US012448379B2

(12) United States Patent
Brubaker et al.

(10) Patent No.: US 12,448,379 B2
(45) Date of Patent: Oct. 21, 2025

(54) WILD TYPE KIT INHIBITORS

(71) Applicant: Blueprint Medicines Corporation, Cambridge, MA (US)

(72) Inventors: Jason D. Brubaker, Cambridge, MA (US); Yinghui Dai, Cambridge, MA (US); Thomas A. Dineen, Cambridge, MA (US); Guangyan Du, Cambridge, MA (US); Cheng Fang, Cambridge, MA (US); Andrew Marc Haidle, Somerville, MA (US); Joseph L. Kim, Cambridge, MA (US); Emanuele Perola, Cambridge, MA (US); Thiwanka Samarakoon, Cambridge, MA (US); Douglas Wilson, Cambridge, MA (US)

(73) Assignee: Blueprint Medicines Corporation, Cambridge, MA (US)

( * ) Notice: Subject to any disclaimer, the term of this patent is extended or adjusted under 35 U.S.C. 154(b) by 0 days.

(21) Appl. No.: 18/603,567

(22) Filed: Mar. 13, 2024

(65) Prior Publication Data

US 2024/0262826 A1 Aug. 8, 2024

Related U.S. Application Data

(63) Continuation of application No. PCT/US2023/081773, filed on Nov. 30, 2023.

(60) Provisional application No. 63/445,787, filed on Feb. 15, 2023, provisional application No. 63/428,804, filed on Nov. 30, 2022.

(51) Int. Cl.

| | |
|---|---|
| ***C07D 471/04*** | (2006.01) |
| ***A61K 31/437*** | (2006.01) |
| ***A61K 31/4545*** | (2006.01) |
| ***A61K 31/496*** | (2006.01) |
| ***A61K 31/4985*** | (2006.01) |
| ***A61K 31/5377*** | (2006.01) |
| ***A61K 31/675*** | (2006.01) |
| ***C07D 519/00*** | (2006.01) |
| ***C07F 9/6524*** | (2006.01) |

(52) U.S. Cl.

CPC .......... *C07D 471/04* (2013.01); *A61K 31/437* (2013.01); *A61K 31/4545* (2013.01); *A61K 31/496* (2013.01); *A61K 31/4985* (2013.01); *A61K 31/5377* (2013.01); *A61K 31/675* (2013.01); *C07D 519/00* (2013.01); *C07F 9/6524* (2013.01)

(58) Field of Classification Search

CPC .................................................... C07D 471/04

See application file for complete search history.

(56) References Cited

U.S. PATENT DOCUMENTS

| | | | |
|---|---|---|---|
| 9,422,285 | B2 | 8/2016 | Vakalopoulos et al. |
| 2013/0059832 | A1 | 3/2013 | Molteni et al. |
| 2013/0059846 | A1 | 3/2013 | Yeh et al. |
| 2013/0237519 | A1 | 9/2013 | Bruce et al. |
| 2014/0031333 | A1 | 1/2014 | Molenti et al. |
| 2020/0299285 | A1 | 9/2020 | Fletcher et al. |
| 2021/0261532 | A1 | 8/2021 | Lennek et al. |

FOREIGN PATENT DOCUMENTS

| | | | | |
|---|---|---|---|---|
| EP | 2147914 | A1 | 1/2010 | |
| WO | 2013/033167 | A1 | 5/2013 | |
| WO | WO-2013088257 | A1 * | 6/2013 | ........... A61K 31/437 |
| WO | 2020/228746 | A1 | 11/2020 | |
| WO | 2021/093795 | A1 | 5/2021 | |
| WO | 2022/109595 | A1 | 5/2022 | |
| WO | 2023/212612 | A1 | 11/2023 | |
| WO | 2024/123966 | A1 | 6/2024 | |
| WO | 2024/124002 | A1 | 6/2024 | |
| WO | 2025/019309 | A2 | 1/2025 | |
| WO | 2025/024503 | A1 | 1/2025 | |
| WO | 2025/034951 | A1 | 2/2025 | |
| WO | 2025/072330 | A1 | 4/2025 | |

OTHER PUBLICATIONS

Baker. Precision at Scale™ Investor Day 2022. Blueprint Medicines Corporation. Slideshow. 113 pages, Oct. 31, 2022.
Granchi et al., Discovery of N-hydroxyindole-based inhibitors of human lactate dehydrogenase isoform A (LDH-A) as starvation agents against cancer cells. J Med Chem. Mar. 24, 2011;54(6):1599-612.
International Search Report and Written Opinion for Application No. PCT/US2023/081773, dated Mar. 20, 2024, 12 pages.

* cited by examiner

*Primary Examiner* — John S Kenyon
*Assistant Examiner* — Rehana Ismail
(74) *Attorney, Agent, or Firm* — McCarter & English, LLP; Steven G. Davis; Xin Zhang

(57) ABSTRACT

Disclosed is a compound represented by Formula (I) or a pharmaceutically acceptable salt thereof. The variables in Formula (I) are defined herein.

(I)

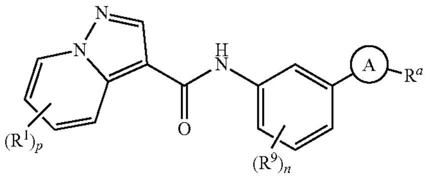

Compounds of Formula (I) are useful for inhibiting wild type c-kit kinase and for treating disorders and diseases mediated by wild type c-kit kinase in humans or non-humans.

33 Claims, No Drawings

WILD TYPE KIT INHIBITORS

RELATED APPLICATIONS

This application is a continuation of International Application No. PCT/US2023/081773, filed Nov. 30, 2023, which, in turn, claims the benefit of U.S. Provisional Application No. 63/428,804 filed on Nov. 30, 2022, and U.S. Provisional Application No. 63/445,787, filed Feb. 15, 2023, the entire teachings of which are incorporated herein by reference in their entirety.

FIELD OF THE INVENTION

The disclosure relates to novel compounds and their use as selective inhibitors of wild type c-kit kinase, a cell surface receptor that acts as the master survival and functional regulator of mast cells.

BACKGROUND OF THE INVENTION

Mast cells are a part of the immune system. They are a main driver of allergic inflammatory responses and are present throughout the body in connective and vascularized tissues, most prominently along surface boundaries with exposure to the external environment: in the skin, the respiratory tract and the gastrointestinal tract. Dysfunctional mast cell activity has been implicated in the pathophysiology of a broad range of allergic and other inflammatory disorders including urticaria, asthma and gastrointestinal disorders.

For many who suffer from allergic conditions, inhibition of mast cell derived mediators, including histamines, leukotrienes, and prostaglandins, has resulted in insufficient therapeutic value to-date given that many mast cell-driven disorders involve multiple pro-inflammatory mediators. One such mast-cell driven disorder is chronic urticaria, which is defined as the occurrence of wheals, angioedema, or both for more than 6 weeks. The international urticaria guideline classifies the disease as chronic spontaneous urticaria (CSU, also called chronic idiopathic urticaria), without a definite eliciting factor involved, or as chronic inducible urticaria (CIndU), where defined and definite eliciting factors reproducibly trigger signs and symptoms and are required for their occurrence. The point prevalence of chronic urticaria is approximately 0.5% to 1%. Chronic urticaria is unpredictable in its course and duration, and it may persist for several years in many patients. Chronic urticaria is a disabling condition that leads to substantial deterioration in quality of life. Furthermore, psychosocial factors, such as anxiety, depression, somatization, interpersonal sensitivity, insomnia, and stressful life events, are present in many of the patients with chronic urticaria. In addition, care of patients with chronic urticaria is time-consuming and costly. No curative treatment exists for chronic urticaria, and all currently recommended treatment options are intended only to control and prevent the symptoms of chronic urticaria.

Wild-type c-kit plays a central role in mast cell survival, proliferation, and activation. Recently in clinical trials, c-kit inhibition has shown positive responses in mast cell mediated diseases. For example, c-kit inhibition in chronic inducible urticaria and chronic spontaneous urticaria has been shown to be an effective treatment in a phase I trial (inducible) and phase 1 and 2 (spontaneous) using a monoclonal antibody, and a c-kit small molecule inhibitor has also shown modulation of tryptase, a mast cell mediator, in normal healthy volunteers and in a phase 1 trial of chronic inducible urticaria the inhibitor has been shown to be an effective treatment. There is need for treatments to target mast cells directly through highly selective inhibition of c-kit to achieve broad symptomatic relief across a range of mast cell mediated diseases.

SUMMARY OF THE INVENTION

Provided herein are compounds, or pharmaceutically acceptable salts thereof, and compositions which are useful for inhibiting wild type c-kit kinase and for treating diseases or disorders mediated by wild type c-kit kinase. The compounds of the disclosure are potent inhibitors of c-kit kinase (see Table 2 in Example 290). Some compounds of the disclosure are orally bioavailable, selective over other kinases such FLT3 kinase and PDGFR and have minimal CNS penetration to reduce CNS side effects.

One embodiment of the disclosure is a compound represented by Formula (I):

(I)

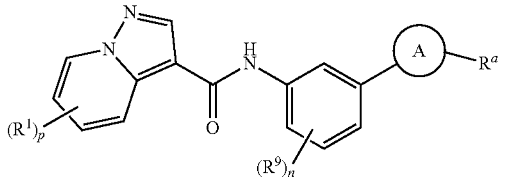

or a pharmaceutically acceptable salt thereof, wherein:

Ring A is selected from tetrazole or triazole, wherein said tetrazole or triazole is optionally substituted with $R^a$;

wherein $R^a$ is selected from hydrogen, $C_{1-6}$ alkyl, $C_{1-6}$haloalkyl, $C_{0-5}$alkylphenyl, $C_{0-5}$alkyl$C_{3-6}$cycloalkyl, $C_{0-5}$alkyl$C_{6-10}$spirocycloalkyl, $C_{0-5}$alkyl$C_{5-10}$bridgedbicycloalkyl, and $C_{0-5}$alkyl(4-6 membered heterocycle), or $C_{0-5}$alkyl(7-10 membered spiroheterocycle) or $C_{0-5}$alkyl(5-10 membered bridgedbicycloheterocycle, each containing at least one N or O, wherein said alkyl, haloalkyl, phenyl, cycloalkyl, spirocycloalkyl, bridgedbicycloalkyl, heterocycle, spiroheterocycle, or bridgedbicycloheterocycle is optionally substituted with 1-5 $R^b$;

each $R^b$ is independently selected from OH, CN, $C_{1-6}$alkoxy, $C_{1-6}$haloalkoxy, $C_{3-5}$ cycloalkoxy, $SO_2C_{1-4}$alkyl, $SO_2C_{1-4}$haloalkyl, $C(O)OC_{1-4}$alkyl, $SO_2$($C_{0-2}$alkyl)(4-6 membered heterocycle containing at least one O or N), $SO_2$($C_{1-4}$alkyl)$C_{1-4}$haloalkoxy, $SO_2$($C_{1-4}$alkyl)$C_{1-4}$alkoxy($C_{0-1}$alkoxy), $SO_2$($C_{1-4}$alkyl)OH, $SO_2$($C_{0-2}$alkyl)$C_{3-6}$ cycloalkyl, $C_{1-3}$alkyl, $C_{1-5}$haloalkyl, halogen and $C_{1-2}$alkylOH, further wherein said cycloalkyl is optionally substituted with $C_{1-3}$alkyl;

each $R^1$ is independently selected from halogen, $C_{1-6}$alkyl, $C_{1-6}$haloalkyl, $C_{3-6}$ cycloalkyl, $C_{0-4}$alkylOH, $C_{6-10}$spirocycloalkyl, $C_{0-6}$alkyl$C_{1-6}$alkoxy, $C_{0-4}$alkyl$C_{1-6}$haloalkoxy, $NH_2$, $NHC_{1-6}$alkyl, $N(C_{1-6}alkyl)_2$, NH-(4-6 membered heterocycle or 5-6 membered heteroaryl containing at least one O or N), and 4-6 membered heterocycle or 7-10 membered fused bicycloheterocycle or 7-10 membered spiroheterocycle, each containing at least one O or N, or 5-6 membered heteroaryl containing at least two N, wherein said alkyl, haloalkyl, alkoxy, cycloalkyl, spirocycloalkyl, heterocycle, or heteroaryl is optionally substituted with 1-3 $R^e$;

each $R^e$ is independently selected from deuterium, deuterated $C_{1-4}$alkyl, deuterated $C_{1-4}$alkoxy, $C_{1-4}$haloalkoxy, halogen, $C_{0-3}$alkyl-$S(O)_2C_{1-3}$alkyl, $C_{0-3}$alkyl-S(O)(NH)$C_{1-3}$alkyl, ($C_{1-4}$alkyl)P(O)($C_{1-3}$alkyl)$_2$, $C_{1-4}$alkyl, CN, $CHF_2$, $C_{3-6}$cycloalkyl, $C_{1-4}$haloalkyl, $C_{0-4}$alkylOH, $C_{2-5}$alkyl$(OH)_2$, $C_{1-4}$alkyl(OH)($C_1$-$C_4$alkoxy), $C_{2-5}$alkyl(OH)($C_{1-5}$alkoxy)($C_{1-5}$alkoxy), $C_{1-4}$alkyl$C_{1-4}$alkoxy, $C_{1-3}$alkyoxy$C_{1-3}$alkoxy, $NH_2$, NH($C_{1-6}$alkyl), N($C_{1-6}$alkyl)$_2$, and ($C_{0-4}$alkyl)-(4-6 membered heterocycle containing at least one O or N), wherein said heterocycle is optionally substituted with 1-3 $C_{1-3}$alkylOH, or $C_{1-3}$alkyl. Alternatively, each $R^e$ is independently selected from deuterium, deuterated $C_{1-4}$alkyl, deuterated $C_{1-4}$alkoxy, $C_{1-4}$haloalkoxy, halogen, $C_{0-3}$alkyl-$S(O)_2C_{1-3}$alkyl, $C_{0-3}$alkyl-S(O)(NH)$C_{1-3}$alkyl, ($C_{1-4}$alkyl)P(O)($C_{1-3}$alkyl)$_2$, $C_{1-4}$alkyl, CN, $CHF_2$, $C_{3-6}$cycloalkyl, $C_{1-4}$haloalkyl, $C_{0-4}$alkylOH, $C_{1-4}$alkyl(OH)($C_1$-$C_4$alkoxy), $C_{0-4}$alkyl$C_{1-4}$alkoxy, $C_{1-3}$alkyoxy$C_{1-3}$alkoxy, $NH_2$, NH($C_{1-4}$alkyl), N($C_{1-6}$alkyl)$_2$, and ($C_{0-4}$alkyl)-(4-6 membered heterocycle containing at least one O or N), wherein said heterocycle is optionally substituted with 1-3 $C_{0-3}$alkylOH. In another alternative, each $R^e$ is independently selected from from deuterium, deuterated $C_{1-4}$alkyl, deuterated $C_{1-4}$alkoxy, $C_{1-4}$haloalkoxy, halogen, $C_{0-3}$alkyl-$S(O)_2C_{1-3}$alkyl, $C_{0-3}$alkyl-S(O)(NH)$C_{1-3}$alkyl, ($C_{1-4}$alkyl)P(O)($C_{1-3}$alkyl)$_2$, $C_{1-4}$alkyl, $C_{1-4}$haloalkyl, $C_{0-4}$alkylOH, $C_{0-4}$alkyl$C_{1-4}$alkoxy, $C_{1-3}$alkyoxy$C_{1-3}$alkoxy, $NH_2$, NH($C_{1-6}$alkyl), N($C_{1-6}$alkyl)$_2$, and ($C_{0-4}$alkyl)-(4-6 membered heterocycle containing at least one O or N), wherein said heterocycle is optionally substituted with 1-3 $C_{0-3}$alkylOH;

each $R^9$ is independently selected from $C_{1-3}$alkyl, $C_{1-3}$haloalkyl, halogen, CN, and $C_{3-4}$cycloalkyl;

n is 1 or 2; and p is 0, 1 or 2.

Another embodiment of the disclosure is a pharmaceutical composition comprising a pharmaceutically acceptable carrier or excipient and a compound of the disclosure, or a pharmaceutically acceptable salt thereof. In one aspect, the composition is for treating a disease or disorder mediated by wild type c-kit kinase. In another aspect, the composition is for inhibiting wild type c-kit kinase.

Another embodiment of the disclosure is a method of treating a subject suffering from a disease or disorder mediated by wild type c-kit kinase. The method comprises administrating to the subject an effective amount of a compound of the disclosure, or pharmaceutically acceptable salt thereof, or an effective amount of a pharmaceutical composition comprising a pharmaceutically acceptable carrier or excipient and a compound of the disclosure, or a pharmaceutically acceptable salt thereof.

Another embodiment of the disclosure is a method of inhibiting wild type c-kit kinase in a subject in need thereof. The method comprises administrating to the subject in need thereof an effective amount of a compound of the disclosure, or a pharmaceutically acceptable salt thereof, or an effective amount of a pharmaceutical composition comprising a pharmaceutically acceptable carrier or excipient and a compound of the disclosure, or a pharmaceutically acceptable salt thereof.

Another embodiment of the disclosure is the use of a compound of the disclosure, or a pharmaceutically acceptable salt thereof, or a pharmaceutical composition comprising a compound of the disclosure and a pharmaceutically acceptable carrier or excipient in the manufacture of a medicament for the treatment of medical condition mediated by wild type c-kit kinase.

Another embodiment of the disclosure is the use of a compound of the disclosure, or a pharmaceutically acceptable salt thereof, or a pharmaceutical composition comprising a compound of the disclosure and a pharmaceutically acceptable carrier or excipient in the manufacture of a medicament for inhibiting wild type c-kit kinase in a subject in need thereof.

Another embodiment of the disclosure is a compound of the disclosure or a pharmaceutically acceptable salt thereof, or a pharmaceutically composition comprising a compound of the disclosure and a pharmaceutically acceptable carrier or excipient for the treatment of a medical condition mediated by wild type c-kit kinase.

Another embodiment of the disclosure is a compound of the disclosure or a pharmaceutically acceptable salt thereof, or a pharmaceutically composition comprising a compound of the disclosure and a pharmaceutically acceptable carrier or excipient for inhibiting wild type c-kit kinase in a subject in need thereof.

DETAILED DESCRIPTION OF THE INVENTION

An object of this disclosure is to provide novel compounds and compositions with highly selective, potent activity against wild type c-kit kinase for the safe and effective treatment of mast cell associated disease in a subject. For example, the $IC_{50}$ values for inhibition of phospho kit provided in Table 2 of Example 290 demonstrate that these compounds are potent inhibitors of c-kit. The term "KIT" or "kit" refers to a human tyrosine kinase that may be referred to as mast/stem cell growth factor receptor (SCFR), proto-oncogene c-kit, tyrosine-protein kinase kit or CD117.

In treating these mast cell associated diseases, especially chronic disorders such as urticaria and asthma, any new therapy should be well-tolerated. The compounds of the disclosure aim to provide treatments having desirable efficacy, safety, and pharmaceutical properties for the treatment of c-kit mediated diseases. In some aspects, compounds of the disclosure are orally administered. In some aspects, compounds of the disclosure are selective inhibitors of c-kit kinase. Selective inhibitors selectively reduce target signaling activity relative to off-target signaling activity, via direct or indirect interaction with the target, which leads to an increased probability of clinical success in comparison with a non-selective inhibitors. In some aspects, compounds of the disclosure have low CNS penetration, which is a desirable property for reducing and minimizing side effects of chronic treatment. Compounds with low CNS penetration often have high levels or active transport out of the brain, i.e., high efflux ratios from the CNS.

Compounds of the disclosure are selective c-kit inhibitors. As used herein, a "selective c-kit inhibitor" refers to a compound or a pharmaceutically acceptable salt thereof that has the ability to selectively inhibit c-kit kinase over other targets. More specifically, a selective c-kit inhibitor has the ability to selectively inhibit c-kit over another kinase. In some aspects, compounds of the disclosure are selective for c-kit over FLT3 kinase and PDGFR kinase. A selective c-kit inhibitor has the ability to selectively reduce target signaling activity relative to off-target signaling activity, via direct or indirect interaction with the target. The ability to selectively target c-kit with a compound of the disclosure or pharmaceutically acceptable salt thereof provides advantages in terms of improved potency, less off-target activity and an increased probability of clinical success in comparison with a non-selective compound or salt.

Some compounds of the disclosure are inhibitors of KIT exon 9 and/or 11. Mutations in exon 9 and 11 of KIT are primary driver mutations in ~10% of gastrointestinal tumors, and high dose imatinib, a KIT ex9/11 inhibitor, has been shown to be an effective treatment option.

In one embodiment, the compounds of the disclosure are represented by Formula (I). The variables in Formula (I) are as described above.

In a first aspect, the compounds of the disclosure are represented by any one of Formulas (IIa), (IIb), (IIIa), (IIIb) or (IV)-(XLIII):

(IIa)

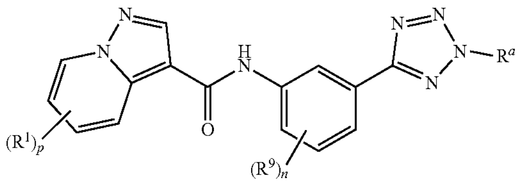

(IIb)

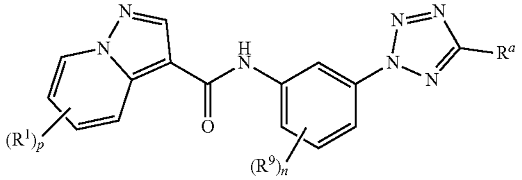

(IIIa)

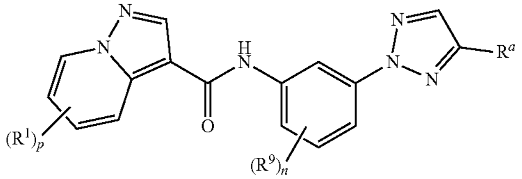

(IIIb)

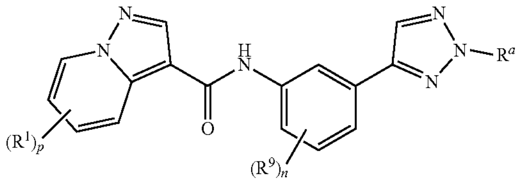

(IV)

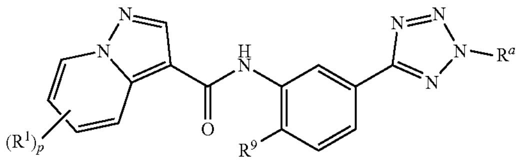

(V)

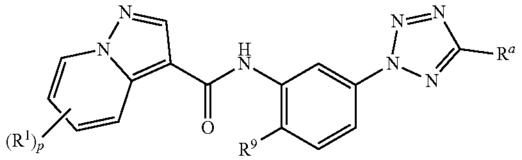

-continued (VI)

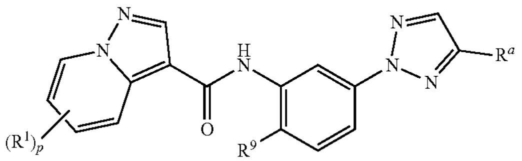

(VII)

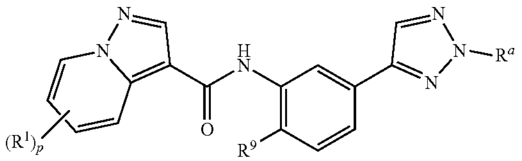

(VIII)

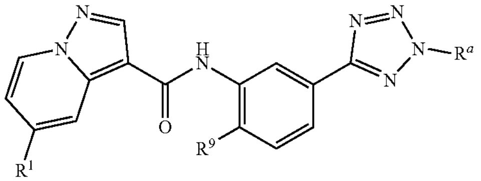

(IX)

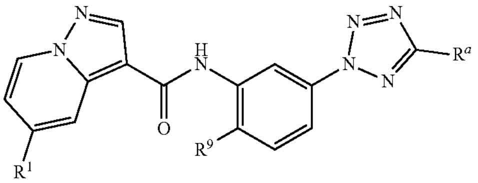

(X)

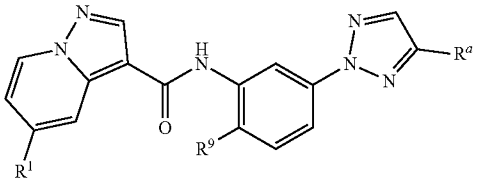

(XI)

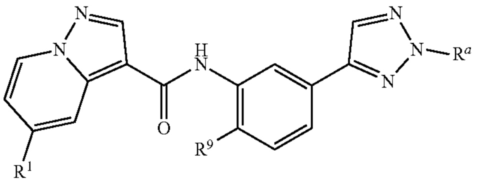

(XII)

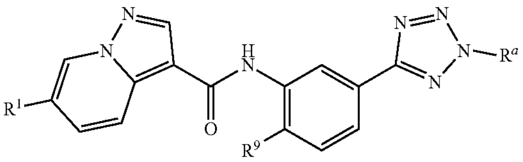

(XIII)

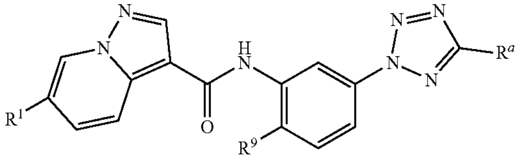

-continued
(XIV)
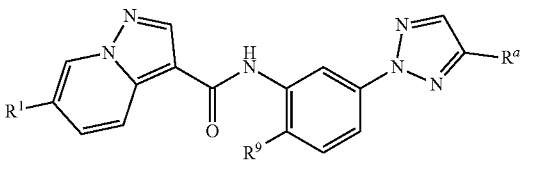
(XV)
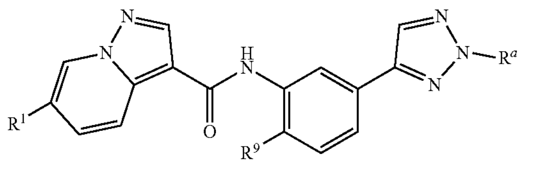
(XVI)
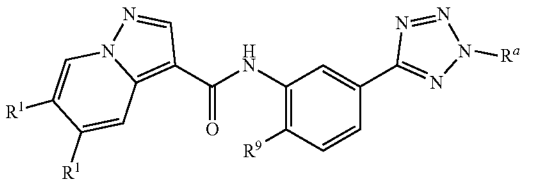
(XVII)
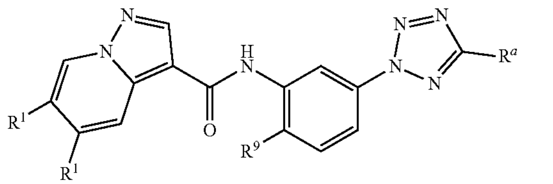
(XVIII)
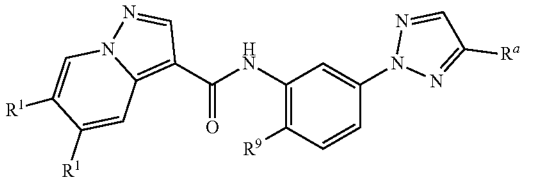
(XIX)
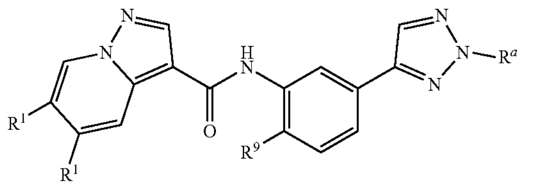
(XX)
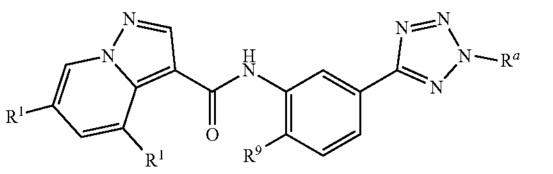
(XXI)
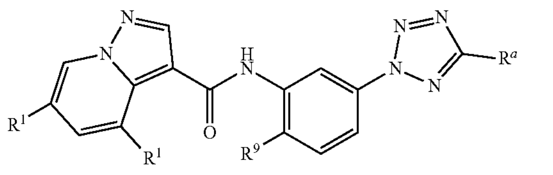
-continued
(XXII)
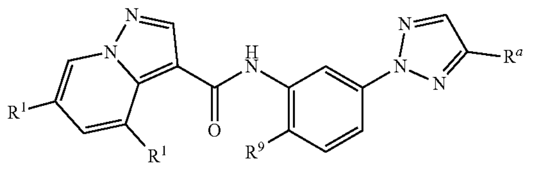
(XXIII)
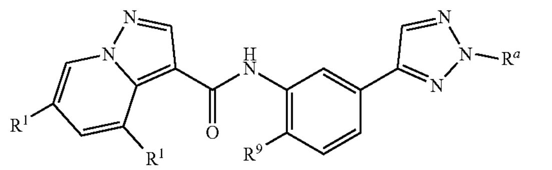
(XXIV)
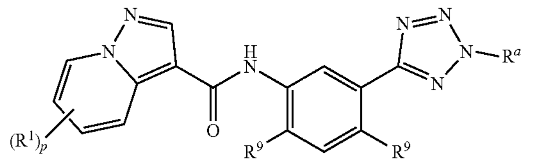
(XXV)
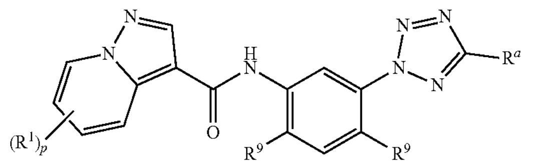
(XXVI)
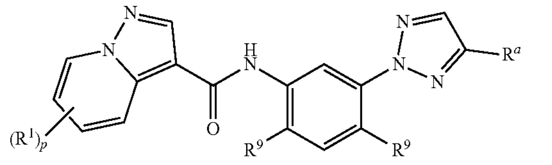
(XXVII)
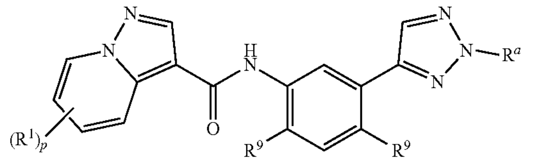
(XXVIII)
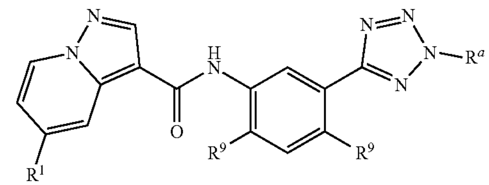
(XXIX)
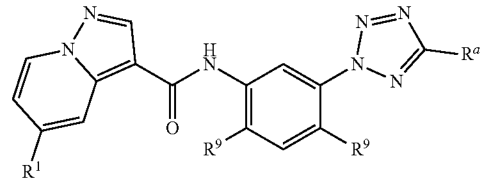

-continued (XXX)

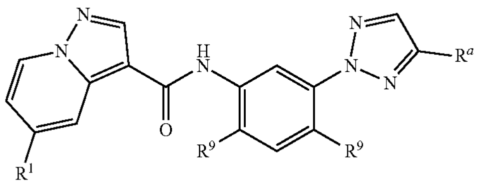

(XXXI)

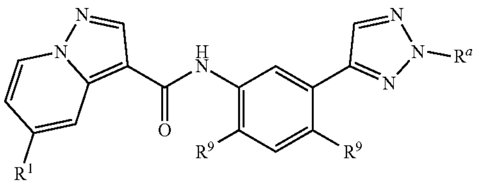

(XXXII)

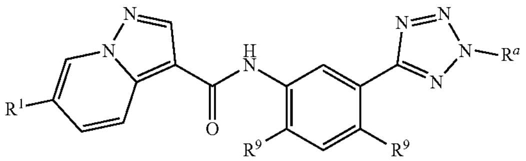

(XXXIII)

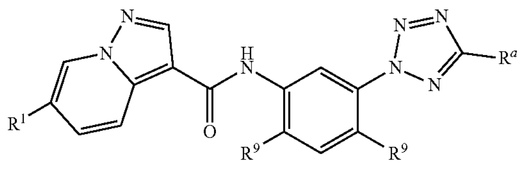

(XXXIV)

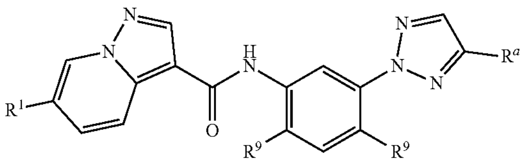

(XXXV)

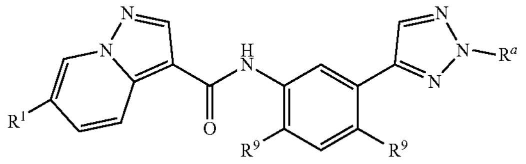

(XXXVI)

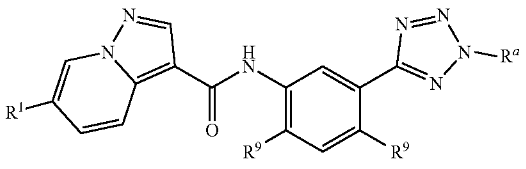

(XXXVII)

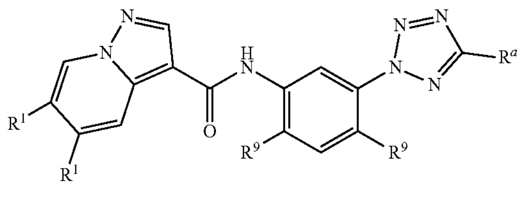

-continued (XXXVIII)

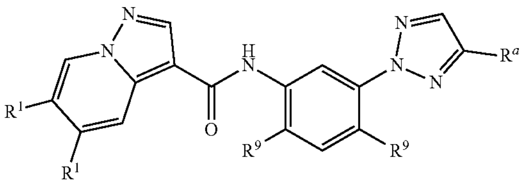

(XXXIX)

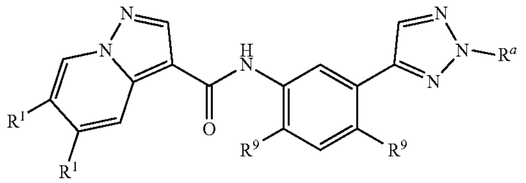

(XL)

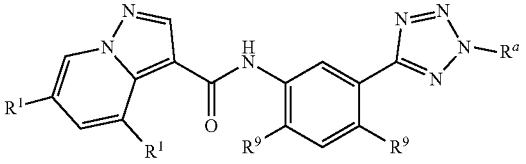

(XLI)

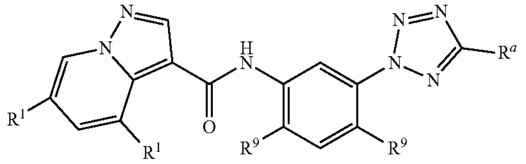

(XLII)

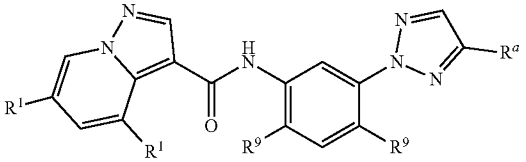

(XLIII)

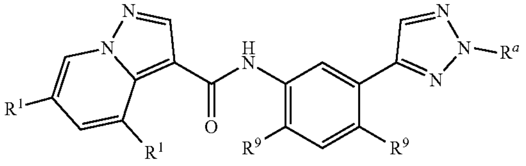

or a pharmaceutically acceptable salt of any of the foregoing. The variables are as described for Formula (I). In one aspect, p is 0 for Formulas (IIa), (IIb), (IIIa), (IIIb), (IV), (V), (VI), (VII), (XXIV), (XXV), (XXVI), and (XXVII), and the remainder of the variables are as described for Formula (I). Alternatively, p is 1 for Formulas (IIa), (IIb), (IIIa), (IIIb), (IV), (V), (VI), (VII), (XXIV), (XXV), (XXVI), and (XXVII), and the remainder of the variables are as described for Formula (I). Alternatively, p is 2 for Formulas (IIa), (IIb), (IIIa), (IIIb), (IV), (V), (VI), (VII), (XXIV), (XXV), (XXVI), and (XXVII), and the remainder of the variables are as described for Formula (I). In yet another alternative, p is 1 or 2 for Formulas (IIa), (IIb), (IIIa), (IIIb), (IV), (V), (VI), (VII), (XXIV), (XXV), (XXVI), and (XXVII), and the remainder of the variables are as described for Formula (I).

In a second aspect, the compounds of the disclosure or a pharmaceutically acceptable salt thereof are represented by any one of Formulas (I), (IIa), (IIb), (IIIa), (IIIb) or (IV)-(XLIII), wherein:

$R^a$ is selected from hydrogen, $C_{1-6}$alkyl, $C_{1-6}$haloalkyl, $C_{0-3}$alkylphenyl, $C_{0-4}$alkyl$C_{3-6}$ cycloalkyl, $C_{0-3}$alkyl$C_{6-10}$spirocycloalkyl, $C_{0-3}$alkyl($C_{5-8}$ bridgedbicycloalkyl), $C_{0-5}$alkyl(4-6 membered heterocycle containing at least one N or O), $C_{0-3}$alkyl(7-10 membered spiroheterocycle containing at least one N or O), and $C_{0-3}$alkyl(5-10 membered bridged bicycloheterocycle containing at least one O or N), wherein:

said alkyl or haloalkyl is optionally substituted with 1-5 $R^b$ each independently selected from $C_{1-5}$alkoxy, $C_{1-5}$haloalkoxy, $C_{3-6}$cycloalkyl, OH and CN;

said cycloalkyl, spirocycloalkyl, or phenyl is optionally substituted with 1-2 $R^b$ each independently selected from methyl, halogen, $C_{1-3}$haloalkyl, $C_{1-3}$alkoxy, and $C_{0-3}$alkylOH; and said heterocycle is optionally substituted with one $R^b$ selected from $SO_2C_{1-5}$alkyl, $SO_2C_{1-5}$haloalkyl, $C(O)OC_{1-4}$alkyl, $SO_2$(4-6 membered heterocycle containing at least one O or N), $SO_2(C_{1-3}$alkyl) $C_{1-3}$ haloalkoxy, $SO_2(C_{1-3}$alkyl)$C_{1-3}$alkoxy, $SO_2$ ($C_{1-4}$alkyl)OH, $SO_2(C_{1-3}$alkyl)$C_{1-3}$alkoxy (methoxy), $SO_2(C_{0-2}$alkyl)$C_{3-6}$cycloalkyl and $C_{1-4}$ haloalkyl, further wherein said cycloalkyl is optionally substituted with $C_{1-2}$alkyl;

and the remainder of the variables are as described for Formula (I) or the first aspect.

In a third aspect, the compounds of the disclosure or a pharmaceutically acceptable salt thereof are represented by any one of Formulas (I), (IIa), (IIb), (IIIa), (IIIb) or (IV)-(XLIII), wherein:

$R^a$ is selected from $C_{1-5}$alkyl, $C_{1-5}$haloalkyl, $C_{0-3}$alkyl$C_{3-6}$cycloalkyl, $C_{0-3}$alkyl(4-6 membered heterocycle containing at least one O or N), $C_{0-2}$alkyl $C_{6-10}$spirocycloalkyl, $C_{0-2}$alkyl(7-9 membered spiroheterocycle containing at least one O), $C_{0-1}$alkylphenyl, $C_{0-2}$alkyl(6-8 membered bridged bicycloheterocycle containing at least one O or N), and $C_{1-2}$alkyl($C_{5-7}$bridgedbicycloalkyl), wherein:

said alkyl or haloalkyl is optionally substituted with 1-3 $R^b$ each independently selected from OH, CN, $C_{1-3}$alkoxy, $C_{1-4}$haloalkoxy, and $C_{3-5}$cycloalkyl;

said cycloalkyl, spirocycloalkyl, or phenyl is optionally substituted with 1-3 $R^b$ each independently selected from halogen, methyl, $C_{1-3}$haloalkyl, $C_{1-2}$alkoxy, and $C_{1-2}$alkylOH; and said heterocycle is optionally substituted with 1-2 $R^b$ each independently selected from $C(O)OC_{1-4}$alkyl, $SO_2C_{1-4}$alkyl, $SO_2C_{1-4}$haloalkyl, $SO_2$(4-5 membered heterocycle containing one O), $SO_2$ ($C_{1-2}$alkyl)$C_{1-2}$haloalkoxy, $SO_2(C_{1-2}$alkyl)$C_{1-2}$ alkoxy, $SO_2(C_{1-3}$alkyl)OH, $SO_2C_{3-4}$cycloalkyl, $SO_2(C_{1-2}$ alkyl)$C_{1-2}$alkoxy(methoxy), $C_{1-4}$haloalkyl, further wherein said cycloalkyl is optionally substituted with $C_{1-2}$alkyl;

and the remainder of the variables are as described for Formula (I) or the first aspect.

In a fourth aspect, the compounds of the disclosure or a pharmaceutically acceptable salt thereof are represented by any one of Formulas (I), (IIa), (IIb), (IIIa), (IIIb) or (IV)-(XLIII), wherein:

$R^a$ is selected from $C_{1-5}$alkyl, $C_{2-5}$haloalkyl, cyclobutyl, cyclopropyl, methylcyclopropyl, $CH(CH_3)$cyclopropyl, methylcyclobutyl, $C_{0-2}$alkyl (tetrahydropyranyl), $C_{6-10}$spirocycloalkyl, $C_{0-2}$alkyl (8-membered spiroheterocycle containing at least one O), benzyl, $CH_2$(6-membered bridged bicycloheterocycle containing one O), $CH_2$(bridgedbicycloalkyl) and azetidinyl, wherein:

said alkyl or haloalkyl is optionally substituted with 1-5 $R^b$ each independently selected from $C_{2-3}$alkoxy, $C_{2-3}$haloalkoxy, $C_{3-4}$cycloalkyl, OH and CN;

said cyclobutyl, cyclopropyl, methylcyclopropyl, methylcyclobutyl, spirocycloalkyl, or benzyl is optionally substituted with 1-3 $R^b$ each independently selected from halogen, methyl, halomethyl, methoxy and methylhydroxy; and said azetitinyl is optionally substituted with one $R^b$ selected from $SO_2C_{1-3}$alkyl, $SO_2C_{1-3}$haloalkyl, $SO_2$tetrahydrofuran, $SO_2$oxetanyl, $SO_2(C_2$alkyl) $C_2$haloalkoxy, $SO_2(C_{1-2}$alkyl)methoxy, $SO_2(C_{1-2}$alkyl)OH, $SO_2$cyclopropyl, $SO_2(C_{1-2}$alkyl)$C_{1-2}$alkoxy(methoxy), $C(O)OC_{1-2}$alkyl, and $C_{1-2}$haloalkyl, further wherein said cyclopropyl is optionally substituted with methyl;

and the remainder of the variables are as described for Formula (I) or the first aspect.

In a fifth aspect, the compounds of the disclosure or a pharmaceutically acceptable salt thereof are represented by any one of Formulas (I), (IIa), (IIb), (IIIa), (IIIb) or (IV)-(XLIII), wherein $R^a$ is independently selected from hydrogen, methyl, ethyl, 2-isopropyl, 2-(cyclopropylmethyl), (S)-(2,2-difluorocyclopropyl)methyl, (R)-4,4,4-trifluoro-3-hydroxy-3-methylbutyl, (S)-4,4,4-trifluoro-3-hydroxy-3-methylbutyl, (R)-1-cyclopropylethyl, (S)-1-cyclopropylethyl, (R)-(2,2-difluorocyclopropyl) methyl, (tetrahydro-2H-pyran-4-yl)methyl, (tetrahydro-2H-pyran-2-yl)methyl, (R)-1-(tetrahydro-2H-pyran-4-yl)ethyl, (S)-1-(tetrahydro-2H-pyran-4-yl)ethyl, 2-isopropoxyethyl, 2-cyclobutoxyethyl, (2,2,2-trifluoroethoxy)ethyl, 4,4,4-trifluorobutyl, cyclopropyl, cyclobutyl, 3-fluorocyclobutyl, 3,3-difluorocyclobutyl, (1s,3s)-3-(trifluoromethyl)cyclobutyl, (1r,3r)-3-(trifluoromethyl)cyclobutyl, 2-fluorocyclopropyl, 2,2-difluorocyclopropyl, (1r,3r)-3-(hydroxymethyl)cyclobutyl, (1s, 3s)-3-methoxycyclobutyl, (2-fluorobenzyl), $CH(CH_3)$(2-fluorophenyl),

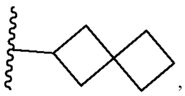,
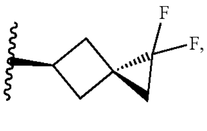,

-continued

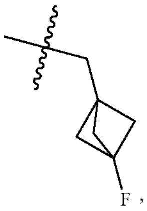 ,

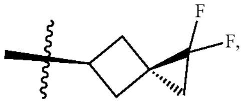

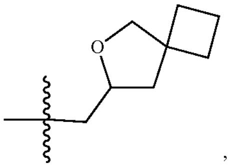 ,

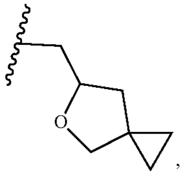 ,

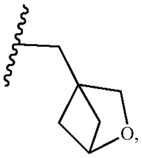

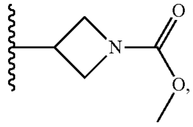

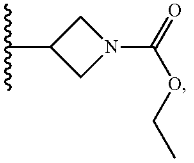

1-(methylsulfonyl)azetidin-3-yl, (ethylsulfonyl)azetidin-3-yl, 1-(propylsulfonyl)azetidin-3-yl, 1-(isopropylsulfonyl)azetidin-3-yl, (2-methoxyethyl)sulfonyl)azetidin-3-yl, 1-(cyclopropylsulfonyl)azetidin-3-yl, 1-((cyclobutylmethyl)sulfonyl)azetidin-3-yl, 1-((1-methylcyclopropyl)sulfonyl)azetidin-3-yl, 1-((trifluoromethyl)sulfonyl)azetidin-3-yl, 1-((3,3-difluoropropyl)sulfonyl)azetidin-3-yl, (2-(2-methoxyethoxy)ethyl)sulfonyl)azetidin-3-yl, (4-cyanobutyl)sulfonyl)azetidin-3-yl, (2,2,2-trifluoroethyl)azetidin-3-yl, (2-hydroxyethyl)sulfonyl)azetidin-3-yl,

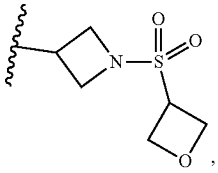 ,

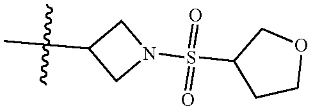

and (2-(2,2-difluoroethoxy)ethyl)sulfonyl)azetidine-3-yl;

and the remainder of the variables are as described for Formula (I) or the first aspect.

In a sixth aspect, the compounds of the disclosure or a pharmaceutically acceptable salt thereof are represented by any one of Formulas (I), (IIa), (IIb), (IIIa), (IIIb) or (IV)-(XLIII), wherein:

each $R^1$ is independently selected from halogen, $C_{1-4}$alkyl, $C_{1-4}$haloalkyl, $C_{0-4}$alkylOH, $C_{0-4}$alkyl$C_{1-6}$alkoxy, $C_{0-4}$alkyl$C_{1-6}$haloalkoxy, $C_{3-4}$cycloalkyl, $NH_2$, $NHC_{1-5}$alkyl, $N(C_{1-3}alkyl)_2$, NH-(4-6 membered heterocycle containing at least one O), NH-(5-6 membered heteroaryl containing at least one N), 4-6 membered heterocycle or 7-9 membered fused bicycloheterocycle or 7-10 membered spiroheterocycle, each containing at least one O or N, and 5-6 membered heteroaryl containing at least one N, wherein:

said alkyl, haloalkyl, or alkoxy is optionally substituted with 1-3 $R^e$ each independently selected from deuterium, deuterated $C_{1-3}$alkoxy, $C_{1-3}$ alkyl, $C_{1-3}$haloalkoxy, $C_{1-4}$alkoxy, $C_{1-2}$alkyoxy$C_{1-2}$alkoxy, OH, halogen, and 4-6 membered heterocycle containing at least one O or N;

said heterocycle or cycloalkyl is optionally substituted with 1-3 $R^e$ each independently selected from deuterated $C_{1-3}$alkyl, di($C_{1-3}$alkyl)amine, $S(O)_2C_{1-3}$alkyl, halogen, 4-6 membered heterocycle containing one O, $C_{1-3}$alkyl, $C_{0-4}$alkylOH, and $C_{1-2}$alkyl$C_{1-3}$alkoxy; and said heteroaryl is optionally substituted with 1-3 $R^e$ each independently selected from $C_{1-4}$alkyl, CN, $CHF_2$, cyclopropyl, $C_{1-4}$alkylOH, $C_{2-5}alkyl(OH)_2$, $C_{2-4}$alkyl(OH)(methoxy), $C_{2-5}$alkyl(OH)($C_{1-5}$alkoxy)($C_{1-5}$alkoxy), $S(O)_2C_{1-3}$alkyl, $C_{1-3}$alkyl-S(O)(NH)$C_{1-3}$alkyl, $(C_{1-3}alkyl)P(O)(C_{1-3}alkyl)_2$, and ($C_{1-3}$alkyl)-(4-6 membered heterocycle containing at least one O or N), wherein said heterocycle is optionally substituted with 1-2 OH or $C_{1-3}$alkyl. Alternatively, said heteroaryl is optionally substituted with 1-3 $R^e$ each independently selected from $C_{1-4}$ alkyl, CN, $CHF_2$, cyclopropyl, $C_{1-4}$alkylOH, $C_{2-4}$alkyl(OH)(methoxy), $S(O)_2C_{1-3}$alkyl, $C_{1-3}$alkyl-S(O)(NH)$C_{1-3}$alkyl, $(C_{1-3}alkyl)P(O)(C_{1-3}alkyl)_2$, and ($C_{1-3}$alkyl)-(4-6 membered heterocycle containing at least one O or N), wherein said heterocycle is optionally substituted with 1-2 OH. In another alternative, said heteroaryl is optionally substituted with 1-3 $R^e$ each independently selected from $C_{1-4}$alkyl, $C_{1-4}$alkylOH, $S(O)_2C_{1-3}$alkyl, $C_{1-3}$alkyl-S(O)(NH)$C_{1-3}$alkyl, $(C_{1-3}alkyl)P(O)(C_{1-3}alkyl)_2$, and ($C_{1-3}$alkyl)-(4-6 membered heterocycle containing at least one O or N), wherein said heterocycle is optionally substituted with 1-2 OH;

and the remainder of the variables are as described for Formula (I) or the first aspect, second, third, fourth or fifth aspects.

In a seventh aspect, the compounds of the disclosure or a pharmaceutically acceptable salt thereof are represented by any one of Formulas (I), (IIa), (IIb), (IIIa), (IIIb) or (IV)-(XLIII), wherein:

each $R^1$ is independently selected from halogen, $C_{1-3}$alkyl, $C_{1-4}$alkylOH, $C_{0-4}$alkyl$C_{1-5}$alkoxy, $C_{0-4}$alkyl$C_{1-5}$haloalkoxy, cyclopropyl, $NH_2$, $NHC_{1-4}$alkyl, $N(C_{1-2}alkyl)_2$, NH-(5 membered heterocycle containing one O), NH-(5 membered heteroaryl containing two N),

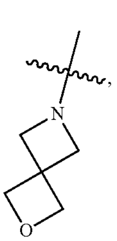 ,

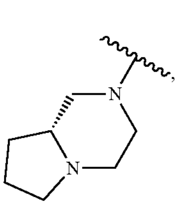 , azetidinyl, pyrrolidinyl, piperidinyl, piperazinyl, morpholino, and pyrazolyl, wherein:

said alkyl or alkoxy is optionally substituted with 1-3 $R^e$ each independently selected from deuterium, $C_{1-3}$alkyl, $C_{1-3}$haloalkoxy, deuterated methoxy, OH, $C_{1-4}$alkoxy, $C_{1-2}$alkyoxy$C_{1-2}$alkoxy, halogen and 4-6 membered heterocycle containing at least one O;

said azetidinyl, pyrrolidinyl, piperidinyl, piperazinyl, tetrahydrofuran or morpholino is optionally substituted with 1-2 $R^e$ each independently selected from deuterated $C_{1-3}$alkyl, di($C_{1-3}$alkyl)amine, $S(O)_2CH_3$, halogen, $C_{0-3}$alkylOH, 4-6 membered heterocycle containing one O, $C_{1-2}$ alkyl, $C_{1-2}$haloalkyl, and $C_{1-2}$alkyl$C_{1-3}$alkoxy; and said pyrazolyl is optionally substituted with 1-3 $R^e$ each independently selected from $C_{1-4}$alkyl, CN, $CHF_2$, cyclopropyl, $C_{0-4}$alkylOH, $C_{2-5}$alkyl$(OH)_2$, $C_{1-4}$alkyl(OH)($C_1$-$C_4$alkoxy), $C_{1-3}$alkyl(OH)($C_{1-3}$alkoxy)($C_{1-3}$alkoxy), $S(O)_2C_{1-3}$alkyl, $C_{1-3}$alkyl-S(O)(NH)$CH_3$, ($C_{1-3}$ alkyl)P(O)$(C_{2-3}alkyl)_2$, and ($C_{1-3}$alkyl)-(6 membered heterocycle containin at least one O or N), further wherein said 6 membered heterocycle is optionally substituted with 1-2 OH or $C_{1-3}$alkyl. Alternatively, said pyrazolyl is optionally substituted with 1-3 $R^e$ each independently selected from $C_{1-4}$alkyl, CN, $CHF_2$, cyclopropyl, $C_{0-4}$alkylOH, $C_{2-4}$alkyl(OH)(methoxy), $S(O)_2C_{1-3}$alkyl, $C_{1-3}$alkyl-S(O)(NH)$CH_3$, ($C_{1-3}$alkyl)P(O)$(C_{2-3}alkyl)_2$ and ($C_{1-3}$alkyl)-(6 membered heterocycle containin at least one O or N), further wherein said 6 membered heterocycle is optionally substituted with 1-2 OH. In another alternative, each $R^e$ is independently selected from $C_{1-4}$alkyl, $C_{0-4}$alkylOH, $S(O)_2C_{1-3}$alkyl, $C_{1-3}$alkyl-S(O)(NH)$CH_3$, ($C_{1-3}$ alkyl)P(O)$(C_{2-3}alkyl)_2$ and ($C_{1-3}$alkyl)-(6 membered heterocycle containin at least one O or N), further wherein said 6 membered heterocycle is optionally substituted with 1-2 OH;

and the remainder of the variables are as described for Formula (I) or the first aspect, second, third, fourth or fifth aspects.

In an eighth aspect, the compounds of the disclosure or a pharmaceutically acceptable salt thereof are represented by any one of Formulas (I), (IIa), (IIb), (IIIa), (IIIb) or (IV)-(XLIII), wherein:

each $R^1$ is independently selected from halogen, $C_{1-3}$alkyl, $C_{2-3}$alkylOH, $C_{0-3}$alkyl$C_{1-5}$alkoxy, cyclopropyl, $NH_2$, NH($C_{1-4}$alkyl), $N(C_{1-2}alkyl)_2$, NH-tetrahydrofuranyl, NH-pyrazolyl, NH-oxetanyl,

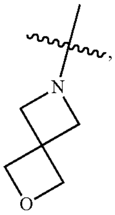
,
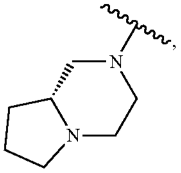
, azetidinyl, pyrrolidinyl, piperidinyl, piperazinyl, morpholino, and pyrazolyl, wherein:

said alkyl or alkoxy is optionally substituted with 1-3 $R^e$ each independently selected from selected from OH, halogen, deuterium, $C_{1-3}$ alkyl, methoxy, ethoxymethoxy, deuterated methoxy, haloethoxy, butoxy, and 4-6 membered heterocycle containing one O;

said azetidinyl, pyrrolidinyl, piperidinyl, piperazinyl, tetrahydrofuranyl or morpholino is optionally substituted with 1-2 $R^e$ each independently selected from $S(O)_2CH_3$, halogen, $C_{0-2}$alkylOH, oxetanyl, $C_1$alkyl, $C_2$haloalkyl, deuterated$C_{1-3}$alkyl, di($C_{1-3}$alkyl)amine and $C_1$alkyl$C_1$alkoxy; and said pyrazolyl is optionally substituted with 1-3 $R^e$ each independently selected from methyl, ethyl, propyl, butyl, cyclopropyl, ethylhydroxy, isobutylhydroxy, $CH_2CH(OH)C(CH_3)_2(OH)$, $CH_2CH(OH)CH_2OH$, $CH_2C(OH)(CH_3)CH_2OH$, $CH(CH_2OH)_2$, propyl(OH)methoxy, $CH_2CH(OH)CH_2OCH_2CH_2OCH_3$, $C_{1-2}$alkyl(morpholino), $C_{1-2}$alkyl(piperazinyl), $C_{1-2}$alkyl(tetrahydropyranyl), S(=O)(=NH)$CH_3$, and ($C_{2-3}$alkyl)P(O)$(CH_3)_2$, further wherein said morpholino, piperazinyl, and tetrahydropyranyl is optionally substituted with 1-2 OH or methyl. Alternatively, said pyrazolyl is optionally substituted with 1-3 $R^e$ each independently selected from methyl, ethyl, propyl, butyl, cyclopropyl, ethylhydroxy, propyl(OH)methoxy, isobutylhydroxy, $C_{1-2}$alkyl(morpholino), $C_{1-2}$alkyl(piperazinyl), $C_{1-2}$alkyl(tetrahydropyranyl), S(=O)(=NH)$CH_3$, ($C_{2-3}$alkyl)P(O)$(CH_3)_2$, further wherein said morpholino, piperazinyl, and tetrahydropyranyl is optionally substituted with 1-2 OH. In another alternative, said pyrazolyl is optionally substituted with 1-3 $R^e$ each independently selected from methyl, ethyl, propyl, butyl, ethylhydroxy, isobutylhydroxy, $C_{1-2}$alkyl(morpholino), $C_{1-2}$alkyl(piperazinyl), $C_{1-2}$alkyl(tetrahydropyranyl), S(=O)(=NH)$CH_3$, ($C_{2-3}$alkyl)P(O)$(CH_3)_2$, further wherein said morpholino, piperazinyl, and tetrahydropyranyl is optionally substituted with 1-2 OH;

and the remainder of the variables are as described for Formula (I) or the first aspect, second, third, fourth or fifth aspects.

In a ninth aspect, the compounds of the disclosure or a pharmaceutically acceptable salt thereof are represented by any one of Formulas (I), (IIa), (IIb), (IIIa), (IIIb) or (IV)-(XLIII), wherein each $R^1$ is independently selected from 1-((4-hydroxytetrahydro-2H-pyran-4-yl)methyl)-3-methyl-1H-pyrazol-4-yl, (S)-1-(2-hydroxy-3-methoxypropyl)-1H-pyrazol-4-yl, 1-(2-hydroxyethyl)-3-methyl-1H-pyrazol-4-yl, 1-(2-hydroxy-2-methylpropyl)-3-methyl-1H-pyrazol-4-yl, 1-(2-hydroxy-2-methylpropyl)-5-methyl-1H-pyrazol-4-yl, 3-cyclopropyl-1-(2-hydroxy-2-methylpropyl)-1H-pyrazol-4-yl, (S)-3-cyclopropyl-1-(2-hydroxy-3-methoxypropyl)-1H-pyrazol-4-yl, 1-(2-hydroxy-2-methylpropyl)-3,5-dimethyl-1H-pyrazol-4-yl, (S)-1-(2-hydroxy-3-methoxypropyl)-3,5-dimethyl-1H-pyrazol-4-yl, 1-(2-hydroxy-2-methylpropyl)-3-methyl-1H-pyrazol-4-yl, (S)-1-(2-hydroxy-3-methoxypropyl)-5-methyl-1H-pyrazol-4-yl, (S)-1-(2-hydroxy-3-methoxy-2-methylpropyl)-3-methyl-1H-pyrazol-4-yl, (R)-1-(2-hydroxy-3-methoxy-2-methylpropyl)-3-methyl-1H-pyrazol-4-yl, (S)-1-(2-hydroxy-3-methoxypropyl)-1H-pyrazol-4-yl, (S)-1-(2-hydroxypropyl)-3,5-dimethyl-1H-pyrazol-4-yl, (R)-1-(2-hydroxypropyl)-3-methyl-1H-pyrazol-4-yl, (S)-1-(2-hydroxypropyl)-3-methyl-1H-pyrazol-4-yl, (S)-3-cyclopropyl-1-(2,3-dihydroxy-3-methylbutyl)-1H-pyrazol-4-yl, (R)-3-cyclopropyl-1-(2,3-dihydroxy-3-methylbutyl)-1H-pyrazol-4-yl, (S)-1-(2-hydroxy-3-(2-methoxyethoxy)propyl)-1H-pyrazol-4-yl, (S)-1-(2-hydroxy-3-methoxypropyl)-3-methyl-1H-pyrazol-4-yl, (S)-1-(2-hydroxypropyl)-5-methyl-1H-pyrazol-4-yl, (R)-1-(2,3-dihydroxy-2-methylpropyl)-1H-pyrazol-4-yl, (R)-1-(2-hydroxy-3-methoxy-2-methylpropyl)-1H-pyrazol-4-yl, (S)-1-(2-hydroxy-3-methoxy-2-methylpropyl)-1H-pyrazol-4-yl, (S)-1-(2-hydroxy-3-methoxy-2-methylpropyl)-1H-pyrazol-4-yl, (R)-1-(2-hydroxy-3-methoxy-2-methylpropyl)-1H-pyrazol-4-yl, 1-((2R,3S)-3-hydroxybutan-2-yl)-3-methyl-1H-pyrazol-4-yl, 1-((2S,3R)-3-hydroxybutan-2-yl)-3-methyl-1H-pyrazol-4-yl, 1-((2S,3S)-3-hydroxybutan-2-yl)-5-methyl-1H-pyrazol-4-yl, 1-((2R,3R)-3-hydroxybutan-2-yl)-5-methyl-1H-pyrazol-4-yl, 1-((R)-2,3-dihydroxy-2-methylpropyl)-1H-pyrazol-4-yl (273), 3,5-dimethyl-1-((4-methylmorpholin-2-yl)methyl)-1H-pyrazol-4-yl (274), (S)-1-(2,3-dihydroxypropyl)-3,5-dimethyl-1H-pyrazol-4-yl, 1-(1,3-dihydroxypropan-2-yl)-3,5-dimethyl-1H-pyrazol-4-yl, (R)-1-(2-hydroxy-3-methoxypropyl)-3-methyl-1H-pyrazol-4-yl, (S)-(1-(2-hydroxypropyl)-3-methyl-1H-pyrazol-4-yl, (R)-1-(2-hydroxypropyl)-3-methyl-1H-pyrazol-4-yl, (S)-1-(2-hydroxy-3-(2-methoxyethoxy)propyl)-3-methyl-1H-pyrazol-4-yl (283), (R)-1-(2-hydroxy-3-(2-methoxyethoxy)propyl)-3-methyl-1H-pyrazol-4-yl, 1-((2R,3R)-3-hydroxybutan-2-yl)-3-methyl-1H-pyrazol-4-yl, and 1-((2S,3S)-3-hydroxybutan-2-yl)-3-methyl-1H-pyrazol-4-yl; and the remainder of the variables are as described for Formula (I) or the first aspect, second, third, fourth or fifth aspects.

In a tenth aspect, the compounds of the disclosure or a pharmaceutically acceptable salt thereof are represented by any one of Formulas (I), (IIa), (IIb), (IIIa), (IIIb) or (IV)-(XLIII), wherein each $R^1$ is independently selected from methyl, —$NH_2$, methylamino, ethylamino, dimethylamino, (2-hydroxyethyl)amino, (S)-(2-hydroxypropyl)amino, (2-hydroxyethyl)(methyl)amino, (2-hydroxy-2-methylpropyl)amino, (2-(tert-butoxy)ethyl)amino, (2-methoxyethyl)amino, (2-(methoxy-$d_3$)ethyl)amino, (2-methoxyethoxy)amino, (R)-(1-methoxypropan-2-yl)amino, (S)-(2-methoxypropyl)amino, (2-methoxy-2-methylpropyl)amino, (2-methoxyethoxy)ethyl)amino, (2,2-difluoroethyl)amino, (2,2-difluoropropyl)amino, (2,2-difluoro-3-hydroxypropyl)amino, (S)-(tetrahydrofuran-3-yl)amino, (oxetan-2-ylmethyl)amino, oxetan-3-ylamino, (oxetan-3-ylmethyl)amino, (1H-pyrazol-4-yl)amino, cyclopropyl, 2-hydroxyethyl, 3-hydroxy-3-methylbutyl, 3-methoxypropyl, (2,2-difluoroethoxy)methyl, (2,2-difluoroethoxy)ethyl, fluoro, methoxy, 3-hydroxy-3-methylbutoxy, 2-methoxyethoxy, 2-hydroxyethoxy, 3-hydroxyazetidin-1-yl, (S)-2-(hydroxymethyl)azetidin-1-yl, 3-methylazetidin-1-yl, (R)-2-(methoxymethyl)azetidin-1-yl, (S)-2-(methoxymethyl)azetidin-1-yl, 3-(methylsulfonyl)azetidin-1-yl

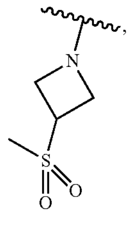

3-(hydroxymethyl)azetidin-1-yl, 3-hydroxy-3-methylazetidin-1-yl, (R)-3-hydroxypyrrolidin-1-yl, (S)-3-hydroxypyrrolidin-1-yl, 3-hydroxy-3-methylpyrrolidin-1-yl, (R)-3-(dimethylamino)pyrrolidin-1-yl, 3,3-difluoropyrrolidin-1-yl, 4-hydroxy-4-methylpiperidin-1-yl, (S)-3-hydroxypiperidin-1-yl, (R)3-hydroxypiperidin-1-yl, 4-(methyl-$d_3$)piperazin-1-yl, 4-(2,2-difluoroethyl)piperazin-1-yl,

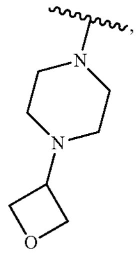

4-methylpiperazin-1-yl, 4-methylpiperazin-1-yl, 4-(2-hydroxyethyl)piperazin-1-yl, 4,4-difluoropiperidin-1-yl, tetrahydrofuran-3-yl, morpholino, (R)-2-(hydroxymethyl)morpholino,

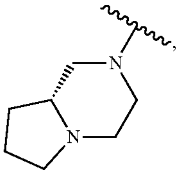 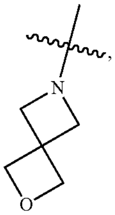

1H-pyrazol-4-yl, 1-(2-hydroxyethyl)-1H-pyrazol-4-yl, 1-(2-hydroxy-2-methylpropyl)-1H-pyrazol-4-yl, (R)-1-(2-hydroxypropyl)-1H-pyrazol-4-yl, (S)-1-(2-hydroxypropyl)-1H-pyrazol-4-yl), (2-hydroxy-2-methylpropyl)-1H-pyrazol-4-yl,

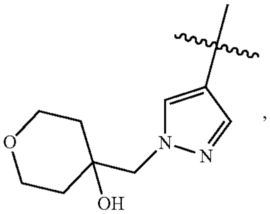, 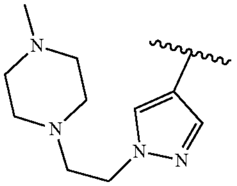,

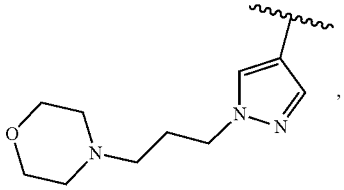,

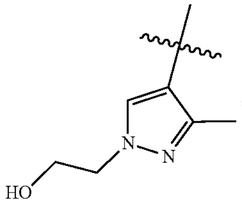, 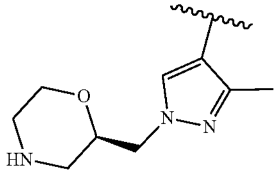,

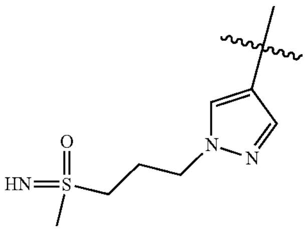,

-continued

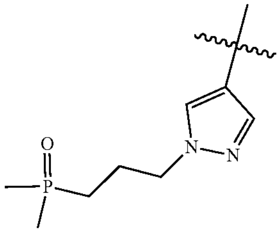,
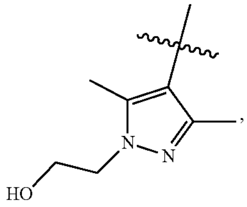,

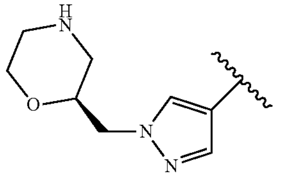 and

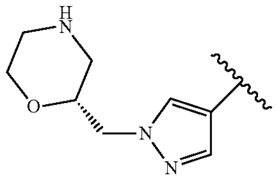;

and the remainder of the variables are as described for Formula (I) or the first aspect, second, third, fourth or fifth aspects.

In an eleventh aspect, the compounds of the disclosure or a pharmaceutically acceptable salt thereof are represented by any one of Formulas (I), (IIa), (IIb), (IIIa), (IIIb) or (IV)-(XLIII), wherein each $R^9$ is independently selected from $CH_3$, Cl, F, $CD_3$, CN, and cyclopropyl; and the remainder of the variables are as described for Formula (I) or the first aspect, second, third, fourth aspects, fifth, sixth, seventh, eighth, ninth or tenth aspects.

In a twelfth aspect, the compounds of the disclosure or a pharmaceutically acceptable salt thereof are represented by any one of Formulas (XLIV) or (XLV):

(XLIV)

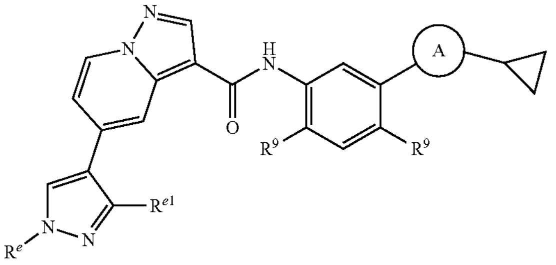

-continued (XLV)

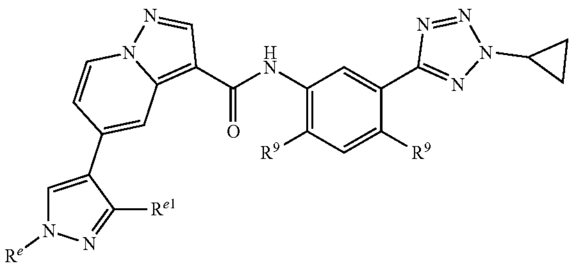

wherein:

Ring A in Formula XLIV is triazolyl or tetrazolyl;

each $R^9$ is independently selected from $CH_3$, Cl, F, $CD_3$, CN, and cyclopropyl. Alternatively, each $R^9$ is independently selected from $CH_3$, Cl, F, $CD_3$, and CN. In another alternative, each $R^9$ is independently selected from $CH_3$, F, $CD_3$, and CN. $R^e$ is selected from $C_{1-4}$alkyl, $C_{0-4}$alkylOH, $C_{1-4}$alkyl(OH)($C_{1-4}$alkoxy), $S(O)_2C_{1-3}$alkyl, $C_{1-3}$alkyl-S(O)(NH)$CH_3$, ($C_{1-3}$alkyl)P(O)($C_{2-3}$alkyl)$_2$, and ($C_{1-3}$alkyl)-(6 membered heterocycle containing at least one O or N), further wherein said 6 membered heterocycle is optionally substituted with 1-2 OH. Alternatively, $R^e$ is selected from $C_{1-4}$alkyl, $C_{0-4}$alkylOH, $S(O)_2C_{1-3}$alkyl, $C_{1-3}$alkyl-S(O)(NH)$CH_3$, ($C_{1-3}$alkyl)P(O)($C_{2-3}$alkyl)$_2$, and ($C_{1-3}$alkyl)-(6 membered heterocycle containing at least one O or N), further wherein said 6 membered heterocycle is optionally substituted with 1-2 OH. In another alternative, $R^e$ is selected from methyl, ethyl, propyl, butyl, ethylhydroxy, isobutylhydroxy, propyl(OH)methoxy, $C_{1-2}$alkyl(morpholino), $C_{1-2}$alkyl(piperazinyl), $C_{1-2}$alkyl(tetrahydropyranyl), S(=O)(=NH)$CH_3$, and ($C_{2-3}$alkyl)P(O)($CH_3$)$_2$, further wherein said morpholino, piperazinyl, and tetrahydropyranyl are optionally substituted with 1-2 OH. In yet another alternative, $R^e$ is selected from methyl, ethyl, propyl, butyl, ethylhydroxy, isobutylhydroxy, propyl(OH)methoxy, $C_{1-2}$alkyl(morpholino), $C_{1-2}$alkyl(piperazinyl), $C_{1-2}$alkyl(tetrahydropyranyl), S(=O)(=NH)$CH_3$, and ($C_{2-3}$alkyl)P(O)($CH_3$)$_2$, further wherein said morpholino, piperazinyl, and tetrahydropyranyl are optionally substituted with 1-2 OH. In yet another alternative, $R^e$ is

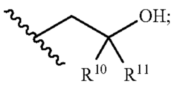

$R^{10}$ and $R^{11}$ are independently H, $CH_3$, $CH_2OCH_3$, provided that $R^{10}$ and $R^{11}$ are not both $CH_2OCH_3$, or $R^{10}$ and $R^{11}$ taken together are 4-tetrahydropyranyl; and $R^{e1}$ is selected from H, $CH_3$ and cyclopropyl.

In a thirteenth aspect, compounds of the disclosure are shown below in Table 1 and in the Exemplification. Pharmaceutically acceptable salts thereof and the corresponding neutral form are included in the disclosure.

TABLE 1

| Compound No | Name, Structure | Scheme |
| --- | --- | --- |
| 1 | N-(2-methyl-5-(2-(4,4,4-trifluorobutyl)-2H-tetrazol-5-yl)phenyl)pyrazolo[1,5-a]pyridine-3-carboxamide 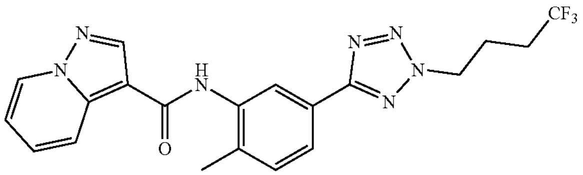 [SMILES: Cc1ccc(-c2nnn(CCCC(F)(F)F)n2)cc1NC(=O)c1cnn2ccccc12] | 13 |
| 2 | N-(2-methyl-5-(2-methyl-2H-tetrazol-5-yl)phenyl)pyrazolo[1,5-a]pyridine-3-carboxamide 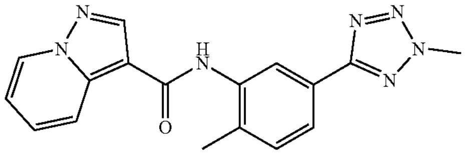 [SMILES: Cc1ccc(-c2nnn(C)n2)cc1NC(=O)c1cnn2ccccc12] | 13 |
| 3 | N-(2-methyl-5-(2-((tetrahydro-2H-pyran-4-yl)methyl)-2H-tetrazol-5-yl)phenyl)pyrazolo[1,5-a]pyridine-3-carboxamide 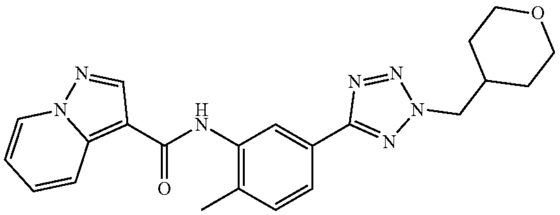 [SMILES: Cc1ccc(-c2nnn(CC3CCOCC3)n2)cc1NC(=O)c1cnn2ccccc12] | 13 |
| 4 | N-(2-methyl-5-(2-(spiro[3.3]heptan-2-yl)-2H-tetrazol-5-yl)phenyl)pyrazolo[1,5-a]pyridine-3-carboxamide 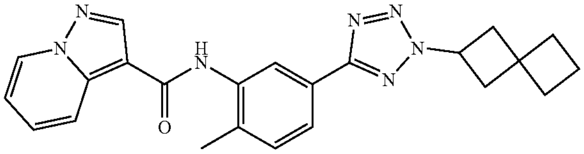 [SMILES: Cc1ccc(-c2nnn(C3CC4(CCC4)C3)n2)cc1NC(=O)c1cnn2ccccc12] | 13 |
| 5 | N-(5-(2-(3,3-difluorocyclobutyl)-2H-tetrazol-5-yl)-2-methylphenyl)pyrazolo[1,5-a]pyridine-3-carboxamide 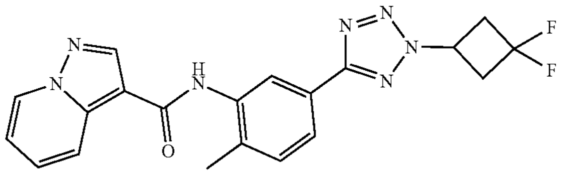 [SMILES: Cc1ccc(-c2nnn(C3CC(F)(F)C3)n2)cc1NC(=O)c1cnn2ccccc12] | 13 |
| 6 | N-(5-(2-((2,2-difluorocyclopropyl)methyl)-2H-tetrazol-5-yl)-2-methylphenyl)pyrazolo[1,5-a]pyridine-3-carboxamide 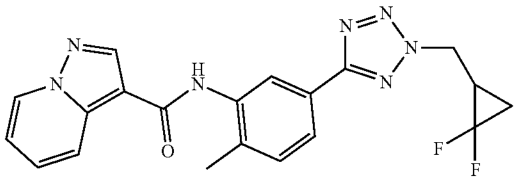 [SMILES: Cc1ccc(-c2nnn(CC3CC3(F)F)n2)cc1NC(=O)c1cnn2ccccc12] | 13 |

TABLE 1-continued

| Compound No | Name, Structure | Scheme |
|---|---|---|
| 7 | N-(5-(2-(cyclopropylmethyl)-2H-tetrazol-5-yl)-2-methylphenyl)pyrazolo[1,5-a]pyridine-3-carboxamide 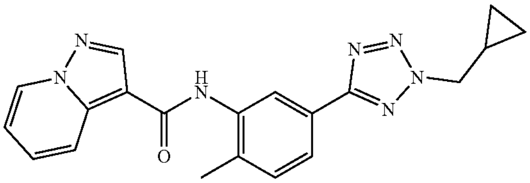 [SMILES: Cc1ccc(-c2nnn(CC3CC3)n2)cc1NC(=O)c1cnn2ccccc12] | 13 |
| 8 | N-(5-(2-cyclobutyl-2H-tetrazol-5-yl)-2-methylphenyl)pyrazolo[1,5-a]pyridine-3-carboxamide 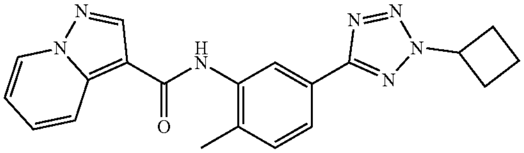 [SMILES: Cc1ccc(-c2nnn(C3CCC3)n2)cc1NC(=O)c1cnn2ccccc12] | 13 |
| 9 | N-(5-(2-((6-oxaspiro[3.4]octan-7-yl)methyl)-2H-tetrazol-5-yl)-2-methylphenyl)pyrazolo[1,5-a]pyridine-3-carboxamide 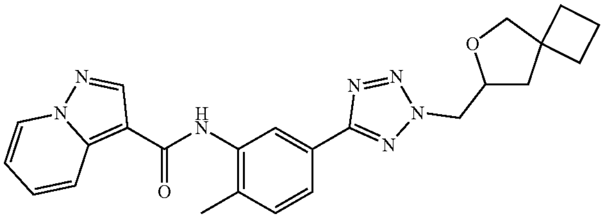 [SMILES: Cc1ccc(-c2nnn(CC3CC4(CCC4)CO3)n2)cc1NC(=O)c1cnn2ccccc12] | 13 |
| 10 | N-(5-(2-((5-oxaspiro[2.4]heptan-6-yl)methyl)-2H-tetrazol-5-yl)-2-methylphenyl)pyrazolo[1,5-a]pyridine-3-carboxamide 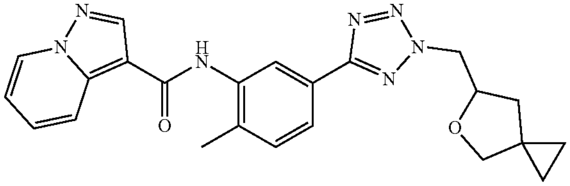 [SMILES: Cc1ccc(-c2nnn(CC3CC4(CC4)CO3)n2)cc1NC(=O)c1cnn2ccccc12] | 13 |
| 11 | N-(5-(2-(2-isopropoxyethyl)-2H-tetrazol-5-yl)-2-methylphenyl)pyrazolo[1,5-a]pyridine-3-carboxamide 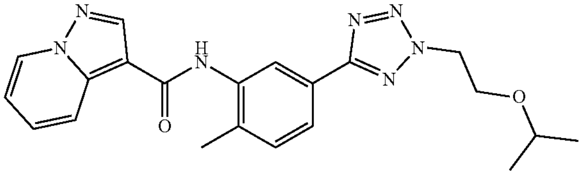 [SMILES: Cc1ccc(-c2nnn(CCOC(C)C)n2)cc1NC(=O)c1cnn2ccccc12] | 13 |
| 12 | N-(5-(2-(2-cyclobutoxyethyl)-2H-tetrazol-5-yl)-2-methylphenyl)pyrazolo[1,5-a]pyridine-3-carboxamide 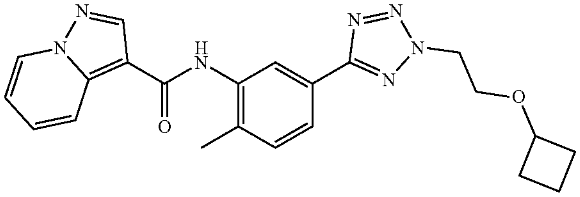 [SMILES: Cc1ccc(-c2nnn(CCOC3CCC3)n2)cc1NC(=O)c1cnn2ccccc12] | 13 |

TABLE 1-continued

| Compound No | Name, Structure | Scheme |
|---|---|---|
| 13 | N-(5-(2-(2-fluorobenzyl)-2H-tetrazol-5-yl)-2-methylphenyl)pyrazolo[1,5-a]pyridine-3-carboxamide 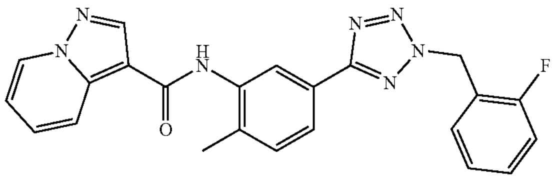 [SMILES: Cc1ccc(-c2nnn(Cc3ccccc3F)n2)cc1NC(=O)c1cnn2ccccc12] | 13 |
| 14 | N-(5-(2-ethyl-2H-tetrazol-5-yl)-2-methylphenyl)pyrazolo[1,5-a]pyridine-3-carboxamide 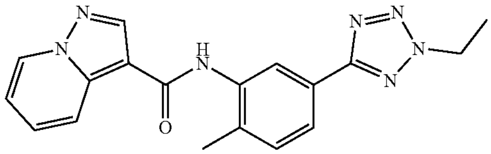 [SMILES: CCn1nnc(-c2ccc(C)c(NC(=O)c3cnn4ccccc34)c2)n1] | 13 |
| 15 | N-(2-chloro-5-(2-(cyclopropylmethyl)-2H-tetrazol-5-yl)phenyl)pyrazolo[1,5-a]pyridine-3-carboxamide 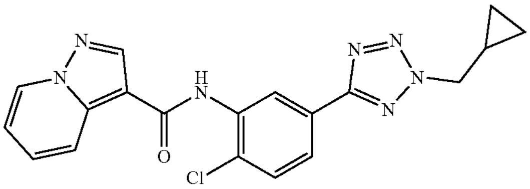 [SMILES: O=C(Nc1cc(-c2nnn(CC3CC3)n2)ccc1Cl)c1cnn2ccccc12] | 13 |
| 16 | N-(2-chloro-5-(2-((2,2-difluorocyclopropyl)methyl)-2H-tetrazol-5-yl)phenyl)pyrazolo[1,5-a]pyridine-3-carboxamide 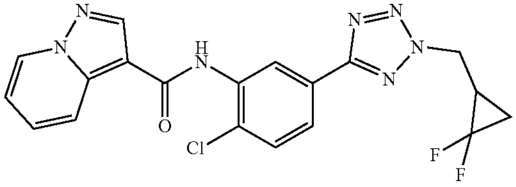 [SMILES: O=C(Nc1cc(-c2nnn(CC3CC3(F)F)n2)ccc1Cl)c1cnn2ccccc12] | 13 |
| 17 | N-(2-chloro-5-(2-(3,3-difluorocyclobutyl)-2H-tetrazol-5-yl)phenyl)pyrazolo[1,5-a]pyridine-3-carboxamide 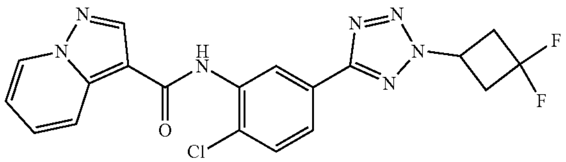 [SMILES: O=C(Nc1cc(-c2nnn(C3CC(F)(F)C3)n2)ccc1Cl)c1cnn2ccccc12] | 13 |
| 18 | N-(5-(2-((2-oxabicyclo[2.1.1]hexan-4-yl)methyl)-2H-tetrazol-5-yl)-2-chlorophenyl)pyrazolo[1,5-a]pyridine-3-carboxamide 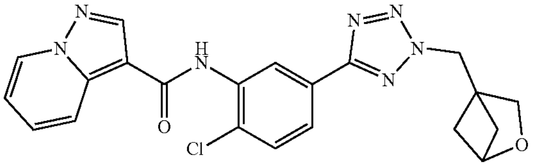 [SMILES: O=C(Nc1cc(-c2nnn(CC34COC(C3)C4)n2)ccc1Cl)c1cnn2ccccc12] | 13 |

TABLE 1-continued

| Compound No | Name, Structure | Scheme |
| --- | --- | --- |
| 19 | N-(2-chloro-5-(2-((3,3-difluorocyclobutyl)methyl)-2H-tetrazol-5-yl)phenyl)pyrazolo[1,5-a]pyridine-3-carboxamide 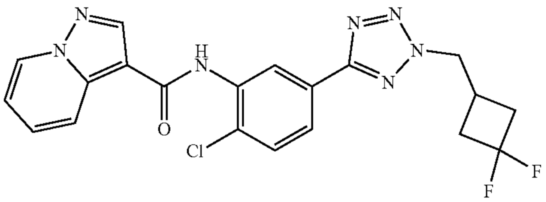 [SMILES: O=C(Nc1cc(-c2nnn(CC3CC(F)(F)C3)n2)ccc1Cl)c1cnn2ccccc12] | 13 |
| 20 | N-(5-(2-((2-oxabicyclo[2.1.1]hexan-4-yl)methyl)-2H-tetrazol-5-yl)-2,4-dimethylphenyl)pyrazolo[1,5-a]pyridine-3-carboxamide 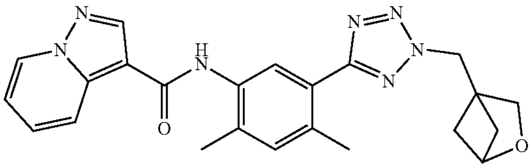 [SMILES: Cc1cc(C)c(-c2nnn(CC34COC(C3)C4)n2)cc1NC(=O)c1cnn2ccccc12] | 13 |
| 21 | N-(5-(2-((2,2-difluorocyclopropyl)methyl)-2H-tetrazol-5-yl)-2,4-dimethylphenyl)pyrazolo[1,5-a]pyridine-3-carboxamide 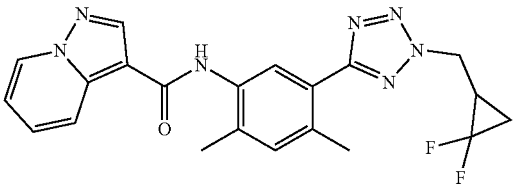 [SMILES: Cc1cc(C)c(-c2nnn(CC3CC3(F)F)n2)cc1NC(=O)c1cnn2ccccc12] | 13 |
| 22 | N-(2-chloro-5-(2-(2-(2,2,2-trifluoroethoxy)ethyl)-2H-tetrazol-5-yl)phenyl)pyrazolo[1,5-a]pyridine-3-carboxamide 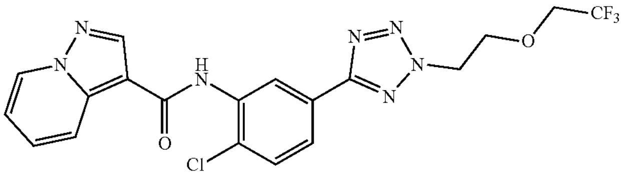 [SMILES: O=C(Nc1cc(-c2nnn(CCOCC(F)(F)F)n2)ccc1Cl)c1cnn2ccccc12] | 13 |
| 23 | N-(2-methyl-5-(2-((1s,3s)-3-(trifluoromethyl)cyclobutyl)-2H-tetrazol-5-yl)phenyl)pyrazolo[1,5-a]pyridine-3-carboxamide or N-(2-methyl-5-(2-((1r,3r)-3-(trifluoromethyl)cyclobutyl)-2H-tetrazol-5-yl)phenyl)pyrazolo[1,5-a]pyridine-3-carboxamide 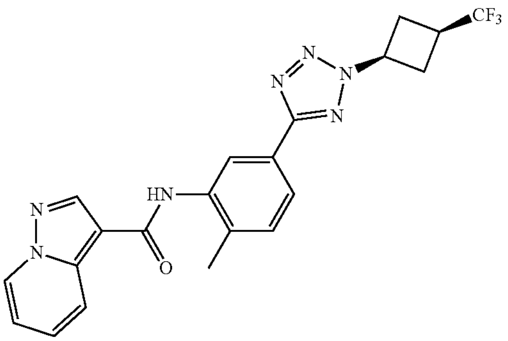 Or | 13<br>Isomer 1 |

TABLE 1-continued

| Compound No | Name, Structure | Scheme |
|---|---|---|
| | 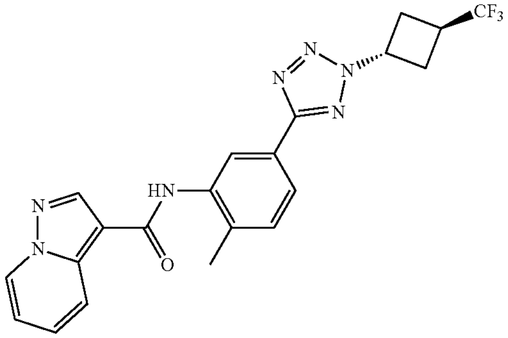 [SMILES: Cc1ccc(-c2nnn([C@H]3C[C@H](C(F)(F)F)C3)n2)cc1NC(=O)c1cnn2ccccc12] | |
| 24 | N-(2-methyl-5-(2-((1r,3r)-3-(trifluoromethyl)cyclobutyl)-2H-tetrazol-5-yl)phenyl)pyrazolo[1,5-a]pyridine-3-carboxamide or N-(2-methyl-5-(2-((1s,3s)-3-(trifluoromethyl)cyclobutyl)-2H-tetrazol-5-yl)phenyl)pyrazolo[1,5-a]pyridine-3-carboxamide | 13 Isomer 2 |
| | 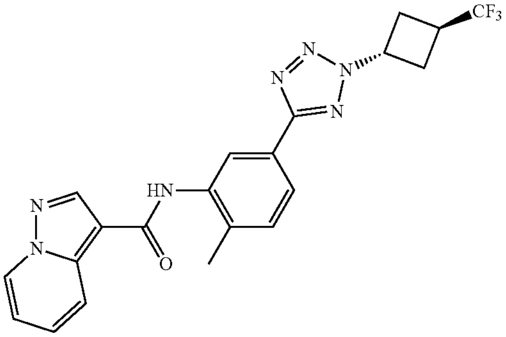 Or 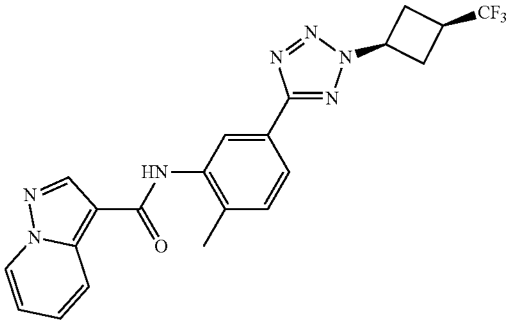 [SMILES: Cc1ccc(-c2nnn([C@H]3C[C@@H](C(F)(F)F)C3)n2)cc1NC(=O)c1cnn2ccccc12] | |
| 25 | (S)-N-(5-(2-((2,2-difluorocyclopropyl)methyl)-2H-tetrazol-5-yl)-2-methylphenyl)pyrazolo[1,5-a]pyridine-3-carboxamide or (R)-N-(5-(2-((2,2-difluorocyclopropyl)methyl)-2H-tetrazol-5-yl)-2-methylphenyl)pyrazolo[1,5-a]pyridine-3-carboxamide | 13 Isomer 1 |

TABLE 1-continued
| Compound No | Name, Structure | Scheme |
|---|---|---|
| | 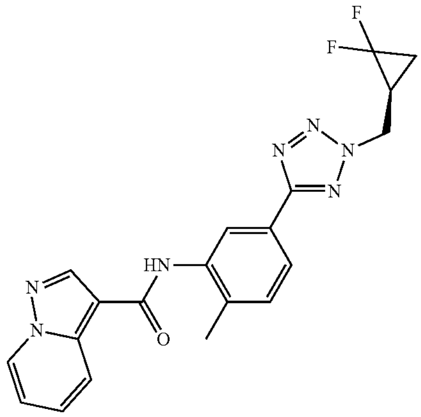 or 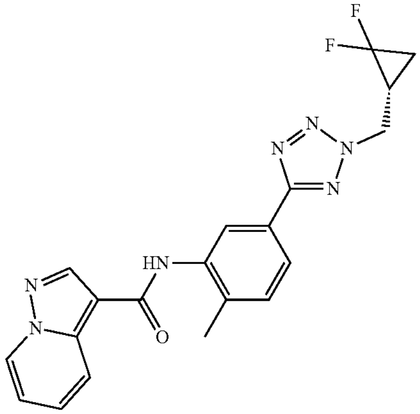 [SMILES: Cc1ccc(-c2nnn(C[C@H]3CC3(F)F)n2)cc1NC(=O)c1cnn2ccccc12] | |
| 26 | (R)-N-(5-(2-((2,2-difluorocyclopropyl)methyl)-2H-tetrazol-5-yl)-2-methylphenyl)pyrazolo[1,5-a]pyridine-3-carboxamide or (S)-N-(5-(2-((2,2-difluorocyclopropyl)methyl)-2H-tetrazol-5-yl)-2-methylphenyl)pyrazolo[1,5-a]pyridine-3-carboxamide | 13 Isomer 2 |
| | 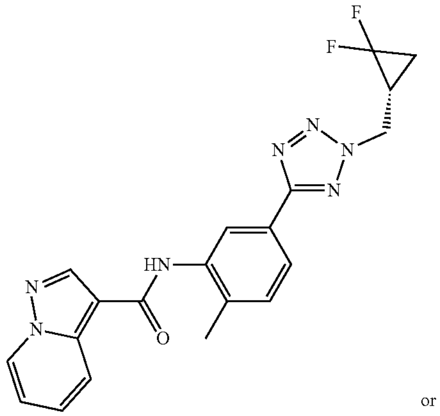 [SMILES: Cc1ccc(-c2nnn(C[C@H]3CC3(F)F)n2)cc1NC(=O)c1cnn2ccccc12] or | |

TABLE 1-continued

| Compound No | Name, Structure | Scheme |
| --- | --- | --- |
| | 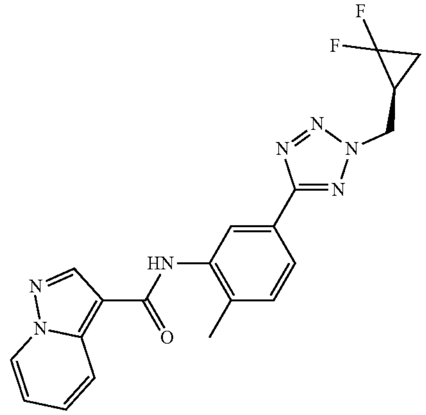 [SMILES: Cc1ccc(-c2nnn(C[C@@H]3CC3(F)F)n2)cc1NC(=O)c1cnn2ccccc12] | |
| 27 | 5-amino-N-(2-chloro-5-(2-((2,2-difluorocyclopropyl)methyl)-2H-tetrazol-5-yl)phenyl)pyrazolo[1,5-a]pyridine-3-carboxamide 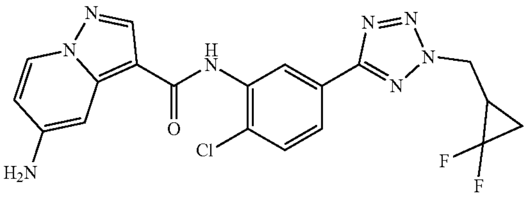 [SMILES: Nc1ccn2ncc(C(=O)Nc3cc(-c4nnn(CC5CC5(F)F)n4)ccc3Cl)c2c1] | 13 |
| 28 | N-(5-(2-cyclopropyl-2H-tetrazol-5-yl)-2-methylphenyl)pyrazolo[1,5-a]pyridine-3-carboxamide 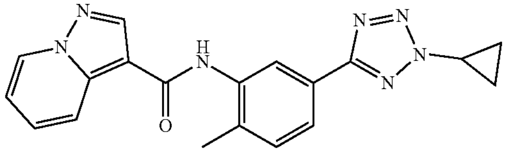 [SMILES: Cc1ccc(-c2nnn(C3CC3)n2)cc1NC(=O)c1cnn2ccccc12] | 14 |
| 29 | N-(5-(2-cyclopropyl-2H-1,2,3-triazol-4-yl)-2-methylphenyl)pyrazolo[1,5-a]pyridine-3-carboxamide 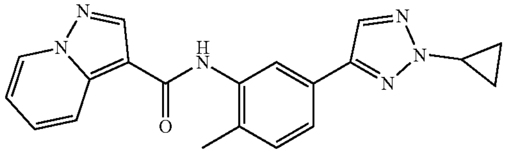 [SMILES: Cc1ccc(-c2cnn(C3CC3)n2)cc1NC(=O)c1cnn2ccccc12] | 14 |
| 30 | N-(5-(2-((3-fluorobicyclo[1.1.1]pentan-1-yl)methyl)-2H-tetrazol-5-yl)-2-methylphenyl)pyrazolo[1,5-a]pyridine-3-carboxamide 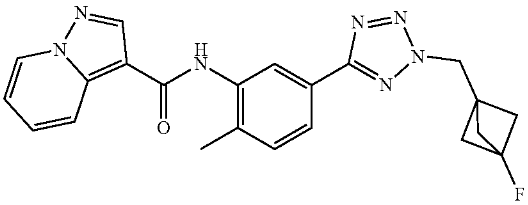 [SMILES: Cc1ccc(-c2nnn(CC34CC(F)(C3)C4)n2)cc1NC(=O)c1cnn2ccccc12] | 15 |

TABLE 1-continued

| Compound No | Name, Structure | Scheme |
|---|---|---|
| 31 | N-(2-methyl-5-(2-(tetrahydro-2H-pyran-4-yl)-2H-tetrazol-5-yl)phenyl)pyrazolo[1,5-a]pyridine-3-carboxamide 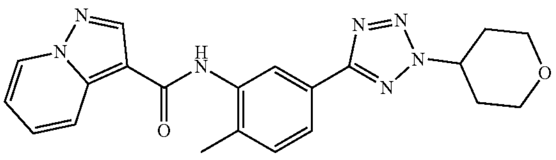 [SMILES: Cc1ccc(-c2nnn(C3CCOCC3)n2)cc1NC(=O)c1cnn2ccccc12] | 15 |
| 32 | N-(5-(2-(3-fluorocyclobutyl)-2H-tetrazol-5-yl)-2-methylphenyl)pyrazolo[1,5-a]pyridine-3-carboxamide 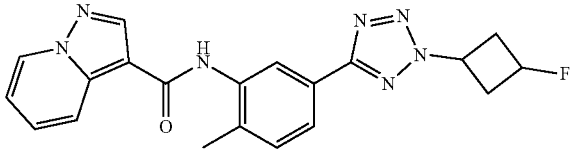 [SMILES: Cc1ccc(-c2nnn(C3CC(F)C3)n2)cc1NC(=O)c1cnn2ccccc12] | 15 |
| 33 | (S)-N-(5-(2-(1-(2-fluorophenyl)ethyl)-2H-tetrazol-5-yl)-2-methylphenyl)pyrazolo[1,5-a]pyridine-3-carboxamide 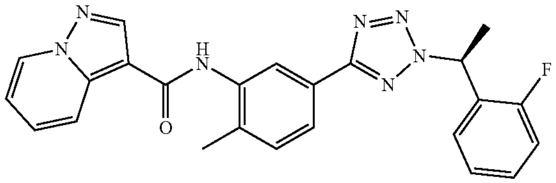 [SMILES: Cc1ccc(-c2nnn([C@@H](C)c3ccccc3F)n2)cc1NC(=O)c1cnn2ccccc12] | 15 |
| 34 | N-(2-methyl-5-(2-((tetrahydro-2H-pyran-2-yl)methyl)-2H-tetrazol-5-yl)phenyl)pyrazolo[1,5-a]pyridine-3-carboxamide 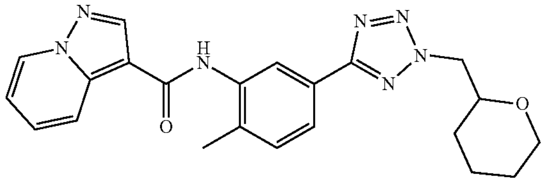 [SMILES: Cc1ccc(-c2nnn(CC3CCCCO3)n2)cc1NC(=O)c1cnn2ccccc12] | 15 |
| 35 | N-(5-(2-((1s,3s)-3-methoxycyclobutyl)-2H-tetrazol-5-yl)-2-methylphenyl)pyrazolo[1,5-a]pyridine-3-carboxamide 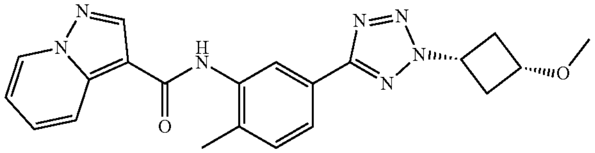 [SMILES: CO[C@H]1C[C@@H](n2nnc(-c3ccc(C)c(NC(=O)c4cnn5ccccc45)c3)n2)C1] | 15 |
| 36 | N-(2,4-dimethyl-5-(2-(4,4,4-trifluoro-3-hydroxy-3-methylbutyl)-2H-tetrazol-5-yl)phenyl)pyrazolo[1,5-a]pyridine-3-carboxamide 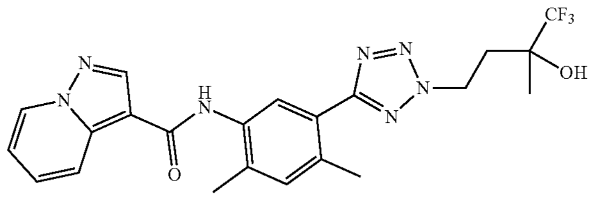 [SMILES: Cc1cc(C)c(-c2nnn(CCC(C)(O)C(F)(F)F)n2)cc1NC(=O)c1cnn2ccccc12] | 15 |

TABLE 1-continued

| Compound No | Name, Structure | Scheme |
|---|---|---|
| 37 | (R)-N-(5-(2-(1-cyclopropylethyl)-2H-tetrazol-5-yl)-2-methylphenyl)pyrazolo[1,5-a]pyridine-3-carboxamide or (S)-N-(5-(2-(1-cyclopropylethyl)-2H-tetrazol-5-yl)-2-methylphenyl)pyrazolo[1,5-a]pyridine-3-carboxamide, 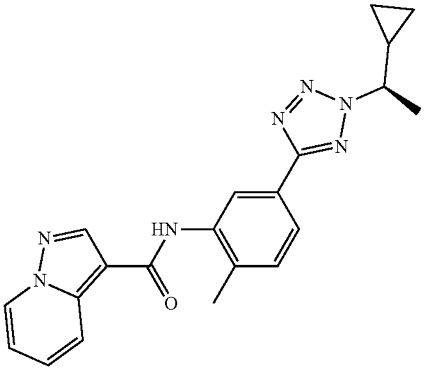 or 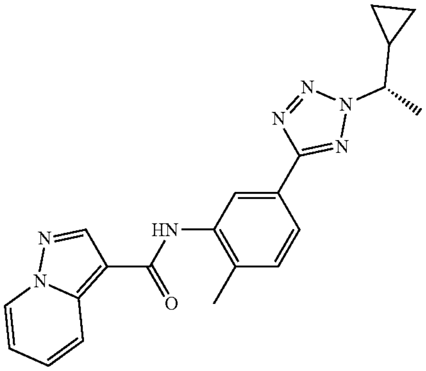 [SMILES: Cc1ccc(-c2nnn([C@@H](C)C3CC3)n2)cc1NC(=O)c1cnn2ccccc12] | 15 Isomer 1 |
| 38 | (S)-N-(5-(2-(1-cyclopropylethyl)-2H-tetrazol-5-yl)-2-methylphenyl) pyrazolo[1,5-a]pyridine-3-carboxamide or (R)-N-(5-(2-(1-cyclopropylethyl)-2H-tetrazol-5-yl)-2-methylphenyl) pyrazolo[1,5-a]pyridine-3-carboxamide 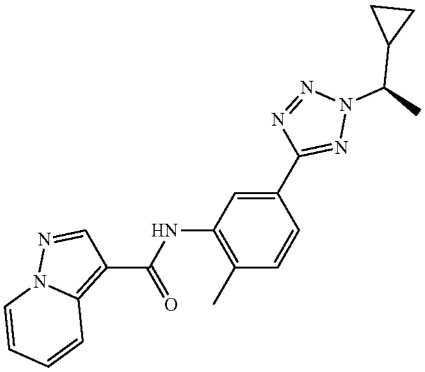 or | 15 Isomer 2 |

TABLE 1-continued

| Compound No | Name, Structure | Scheme |
|---|---|---|
| | 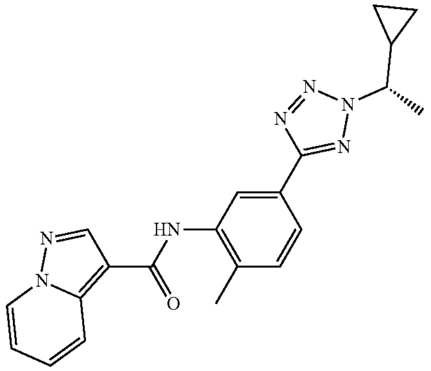 | |
| 39 | (R)-N-(2-methyl-5-(2-(1 -(tetrahydro-2H-pyran-4-yl)ethyl)-2H-tetrazol-5-yl)phenyl)pyrazolo[1,5-a]pyridine-3-carboxamide or (S)-N-(2-methyl-5-(2-(1-(tetrahydro-2H-pyran-4-yl)ethyl)-2H-tetrazol-5-yl)phenyl)pyrazolo[1,5-a]pyridine-3-carboxamide 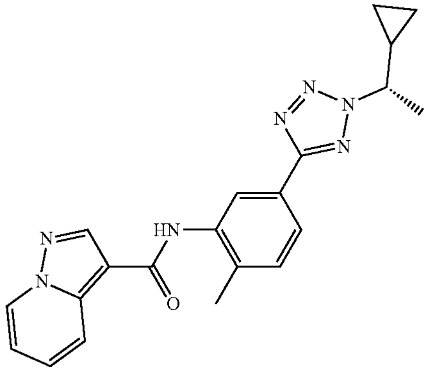 [SMILES: Cc1ccc(-c2nnn([C@@H](C)C3CC3)n2)cc1NC(=O)c1cnn2ccccc12] or 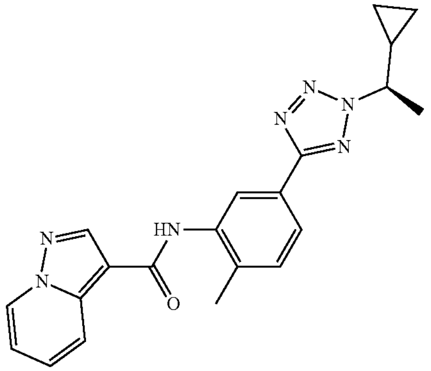 [SMILES: Cc1ccc(-c2nnn([C@H](C)C3CC3)n2)cc1NC(=O)c1cnn2ccccc12] | 15 Isomer 1 |
| 40 | (S)-N-(2-methyl-5-(2-((tetrahydro-2H-pyran-2-yl)methyl)-2H-tetrazol-5-yl)phenyl)pyrazolo[1,5-a]pyridine-3-carboxamide or (R)-N-(2-methyl-5-(2-((tetrahydro-2H-pyran-2-yl)methyl)-2H-tetrazol-5-yl)phenyl)pyrazolo[1,5-a]pyridine-3-carboxamide 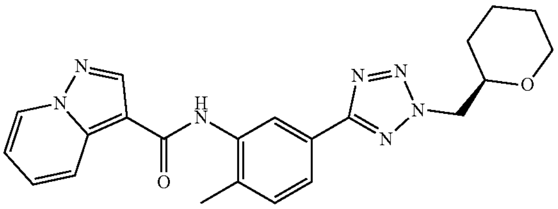 OR | 15 Isomer 2 |

TABLE 1-continued

| Compound No | Name, Structure | Scheme |
| --- | --- | --- |
| | 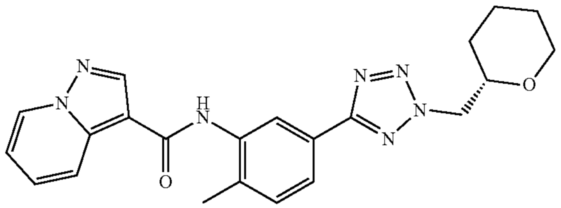 [SMILES: Cc1ccc(-c2nnn(C[C@@H]3CCCCO3)n2)cc1NC(=O)c1cnn2ccccc12] | |
| 41 | (R)-N-(2-methyl-5-(2-(4,4,4-trifluoro-3-hydroxy-3-methylbutyl)-2H-tetrazol-5-yl)phenyl)pyrazolo[1,5-a]pyridine-3-carboxamide or (S)-N-(2-methyl-5-(2-(4,4,4-trifluoro-3-hydroxy-3-methylbutyl)-2H-tetrazol-5-yl)phenyl)pyrazolo[1,5-a]pyridine-3-carboxamide<br>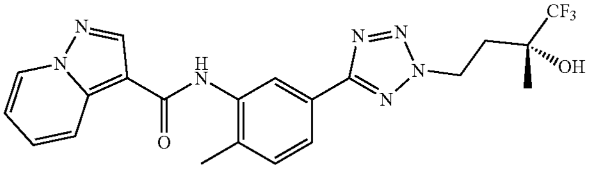<br>OR<br>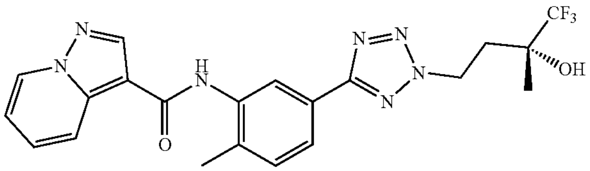 [SMILES: Cc1ccc(-c2nnn(CC[C@@](C)(O)C(F)(F)F)n2)cc1NC(=O)c1cnn2ccccc12] | 15<br>Isomer 1 |
| 42 | N-(5-(2-((3r,5r)-1,1-difluorospiro[2.3]hexan-5-yl)-2H-tetrazol-5-yl)-2-methylphenyl)pyrazolo[1,5-a]pyridine-3-carboxamide or N-(5-(2-((3s,5s)-1,1-difluorospiro[2.3]hexan-5-yl)-2H-tetrazol-5-yl)-2-methylphenyl)pyrazolo[1,5-a]pyridine-3-carboxamide<br>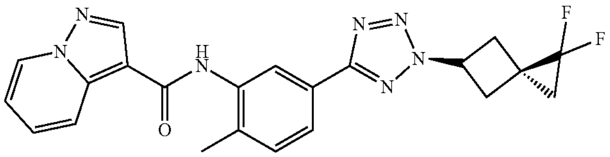<br>OR<br>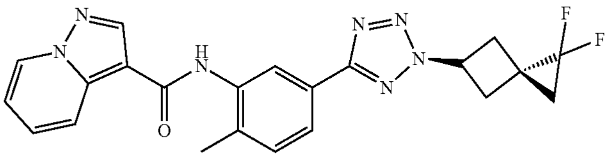 | 15<br>Isomer 2 |
| 43 | N-(2-methyl-5-(2-methyl-2H-tetrazol-5-yl)phenyl)-5-(1H-pyrazol-4-yl)pyrazolo[1,5-a]pyridine-3-carboxamide<br>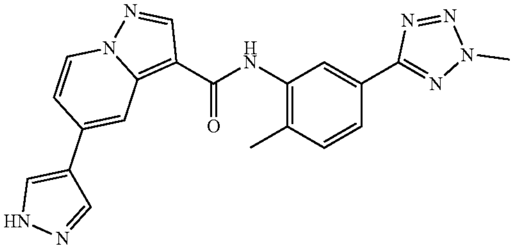 [SMILES: Cc1ccc(-c2nnn(C)n2)cc1NC(=O)c1cnn2ccc(-c3cn[nH]c3)cc12] | 16 |

TABLE 1-continued

| Compound No | Name, Structure | Scheme |
|---|---|---|
| 44 | N-(2-methyl-5-(2-((1r,3r)-3-(trifluoromethyl)cyclobutyl)-2H-tetrazol-5-yl)phenyl)-5-(1H-pyrazol-4-yl)pyrazolo[1,5-a]pyridine-3-carboxamide or N-(2-methyl-5-(2-((1s,3s)-3-(trifluoromethyl)cyclobutyl)-2H-tetrazol-5-yl)phenyl)-5-(1H-pyrazol-4-yl)pyrazolo[1,5-a]pyridine-3-carboxamide 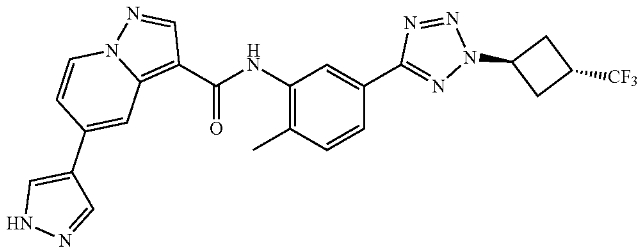 OR 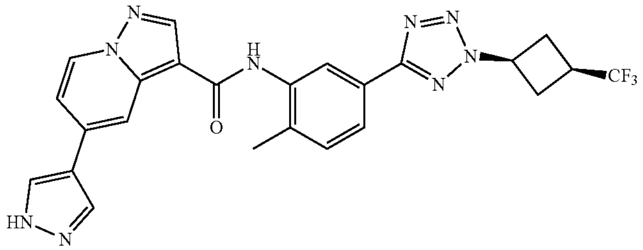 [SMILES: Cc1ccc(-c2nnn([C@H]3C[C@@H](C(F)(F)F)C3)n2)cc1NC(=O)c1cnn2ccc(-c3cn[nH]c3)cc12] | 16 Isomer 1 |
| 45 | methyl 3-(5-(3-(5-((2-methoxyethyl)amino)-4-methylpyrazolo[1,5-a]pyridine-3-carboxamido)-4-methylphenyl)-2H-tetrazol-2-yl)azetidine-1-carboxylate 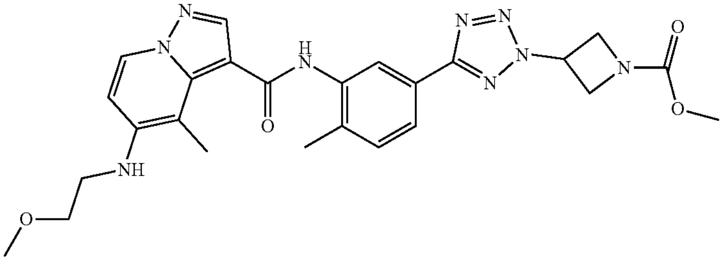 | 16 |
| 46 | N-(5-(2-(3,3-difluorocyclobutyl)-2H-tetrazol-5-yl)-2-methylphenyl)-5-(1-(2-hydroxyethyl)-1H-pyrazol-4-yl)pyrazolo[1,5-a]pyridine-3-carboxamide 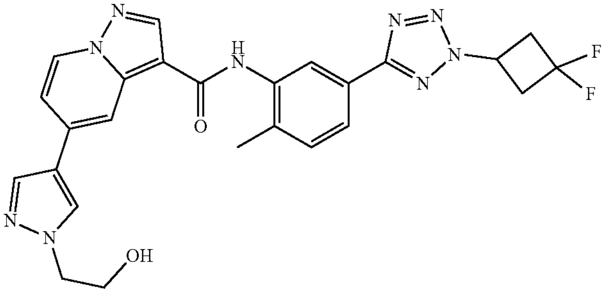 [SMILES: Cc1ccc(-c2nnn(C3CC(F)(F)C3)n2)cc1NC(=O)c1cnn2ccc(-c3cnn(CCO)c3)cc12] | 16 |

TABLE 1-continued

| Compound No | Name, Structure | Scheme |
|---|---|---|
| 47 | 5-(1-(2-hydroxyethyl)-1H-pyrazol-4-yl)-N-(2-methyl-5-(2-methyl-2H-tetrazol-5-yl)phenyl)pyrazolo[1,5-a]pyridine-3-carboxamide 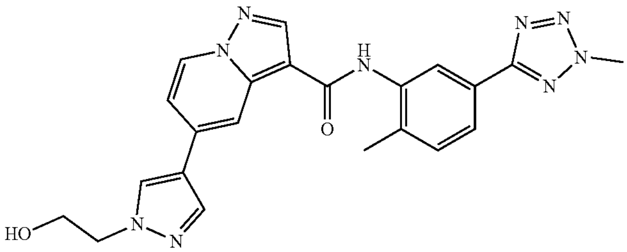 [SMILES: Cc1ccc(-c2nnn(C)n2)cc1NC(=O)c1cnn2ccc(-c3cnn(CCO)c3)cc12] | 16 |
| 48 | 5-(1-(2-hydroxy-2-methylpropyl)-1H-pyrazol-4-yl)-N-(2-methyl-5-(2-methyl-2H-tetrazol-5-yl)phenyl)pyrazolo[1,5-a]pyridine-3-carboxamide 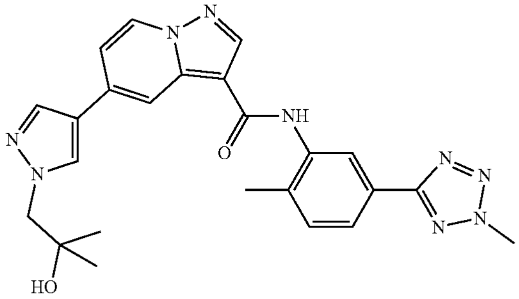 [SMILES: Cc1ccc(-c2nnn(C)n2)cc1NC(=O)c1cnn2ccc(-c3cnn(CC(C)(C)O)c3)cc12] | 16 |
| 49 | 5-(1-(2-hydroxyethyl)-1H-pyrazol-4-yl)-N-(5-(2-isopropyl-2H-tetrazol-5-yl)-2-methylphenyl)pyrazolo[1,5-a]pyridine-3-carboxamide 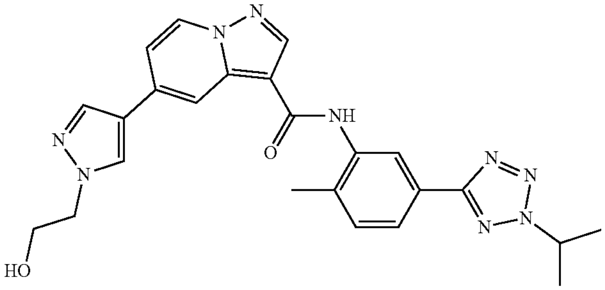 [SMILES: Cc1ccc(-c2nnn(C(C)C)n2)cc1NC(=O)c1cnn2ccc(-c3cnn(CCO)c3)cc12] | 16 |
| 50 | 5-cyclopropyl-N-(2-methyl-5-(2-(1-(methylsulfonyl)azetidin-3-yl)-2H-tetrazol-5-yl)phenyl)pyrazolo[1,5-a]pyridine-3-carboxamide 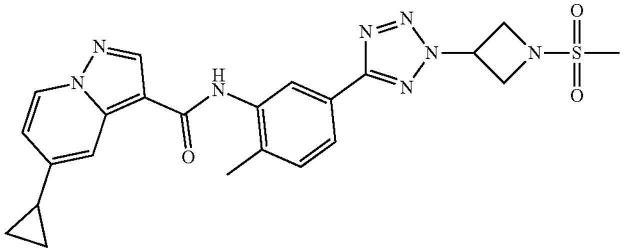 [SMILES: Cc1ccc(-c2nnn(C3CN(S(C)(=O)=O)C3)n2)cc1NC(=O)c1cnn2ccc(C3CC3)cc12] | 16 |

TABLE 1-continued

| Compound No | Name, Structure | Scheme |
|---|---|---|
| 51 | 5-(1-(2-hydroxyethyl)-1H-pyrazol-4-yl)-N-(2-methyl-5-(5-methyl-2H-tetrazol-2-yl)phenyl)pyrazolo[1,5-a]pyridine-3-carboxamide 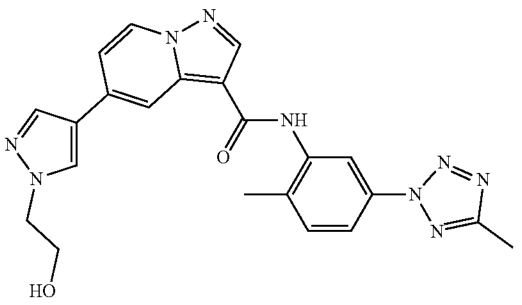 [SMILES: Cc1nnn(-c2ccc(C)c(NC(=O)c3cnn4ccc(-c5cnn(CCO)c5)cc34)c2)n1] | 16 |
| 52 | N-(5-(5-cyclopropyl-2H-tetrazol-2-yl)-2-methylphenyl)-5-(1-(2-hydroxyethyl)-1H-pyrazol-4-yl)pyrazolo[1,5-a]pyridine-3-carboxamide 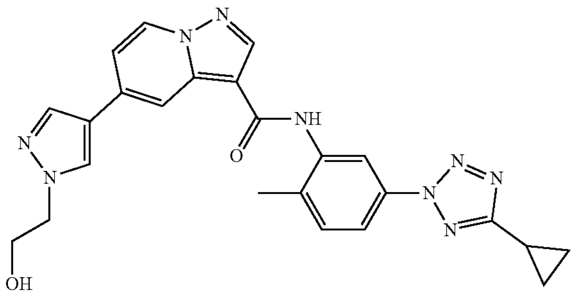 [SMILES: Cc1ccc(-n2nnc(C3CC3)n2)cc1NC(=O)c1cnn2ccc(-c3cnn(CCO)c3)cc12] | 16 |
| 53 | (R)-5-(1-(2-hydroxypropyl)-1H-pyrazol-4-yl)-N-(2-methyl-5-(2-methyl-2H-tetrazol-5-yl)phenyl)pyrazolo[1,5-a]pyridine-3-carboxamide or (S)-5-(1-(2-hydroxypropyl)-1H-pyrazol-4-yl)-N-(2-methyl-5-(2-methyl-2H-tetrazol-5-yl)phenyl)pyrazolo[1,5-a]pyridine-3-carboxamide 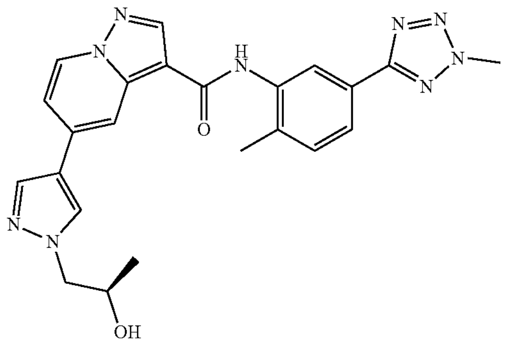 OR 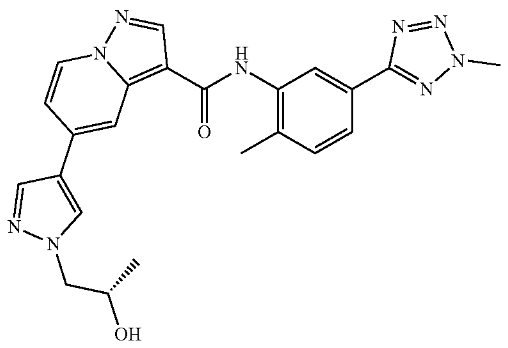 [SMILES: Cc1ccc(-c2nnn(C)n2)cc1NC(=O)c1cnn2ccc(-c3cnn(C[C@H](C)O)c3)cc12] | 16 Isomer 1 |

TABLE 1-continued

| Compound No | Name, Structure | Scheme |
| --- | --- | --- |
| 54 | (S)-5-(1-(2-hydroxypropyl)-1H-pyrazol-4-yl)-N-(2-methyl-5-(2-methyl-2H-tetrazol-5-yl)phenyl)pyrazolo[1,5-a]pyridine-3-carboxamide or (R)-5-(1-(2-hydroxypropyl)-1H-pyrazol-4-yl)-N-(2-methyl-5-(2-methyl-2H-tetrazol-5-yl)phenyl)pyrazolo[1,5-a]pyridine-3-carboxamide 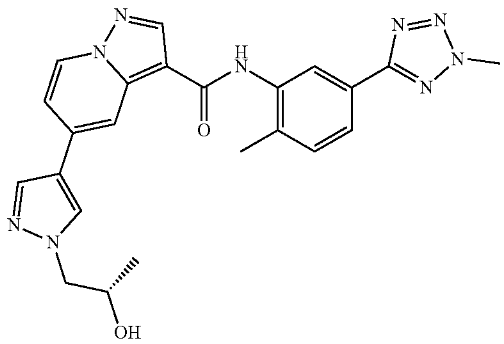 OR 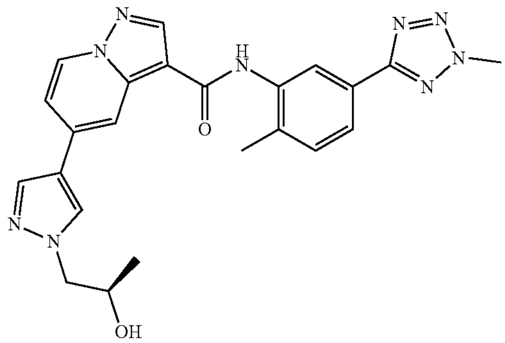 [SMILES: Cc1ccc(-c2nnn(C)n2)cc1NC(=O)c1cnn2ccc(-c3cnn(C[C@@H](C)O)c3)cc12] | 16 Isomer 2 |
| 55 | (R)-N-(5-(2-((2,2-difluorocyclopropyl)methyl)-2H-tetrazol-5-yl)-2-methylphenyl)-5-(1H-pyrazol-4-yl)pyrazolo[1,5-a]pyridine-3-carboxamide or (S)-N-(5-(2-((2,2-difluorocyclopropyl)methyl)-2H-tetrazol-5-yl)-2-methylphenyl)-5-(1H-pyrazol-4-yl)pyrazolo[1,5-a]pyridine-3-carboxamide 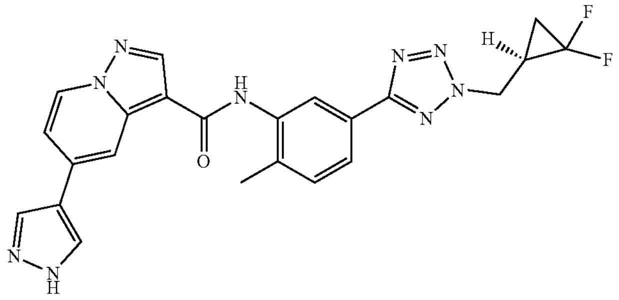 Or 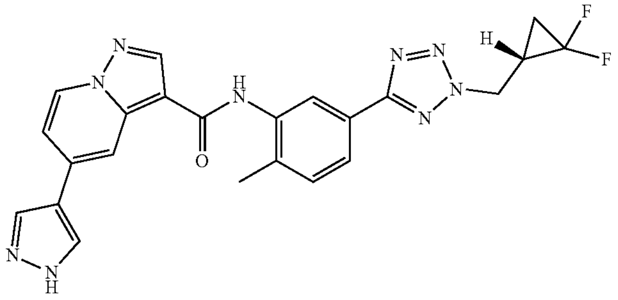 | 16 Isomer 1 |

TABLE 1-continued

| Compound No | Name, Structure | Scheme |
| --- | --- | --- |
| 56 | (S)-N-(5-(2-((2,2-difluorocyclopropyl)methyl)-2H-tetrazol-5-yl)-2-methylphenyl)-5-(1H-pyrazol-4-yl)pyrazolo[1,5-a]pyridine-3-carboxamide or (R)-N-(5-(2-((2,2-difluorocyclopropyl)methyl)-2H-tetrazol-5-yl)-2-methylphenyl)-5-(1H-pyrazol-4-yl)pyrazolo[1,5-a]pyridine-3-carboxamide 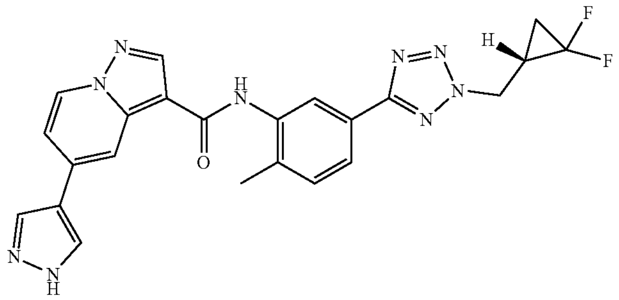 [SMILES: Cc1ccc(-c2nnn(C[C@@H]3CC3(F)F)n2)cc1NC(=O)c1cnn2ccc(-c3cn[nH]c3)cc12] Or 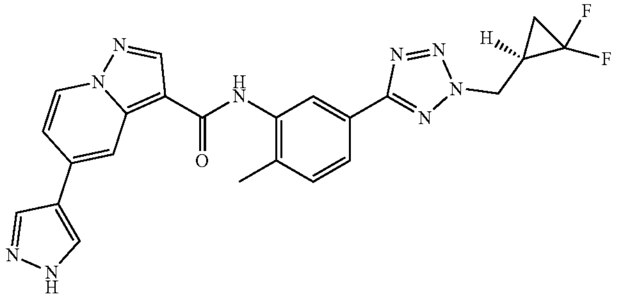 [SMILES: Cc1ccc(-c2nnn(C[C@H]3CC3(F)F)n2)cc1NC(=O)c1cnn2ccc(-c3cn[nH]c3)cc12] | 16 Isomer 2 |
| 57 | 5-(1-(2-hydroxyethyl)-1H-pyrazol-4-yl)-N-(2-methyl-5-(4-methyl-2H-1,2,3-triazol-2-yl)phenyl)pyrazolo[1,5-a]pyridine-3-carboxamide 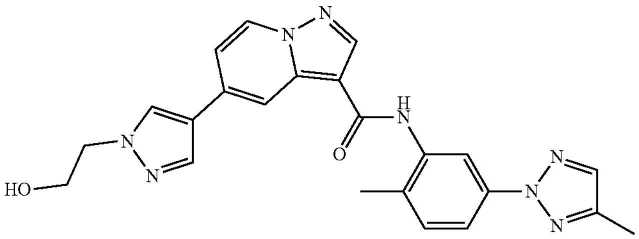 [SMILES: Cc1cnn(-c2ccc(C)c(NC(=O)c3cnn4ccc(-c5cnn(CCO)c5)cc34)c2)n1] | 16 |
| 58 | methyl 3-(5-(3-(5-(3-methoxypropyl)pyrazolo[1,5-a]pyridine-3-carboxamido)-4-methylphenyl)-2H-tetrazol-2-yl)azetidine-1-carboxylate 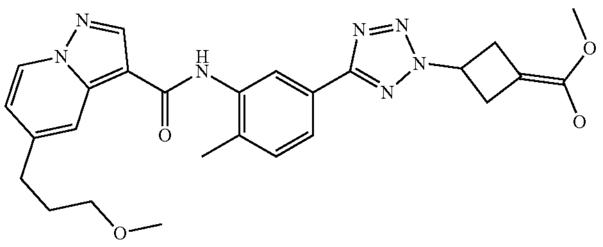 [SMILES: COCCCc1ccn2ncc(C(=O)Nc3cc(-c4nnn(C5CC(=C(O)OC)C5)n4)ccc3C)c2c1] | 17 |
| 59 | N-(5-(2-(3,3-difluorocyclobutyl)-2H-tetrazol-5-yl)-4-fluoro-2-methylphenyl)-5-morpholinopyrazolo[1,5-a]pyridine-3-carboxamide | 18 |

TABLE 1-continued

| Compound No | Name, Structure | Scheme |
|---|---|---|
| | 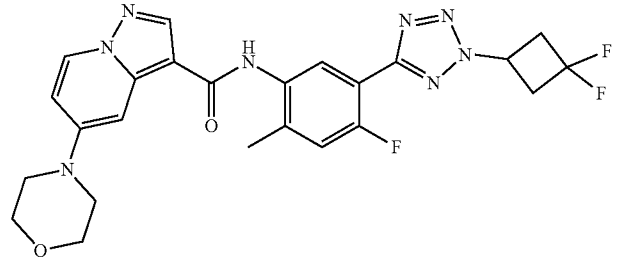 [SMILES: Cc1cc(F)c(-c2nnn(C3CC(F)(F)C3)n2)cc1NC(=O)c1cnn2ccc(N3CCOCC3)cc12] | |
| 60 | N-(5-(2-(3,3-difluorocyclobutyl)-2H-tetrazol-5-yl)-2-methylphenyl)-5-(3-hydroxyazetidin-1-yl)pyrazolo[1,5-a]pyridine-3-carboxamide | 18 |
| | 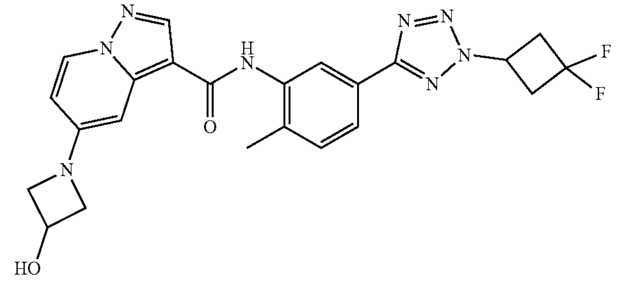 [SMILES: Cc1ccc(-c2nnn(C3CC(F)(F)C3)n2)cc1NC(=O)c1cnn2ccc(N3CC(O)C3)cc12] | |
| 61 | N-(5-(2-(3,3-difluorocyclobutyl)-2H-tetrazol-5-yl)-2-methylphenyl)-5-(4-hydroxy-4-methylpiperidin-1-yl)pyrazolo[1,5-a]pyridine-3-carboxamide | 18 |
| | 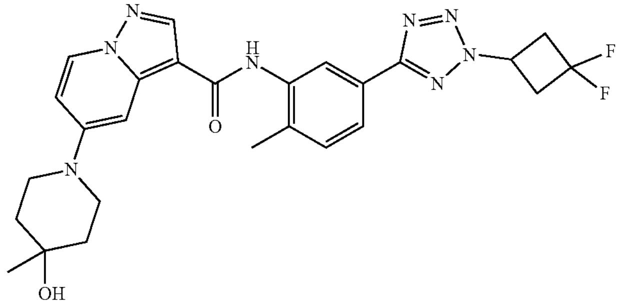 [SMILES: Cc1ccc(-c2nnn(C3CC(F)(F)C3)n2)cc1NC(=O)c1cnn2ccc(N3CCC(C)(O)CC3)cc12] | |
| 62 | (S)-N-(5-(2-(3,3-difluorocyclobutyl)-2H-tetrazol-5-yl)-2-methylphenyl)-5-(3-hydroxypyrrolidin-1-yl)pyrazolo[1,5-a]pyridine-3-carboxamide | 18 |
| | 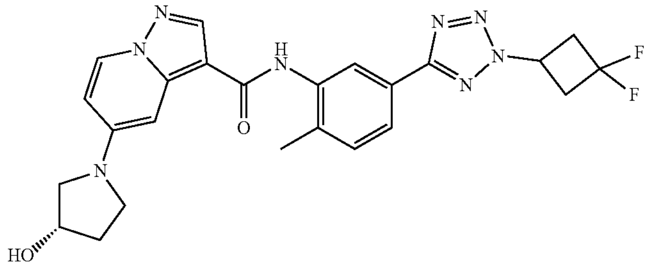 [SMILES: Cc1ccc(-c2nnn(C3CC(F)(F)C3)n2)cc1NC(=O)c1cnn2ccc(N3CC[C@H](O)C3)cc12] | |
| 63 | N-(2-chloro-5-(2-(3,3-difluorocyclobutyl)-2H-tetrazol-5-yl)-4-fluorophenyl)-5-morpholinopyrazolo[1,5-a]pyridine-3-carboxamide | 18 |

TABLE 1-continued

| Compound No | Name, Structure | Scheme |
|---|---|---|
| | 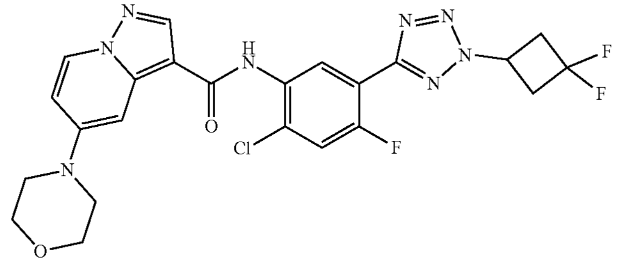 | |
| 64 | N-(4-fluoro-2-methyl-5-(2-((1s,3s)-3-(trifluoromethyl)cyclobutyl)-2H-tetrazol-5-yl)phenyl)-5-(3-hydroxy-3-methylazetidin-1-yl)pyrazolo[1,5-a]pyridine-3-carboxamide 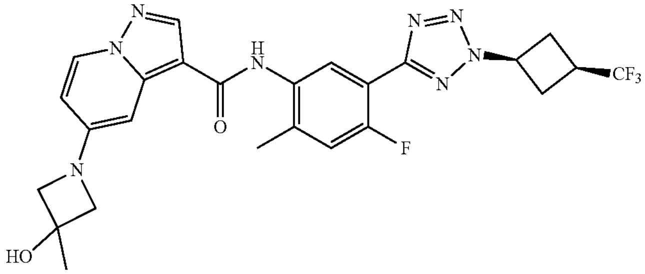 [SMILES: Cc1cc(F)c(-c2nnn([C@H]3C[C@@H](C(F)(F)F)C3)n2)cc1NC(=O)c1cnn2ccc(N3CC(C)(O)C3)cc12] | 18 |
| 65 | methyl 3-(5-(3-(5-(3-hydroxy-3-methylbutoxy)pyrazolo[1,5-a]pyridine-3-carboxamido)-4-methylphenyl)-2H-tetrazol-2-yl)azetidine-1-carboxylate 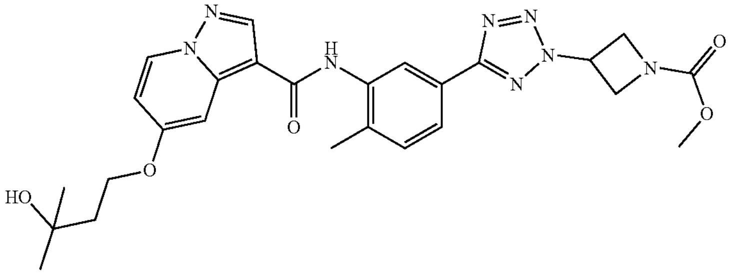 [SMILES: COC(=O)N1CC(n2nnc(-c3ccc(C)c(NC(=O)c4cnn5ccc(OCCC(C)(C)O)cc45)c3)n2)C1] | 18 |
| 66 | methyl 3-(5-(4-methyl-3-(5-(4-methylpiperazin-1-yl)pyrazolo[1,5-a]pyridine-3-carboxamido)phenyl)-2H-tetrazol-2-yl)azetidine-1-carboxylate 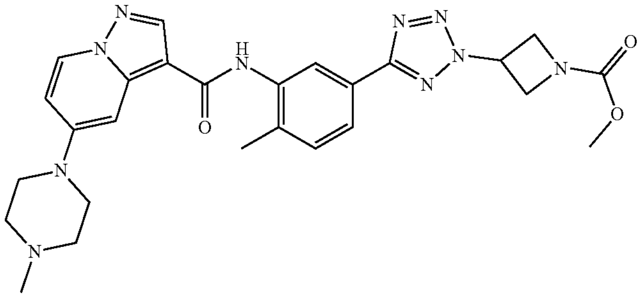 [SMILES: COC(=O)N1CC(n2nnc(-c3ccc(C)c(NC(=O)c4cnn5ccc(N6CCN(C)CC6)cc45)c3)n2)C1] | 18 |
| 67 | methyl 3-(5-(3-(5-(3,3-difluoropyrrolidin-1-yl)pyrazolo[1,5-a]pyridine-3-carboxamido)-4-methylphenyl)-2H-tetrazol-2-yl)azetidine-1-carboxylate | 18 |

TABLE 1-continued

| Compound No | Name, Structure | Scheme |
| --- | --- | --- |
| | 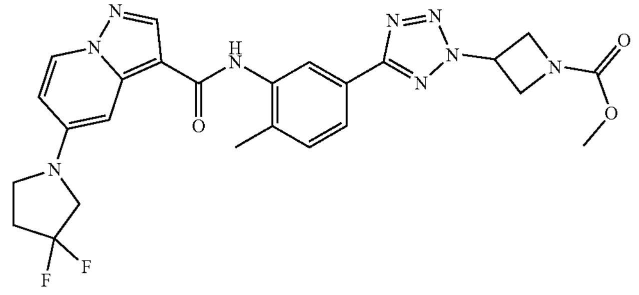 [SMILES: COC(=O)N1CC(n2nnc(-c3ccc(C)c(NC(=O)c4cnn5ccc(N6CCC(F)(F)C6)cc45)c3)n2)C1] | |
| 68 | methyl (S)-3-(5-(3-(5-(2-(hydroxymethyl)morpholino)pyrazolo[1,5-a]pyridine-3-carboxamido)-4-methylphenyl)-2H-tetrazol-2-yl)azetidine-1-carboxylate<br>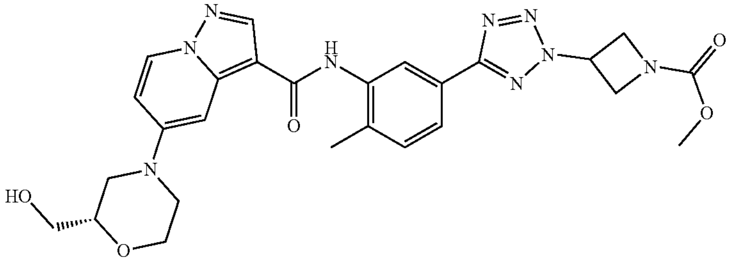 [SMILES: COC(=O)N1CC(n2nnc(-c3ccc(C)c(NC(=O)c4cnn5ccc(N6CCO[C@H](CO)C6)cc45)c3)n2)C1] | 18 |
| 69 | methyl 3-(5-(4-methyl-3-(5-morpholinopyrazolo[1,5-a]pyridine-3-carboxamido)phenyl)-2H-tetrazol-2-yl)azetidine-1-carboxylate<br>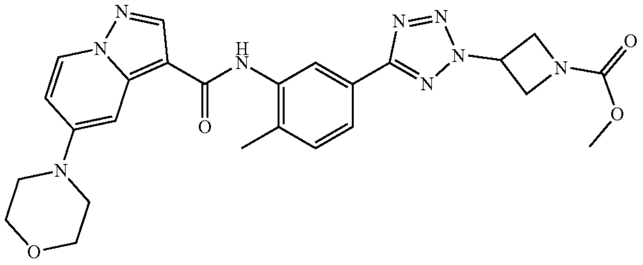 [SMILES: COC(=O)N1CC(n2nnc(-c3ccc(C)c(NC(=O)c4cnn5ccc(N6CCOCC6)cc45)c3)n2)C1] | 18 |
| 70 | methyl (S)-3-(5-(3-(5-(3-hydroxypiperidin-1-yl)pyrazolo[1,5-a]pyridine-3-carboxamido)-4-methylphenyl)-2H-tetrazol-2-yl)azetidine-1-carboxylate<br>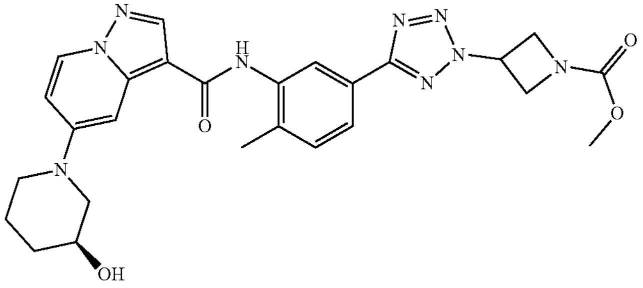 [SMILES: COC(=O)N1CC(n2nnc(-c3ccc(C)c(NC(=O)c4cnn5ccc(N6CCC[C@H](O)C6)cc45)c3)n2)C1] | 18 |
| 71 | methyl (R)-3-(5-(3-(5-(3-hydroxypiperidin-1-yl)pyrazolo[1,5-a]pyridine-3-carboxamido)-4-methylphenyl)-2H-tetrazol-2-yl)azetidine-1-carboxylate | 18 |

TABLE 1-continued

| Compound No | Name, Structure | Scheme |
|---|---|---|
| | 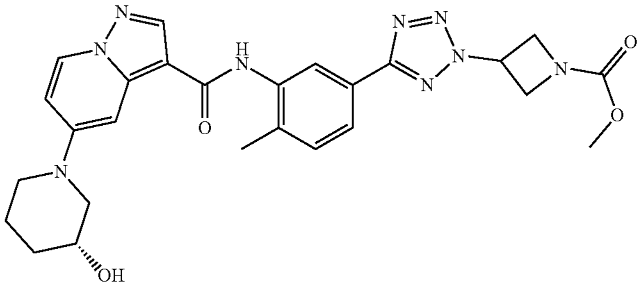 [SMILES: COC(=O)N1CC(n2nnc(-c3ccc(C)c(NC(=O)c4cnn5ccc(N6CCC[C@@H](O)C6)cc45)c3)n2)C1] | |
| 72 | methyl 3-(5-(4-methyl-3-(5-(4-(methyl-d3)piperazin-1-yl)pyrazolo[1,5-a]pyridine-3-carboxamido)phenyl)-2H-tetrazol-2-yl)azetidine-1-carboxylate | 18 |
| | 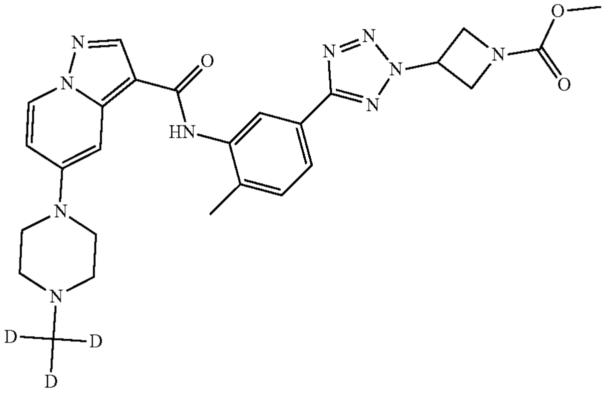 [SMILES: [2H]C([2H])([2H])N1CCN(c2ccn3ncc(C(=O)Nc4cc(-c5nnn(C6CN(C(=O)OC)C6)n5)ccc4C)c3c2)CC1] | |
| 73 | methyl 3-(5-(3-(5-(4-(2,2-difluoroethyl)piperazin-1-yl)pyrazolo[1,5-a]pyridine-3-carboxamido)-4-methylphenyl)-2H-tetrazol-2-yl)azetidine-1-carboxylate | 18 |
| | 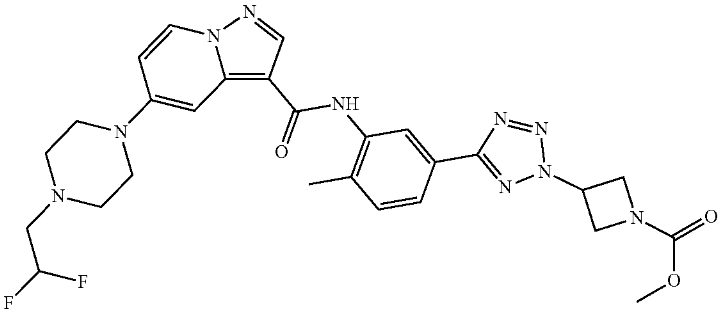 [SMILES: COC(=O)N1CC(n2nnc(-c3ccc(C)c(NC(=O)c4cnn5ccc(N6CCN(CC(F)F)CC6)cc45)c3)n2)C1] | |
| 74 | methyl 3-(5-(4-methyl-3-(5-(4-(oxetan-3-yl)piperazin-1-yl)pyrazolo[1,5-a]pyridine-3-carboxamido)phenyl)-2H-tetrazol-2-yl)azetidine-1-carboxylate | 18 |

TABLE 1-continued

| Compound No | Name, Structure | Scheme |
|---|---|---|
| | 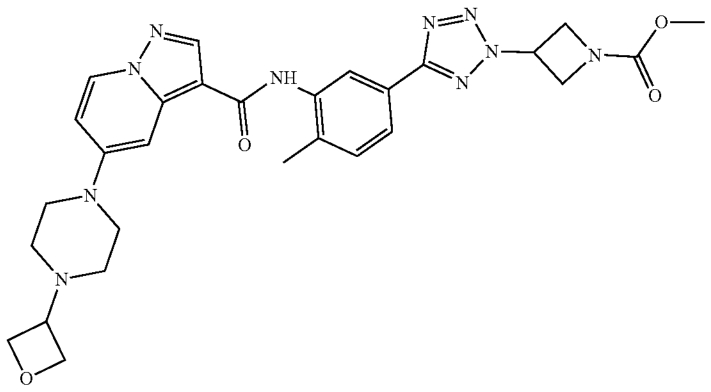 [SMILES: COC(=O)N1CC(n2nnc(-c3ccc(C)c(NC(=O)c4cnn5ccc(N6CCN(C7COC7)CC6)cc45)c3)n2)C1] | |
| 75 | methyl (R)-3-(5-(3-(5-(hexahydropyrrolo[1,2-a]pyrazin-2(1H)-yl)pyrazolo[1,5-a]pyridine-3-carboxamido)-4-methylphenyl)-2H-tetrazol-2-yl)azetidine-1-carboxylate 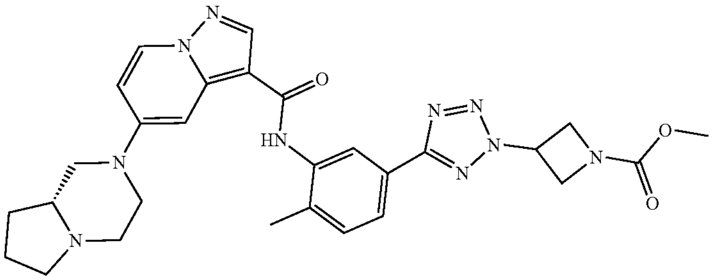 [SMILES: COC(=O)N1CC(n2nnc(-c3ccc(C)c(NC(=O)c4cnn5ccc(N6CCN7CCC[C@@H]7C6)cc45)c3)n2)C1] | 18 |
| 76 | ethyl 3-(5-(4-methyl-3-(5-(4-methylpiperazin-1-yl)pyrazolo[1,5-a]pyridine-3-carboxamido)phenyl)-2H-tetrazol-2-yl)azetidine-1-carboxylate 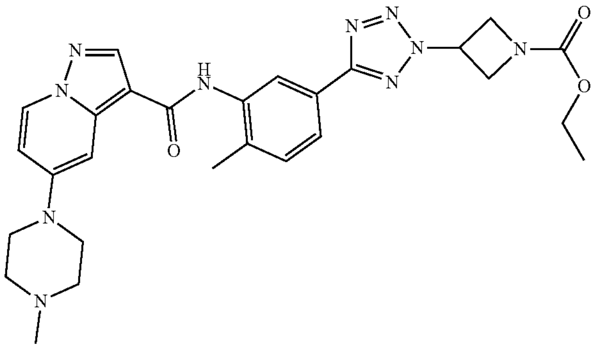 [SMILES: CCOC(=O)N1CC(n2nnc(-c3ccc(C)c(NC(=O)c4cnn5ccc(N6CCN(C)CC6)cc45)c3)n2)C1] | 18 |
| 77 | ethyl 3-(5-(4-methyl-3-(5-morpholinopyrazolo[1,5-a]pyridine-3-carboxamido)phenyl)-2H-tetrazol-2-yl)azetidine-1-carboxylate 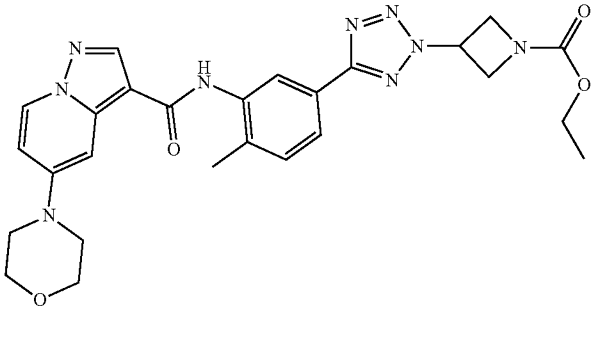 [SMILES: CCOC(=O)N1CC(n2nnc(-c3ccc(C)c(NC(=O)c4cnn5ccc(N6CCOCC6)cc45)c3)n2)C1] | 18 |

TABLE 1-continued

| Compound No | Name, Structure | Scheme |
|---|---|---|
| 78 | (R)-N-(5-(2-(3,3-difluorocyclobutyl)-2H-tetrazol-5-yl)-2-methylphenyl)-5-(3-hydroxypyrrolidin-1-yl)pyrazolo[1,5-a]pyridine-3-carboxamide 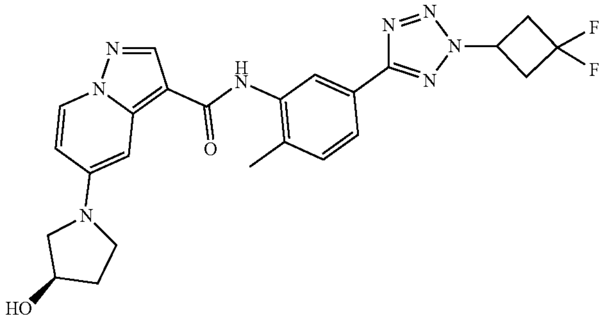 [SMILES: Cc1ccc(-c2nnn(C3CC(F)(F)C3)n2)cc1NC(=O)c1cnn2ccc(N3CC[C@@H](O)C3)cc12] | 18 |
| 79 | N-(5-(2-(3,3-difluorocyclobutyl)-2H-tetrazol-5-yl)-2-methylphenyl)-5-morpholinopyrazolo[1,5-a]pyridine-3-carboxamide 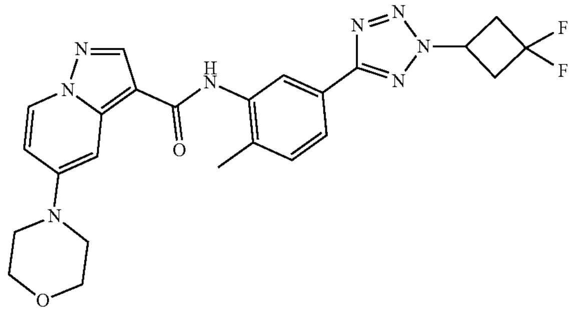 [SMILES: Cc1ccc(-c2nnn(C3CC(F)(F)C3)n2)cc1NC(=O)c1cnn2ccc(N3CCOCC3)cc12] | 18 |
| 80 | methyl 3-(2-(4-methyl-3-(5-morpholinopyrazolo[1,5-a]pyridine-3-carboxamido)phenyl)-2H-1,2,3-triazol-4-yl)azetidine-1-carboxylate 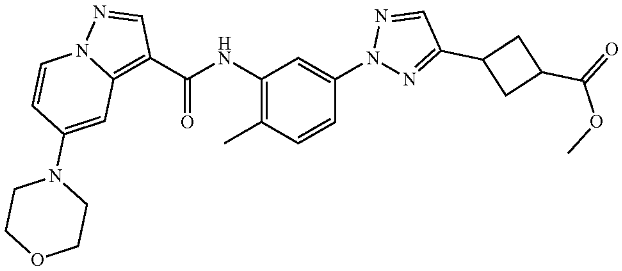 [SMILES: COC(=O)C1CC(c2cnn(-c3ccc(C)c(NC(=O)c4cnn5ccc(N6CCOCC6)cc45)c3)n2)C1] | 18 |
| 81 | methyl 3-(2-(4-methyl-3-(5-(4-methylpiperazin-1-yl)pyrazolo[1,5-a]pyridine-3-carboxamido)phenyl)-2H-1,2,3-triazol-4-yl)azetidine-1-carboxylate 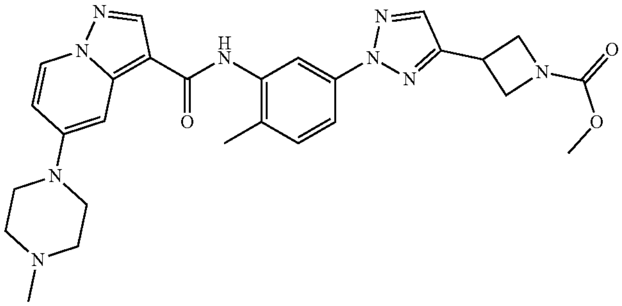 [SMILES: COC(=O)N1CC(c2cnn(-c3ccc(C)c(NC(=O)c4cnn5ccc(N6CCN(C)CC6)cc45)c3)n2)C1] | 18 |

TABLE 1-continued

| Compound No | Name, Structure | Scheme |
|---|---|---|
| 82 | methyl 3-(2-(4-methyl-3-(5-(4-(methyl-d3)piperazin-1-yl)pyrazolo[1,5-a]pyridine-3-carboxamido)phenyl)-2H-1,2,3-triazol-4-yl)azetidine-1-carboxylate<br>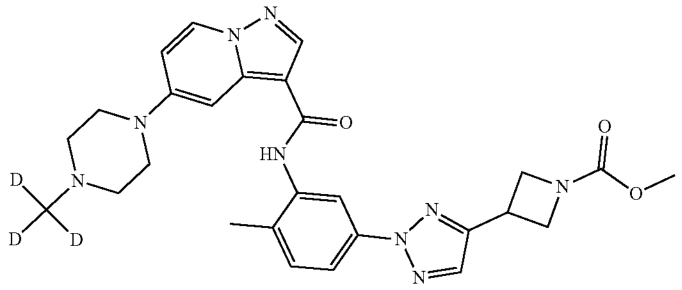 [SMILES: [2H]C([2H])([2H])N1CCN(c2ccn3ncc(C(=O)Nc4cc(-n5ncc(C6CN(C(=O)OC)C6)n5)ccc4C)c3c2)CC1] | 18 |
| 83 | methyl 3-(2-(4-methyl-3-(5-(4-(oxetan-3-yl)piperazin-1-yl)pyrazolo[1,5-a]pyridine-3-carboxamido)phenyl)-2H-1,2,3-triazol-4-yl)azetidine-1-carboxylate<br>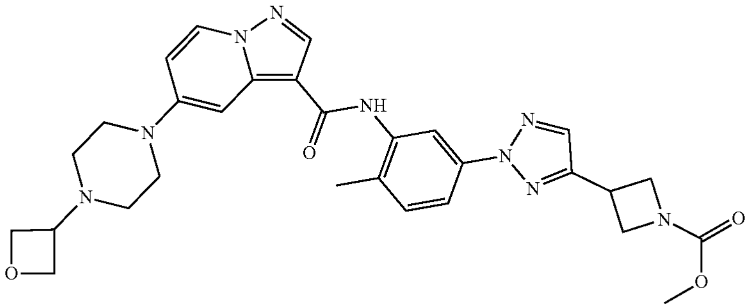 [SMILES: COC(=O)N1CC(c2cnn(-c3ccc(C)c(NC(=O)c4cnn5ccc(N6CCN(C7COC7)CC6)cc45)c3)n2)C1] | 18 |
| 84 | methyl 3-(2-(3-(5-((2-hydroxyethyl)(methyl)amino)pyrazolo[1,5-a]pyridine-3-carboxamido)-4-methylphenyl)-2H-1,2,3-triazol-4-yl)azetidine-1-carboxylate<br>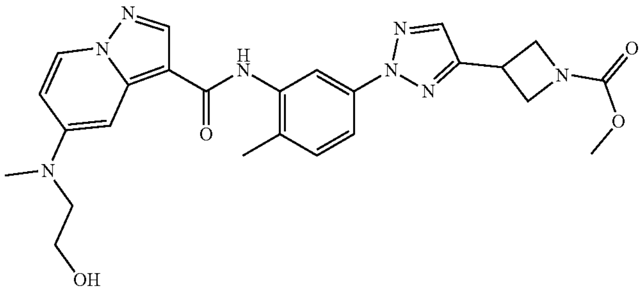 [SMILES: COC(=O)N1CC(c2cnn(-c3ccc(C)c(NC(=O)c4cnn5ccc(N(C)CCO)cc45)c3)n2)C1] | 18 |
| 85 | methyl (S)-3-(5-(3-(5-(2-(methoxymethyl)azetidin-1-yl)pyrazolo[1,5-a]pyridine-3-carboxamido)-4-methylphenyl)-2H-tetrazol-2-yl)azetidine-1-carboxylate or methyl (R)-3-(5-(3-(5-(2-(methoxymethyl)azetidin-1-yl)pyrazolo[1,5-a]pyridine-3-carboxamido)-4-methylphenyl)-2H-tetrazol-2-yl)azetidine-1-carboxylate | 18<br>Isomer 1 |

TABLE 1-continued
| Compound No | Name, Structure | Scheme |
|---|---|---|
| | 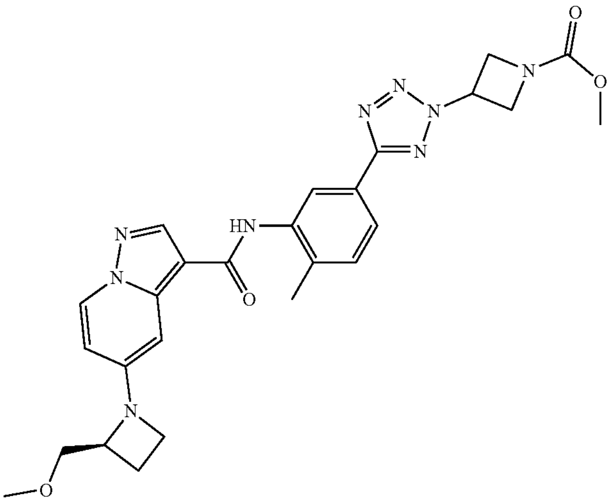 Or 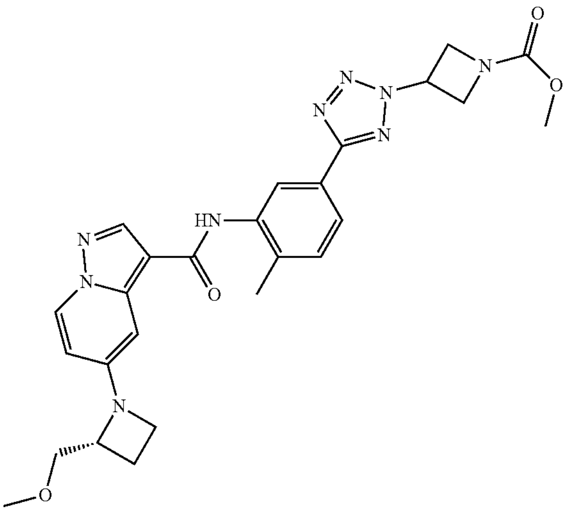 [SMILES: COC[C@H]1CCN1c1ccn2ncc(C(=O)Nc3cc(-c4nnn(C5CN(C(=O)OC)C5)n4)ccc3C)c2c1] | |
| 86 | (S)-N-(5-(2-(3,3-difluorocyclobutyl)-2H-tetrazol-5-yl)-2-methylphenyl)-5-(3-hydroxy-3-methylpyrrolidin-1-yl)pyrazolo[1,5-a]pyridine-3-carboxamide or (R)-N-(5-(2-(3,3-difluorocyclobutyl)-2H-tetrazol-5-yl)-2-methylphenyl)-5-(3-hydroxy-3-methylpyrrolidin-1-yl)pyrazolo[1,5-a]pyridine-3-carboxamide | 18 Isomer 2 |

TABLE 1-continued
| Compound No | Name, Structure | Scheme |
|---|---|---|
| | 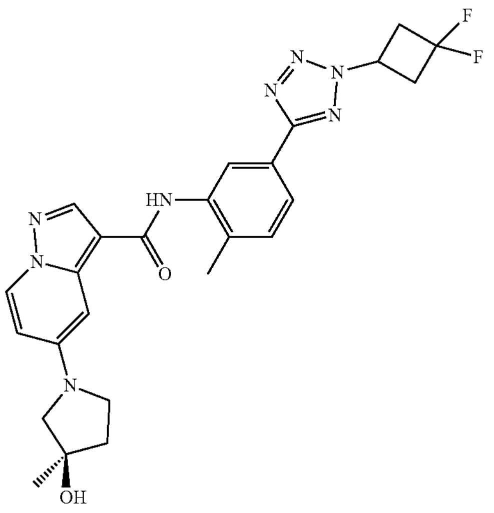 Or 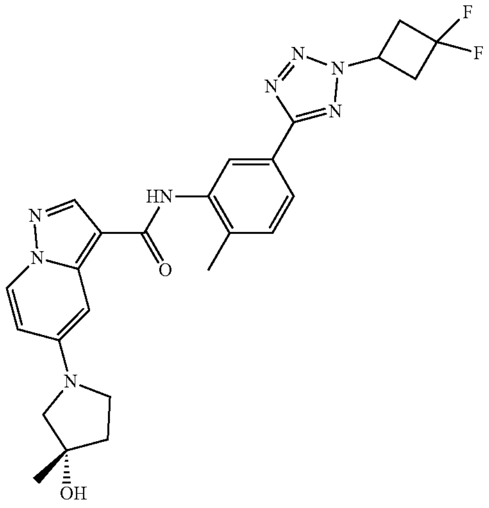 [SMILES: Cc1ccc(-c2nnn(C3CC(F)(F)C3)n2)cc1NC(=O)c1cnn2ccc(N3CC[C@](C)(O)C3)cc12] | |
| 87 | 5-((2-methoxyethyl)amino)-N-(2-methyl-5-(2-methyl-2H-tetrazol-5-yl)phenyl)pyrazolo[1,5-a]pyridine-3-carboxamide 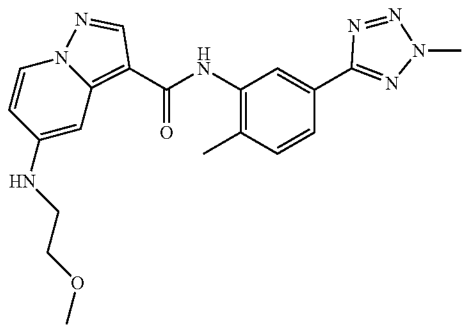 [SMILES: COCCNc1ccn2ncc(C(=O)Nc3cc(-c4nnn(C)n4)ccc3C)c2c1] | 18 |
| 88 | N-(5-(2-cyclopropyl-2H-tetrazol-5-yl)-2-methylphenyl)-5-((2-methoxyethyl)amino)pyrazolo[1,5-a]pyridine-3-carboxamide | 18 |

TABLE 1-continued

| Compound No | Name, Structure | Scheme |
|---|---|---|
| | 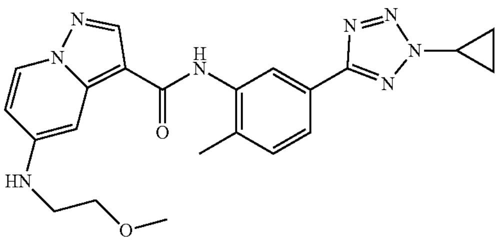 [SMILES: COCCNc1ccn2ncc(C(=O)Nc3cc(-c4nnn(C5CC5)n4)ccc3C)c2c1] | |
| 89 | methyl 3-(5-(3-(5-((2-hydroxy-2-methylpropyl)amino)pyrazolo[1,5-a]pyridine-3-carboxamido)-4-methylphenyl)-2H-tetrazol-2-yl)azetidine-1-carboxylate 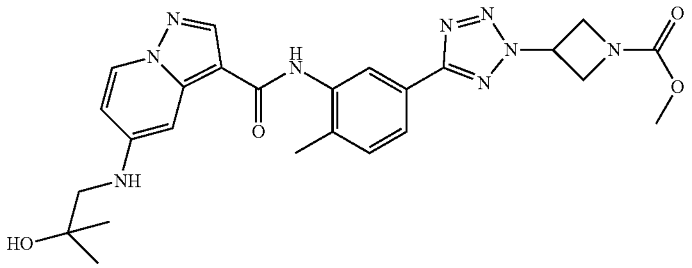 [SMILES: COC(=O)N1CC(n2nnc(-c3ccc(C)c(NC(=O)c4cnn5ccc(NCC(C)(C)O)cc45)c3)n2)C1] | 18 |
| 90 | methyl (S)-3-(5-(3-(5-(2-(hydroxymethyl)azetidin-1-yl)pyrazolo[1,5-a]pyridine-3-carboxamido)-4-methylphenyl)-2H-tetrazol-2-yl)azetidine-1-carboxylate 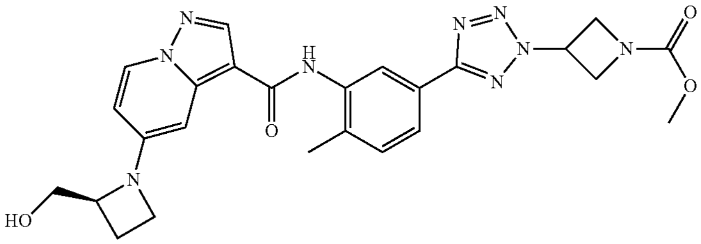 [SMILES: COC(=O)N1CC(n2nnc(-c3ccc(C)c(NC(=O)c4cnn5ccc(N6CC[C@H]6CO)cc45)c3)n2)C1] | 18 |
| 91 | methyl (R)-3-(5-(3-(5-(2-(hydroxymethyl)morpholino)pyrazolo[1,5-a]pyridine-3-carboxamido)-4-methylphenyl)-2H-tetrazol-2-yl)azetidine-1-carboxylate 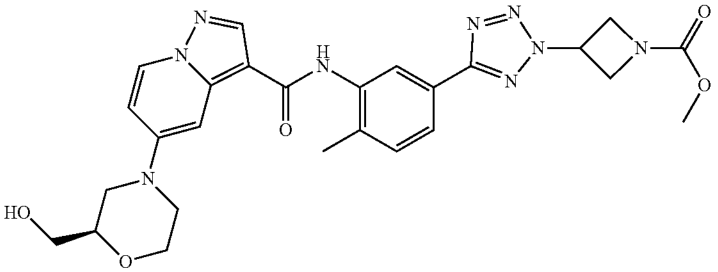 [SMILES: COC(=O)N1CC(n2nnc(-c3ccc(C)c(NC(=O)c4cnn5ccc(N6CCO[C@@H](CO)C6)cc45)c3)n2)C1] | 18 |
| 92 | methyl 3-(5-(3-(5-((2,2-difluoropropyl)amino)pyrazolo[1,5-a]pyridine-3-carboxamido)-4-methylphenyl)-2H-tetrazol-2-yl)azetidine-1-carboxylate | 18 |

TABLE 1-continued

| Compound No | Name, Structure | Scheme |
|---|---|---|
| | 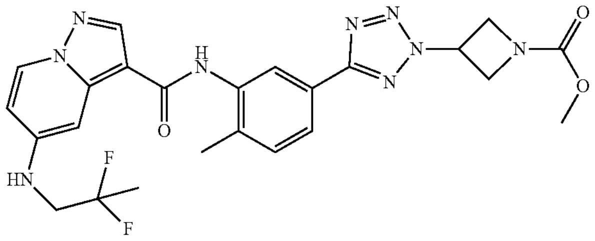 [SMILES: COC(=O)N1CC(n2nnc(-c3ccc(C)c(NC(=O)c4cnn5ccc(NCC(C)(F)F)cc45)c3)n2)C1] | |
| 93 | methyl 3-(5-(3-(5-((2-(tert-butoxy)ethyl)amino)pyrazolo[1,5-a]pyridine-3-carboxamido)-4-methylphenyl)-2H-tetrazol-2-yl)azetidine-1-carboxylate | 18 |
| | 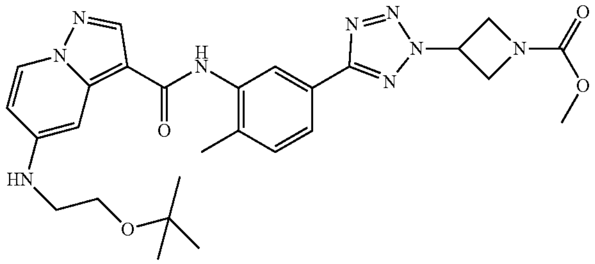 [SMILES: COC(=O)N1CC(n2nnc(-c3ccc(C)c(NC(=O)c4cnn5ccc(NCCOC(C)(C)C)cc45)c3)n2)C1] | |
| 94 | methyl (S)-3-(5-(3-(5-((2-hydroxypropyl)amino)pyrazolo[1,5-a]pyridine-3-carboxamido)-4-methylphenyl)-2H-tetrazol-2-yl)azetidine-1-carboxylate | 18 |
| | 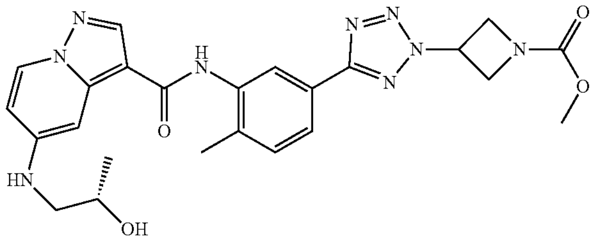 [SMILES: COC(=O)N1CC(n2nnc(-c3ccc(C)c(NC(=O)c4cnn5ccc(NC[C@H](C)O)cc45)c3)n2)C1] | |
| 95 | methyl 3-(5-(4-methyl-3-(5-((oxetan-2-ylmethyl)amino)pyrazolo[1,5-a]pyridine-3-carboxamido)phenyl)-2H-tetrazol-2-yl)azetidine-1-carboxylate | 18 |
| | 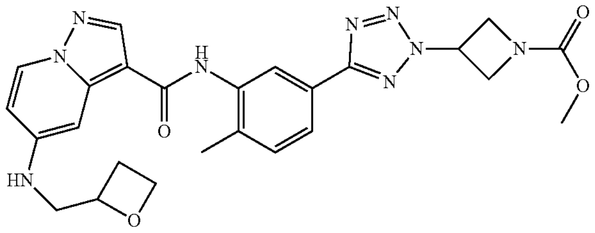 [SMILES: COC(=O)N1CC(n2nnc(-c3ccc(C)c(NC(=O)c4cnn5ccc(NCC6CCO6)cc45)c3)n2)C1] | |
| 96 | methyl 3-(5-(3-(5-((2-methoxy-2-methylpropyl)amino)pyrazolo[1,5-a]pyridine-3-carboxamido)-4-methylphenyl)-2H-tetrazol-2-yl)azetidine-1-carboxylate | 18 |

TABLE 1-continued

| Compound No | Name, Structure | Scheme |
|---|---|---|
| | 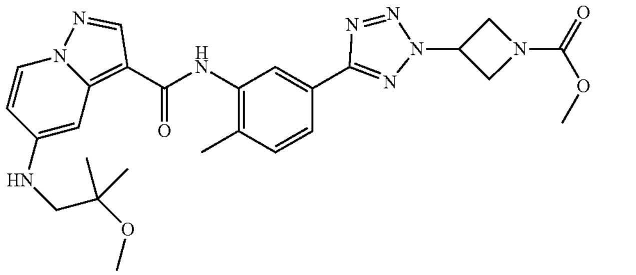 [SMILES: COC(=O)N1CC(n2nnc(-c3ccc(C)c(NC(=O)c4cnn5ccc(NCC(C)(C)OC)cc45)c3)n2)C1] | |
| 97 | methyl (R)-3-(5-(3-(5-(3-(dimethylamino)pyrrolidin-1-yl)pyrazolo[1,5-a]pyridine-3-carboxamido)-4-methylphenyl)-2H-tetrazol-2-yl)azetidine-1-carboxylate<br>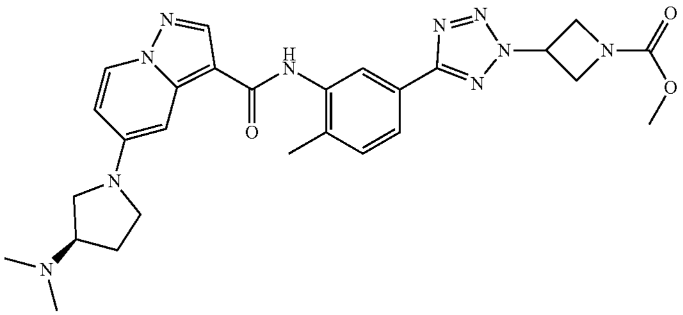 [SMILES: COC(=O)N1CC(n2nnc(-c3ccc(C)c(NC(=O)c4cnn5ccc(N6CC[C@@H](N(C)C)C6)cc45)c3)n2)C1] | 18 |
| 98 | methyl 3-(5-(3-(5-(2-oxa-6-azaspiro[3.3]heptan-6-yl)pyrazolo[1,5-a]pyridine-3-carboxamido)-4-methylphenyl)-2H-tetrazol-2-yl)azetidine-1-carboxylate<br>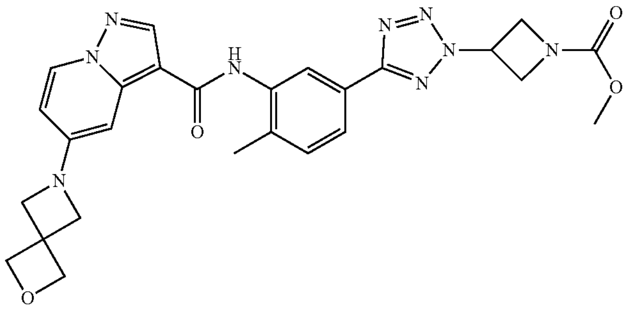 [SMILES: COC(=O)N1CC(n2nnc(-c3ccc(C)c(NC(=O)c4cnn5ccc(N6CC7(COC7)C6)cc45)c3)n2)C1] | 18 |
| 99 | Methyl 3-(5-(4-methyl-3-(5-(3-(methylsulfonyl)azetidin-1-yl)pyrazolo[1,5-a]pyridine-3-carboxamido)phenyl)-2H-tetrazol-2-yl)azetidine-1-carboxylate<br>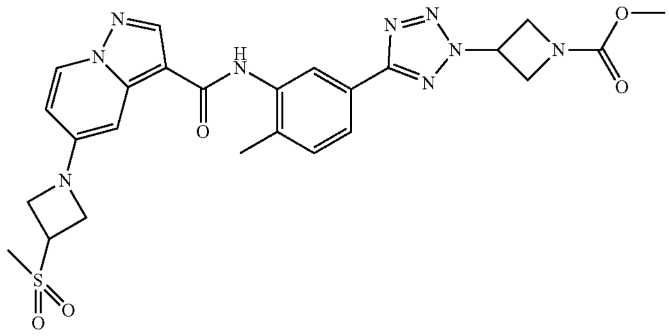 | 18 |
| 100 | methyl 3-(5-(3-(5-((2-(methoxy-d3)ethyl)amino)pyrazolo[1,5-a]pyridine-3-carboxamido)-4-methylphenyl)-2H-tetrazol-2-yl)azetidine-1-carboxylate | 18 |

TABLE 1-continued

| Compound No | Name, Structure | Scheme |
|---|---|---|
| | 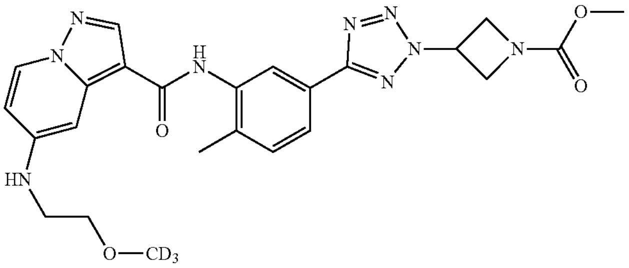 [SMILES: [2H]C([2H])([2H])OCCNc1ccn2ncc(C(=O)Nc3cc(-c4nnn(C5CN(C(=O)OC)C5)n4)ccc3C)c2c1] | |
| 101 | N-(5-(2-(3,3-difluorocyclobutyl)-2H-tetrazol-5-yl)-2-methylphenyl)-5-((2-hydroxyethyl)amino)pyrazolo[1,5-a]pyridine-3-carboxamide 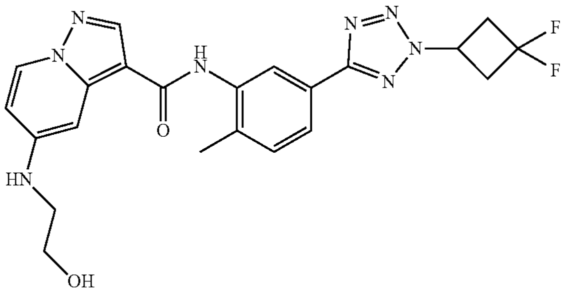 [SMILES: Cc1ccc(-c2nnn(C3CC(F)(F)C3)n2)cc1NC(=O)c1cnn2ccc(NCCO)cc12] | 18 |
| 102 | 5-((2,2-difluoro-3-hydroxypropyl)amino)-N-(5-(2-(3,3-difluorocyclobutyl)-2H-tetrazol-5-yl)-2-methylphenyl)pyrazolo[1,5-a]pyridine-3-carboxamide 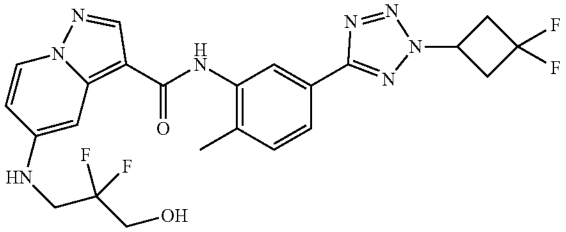 [SMILES: Cc1ccc(-c2nnn(C3CC(F)(F)C3)n2)cc1NC(=O)c1cnn2ccc(NCC(F)(F)CO)cc12] | 18 |
| 103 | N-(5-(2-(3,3-difluorocyclobutyl)-2H-tetrazol-5-yl)-2-methylphenyl)-5-(3-(hydroxymethyl)azetidin-1-yl)pyrazolo[1,5-a]pyridine-3-carboxamide 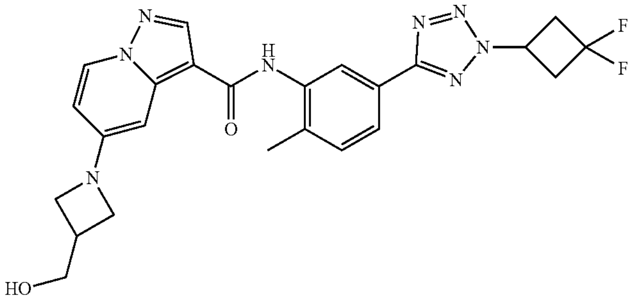 [SMILES: Cc1ccc(-c2nnn(C3CC(F)(F)C3)n2)cc1NC(=O)c1cnn2ccc(N3CC(CO)C3)cc12] | 18 |
| 104 | (S)-N-(5-(2-(3,3-difluorocyclobutyl)-2H-tetrazol-5-yl)-2-methylphenyl)-5-(2-(hydroxymethyl)azetidin-1-yl)pyrazolo[1,5-a]pyridine-3-carboxamide | 18 |

TABLE 1-continued

| Compound No | Name, Structure | Scheme |
|---|---|---|
| | 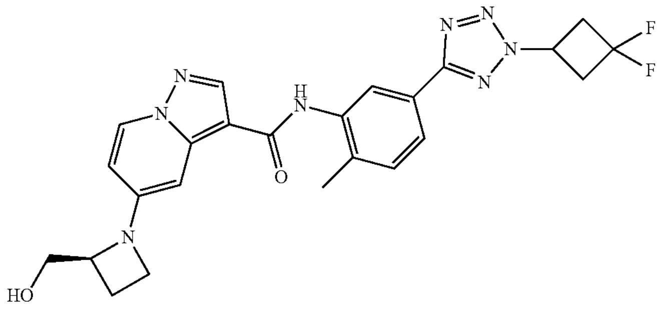 [SMILES: Cc1ccc(-c2nnn(C3CC(F)(F)C3)n2)cc1NC(=O)c1cnn2ccc(N3CC[C@H]3CO)cc12] | |
| 105 | N-(5-(2-(3,3-difluorocyclobutyl)-2H-tetrazol-5-yl)-4-fluoro-2-methylphenyl)-5-((2-methoxyethyl)amino)pyrazolo[1,5-a]pyridine-3-carboxamide<br>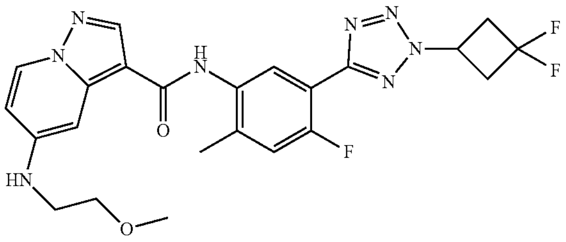 [SMILES: COCCNc1ccn2ncc(C(=O)Nc3cc(-c4nnn(C5CC(F)(F)C5)n4)c(F)cc3C)c2c1] | 18 |
| 106 | 5-(4-(2-hydroxyethyl)piperazin-1-yl)-N-(2-methyl-5-(2-((1s,3s)-3-(trifluoromethyl)cyclobutyl)-2H-tetrazol-5-yl)phenyl)pyrazolo[1,5-a]pyridine-3-carboxamide<br>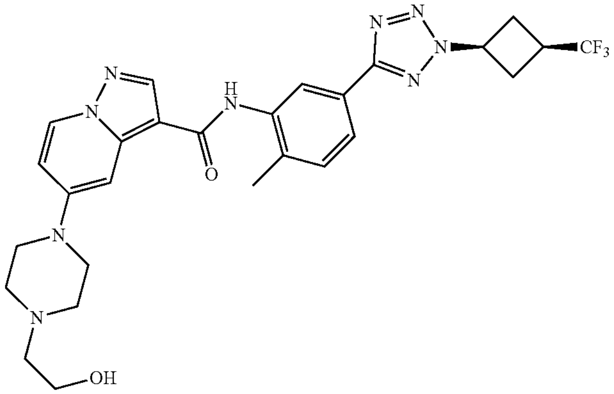 [SMILES: Cc1ccc(-c2nnn([C@H]3C[C@@H](C(F)(F)F)C3)n2)cc1NC(=O)c1cnn2ccc(N3CCN(CCO)CC3)cc12] | 18 |
| 107 | 5-(3-hydroxy-3-methylazetidin-1-yl)-N-(2-methyl-5-(2-((1s,3s)-3-(trifluoromethyl)cyclobutyl)-2H-tetrazol-5-yl)phenyl)pyrazolo[1,5-a]pyridine-3-carboxamide<br>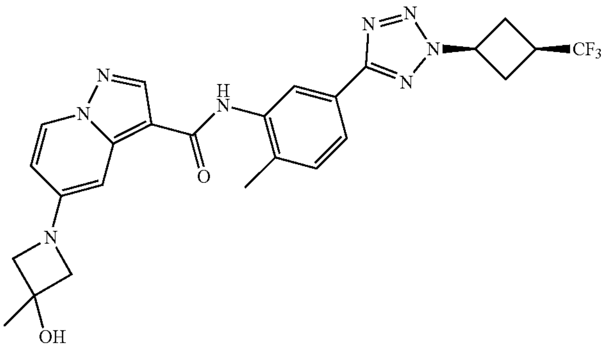 [SMILES: Cc1ccc(-c2nnn([C@H]3C[C@@H](C(F)(F)F)C3)n2)cc1NC(=O)c1cnn2ccc(N3CC(C)(O)C3)cc12] | 18 |

TABLE 1-continued

| Compound No | Name, Structure | Scheme |
|---|---|---|
| 108 | N-(4-fluoro-2-methyl-5-(2-((1s,3s)-3-(trifluoromethyl)cyclobutyl)-2H-tetrazol-5-yl)phenyl)-5-((2-methoxyethyl)amino)pyrazolo[1,5-a]pyridine-3-carboxamide 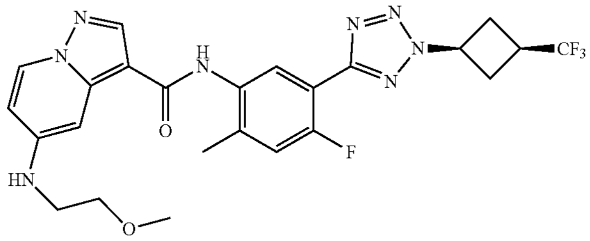 [SMILES: COCCNc1ccn2ncc(C(=O)Nc3cc(-c4nnn([C@H]5C[C@@H](C(F)(F)F)C5)n4)c(F)cc3C)c2c1] | 18 |
| 109 | N-(4-fluoro-2-methyl-5-(2-((1s,3s)-3-(trifluoromethyl)cyclobutyl)-2H-tetrazol-5-yl)phenyl)-5-(4-hydroxy-4-methylpiperidin-1-yl)pyrazolo[1,5-a]pyridine-3-carboxamide 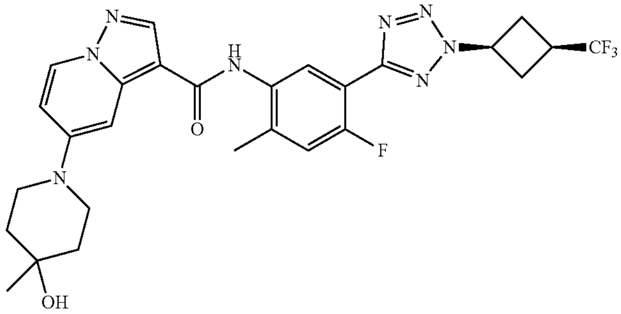 [SMILES: Cc1cc(F)c(-c2nnn([C@H]3C[C@@H](C(F)(F)F)C3)n2)cc1NC(=O)c1cnn2ccc(N3CCC(C)(O)CC3)cc12] | 18 |
| 110 | methyl 3-(2-(3-(5-((2-methoxyethyl)amino)pyrazolo[1,5-a]pyridine-3-carboxamido)-4-methylphenyl)-2H-1,2,3-triazol-4-yl)azetidine-1-carboxylate 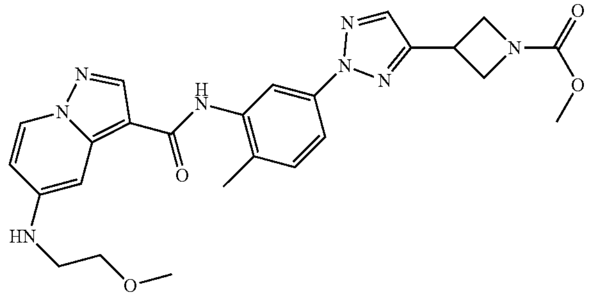 [SMILES: COCCNc1ccn2ncc(C(=O)Nc3cc(-n4ncc(C5CN(C(=O)OC)C5)n4)ccc3C)c2c1] | 18 |
| 111 | methyl 3-(2-(4-chloro-3-(5-((2-methoxyethyl)amino)pyrazolo[1,5-a]pyridine-3-carboxamido)phenyl)-2H-1,2,3-triazol-4-yl)azetidine-1-carboxylate 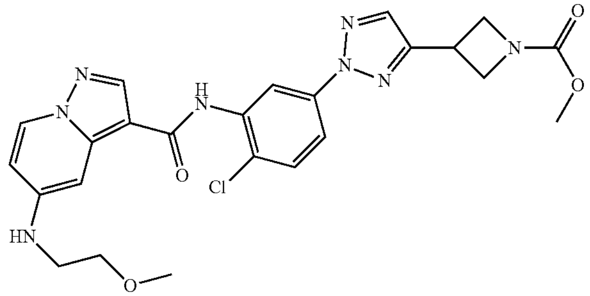 [SMILES: COCCNc1ccn2ncc(C(=O)Nc3cc(-n4ncc(C5CN(C(=O)OC)C5)n4)ccc3Cl)c2c1] | 18 |

TABLE 1-continued

| Compound No | Name, Structure | Scheme |
|---|---|---|
| 112 | methyl 3-(2-(4-methyl-3-(5-(4-methylpiperazin-1-yl)pyrazolo[1,5-a]pyridine-3-carboxamido)phenyl)-2H-tetrazol-5-yl)azetidine-1-carboxylate 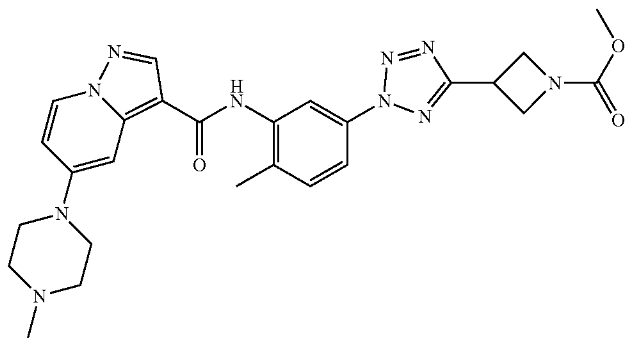 [SMILES: COC(=O)N1CC(c2nnn(-c3ccc(C)c(NC(=O)c4cnn5ccc(N6CCN(C)CC6)cc45)c3)n2)C1] | 18 |
| 113 | methyl 3-(2-(4-chloro-3-(5-((2-methoxyethyl)amino)pyrazolo[1,5-a]pyridine-3-carboxamido)phenyl)-2H-tetrazol-5-yl)azetidine-1-carboxylate 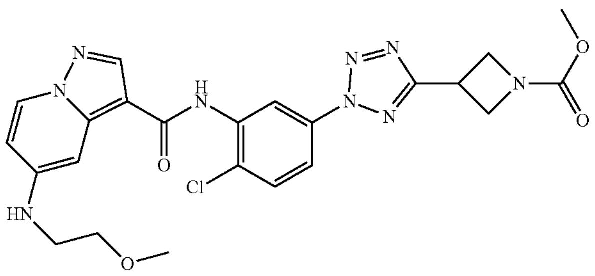 [SMILES: COCCNc1ccn2ncc(C(=O)Nc3cc(-n4nnc(C5CN(C(=O)OC)C5)n4)ccc3Cl)c2c1] | 18 |
| 114 | methyl 3-(5-(2-fluoro-5-(5-((2-methoxyethyl)amino)pyrazolo[1,5-a]pyridine-3-carboxamido)-4-methylphenyl)-2H-tetrazol-2-yl)azetidine-1-carboxylate 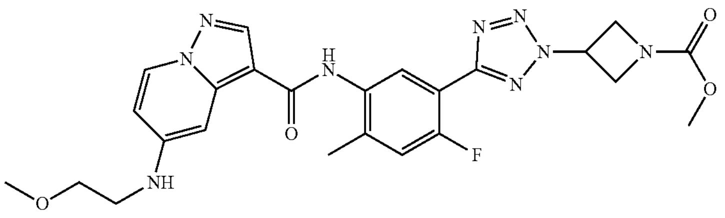 [SMILES: COCCNc1ccn2ncc(C(=O)Nc3cc(-c4nnn(C5CN(C(=O)OC)C5)n4)c(F)cc3C)c2c1] | 18 |
| 115 | methyl 3-(5-(4-fluoro-3-(5-((2-methoxyethyl)amino)pyrazolo[1,5-a]pyridine-3-carboxamido)phenyl)-2H-tetrazol-2-yl)azetidine-1-carboxylate 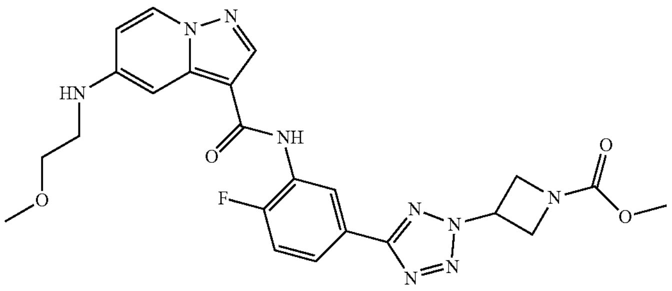 | 18 |
| 116 | 5-((2-methoxyethyl)amino)-N-(2-methyl-5-(2-(4,4,4-trifluorobutyl)-2H-tetrazol-5-yl)phenyl)pyrazolo[1,5-a]pyridine-3-carboxamide | 18 |

TABLE 1-continued

| Compound No | Name, Structure | Scheme |
|---|---|---|
| | 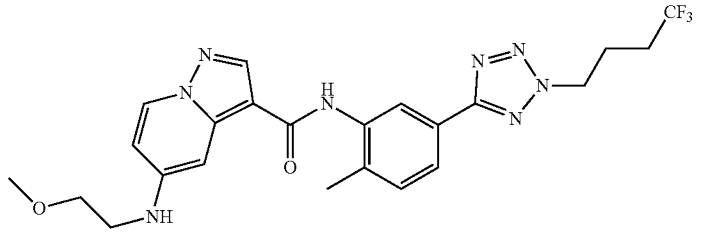 [SMILES: COCCNc1ccn2ncc(C(=O)Nc3cc(-c4nnn(CCCC(F)(F)F)n4)ccc3C)c2c1] | |
| 117 | N-(2-chloro-4-cyclopropyl-5-(2-(3,3-difluorocyclobutyl)-2H-tetrazol-5-yl)phenyl)-5-morpholinopyrazolo[1,5-a]pyridine-3-carboxamide 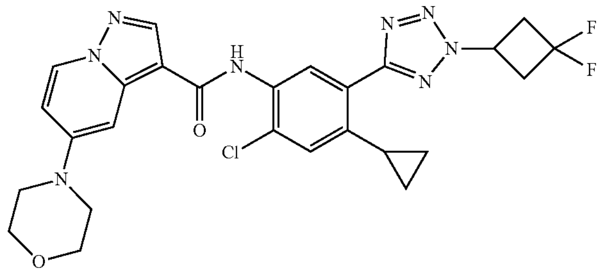 [SMILES: O=C(Nc1cc(-c2nnn(C3CC(F)(F)C3)n2)c(C2CC2)cc1Cl)c1cnn2ccc(N3CCOCC3)cc12] | 18 |
| 118 | methyl 3-(5-(3-(5-((2-methoxyethyl)amino)pyrazolo[1,5-a]pyridine-3-carboxamido)-4-(methyl-d3)phenyl)-2H-tetrazol-2-yl)azetidine-1-carboxylate 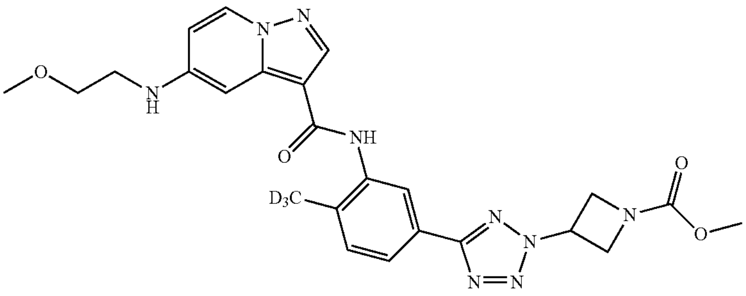 | 18 |
| 119 | 5-((2-methoxyethyl)amino)-N-(2-methyl-5-(2-((1s,3s)-3-(trifluoromethyl)cyclobutyl)-2H-tetrazol-5-yl)phenyl)pyrazolo[1,5-a]pyridine-3-carboxamide or 5-((2-methoxyethyl)amino)-N-(2-methyl-5-(2-((1r,3r)-3-(trifluoromethyl)cyclobutyl)-2H-tetrazol-5-yl)phenyl)pyrazolo[1,5-a]pyridine-3-carboxamide | 18 Isomer 1 |

TABLE 1-continued
| Compound No | Name, Structure | Scheme |
|---|---|---|
| | 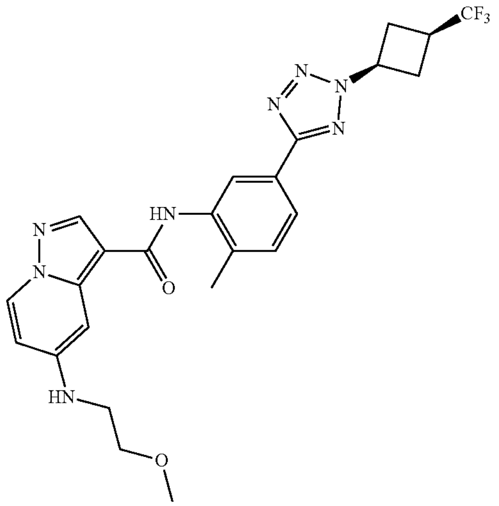 OR | |
| | 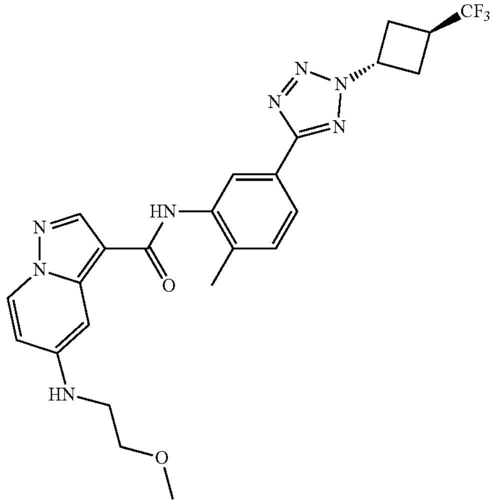 | |
| 120 | 5-((2-hydroxyethyl)amino)-N-(2-methyl-5-(2-((1s,3s)-3-(trifluoromethyl)cyclobutyl)-2H-tetrazol-5-yl)phenyl)pyrazolo[1,5-a]pyridine-3-carboxamide or 5-((2-hydroxyethyl)amino)-N-(2-methyl-5-(2-((1r,3r)-3-(trifluoromethyl)cyclobutyl)-2H-tetrazol-5-yl)phenyl)pyrazolo[1,5-a]pyridine-3-carboxamide | 18 Isomer 1 |
| | 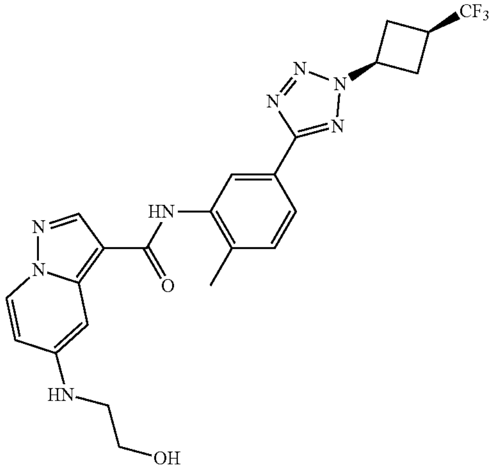 OR | |

TABLE 1-continued
| Compound No | Name, Structure | Scheme |
| --- | --- | --- |
| | 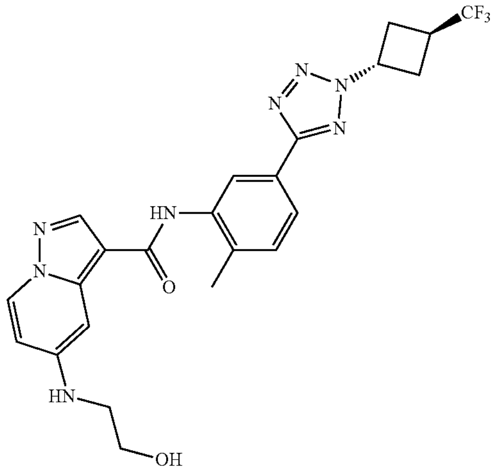 | |
| 121 | 5-((2-hydroxyethyl)amino)-N-(2-methyl-5-(2-((1r,3r)-3-(trifluoromethyl)cyclobutyl)-2H-tetrazol-5-yl)phenyl)pyrazolo[1,5-a]pyridine-3-carboxamide or 5-((2-hydroxyethyl)amino)-N-(2-methyl-5-(2-((1s,3s)-3-(trifluoromethyl)cyclobutyl)-2H-tetrazol-5-yl)phenyl)pyrazolo[1,5-a]pyridine-3-carboxamide CF3 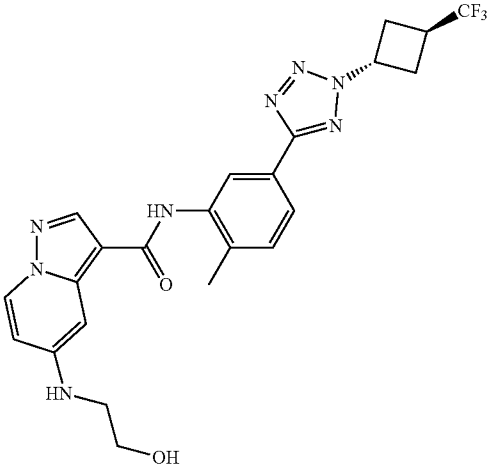 [SMILES: Cc1ccc(-c2nnn([C@H]3C[C@H](C(F)(F)F)C3)n2)cc1NC(=O)c1cnn2ccc(NCCO)cc12] OR 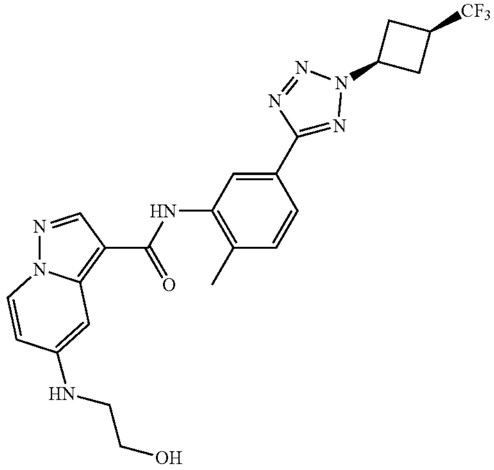 [SMILES: Cc1ccc(-c2nnn([C@H]3C[C@@H](C(F)(F)F)C3)n2)cc1NC(=O)c1cnn2ccc(NCCO)cc12] | 18 Isomer 2 |

TABLE 1-continued

| Compound No | Name, Structure | Scheme |
|---|---|---|
| 122 | 5-(4-hydroxy-4-methylpiperidin-1-yl)-N-(2-methyl-5-(2-((1s,3s)-3-(trifluoromethyl)cyclobutyl)-2H-tetrazol-5-yl)phenyl)pyrazolo[1,5-a]pyridine-3-carboxamide or 5-(4-hydroxy-4-methylpiperidin-1-yl)-N-(2-methyl-5-(2-((1r,3r)-3-(trifluoromethyl)cyclobutyl)-2H-tetrazol-5-yl)phenyl)pyrazolo[1,5-a]pyridine-3-carboxamide 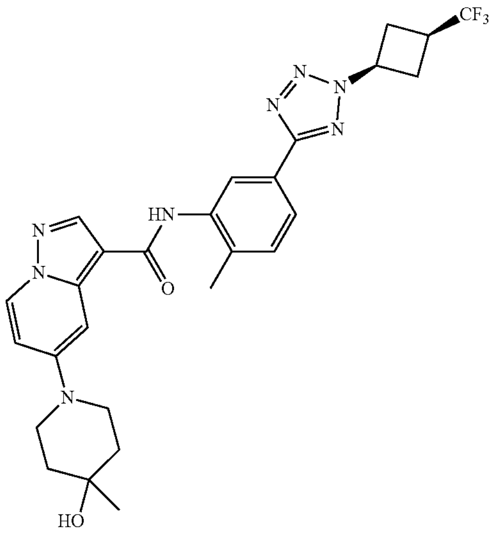 OR 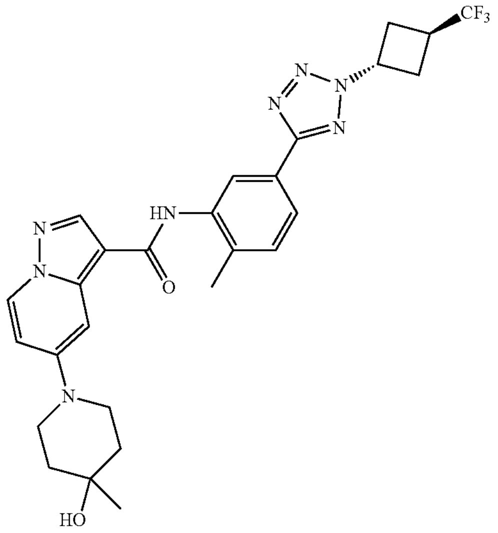 [SMILES: Cc1ccc(-c2nnn([C@H]3C[C@H](C(F)(F)F)C3)n2)cc1NC(=O)c1cnn2ccc(N3CCC(C)(O)CC3)cc12] | 18 Isomer 1 |
| 123 | (S)-N-(5-(2-((2,2-difluorocyclopropyl)methyl)-2H-tetrazol-5-yl)-2-methylphenyl)-5-((2-methoxyethyl)amino)pyrazolo[1,5-a]pyridine-3-carboxamide or (R)-N-(5-(2-((2,2-difluorocyclopropyl)methyl)-2H-tetrazol-5-yl)-2-methylphenyl)-5-((2-methoxyethyl)amino)pyrazolo[1,5-a]pyridine-3-carboxamide | 18 Isomer 1 |

TABLE 1-continued
| Compound No | Name, Structure | Scheme |
|---|---|---|
| | 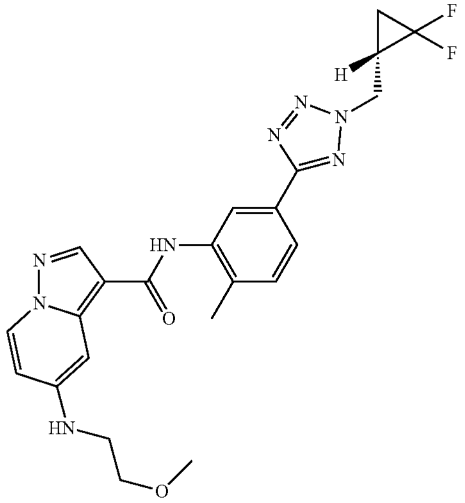 Or 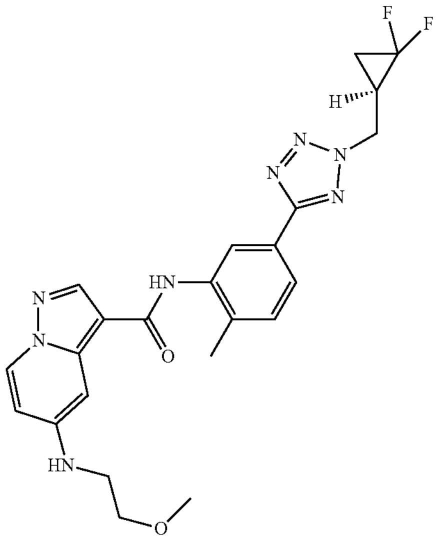 [SMILES: COCCNc1ccn2ncc(C(=O)Nc3cc(-c4nnn(C[C@H]5CC5(F)F)n4)ccc3C)c2c1] | |
| 124 | (R)-N-(5-(2-((2,2-difluorocyclopropyl)methyl)-2H-tetrazol-5-yl)-2-methylphenyl)-5-((2-methoxyethyl)amino)pyrazolo[1,5-a]pyridine-3-carboxamide or (S)-N-(5-(2-((2,2-difluorocyclopropyl)methyl)-2H-tetrazol-5-yl)-2-methylphenyl)-5-((2-methoxyethyl)amino)pyrazolo[1,5-a]pyridine-3-carboxamide | 18 |

TABLE 1-continued
| Compound No | Name, Structure | Scheme |
|---|---|---|
| | 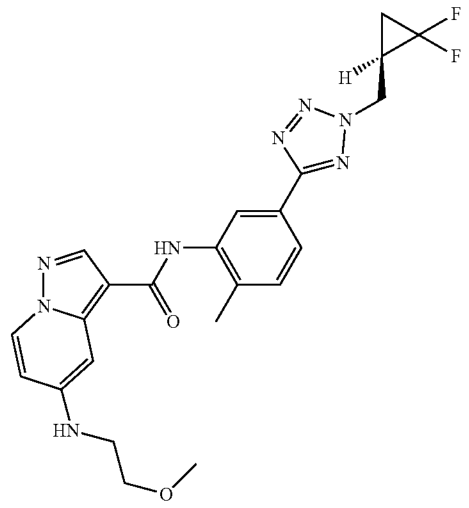 Or | |
| | 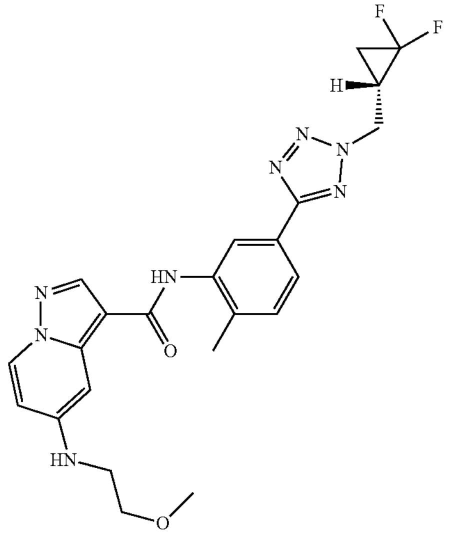 [SMILES: COCCNc1ccn2ncc(C(=O)Nc3cc(-c4nnn(C[C@@H]5CC5(F)F)n4)ccc3C)c2c1] | |
| 125 | methyl 3-(2-(3-(5-((2-methoxyethyl)amino)pyrazolo[1,5-a]pyridine-3-carboxamido)-4-methylphenyl)-2H-tetrazol-5-yl)azetidine-1-carboxylate 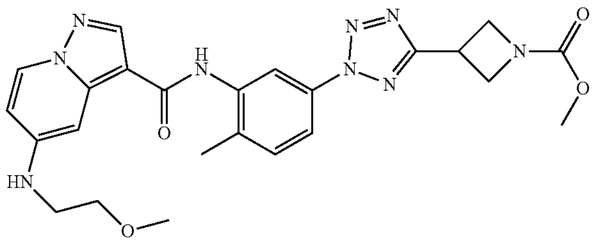 [SMILES: COCCNc1ccn2ncc(C(=O)Nc3cc(-n4nnc(C5CN(C(=O)OC)C5)n4)ccc3C)c2c1] | 18 |
| 126 | ethyl 3-(5-(4-methyl-3-(5-(methylamino)pyrazolo[1,5-a]pyridine-3-carboxamido)phenyl)-2H-tetrazol-2-yl)azetidine-1-carboxylate | 18 |

TABLE 1-continued

| Compound No | Name, Structure | Scheme |
|---|---|---|
| | 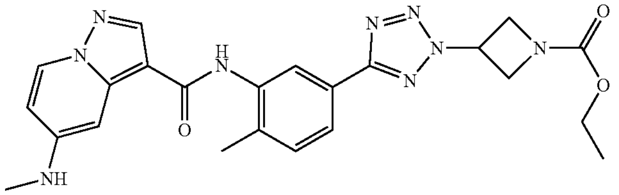 | |
| 127 | methyl 3-(5-(3-(5-(ethylamino)pyrazolo[1,5-a]pyridine-3-carboxamido)-4-methylphenyl)-2H-tetrazol-2-yl)azetidine-1-carboxylate 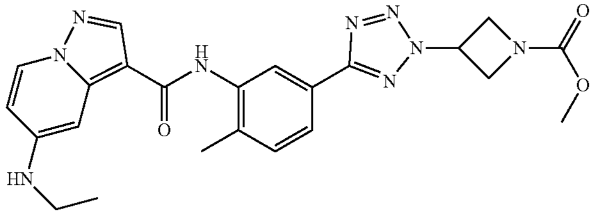 [SMILES: CCNc1ccn2ncc(C(=O)Nc3cc(-c4nnn(C5CN(C(=O)OC)C5)n4)ccc3C)c2c1] | 18 |
| 128 | methyl (S)-3-(5-(3-(5-((1-methoxypropan-2-yl)amino)pyrazolo[1,5-a]pyridine-3-carboxamido)-4-methylphenyl)-2H-tetrazol-2-yl)azetidine-1-carboxylate 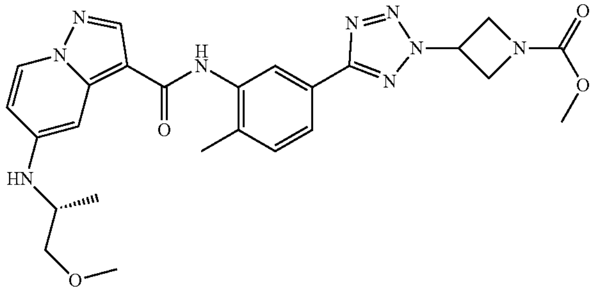 [SMILES: COC[C@@H](C)Nc1ccn2ncc(C(=O)Nc3cc(-c4nnn(C5CN(C(=O)OC)C5)n4)ccc3C)c2c1] | 18 |
| 129 | methyl (R)-3-(5-(4-methyl-3-(5-((tetrahydrofuran-3-yl)amino)pyrazolo[1,5-a]pyridine-3-carboxamido)phenyl)-2H-tetrazol-2-yl)azetidine-1-carboxylate 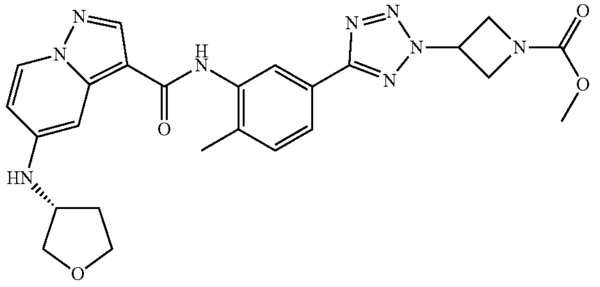 [SMILES: COC(=O)N1CC(n2nnc(-c3ccc(C)c(NC(=O)c4cnn5ccc(N[C@@H]6CCOC6)cc45)c3)n2)C1] | 18 |
| 130 | ethyl 3-(5-(3-(5-(ethylamino)pyrazolo[1,5-a]pyridine-3-carboxamido)-4-methylphenyl)-2H-tetrazol-2-yl)azetidine-1-carboxylate 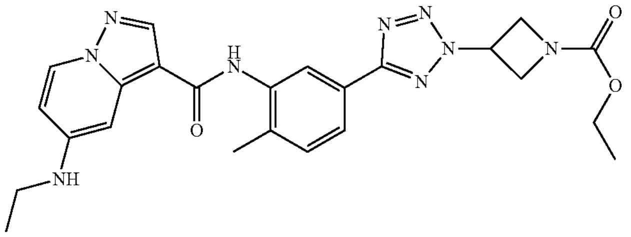 [SMILES: CCNc1ccn2ncc(C(=O)Nc3cc(-c4nnn(C5CN(C(=O)OCC)C5)n4)ccc3C)c2c1] | 18 |

TABLE 1-continued

| Compound No | Name, Structure | Scheme |
|---|---|---|
| 131 | methyl 3-(5-(3-(5-((2,2-difluoroethyl)amino)pyrazolo[1,5-a]pyridine-3-carboxamido)-4-methylphenyl)-2H-tetrazol-2-yl)azetidine-1-carboxylate 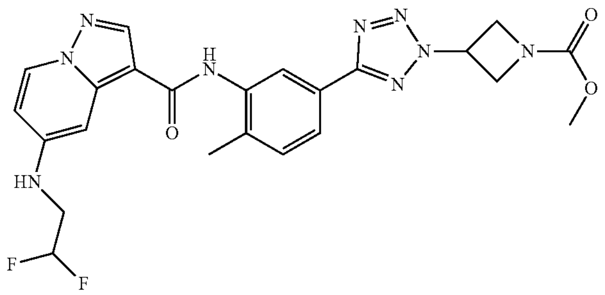 [SMILES: COC(=O)N1CC(n2nnc(-c3ccc(C)c(NC(=O)c4cnn5ccc(NCC(F)F)cc45)c3)n2)C1] | 18 |
| 132 | methyl 3-(5-(3-(5-(dimethylamino)pyrazolo[1,5-a]pyridine-3-carboxamido)-4-methylphenyl)-2H-tetrazol-2-yl)azetidine-1-carboxylate 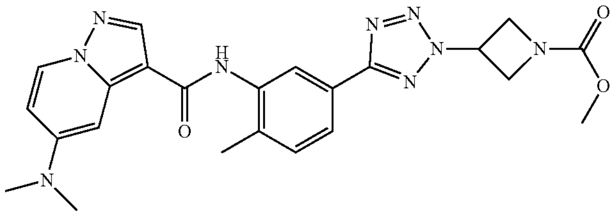 [SMILES: COC(=O)N1CC(n2nnc(-c3ccc(C)c(NC(=O)c4cnn5ccc(N(C)C)cc45)c3)n2)C1] | 18 |
| 133 | methyl 3-(5-(4-methyl-3-(5-(methylamino)pyrazolo[1,5-a]pyridine-3-carboxamido)phenyl)-2H-tetrazol-2-yl)azetidine-1-carboxylate 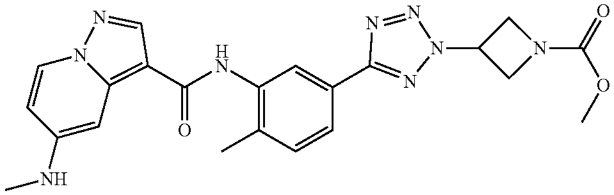 [SMILES: CNc1ccn2ncc(C(=O)Nc3cc(-c4nnn(C5CN(C(=O)OC)C5)n4)ccc3C)c2c1] | 18 |
| 134 | methyl (S)-3-(5-(3-(5-((2-methoxypropyl)amino)pyrazolo[1,5-a]pyridine-3-carboxamido)-4-methylphenyl)-2H-tetrazol-2-yl)azetidine-1-carboxylate 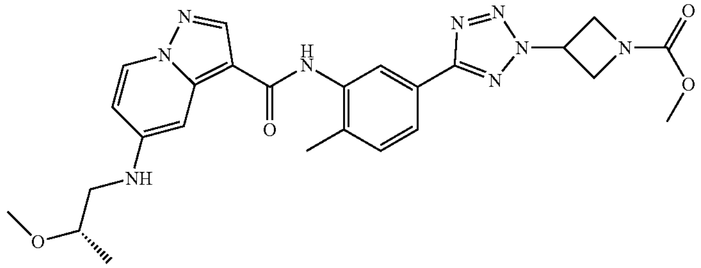 [SMILES: COC(=O)N1CC(n2nnc(-c3ccc(C)c(NC(=O)c4cnn5ccc(NC[C@H](C)OC)cc45)c3)n2)C1] | 18 |
| 135 | methyl (R)-3-(5-(3-(5-((1-methoxypropan-2-yl)amino)pyrazolo[1,5-a]pyridine-3-carboxamido)-4-methylphenyl)-2H-tetrazol-2-yl)azetidine-1-carboxylate | 18 |

TABLE 1-continued

| Compound No | Name, Structure | Scheme |
| --- | --- | --- |
| | 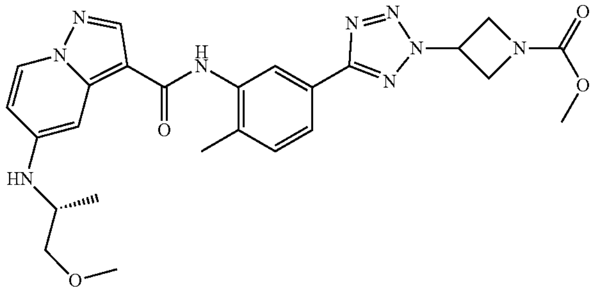 [SMILES: COC[C@@H](C)Nc1ccn2ncc(C(=O)Nc3cc(-c4nnn(C5CN(C(=O)OC)C5)n4)ccc3C)c2c1] | |
| 136 | methyl (S)-3-(5-(4-methyl-3-(5-((tetrahydrofuran-3-yl)amino)pyrazolo[1,5-a]pyridine-3-carboxamido)phenyl)-2H-tetrazol-2-yl)azetidine-1-carboxylate | 18 |
| | 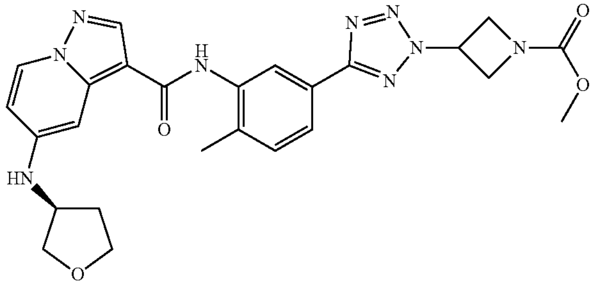 [SMILES: COC(=O)N1CC(n2nnc(-c3ccc(C)c(NC(=O)c4cnn5ccc(N[C@H]6CCOC6)cc45)c3)n2)C1] | |
| 137 | methyl 3-(2-(3-(5-(ethylamino)pyrazolo[1,5-a]pyridine-3-carboxamido)-4-methylphenyl)-2H-1,2,3-triazol-4-yl)azetidine-1-carboxylate | 18 |
| | 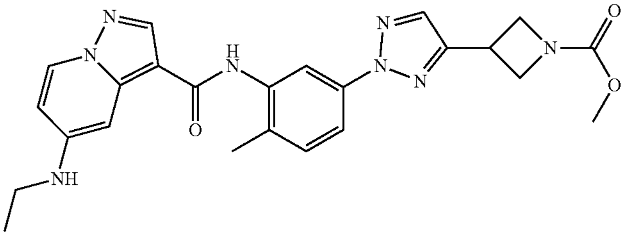 [SMILES: CCNc1ccn2ncc(C(=O)Nc3cc(-n4ncc(C5CN(C(=O)OC)C5)n4)ccc3C)c2c1] | |
| 138 | methyl 3-(2-(4-methyl-3-(5-(methylamino)pyrazolo[1,5-a]pyridine-3-carboxamido)phenyl)-2H-1,2,3-triazol-4-yl)azetidine-1-carboxylate | 18 |
| | 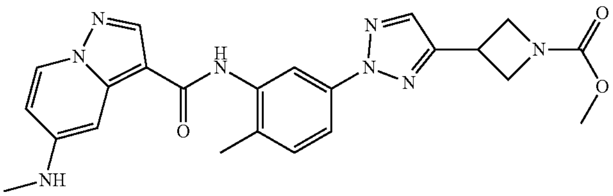 [SMILES: CNc1ccn2ncc(C(=O)Nc3cc(-n4ncc(C5CN(C(=O)OC)C5)n4)ccc3C)c2c1] | |
| 139 | methyl 3-(2-(3-(5-((2,2-difluoroethyl)amino)pyrazolo[1,5-a]pyridine-3-carboxamido)-4-methylphenyl)-2H-1,2,3-triazol-4-yl)azetidine-1-carboxylate | 18 |

TABLE 1-continued

| Compound No | Name, Structure | Scheme |
|---|---|---|
| | 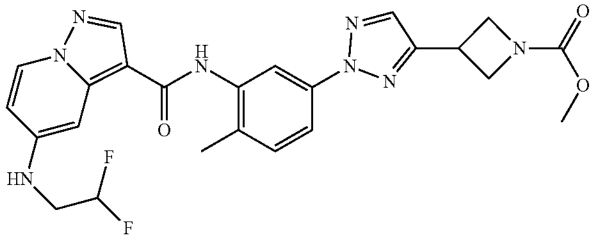 [SMILES: COC(=O)N1CC(c2cnn(-c3ccc(C)c(NC(=O)c4cnn5ccc(NCC(F)F)cc45)c3)n2)C1] | |
| 140 | methyl 3-(2-(4-methyl-3-(5-((oxetan-3-ylmethyl)amino)pyrazolo[1,5-a]pyridine-3-carboxamido)phenyl)-2H-1,2,3-triazol-4-yl)azetidine-1-carboxylate<br>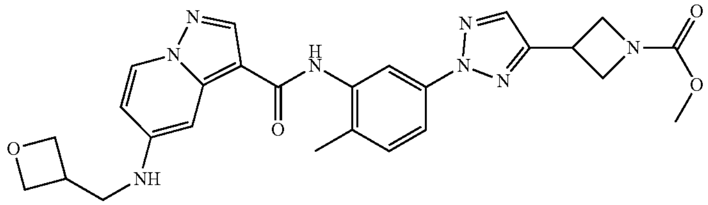 [SMILES: COC(=O)N1CC(c2cnn(-c3ccc(C)c(NC(=O)c4cnn5ccc(NCC6COC6)cc45)c3)n2)C1] | 18 |
| 141 | methyl 3-(2-(4-methyl-3-(5-(oxetan-3-ylamino)pyrazolo[1,5-a]pyridine-3-carboxamido)phenyl)-2H-1,2,3-triazol-4-yl)azetidine-1-carboxylate<br>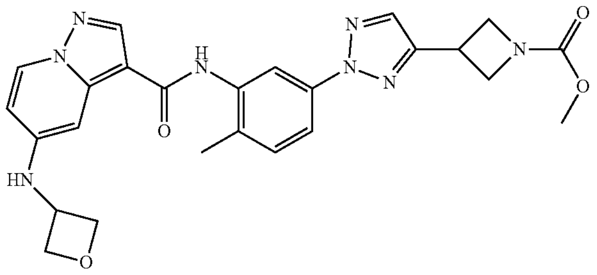 [SMILES: COC(=O)N1CC(c2cnn(-c3ccc(C)c(NC(=O)c4cnn5ccc(NC6COC6)cc45)c3)n2)C1] | 18 |
| 142 | methyl 3-(5-(3-(5-((2-hydroxyethyl)amino)pyrazolo[1,5-a]pyridine-3-carboxamido)-4-methylphenyl)-2H-tetrazol-2-yl)azetidine-1-carboxylate<br>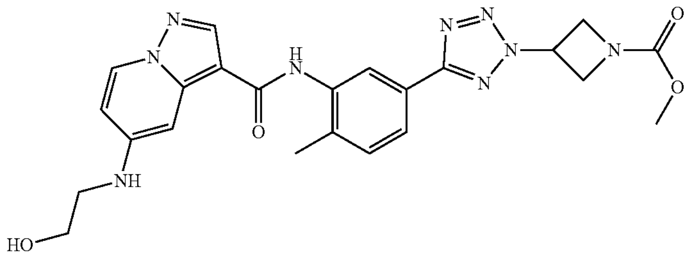 [SMILES: COC(=O)N1CC(n2nnc(-c3ccc(C)c(NC(=O)c4cnn5ccc(NCCO)cc45)c3)n2)C1] | 18 |
| 143 | methyl 3-(5-(3-(6-(2-methoxyethoxy)pyrazolo[1,5-a]pyridine-3-carboxamido)-4-methylphenyl)-2H-tetrazol-2-yl)azetidine-1-carboxylate<br>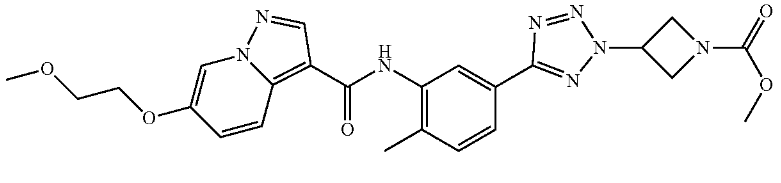 [SMILES: COCCOc1ccc2c(C(=O)Nc3cc(-c4nnn(C5CN(C(=O)OC)C5)n4)ccc3C)cnn2c1] | 18 |
| 144 | methyl 3-(5-(3-(5-((2-methoxyethyl)amino)-6-methylpyrazolo[1,5-a]pyridine-3-carboxamido)-4-methylphenyl)-2H-tetrazol-2-yl)azetidine-1-carboxylate | 16 |

TABLE 1-continued

| Compound No | Name, Structure | Scheme |
| --- | --- | --- |
| | 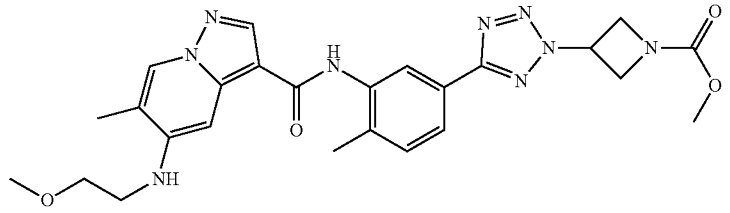 [SMILES: COCCNc1cc2c(C(=O)Nc3cc(-c4nnn(C5CN(C(=O)OC)C5)n4)ccc3C)cnn2cc1C] | |
| 145 | methyl 3-(5-(3-(6-chloro-5-((2-methoxyethyl)amino)pyrazolo[1,5-a]pyridine-3-carboxamido)-4-methylphenyl)-2H-tetrazol-2-yl)azetidine-1-carboxylate | 19 |
| | 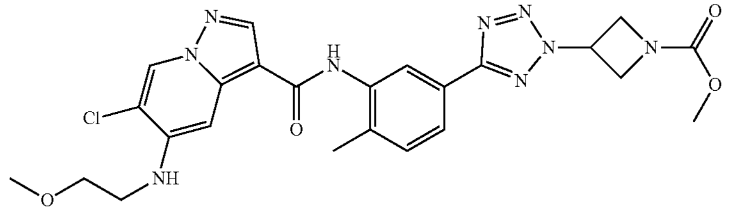 [SMILES: COCCNc1cc2c(C(=O)Nc3cc(-c4nnn(C5CN(C(=O)OC)C5)n4)ccc3C)cnn2cc1Cl] | |
| 146 | methyl 3-(5-(3-(5-((2-(2-methoxyethoxy)ethyl)amino)pyrazolo[1,5-a]pyridine-3-carboxamido)-4-methylphenyl)-2H-tetrazol-2-yl)azetidine-1-carboxylate | 18 |
| | 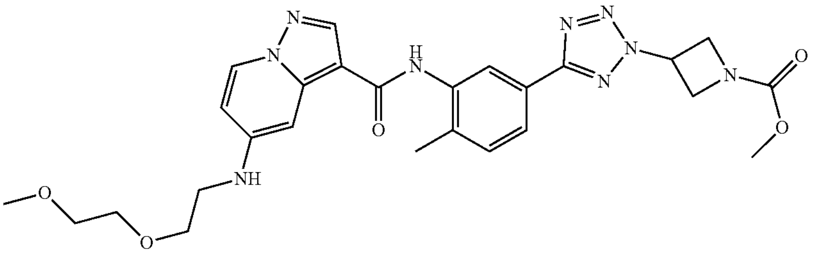 [SMILES: COCCOCCNc1ccn2ncc(C(=O)Nc3cc(-c4nnn(C5CN(C(=O)OC)C5)n4)ccc3C)c2c1] | |
| 147 | methyl 3-(5-(3-(5-(4,4-difluoropiperidin-1-yl)pyrazolo[1,5-a]pyridine-3-carboxamido)-4-methylphenyl)-2H-tetrazol-2-yl)azetidine-1-carboxylate | 18 |
| | 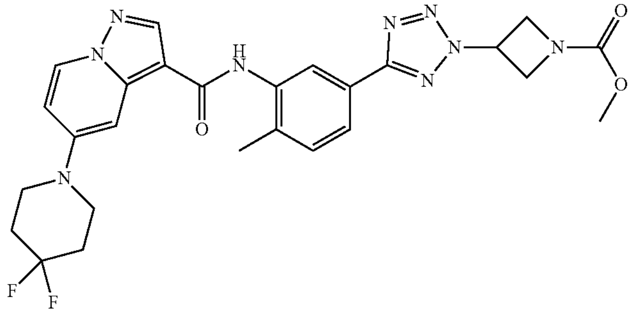 [SMILES: COC(=O)N1CC(n2nnc(-c3ccc(C)c(NC(=O)c4cnn5ccc(N6CCC(F)(F)CC6)cc45)c3)n2)C1] | |
| 148 | methyl 3-(5-(3-(5-((2-methoxyethyl)amino)pyrazolo[1,5-a]pyridine-3-carboxamido)-4-methylphenyl)-2H-tetrazol-2-yl)azetidine-1-carboxylate | 19 |

TABLE 1-continued

| Compound No | Name, Structure | Scheme |
|---|---|---|
| | 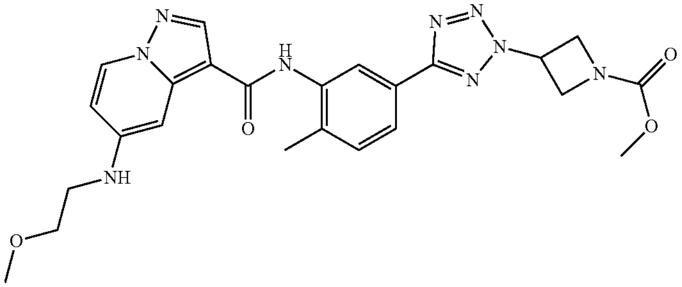 [SMILES: COCCNc1ccn2ncc(C(=O)Nc3cc(-c4nnn(C5CN(C(=O)OC)C5)n4)ccc3C)c2c1] | |
| 149 | ethyl 3-(5-(3-(5-((2-methoxyethyl)amino)pyrazolo[1,5-a]pyridine-3-carboxamido)-4-methylphenyl)-2H-tetrazol-2-yl)azetidine-1-carboxylate | 19 |
| | 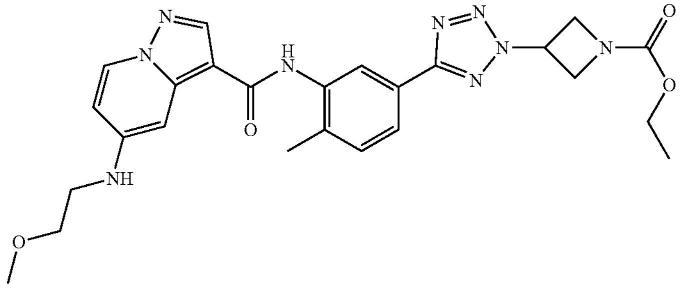 [SMILES: CCOC(=O)N1CC(n2nnc(-c3ccc(C)c(NC(=O)c4cnn5ccc(NCCOC)cc45)c3)n2)C1] | |
| 150 | 5-((2-methoxyethyl)amino)-N-(2-methyl-5-(2-(spiro[3.3]heptan-2-yl)-2H-tetrazol-5-yl)phenyl)pyrazolo[1,5-a]pyridine-3-carboxamide | 19 |
| | 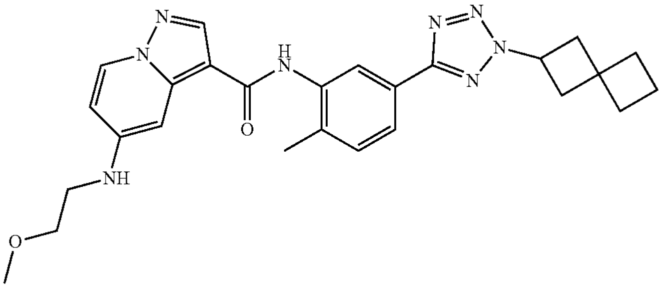 [SMILES: COCCNc1ccn2ncc(C(=O)Nc3cc(-c4nnn(C5CC6(CCC6)C5)n4)ccc3C)c2c1] | |
| 151 | N-(5-(2-(3-fluorocyclobutyl)-2H-tetrazol-5-yl)-2-methylphenyl)-5-((2-methoxyethyl)amino)pyrazolo[1,5-a]pyridine-3-carboxamide | 19 |
| | 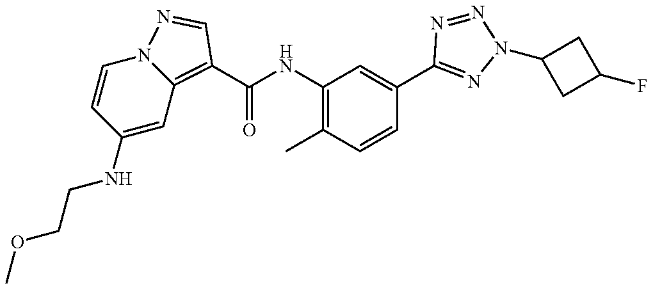 [SMILES: COCCNc1ccn2ncc(C(=O)Nc3cc(-c4nnn(C5CC(F)C5)n4)ccc3C)c2c1] | |
| 152 | N-(5-(5-cyclopropyl-2H-tetrazol-2-yl)-2-methylphenyl)pyrazolo[1,5-a]pyridine-3-carboxamide | 19 |

TABLE 1-continued

| Compound No | Name, Structure | Scheme |
|---|---|---|
| | 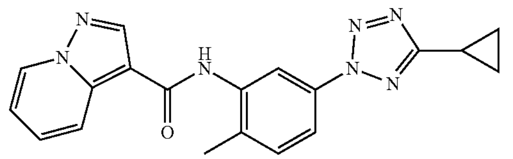 [SMILES: Cc1ccc(-n2nnc(C3CC3)n2)cc1NC(=O)c1cnn2ccccc12] | |
| 153 | 5-methoxy-N-(2-methyl-5-(2-(1-(methylsulfonyl)azetidin-3-yl)-2H-tetrazol-5-yl)phenyl)pyrazolo[1,5-a]pyridine-3-carboxamide 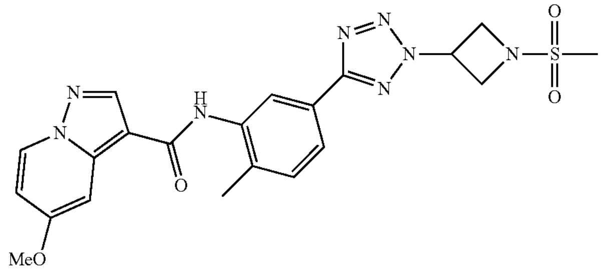 [SMILES: COc1ccn2ncc(C(=O)Nc3cc(-c4nnn(C5CN(S(C)(=O)=O)C5)n4)ccc3C)c2c1] | 19 |
| 154 | 5-((2,2-difluoroethoxy)methyl)-N-(2-methyl-5-(2-(1-(methylsulfonyl)azetidin-3-yl)-2H-tetrazol-5-yl)phenyl)pyrazolo[1,5-a]pyridine-3-carboxamide 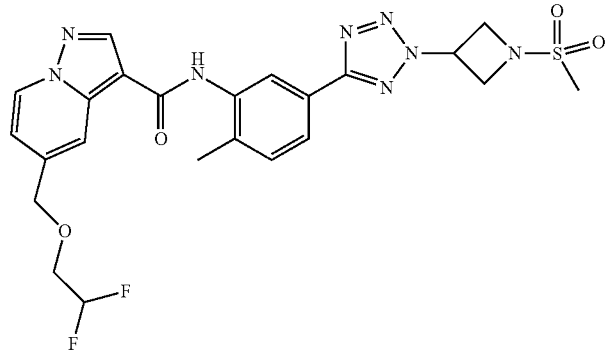 [SMILES: Cc1ccc(-c2nnn(C3CN(S(C)(=O)=O)C3)n2)cc1NC(=O)c1cnn2ccc(COCC(F)F)cc12] | 19 |
| 155 | 5-(3-hydroxy-3-methylbutyl)-N-(2-methyl-5-(2-(1-(methylsulfonyl)azetidin-3-yl)-2H-tetrazol-5-yl)phenyl)pyrazolo[1,5-a]pyridine-3-carboxamide 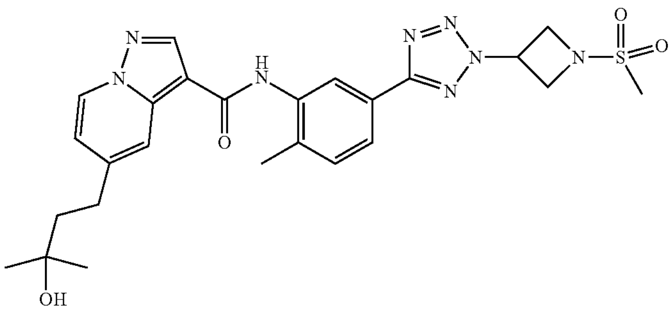 [SMILES: Cc1ccc(-c2nnn(C3CN(S(C)(=O)=O)C3)n2)cc1NC(=O)c1cnn2ccc(CCC(C)(C)O)cc12] | 19 |
| 156 | N-(5-(2-(3,3-difluorocyclobutyl)-2H-tetrazol-5-yl)-2,4-dimethylphenyl)-5-morpholinopyrazolo[1,5-a]pyridine-3-carboxamide | 19 |

TABLE 1-continued

| Compound No | Name, Structure | Scheme |
|---|---|---|
| | 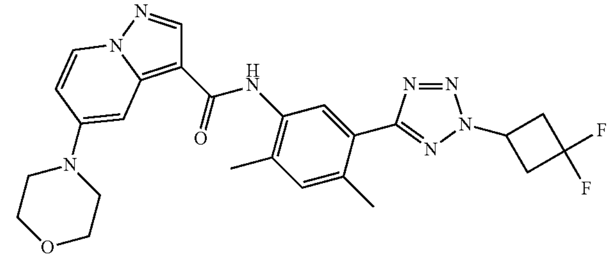 [SMILES: Cc1cc(C)c(-c2nnn(C3CC(F)(F)C3)n2)cc1NC(=O)c1cnn2ccc(N3CCOCC3)cc12] | |
| 157 | methyl 3-(5-(4-chloro-3-(6-((2-methoxyethyl)amino)pyrazolo[1,5-a]pyridine-3-carboxamido)phenyl)-2H-tetrazol-2-yl)azetidine-1-carboxylate 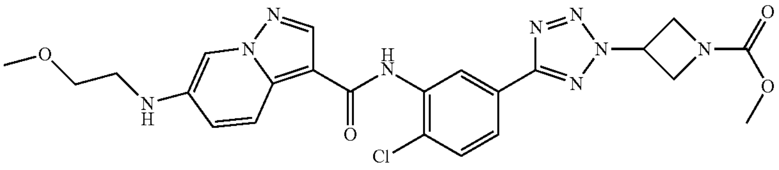 [SMILES: COCCNc1ccc2c(C(=O)Nc3cc(-c4nnn(C5CN(C(=O)OC)C5)n4)ccc3Cl)cnn2c1] | 19 |
| 158 | N-(2-methyl-5-(2-(2-(2,2,2-trifluoroethoxy)ethyl)-2H-tetrazol-5-yl)phenyl)pyrazolo[1,5-a]pyridine-3-carboxamide 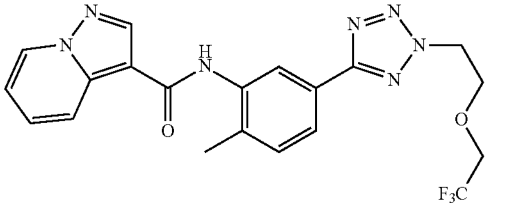 [SMILES: Cc1ccc(-c2nnn(CCOCC(F)(F)F)n2)cc1NC(=O)c1cnn2ccccc12] | 19 |
| 159 | methyl 3-(5-(4-methyl-3-(6-morpholinopyrazolo[1,5-a]pyridine-3-carboxamido)phenyl)-2H-tetrazol-2-yl)azetidine-1-carboxylate 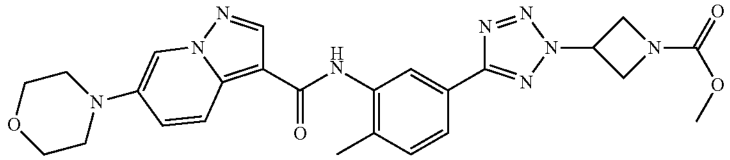 [SMILES: COC(=O)N1CC(n2nnc(-c3ccc(C)c(NC(=O)c4cnn5cc(N6CCOCC6)ccc45)c3)n2)C1] | 19 |
| 160 | methyl 3-(2-(4-methyl-3-(6-morpholinopyrazolo[1,5-a]pyridine-3-carboxamido)phenyl)-2H-1,2,3-triazol-4-yl)azetidine-1-carboxylate 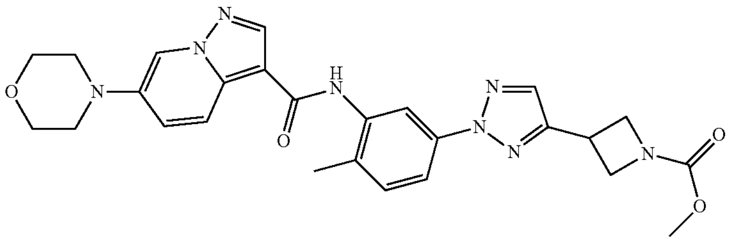 [SMILES: COC(=O)N1CC(c2cnn(-c3ccc(C)c(NC(=O)c4cnn5cc(N6CCOCC6)ccc45)c3)n2)C1] | 19 |
| 161 | N-(5-(4-(3,3-difluorocyclobutyl)-2H-1,2,3-triazol-2-yl)-2-methylphenyl)pyrazolo[1,5-a]pyridine-3-carboxamide | 19 |

TABLE 1-continued

| Compound No | Name, Structure | Scheme |
|---|---|---|
| | 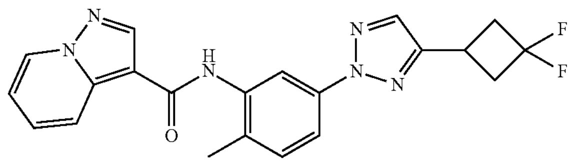 [SMILES: Cc1ccc(-n2ncc(C3CC(F)(F)C3)n2)cc1NC(=O)c1cnn2ccccc12] | |
| 162 | methyl 3-(5-(3-(5-((2,2-difluoroethoxy)methyl)pyrazolo[1,5-a]pyridine-3-carboxamido)-4-methylphenyl)-2H-tetrazol-2-yl)azetidine-1-carboxylate | 19 |
| | 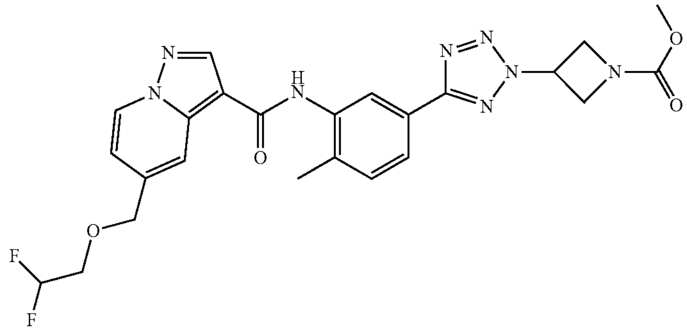 [SMILES: COC(=O)N1CC(n2nnc(-c3ccc(C)c(NC(=O)c4cnn5ccc(COCC(F)F)cc45)c3)n2)C1] | |
| 163 | methyl 3-(5-(4-chloro-3-(6-morpholinopyrazolo[1,5-a]pyridine-3-carboxamido)phenyl)-2H-tetrazol-2-yl)azetidine-1-carboxylate | 19 |
| | 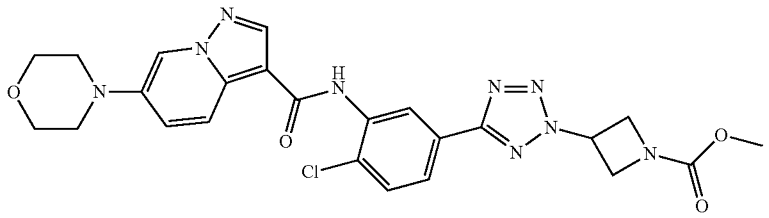 [SMILES: COC(=O)N1CC(n2nnc(-c3ccc(Cl)c(NC(=O)c4cnn5cc(N6CCOCC6)ccc45)c3)n2)C1] | |
| 164 | Methyl 3-(5-(4-chloro-3-(6-((2-methoxyethyl)amino)pyrazolo[1,5-a]pyridine-3-carboxamido)phenyl)-2H-tetrazol-2-yl)azetidine-1-carboxylate | 19 |
| | 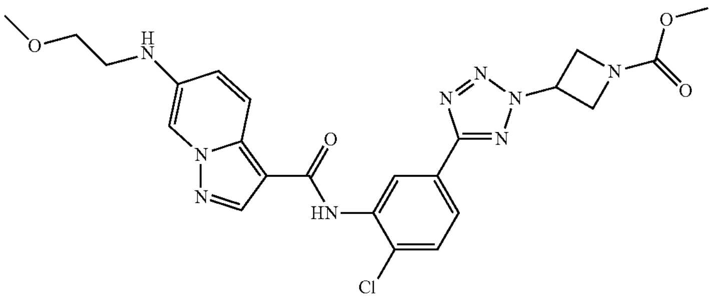 | |
| 165 | N-(4-cyano-5-(2-(3,3-difluorocyclobutyl)-2H-tetrazol-5-yl)-2-methylphenyl)-5-morpholinopyrazolo[1,5-a]pyridine-3-carboxamide | 19 |

TABLE 1-continued

| Compound No | Name, Structure | Scheme |
| --- | --- | --- |
| | 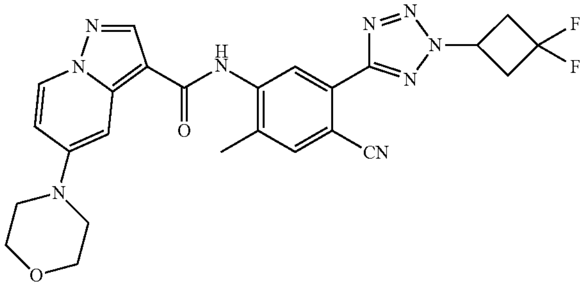 [SMILES: Cc1cc(C#N)c(-c2nnn(C3CC(F)(F)C3)n2)cc1NC(=O)c1cnn2ccc(N3CCOCC3)cc12] | |
| 166 | N-(4-cyclopropyl-5-(2-(3,3-difluorocyclobutyl)-2H-tetrazol-5-yl)-2-methylphenyl)-5-morpholinopyrazolo[1,5-a]pyridine-3-carboxamide 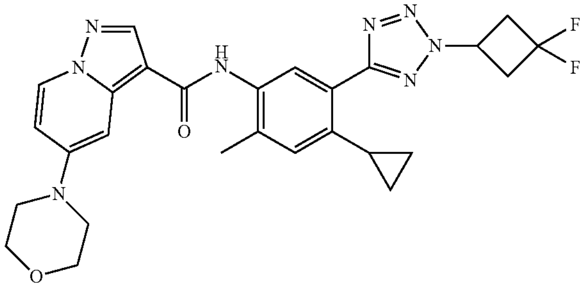 [SMILES: Cc1cc(C2CC2)c(-c2nnn(C3CC(F)(F)C3)n2)cc1NC(=O)c1cnn2ccc(N3CCOCC3)cc12] | 19 |
| 167 | N-(2,4-dichloro-5-(2-(3,3-difluorocyclobutyl)-2H-tetrazol-5-yl)phenyl)-5-morpholinopyrazolo[1,5-a]pyridine-3-carboxamide 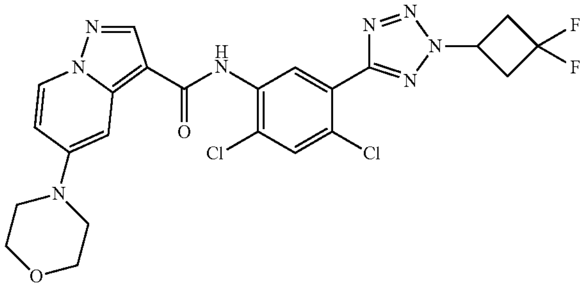 [SMILES: O=C(Nc1cc(-c2nnn(C3CC(F)(F)C3)n2)c(Cl)cc1Cl)c1cnn2ccc(N3CCOCC3)cc12] | 19 |
| 168 | N-(4-chloro-5-(2-(3,3-difluorocyclobutyl)-2H-tetrazol-5-yl)-2-methylphenyl)-5-morpholinopyrazolo[1,5-a]pyridine-3-carboxamide 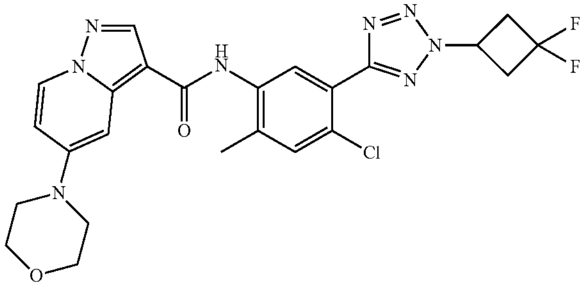 [SMILES: Cc1cc(Cl)c(-c2nnn(C3CC(F)(F)C3)n2)cc1NC(=O)c1cnn2ccc(N3CCOCC3)cc12] | 19 |
| 169 | N-(2-chloro-5-(2-(3,3-difluorocyclobutyl)-2H-tetrazol-5-yl)phenyl)-5-morpholinopyrazolo[1,5-a]pyridine-3-carboxamide | 19 |

TABLE 1-continued

| Compound No | Name, Structure | Scheme |
| --- | --- | --- |
| | 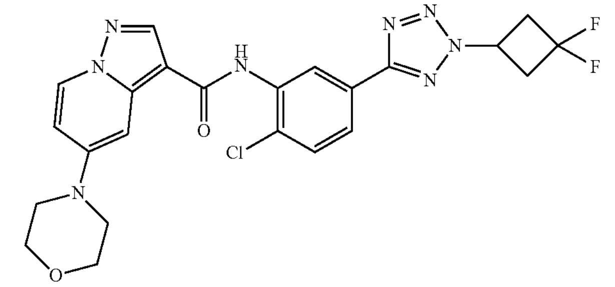 [SMILES: O=C(Nc1cc(-c2nnn(C3CC(F)(F)C3)n2)ccc1Cl)c1cnn2ccc(N3CCOCC3)cc12] | |
| 170 | N-(2-chloro-5-(2-(3,3-difluorocyclobutyl)-2H-tetrazol-5-yl)-4-methylphenyl)-5-morpholinopyrazolo[1,5-a]pyridine-3-carboxamide | 19 |
| | 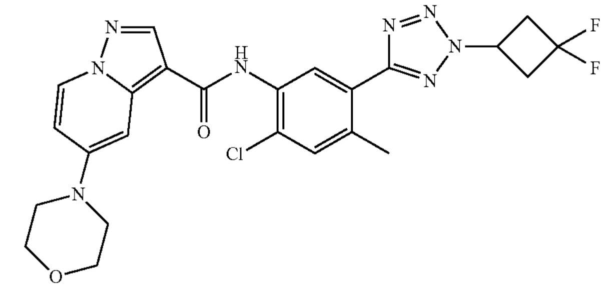 [SMILES: Cc1cc(Cl)c(NC(=O)c2cnn3ccc(N4CCOCC4)cc23)cc1-c1nnn(C2CC(F)(F)C2)n1] | |
| 171 | methyl 3-(5-(3-(6-fluoro-5-((2-methoxyethyl)amino)pyrazolo[1,5-a]pyridine-3-carboxamido)-4-methylphenyl)-2H-tetrazol-2-yl)azetidine-1-carboxylate | 19 |
| | 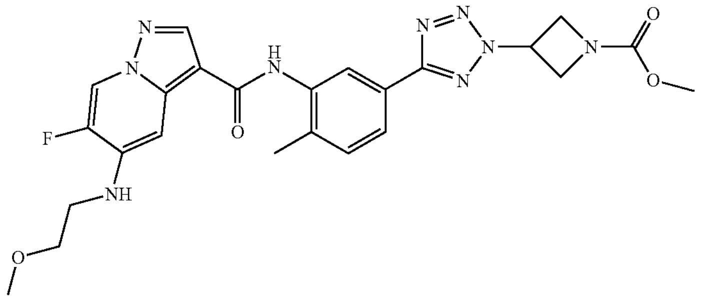 | |
| 172 | N-(2-methyl-5-(2-(1-(methylsulfonyl)azetidin-3-yl)-2H-tetrazol-5-yl)phenyl)pyrazolo[1,5-a]pyridine-3-carboxamide | 20 |
| | 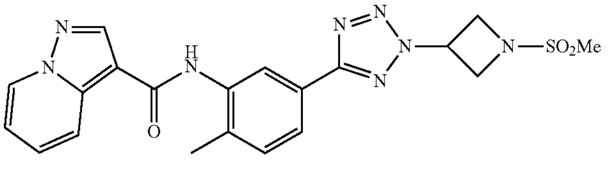 [SMILES: Cc1ccc(-c2nnn(C3CN(S(C)(=O)=O)C3)n2)cc1NC(=O)c1cnn2ccccc12] | |
| 173 | N-(5-(2-(1-(ethylsulfonyl)azetidin-3-yl)-2H-tetrazol-5-yl)-2-methylphenyl)pyrazolo[1,5-a]pyridine-3-carboxamide | 20 |
| | 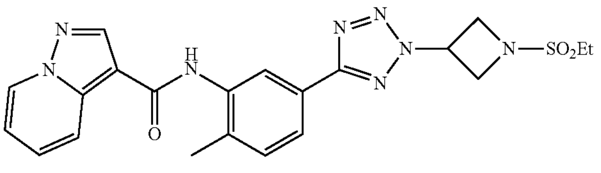 | |

TABLE 1-continued

| Compound No | Name, Structure | Scheme |
|---|---|---|
| 174 | N-(2-methyl-5-(2-(1-(propylsulfonyl)azetidin-3-yl)-2H-tetrazol-5-yl)phenyl)pyrazolo[1,5-a]pyridine-3-carboxamide 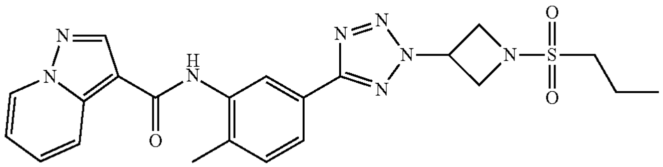 [SMILES: CCCS(=O)(=O)N1CC(n2nnc(-c3ccc(C)c(NC(=O)c4cnn5ccccc45)c3)n2)C1] | 20 |
| 175 | N-(2-methyl-5-(2-(1-((tetrahydrofuran-3-yl)sulfonyl)azetidin-3-yl)-2H-tetrazol-5-yl)phenyl)pyrazolo[1,5-a]pyridine-3-carboxamide 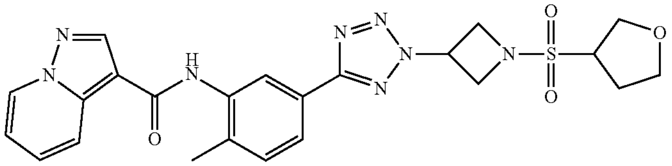 [SMILES: Cc1ccc(-c2nnn(C3CN(S(=O)(=O)C4CCOC4)C3)n2)cc1NC(=O)c1cnn2ccccc12] | 20 |
| 176 | N-(5-(2-(1-((2-(2,2-difluoroethoxy)ethyl)sulfonyl)azetidin-3-yl)-2H-tetrazol-5-yl)-2-methylphenyl)pyrazolo[1,5-a]pyridine-3-carboxamide 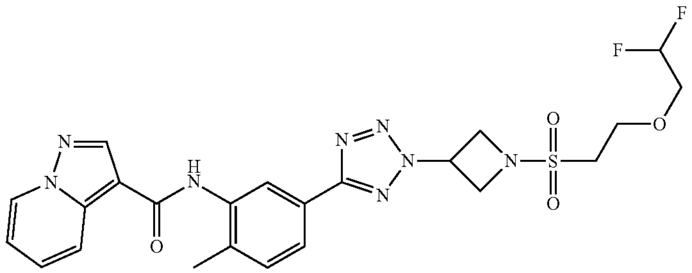 [SMILES: Cc1ccc(-c2nnn(C3CN(S(=O)(=O)CCOCC(F)F)C3)n2)cc1NC(=O)c1cnn2ccccc12] | 20 |
| 177 | N-(5-(2-(1-(isopropylsulfonyl)azetidin-3-yl)-2H-tetrazol-5-yl)-2-methylphenyl)pyrazolo[1,5-a]pyridine-3-carboxamide 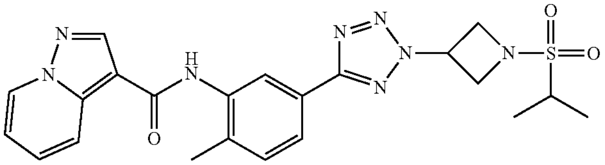 [SMILES: Cc1ccc(-c2nnn(C3CN(S(=O)(=O)C(C)C)C3)n2)cc1NC(=O)c1cnn2ccccc12] | 20 |
| 178 | N-(5-(2-(1-((2-methoxyethyl)sulfonyl)azetidin-3-yl)-2H-tetrazol-5-yl)-2-methylphenyl)pyrazolo[1,5-a]pyridine-3-carboxamide 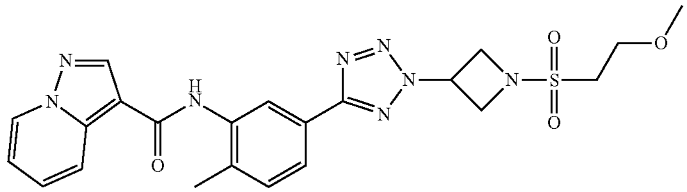 [SMILES: COCCS(=O)(=O)N1CC(n2nnc(-c3ccc(C)c(NC(=O)c4cnn5ccccc45)c3)n2)C1] | 20 |

TABLE 1-continued

| Compound No | Name, Structure | Scheme |
|---|---|---|
| 179 | N-(5-(2-(1-(cyclopropylsulfonyl)azetidin-3-yl)-2H-tetrazol-5-yl)-2-methylphenyl)pyrazolo[1,5-a]pyridine-3-carboxamide 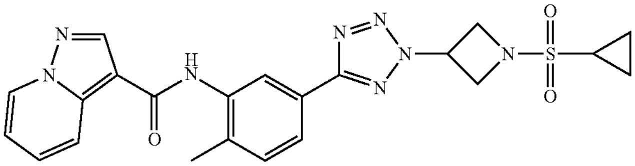 [SMILES: Cc1ccc(-c2nnn(C3CN(S(=O)(=O)C4CC4)C3)n2)cc1NC(=O)c1cnn2ccccc12] | 20 |
| 180 | N-(5-(2-(1-((cyclobutylmethyl)sulfonyl)azetidin-3-yl)-2H-tetrazol-5-yl)-2-methylphenyl)pyrazolo[1,5-a]pyridine-3-carboxamide 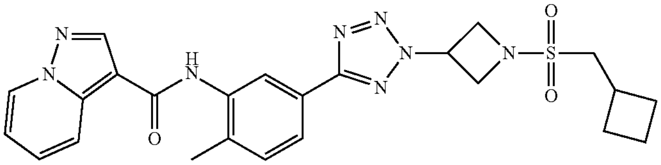 [SMILES: Cc1ccc(-c2nnn(C3CN(S(=O)(=O)CC4CCC4)C3)n2)cc1NC(=O)c1cnn2ccccc12] | 20 |
| 181 | N-(2-methyl-5-(2-(1-((1-methylcyclopropyl)sulfonyl)azetidin-3-yl)-2H-tetrazol-5-yl)phenyl)pyrazolo[1,5-a]pyridine-3-carboxamide 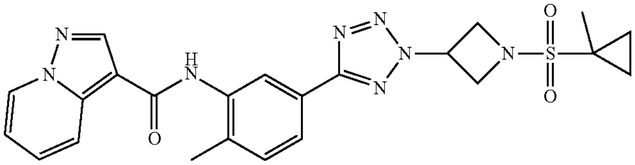 [SMILES: Cc1ccc(-c2nnn(C3CN(S(=O)(=O)C4(C)CC4)C3)n2)cc1NC(=O)c1cnn2ccccc12] | 20 |
| 182 | N-(2-methyl-5-(2-(1-((trifluoromethyl)sulfonyl)azetidin-3-yl)-2H-tetrazol-5-yl)phenyl)pyrazolo[1,5-a]pyridine-3-carboxamide 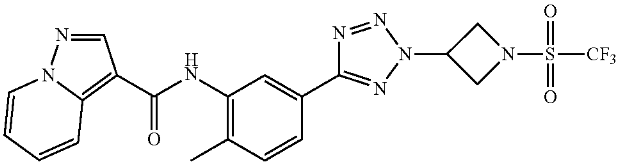 [SMILES: Cc1ccc(-c2nnn(C3CN(S(=O)(=O)C(F)(F)F)C3)n2)cc1NC(=O)c1cnn2ccccc12] | 20 |
| 183 | N-(2-methyl-5-(2-(1-(oxetan-3-ylsulfonyl)azetidin-3-yl)-2H-tetrazol-5-yl)phenyl)pyrazolo[1,5-a]pyridine-3-carboxamide 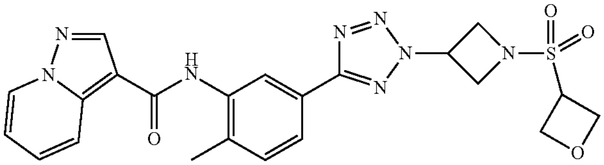 [SMILES: Cc1ccc(-c2nnn(C3CN(S(=O)(=O)C4COC4)C3)n2)cc1NC(=O)c1cnn2ccccc12] | 20 |
| 184 | N-(5-(2-(1-((3,3-difluoropropyl)sulfonyl)azetidin-3-yl)-2H-tetrazol-5-yl)-2-methylphenyl)pyrazolo[1,5-a]pyridine-3-carboxamide 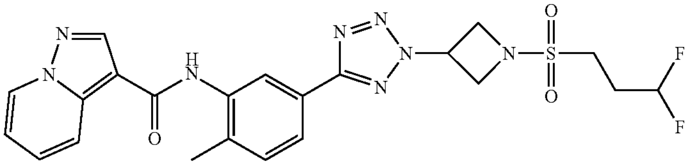 [SMILES: Cc1ccc(-c2nnn(C3CN(S(=O)(=O)CCC(F)F)C3)n2)cc1NC(=O)c1cnn2ccccc12] | 20 |

TABLE 1-continued

| Compound No | Name, Structure | Scheme |
|---|---|---|
| 185 | N-(5-(2-(1-((2-(2-methoxyethoxy)ethyl)sulfonyl)azetidin-3-yl)-2H-tetrazol-5-yl)-2-methylphenyl)pyrazolo[1,5-a]pyridine-3-carboxamide 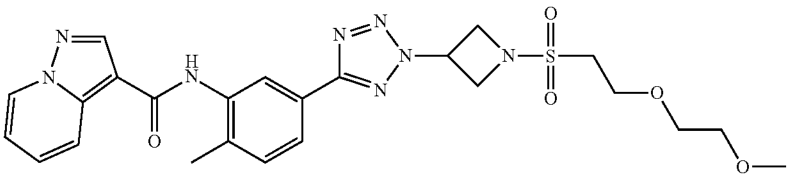 [SMILES: COCCOCCS(=O)(=O)N1CC(n2nnc(-c3ccc(C)c(NC(=O)c4cnn5ccccc45)c3)n2)C1] | 20 |
| 186 | N-(5-(2-(1-((4-cyanobutyl)sulfonyl)azetidin-3-yl)-2H-tetrazol-5-yl)-2-methylphenyl)pyrazolo[1,5-a]pyridine-3-carboxamide 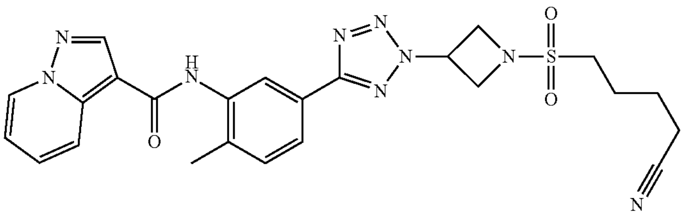 [SMILES: Cc1ccc(-c2nnn(C3CN(S(=O)(=O)CCCCC#N)C3)n2)cc1NC(=O)c1cnn2ccccc12] | 20 |
| 187 | N-(2-chloro-5-(5-(1-(methylsulfonyl)azetidin-3-yl)-2H-tetrazol-2-yl)phenyl)pyrazolo[1,5-a]pyridine-3-carboxamide 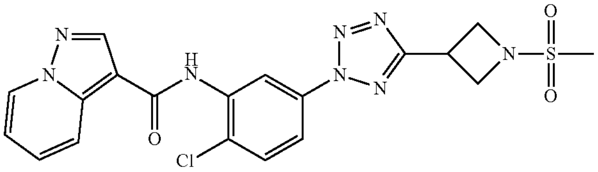 [SMILES: CS(=O)(=O)N1CC(c2nnn(-c3ccc(Cl)c(NC(=O)c4cnn5ccccc45)c3)n2)C1] | 20 |
| 188 | N-(5-(5-(1-(cyclopropylsulfonyl)azetidin-3-yl)-2H-tetrazol-2-yl)-2-methylphenyl)pyrazolo[1,5-a]pyridine-3-carboxamide 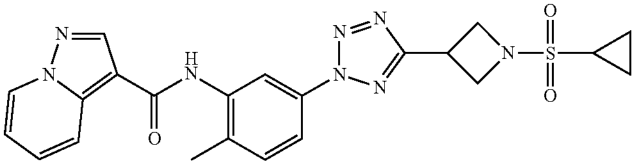 [SMILES: Cc1ccc(-n2nnc(C3CN(S(=O)(=O)C4CC4)C3)n2)cc1NC(=O)c1cnn2ccccc12] | 20 |
| 189 | N-(5-(5-(1-((2-methoxyethyl)sulfonyl)azetidin-3-yl)-2H-tetrazol-2-yl)-2-methylphenyl)pyrazolo[1,5-a]pyridine-3-carboxamide 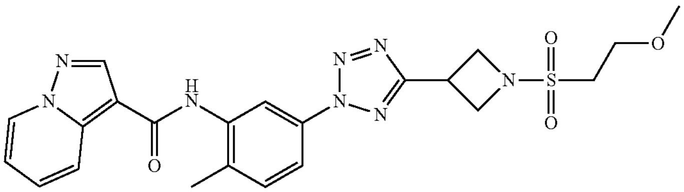 [SMILES: COCCS(=O)(=O)N1CC(c2nnn(-c3ccc(C)c(NC(=O)c4cnn5ccccc45)c3)n2)C1] | 20 |
| 190 | N-(2-methyl-5-(5-(1-(methylsulfonyl)azetidin-3-yl)-2H-tetrazol-2-yl)phenyl)pyrazolo[1,5-a]pyridine-3-carboxamide 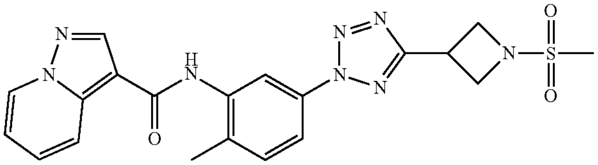 [SMILES: Cc1ccc(-n2nnc(C3CN(S(C)(=O)=O)C3)n2)cc1NC(=O)c1cnn2ccccc12] | 20 |

TABLE 1-continued

| Compound No | Name, Structure | Scheme |
|---|---|---|
| 191 | methyl 3-(5-(4-methyl-3-(pyrazolo[1,5-a]pyridine-3-carboxamido)phenyl)-2H-tetrazol-2-yl)azetidine-1-carboxylate 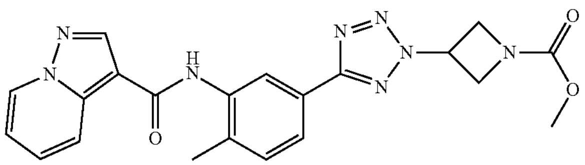 [SMILES: COC(=O)N1CC(n2nnc(-c3ccc(C)c(NC(=O)c4cnn5ccccc45)c3)n2)C1] | 20 |
| 192 | methyl 3-(5-(4-chloro-3-(pyrazolo[1,5-a]pyridine-3-carboxamido)phenyl)-2H-tetrazol-2-yl)azetidine-1-carboxylate 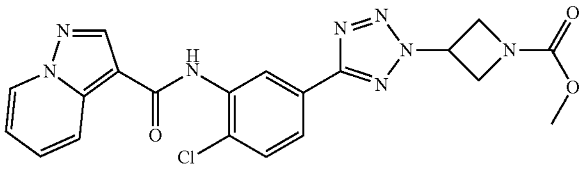 [SMILES: COC(=O)N1CC(n2nnc(-c3ccc(Cl)c(NC(=O)c4cnn5ccccc45)c3)n2)C1] | 20 |
| 193 | methyl 3-(2-(4-chloro-3-(pyrazolo[1,5-a]pyridine-3-carboxamido)phenyl)-2H-1,2,3-triazol-4-yl)azetidine-1-carboxylate 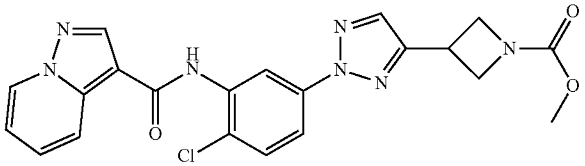 [SMILES: COC(=O)N1CC(c2cnn(-c3ccc(Cl)c(NC(=O)c4cnn5ccccc45)c3)n2)C1] | 20 |
| 194 | methyl 3-(2-(4-chloro-3-(pyrazolo[1,5-a]pyridine-3-carboxamido)phenyl)-2H-tetrazol-5-yl)azetidine-1-carboxylate 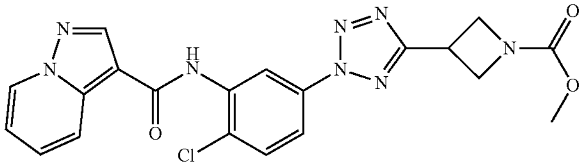 [SMILES: COC(=O)N1CC(c2nnn(-c3ccc(Cl)c(NC(=O)c4cnn5ccccc45)c3)n2)C1] | 20 |
| 195 | N-(2-chloro-5-(2-(1-(2,2,2-trifluoroethyl)azetidin-3-yl)-2H-tetrazol-5-yl)phenyl)pyrazolo[1,5-a]pyridine-3-carboxamide 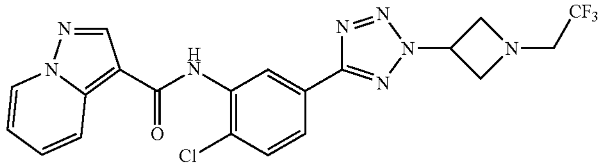 [SMILES: O=C(Nc1cc(-c2nnn(C3CN(CC(F)(F)F)C3)n2)ccc1Cl)c1cnn2ccccc12] | 20 |
| 196 | N-(2-methyl-5-(2-(1-(2,2,2-trifluoroethyl)azetidin-3-yl)-2H-tetrazol-5-yl)phenyl)pyrazolo[1,5-a]pyridine-3-carboxamide 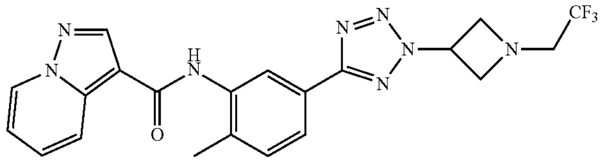 [SMILES: Cc1ccc(-c2nnn(C3CN(CC(F)(F)F)C3)n2)cc1NC(=O)c1cnn2ccccc12] | 20 |
| 197 | N-(2-methyl-5-(2-(2-(2,2,2-trifluoroethoxy)ethyl)-2H-tetrazol-5-yl)phenyl)-5-(1H-pyrazol-4-yl)pyrazolo[1,5-a]pyridine-3-carboxamide | 21 |

TABLE 1-continued

| Compound No | Name, Structure | Scheme |
|---|---|---|
| | 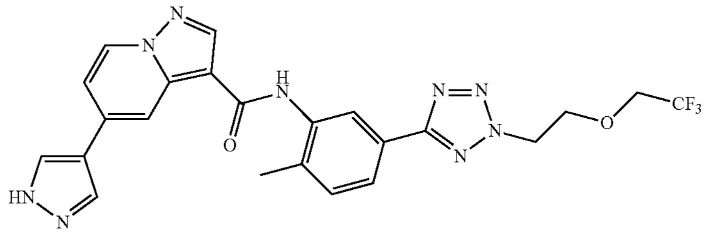 [SMILES: Cc1ccc(-c2nnn(CCOCC(F)(F)F)n2)cc1NC(=O)c1cnn2ccc(-c3cn[nH]c3)cc12] | |
| 198 | N-(5-(2-(3,3-difluorocyclobutyl)-2H-tetrazol-5-yl)-2-methylphenyl)-5-(1H-pyrazol-4-yl)pyrazolo[1,5-a]pyridine-3-carboxamide 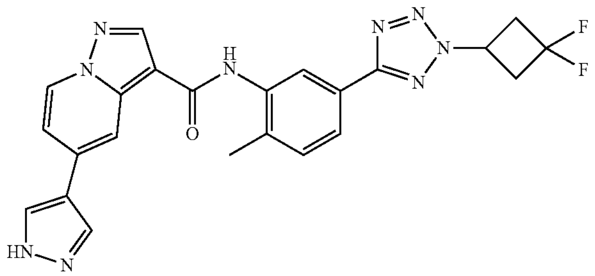 [SMILES: Cc1ccc(-c2nnn(C3CC(F)(F)C3)n2)cc1NC(=O)c1cnn2ccc(-c3cn[nH]c3)cc12] | 21 |
| 199 | methyl 3-(5-(3-(5-(2-hydroxyethoxy)pyrazolo[1,5-a]pyridine-3-carboxamido)-4-methylphenyl)-2H-tetrazol-2-yl)azetidine-1-carboxylate 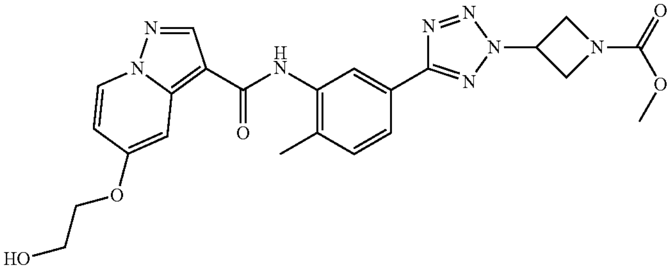 [SMILES: COC(=O)N1CC(n2nnc(-c3ccc(C)c(NC(=O)c4cnn5ccc(OCCO)cc45)c3)n2)C1] | 21 |
| 200 | N-(5-(2-((1r,3r)-3-(hydroxymethyl)cyclobutyl)-2H-tetrazol-5-yl)-2-methylphenyl)pyrazolo[1,5-a]pyridine-3-carboxamide 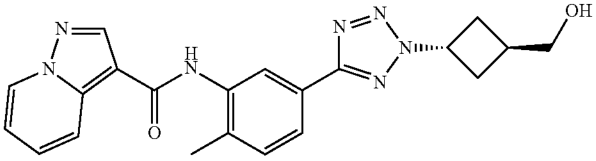 [SMILES: Cc1ccc(-c2nnn([C@H]3C[C@H](CO)C3)n2)cc1NC(=O)c1cnn2ccccc12] | 23 |
| 201 | N-(5-(2-((1r,3r)-3-(hydroxymethyl)cyclobutyl)-2H-tetrazol-5-yl)-2-methylphenyl)-5-((2-methoxyethyl)amino)pyrazolo[1,5-a]pyridine-3-carboxamide 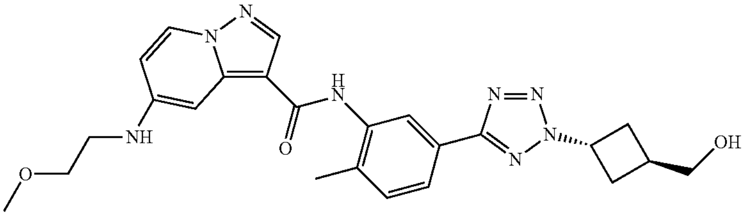 [SMILES: COCCNc1ccn2ncc(C(=O)Nc3cc(-c4nnn([C@H]5C[C@H](CO)C5)n4)ccc3C)c2c1] | 23 |
| 202 | N-(4-fluoro-5-(2-((1r,3r)-3-(hydroxymethyl)cyclobutyl)-2H-tetrazol-5-yl)-2-methylphenyl)-5-((2-methoxyethyl)amino)pyrazolo[1,5-a]pyridine-3-carboxamide | 23 |

TABLE 1-continued

| Compound No | Name, Structure | Scheme |
|---|---|---|
| | 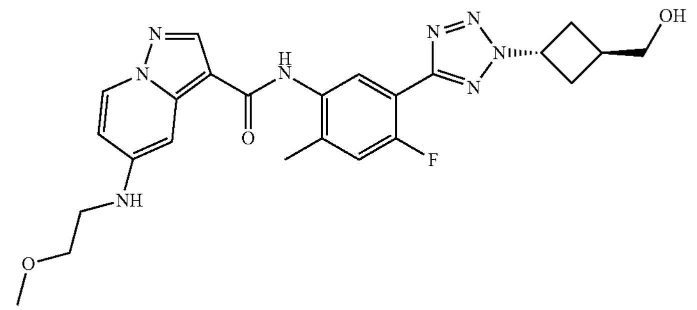 [SMILES: COCCNc1ccn2ncc(C(=O)Nc3cc(-c4nnn([C@H]5C[C@H](CO)C5)n4)c(F)cc3C)c2c1] | |
| 203 | N-(5-(2-(1-((2-hydroxyethyl)sulfonyl)azetidin-3-yl)-2H-tetrazol-5-yl)-2-methylphenyl)pyrazolo[1,5-a]pyridine-3-carboxamide 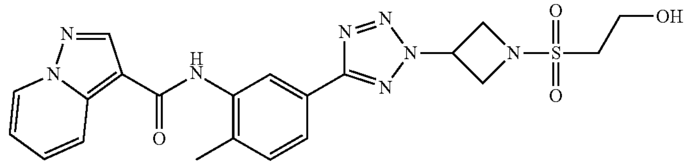 [SMILES: Cc1ccc(-c2nnn(C3CN(S(=O)(=O)CCO)C3)n2)cc1NC(=O)c1cnn2ccccc12] | 23 |
| 204 | (S)-N-(2-methyl-5-(4-methyl-2H-1,2,3-triazol-2-yl)phenyl)-5-(1-(morpholin-2-ylmethyl)-1H-pyrazol-4-yl)pyrazolo[1,5-a]pyridine-3-carboxamide 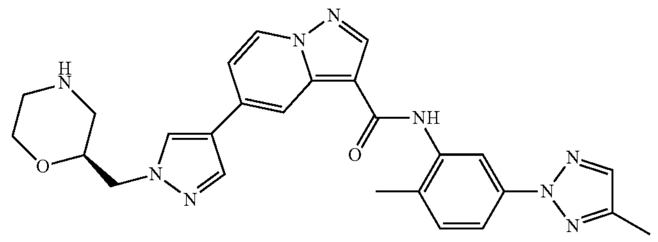 [SMILES: Cc1cnn(-c2ccc(C)c(NC(=O)c3cnn4ccc(-c5cnn(C[C@@H]6CNCCO6)c5)cc34)c2)n1] | 21 |
| 205 | (R)-N-(2-methyl-5-(4-methyl-2H-1,2,3-triazol-2-yl)phenyl)-5-(1-(morpholin-2-ylmethyl)-1H-pyrazol-4-yl)pyrazolo[1,5-a]pyridine-3-carboxamide 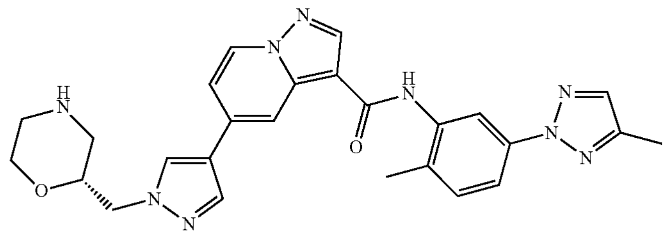 [SMILES: Cc1cnn(-c2ccc(C)c(NC(=O)c3cnn4ccc(-c5cnn(C[C@H]6CNCCO6)c5)cc34)c2)n1] | 21 |
| 206 | N-(5-(2-cyclopropyl-2H-tetrazol-5-yl)-2-methylphenyl)-5-(1-((4-hydroxytetrahydro-2H-pyran-4-yl)methyl)-1H-pyrazol-4-yl)pyrazolo[1,5-a]pyridine-3-carboxamide | 16 |

TABLE 1-continued

| Compound No | Name, Structure | Scheme |
|---|---|---|
| | 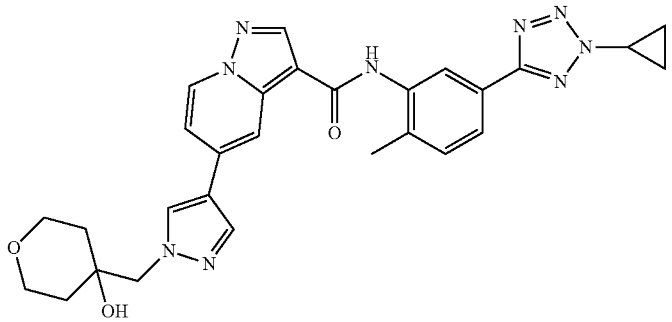 [SMILES: Cc1ccc(-c2nnn(C3CC3)n2)cc1NC(=O)c1cnn2ccc(-c3cnn(CC4(O)CCOCC4)c3)cc12] | |
| 207 | N-(5-(2-cyclopropyl-2H-tetrazol-5-yl)-4-fluoro-2-methylphenyl)-5-(1-(2-hydroxy-2-methylpropyl)-1H-pyrazol-4-yl)pyrazolo[1,5-a]pyridine-3-carboxamide 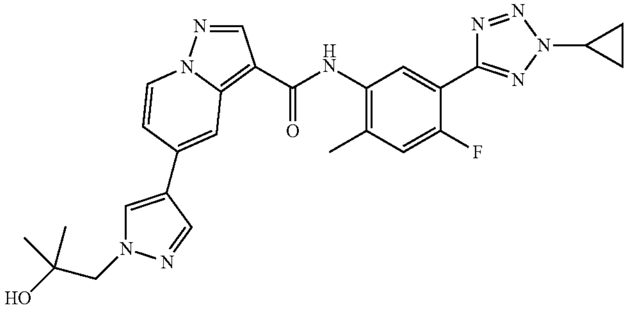 [SMILES: Cc1cc(F)c(-c2nnn(C3CC3)n2)cc1NC(=O)c1cnn2ccc(-c3cnn(CC(C)(C)O)c3)cc12] | 16 |
| 208 | N-(5-(2-cyclopropyl-2H-tetrazol-5-yl)-2-methylphenyl)-5-(1-(2-hydroxyethyl)-3,5-dimethyl-1H-pyrazol-4-yl)pyrazolo[1,5-a]pyridine-3-carboxamide 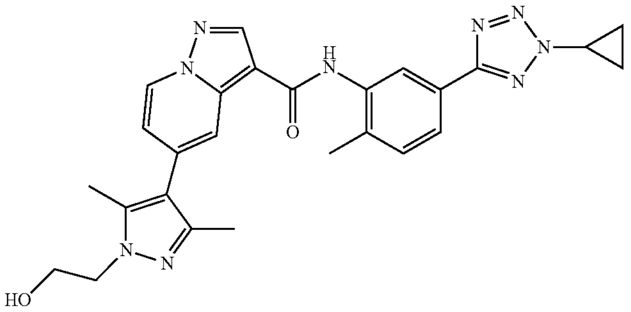 [SMILES: Cc1ccc(-c2nnn(C3CC3)n2)cc1NC(=O)c1cnn2ccc(-c3c(C)nn(CCO)c3C)cc12] | 21 |
| 209 | 5-(1-(2-hydroxy-2-methylpropyl)-1H-pyrazol-4-yl)-N-(2-methyl-5-(5-methyl-2H-tetrazol-2-yl)phenyl)pyrazolo[1,5-a]pyridine-3-carboxamide 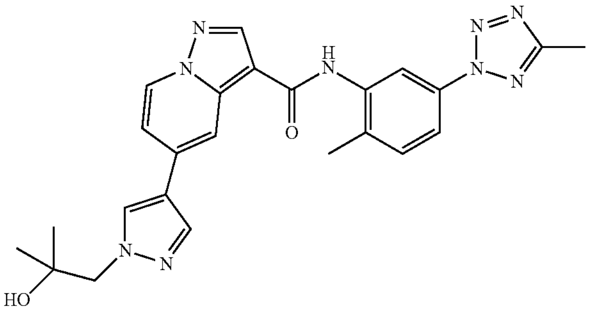 [SMILES: Cc1nnn(-c2ccc(C)c(NC(=O)c3cnn4ccc(-c5cnn(CC(C)(C)O)c5)cc34)c2)n1] | 16 |
| 210 | N-(2-chloro-5-(2-methyl-2H-tetrazol-5-yl)phenyl)-5-(1-(2-hydroxy-2-methylpropyl)-1H-pyrazol-4-yl)pyrazolo[1,5-a]pyridine-3-carboxamide | 16 |

TABLE 1-continued

| Compound No | Name, Structure | Scheme |
|---|---|---|
| | 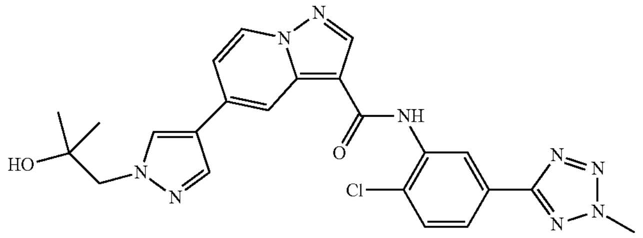 [SMILES: Cn1nnc(-c2ccc(Cl)c(NC(=O)c3cnn4ccc(-c5cnn(CC(C)(C)O)c5)cc34)c2)n1] | |
| 211 | (R)-N-(5-(5-(2,2-difluorocyclopropyl)-2H-tetrazol-2-yl)-2-methylphenyl)-5-(1-(2-hydroxyethyl)-1H-pyrazol-4-yl)pyrazolo[1,5-a]pyridine-3-carboxamide or (S)-N-(5-(5-(2,2-difluorocyclopropyl)-2H-tetrazol-2-yl)-2-methylphenyl)-5-(1-(2-hydroxyethyl)-1H-pyrazol-4-yl)pyrazolo[1,5-a]pyridine-3-carboxamide 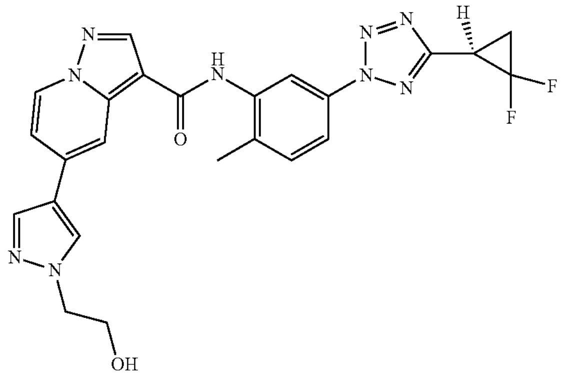 [SMILES: Cc1ccc(-n2nnc([C@H]3CC3(F)F)n2)cc1NC(=O)c1cnn2ccc(-c3cnn(CCO)c3)cc12] Or 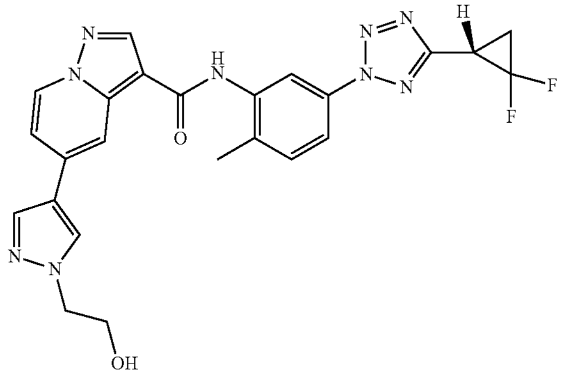 [SMILES: Cc1ccc(-n2nnc([C@@H]3CC3(F)F)n2)cc1NC(=O)c1cnn2ccc(-c3cnn(CCO)c3)cc12] | 16 Isomer 1 |
| 212 | N-(2-chloro-5-(5-methyl-2H-tetrazol-2-yl)phenyl)-5-(1-(2-hydroxy-2-methylpropyl)-1H-pyrazol-4-yl)pyrazolo[1,5-a]pyridine-3-carboxamide 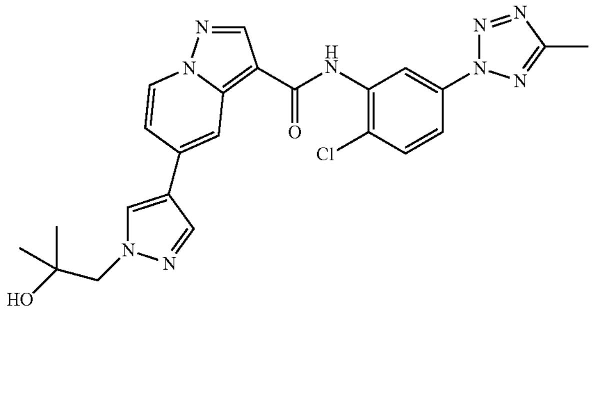 [SMILES: Cc1nnn(-c2ccc(Cl)c(NC(=O)c3cnn4ccc(-c5cnn(CC(C)(C)O)c5)cc34)c2)n1] | 16 |

TABLE 1-continued

| Compound No | Name, Structure | Scheme |
| --- | --- | --- |
| 213 | N-(2-fluoro-5-(2-methyl-2H-tetrazol-5-yl)phenyl)-5-(1-(2-hydroxy-2-methylpropyl)-1H-pyrazol-4-yl)pyrazolo[1,5-a]pyridine-3-carboxamide 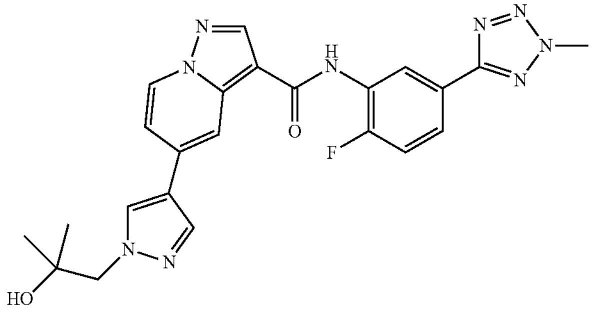 [SMILES: Cn1nnc(-c2ccc(F)c(NC(=O)c3cnn4ccc(-c5cnn(CC(C)(C)O)c5)cc34)c2)n1] | 16 |
| 214 | 4-fluoro-6-(1-(2-hydroxy-2-methylpropyl)-1H-pyrazol-4-yl)-N-(2-methyl-5-(2-methyl-2H-tetrazol-5-yl)phenyl)pyrazolo[1,5-a]pyridine-3-carboxamide 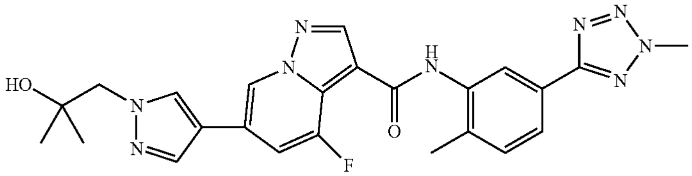 [SMILES: Cc1ccc(-c2nnn(C)n2)cc1NC(=O)c1cnn2cc(-c3cnn(CC(C)(C)O)c3)cc(F)c12] | 16 |
| 215 | N-(5-(2-cyclopropyl-2H-tetrazol-5-yl)-2-fluoro-4-methylphenyl)-5-(1-(2-hydroxy-2-methylpropyl)-1H-pyrazol-4-yl)pyrazolo[1,5-a]pyridine-3-carboxamide 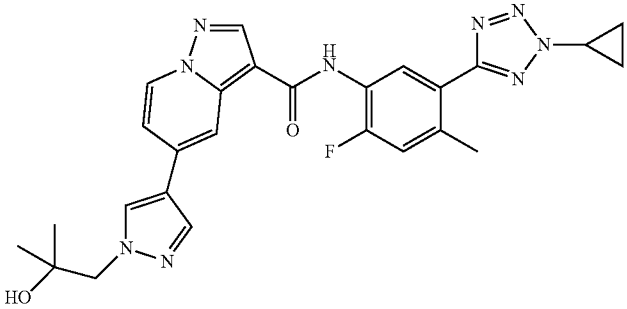 [SMILES: Cc1cc(F)c(NC(=O)c2cnn3ccc(-c4cnn(CC(C)(C)O)c4)cc23)cc1-c1nnn(C2CC2)n1] | 16 |
| 216 | N-(2-chloro-5-(5-cyclopropyl-2H-tetrazol-2-yl)phenyl)-5-(1-(2-hydroxy-2-methylpropyl)-1H-pyrazol-4-yl)pyrazolo[1,5-a]pyridine-3-carboxamide 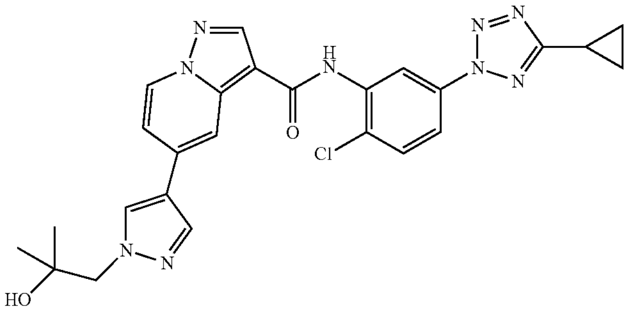 [SMILES: CC(C)(O)Cn1cc(-c2ccn3ncc(C(=O)Nc4cc(-n5nnc(C6CC6)n5)ccc4Cl)c3c2)cn1] | 16 |
| 217 | N-(5-(5-cyclopropyl-2H-tetrazol-2-yl)-2-fluorophenyl)-5-(1-(2-hydroxy-2-methylpropyl)-1H-pyrazol-4-yl)pyrazolo[1,5-a]pyridine-3-carboxamide | 16 |

TABLE 1-continued

| Compound No | Name, Structure | Scheme |
|---|---|---|
| | 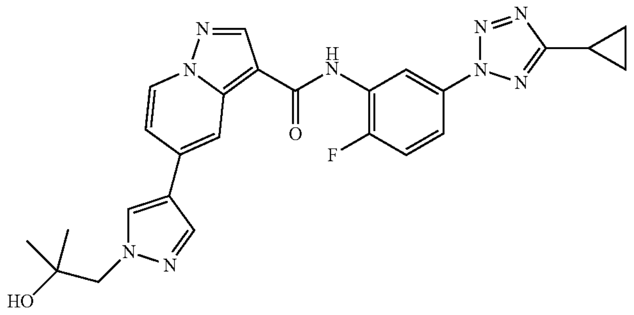 [SMILES: CC(C)(O)Cn1cc(-c2ccn3ncc(C(=O)Nc4cc(-n5nnc(C6CC6)n5)ccc4F)c3c2)cn1] | |
| 218 | N-(2-chloro-5-(2-methyl-2H-tetrazol-5-yl)phenyl)-5-(1-(2-hydroxyethyl)-1H-pyrazol-4-yl)pyrazolo[1,5-a]pyridine-3-carboxamide | 16 |
| | 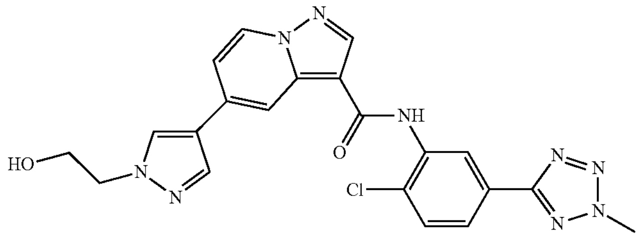 [SMILES: Cn1nnc(-c2ccc(Cl)c(NC(=O)c3cnn4ccc(-c5cnn(CCO)c5)cc34)c2)n1] | |
| 219 | N-(5-(2-cyclopropyl-2H-tetrazol-5-yl)-2-methylphenyl)-5-(1-(2-(4-methylpiperazin-1-yl)ethyl)-1H-pyrazol-4-yl)pyrazolo[1,5-a]pyridine-3-carboxamide | 16 |
| | 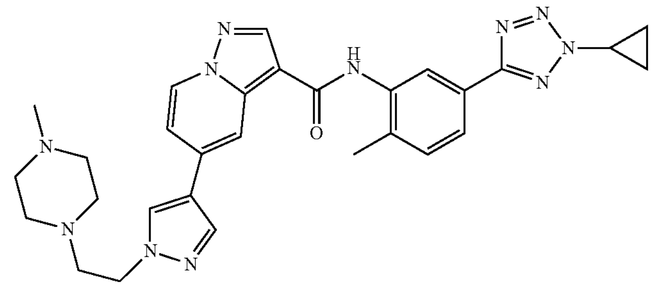 [SMILES: Cc1ccc(-c2nnn(C3CC3)n2)cc1NC(=O)c1cnn2ccc(-c3cnn(CCN4CCN(C)CC4)c3)cc12] | |
| 220 | N-(5-(2-cyclopropyl-2H-tetrazol-5-yl)-2-methylphenyl)-5-(1-(3-morpholinopropyl)-1H-pyrazol-4-yl)pyrazolo[1,5-a]pyridine-3-carboxamide | 16 |
| | 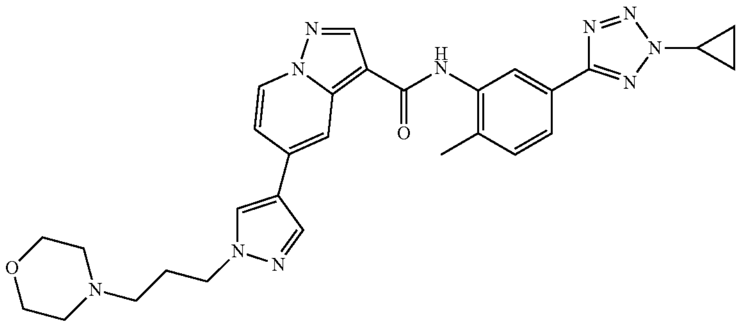 [SMILES: Cc1ccc(-c2nnn(C3CC3)n2)cc1NC(=O)c1cnn2ccc(-c3cnn(CCCN4CCOCC4)c3)cc12] | |
| 221 | 5-(1-(3-(dimethylphosphoryl)propyl)-1H-pyrazol-4-yl)-N-(2-methyl-5-(2-methyl-2H-tetrazol-5-yl)phenyl)pyrazolo[1,5-a]pyridine-3-carboxamide | 16 |

TABLE 1-continued

| Compound No | Name, Structure | Scheme |
|---|---|---|
| | 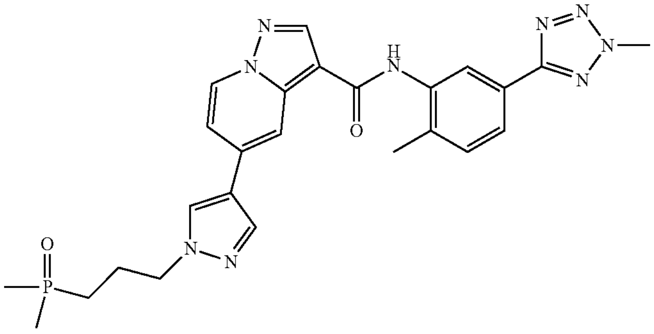 | |
| 222 | N-(5-(5-(2-fluorocyclopropyl)-2H-tetrazol-2-yl)-2-methylphenyl)-5-(1-(2-hydroxy-2-methylpropyl)-1H-pyrazol-4-yl)pyrazolo[1,5-a]pyridine-3-carboxamide 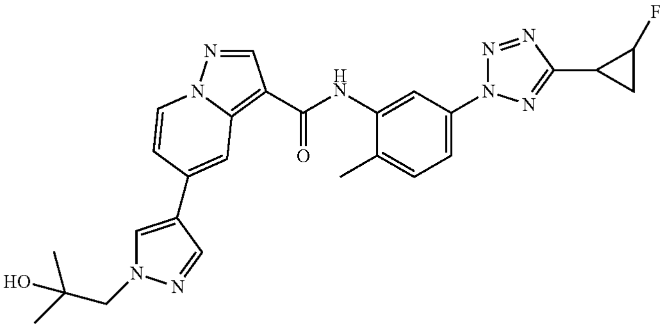 [SMILES: Cc1ccc(-n2nnc(C3CC3F)n2)cc1NC(=O)c1cnn2ccc(-c3cnn(CC(C)(C)O)c3)cc12] | 16 |
| 223 | methyl 3-(5-(2-fluoro-5-(6-(2-hydroxyethoxy)pyrazolo[1,5-a]pyridine-3-carboxamido)-4-methylphenyl)-2H-tetrazol-2-yl)azetidine-1-carboxylate 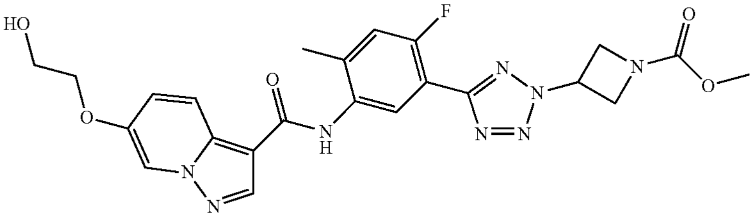 [SMILES: COC(=O)N1CC(n2nnc(-c3cc(NC(=O)c4cnn5cc(OCCO)ccc45)c(C)cc3F)n2)C1] | 18 |
| 224 | methyl 3-(5-(2-fluoro-4-methyl-5-(6-morpholinopyrazolo[1,5-a]pyridine-3-carboxamido)phenyl)-2H-tetrazol-2-yl)azetidine-1-carboxylate 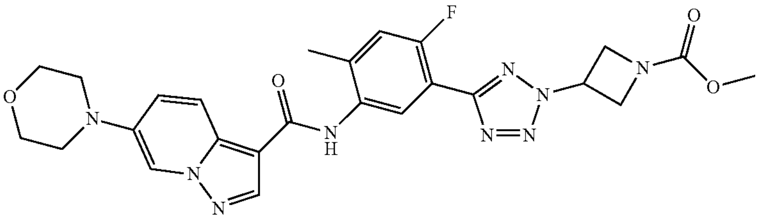 [SMILES: COC(=O)N1CC(n2nnc(-c3cc(NC(=O)c4cnn5cc(N6CCOCC6)ccc45)c(C)cc3F)n2)C1] | 18 |
| 225 | N-(5-(5-cyclopropyl-2H-tetrazol-2-yl)-2-methylphenyl)-5-(1-(2-hydroxy-2-methylpropyl)-1H-pyrazol-4-yl)pyrazolo[1,5-a]pyridine-3-carboxamide | 19 |

TABLE 1-continued

| Compound No | Name, Structure | Scheme |
| --- | --- | --- |
| | 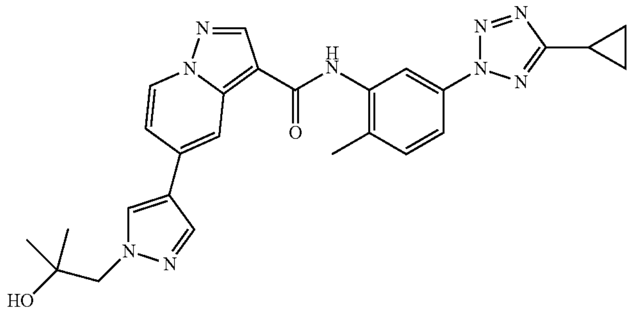 [SMILES: Cc1ccc(-n2nnc(C3CC3)n2)cc1NC(=O)c1cnn2ccc(-c3cnn(CC(C)(C)O)c3)cc12] | |
| 226 | N-(4-chloro-5-(2-cyclopropyl-2H-tetrazol-5-yl)-2-methylphenyl)-5-(1-(2-hydroxy-2-methylpropyl)-1H-pyrazol-4-yl)pyrazolo[1,5-a]pyridine-3-carboxamide | 19 |
| | 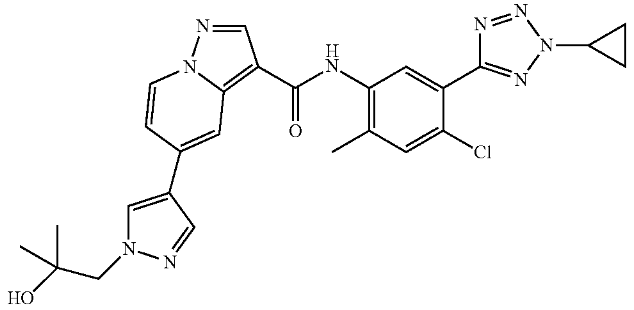 [SMILES: Cc1cc(Cl)c(-c2nnn(C3CC3)n2)cc1NC(=O)c1cnn2ccc(-c3cnn(CC(C)(C)O)c3)cc12] | |
| 227 | N-(2-chloro-5-(2-cyclopropyl-2H-tetrazol-5-yl)-4-methylphenyl)-5-(1-(2-hydroxy-2-methylpropyl)-1H-pyrazol-4-yl)pyrazolo[1,5-a]pyridine-3-carboxamide | 19 |
| | 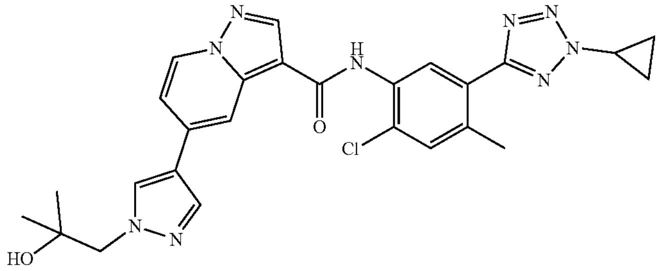 [SMILES: Cc1cc(Cl)c(NC(=O)c2cnn3ccc(-c4cnn(CC(C)(C)O)c4)cc23)cc1-c1nnn(C2CC2)n1] | |
| 228 | 5-(1-(2-hydroxyethyl)-3-methyl-1H-pyrazol-4-yl)-N-(2-methyl-5-(2-methyl-2H-tetrazol-5-yl)phenyl)pyrazolo[1,5-a]pyridine-3-carboxamide | 21 |
| | 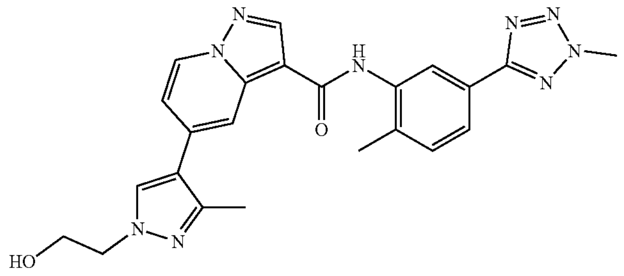 [SMILES: Cc1ccc(-c2nnn(C)n2)cc1NC(=O)c1cnn2ccc(-c3cn(CCO)nc3C)cc12] | |
| 229 | (R)-N-(5-(2-cyclopropyl-2H-tetrazol-5-yl)-2-methylphenyl)-5-(1-(morpholin-2-ylmethyl)-1H-pyrazol-4-yl)pyrazolo[1,5-a]pyridine-3-carboxamide | 21 |

TABLE 1-continued

| Compound No | Name, Structure | Scheme |
|---|---|---|
| | 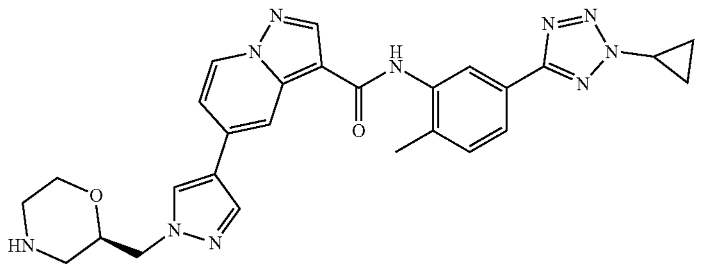 [SMILES: Cc1ccc(-c2nnn(C3CC3)n2)cc1NC(=O)c1cnn2ccc(-c3cnn(C[C@H]4CNCCO4)c3)cc12] | |
| 230 | (R)-5-(3-methyl-1-(morpholin-2-ylmethyl)-1H-pyrazol-4-yl)-N-(2-methyl-5-(5-methyl-2H-tetrazol-2-yl)phenyl)pyrazolo[1,5-a]pyridine-3-carboxamide | 21 |
| | 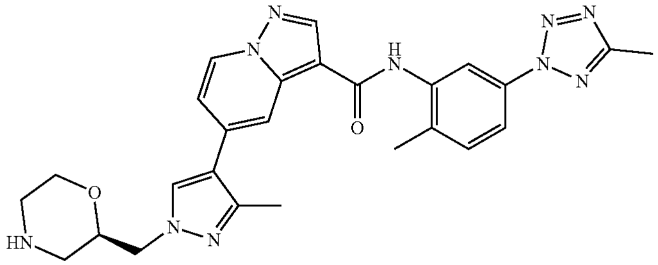 [SMILES: Cc1nnn(-c2ccc(C)c(NC(=O)c3cnn4ccc(-c5cn(C[C@H]6CNCCO6)nc5C)cc34)c2)n1] | |
| 231 | 5-((1H-pyrazol-4-yl)amino)-N-(2-methyl-5-(5-methyl-2H-tetrazol-2-yl)phenyl)pyrazolo[1,5-a]pyridine-3-carboxamide | 21 |
| | 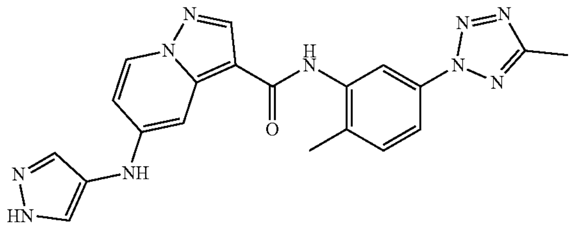 [SMILES: Cc1nnn(-c2ccc(C)c(NC(=O)c3cnn4ccc(Nc5cn[nH]c5)cc34)c2)n1] | |
| 232 | N-(2-methyl-5-(2-methyl-2H-tetrazol-5-yl)phenyl)-5-(1-(3-(S-methylsulfonimidoyl)propyl)-1H-pyrazol-4-yl)pyrazolo[1,5-a]pyridine-3-carboxamide | 22 |
| | 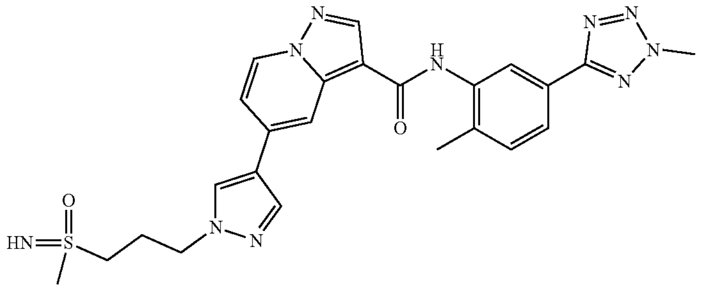 [SMILES: Cc1ccc(-c2nnn(C)n2)cc1NC(=O)c1cnn2ccc(-c3cnn(CCCS(C)(=N)=O)c3)cc12] | |
| 233 | (S)-N-(5-(5-(2,2-difluorocyclopropyl)-2H-tetrazol-2-yl)-2-methylphenyl)-5-(1-(2-hydroxyethyl)-1H-pyrazol-4-yl)pyrazolo[1,5-a]pyridine-3-carboxamide or (R)-N-(5-(5-(2,2-difluorocyclopropyl)-2H-tetrazol-2-yl)-2-methylphenyl)-5-(1-(2-hydroxyethyl)-1H-pyrazol-4-yl)pyrazolo[1,5-a]pyridine-3-carboxamide | 16 Isomer 2 |

TABLE 1-continued

| Compound No | Name, Structure | Scheme |
|---|---|---|
| | 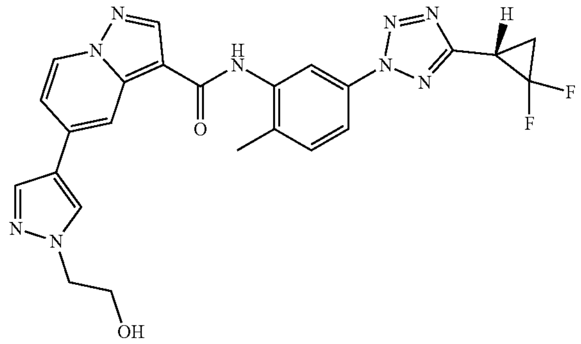 [SMILES: Cc1ccc(-n2nnc([C@@H]3CC3(F)F)n2)cc1NC(=O)c1cnn2ccc(-c3cnn(CCO)c3)cc12] | |
| | 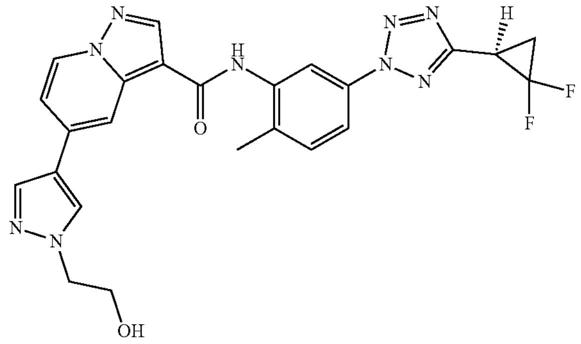 [SMILES: Cc1ccc(-n2nnc([C@H]3CC3(F)F)n2)cc1NC(=O)c1cnn2ccc(-c3cnn(CCO)c3)cc12] | |
| 234 | N-(2-chloro-5-(2-cyclopropyl-2H-tetrazol-5-yl)phenyl)-5-(1-(2-hydroxy-2-methylpropyl)-1H-pyrazol-4-yl)pyrazolo[1,5-a]pyridine-3-carboxamide 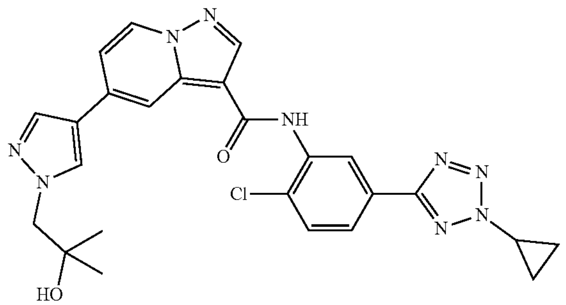 [SMILES: CC(C)(O)Cn1cc(-c2ccn3ncc(C(=O)Nc4cc(-c5nnn(C6CC6)n5)ccc4Cl)c3c2)cn1] | 19 |
| 235 | N-(2-chloro-5-(2-cyclopropyl-2H-tetrazol-5-yl)-4-methylphenyl)-5-(1-((4-hydroxytetrahydro-2H-pyran-4-yl)methyl)-3-methyl-1H-pyrazol-4-yl)pyrazolo[1,5-a]pyridine-3-carboxamide 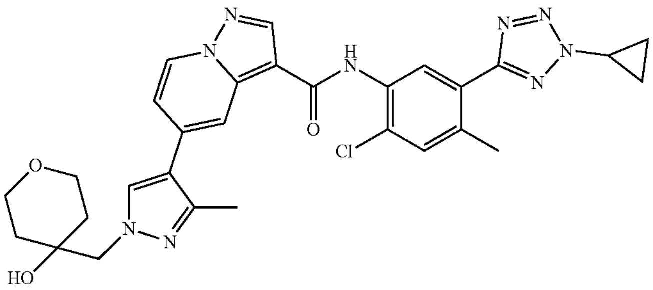 [SMILES: Cc1cc(Cl)c(NC(=O)c2cnn3ccc(-c4cn(CC5(O)CCOCC5)nc4C)cc23)cc1-c1nnn(C2CC2)n1] | 19 |
| 236 | N-(2-chloro-5-(2-cyclopropyl-2H-tetrazol-5-yl)phenyl)-5-(1-((4-hydroxytetrahydro-2H-pyran-4-yl)methyl)-1H-pyrazol-4-yl)pyrazolo[1,5-a]pyridine-3-carboxamide | 16 |

TABLE 1-continued

| Compound No | Name, Structure | Scheme |
|---|---|---|
| | 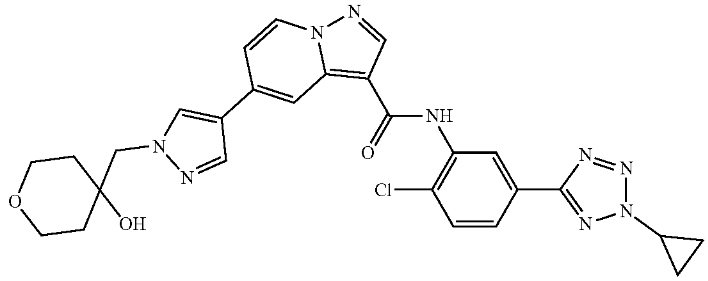 [SMILES: O=C(Nc1cc(-c2nnn(C3CC3)n2)ccc1Cl)c1cnn2ccc(-c3cnn(CC4(O)CCOCC4)c3)cc12] | |
| 237 | (S)-N-(2-chloro-5-(2-cyclopropyl-2H-tetrazol-5-yl)phenyl)-5-(1-(2-hydroxy-3-methoxypropyl)-1H-pyrazol-4-yl)pyrazolo[1,5-a]pyridine-3-carboxamide 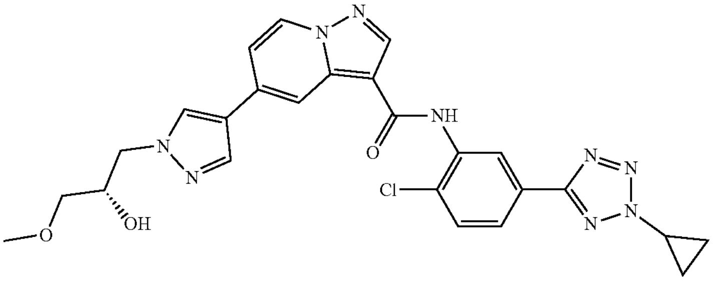 [SMILES: COC[C@@H](O)Cn1cc(-c2ccn3ncc(C(=O)Nc4cc(-c5nnn(C6CC6)n5)ccc4Cl)c3c2)cn1] | 16 |
| 238 | N-[2-chloro-5-(2-cyclopropyl-2H-1,2,3,4-tetrazol-5-yl)phenyl]-5-[1-(2-hydroxyethyl)-3-methyl-1H-pyrazol-4-yl]pyrazolo[1,5-a]pyridine-3-carboxamide 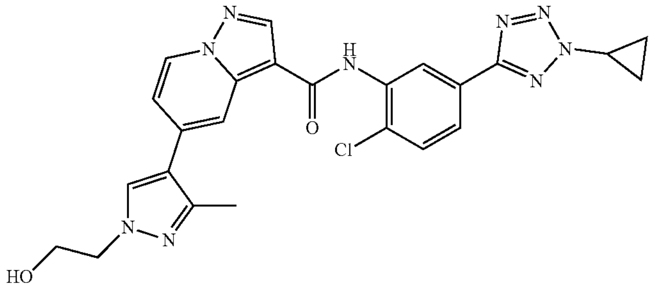 [SMILES: Cc1nn(CCO)cc1-c1ccn2ncc(C(=O)Nc3cc(-c4nnn(C5CC5)n4)ccc3Cl)c2c1] | 21 |
| 239 | N-(5-(2-cyclopropyl-2H-tetrazol-5-yl)-4-fluoro-2-methylphenyl)-5-(1-(2-hydroxy-2-methylpropyl)-3-methyl-1H-pyrazol-4-yl)pyrazolo[1,5-a]pyridine-3-carboxamide 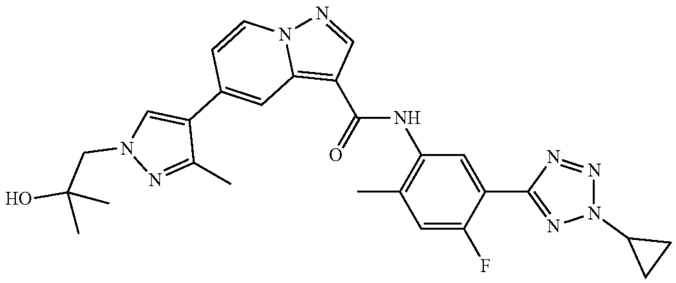 [SMILES: Cc1cc(F)c(-c2nnn(C3CC3)n2)cc1NC(=O)c1cnn2ccc(-c3cn(CC(C)(C)O)nc3C)cc12] | 19 |
| 240 | N-(5-(2-cyclopropyl-2H-tetrazol-5-yl)-4-fluoro-2-methylphenyl)-5-(1-(2-hydroxy-2-methylpropyl)-5-methyl-1H-pyrazol-4-yl)pyrazolo[1,5-a]pyridine-3-carboxamide | 19 |

TABLE 1-continued

| Compound No | Name, Structure | Scheme |
|---|---|---|
| | 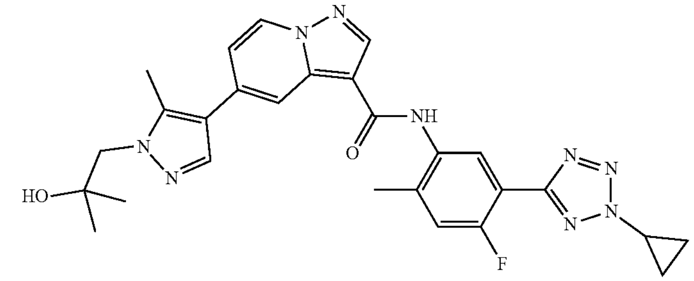 [SMILES: Cc1cc(F)c(-c2nnn(C3CC3)n2)cc1NC(=O)c1cnn2ccc(-c3cnn(CC(C)(C)O)c3C)cc12] | |
| 241 | 5-(3-cyclopropyl-1-(2-hydroxy-2-methylpropyl)-1H-pyrazol-4-yl)-N-(5-(2-cyclopropyl-2H-tetrazol-5-yl)-4-fluoro-2-methylphenyl)pyrazolo[1,5-a]pyridine-3-carboxamide | 19 |
| | 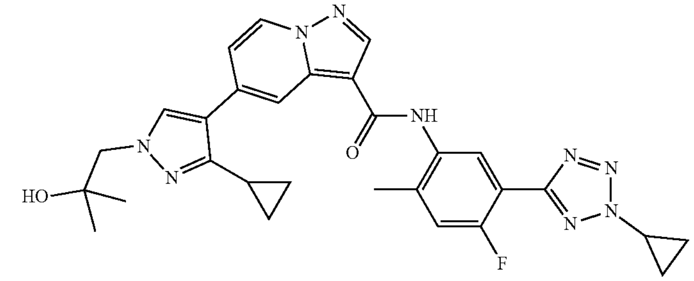 [SMILES: Cc1cc(F)c(-c2nnn(C3CC3)n2)cc1NC(=O)c1cnn2ccc(-c3cn(CC(C)(C)O)nc3C3CC3)cc12] | |
| 242 | N-(5-(2-cyclopropyl-2H-tetrazol-5-yl)-2-methylphenyl)-5-(1-(2-hydroxy-2-methylpropyl)-1H-pyrazol-4-yl)pyrazolo[1,5-a]pyridine-3-carboxamide | 16 |
| | 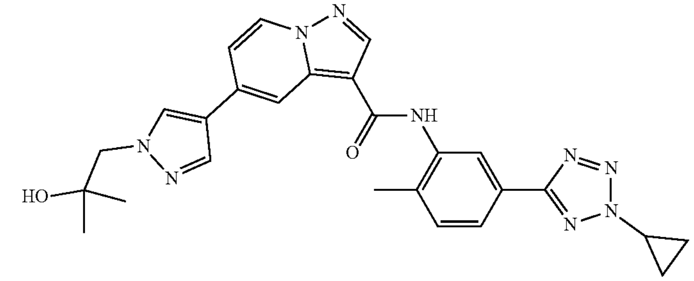 [SMILES: Cc1ccc(-c2nnn(C3CC3)n2)cc1NC(=O)c1cnn2ccc(-c3cnn(CC(C)(C)O)c3)cc12] | |
| 243 | (S)-5-(3-cyclopropyl-1-(2-hydroxy-3-methoxypropyl)-1H-pyrazol-4-yl)-N-(5-(2-cyclopropyl-2H-tetrazol-5-yl)-2-methylphenyl)pyrazolo[1,5-a]pyridine-3-carboxamide | 24 |
| | 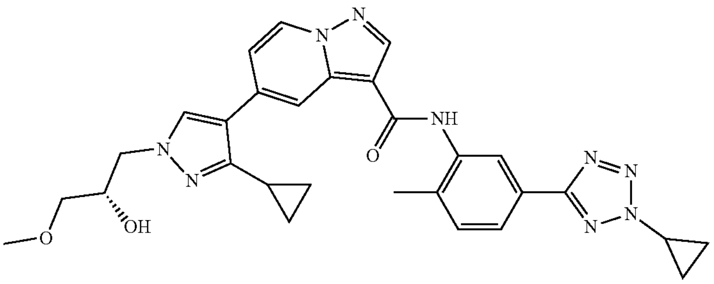 [SMILES: COC[C@@H](O)Cn1cc(-c2ccn3ncc(C(=O)Nc4cc(-c5nnn(C6CC6)n5)ccc4C)c3c2)c(C2CC2)n1] | |
| 244 | 5-(1-(2-hydroxy-2-methylpropyl)-3,5-dimethyl-1H-pyrazol-4-yl)-N-(2-methyl-5-(5-methyl-2H-tetrazol-2-yl)phenyl)pyrazolo[1,5-a]pyridine-3-carboxamide | 19 |

TABLE 1-continued

| Compound No | Name, Structure | Scheme |
|---|---|---|
| | 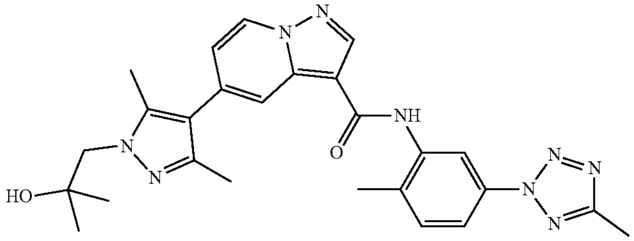 [SMILES: Cc1nnn(-c2ccc(C)c(NC(=O)c3cnn4ccc(-c5c(C)nn(CC(C)(C)O)c5C)cc34)c2)n1] | |
| 245 | (S)-5-(1-(2-hydroxy-3-methoxypropyl)-3,5-dimethyl-1H-pyrazol-4-yl)-N-(2-methyl-5-(2-methyl-2H-tetrazol-5-yl)phenyl)pyrazolo[1,5-a]pyridine-3-carboxamide | 16 |
| | 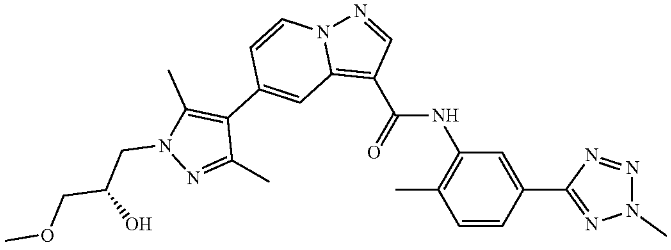 | |
| 246 | N-(5-(2-ethyl-2H-tetrazol-5-yl)-4-fluoro-2-methylphenyl)-5-(1-(2-hydroxy-2-methylpropyl)-3,5-dimethyl-1H-pyrazol-4-yl)pyrazolo[1,5-a]pyridine-3-carboxamide | 16 |
| | 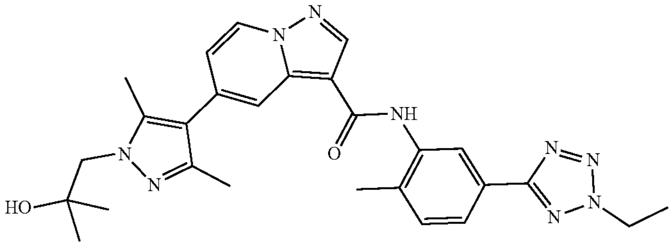 [SMILES: CCn1nnc(-c2ccc(C)c(NC(=O)c3cnn4ccc(-c5c(C)nn(CC(C)(C)O)c5C)cc34)c2)n1] | |
| 247 | N-(5-(2-cyclopropyl-2H-tetrazol-5-yl)-4-fluoro-2-methylphen yl)-6-fluoro-5-(1-(2-hydroxy-2-methylpropyl)-3-methyl-1H-pyrazol-4-yl)pyrazolo[1,5-a]pyridine-3-carboxamide | 16 |
| | 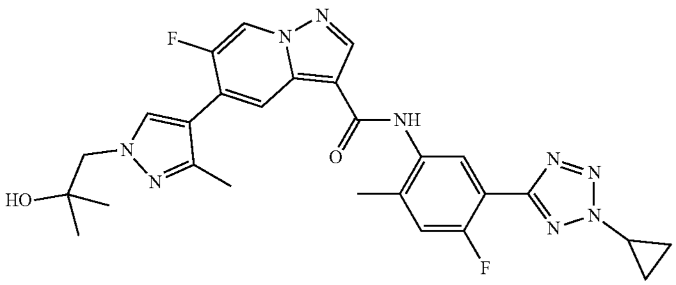 [SMILES: Cc1cc(F)c(-c2nnn(C3CC3)n2)cc1NC(=O)c1cnn2cc(F)c(-c3cn(CC(C)(C)O)nc3C)cc12] | |
| 248 | (S)-N-(2-chloro-5-(2-cyclopropyl-2H-tetrazol-5-yl)phenyl)-5-(1-(2-hydroxy-3-methoxypropyl)-5-methyl-1H-pyrazol-4-yl)pyrazolo[1,5-a]pyridine-3-carboxamide | 16 |

TABLE 1-continued

| Compound No | Name, Structure | Scheme |
|---|---|---|
| | 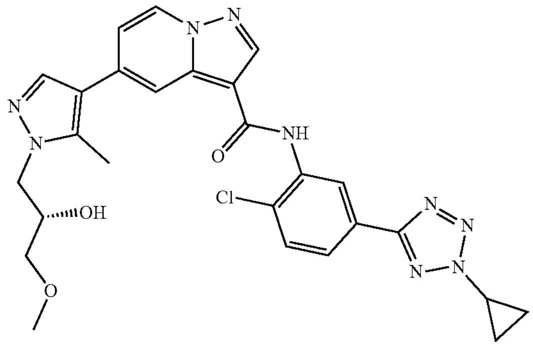 [SMILES: COC[C@@H](O)Cn1ncc(-c2ccn3ncc(C(=O)Nc4cc(-c5nnn(C6CC6)n5)ccc4Cl)c3c2)c1C] | |
| 249 | (S)-N-(5-(2-cyclopropyl-2H-tetrazol-5-yl)-4-fluoro-2-methylphenyl)-5-(1-(2-hydroxy-3-methoxy-2-methylpropyl)-3-methyl-1H-pyrazol-4-yl)pyrazolo[1,5-a]pyridine-3-carboxamide or (R)-N-(5-(2-cyclopropyl-2H-tetrazol-5-yl)-4-fluoro-2-methylphenyl)-5-(1-(2-hydroxy-3-methoxy-2-methylpropyl)-3-methyl-1H-pyrazol-4-yl)pyrazolo[1,5-a]pyridine-3-carboxamide | 16 |
| | 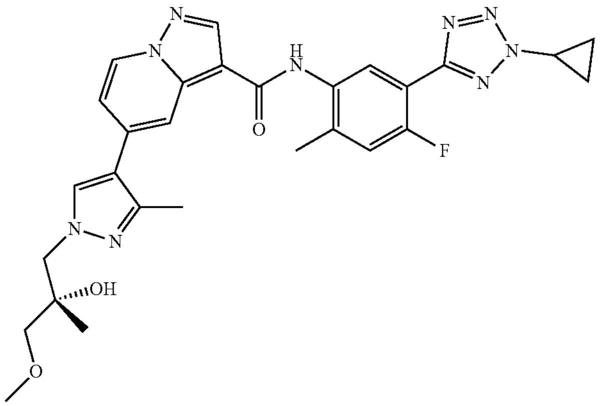 or 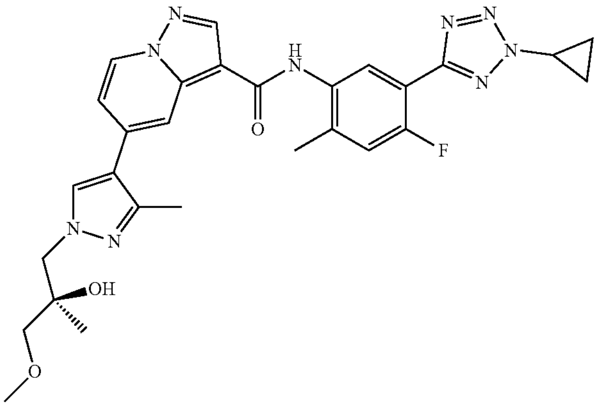 [SMILES: COC[C@](C)(O)Cn1cc(-c2ccn3ncc(C(=O)Nc4cc(-c5nnn(C6CC6)n5)c(F)cc4C)c3c2)c(C)n1] | |
| 250 | N-(2-chloro-5-(2-cyclopropyl-2H-tetrazol-5-yl)phenyl)-5-(1-(2-hydroxy-2-methylpropyl)-3-methyl-1H-pyrazol-4-yl)pyrazolo[1,5-a]pyridine-3-carboxamide | 16 |

TABLE 1-continued

| Compound No | Name, Structure | Scheme |
|---|---|---|
| | 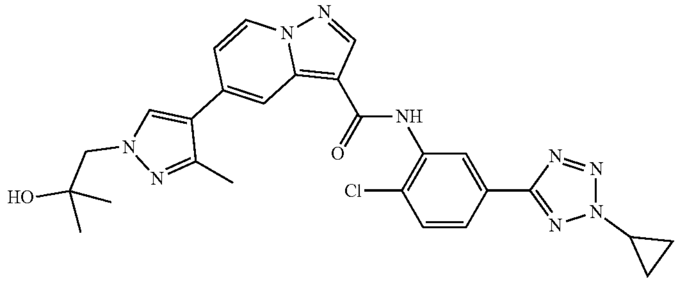 [SMILES: Cc1nn(CC(C)(C)O)cc1-c1ccn2ncc(C(=O)Nc3cc(-c4nnn(C5CC5)n4)ccc3Cl)c2c1] | |
| 251 | N-(2-chloro-5-(2-cyclopropyl-2H-tetrazol-5-yl)-4-fluorophenyl)-5-(1-(2-hydroxy-2-methylpropyl)-3-methyl-1H-pyrazol-4-yl)pyrazolo[1,5-a]pyridine-3-carboxamide | 19 |
| | 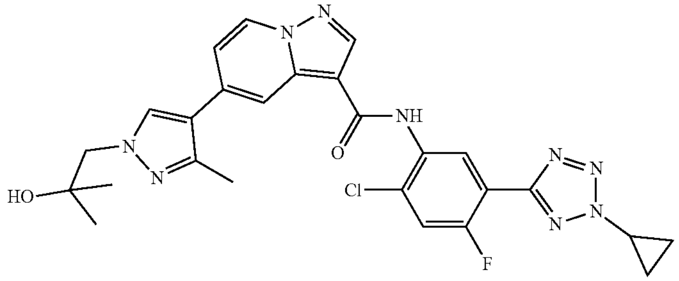 [SMILES: Cc1nn(CC(C)(C)O)cc1-c1ccn2ncc(C(=O)Nc3cc(-c4nnn(C5CC5)n4)c(F)cc3Cl)c2c1] | |
| 252 | (S)-N-(2-chloro-5-(2-cyclopropyl-2H-tetrazol-5-yl)-4-methylphenyl)-5-(1-(2-hydroxy-3-methoxypropyl)-1H-pyrazol-4-yl)pyrazolo[1,5-a]pyridine-3-carboxamide | 19 |
| | 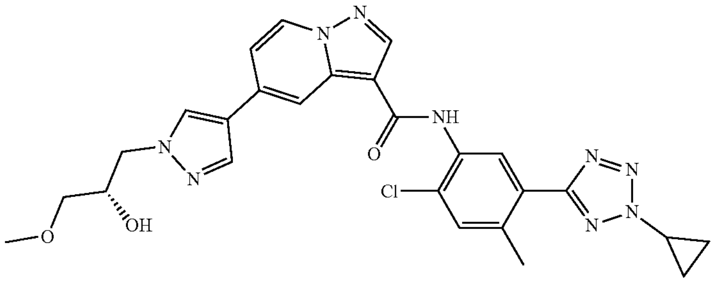 | |
| 253 | (S)-N-(2-chloro-5-(2-ethyl-2H-tetrazol-5-yl)phenyl)-5-(1-(2-hydroxypropyl)-3,5-dimethyl-1H-pyrazol-4-yl)pyrazolo[1,5-a]pyridine-3-carboxamide | 19 |
| | 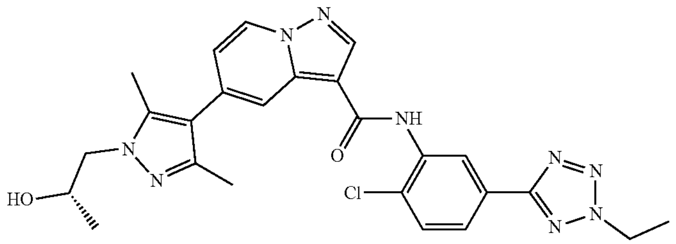 [SMILES: CCn1nnc(-c2ccc(Cl)c(NC(=O)c3cnn4ccc(-c5c(C)nn(C[C@H](C)O)c5C)cc34)c2)n1] | |
| 254 | (S)-N-(5-(2-cyclopropyl-2H-tetrazol-5-yl)-4-fluoro-2-methylphenyl)-5-(1-(2-hydroxypropyl)-3,5-dimethyl-1H-pyrazol-4-yl)pyrazolo[1,5-a]pyridine-3-carboxamide | 19 |

TABLE 1-continued

| Compound No | Name, Structure | Scheme |
| --- | --- | --- |
| | 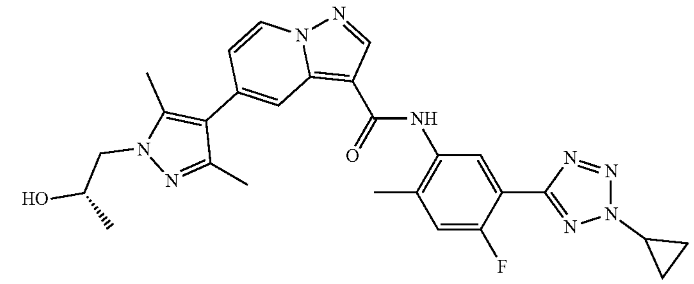 [SMILES: Cc1cc(F)c(-c2nnn(C3CC3)n2)cc1NC(=O)c1cnn2ccc(-c3c(C)nn(C[C@H](C)O)c3C)cc12] | |
| 255 | (R)-N-(5-(2-cyclopropyl-2H-tetrazol-5-yl)-4-fluoro-2-methylphenyl)-5-(1-(2-hydroxypropyl)-3-methyl-1H-pyrazol-4-yl)pyrazolo[1,5-a]pyridine-3-carboxamide | 19 |
| | 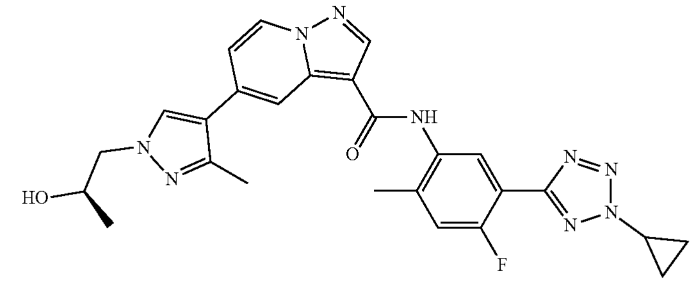 [SMILES: Cc1cc(F)c(-c2nnn(C3CC3)n2)cc1NC(=O)c1cnn2ccc(-c3cn(C[C@@H](C)O)nc3C)cc12] | |
| 256 | (S)-N-(5-(2-cyclopropyl-2H-tetrazol-5-yl)-4-fluoro-2-methylphenyl)-5-(1-(2-hydroxypropyl)-3-methyl-1H-pyrazol-4-yl)pyrazolo[1,5-a]pyridine-3-carboxamide | 19 |
| | 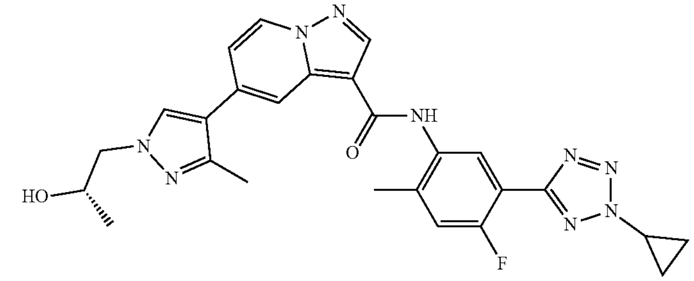 [SMILES: Cc1cc(F)c(-c2nnn(C3CC3)n2)cc1NC(=O)c1cnn2ccc(-c3cn(C[C@H](C)O)nc3C)cc12] | |
| 257 | (S)-5-(3-cyclopropyl-1-(2-hydroxy-3-methoxypropyl)-1H-pyrazol-4-yl)-N-(5-(2-cyclopropyl-2H-tetrazol-5-yl)-4-fluoro-2-methylphenyl)pyrazolo[1,5-a]pyridine-3-carboxamide | 19 |
| | 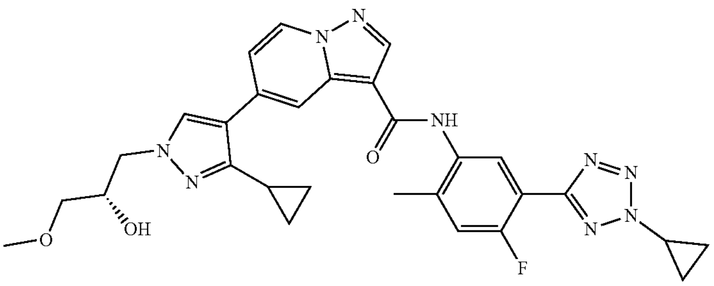 [SMILES: COC[C@@H](O)Cn1cc(-c2ccn3ncc(C(=O)Nc4cc(-c5nnn(C6CC6)n5)c(F)cc4C)c3c2)c(C2CC2)n1] | |
| 258 | (S)-5-(3-cyclopropyl-1-(2,3-dihydroxy-3-methylbutyl)-1H-pyrazol-4-yl)-N-(5-(2-cyclopropyl-2H-tetrazol-5-yl)-4-fluoro-2-methylphenyl)pyrazolo[1,5-a]pyridine-3-carboxamide | 19 |

TABLE 1-continued

| Compound No | Name, Structure | Scheme |
|---|---|---|
| | 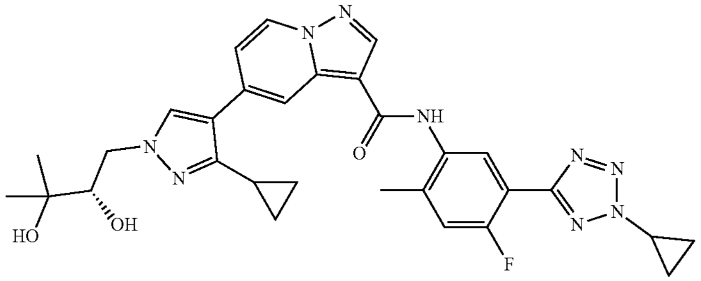 [SMILES: Cc1cc(F)c(-c2nnn(C3CC3)n2)cc1NC(=O)c1cnn2ccc(-c3cn(C[C@H](O)C(C)(C)O)nc3C3CC3)cc12] | |
| 259 | (R)-5-(3-cyclopropyl-1-(2,3-dihydroxy-3-methylbutyl)-1H-pyrazol-4-yl)-N-(5-(2-cyclopropyl-2H-tetrazol-5-yl)-4-fluoro-2-methylphenyl)pyrazolo[1,5-a]pyridine-3-carboxamide | 19 |
| | 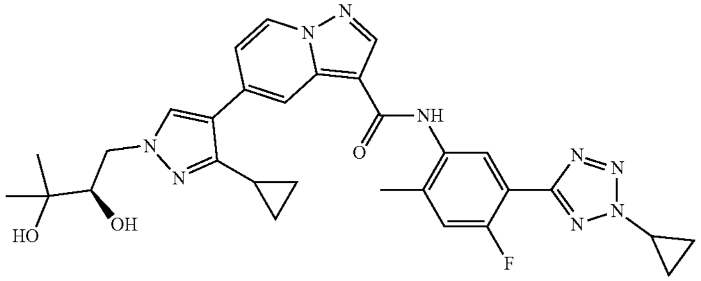 [SMILES: Cc1cc(F)c(-c2nnn(C3CC3)n2)cc1NC(=O)c1cnn2ccc(-c3cn(C[C@@H](O)C(C)(C)O)nc3C3CC3)cc12] | |
| 260 | N-(2-chloro-5-(2-cyclopropyl-2H-tetrazol-5-yl)-4-fluorophenyl)-5-(1-(2-hydroxy-2-methylpropyl)-3-methyl-1H-pyrazol-4-yl)pyrazolo[1,5-a]pyridine-3-carboxamide | 19 |
| | 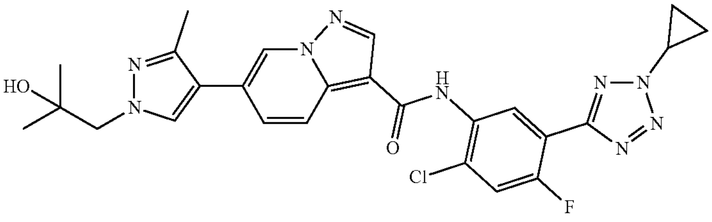 [SMILES: Cc1nn(CC(C)(C)O)cc1-c1ccc2c(C(=O)Nc3cc(-c4nnn(C5CC5)n4)c(F)cc3Cl)cnn2c1] | |
| 261 | (S)-N-(2-chloro-5-(2-cyclopropyl-2H-tetrazol-5-yl)-4-methylphenyl)-5-(1-(2-hydroxy-3-(2-methoxyethoxy)propyl)-1H-pyrazol-4-yl)pyrazolo[1,5-a]pyridine-3-carboxamide | 19 |
| | 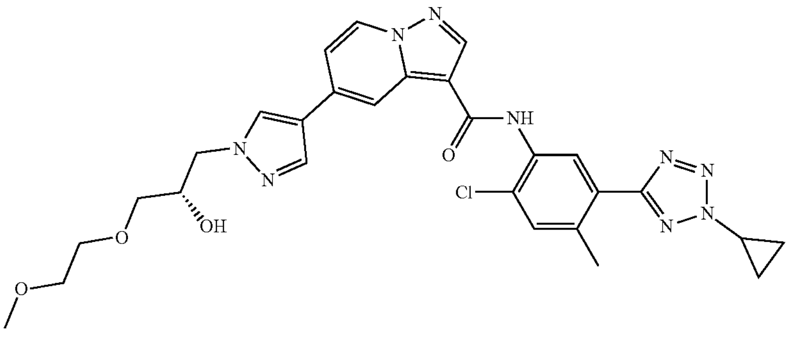 [SMILES: COCCOC[C@@H](O)Cn1cc(-c2ccn3ncc(C(=O)Nc4cc(-c5nnn(C6CC6)n5)c(C)cc4Cl)c3c2)cn1] | |
| 262 | (S)-N-(2-chloro-5-(2-cyclopropyl-2H-tetrazol-5-yl)-4-methylphenyl)-5-(1-(2-hydroxy-3-methoxypropyl)-5-methyl-1H-pyrazol-4-yl)pyrazolo[1,5-a]pyridine-3-carboxamide | 19 |

TABLE 1-continued

| Compound No | Name, Structure | Scheme |
|---|---|---|
| | 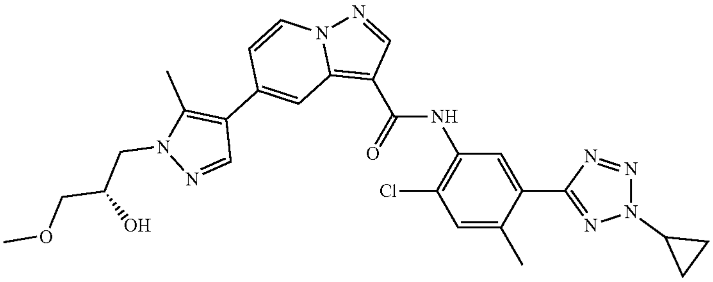 [SMILES: COC[C@@H](O)Cn1ncc(-c2ccn3ncc(C(=O)Nc4cc(-c5nnn(C6CC6)n5)c(C)cc4Cl)c3c2)c1C] | |
| 263 | (S)-N-(2-chloro-5-(2-cyclopropyl-2H-tetrazol-5-yl)phenyl)-5-(1-(2-hydroxy-3-methoxypropyl)-3-methyl-1H-pyrazol-4-yl)pyrazolo[1,5-a]pyridine-3-carboxamide | 16 |
| | 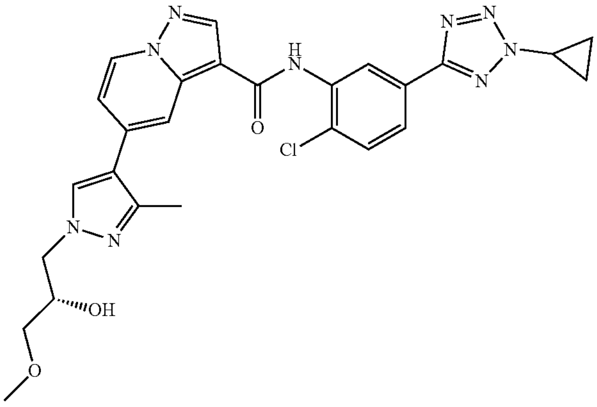 [SMILES: COC[C@@H](O)Cn1cc(-c2ccn3ncc(C(=O)Nc4cc(-c5nnn(C6CC6)n5)ccc4Cl)c3c2)c(C)n1] | |
| 264 | (S)-N-(2-chloro-5-(2-cyclopropyl-2H-tetrazol-5-yl)-4-fluorophenyl)-5-(1-(2-hydroxypropyl)-5-methyl-1H-pyrazol-4-yl)pyrazolo[1,5-a]pyridine-3-carboxamide | 19 |
| | 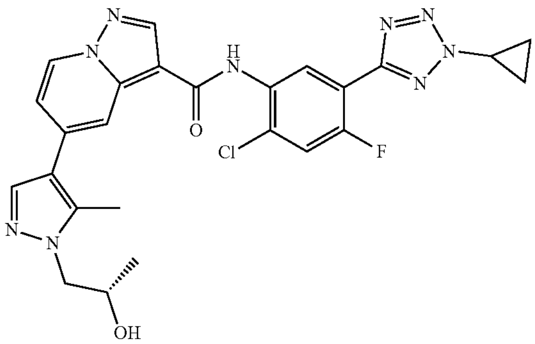 [SMILES: Cc1c(-c2ccn3ncc(C(=O)Nc4cc(-c5nnn(C6CC6)n5)c(F)cc4Cl)c3c2)cnn1C[C@H](C)O] | |
| 265 | N-(2-chloro-5-(2-ethyl-2H-tetrazol-5-yl)-4-fluorophenyl)-5-(1-(2-hydroxy-2-methylpropyl)-3-methyl-1H-pyrazol-4-yl)pyrazolo[1,5-a]pyridine-3-carboxamide | 19 |

TABLE 1-continued

| Compound No | Name, Structure | Scheme |
|---|---|---|
| | 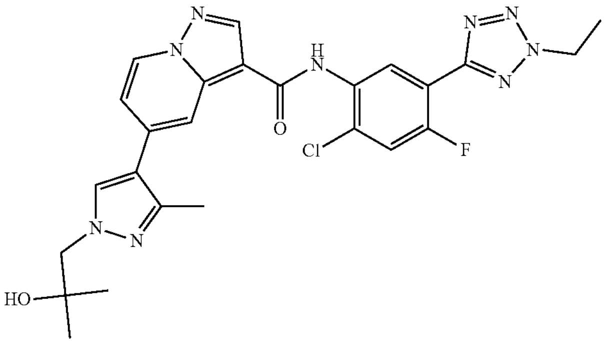 [SMILES: CCn1nnc(-c2cc(NC(=O)c3cnn4ccc(-c5cn(CC(C)(C)O)nc5C)cc34)c(Cl)cc2F)n1] | |
| 266 | (R)-N-(2-chloro-5-(2-cyclopropyl-2H-tetrazol-5-yl)phenyl)-5-(1-(2,3-dihydroxy-2-methylpropyl)-1H-pyrazol-4-yl)pyrazolo[1,5-a]pyridine-3-carboxamide 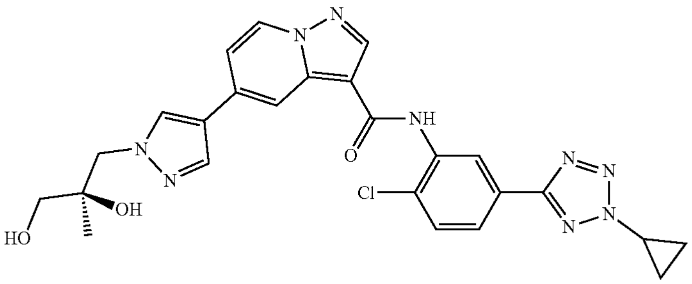 [SMILES: C[C@](O)(CO)Cn1cc(-c2ccn3ncc(C(=O)Nc4cc(-c5nnn(C6CC6)n5)ccc4Cl)c3c2)cn1] | 16 |
| 267 | (R)-N-(5-(2-cyclopropyl-2H-tetrazol-5-yl)-2-methylphenyl)-5-(1-(2-hydroxy-3-methoxy-2-methylpropyl)-1H-pyrazol-4-yl)pyrazolo[1,5-a]pyridine-3-carboxamide or (S)-N-(5-(2-cyclopropyl-2H-tetrazol-5-yl)-2-methylphenyl)-5-(1-(2-hydroxy-3-methoxy-2-methylpropyl)-1H-pyrazol-4-yl)pyrazolo[1,5-a]pyridine-3-carboxamide 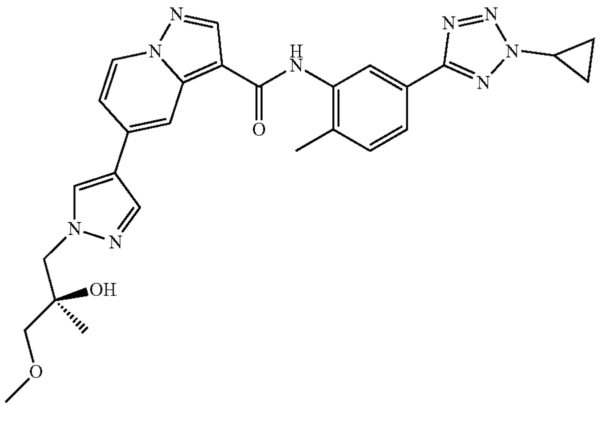 or | 16 |

TABLE 1-continued

| Compound No | Name, Structure | Scheme |
|---|---|---|
| | 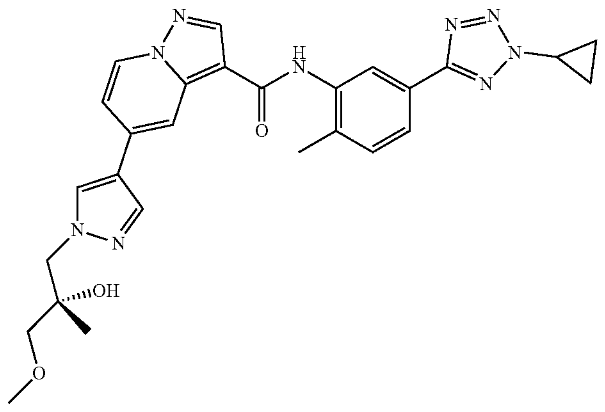 | |
| 268 | (S)-N-(5-(2-cyclopropyl-2H-tetrazol-5-yl)-2-methylphenyl)-5-(1-(2-hydroxy-3-methoxy-2-methylpropyl)-1H-pyrazol-4-yl)pyrazolo[1,5-a]pyridine-3-carboxamide or (R)-N-(5-(2-cyclopropyl-2H-tetrazol-5-yl)-2-methylphenyl)-5-(1-(2-hydroxy-3-methoxy-2-methylpropyl)-1H-pyrazol-4-yl)pyrazolo[1,5-a]pyridine-3-carboxamide | 16 |
| | 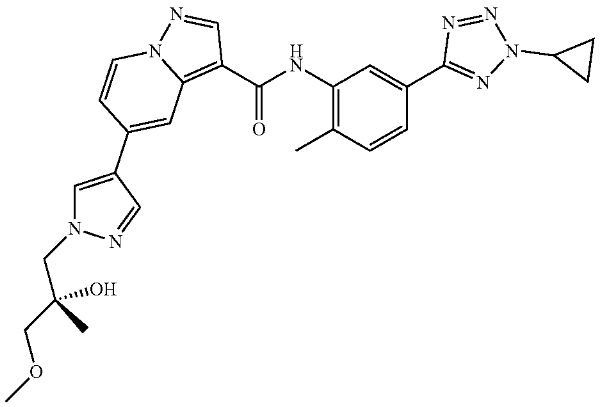 [SMILES: COC[C@@](C)(O)Cn1cc(-c2ccn3ncc(C(=O)Nc4cc(-c5nnn(C6CC6)n5)ccc4C)c3c2)cn1] or 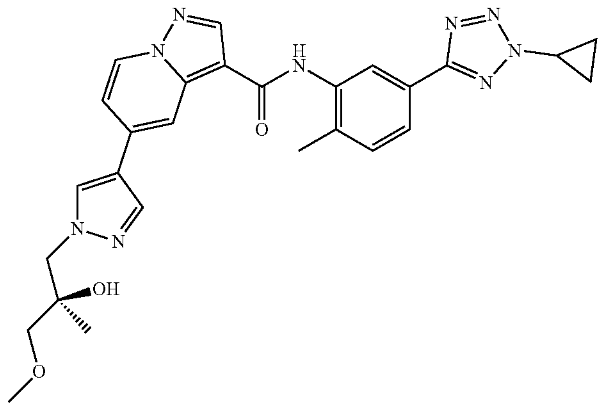 [SMILES: COC[C@](C)(O)Cn1cc(-c2ccn3ncc(C(=O)Nc4cc(-c5nnn(C6CC6)n5)ccc4C)c3c2)cn1] | |
| 269 | N-(5-(2-cyclopropyl-2H-tetrazol-5-yl)-2-methylphenyl)-5-(1-((2R,3S)-3-hydroxybutan-2-yl)-3-methyl-1H-pyrazol-4-yl)pyrazolo[1,5-a]pyridine-3-carboxamide or N-(5-(2-cyclopropyl-2H-tetrazol-5-yl)-2-methylphenyl)-5-(1-((2S,3R)-3-hydroxybutan-2-yl)-3-methyl-1H-pyrazol-4-yl)pyrazolo[1,5-a]pyridine-3-carboxamide | 16 |

TABLE 1-continued

| Compound No | Name, Structure | Scheme |
|---|---|---|
| | 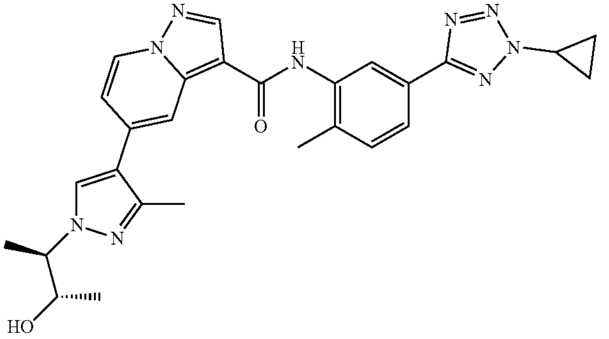 or | |
| | 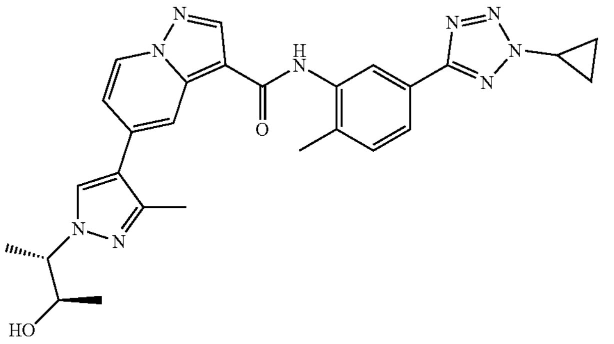 [SMILES: Cc1ccc(-c2nnn(C3CC3)n2)cc1NC(=O)c1cnn2ccc(-c3cn([C@@H](C)[C@@H](C)O)nc3C)cc12] | |
| 270 | N-(5-(2-cyclopropyl-2H-tetrazol-5-yl)-2-methylphenyl)-5-(1-((2S,3S)-3-hydroxybutan-2-yl)-5-methyl-1H-pyrazol-4-yl)pyrazolo[1,5-a]pyridine-3-carboxamide or N-(5-(2-cyclopropyl-2H-tetrazol-5-yl)-2-methylphenyl)-5-(1-((2R,3R)-3-hydroxybutan-2-yl)-5-methyl-1H-pyrazol-4-yl)pyrazolo[1,5-a]pyridine-3-carboxamide | 16 |
| | 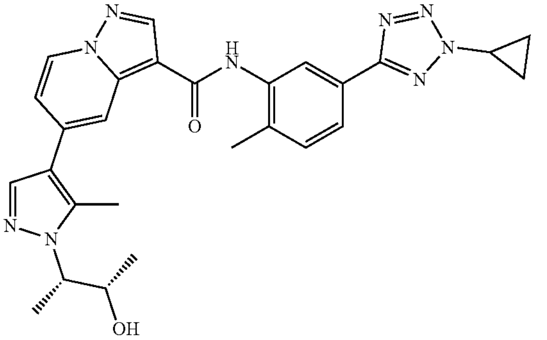 or | |
| | 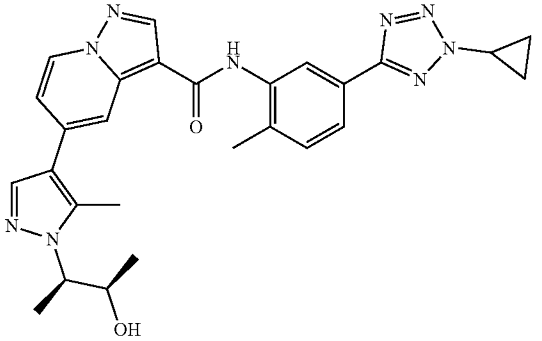 [SMILES: Cc1ccc(-c2nnn(C3CC3)n2)cc1NC(=O)c1cnn2ccc(-c3cnn([C@H](C)[C@@H](C)O)c3C)cc12] | |
| 271 | N-(2-chloro-5-(5-((1R,2S)-2-fluorocyclopropyl)-2H-tetrazol-2-yl)phenyl)-5-(1-((4-hydroxytetrahydro-2H-pyran-4-yl)methyl)-1H-pyrazol-4-yl)pyrazolo[1,5-a]pyridine-3- | 16 |

TABLE 1-continued

| Compound No | Name, Structure | Scheme |
|---|---|---|
| | carboxamide or N-(2-chloro-5-(5-((1S,2R)-2-fluorocyclopropyl)-2H-tetrazol-2-yl)phenyl)-5-(1-((4-hydroxytetrahydro-2H-pyran-4-yl)methyl)-1H-pyrazol-4-yl)pyrazolo[1,5-a]pyridine-3-carboxamide 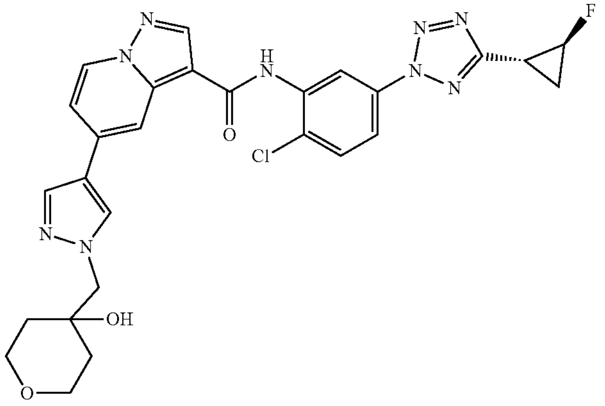 or 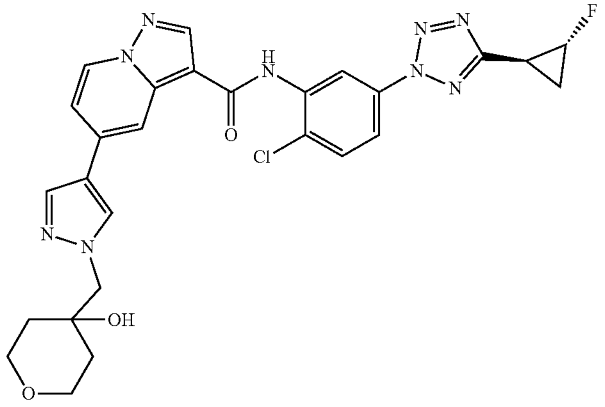 [SMILES: O=C(Nc1cc(-n2nnc([C@@H]3C[C@H]3F)n2)ccc1Cl)c1cnn2ccc(-c3cnn(CC4(O)CCOCC4)c3)cc12] | |
| 272 | N-(2-chloro-5-(5-((1R,2S)-2-fluorocyclopropyl)-2H-tetrazol-2-yl)phenyl)-5-(1-((4-hydroxytetrahydro-2H-pyran-4-yl)methyl)-3-methyl-1H-pyrazol-4-yl)pyrazolo[1,5-a]pyridine-3-carboxamide or N-(2-chloro-5-(5-((1S,2R)-2-fluorocyclopropyl)-2H-tetrazol-2-yl)phenyl)-5-(1 -((4-hydroxytetrahydro-2H-pyran-4-yl)methyl)-3-methyl-1H-pyrazol-4-yl)pyrazolo[1,5-a]pyridine-3-carboxamide 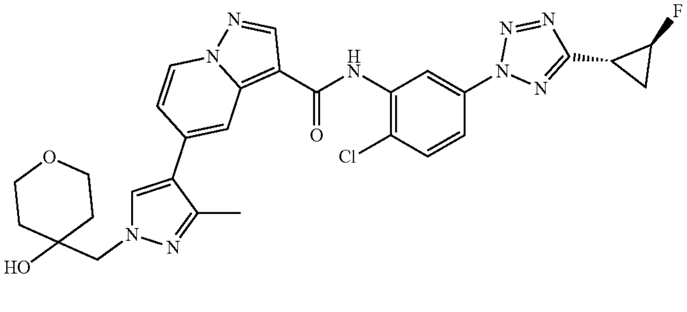 or | 16 |

TABLE 1-continued

| Compound No | Name, Structure | Scheme |
|---|---|---|
| | 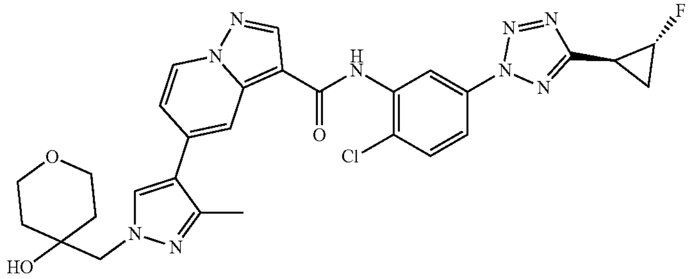 [SMILES: Cc1nn(CC2(O)CCOCC2)cc1-c1ccn2ncc(C(=O)Nc3cc(-n4nnc([C@@H]5C[C@H]5F)n4)ccc3Cl)c2c1] | |
| 273 | N-(2-chloro-5-(5-((1S,2R)-2-fluorocyclopropyl)-2H-tetrazol-2-yl)phenyl)-5-(1-((R)-2,3-dihydroxy-2-methylpropyl)-1H-pyrazol-4-yl)pyrazolo[1,5-a]pyridine-3-carboxamide or N-(2-chloro-5-(5-((1R,2S)-2-fluorocyclopropyl)-2H-tetrazol-2-yl)phenyl)-5-(1-((R)-2,3-dihydroxy-2-methylpropyl)-1H-pyrazol-4-yl)pyrazolo[1,5-a]pyridine-3-carboxamide<br>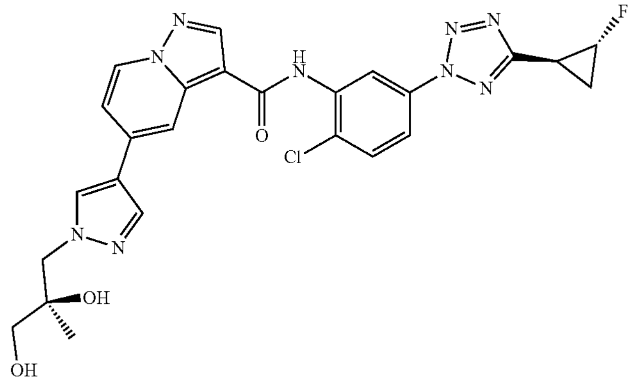 or<br>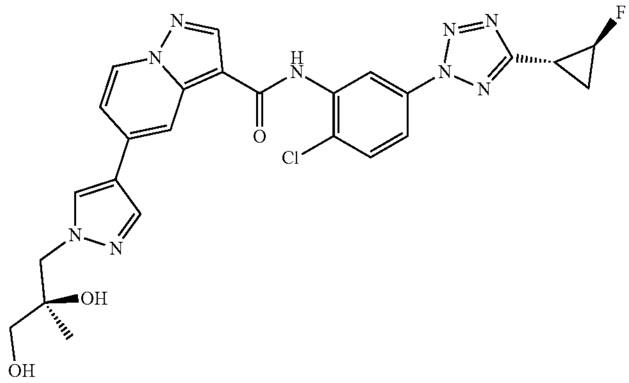 [SMILES: C[C@](O)(CO)Cn1cc(-c2ccn3ncc(C(=O)Nc4cc(-n5nnc([C@H]6C[C@@H]6F)n5)ccc4Cl)c3c2)cn1] | 16 |
| 274 | (R)-N-(2-chloro-5-(2-cyclopropyl-2H-tetrazol-5-yl)phenyl)-5-(3,5-dimethyl-1-((4-methylmorpholin-2-yl)methyl)-1H-pyrazol-4-yl)pyrazolo[1,5-a]pyridine-3-carboxamide<br>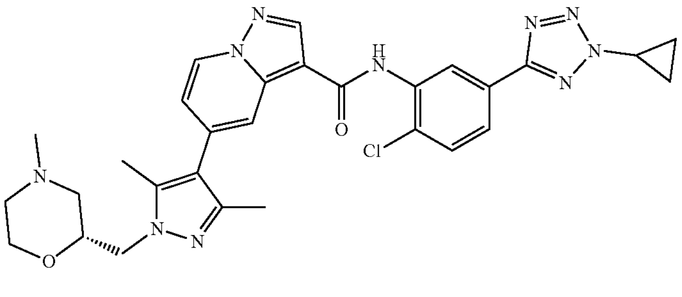 [SMILES: Cc1nn(C[C@H]2CN(C)CCO2)c(C)c1-c1ccn2ncc(C(=O)Nc3cc(-c4nnn(C5CC5)n4)ccc3Cl)c2c1] | 16 |

TABLE 1-continued

| Compound No | Name, Structure | Scheme |
|---|---|---|
| 275 | (S)-N-(2-chloro-5-(2-cyclopropyl-2H-tetrazol-5-yl)phenyl)-5-(1-(2,3-dihydroxypropyl)-3,5-dimethyl-1H-pyrazol-4-yl)pyrazolo[1,5-a]pyridine-3-carboxamide 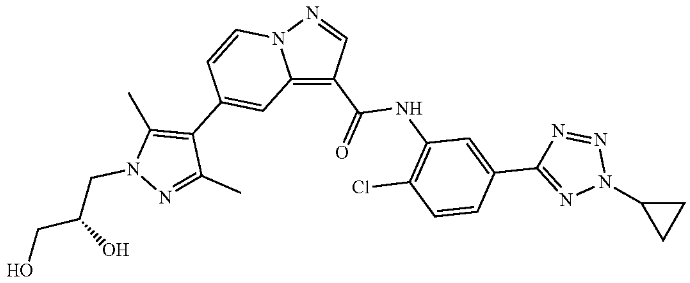 [SMILES: Cc1nn(C[C@H](O)CO)c(C)c1-c1ccn2ncc(C(=O)Nc3cc(-c4nnn(C5CC5)n4)ccc3Cl)c2c1] | 16 |
| 276 | N-(2-chloro-5-(2-cyclopropyl-2H-tetrazol-5-yl)phenyl)-5-(1-(1,3-dihydroxypropan-2-yl)-3,5-dimethyl-1H-pyrazol-4-yl)pyrazolo[1,5-a]pyridine-3-carboxamide 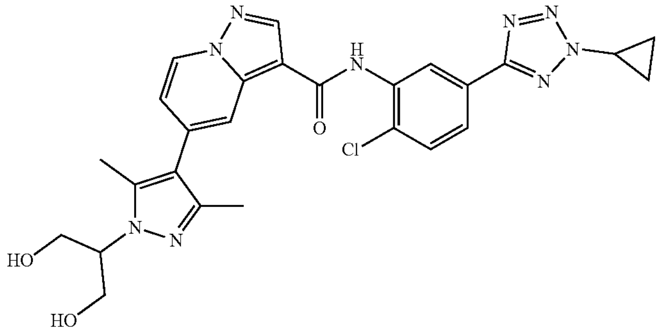 [SMILES: Cc1nn(C(CO)CO)c(C)c1-c1ccn2ncc(C(=O)Nc3cc(-c4nnn(C5CC5)n4)ccc3Cl)c2c1] | 16 |
| 277 | N-(5-(5-cyclopropyl-2H-tetrazol-2-yl)-2-methylphenyl)-4-fluoro-6-(1-((4-hydroxytetrahydro-2H-pyran-4-yl)methyl)-1H-pyrazol-4-yl)pyrazolo[1,5-a]pyridine-3-carboxamide 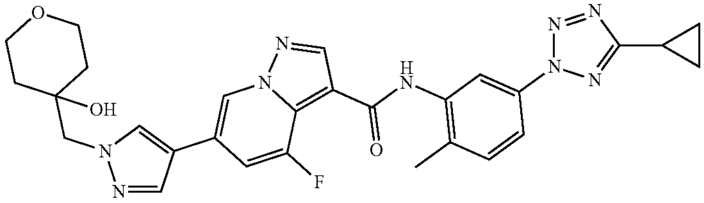 [SMILES: Cc1ccc(-n2nnc(C3CC3)n2)cc1NC(=O)c1cnn2cc(-c3cnn(CC4(O)CCOCC4)c3)cc(F)c12] | 16 |
| 278 | (S)-N-(2-chloro-5-(2-cyclopropyl-2H-tetrazol-5-yl)phenyl)-5-(1-(2-hydroxypropyl)-3-methyl-1H-pyrazol-4-yl)pyrazolo[1,5-a]pyridine-3-carboxamide 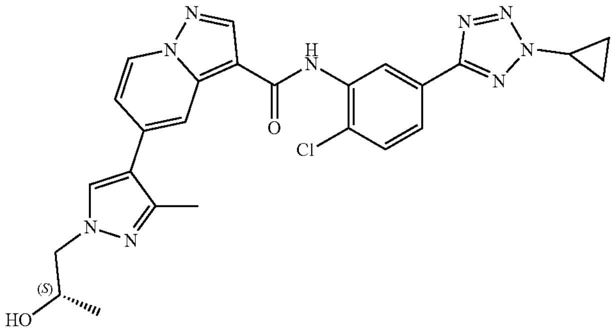 | 16 |
| 279 | (R)-N-(2-chloro-5-(2-cyclopropyl-2H-tetrazol-5-yl)-4-fluorophenyl)-5-(1-(2-hydroxy-3-methoxypropyl)-3-methyl-1H-pyrazol-4-yl)pyrazolo[1,5-a]pyridine-3-carboxamide | 19 |

TABLE 1-continued

| Compound No | Name, Structure | Scheme |
|---|---|---|
| | 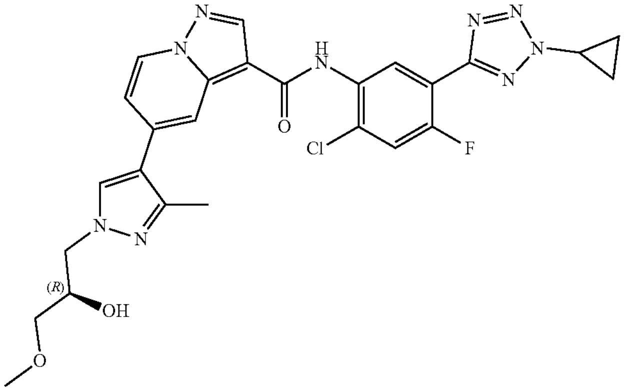 | |
| 280 | (S)-N-(2-chloro-5-(2-cyclopropyl-2H-tetrazol-5-yl)-4-fluorophenyl)-5-(1-(2-hydroxypropyl)-3-methyl-1H-pyrazol-4-yl)pyrazolo[1,5-a]pyridine-3-carboxamide | 19 |
| | 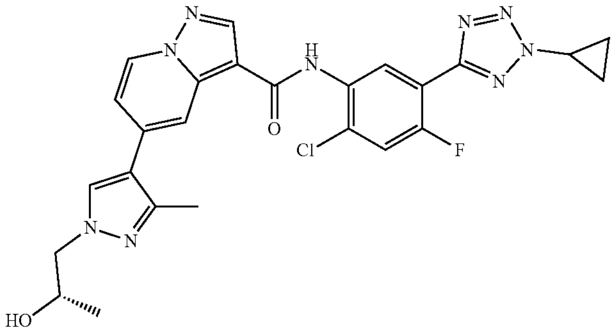 [SMILES: Cc1nn(C[C@H](C)O)cc1-c1ccn2ncc(C(=O)Nc3cc(-c4nnn(C5CC5)n4)c(F)cc3Cl)c2c1] | |
| 281 | (R)-N-(2-chloro-5-(2-cyclopropyl-2H-tetrazol-5-yl)-4-fluorophenyl)-5-(1-(2-hydroxypropyl)-3-methyl-1H-pyrazol-4-yl)pyrazolo[1,5-a]pyridine-3-carboxamide | 19 |
| | 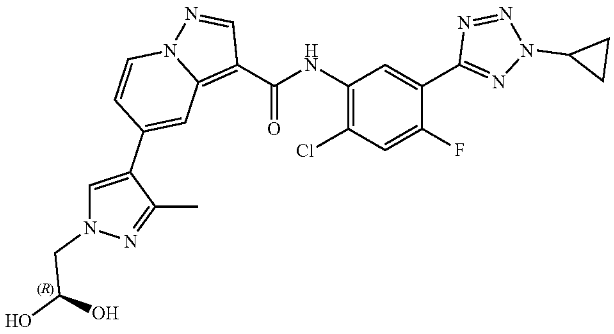 | |
| 282 | (S)-N-(2-chloro-5-(2-ethyl-2H-tetrazol-5-yl)-4-fluorophenyl)-5-(1-(2-hydroxy-3-methoxypropyl)-3-methyl-1H-pyrazol-4-yl)pyrazolo[1,5-a]pyridine-3-carboxamide | 19 |

TABLE 1-continued

| Compound No | Name, Structure | Scheme |
|---|---|---|
| | 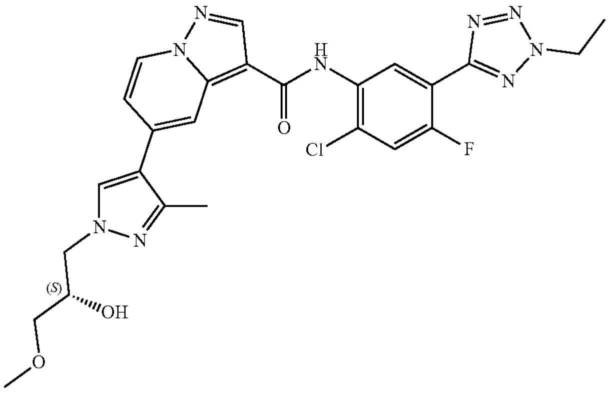 | |
| 283 | (S)-N-(2-chloro-5-(2-ethyl-2H-tetrazol-5-yl)-4-fluorophenyl)-5-(1-(2-hydroxy-3-(2-methoxyethoxy)propyl)-3-methyl-1H-pyrazol-4-yl)pyrazolo[1,5-a]pyridine-3-carboxamide | 19 |
| | 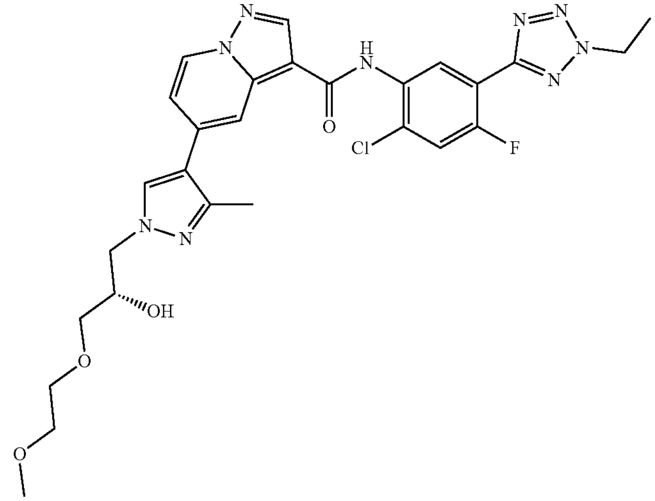 [SMILES: CCn1nnc(-c2cc(NC(=O)c3cnn4ccc(-c5cn(C[C@H](O)COCCOC)nc5C)cc34)c(Cl)cc2F)n1] | |
| 284 | (S)-N-(2-chloro-5-(2-ethyl-2H-tetrazol-5-yl)phenyl)-5-(1-(2-hydroxy-3-methoxypropyl)-3-methyl-1H-pyrazol-4-yl)pyrazolo[1,5-a]pyridine-3-carboxamide | 19 |
| | 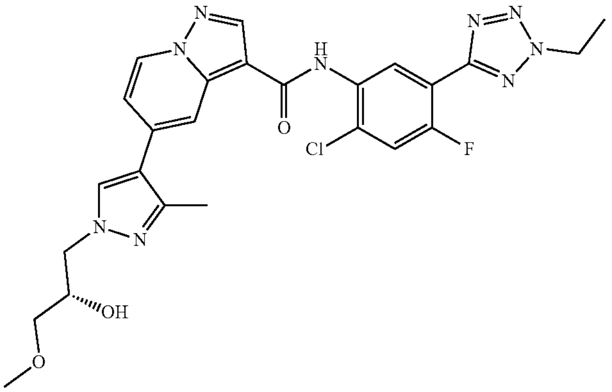 [SMILES: CCn1nnc(-c2cc(NC(=O)c3cnn4ccc(-c5cn(C[C@H](O)COC)nc5C)cc34)c(Cl)cc2F)n1] | |
| 285 | (S)-N-(2-chloro-5-(2-cyclopropyl-2H-tetrazol-5-yl)-4-fluorophenyl)-5-(1-(2-hydroxy-3-(2-methoxyethoxy)propyl)-3-methyl-1H-pyrazol-4-yl)pyrazolo[1,5-a]pyridine-3-carboxamide | 19 |

TABLE 1-continued

| Compound No | Name, Structure | Scheme |
|---|---|---|
| | 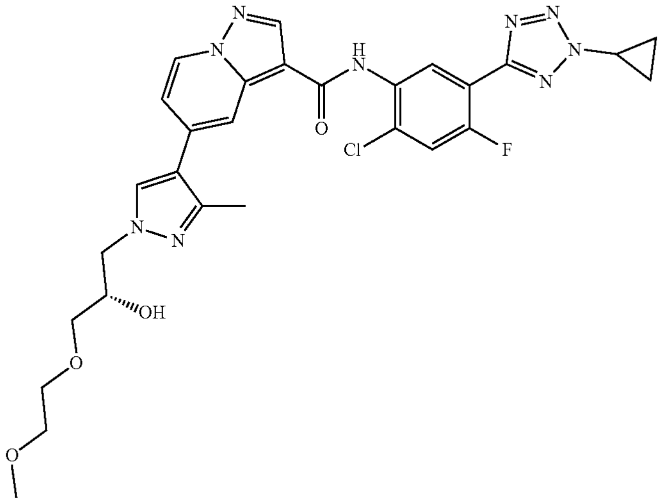 [SMILES: COCCOC[C@@H](O)Cn1cc(-c2ccn3ncc(C(=O)Nc4cc(-c5nnn(C6CC6)n5)c(F)cc4Cl)c3c2)c(C)n1] | |
| 286 | (R)-N-(2-chloro-5-(2-cyclopropyl-2H-tetrazol-5-yl)-4-fluorophenyl)-5-(1-(2-hydroxy-3-(2-methoxyethoxy)propyl)-3-methyl-1H-pyrazol-4-yl)pyrazolo[1,5-a]pyridine-3-carboxamide | 19 |
| | 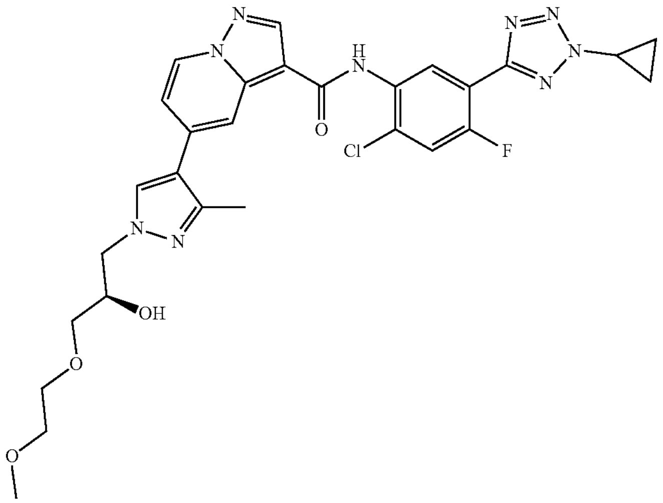 [SMILES: COCCOC[C@H](O)Cn1cc(-c2ccn3ncc(C(=O)Nc4cc(-c5nnn(C6CC6)n5)c(F)cc4Cl)c3c2)c(C)n1] | |
| 287 | N-(2-chloro-5-(2-cyclopropyl-2H-tetrazol-5-yl)-4-fluorophenyl)-5-(1-((2R,3R)-3-hydroxybutan-2-yl)-3-methyl-1H-pyrazol-4-yl)pyrazolo[1,5-a]pyridine-3-carboxamide or N-(2-chloro-5-(2-cyclopropyl-2H-tetrazol-5-yl)-4-fluorophenyl)-5-(1-((2S,3S)-3-hydroxybutan-2-yl)-3-methyl-1H-pyrazol-4-yl)pyrazolo[1,5-a]pyridine-3-carboxamide | 19 |
| | 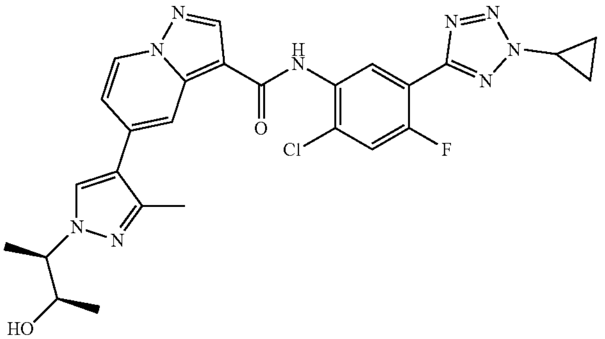 or | |

TABLE 1-continued

| Compound No | Name, Structure | Scheme |
|---|---|---|
| | 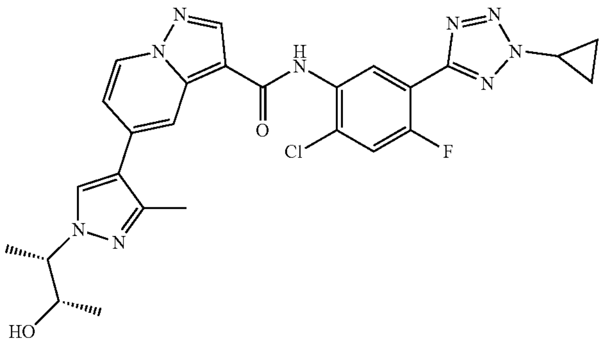 | |
| 288 | N-(2-chloro-5-(2-cyclopropyl-2H-tetrazol-5-yl)-4-fluorophenyl)-5-(1-((2S,3S)-3-hydroxybutan-2-yl)-3-methyl-1H-pyrazol-4-yl)pyrazolo[1,5-a]pyridine-3-carboxamide or N-(2-chloro-5-(2-cyclopropyl-2H-tetrazol-5-yl)-4-fluorophenyl)-5-(1-((2R,3R)-3-hydroxybutan-2-yl)-3-methyl-1H-pyrazol-4-yl)pyrazolo[1,5-a]pyridine-3-carboxamide | 19 |
| | 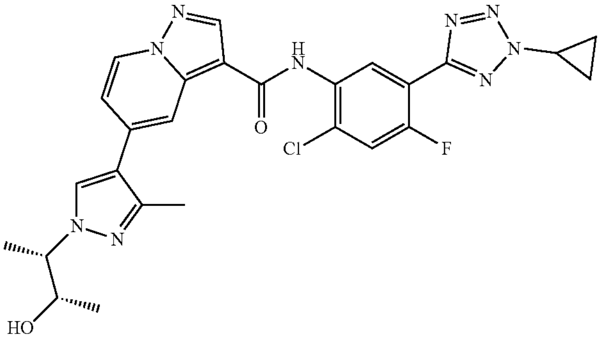 [SMILES: Cc1nn([C@@H](C)[C@H](C)O)cc1-c1ccn2ncc(C(=O)Nc3cc(-c4nnn(C5CC5)n4)c(F)cc3Cl)c2c1] or 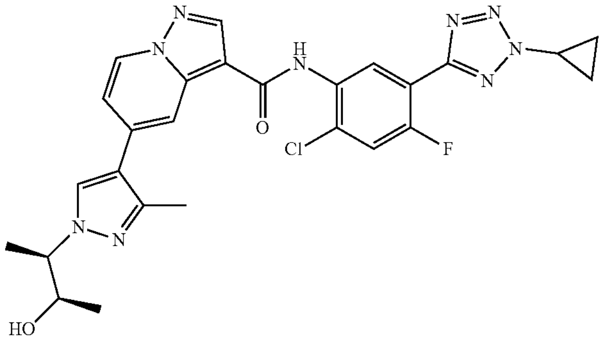 [SMILES: Cc1nn([C@H](C)[C@@H](C)O)cc1-c1ccn2ncc(C(=O)Nc3cc(-c4nnn(C5CC5)n4)c(F)cc3Cl)c2c1] | |
| 289 | N-(2-chloro-5-(2-cyclopropyl-2H-tetrazol-5-yl)-4-fluorophenyl)-5-(1-((2R,3S)-3-hydroxybutan-2-yl)-3-methyl-1H-pyrazol-4-yl)pyrazolo[1,5-a]pyridine-3-carboxamide or N-(2-chloro-5-(2-cyclopropyl-2H-tetrazol-5-yl)-4-fluorophenyl)-5-(1-((2S,3R)-3-hydroxybutan-2-yl)-3-methyl-1H-pyrazol-4-yl)pyrazolo[1,5-a]pyridine-3-carboxamide | 19 |

TABLE 1-continued

| Compound No | Name, Structure | Scheme |
|---|---|---|
| | 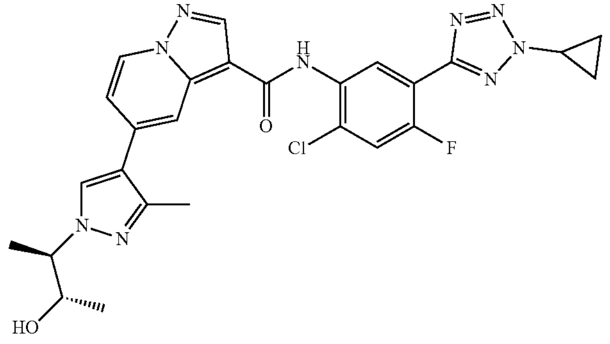 or | |
| | 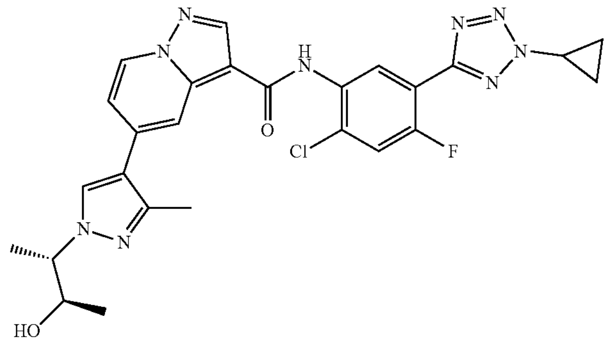 [SMILES: Cc1nn([C@@H](C)[C@@H](C)O)cc1-c1ccn2ncc(C(=O)Nc3cc(-c4nnn(C5CC5)n4)c(F)cc3Cl)c2c1] | |

As used herein, the term "pharmaceutically acceptable salt" refers to pharmaceutical salts that are, within the scope of sound medical judgment, suitable for use in contact with the tissues of humans and lower animals without undue toxicity, irritation, and allergic response, and are commensurate with a reasonable benefit/risk ratio.

Pharmaceutically acceptable salts are known in the art. For example, S. M. Berge et al. describes pharmacologically acceptable salts in J. Pharm. Sci. (1977) 66:1-19. Compounds of this disclosure with basic groups can form pharmaceutically acceptable salts with pharmaceutically acceptable acid(s). Suitable pharmaceutically acceptable acid addition salts of the compounds described herein include salts of inorganic acids (such as hydrochloric acid, hydrobromic, phosphoric, nitric, and sulfuric acids) and of organic acids (such as acetic acid, benzenesulfonic, benzoic, methanesulfonic, and p-toluenesulfonic acids). Compounds of this disclosure with acidic groups can form pharmaceutically acceptable salts with pharmaceutically acceptable base(s). Suitable pharmaceutically acceptable basic salts include ammonium salts, alkali metal salts (such as sodium and potassium salts) and alkaline earth metal salts (such as magnesium and calcium salts).

The following abbreviations and terms have the indicated meanings throughout:

The term "alkyl" used alone or as part of a larger moiety, such as "alkoxy", "alkylphenyl", alkylspirocycloalkyl" and the like, means a saturated aliphatic straight-chain or branched monovalent hydrocarbon radical. Unless otherwise specified, an alkyl group typically has 1 to 6 carbon atoms ($C_{1-6}$ alkyl) (i.e., 1, 2, 3, 4, 5 or 6), alternatively, 1 to 4 carbon atoms ($C_{1-4}$ alkyl) (i.e., 1, 2, 3, or 4), alternatively, 1 to 3 carbon atoms ($C_{1-3}$ alkyl) (i.e., 1, 2 or 3). Examples include methyl, ethyl, propyl, isopropyl, butyl, tert-butyl, and the like.

The term "alkoxy", used alone or as part of a larger moiety, such as haloalkoxy or alkylalkoxy, means a saturated aliphatic straight-chain or branched monovalent radical composed of an alkyl group bonded to oxygen. Unless otherwise specified, an alkoxy group typically has 1 to 6 (i.e., 1, 2, 3, 4, 5, or 6) carbon atoms and an oxygen atom ($C_{1-6}$alkoxy), alternatively, 1 to 4 (i.e., 1, 2, 3, or 4) carbon atom and an oxygen atom ($C_{1-4}$ alkoxy). Examples of alkoxy include methoxy, ethoxy, and the like.

The term "halogen" or "halo" means fluorine or fluoro (F), chlorine or chloro (Cl) or bromine or bromo (Br).

The term "haloalkyl", used alone or as part of a large moiety, such as haloalkoxy or alkylhaloalkoxy, means an alkyl group wherein at least one hydrogen substituent is replaced by a halogen group. Unless otherwise specified, a haloalkyl group typically has 1 to 6 (i.e., 1, 2, 3, 4, 5, or 6) carbon atoms ($C_{1-6}$haloalkyl), alternatively, 1 to 4 (i.e., 1, 2, 3, or 4) carbon atoms ($C_{1-4}$ haloalkyl). Examples include trifluoromethyl, trifluoroethyl, difluoroethyl, and the like.

The term "haloalkoxy", used alone or as part of a larger moiety, such as alkylhaloalkoxy, means an alkoxy group wherein at least one hydrogen substituent is replaced by a halogen. Unless otherwise specified, an haloalkoxy typically has 1 to 6 (i.e., 1, 2, 3, 4, 5 or 6), carbon atoms ($C_{1-6}$ haloalkoxy), alternatively 1 to 4 (i.e., 1, 2, 3, or 4), carbon atoms ($C_{1-4}$ haloalkoxy). Examples include difluoroethoxy and the like.

The term "cycloalkyl", used alone or as part of a larger moiety, such as alkylcycloalkyl, means a saturated aliphatic monocyclic hydrocarbon ring radical. Unless otherwise specified, a cycloalkyl has 3 to 6 (i.e., 3, 4, 5, or 6) ring carbon atoms ($C_{3-6}$ cycloalkyl), alternatively, 3 to 5 (i.e., 3, 4, or 5) ring carbon atoms ($C_{3-5}$ cycloalkyl), alternatively, 3 to 4 carbon atoms ($C_{3-4}$ cycloalkyl). Examples of cycloalkyl include cyclopropyl, cyclobutyl, and the like.

The term "spirocycloalkyl", used alone or as part of a large moiety such as alkylspirocycloalkyl, means a group comprising two cycloalkyls which share one common ring atom. Unless otherwise specific, a spirocycloalkyl has 6 to 11 (i.e., 6, 7, 8, 9, 10, or 11) ring carbon atoms. Examples include 3,4-bicyclooctanyl, 4,4-bicyclononanyl, 3,5-bicyclononanyl, 3,6-bicyclodecanyl, 4,5-bicyclodecanyl, 3,7-bicycloundecanyl, 4,6-bicycloundecanyl and 5,5-bicycloundecanyl.

The term "bridgedbicycloalkyl", used alone or a part of a larger moiety such as alkylbridgedbicycloalkyl, means a group comprising two cycloalkyl groups sharing 3 or 4 adjacent ring atoms. Unless otherwise specified, a bridgedbicycloalkyl has 5-10 ring carbon atoms. Examples include bicyclo[2.2.1]hepantyl, bicyclo[2.2.2]octantyl, bicyclo[3.2.1]octanyl, bicyclo[3.2.2]nonanyl and bicyclo[3.3.1]nonanyl.

The term "heterocycle", used alone or a part of a larger moiety such as alkylheterocycle, refers to a monocyclic non-aromatic ring radical containing unless otherwise specified, 4 to 6 ring atoms (i.e., "4, 5, or 6 membered") selected from carbon atoms and 1 or 2 heteroatoms. Each heteroatom is independently selected from nitrogen (N) and oxygen (O). Nitrogen containing heterocycles include azetidinyl, pyrrolidinyl, piperidinyl, piperazinyl, morpholinyl, and the like. Oxygen containing heterocycles include oxetanyl, tetrahydrofuranyl, tetrahydropyranyl, and the like. Heterocycles that contain both N and O include morpholinyl and the like.

The term "spiroheterocycle", used alone or a part of a larger moiety such as alkylspiroheterocycle, refers to a bicyclic non-aromatic ring radical comprising a heterocycle which shares one ring atom with a cycloalkyl or a second heterocycle. Unless otherwise specified, a spiroheterocycle has 7 to 11 ring atoms (i.e., "7, 8, 9, 10 or 11 membered") selected from carbon atoms and 1 or 2 heteroatoms. Each heteroatom is independently selected from nitrogen and oxygen. Examples of 7 to 11 nitrogen containing spiro rings systems include, but not limited to, 3,3-azabicycloheptanyl, 3,4-azabicyclooctanyl, 4,4-azabicyclononanyl, 3,5-azabicyclononanyl, 3,6-azabicyclodecanyl, 4,5-azabicyclodecanyl, 3,7-azabicycloundecanyl, 4,6-azabicycloundecanyl and 5,5-azabicycloundecanyl. Examples of 7-11 oxygen containing spiro ring systems include, but not limited to, 3,3-oxobicycloheptanyl, 3,4-oxobicyclooctanyl, 4,4-oxobicyclononanyl, 3,5-oxobicyclononanyl, 3,6-oxobicyclodecanyl, 4,5-oxobicyclodecanyl, 3,7-oxobicycloundecanyl, 4,6-oxobicycloundecanyl, 5,5-oxobicycloundecanyl, 2-oxa-6$\lambda^2$-asaspiro[3,3]hepatanyl, 2-oxa-6$\lambda^2$-asaspiro[3,4]octanyl, 2-oxa-6$\lambda^2$-asaspiro[3,5]nonanyl, 6-oxa-2$\lambda^2$-asaspiro[3,3]hepatanyl, 6-oxa-2$\lambda^2$-asaspiro[3,4]octanyl and 6-oxa-2$\lambda^2$-asaspiro[3,5]nonany.

The term "fused bicycloheterocycle" refers to a bicyclic non-aromatic ring radical wherein a heterocycle shares two adjacent ring atoms with a cycloalkyl or a second heterocyle. Unless otherwise specified, a bicycloheterocycle has 7 to 10 ring atoms (i.e., "7, 8, 9, or 10 membered") selected from carbon atoms and 1 or 2 heteroatoms. Each heteroatom is independently selected from nitrogen and oxygen. Examples of nitrogen containing bicycloheterocycle include, but not limited to, azabicyclo[3.2.0]hepantyl, azabicyclo[4.2.0]octantyl, azabicyclo[3.3.0]octanyl, azabicyclo[4.3.0]nonanyl, azabicyclo[5.2.0]nonanyl, diazabicyclo[3.2.0]hepantyl, diazabicyclo[3.3.0]octanyl and diazabicyclo[4.3.0]nonanyl. Examples of oxygen containing bicycloheterocycle include, but not limited, oxobicyclo[3.2.0]hepantyl, oxobicyclo[4.2.0]octantyl, oxobicyclo[3.3.0]octanyl, oxobicyclo[4.3.0]nonanyl, oxobicyclo[5.2.0]nonanyl, dioxobicyclo[3.2.0]hepantyl, dioxobicyclo[3.3.0]octanyl, and dioxobicyclo[4.3.0]nonanyl. Examples of fused bicycloheterocycles containing both nitrogen and oxygen atoms include hexahydro-1H-2λ-pyrrolo-[2,1-c]pyrazine.

The term "bridgedbicycloheterocycle", used alone or a part of a larger moiety such as alkylbridgedbicycloheterocycle, refers to a bicyclic non-aromatic ring radical comprising a heterocycle which shares three or four adjacent ring atoms with a cycloalkyl or a second heterocyle. Unless otherwise specified, a bridgedbicyclheterocycle has 5 to 10 ring atoms (i.e., "5, 6, 7, 8, 9 or 10 membered") selected from carbon atoms and 1 or 2 heteroatoms. Each heteroatom is independently selected from nitrogen and oxygen. Examples nitrogen containing bridged bicyclics include, but not limited to, azabicyclo[2.2.1]hepantyl, azabicyclo[2.2.2]octantyl, azabicyclo[3.2.1]octanyl, azabicyclo[3.2.2]nonanyl, azabicyclo[3.3.1]nonanyl, diazabicyclo[2.2.1]hepantyl, diazabicyclo[3.2.1]octanyl and diazabicyclo[3.3.1]nonanyl. Examples of oxygen containing bridged bicyclics include, but not limited to, oxobicyclo[2.2.1]hepantyl, oxobicyclo[2.2.2]octantyl, oxobicyclo[3.2.1]octanyl, oxobicyclo[3.2.2]nonanyl, and oxobicyclo[3.3.1]nonanyl. Examples of bridgedbicycloheterocycles containing both oxygen and nitrogen atoms include: oxa-azabicyclo[2.2.1]hepantyl, oxa-azabicyclo[3.2.1]octanyl and oxa-azabicyclo[3.3.1]nonanyl.

"Heteroaryl" refers to an aromatic 5- to 6-membered monocyclic ring system, having 1 to 4 (i.e., 1, 2, 3, or 4) heteroatoms independently selected from O, N and S, and wherein N can be oxidized (e.g., N(O)) or quaternized, and S can be optionally oxidized to sulfoxide and sulfone. Examples of 5- to 6-membered monocyclic heteroaryls include, but are not limited to, pyrrolyl, furanyl, thienyl, imidazolyl, pyrazolyl, oxazolyl, isoxazolyl, thiazolyl, isothiazolyl, oxadiazolyl, thiadiazolyl, triazolyl, tetrazolyl, pyridinyl, pyrazinyl, pyrimidinyl, pyridazinyl and the like.

The term "substituted", whether preceded by the term "optionally" or not, refers to the replacement of a hydrogen substituent in a given structure with a non-hydrogen substituent. Thus, for example, a substituted alkyl is an alkyl wherein at least one non-hydrogen substituent is in the place of a hydrogen substituent on the alkyl group. To illustrate, monofluoroalkyl is an alkyl substituted with a fluoro substituent, and difluoroalkyl is an alkyl substituted with two fluoro substituents. It should be recognized that if there is more than one substitution on a substituent, each non-hydrogen substituent can be identical or different (unless otherwise stated).

When a substituent is described as a string or series of groups, such as "$C_{0-5}$alkylphenyl", "$C_{0-5}$alkyl$C_{3-6}$cycloalkyl", "$C_{0-5}$alkyl$C_{6-10}$spirocycloalkyl" or "$C_{0-5}$alkyl$C_{5-10}$bridgedbicycloalkyl", the substitutent is attached to the remainder of the compound via the first group in the sequence. By the way of example, $C_{0-5}$alkylphenyl is attached to the remainder of the compound via the $C_{0-5}$alkyl, which, in turn, is attached to the phenyl. $C_{0-5}$alkylphenyl could also be designated as $-(CH_2)_{0-5}$phenyl. $C_{0-5}$alkyl$C_{3-6}$ cycloalkyl is attached to the remainder of the compound via the $C_{0-5}$ alkyl, which, in turn is bonded to the $C_{3-6}$cycloalkyl. $C_{0-5}$alkyl$C_{3-6}$ cycloalkyl could also be drafted as $-(CH_2)_{0-5}$($C_{3-6}$cycloalkyl). $C_{0-5}$alkyl$C_{6-10}$spirocycloalkyl is attached to the remainder of the compound via the $C_{0-5}$alkyl, which, in turn, is bonded to the $C_{6-10}$spirocycloalkyl. $C_{0-5}$alkyl$C_{6-10}$spirocycloalkyl could also be drafted as $-(CH_2)_{0-5}$($C_{6-10}$spirocycloalkyl. $C_{0-4}$alkyl$C_{1-6}$alkoxy is attached to reminder of the compound via $C_{0-4}$alkyl which, in turn, is attached to the $C_{1-6}$alkoxy. $C_{0-4}$alkyl$C_{1-6}$alkoxy could also be drafted as —$(CH_2)_{0-4}(C_{1-6}$alkoxy). "$C_{1-4}$alkyl (OH)$C_1$-$C_4$alkoxy" (e.g., propyl(OH)methoxy) refers to a $C_{1-4}$ alkyl group that is bonded to a hydroxyl and alkoxy group; and "$C_{2-5}$alkyl(OH)($C_{1-5}$alkoxy)($C_{1-5}$alkoxy)" refers to a $C_{2-5}$alkyl group which is bonded to a hydroxyl and $C_{1-5}$alkoxy group and wherein the $C_{1-5}$alkxoy group is in turn bonded to another $C_{1-5}$alkoxy group.

If a group is described as "optionally substituted", the group can be either (1) not substituted or (2) substituted. If a group is described as optionally substituted with up to a particular number of non-hydrogen substituents, that group can be either (1) not substituted; or (2) substituted by up to that particular number of non-hydrogen substituents or by up to the maximum number of substitutable positions on the substituent, whichever is less. Thus, for example, if a group is described as a cycloalkyl optionally substituted with up to 3 non-hydrogen substituents, then any cycloalkyl with less than 3 substitutable positions would be optionally substituted by up to only as many non-hydrogen substituents as the cycloalkyl has substitutable positions.

Compounds having one or more chiral centers can exist in various stereoisomeric forms, i.e., each chiral center can have an R or S configuration or can be a mixture of both. Stereoisomers are compounds that differ only in their spatial arrangement. Stereoisomers include all diastereomeric and enantiomeric forms of a compound. Enantiomers are stereoisomers that are non-superimposable mirror images of each other. Diastereomers are stereoisomers having two or more chiral centers that are not identical and are not mirror images of each other.

When the stereochemical configuration at a chiral center in a compound having one or more chiral centers is depicted by its chemical name (e.g., where the configuration is indicated in the chemical name by "R" or "S") or structure (e.g., the configuration is indicated by "wedge" bonds), the enrichment of the indicated configuration relative to the opposite configuration is greater than 50%, 60%, 70%, 80%, 90%, 99% or 99.9%.

"Enrichment of the indicated configuration relative to the opposite configuration" is a mole percent and is determined by dividing the number of compounds with the indicated stereochemical configuration at the chiral center(s) by the total number of all of the compounds with the same or opposite stereochemical configuration in a mixture.

When two or more stereoisomers are depicted by their chemical names or structures, and the names or structures are connected by an "or", one or the other of the two or more stereoisomers is intended, but not both. The enrichment of one stereoisomer relative to the other is as indicated above.

When a disclosed compound having a chiral center is depicted by a structure without showing a configuration at that chiral center, the structure is meant to encompass the compound with the S configuration at that chiral center, the compound with the R configuration at that chiral center, or the compound with a mixture of the R and S configuration at that chiral center. When a disclosed compound having a chiral center is depicted by its chemical name without indicating a configuration at that chiral center with "S" or "R", the name is meant to encompass the compound with the S configuration at that chiral center, the compound with the R configuration at that chiral center or the compound with a mixture of the R and S configuration at that chiral center.

A racemic mixture means a mixture of 50% of one enantiomer and 50% of its corresponding enantiomer. The present teachings encompass all enantiomerically-pure, enantiomerically-enriched, diastereomerically pure, diastereomerically enriched, and racemic mixtures, and diastereomeric mixtures of the compounds described herein.

Enantiomeric and diastereomeric mixtures can be resolved into their component enantiomers or stereoisomers by well known methods, such as chiral-phase gas chromatography, chiral-phase high performance liquid chromatography, crystallizing the compound as a chiral salt complex, or crystallizing the compound in a chiral solvent. Enantiomers and diastereomers can also be obtained from diastereomerically or enantiomerically pure intermediates, reagents, and catalysts by known asymmetric synthetic methods.

"Peak 1" or "first eluting isomer" or "isomer 1" in the Experimental section refers to an intended reaction product compound obtained from a chromatography separation/purification that elutes earlier than a second intended reaction product compound from the same preceding reaction. The second intended product compound is referred to as "peak 2" or "second eluting isomer" or "isomer 2".

When a compound is designated by a name or structure that indicates a single enantiomer, unless indicated otherwise, the compound is at least 60%, 70%, 80%, 90%, 99% or 99.9% optically pure (also referred to as "enantiomerically pure"). Optical purity is the weight in the mixture of the named or depicted enantiomer divided by the total weight in the mixture of both enantiomers.

When the stereochemistry of a disclosed compound is named or depicted by structure, and the named or depicted structure encompasses more than one stereoisomer (e.g., as in a diastereomeric pair), it is to be understood that, unless otherwise indicated, one of the encompassed stereoisomers or any mixture of the encompassed stereoisomers are included. It is to be further understood that the stereoisomeric purity of the named or depicted stereoisomers at least 60%, 70%, 80%, 90%, 99% or 99.9% by weight. The stereoisomeric purity in this case is determined by dividing the total weight in the mixture of the stereoisomers encompassed by the name or structure by the total weight in the mixture of all of the stereoisomers.

The deuterium enrichment at any one of the sites where hydrogen has been replaced by deuterium is at least 50%, 75%, 85%, 90%, 95%, 98% or 99%. Deuterium enrichment is a mole percent and is obtained by dividing the number of compounds with deuterium enrichment at the site of enrichment with the number of compounds having hydrogen or deuterium at the site of enrichment. A deuterated group such as a "deuterated alkyl" or "deuterated alkoxy" has hydrogen atoms at one or more positions replaced or enriched with deuterium.

The c-kit kinase inhibitors described herein are useful for treating diseases and disorders mediated by wild type c-kit. In some aspects c-kit mediated diseases and disorders include mast cell related disorder, an eosinophil related disorder, cancer, asthma, an inflammatory condition, rheumatoid arthritis, an allergic inflammation, inflammatory bowel disease, a gastrointestinal disorder, or fibrosis.

Wild-type KIT plays a central role in mast cell survival, proliferation, and activation. Specifically, inhibitors of c-kit are useful for the inhibition and/or depletion of mast cells and thus are useful for treating mast cell related disorders. As used herein, the term "mast cell related disorder" or "mast cell related disorders" or "mast cell mediated disorder" or "mast cell mediated disorders" refers to disorders where mast cell activity contributes to the pathology and/or mast cells are found in abnormal amounts, such as above-normal amounts or below-normal amounts, in various parts of the body. For example, mast cell related disorders can exhibit accumulation of pathological mast cells and/or can be characterized by mast cells that are aberrantly activated in potentially any or all organs and tissues and/or aberrant release of one or more mast cell mediators such as inflammatory mediators. Non-limiting examples of inflammatory mediators released by mast cells include any of (i) granule-associated mediators, including histamine, serotonin (5-hydroxytryptamine), and a variety of proteases such as tryptase and chymase) and peptidases; (ii) eicosanoids such as prostaglandin D2 (PGD2) and leukotriene C4 (LTC4); and (iii) cytokines including interleukin-2 (IL-2), IL-3, IL-4, IL-5, IL-6, IL-10, IL-13, granulocyte-macrophage colony-stimulating factor (GM-CSF), and tumor necrosis factor a (TNFa), and chemokines including CCL-2, CCL-3, CCL-5, and CXCL8.

Compounds of the disclosure are useful for treating chronic urticaria. Chronic urticaria includes chronic spontaneous urticaria (CSU), chronic idiopathic urticaria and chronic induced urticaria (i.e., chronic inducible urticaria (CIndU). In certain aspects, the mast cell related disorder is CSU. In certain aspects, the mast cell related disorder is CindU. Chronic inducible urticarias are forms of urticaria that have an attributable trigger associated with them, typically resulting in inflammation of the skin characterized by wheals (hives) or angioedema. Complications of both CSU and CIndU include swelling/hives in inopportune sites (mouth, airway, genitals) and anaphylaxis. Sleep disruption, stress, & anxiety due to severe itching are major contributors to disease burden. In a specific aspect, the chronic inducible urticaria is cold urticaria (ColdU). People afflicted with cold urticaria experience symptoms like itching, burning wheals and angioedema when their skin is exposed to temperatures below skin temperature. In another aspect, the chronic inducible urticaria is symptomatic dermographism (SD). Symptomatic dermographism is characterized by the development of a wheal and flare reaction in response to stroking, scratching or rubbing of the skin and usually occurs within minutes of the inciting stimulus. In another aspect, the chronic inducible urticaria is cholinergic urticaria. Cholinergic urticaria is triggered by the body's sweating response to active or passive body warming and is characterized by small (1-4 mm) wheals surrounded by bright red flares. Common triggers include exercise, hot baths/showers, fever, occlusive dressings, eating spicy foods and emotional stress. In another aspect, the chronic inducible urticaria is heat urticaria. In another specific embodiment, the chronic inducible urticaria is delayed pressure urticaria. In another aspect, the chronic inducible urticaria is solar urticaria. In another specific embodiment, the chronic inducible urticaria is vibratory urticaria. In another aspect, the chronic inducible urticaria is contact urticaria. In one aspect, the vibratory urticaria is characterized by a missense mutation in EMR2. In another aspect, the chronic inducible urticaria is aquagenic urticaria.

Other mast cell related disorders and diseases include dermatosis, including: atopic dermatitis and allergic contact dermatitis; idiopathic angioedema; idiopathic anaphylaxis; asthma, including allergic asthma; hereditary alpha tryptasemia (HAT); idiopathic mast cell activation syndrome (MCAS); monoclonal MCAS; neurofibromatosis; idiopathic pulmonary fibrosis; bullous pemphigoid; and prurigo nodularis.

Additional diseases with mast cell involvement include: age-related macular degeneration; allergic conjunctivitis; allergic rhinitis; non-allergic rhinitis; alpha-1 antitrypsin deficiency; Alzheimer's disease; amyotrophic lateral sclerosis (AML); bronchiectasis; Celiac disease; chronic graft verse host disease; chronic rhinosinusitis with nasal polyps; allergic fungal rhinosinusitis; aspirin-exacerbated respiratory disease; allergic broncho pulmonary aspergillosis; colorectal cancer; dermatitis herpetiformis; irritable bowel syndrome (IBS), including diarrhea-prominent IBS; fibromyalgia; fibrosis, including hepatic fibrosis, pulmonary, and cardiac fibrosis; food allergies, including Igf-mediated food allergies and peanut allergies; insect venom allergy; drug allergy; insulin-dependent diabetes mellitus; mast cell leukemia; migraine; multiple sclerosis; Parkinson's disease; psoriasis; and rheumatoid arthritis.

Other diseases modulated by c-kit include pulmonary arterial hypertension (PAH); inflammatory bowel disease (IBD), cholestatic pruritis; uremic pruritis; chronic pruritis of unknown origin; pulmonary fibrosis; scleroderma; dermatosis; dermatitis herpetiformis; melanoma; gastrointestinal stromal tumor; mast cell tumor; anaphylactic syndrome; idiopathic anaphylaxis; diabetes, type I or type II, eosinophilic esophagitis (EoE); eosinophilic gastritis & duodenitis; interstitial cystitis/bladder pain syndrome, chronic prostatitis/chronic pelvic pain syndrome; endometriosis; and mastocytosis, including cutaneous mastocytosis and systemic mastocytosis.

Compounds of the disclosure are useful for treating gastrointestinal stromal tumor (GIST). GISTs are the most common malignant subepithelial lesions of the gastrointestinal tract, and the most common symptoms of GISTs are gastrointestinal bleeding, acute melena (dark feces containing blood), hematemesis (vomiting of blood) with anemia, weakness, and abdominal pain and distension. Nearly 80% of metastatic GISTs have a primary activating mutation in either the extracellular region (exon 9) or the juxtamembrane (TM) domain (exon 11) of KIT. Imatinib is a standard therapy used to treat GIST. Side effects of imatinib include mild stomach upset, diarrhea, muscle pain, and skin rashes. There is a need for new therapies for the treatment of GIST.

Compounds of the disclosure can be administered in combination with another agent. In one aspect, compounds of the disclosure are administered in combination with one or more antihistamine agents such as loratadine, cetirizine, fexofenadine, cimetidine, famotidine or diphenhydramine. In another aspect, compounds of the disclosure are administered in combination with one or more asthma agents such as montelukast and zafirlukast.

In another aspect, compounds of the disclosure can be administered in combination with one or more other agents that are used in the treatment of urticaria. For example, compounds of the disclosure are administered in combination with omalizumab, dupilumab, reslizumab, mepolizumab, and benralizumab. In some aspects, compounds of the disclosure can be administered with novel anti-IgE monoclonal antibodies such as ligelizumab and UB-221. Compounds of the disclosure can also be administered with a monoclonal antibody to Siglec-8 (AK002), Bruton tyrosine kinase inhibitors (fenebrutinib and Lou064), a spleen tyrosine kinase inhibitor, and dupilumab. The compound of the disclosure and agent can be co-administered or administered in alternating regimen. In some aspects, compounds of the disclosure can be administered with antihistamines. Examples of antihistamine agents include Classic H1 antihistamines with sedation as a side effect including chlorpheniramine, hydroxyzine, and diphenhydramine, nonsedating second generation H1 antihistamines including loratadine, cetirizine, terfenadine, and mizolastine, second generation H1 antihistamine derivatives including desloratadine, levocetirizine, and fexofenadine, and H2 antihistamines including cimetidine, ranitidine, famotidine and nizatadine. Other antihistamine agents include bilastine, cetirizine, desloratadine, ebastine, fexofenadine, levocetirizine, loratadine, and rupatadine. In some aspects, compounds of the disclosure can be administered in combination with an MRGPRX2 inhibitor. Examples of MRGPRX2 inhibitors are EP-262 and EVO-756.

In some aspects, compounds of the disclosure are administered to a subject in need thereof. In some aspects, compounds of the disclosure are administered as a pharmaceutical formulation, wherein the compound is combined with one or more pharmaceutically acceptable excipients or carriers. Thus, in some aspects, disclosed herein are compositions comprising at least one entity chosen from compounds of Formula I and pharmaceutically acceptable salts thereof and optionally further comprising at least one pharmaceutically acceptable excipient.

The compounds of the disclosure or pharmaceutically acceptable salts thereof may be formulated for administration in any convenient way for use in human or veterinary medicine. In certain embodiments, the compound included in the pharmaceutical preparation may be active itself, or may be a prodrug, e.g., capable of being converted to an active compound in a physiological setting.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Examples of pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; (21) cyclodextrins; and (22) other non-toxic compatible substances employed in pharmaceutical formulations.

Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Solid dosage forms (e.g., capsules, tablets, pills, dragees, powders, granules and the like) can include one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents.

Liquid dosage forms can include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Suspensions, in addition to compounds of the disclosure or pharmaceutically acceptable salts thereof, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Ointments, pastes, creams and gels may contain, in addition to compounds of the disclosure or pharmaceutically acceptable salts thereof, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to compounds of the disclosure or pharmaceutically acceptable salts thereof, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of compound of the disclosure or pharmaceutically acceptable salt thereof that can be combined with a carrier material to produce a single dosage form will generally be that amount of the compound which produces a therapeutic effect.

Dosage forms for the topical or transdermal administration of a compound of this disclosure or pharmaceutically acceptable salts thereof, include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

When the compounds of the disclosure or pharmaceutically acceptable salts thereof are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

The formulations can be administered topically, orally, transdermally, rectally, vaginally, parentally, intranasally, intrapulmonary, intraocularly, intravenously, intramuscularly, intraarterially, intrathecally, intracapsularly, intradermally, intraperitoneally, subcutaneously, subcuticularly, or by inhalation.

Actual dosage levels of the active ingredients in the pharmaceutical compositions of this disclosure may be varied so as to obtain an amount of the active ingredient that is effective to achieve the desired therapeutic response for a particular patient, composition, and mode of administration, without being toxic to the patient.

The term "effective amount" means an amount when administered to the subject or patient which results in beneficial or desired results, including clinical results, e.g., inhibits, suppresses or reduces the symptoms of the condition being treated in the subject as compared to a control. For example, an effective amount can be given in unit dosage form (e.g., 0.1 mg to about 50 g per day, alternatively from 1 mg to about 5 grams per day. The precise amount of compound or pharmaceutically acceptable salt thereof administered to provide an "effective amount" to the subject will depend on the mode of administration, the type, and severity of the disease or condition, and on the characteristics of the subject, such as general the route of administration, the time of administration, the rate of excretion of the particular active ingredient being employed, the duration of the treatment, other drugs, compounds and/or materials used in combination with the particular active ingredient employed, the age, sex, weight, condition, general health and prior medical history of the patient being treated, and like factors well known in the medical arts. The skilled artisan will be able to determine appropriate dosages depending on these and other factors. When administered in combination with other therapeutic agents, an "effective amount" of any additional therapeutic agent(s) will depend on the type of drug used. Suitable dosages are known for approved therapeutic agents and can be adjusted by the skilled artisan according to the condition of the subject, the type of condition(s) being treated and the amount of a compound of the disclosure or a pharmaceutically acceptable salt thereof being used by following, for example, dosages reported in the literature and recommended in the *Physician's Desk Reference* (57th ed., 2003). A physician having ordinary skill in the art can readily determine and prescribe the effective amount of the pharmaceutical composition required. For example, the physician could start doses of the compounds of the disclosure employed in the pharmaceutical composition at levels lower than that required in order to achieve the desired therapeutic effect and gradually increase the dosage until the desired effect is achieved.

In general, a suitable daily dose of a compound of the disclosure will be that amount of the compound that is the lowest dose effective to produce a therapeutic effect. Such an effective dose will generally depend upon the factors described above.

The terms "administer", "administering", "administration", and the like, as used herein, refer to methods that may be used to enable delivery of compositions to the desired site of biological action. These methods include, but are not limited to, intraarticular (in the joints), intravenous, intramuscular, intratumoral, intradermal, intraperitoneal, subcutaneous, orally, topically, intrathecally, inhalationally, transdermally, rectally, and the like. Administration techniques that can be employed with the agents and methods described herein are found in e.g., Goodman and Gilman, *The Pharmacological Basis of Therapeutics*, current ed.; Pergamon; and Remington's, *Pharmaceutical Sciences* (current edition), Mack Publishing Co., Easton, PA.

The particular mode of administration and the dosage regimen will be selected by the attending clinician, taking into account the particulars of the case (e.g. the subject, the disease, the disease state involved, the particular treatment, and whether the treatment is prophylactic). Treatment can involve daily or multi-daily or less than daily (such as weekly or monthly etc.) doses over a period of a few days to months, or even years.

"Pharmaceutically acceptable excipient" and "pharmaceutically acceptable carrier" refer to a substance that aids the formulation and/or administration of an active agent to and/or absorption by a subject and can be included in the compositions of the disclosure without causing a significant adverse toxicological effect on the subject. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with or interfere with the activity of the compounds provided herein. One of ordinary skill in the art will recognize that other pharmaceutical excipients are suitable for use with disclosed compounds.

A "subject" or "patient" is a mammal in need of medical treatment, preferably a human, but can also be an animal in need of veterinary treatment, e.g., companion animals (e.g., dogs, cats, and the like), farm animals (e.g., cows, sheep, pigs, horses, and the like) and laboratory animals (e.g., rats, mice, guinea pigs, and the like). In one aspect, the patient is a human. In one aspect, the patient is an adult human.

The compounds of the disclosure can be prepared according to the following general synthetic methods.

General Synthetic Methods (I)

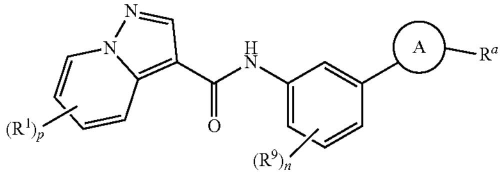

-continued (IIa)

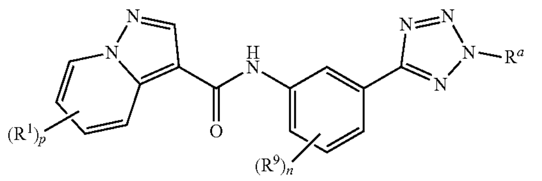

(IIb)

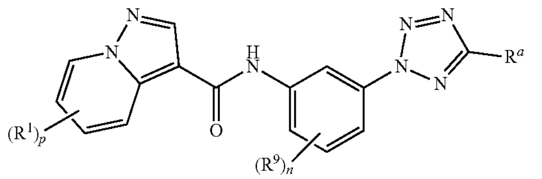

(IIIa)

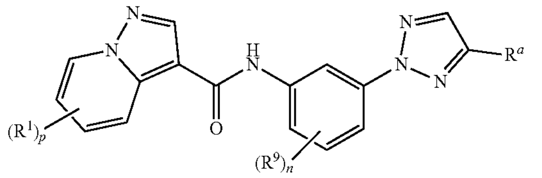

(IIIb)

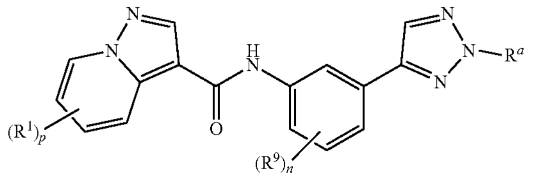

Scheme 1

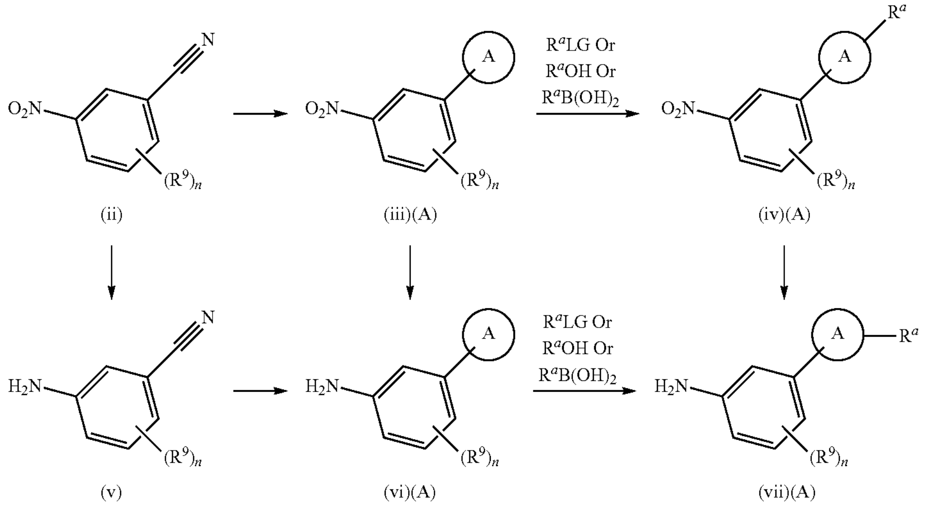

LG is a leaving group, typically a Cl, Br, I or mesylate.

In Scheme 1, Ring A is tetrazole linked to $R^a$ through a N.

The aryl nitrile compounds (ii) and (v) can be treated with an azide source, such as $Bu_3SnN_3$ or $TMSN_3$ in the presence of $Bu_2SnO$ or $NaN_3$ and $NH_4Cl$ in DMF or toluene at elevated temperature, optionally under microwave irradiation, to give the tetrazoles (iii)(A) and (vi)(A) respectively.

The tetrazoles (iii)(A) and (vi)(A) can be alkylated with $R^aLG$, using a base such as DIPEA or $K_2CO_3$ in DMF to give the compounds (iv)(A) and (vii)(A) respectively.

Alternatively, the tetrazoles (iii)(A) and (vi)(A) can undergo a Mitsunobu reaction with $R^aOH$ to give compounds (iv)(A) and (vii)(A) respectively.

Alternatively, the tetrazoles (iii)(A) and (vi)(A) can undergo a Chan-Lam type coupling reaction with $R^aB(OH)_2$ to give compounds (iv)(A) and (vii)(A) respectively.

The nitroaryls (ii), (iii)(A) and (iv)(A) can be reduced to the corresponding anilines under hydrogenation conditions, such as Pd/C or Pt on C under $H_2$, or by reduction with Fe under acidic conditions in an alcoholic solvent to give the compounds (v), (vi)(A) and (vii)(A) respectively.

Scheme 2

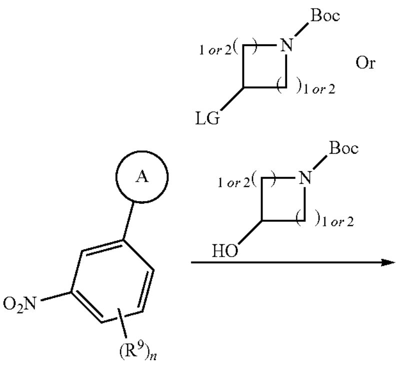

(iii)(A) or (D)

-continued

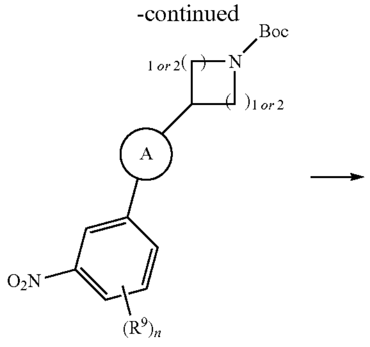

(viiii)(A) or (D)

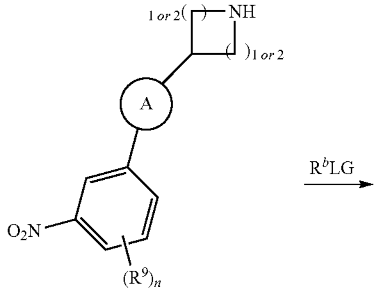

(ix)(A) or (D)

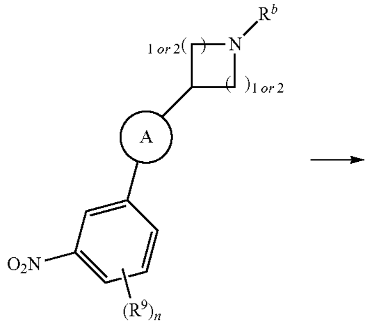

(x)(A) or (D)

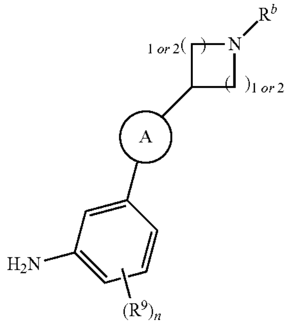

(xi)(A) or (D)

In Scheme 2, Ring A is tetrazole or triazole linked to $R^a$ through N and $R^a$ is a 4-6 membered ring heterocycle containing at least one N atom, substituted by $R^b$.

The tetrazole (iii)(A) or (D) may be alkylated by

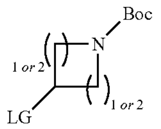

or undergo a Mitsunobu reaction with

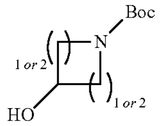

as previously described in Scheme 1, to give the compound (viii)(A) or (D). Compound (viii)(A) or (D) can be deprotected under Boc-deprotection conditions such as HCl or TFA to give the amine (ix)(A) or (D).

Wherein $R^b$ is $SO_2R^4$, $C(O)OR^5$, $C_{1-3}$alkyl, $C_{1-3}$alkoxy, $CH_2OR^3$ or $C_{3-4}$cycloalkyl, the amine (ix)(A) or (D) can be treated with $R^b$LG, in the presence of a base, to give compound (x)(A) or (D). Compound (x)(A) or (D) can be reduced to give the amine (xi)(A) or (D), using the reduction methods previously described in Scheme 1.

Scheme 3

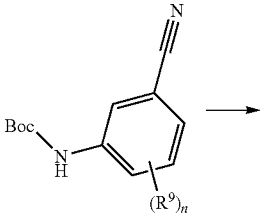

(xii)

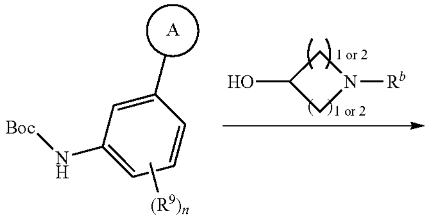

(xiii)(A)

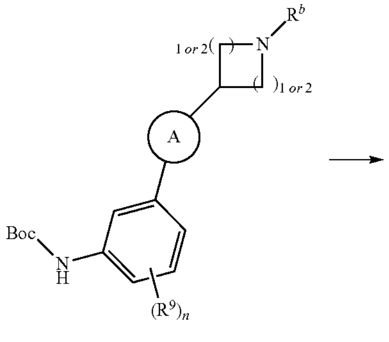

(xiv)(A)

-continued

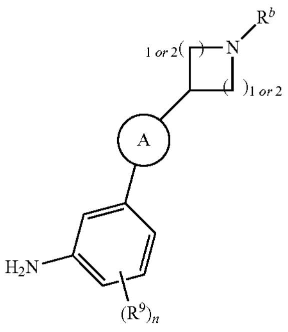

(xi)(A)

In Scheme 3, Ring A is tetrazole linked to $R^a$ through N and $R^a$ is a 4-6 membered ring heterocycle containing at least one N atom, substituted by R.

The tetrazole (xiii)(A) can be obtained from nitrile (xii) and an azide source, as previously described in Scheme 1. The tetrazole (xiii)(A) can be reacted with

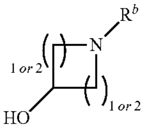

under Mitsunobu type conditions to give compound (xiv)(A). Compound (xiv)(A) can be deprotected under Boc-deprotection conditions such as HCl or TFA to give the amine (xi)(A).

Scheme 4

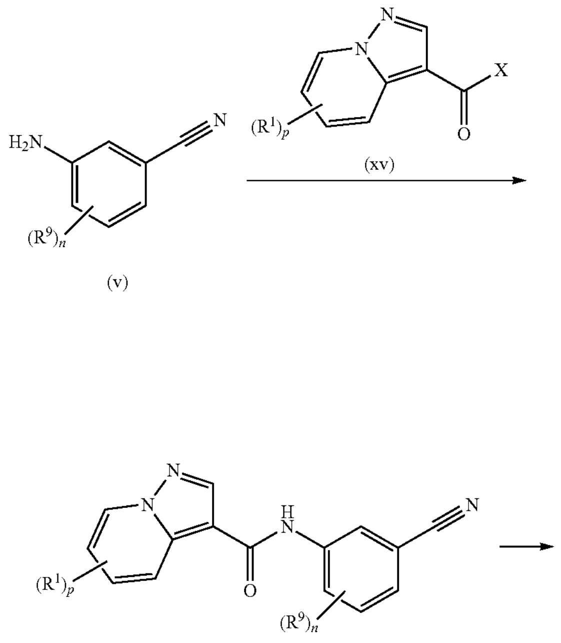

(v)

(xv)

(xvi)

-continued

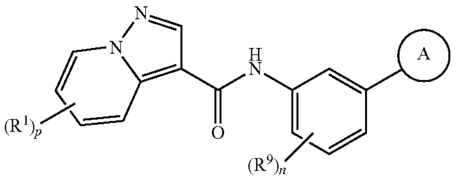

(xvii)(A)

X is Cl, OH or $O(C_1-C_4)$alkyl.

In Scheme 4, Ring A is tetrazole linked to $R^a$ through N.

Wherein X is Cl, the compound (xvi), can be obtained by reaction of the acid chloride (xv) with the aniline (v) in the presence of an organic base, such as pyridine, TEA or DIPEA.

Wherein X is OH, the acid (xv) can be coupled with aniline (v) using an amide coupling agent, such as EDCI, T3P® or HATU, or an activating agent such as 2,4,6-trichlorobenzoyl chloride, or via the in-situ preparation of the acid chloride, to give compound (xvi).

Wherein X is $O(C_1-C_4)$alkyl, the ester (xv) can be coupled with aniline (v) using trimethylaluminium or LiHMDS to give the compound (xvi).

The tetrazole (xvii)(A) can be obtained from nitrile (xvi) and an azide source, as previously described in Scheme 1.

Scheme 5

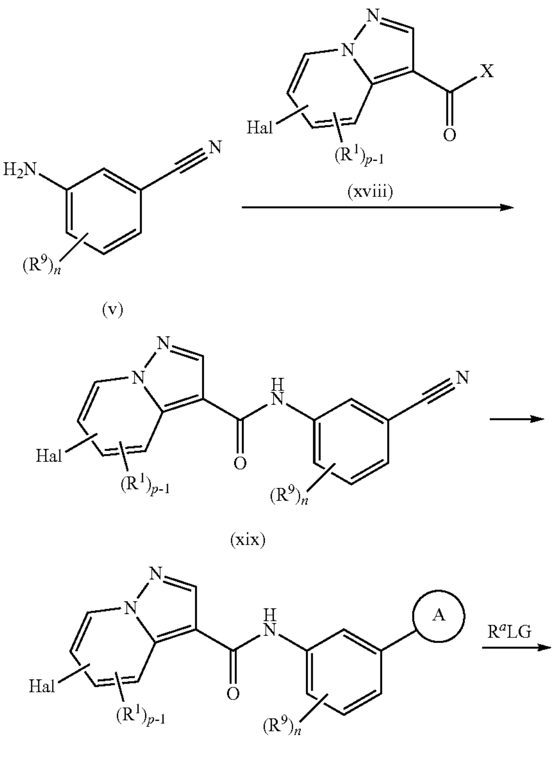

(xviii)

(v)

(xix)

(xx)(A)

-continued

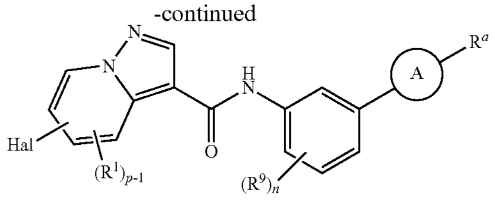

(xxi)(A)

X and LG are as previously described.

Hal is halogen, preferably Br or Cl.

In Scheme 5, Ring A is tetrazole linked to $R^a$ through N.

The aniline (v) can be coupled with compound (xviii) to give compound (xix) using the conditions described previously in Scheme 4. The compound (xx)(A) can be obtained from the compound (xix) and an azide source, using the conditions previously described in Scheme 1. The compound (xxi)(A) can be obtained from the compound (xx)(A) and $R^a$LG, using the conditions previously described in Scheme 1.

Scheme 6

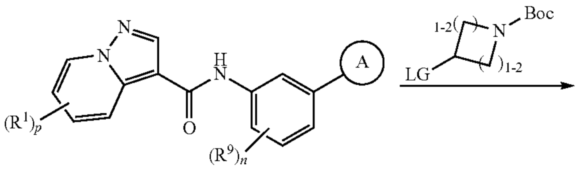

(xvii)(A)

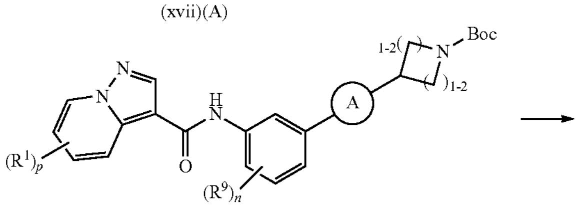

(xxii)(A)

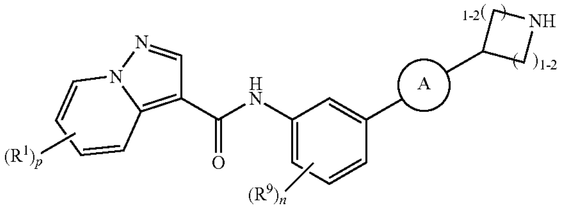

(xxiii)(A)

In Scheme 6, Ring A is tetrazole linked to $R^a$ through N. LG is as previously described.

The tetrazole (xvii)(A) can be alkylated under basic conditions with

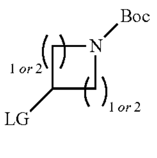

to give (xxii)(A), using the conditions previously described in Scheme 2. Compound (xxii)(A) can be deprotected under Boc-deprotection conditions such as HCl or TFA to give the amine (xxiii)(A).

Scheme 7

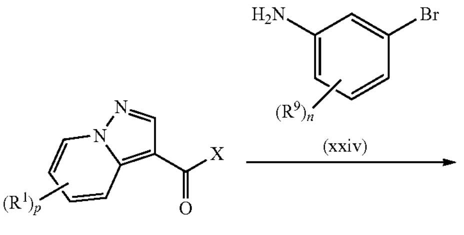

(xxiv)

(xv)

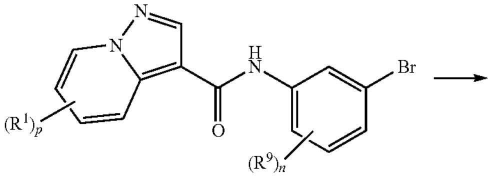

(xxv)

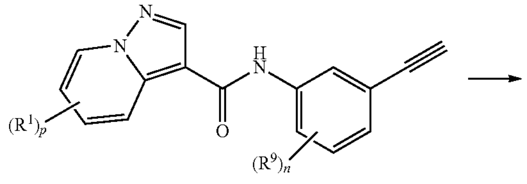

(xxvi)

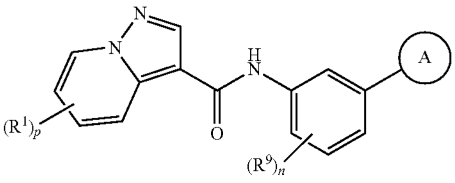

(xvii)(D)

In Scheme 7, Ring A is a triazole, linked to $R^a$ through N. X is as previously defined.

The aniline (xxiv) can be coupled to compound (xv) to give compound (xxv), using conditions previously described in Scheme 4. The compound (xxv) can be treated with trimethyl(2-(tributylstannyl)ethynyl)silane under palladium coupling conditions, followed by removal of the TMS protecting group, to give the compound (xxvi). Compound (xxvi) can be treated with a suitable azide source, to give the triazole (xvii)(D).

Scheme 8

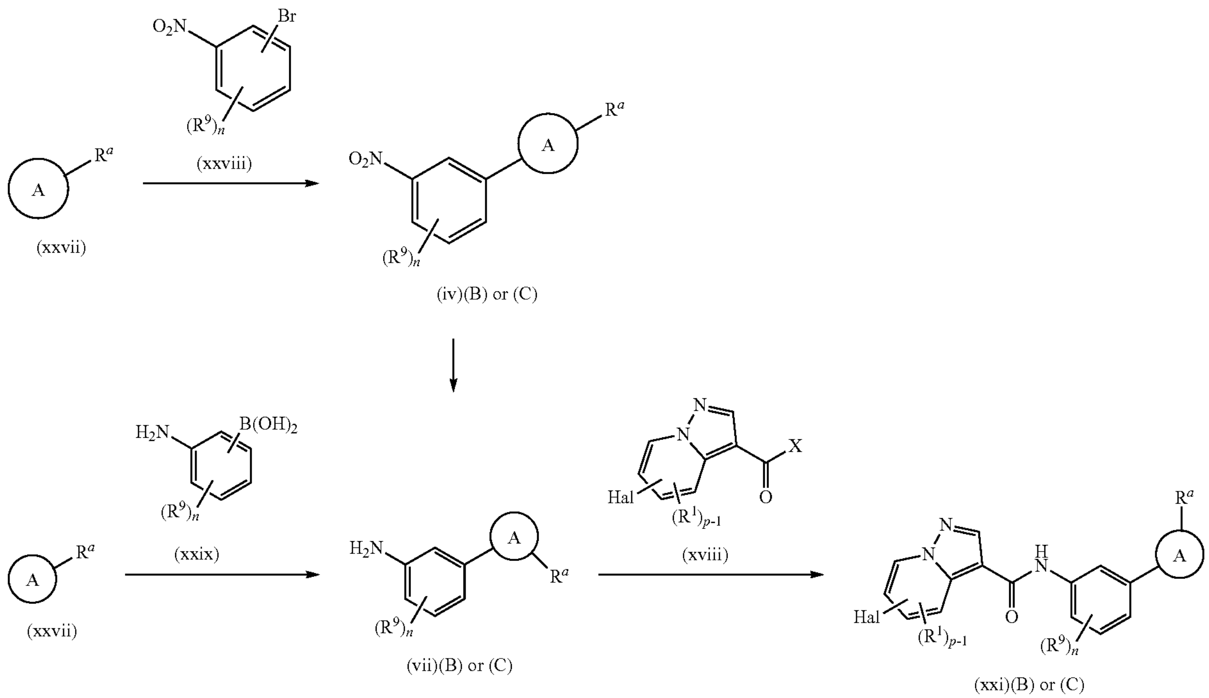

(xxvii) (xxviii) (iv)(B) or (C) (xxix) (vii)(B) or (C) (xviii) (xxi)(B) or (C)

In Scheme 8, Ring A is attached to $R^a$ through a C atom. The compound (xxvii) can be coupled with the aromatic bromide (xxviii) under palladium coupling conditions to give compound (iv)(B) or (C). Compound (iv)(B) or (C) can be reduced using the methods previously described in Scheme 1, to give the aniline (vii)(B) or (C). Alternatively, the compound (xxvii) can be coupled with the boronic acid (xxix) under Chan-Lam type coupling conditions to give compound (vii)(B) or (C). The aniline (vii)(B) or (C) can be coupled with compound (xviii) as described previously in Scheme 4 to give the amide (xxi)(B) or (C).

Scheme 9

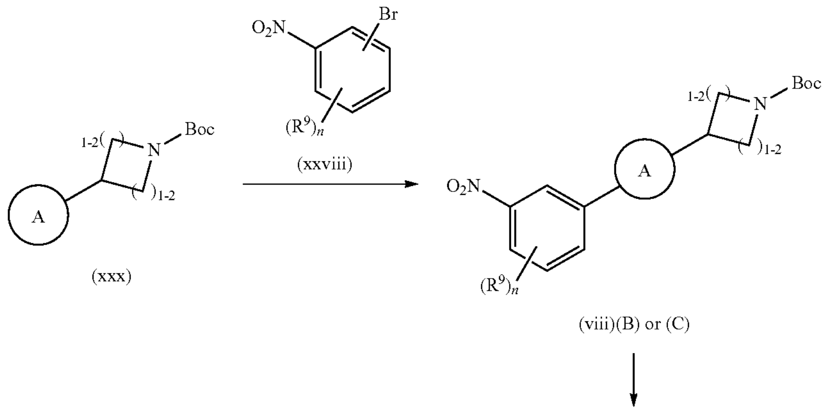

(xxx) (xxviii) (viii)(B) or (C)

-continued

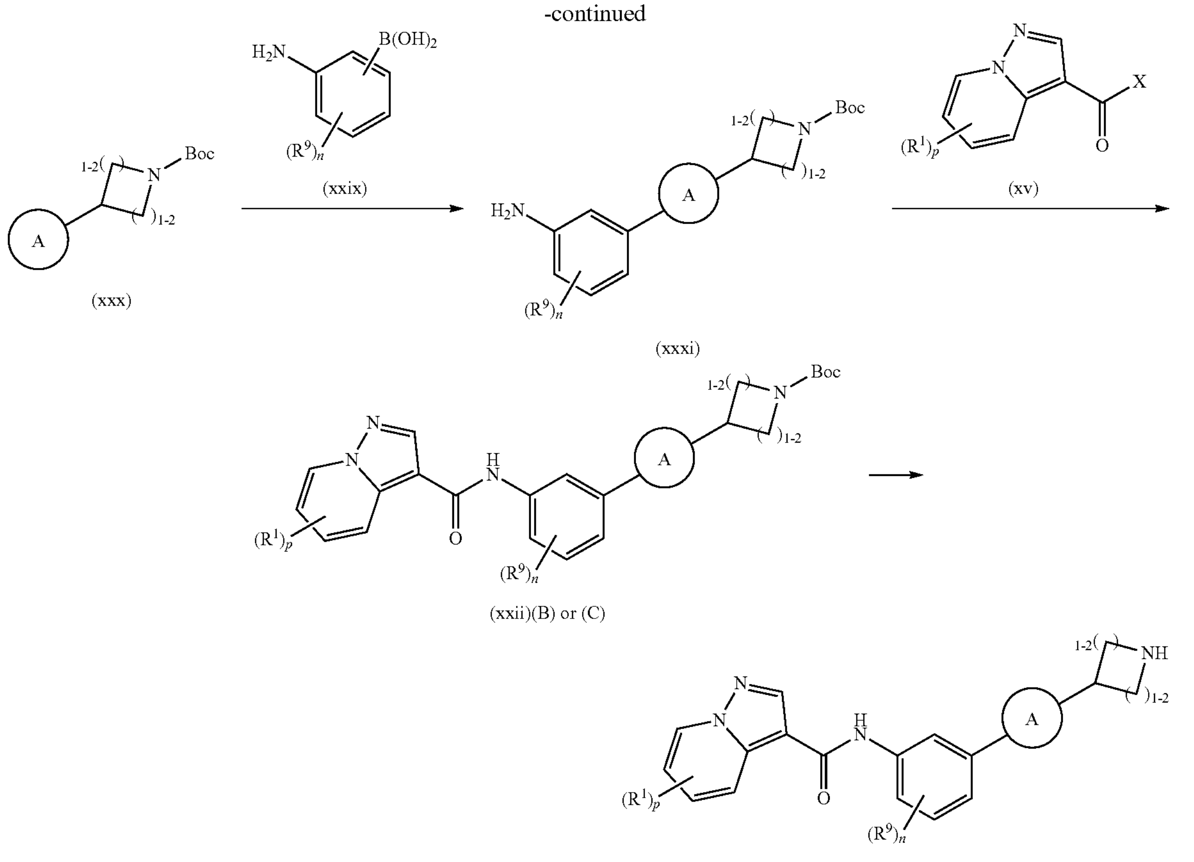

(xxx)

(xxix)

(xxxi)

(xv)

(xxii)(B) or (C)

(xxiii)(B) or (C)

In Scheme 9, Ring A is attached to $R^a$ through a C atom. Compound (xxx) can be coupled to the bromide (xxviii) under palladium coupling conditions to give the compound (viii)(B) or (C). Compound (viii)(B) or (C) can be reduced using the methods previously described in Scheme 1, to give the aniline (xxxi). Alternatively, the aniline (xxxi) can be obtained by reaction of the compound (xxx) with the boronic acid (xxix) under Chan-Lam type reaction conditions. The aniline (xxxi) can be coupled with the compound (xv) to give amide (xxii)(B) or (C) using conditions described previously in Scheme 4. The compound (xxii)(B) or (C) can be obtained by the deprotection of the compound (xxii)(B) or (C) using conditions previously described in Scheme 6.

Scheme 10

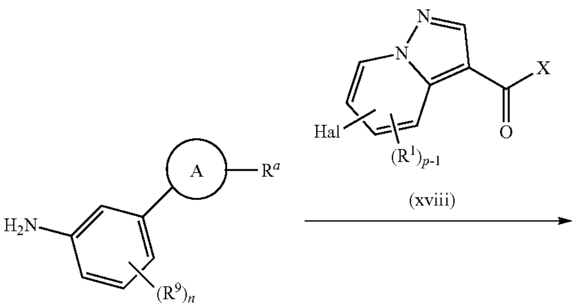

(xviii)

(vii)

-continued

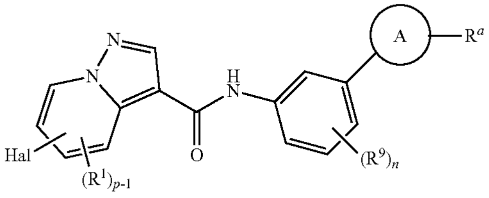

(xxi)

The aniline (vii) can be coupled with compound (xviii) to give the amide (xxi), using conditions previously described in Scheme 4.

Scheme 11

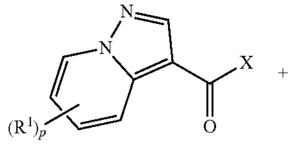

(xv)

-continued

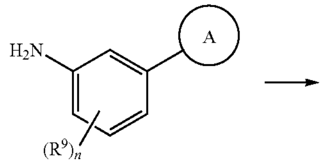

(vi)

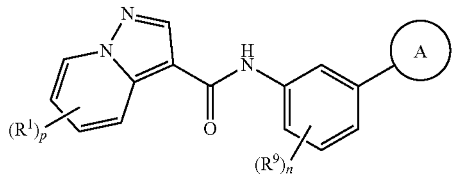

(xvii)

The aniline (vi) can be coupled with compound (xv) to give amide (xvii) using the conditions described previously in Scheme 4.

[Scheme 12 intentionally omitted]

Scheme 13

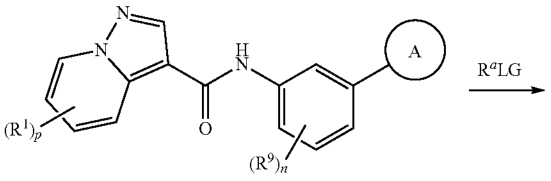

(xvii)(A) or (D)

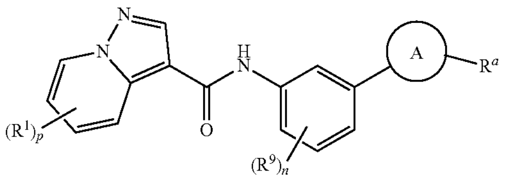

(I)(A) or (D)

LG is as previously defined.

In Scheme 13, Ring A is attached to $R^a$ through a N atom.

The compound (xvii)(A) or (D) may be alkylated with $R^a$LG under basic conditions to give the amide (I)(A) or (D).

Scheme 14

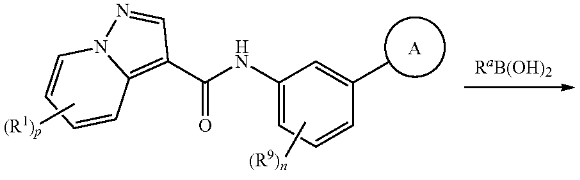

(xvii)(A) or (D)

-continued

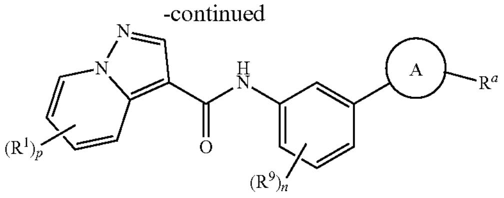

(I)(A) or (D)

In Scheme 14, Ring A is attached to $R^a$ through a N atom

The compound (xvii)(A) or (D) can be coupled with $R^aB(OH)_2$ under Chan-Lam type coupling conditions to give the amide (I)(A) or (D).

Scheme 15

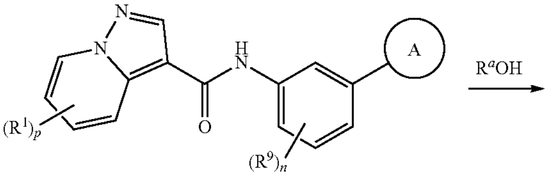

(xvii)(A) or (D)

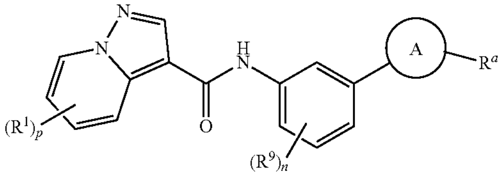

(I)(A) or (D)

In Scheme 15, Ring A is attached to $R^a$ through a N atom.

Compound (I)(A) or (D) can be obtained from the compound (xvii)(A) or (D) via a Mitsunobu type reaction with $R^a$OH.

Scheme 16

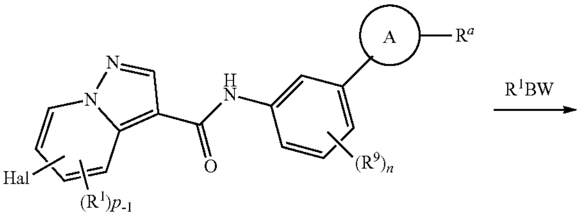

(xxi)

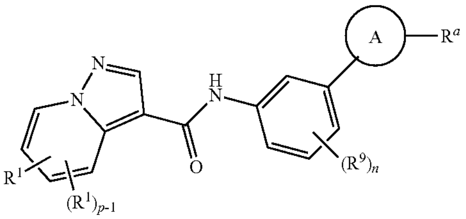

(I)

W is a suitable boronate ester, such as a pinacol ester.

$R^1$ is a C linked hetereocycle, or optionally substituted $C_1$-$C_6$ alkyl.

The halide (xxi) can be coupled with the boronate ester, $R^1BW$, under Suzuki reaction coupling conditions to give the amide (I).

Scheme 17

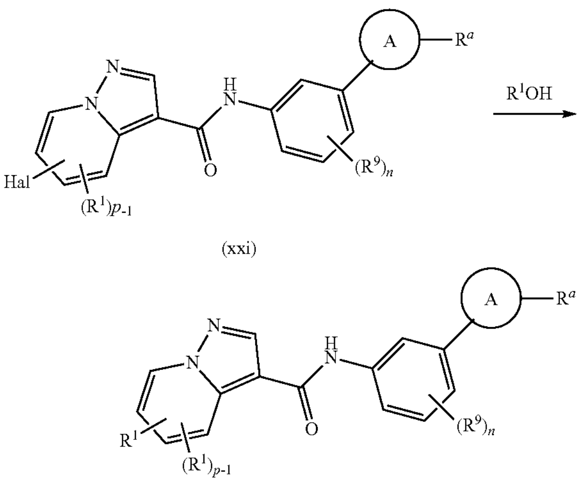

(xxi)

(I)

Wherein $R^1$ is $C_1$-$C_6$ alkyl, the compound (I) can be obtained from the halide (xxi) via a photo-catalysed iridium-nickel cross coupling with $R^1OH$.

Scheme 18

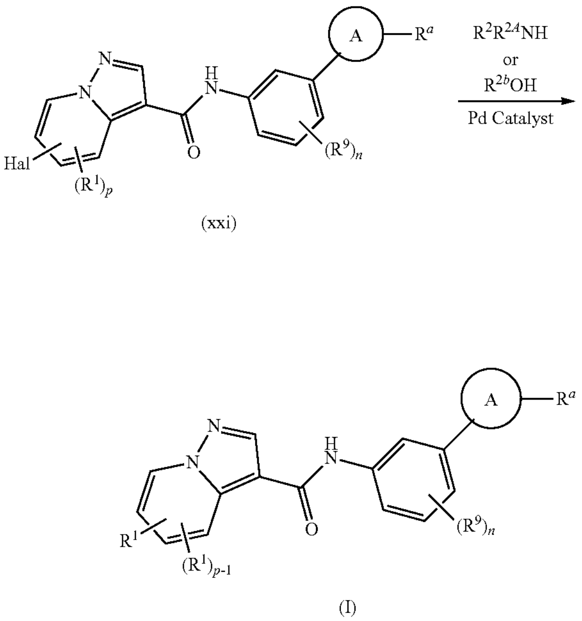

(xxi)

(I)

In Scheme 18, $R^1$ is $NR^2R^{2a}$ or $OR^{2b}$

The compound of Formula (I) may be obtained from the halide of Formula (xxi) and the amine, $NHR^2R^{2A}$ or alcohol $OR^{2b}$ by a palladium catalysed cross coupling reaction using a suitable palladium catalyst in the presence of suitable phosphine ligands, in the presence of a suitable inorganic base, in a solvent at elevated temperature.

Scheme 19

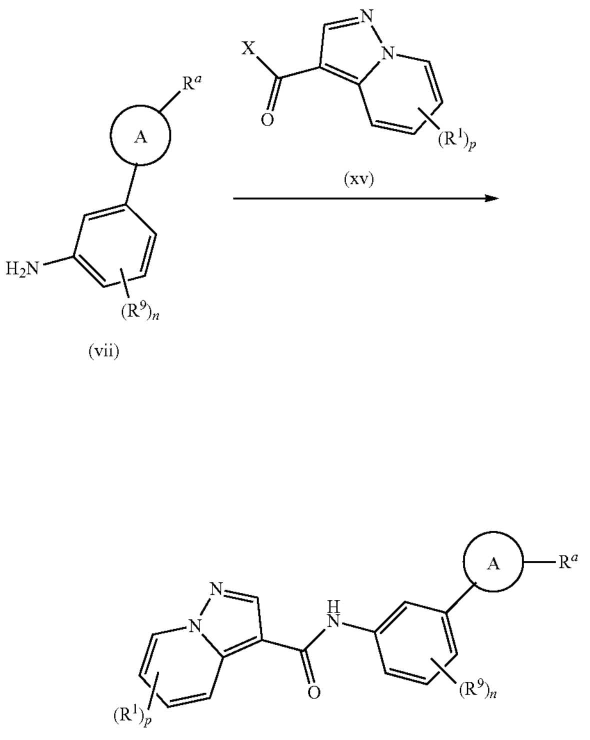

(vii)

(xv)

(I)

The aniline (vii) can be coupled with the carboxylic acid derivative (xv) to give the amide (I) using coupling conditions previously described in Scheme 4.

Scheme 20

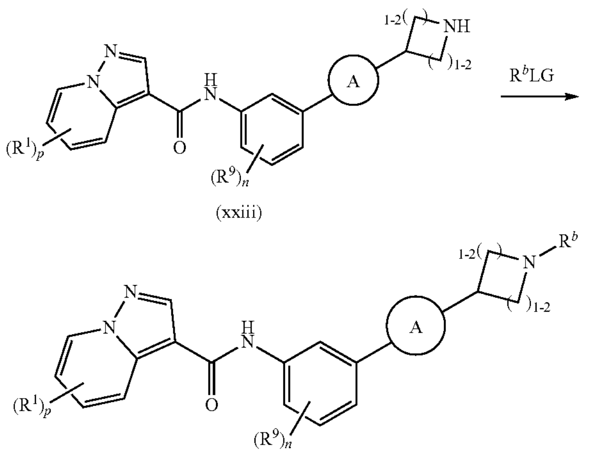

(xxiii)

(I)

LG is a suitable leaving group as previously defined.

Wherein $R^b$ is $SO_2R^4$, $C(O)OR^5$, $C_{1-3}$alkyl, $C_{1-3}$alkoxy, $CH_2OR^3$ or $C_{3-4}$cycloalkyl, the amide (I) can be obtained from the compound (xxiii) by reaction with $R^bLG$ as previously described in Scheme 2.

Scheme 21

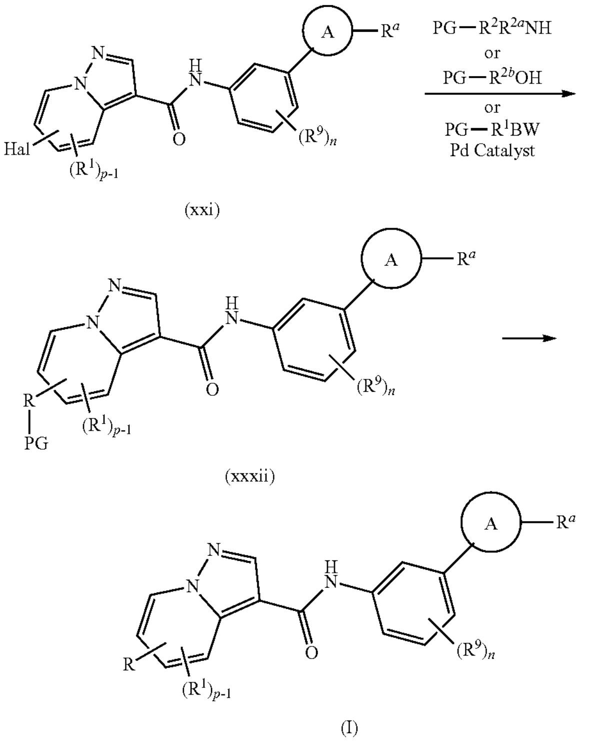

(xxi)

(xxxii)

(I)

Note: $R = R^2R^{2a}$, $R^{2b}$, or $R^1$

PG is a suitable protecting group for a N or O atom, such as THP to protect a heteroaromatic N atom, Boc to protect a primary or secondary N, or TBDMS to protect an aliphatic alcohol.

Scheme 22

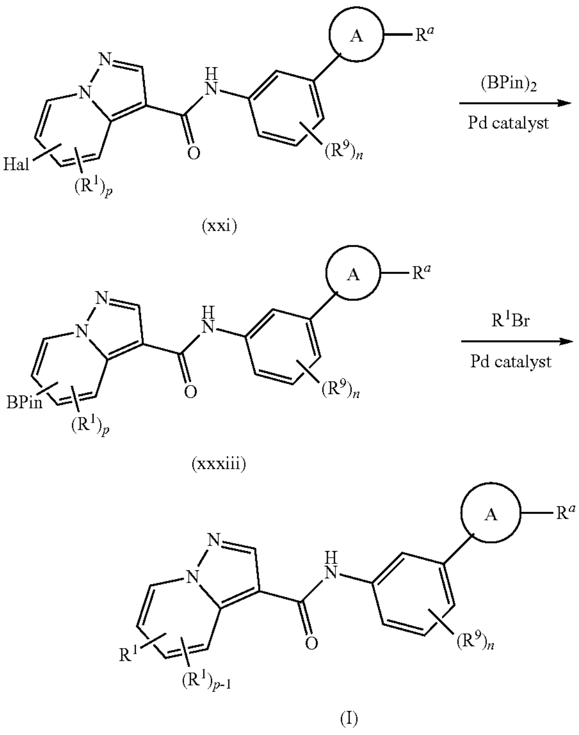

(xxi)

(xxxiii)

(I)

The compound (xxi) can be treated with $(BPin)_2$ under palladium coupling conditions, to give the boronate ester (xxxiii). The compound (xxxiii) can be treated with $R^1Br$ under Suzuki type reaction conditions, to give compound (I).

Scheme 23

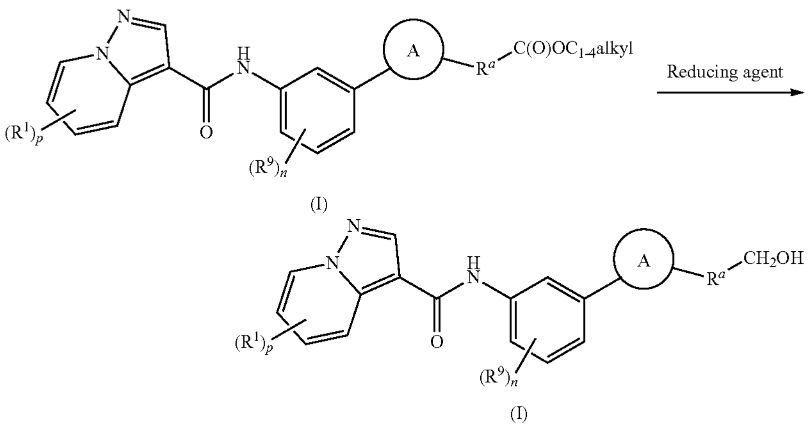

(I)

(I)

The compound (xxi) can be coupled with $PG-R^2R^{2A}NH$ or $PG-R^{2b}OH$ under palladium coupling conditions to obtain compound (xxxii). Alternatively, the compound (xxi) can be coupled with $PG-R^1BW$ under Suzuki type reaction conditions to give compound (xxxii). Compound (xxxii) can be deprotected under typical conditions, such as TBAF for the removal of a TBDMS group, or TFA for the removal of a THP group, to give compound (I).

Compounds of formula (I), wherein $R^b$ is $C(O)OR^5$ can be reduced to a compound of formula (I), wherein $R^b$ is $CH_2OH$ by treatment with a suitable reducing agent, such as $NaBH_4$.

Compounds that contain one or more stereocenters can be separated into their separate steroisomers by typical methods such as chiral SFC or chiral HPLC techniques as indicated in Examples below.

Compounds of Formulae (i) to (xxxiii) can be converted to alternative compounds of Formulae (i) to (xxxiii) by chemical transformations. Examples of these transformations include, but are not limited to:

the cyanation of an aryl bromide, using $Zn(CN)_2$ under palladium coupling conditions;

the transformation of an aryl bromide to an arylalkyl by reaction with an alkyl boronic acid under Chan-Lam type coupling conditions;

the alkylation of aryl amine with an alkylhalide to give a secondary amine;

the alkylation of a heterocyclic N atom with an alkyl halide or epoxide to give an N-substituted heterocycle, and the reductive amination of a primary or secondary amine with an aldehyde to provide a secondary or tertiary amine.

Compounds (ii), (iii), (x), (xii), (xv), (xviii), (xxiv), (xxvii), (xxviii), (xxix) and (xxx) are commercially available or may be prepared by the methods described in the Intermediates and Examples below.

It will be appreciated by those skilled in the art that it may be necessary to utilize a suitable protecting group strategy for the preparation of compounds of Formula (II), (II) or (III). Typical protecting groups may comprise, a carbamate, in certain aspects, a Boc or CBz group for the protection of primary or secondary aliphatic amines.

The invention is illustrated by the following examples, which are not intended to be limiting in any way.

EXEMPLIFICATION

Abbreviations

Abbreviations and acronyms used herein include the following:

AcOH means acetic acid;
$AlMe_3$ means trimethylaluminium;
Aq. means aqueous;
Boc means tert-butoxy carbonyl;
Brettphos means 2-(Dicyclohexylphosphino)3,6-dimethoxy-2',4',6'-triisopropyl-1,1'-biphenyl;
BrettPhos Pd G3 means [(2-Di-cyclohexylphosphino-3,6-dimethoxy-2',4',6'-triisopropyl-1,1'-biphenyl)-2-(2'-amino-1,1'-biphenyl)]palladium(II) methanesulfonate;
BrettPhos Pd G4 means dicyclohexyl-[3,6-dimethoxy-2-[2,4,6-tri(propan-2-yl)phenyl]phenyl]phosphane; methanesulfonic acid; N-methyl-2-phenylaniline; palladium
$Bu_3SnN_3$ means azido(tributyl)stannane;
$Bu_2SnO$ means dibutyl(oxo)tin;
d means doublet;
dd means doublet of doublets;
ddd means doublet of doublet of doublets;
ddt means doublet of doublet of triplets;
dq means doublet of quartets;
dt means doublet of triplets;
DCE means 1,2-dichloroethane;
DCM means dichloromethane;
DIAD means diisopropyl azodicarboxylate;
DIPEA means N-ethyldiisopropylamine or N,N-diisopropylethylamine;
DMA means N,N-Dimethylacetamide;
DMAP means N,N-dimethylpyridin-4-amine;
DMF means N,N-dimethylformamide;
DMSO means Dimethylsulfoxide;
DMSO-$d_6$ means trideuterio(trideuteriomethylsulfinyl)methane;
EDCI means 1-Ethyl-3-(3'-dimethylaminopropyl)carbodiimide;
EtOAc means ethyl acetate;
EtOH means ethanol;
FA means formic acid;
HATU means 1-[bis(dimethylamino)methylene]-1H-1,2,3-triazolo[4,5-b]pyridinium 3-oxide hexafluorophosphate;
HPLC means high performance liquid chromatography;
IPA means 2-propanol;
LG means leaving group;
LCMS means liquid chromatography mass spectrometry;
m means multiplet;
MeCN means acetonitrile;
Mel means iodomethane;
MeOH means methanol;
MS m/z means mass spectrum peak;
NMR means nuclear magnetic resonance;
PE means petroleum ether;
$Pd_2(dba)_3$ means tris(dibenzylideneacetone)dipalladium (0);
$Pd(dppf)Cl_2$ means [1,1'-bis(diphenylphosphino)ferrocene]dichloropalladium(II);
q means quartet;
rt means room temperature;
s means singlet;
sat. means saturated;
SFC means supercritical fluid chromatography;
t means triplet;
td means triplet of doublets;
tq means triplet of quartets;
tt means triplet of triplets;
T3P® means 2,4,6-Tripropyl-1,3,5,2,4,6-trioxatriphosphorinane-2,4,6-trioxide;
TBAF means tetrabutylammonium fluoride;
TBDMS means tert-Butyldimethylsilane;
TEA means triethylamine;
TFA means trifluoroacetic acid;
THF means tetrahydrofuran;
THP means tetrahydropyran;
TLC means thin layer chromatography;
$TMSN_3$ means trimethylsilyl azide;
Xantphos means 4,5-Bis(diphenylphosphino)-9,9-dimethylxanthene;
XPhos means dicyclohexyl-[2-[2,4,6-tri(propan-2-yl)phenyl]phenyl]phosphane;
XPhos Pd G3 means dicyclohexyl-[2-[2,4,6-tri(propan-2-yl)phenyl]phenyl]phosphane; methanesulfonate; palladium; 2-phenylaniline.

HPLC Conditions

Basic:

Method A: X Bridge Prep OBD C18 Column, 30*150 mm, 5 μm; Mobile Phase A: Water (10 mmol/L $NH_4HCO_3$+0.1% $NH_3 \cdot H_2O$), Mobile Phase B: ACN; Flow rate: 60 mL/min;

Method B: XBridge Shield RP18 OBD Column, 30*150 mm, 5 μm; Mobile Phase A: Water (10 mmol/L NH4HCO3+0.1% $NH_3 \cdot$H2O), Mobile Phase B: ACN; Flow rate: 60 mL/min;

Method B2: XBridge Shield RP18 OBD Column, 30*150 mm, 5 μm; Mobile Phase A: Water (10 mmol/L NH4HCO3+0.05% NH3·H2O), Mobile Phase B: ACN; Flow rate: 60 mL/min;

Method C: XBridge Prep OBD C18 Column, 30*150 mm, 5 μm; Mobile Phase A: Water (10 mmol/L $NH_4HCO_3$), Mobile Phase B: MeCN; Flow rate: 60 mL/min;

Method D: XBridge OBD Column, 19*250 mm, 5 μm; Mobile Phase A: Water (10 mmol/L $NH_4HCO_3$+0.1% $NH_3 \cdot H_2O$), Mobile Phase B: ACN; Flow rate: 25 mL/min;

Method E: YMC-Actus Triart C18, 30*150 mm, 5 μm; Mobile Phase A: Water (10 mmol/L $NH_4HCO_3$+0.1% $NH_3 \cdot H_2O$), Mobile Phase B: ACN; Flow rate: 60 mL/min;

Method F: YMC-Actus Triart C18 ExRS, 30*150 mm, 5 μm; Mobile Phase A: Water (10 mmol/L $NH_4HCO_3$), Mobile Phase B: MeCN; Flow rate: 60 mL/min Method G: Aeris PEPTIDE 5 um XB-C18 Axia, 21.2 mm×250 mm, 5 μm; Mobile Phase A: Water (10 mmol/L NH4HCO3), Mobile Phase B: ACN; Flow rate: 60 mL/min;

Method H: Sunfire prep C18 column, 30*150 mm, 5 μm; Mobile Phase A: Water (10 mmol/L $NH_4HCO_3$), Mobile Phase B: ACN; Flow rate: 60 mL/min Method I: Xselect CSH F-pheny OBD Column, 19*250 mm, 5 μm; Mobile Phase A: Water (10 mmol/L $NH_4HCO_3$+0.1% $NH_3 \cdot H_2O$), Mobile Phase B: ACN; Flow rate: 25 mL/min;

Acidic:

Method J: Xselect CSH C18 OBD Column 30*150 mm 5 μm, n; Mobile Phase A: Water (0.1% FA), Mobile Phase B: ACN; Flow rate: 60 mL/min Method K: XBridge Prep OBD C18 Column, 30×150 mm 5 μm; Mobile Phase A: Water (0.1% FA), Mobile Phase B: ACN; Flow rate: 60 mL/min;

Method L: XBridge Prep OBD C18 Column, 19*250 mm, 5 μm; Mobile Phase A: Water (0.1% FA), Mobile Phase B: ACN; Flow rate: 25 mL/min Method M: Sunfire prep C18 column, 30*150 mm, 5 μm; Mobile Phase A: Water (0.1% FA), Mobile Phase B: ACN; Flow rate: 60 mL/min;

Method N: Column: XSelect CSH Fluoro Phenyl, 30*150 mm, 5 μm; Mobile Phase A: Water (0.1% FA), Mobile Phase B: ACN; Flow rate: 60 mL/min;

Method O: Column: XBridge Prep Phenyl OBD Column, 19*250 mm, 5 μm; Mobile Phase A: Water (0.05% TFA), Mobile Phase B: ACN; Flow rate: 25 mL/min;

Method P: CHIRALPAK IC, 2*25 cm, 5 μm; Mobile Phase A: Hex (0.5% 2M $NH_3$-MeOH), Mobile Phase B: EtOH:DCM=1:1; Flow rate: 20 mL/min;

Method Q: CHIRALPAK ID, 2*25 cm, 5 μm; Mobile Phase A: Hex (0.5% 2M $NH_3$-MeOH), Mobile Phase B: EtOH:DCM; Flow rate: 20 mL/min;

Method R: Lux 5 um Cellulose-2 2.12*25 cm, 5 μm; Mobile Phase A: Hex (0.5% 2M $NH_3$-MeOH), Mobile Phase B: MeOH:EtOH=1:1; Flow rate: 20 mL/min Preparation of Intermediates Intermediate 1

N-(2-methyl-5-(2H-tetrazol-5-yl)phenyl)pyrazolo[1,5-a]pyridine-3-carboxamide

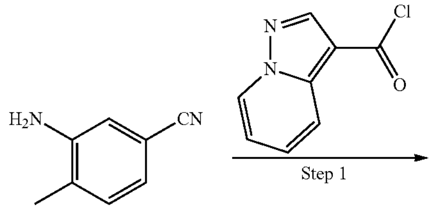

-continued

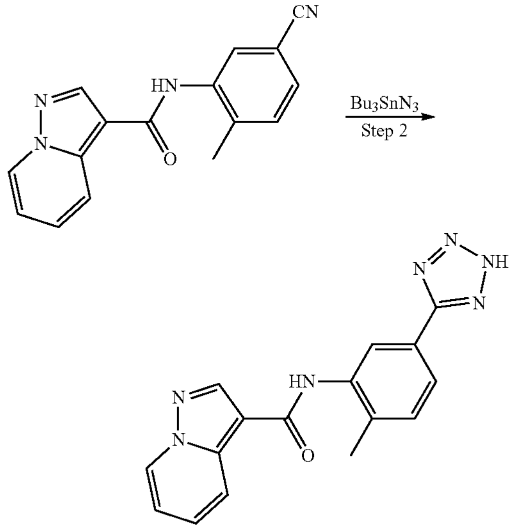

Step 1: Synthesis of N-(5-cyano-2-methylphenyl) pyrazolo[1,5-a]pyridine-3-carboxamide To a stirred solution of 3-amino-4-methylbenzonitrile (18.74 g, 141.8 mmol) in pyridine (300 mL) was added pyrazolo[1,5-a]pyridine-3-carbonyl chloride (25.6 g, 141.8 mmol) in portions at 0° C. The resulting mixture was stirred for an additional 1 h at rt then concentrated under reduced pressure. The residue was poured into water, the precipitated solid was filtered, the filter cake was washed with water and dried to give the title compound (37 g, 94.5%) as a light brown solid. LCMS m/z=277 $[M+H]^+$ Step 2: Synthesis of N-(2-methyl-5-(2H-tetrazol-5-yl)phenyl)pyrazolo[1,5-a]pyridine-3-carboxamide A solution of N-(5-cyano-2-methylphenyl)pyrazolo[1,5-a]pyridine-3-carboxamide (37.0 g, 133.9 mmol) and $Bu_3SnN_3$ (88.9 g, 267.8 mmol) in DMF (370 mL) was stirred for 16 h at 100° C. The mixture was allowed to cool to rt and poured into saturated $NaHCO_3$ solution. KF solution was added and the mixture was washed with PE/MTBE=1/1 (2 L×3) and the aqueous layer was adjusted to pH 3 with HCl. The mixture was filtered and the filter cake washed with PE/MTBE=1/1 (500 mL) and dried to afford the title compound (25.0 g, 58.5%) as an off-white solid. LCMS m/z=320 $[M+H]^+$ Intermediate 2

N-(2-chloro-5-(2H-tetrazol-5-yl)phenyl)pyrazolo[1,5-a]pyridine-3-carboxamide

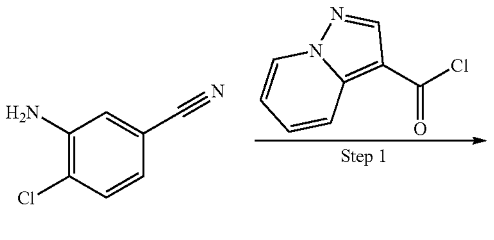

-continued

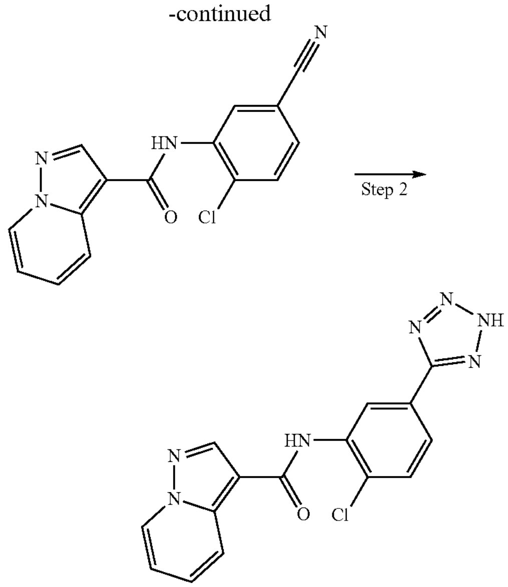

Step 1: Synthesis of N-(2-chloro-5-cyanophenyl) pyrazolo[1,5-a]pyridine-3-carboxamide Pyrazolo[1,5-a]pyridine-3-carbonyl chloride (0.6 g, 3.32 mmol) was added portion-wise to a solution of 3-amino-4-chlorobenzonitrile (507 mg, 3.32 mmol) in pyridine (7 mL). The mixture was diluted with DCM (7 mL) and stirred at rt overnight. The mixture was concentrated in vacuo, the residue triturated with water and the resulting solid filtered off, to give the title compound as a tan colored solid, 904 mg, 92%. LCMS m/z=297 $[M+H]^+$

Step 2: Synthesis of N-(2-chloro-5-(2H-tetrazol-5-yl)phenyl)pyrazolo[1,5-a]pyridine-3-carboxamide A mixture of N-(2-chloro-5-cyanophenyl)pyrazolo[1,5-a]pyridine-3-carboxamide (100 mg, 0.34 mmol), sodium azide (66 mg, 1.01 mmol) and $NH_4Cl$ (54 mg, 1.01 mmol) in DMF (1 mL) was heated under microwave irradiation at 150° C. for 1 h. The reaction was added dropwise to stirring water (25 mL), the pH adjusted to 3 using 1M HCl and the resulting mixture stirred for 45 mins. The mixture was filtered, the resulting solid washed with water and dried to afford the title compound, 92 mg, 80%. LCMS m/z=340 $[M+H]^+$

Intermediate 3

N-(2,4-dimethyl-5-(2H-tetrazol-5-yl)phenyl)pyrazolo[1,5-a]pyridine-3-carboxamide

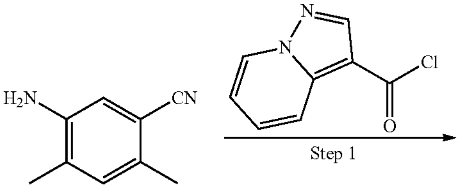

-continued

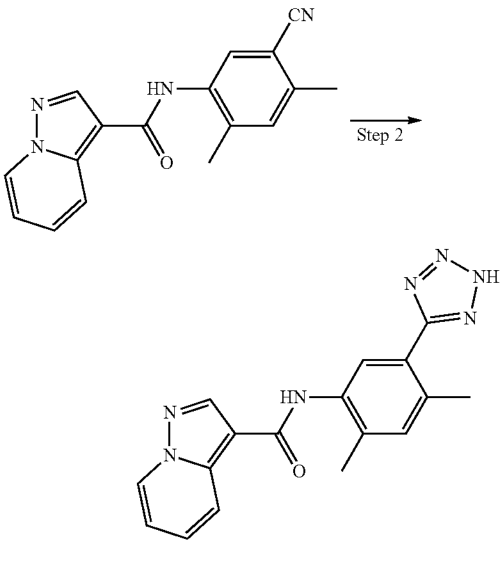

The title compound was obtained as a white solid, 545 mg, from 5-amino-2,4-dimethylbenzonitrile and pyrazolo[1,5-a]pyridine-3-carbonyl chloride, following a similar 2-step procedure to that described in Intermediate 2. LCMS m/z=334 $[M+H]^+$

Intermediate 4

5-bromo-N-(5-(2-(3,3-difluorocyclobutyl)-2H-tetrazol-5-yl)-2-methylphenyl)pyrazolo[1,5-a]pyridine-3-carboxamide

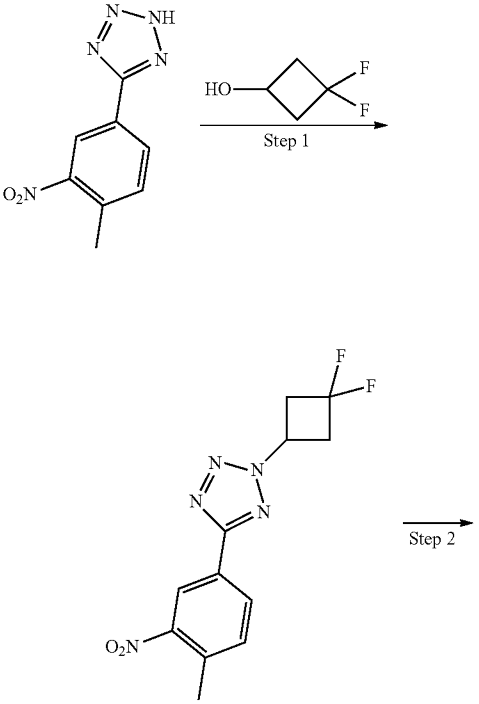

-continued

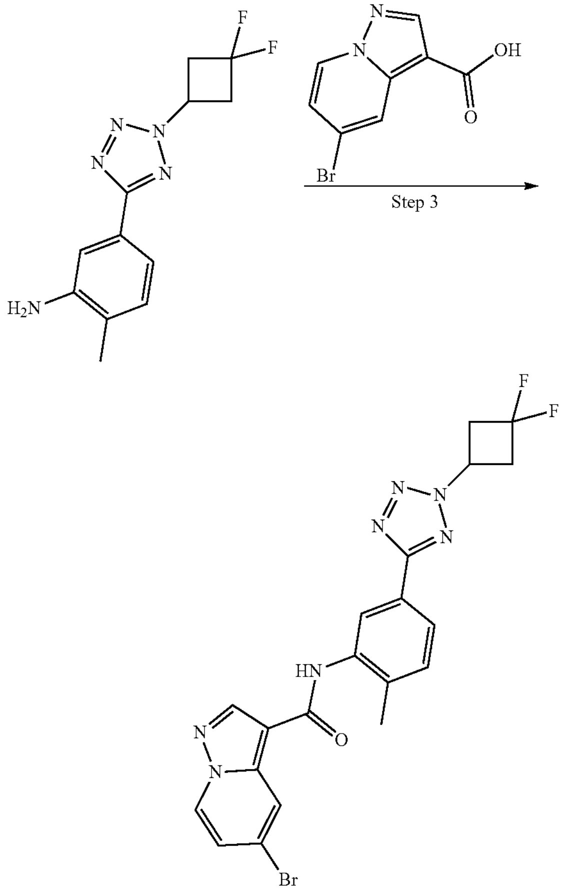

Step 1: Synthesis of 2-(3,3-difluorocyclobutyl)-5-(4-methyl-3-nitrophenyl)-2H-tetrazole To a stirred solution of 5-(4-methyl-3-nitrophenyl)-2H-tetrazole (J. Med. Chem. 54(6), 1599-1612, 2 g, 9.75 mmol) and $PPh_3$ (5.11 g, 19.5 mmol) in THF (20 mL) was added DIAD (3.94 g, 19.5 mmol) dropwise at 0° C. and the reaction mixture stirred at 50° C. for 16 h. The resulting mixture was concentrated under reduced pressure. The residue was purified by silica gel column chromatography, eluting with PE/EtOAc (15/1) to afford the title compound (1.6 g, 55.6%) as a white solid. LCMS m/z=296 $[M+H]^+$ Step 2: Synthesis of 5-(2-(3,3-difluorocyclobutyl)-2H-tetrazol-5-yl)-2-methylaniline To a stirred solution of 2-(3,3-difluorocyclobutyl)-5-(4-methyl-3-nitrophenyl)-1,2,3,4-tetrazole (20 g, 67.7 mmol) and $NH_4Cl$ (36.23 g, 677 mmol) in EtOH (180 mL) and $H_2O$ (20 mL) was added Fe dust (37.9 g, 677 mmol) at rt and the solution stirred at 80° C. for 1 h. The resulting mixture was filtered and the filter cake was washed with EtOH (3x30 mL). The filtrate was concentrated under reduced pressure and the residue purified by silica gel column chromatography, eluting with PE/EtOAc (2/1) to afford the title compound (12.3 g, 67.0%) as a white solid. LCMS m/z=266 $[M+H]^+$ Step 3: Synthesis of 5-bromo-N-(5-(2-(3,3-difluorocyclobutyl)-2H-tetrazol-5-yl)-2-methylphenyl)pyrazolo[1,5-a]pyridine-3-carboxamide A suspension of 5-bromopyrazolo[1,5-a]pyridine-3-carboxylic acid (500 mg, 2.07 mmol) and DMF (0.1 mL) in DCM (20 mL) was cooled to 0° C. and treated slowly with oxalyl chloride (1.3 g, 10.35 mmol). The mixture was removed from the cold bath and stirred at rt for 2.5 h. The mixture was filtered through filter paper and concentrated in vacuo to afford the crude acid chloride as a yellow solid. This was added to a mixture of 5-(2-(3,3-difluorocyclobutyl)-2H-tetrazol-5-yl)-2-methylaniline (549 mg, 2.07 mmol) in DCM (8 mL) and pyridine (8 mL) and the reaction mixture was stirred at rt for 3 h. The resulting solution was concentrated in vacuo and the product purified by column chromatography (DCM:MeOH 90:10) gave the title compound (400 mg, 39.6%) as a yellow solid. LCMS m/z=488, 490 $[M+H]^+$ Intermediate 5

5-bromo-N-(5-(2-((2,2-difluorocyclopropyl)methyl)-2H-tetrazol-5-yl)-2-methylphenyl)pyrazolo[1,5-a]pyridine-3-carboxamide

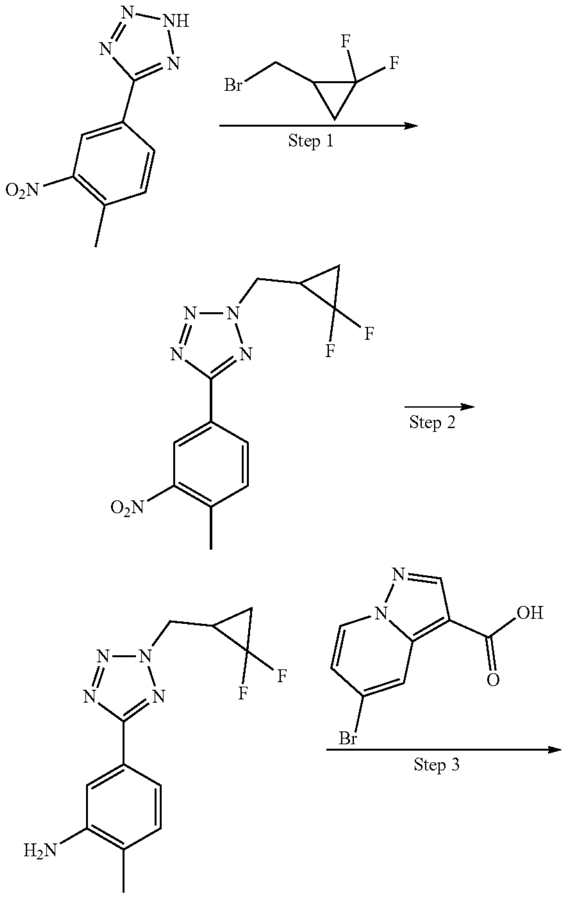

-continued

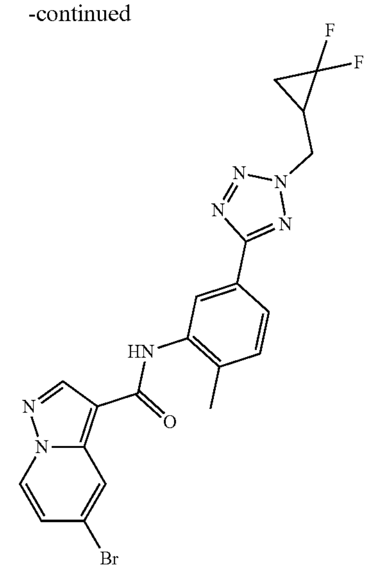

Step 1: Synthesis of 2-((2,2-difluorocyclopropyl) methyl)-5-(4-methyl-3-nitrophenyl)-2H-tetrazole To a stirred solution of 5-(4-methyl-3-nitrophenyl)-2H-tetrazole (1 g, 4.87 mmol) in DMF (10 mL) were added DIPEA (1.88 g, 14.6 mmol) and 2-(bromomethyl)-1,1-difluorocyclopropane (998 mg, 5.84 mmol) at rt. The mixture was stirred for 3 h at 120° C. and then cooled to rt. Water (10 mL) was added and the resulting solution extracted with EtOAc (3×40 mL) and the combined organic phase washed with brine (3×10 mL), dried over $Na_2SO_4$ and concentrated in vacuo. The crude product was purified by silica gel column with PE:EtOAc=3:1 to give the title compound (1 g, 70%) as a colorless oil. LCMS: m/z=296 $[M+H]^+$ Step 2: Synthesis of 5-(2-((2,2-difluorocyclopropyl) methyl)-2H-tetrazol-5-yl)-2-methylaniline To a stirred solution of 2-((2,2-difluorocyclopropyl) methyl)-5-(4-methyl-3-nitrophenyl)-2H-tetrazole (990 mg, 3.35 mmol) in EtOAc (10 mL) was added Pd/C (35.5 mg, 0.34 mmol) at rt. The flask was evacuated and flushed with $N_2$ (3×), followed by $H_2$ and the reaction was stirred for 4 h at rt under an atmosphere of $H_2$ (balloon). The mixture was filtered, the filter cake washed with EtOAc and the filtrate concentrated in vacuo to give the title compound (850 mg, 96%) as a white solid. LCMS: m/z=266 $[M+H]^+$ Step 3: Synthesis of 5-bromo-N-(5-(2-((2,2-difluorocyclopropyl)methyl)-2H-tetrazol-5-yl)-2-methylphenyl)pyrazolo[1,5-a]pyridine-3-carboxamide To a stirred solution of 5-(2-((2,2-difluorocyclopropyl) methyl)-2H-tetrazol-5-yl)-2-methylaniline (150 mg, 0.565 mmol) and 5-bromopyrazolo[1,5-a]pyridine-3-carboxylic acid (272 mg, 1.13 mmol) in THF (3 mL) was added T3P® (537 mg, 1.69 mmol) and pyridine (89.2 mg, 1.13 mmol). The mixture was stirred for 12 h at 60° C. and then cooled to rt. Water was added and the resulting solution was extracted with DCM (3×20 mL). The organic layer was dried over $Na_2SO_4$ and concentrated in vacuo. The crude product was purified by silica gel column eluting with PE:EtOAc=1:1 to give the title compound (210 mg; 76%) as an off-white solid. LCMS m/z=488, 490 $[M+H]^+$ Intermediate 6

5-bromo-N-(2-methyl-5-(2-((1s,3s)-3-(trifluoromethyl)cyclobutyl)-2H-tetrazol-5-yl)phenyl)pyrazolo[1,5-a]pyridine-3-carboxamide

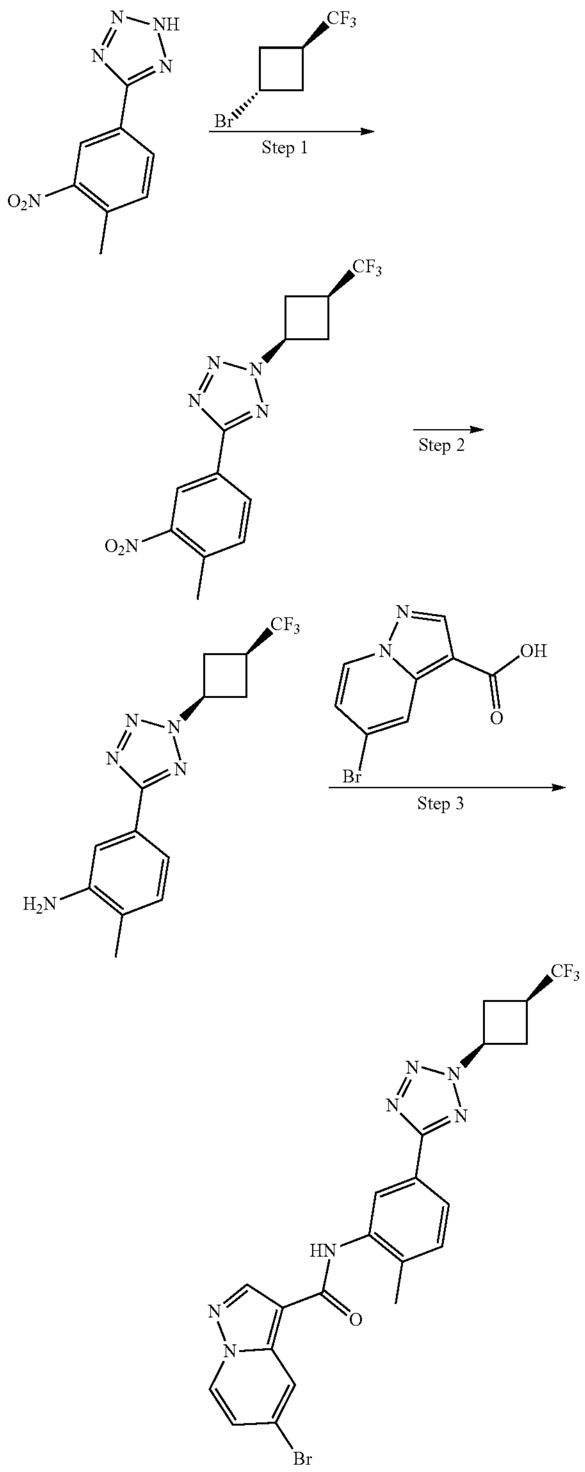

The title compound was obtained as a white solid, 220 mg, from 5-(4-methyl-3-nitrophenyl)-2H-1,2,3,4-tetrazole, (1r,3r)-1-bromo-3-(trifluoromethyl)cyclobutane and 5-bromopyrazolo[1,5-a]pyridine-3-carboxylic acid, following a similar 3 step procedure to that described for Intermediate 5. LCMS: m/z=522 $[M+H]^+$ Intermediate 7

5-bromo-N-(5-(2-(3,3-difluorocyclobutyl)-2H-tetrazol-5-yl)-4-fluoro-2-methylphenyl)pyrazolo[1,5-a]pyridine-3-carboxamide

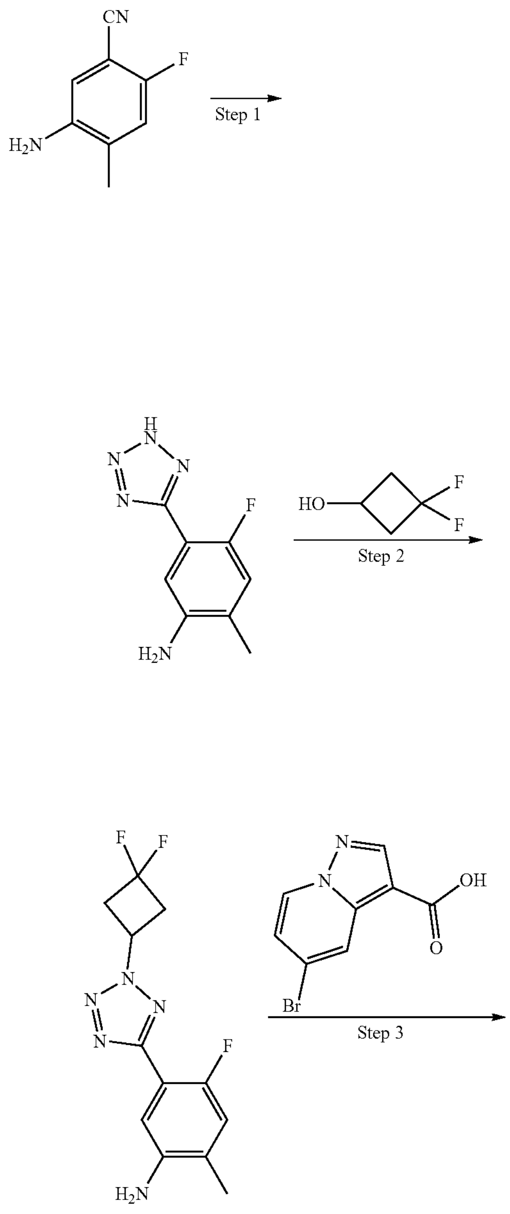

-continued

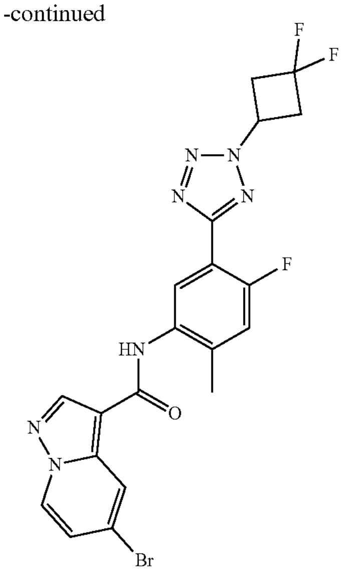

Step 1: Synthesis of 4-fluoro-2-methyl-5-(2H-tetrazol-5-yl)aniline

To a solution of 5-amino-2-fluoro-4-methylbenzonitrile (500 mg, 3.32 mmol) in DMF (5 mL) was added $Bu_3SnN_3$ (3.30 g, 9.95 mmol) and the reaction mixture stirred at 100° C. for 12 h. The mixture was diluted with EtOAc (50 mL) and water (50 mL) and the layers separated. The aqueous phase was extracted with EtOAc (3×20 mL) and the combined organic phase was washed with brine (30 mL). The organic layer was dried over $Na_2SO_4$ and concentrated under vacuum. The residue was purified by prep-TLC with PE:EtOAc=3:1 to give the title compound (330 mg, 51%) as a white solid. LCMS m/z=194 $[M+H]^+$ Step 2: Synthesis of 5-(2-(3,3-difluorocyclobutyl)-2H-tetrazol-5-yl)-4-fluoro-2-methylaniline To a solution of 4-fluoro-2-methyl-5-(2H-tetrazol-5-yl) aniline (200 mg, 1.03 mmol) in THF (5 mL) was added 3,3-difluorocyclobutan-1-ol (166 mg, 1.54 mmol), $PPh_3$ (540 mg, 2.06 mmol) and DIAD (416 mg, 2.06 mmol) at 0° C. The mixture was stirred at rt for 3 h then diluted with EtOAc (50 mL) and water (50 mL). The aqueous phase was extracted with EtOAc (3×50 mL) and the combined organic phase was washed with brine (50 mL). The organic layer was dried over $Na_2SO_4$ and concentrated under vacuum. The residue was purified by prep-TLC (DCM:MeOH=15:1) to give the title compound (200 mg, 68%) as a white solid. LCMS m/z=282 $[M+H]^+$ Step 3: Synthesis of 5-bromo-N-(5-(2-(3,3-difluorocyclobutyl)-2H-tetrazol-5-yl)-4-fluoro-2-methylphenyl)pyrazolo[1,5-a]pyridine-3-carboxamide To a solution of 5-(2-(3,3-difluorocyclobutyl)-2H-tetrazol-5-yl)-4-fluoro-2-methylaniline (200 mg, 0.71 mmol) and pyridine (111 mg, 1.41 mmol) in THF (5 mL) was added 5-bromopyrazolo[1,5-a]pyridine-3-carboxylic acid (203 mg, 0.85 mmol) and T3P® (670 mg, 2.11 mmol) and the reaction mixture stirred at 60° C. for 3 h. The mixture was diluted with EtOAc (30 mL) and water (30 mL). The aqueous phase was extracted with EtOAc (3×20 mL) and the combined organic phase washed with brine (30 mL) dried over $Na_2SO_4$ and concentrated under vacuum. The residue was purified by prep-TLC (DCM:MeOH=15:1) to give the title compound (200 mg, 56%) as a white solid. LCMS m/z=506 $[M+H]^+$ Intermediate 8

5-bromo-N-(2-chloro-5-(2-(3,3-difluorocyclobutyl)-2H-tetrazol-5-yl)-4-fluorophenyl)pyrazolo[1,5-a]pyridine-3-carboxamide

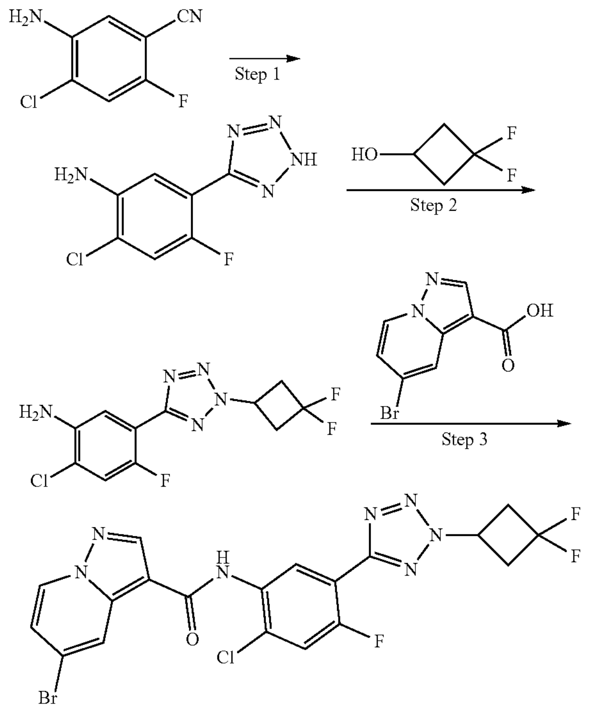

Step 1: Synthesis of 2-chloro-4-fluoro-5-(2H-tetrazol-5-yl)aniline

To a solution of 5-amino-4-chloro-2-fluorobenzonitrile (880 mg, 5.15 mmol) in DMF (8 mL) was added $Bu_3SnN_3$ (5.12 g, 15.4 mmol) and the reaction mixture heated to 100° C. for 24 h. Sat. $NaHCO_3$ solution was added and the mixture washed with MTBE:PE=1:1 (3×30 mL). The aqueous phase was adjusted to pH 4-5 with 1M HCl and the resulting solution extracted with EtOAc (3×100 mL). The combined organic phase was washed with brine (50 mL), dried over $Na_2SO_4$ and concentrated under vacuum. The crude product was purified by silica gel column with DCM:MeOH=10:1 to give the title compound (773 mg, 90%) as an off-white solid. LCMS: m/z=214 $[M+H]^+$ Step 2: Synthesis of 2-chloro-5-(2-(3,3-difluorocyclobutyl)-2H-tetrazol-5-yl)-4-fluoroaniline The title compound was obtained as a white solid, 250 mg, 88% yield, from 2-chloro-4-fluoro-5-(2H-tetrazol-5-yl) aniline and 3,3,-difluorocyclobutan-3-ol, following the method described in Intermediate 7, step 2. LCMS m/z=302 $[M+H]^+$ Step 3: Synthesis of 5-bromo-N-(2-chloro-5-(2-(3,3-difluorocyclobutyl)-2H-tetrazol-5-yl)-4-fluorophenyl)pyrazolo[1,5-a]pyridine-3-carboxamide The title compound was obtained as a white solid, 350 mg, 84%, from 2-chloro-5-(2-(3,3-difluorocyclobutyl)-2H-tetrazol-5-yl)-4-fluoroaniline and 5-bromopyrazolo[1,5-a] pyridine-3-carboxylic acid, following the procedure described in Intermediate 5, step 3. LCMS: m/z=526 $[M+H]^+$ Intermediate 9

5-bromo-N-(4-fluoro-2-methyl-5-(2-((1s,3s)-3-(trifluoromethyl)cyclobutyl)-2H-tetrazol-5-yl)phenyl) pyrazolo[1,5-a]pyridine-3-carboxamide

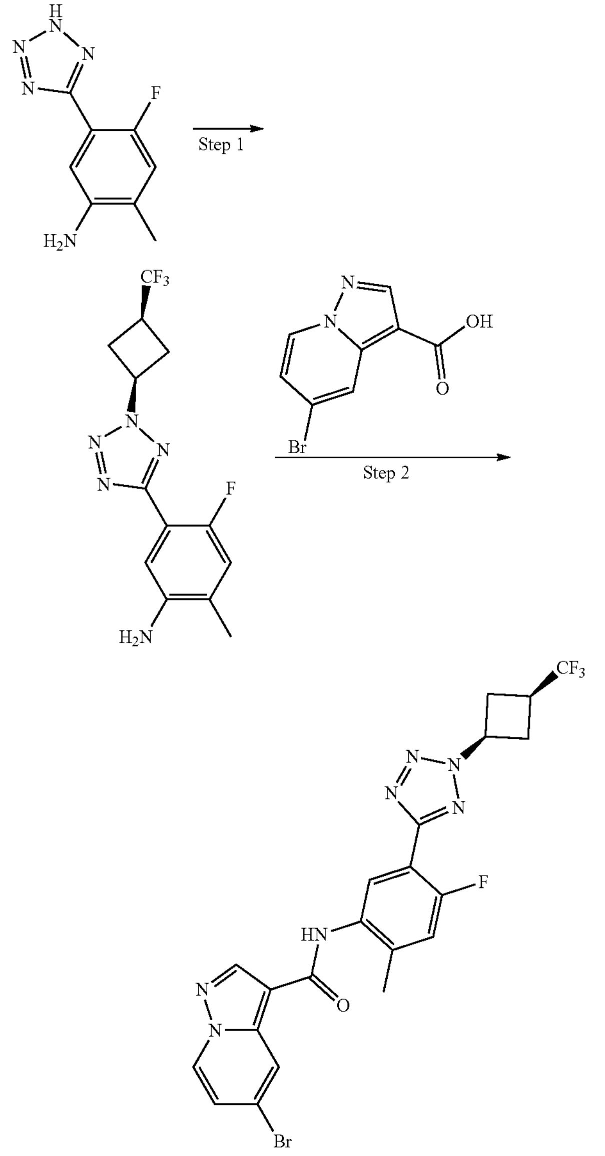

Step 1: Synthesis of 4-fluoro-2-methyl-5-(2-((1s, 3s)-3-(trifluoromethyl)cyclobutyl)-2H-tetrazol-5-yl) aniline To a solution of Intermediate 7, step 1, (300 mg, 1.55 mmol) and DIPEA (399 mg, 3.10 mmol) in DMF (5 mL) was added (1r,3r)-1-bromo-3-(trifluoromethyl)cyclobutane (470 mg, 2.32 mmol) at rt. The mixture was stirred at 100° C. for 2 h and cooled to rt. Water (30 mL) and EtOAc (50 mL) were added, the layers separated, and the aqueous phase was extracted with EtOAc (3×30 mL). The combined organic extracts were dried over $Na_2SO_4$ and concentrated. The crude product was purified by prep-TLC with DCM: MeOH=10:1 to give the title compound (300 mg; 61%) as a yellow solid. LCMS: m/z=316 $[M+H]^+$.

Step 2: Synthesis of N-(4-fluoro-2-methyl-5-(2-((1s, 3s)-3-(trifluoromethyl)cyclobutyl)-2H-tetrazol-5-yl) phenyl)-5-((2-methoxyethyl)amino)pyrazolo[1,5-a] pyridine-3-carboxamide The title compound was obtained as a yellow solid, 60 mg, 70% yield, from 4-fluoro-2-methyl-5-(2-((1s,3s)-3-(trifluoromethyl)cyclobutyl)-2H-tetrazol-5-yl)aniline and 5-bromopyrazolo[1,5-a]pyridine-3-carboxylic acid following the procedure described in Intermediate 7, step 3. LCMS: m/z=538 $[M+H]^+$ Intermediate 10 methyl 3-(5-(3-amino-4-chlorophenyl)-2H-tetrazol-2-yl)azetidine-1-carboxylate

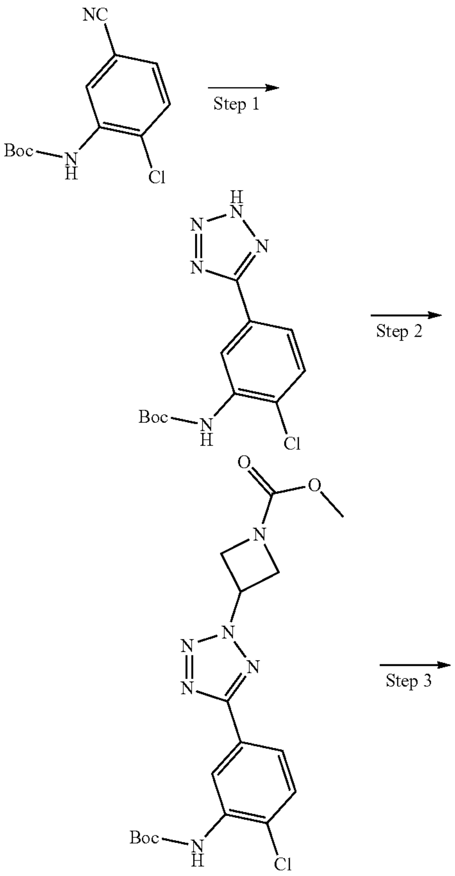

-continued

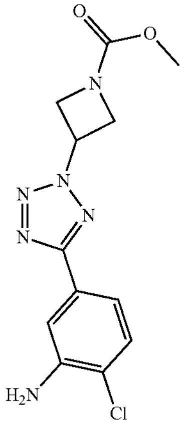

Steps 1 and 2: Synthesis of methyl 3-(5-(3-((tert-butoxycarbonyl)amino)-4-chlorophenyl)-2H-tetrazol-2-yl)azetidine-1-carboxylate The title compound was obtained as a white solid, 2.8 g, from tert-butyl N-(2-chloro-5-cyanophenyl)carbamate and methyl 3-hydroxyazetidine-1-carboxylate, following the same 2 step procedure described in Intermediate 7, steps 1-2. LCMS: m/z=409 $[M+H]^+$ Step 3: Synthesis of methyl 3-(5-(3-amino-4-chlorophenyl)-2H-tetrazol-2-yl)azetidine-1-carboxylate TFA (10 mL) was added dropwise to methyl 3-(5-(3-((tert-butoxycarbonyl)amino)-4-chlorophenyl)-2H-tetrazol-2-yl)azetidine-1-carboxylate (2.8 g, 6.84 mmol) in DCM (30 mL) and the reaction mixture was stirred at rt for 2 h. The mixture was concentrated in vacuo, the residue diluted with DCM and adjusted to pH=8-9 with (sat) $NaHCO_3$ (aq). The organic layer was dried with $Na_2SO_4$ and evaporated under reduced pressure to give the title compound (1.9 g, 90%) as a white solid. LCMS: m/z=309 $[M+H]^+$ Intermediate 11 methyl 3-(5-(3-(5-bromopyrazolo[1,5-a]pyridine-3-carboxamido)-4-methylphenyl)-2H-tetrazol-2-yl) azetidine-1-carboxylate

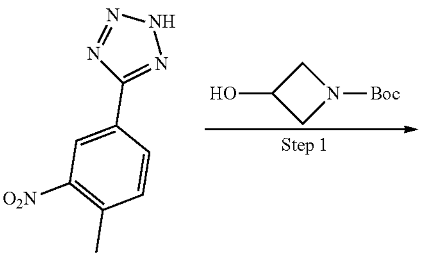

-continued

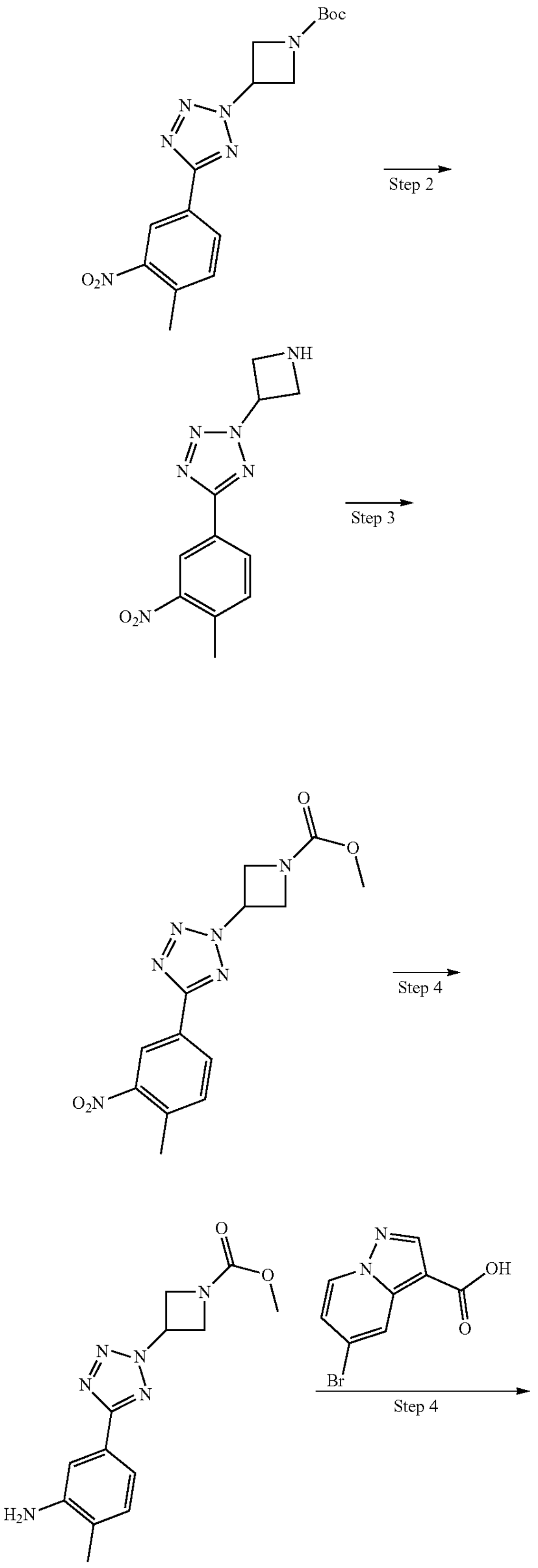

-continued

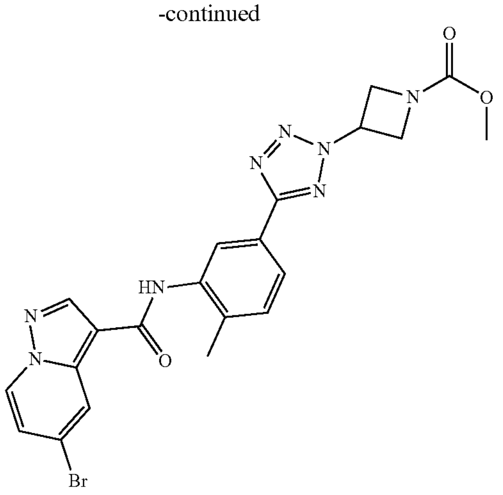

Step 1: Synthesis of tert-butyl 3-(5-(4-methyl-3-nitrophenyl)-2H-tetrazol-2-yl)azetidine-1-carboxylate DIAD (38.24 g, 189.1 mmol) was added dropwise to 5-(4-methyl-3-nitrophenyl)-2H-tetrazole (J. Med. Chem. 54(6), 1599-1612; 2011, 19.4 g, 94.6 mmol), tert-butyl 3-hydroxyazetidine-1-carboxylate (24.57 g, 141.8 mmol) and $PPh_3$ (49.60 g, 189.1 mmol) in THF (200 mL) at 0° C. under $N_2$ and the resulting mixture was stirred for an additional 16 h at 50° C. The reaction mixture was extracted with EtOAc (3×500 mL), the combined organic layers were washed with brine (2×600 mL), dried over $Na_2SO_4$, filtered and the filtrate concentrated under reduced pressure. The solid was washed with anhydrous ether, and the precipitated solid filtered off to give the title compound (32.9 g, 96.6%) as a brown solid. LCMS: m/z=361 $[M+H]^+$ Step 2: Synthesis of 2-(azetidin-3-yl)-5-(4-methyl-3-nitrophenyl)-2H-tetrazole trifluoroacetate A solution of tert-butyl 3-(5-(4-methyl-3-nitrophenyl)-2H-tetrazol-2-yl)azetidine-1-carboxylate (32.9 g, 91.29 mmol) and TFA (161.6 mL) in DCM (300 mL) was stirred for 1 h at rt. The resulting mixture was concentrated under reduced pressure and the residue washed with DCM (3×50 mL). The solid was washed with anhydrous ether, and the precipitated solid, filtered and dried to give the title compound (22.5 g, 94.70%) as a brown solid. LCMS m/z=261 $[M+H]^+$ Step 3: Synthesis of methyl 3-(5-(4-methyl-3-nitrophenyl)-2H-tetrazol-2-yl)azetidine-1-carboxylate To a solution of 2-(azetidin-3-yl)-5-(4-methyl-3-nitrophenyl)-1,2,3,4-tetrazole (8.6 g, 33.0 mmol) trifluoroacetate and TEA (10.03 g, 99.1 mmol) in DCM (90 mL) was added methyl chloroformate (6.24 g, 66.1 mmol) dropwise at 0° C. and the reaction mixture stirred for 45 mins at rt. The resulting mixture was diluted with water, the layers separated and the aqueous layer extracted with DCM (3×150 mL). The combined organic layers were washed with brine (2×200 mL), dried over $Na_2SO_4$, filtered and the filtrate concentrated under reduced pressure to afford the title compound (8.1 g, 77.0%) as a light brown solid. LCMS m/z=319 $[M+H]^+$

Step 4: Synthesis of methyl 3-(5-(3-amino-4-methylphenyl)-2H-tetrazol-2-yl)azetidine-1-carboxylate Pd/C (0.76 g, 7.163 mmol) was added to methyl 3-(5-(4-methyl-3-nitrophenyl)-2H-tetrazol-2-yl)azetidine-1-carboxylate (3.8 g, 11.9 mmol) in EtOAc (50 mL) at rt. The flask was evacuated and flushed three times with $N_2$, followed by flushing with $H_2$. The mixture was stirred for 2 h at rt under an atmosphere of $H_2$ (balloon). The resulting mixture was filtered and the filter cake was washed with MeOH (3×10 mL). The filtrate was concentrated under reduced pressure to give the title compound (3.24 g, 94.3%) as a white solid. LCMS m/z=289 $[M+H]^+$

Step 5: Synthesis of methyl 3-(5-(3-(5-bromopyrazolo[1,5-a]pyridine-3-carboxamido)-4-methylphenyl)-2H-tetrazol-2-yl)azetidine-1-carboxylate A mixture of methyl 3-(5-(3-amino-4-methylphenyl)-2H-tetrazol-2-yl)azetidine-1-carboxylate (600 mg, 2.1 mmol), 5-bromopyrazolo[1,5-a]pyridine-3-carboxylic acid (549 mg, 2.3 mmol), T3P® (5 mL, 50% in EtOAc), pyridine (3 mL) and THF (15 mL) was stirred at 60° C. for 2 h. The mixture was concentrated to dryness and the residue purified by silica gel column to afford the title compound (700 mg, 66%) as an off-white solid. LCMS m/z=511 $[M+H]^+$

Intermediate 12

5-bromo-N-(2-methyl-5-(2-(3-(trifluoromethyl)cyclobutyl)-2H-tetrazol-5-yl)phenyl)pyrazolo[1,5-a]pyridine-3-carboxamide

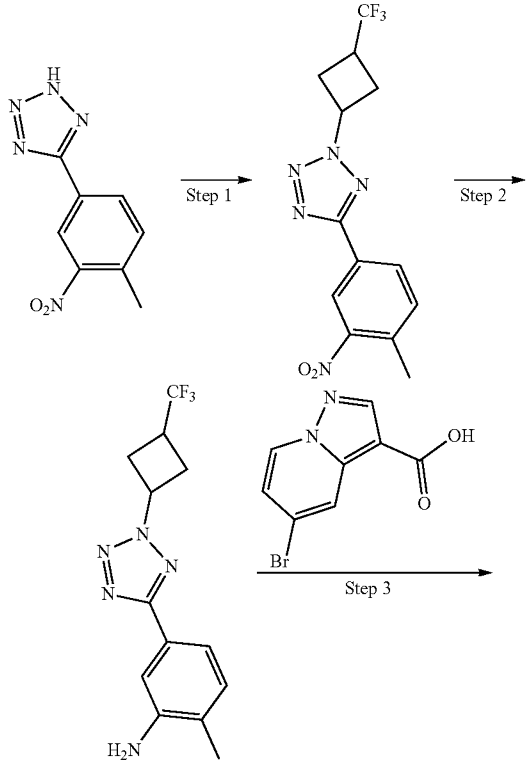

-continued

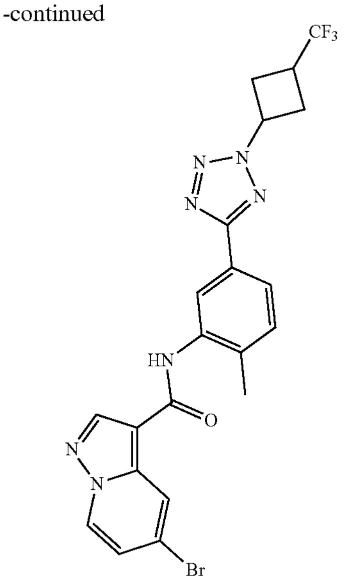

Step 1: Synthesis of 5-(4-methyl-3-nitrophenyl)-2-(3-(trifluoromethyl)cyclobutyl)-2H-tetrazole To a stirred solution of 5-(4-methyl-3-nitrophenyl)-2H-tetrazole (J. Med. Chem. 54(6), 1599-1612, 440 mg, 2.14 mmol) in DMF (0.50 mL) was added DIPEA (553 mg, 4.28 mmol) and (1r,3r)-1-bromo-3-(trifluoromethyl)cyclobutane (434 mg, 2.14 mmol) in portions at rt and the solution was stirred at 120° C. for 16 h. The resulting mixture was concentrated under reduced pressure. The residue was purified by prep-TLC (PE:EtOAc=3:1) to afford the title compound (550 mg, 78.5%) as a yellow solid. LCMS: m/z=328 $[M+H]^+$

Step 2: Synthesis of 2-methyl-5-(2-(3-(trifluoromethyl)cyclobutyl)-2H-tetrazol-5-yl)aniline The title compound was obtained as a yellow solid, 160 mg, 88.3%, from 5-(4-methyl-3-nitrophenyl)-2-(3-(trifluoromethyl)cyclobutyl)-2H-tetrazole following the procedure described in Intermediate 5, step 2. LCMS: m/z=298 $[M+H]^+$

Step 3: Synthesis of 5-bromo-N-(2-methyl-5-(2-(3-(trifluoromethyl)cyclobutyl)-2H-tetrazol-5-yl)phenyl)pyrazolo[1,5-a]pyridine-3-carboxamide To a solution of 2-methyl-5-(2-(3-(trifluoromethyl)cyclobutyl)-2H-tetrazol-5-yl)aniline (200 mg, 0.67 mmol) and 5-bromopyrazolo[1,5-a]pyridine-3-carboxylic acid (194 mg, 0.81 mmol) in DMF (4 mL) were added HATU (380 mg, 1.0 mmol) and DIPEA (173 mg, 1.34 mmol) dropwise at rt and the solution stirred at 80° C. for 3 h. The resulting mixture was concentrated under reduced pressure and the residue purified by prep-TLC (PE:EtOAc=2:1) to afford the title compound (160 mg, 45.9%) as a yellow solid. LCMS: m/z=522 $[M+H]^+$ Intermediate 13

5-bromo-N-(2-methyl-5-(2-methyl-2H-tetrazol-5-yl)phenyl)pyrazolo[1,5-a]pyridine-3-carboxamide

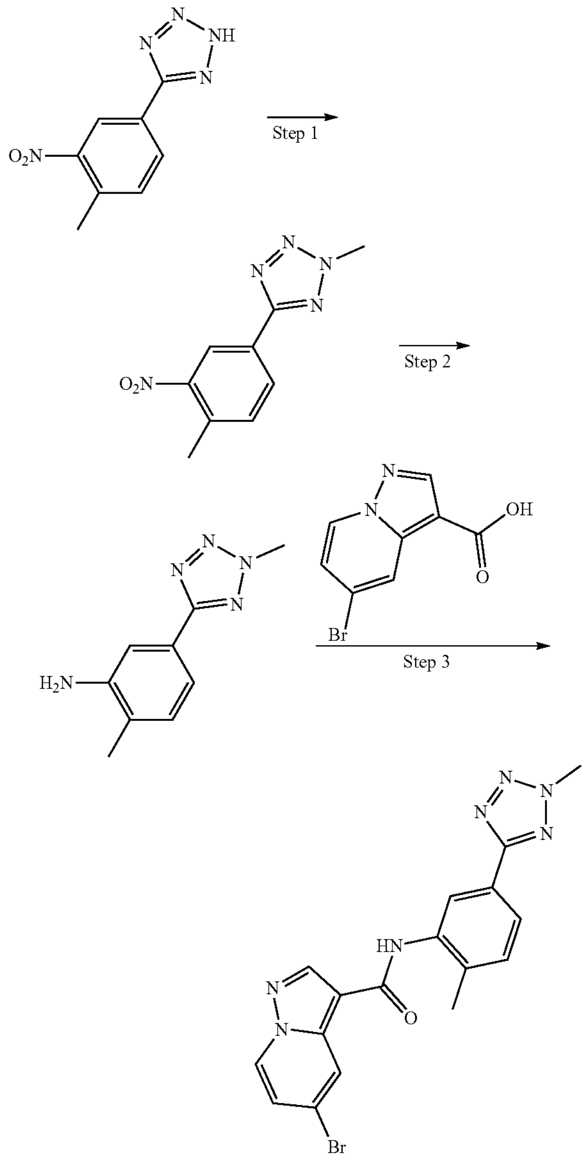

Step 1: Synthesis of 2-methyl-5-(4-methyl-3-nitrophenyl)-2H-1,2,3,4-tetrazole

To a solution of 5-(4-methyl-3-nitrophenyl)-2H-tetrazole (J. Med. Chem. 54(6), 1599-1612, 1 g, 4.87 mmol) and $K_2CO_3$ (1.34 g, 9.74 mmol) in DMF/dioxane (10/10 mL) was added MeI (823 mg, 5.84 mmol) dropwise under $N_2$ at 0° C. and the reaction mixture stirred for 2 h at rt. The mixture was quenched with ice water and extracted with DCM. The organic layer was washed with brine, concentrated in vacuo and the residue purified by silica gel column eluting with PE:EtOAc=1:1 to give the title compound (0.8 g, 75%) as a white solid. LCMS m/z=220 [M+H]$^+$ Step 2: Synthesis of 2-methyl-5-(2-methyl-2H-1,2,3,4-tetrazol-5-yl)aniline To a solution of 2-methyl-5-(4-methyl-3-nitrophenyl)-2H-tetrazole (0.8 g, 3.64 mmol) in MeOH (10 mL) was added Pd/C (771 mg, 7.27 mmol, 10%). The flask was evacuated and flushed with $N_2$, and then $H_2$. The mixture was stirred for 2 h at rt under an atmosphere of $H_2$ (balloon). The reaction mixture was filtered, the filter cake was washed with MeOH and the filtrate concentrated under vacuum to give the title compound (0.6 g; 87%) as a white solid. LCMS m/z=190 [M+H]$^+$ Step 3: Synthesis of 5-bromo-N-(2-methyl-5-(2-methyl-2H-tetrazol-5-yl)phenyl)pyrazolo[1,5-a]pyridine-3-carboxamide To a stirred solution of 2-methyl-5-(2-methyl-2H-1,2,3,4-tetrazol-5-yl)aniline (0.6 g, 3.17 mmol) and 5-bromopyrazolo[1,5-a]pyridine-3-carboxylic acid (915 mg, 3.80 mmol) in THF (10 mL) were added pyridine (501 mg, 6.34 mmol) and T3P® (190 mg, 4.75 mmol) under $N_2$. The reaction was stirred for 2 h at 60° C. and quenched with water. The mixture was extracted with DCM (100 mL×2), the combined organic layer was dried over $Na_2SO_4$ and concentrated under vacuum. The product was purified by prep-TLC with PE:EtOAc=2:1 to give the title compound (0.7 g, 53%) as a white solid. LCMS m/z=412 [M+H]$^+$ Intermediate 14 ethyl 3-(5-(3-(5-bromopyrazolo[1,5-a]pyridine-3-carboxamido)-4-methylphenyl)-2H-tetrazol-2-yl)azetidine-1-carboxylate

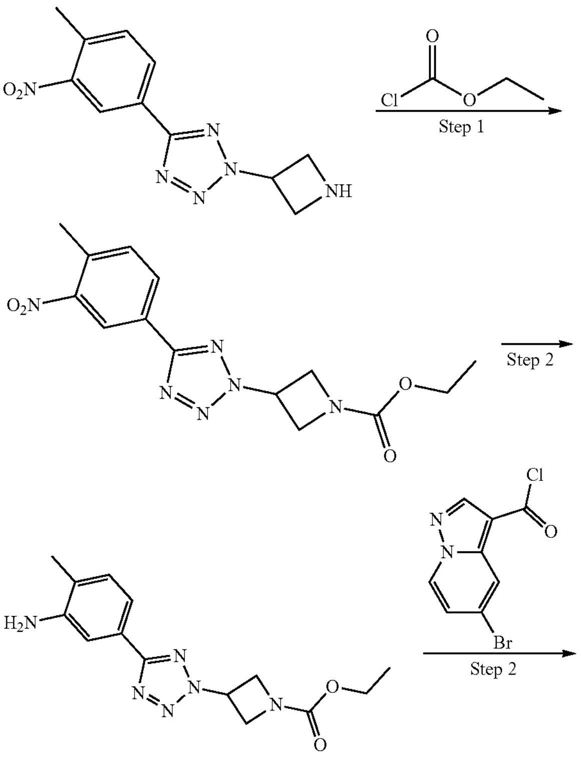

-continued

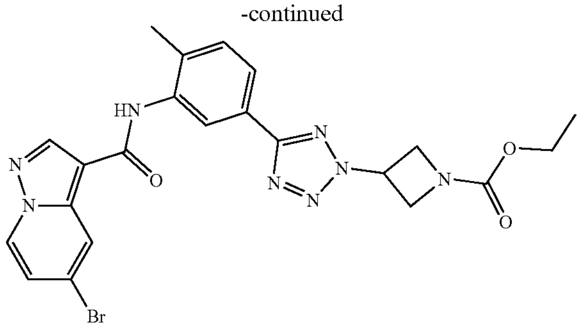

Step 1: Synthesis of ethyl 3-(5-(4-methyl-3-nitrophenyl)-2H-tetrazol-2-yl)azetidine-1-carboxylate Ethyl chloroformate (375 mg, 3.46 mmol) was added dropwise to a solution of Intermediate 11, step 2, (750 mg, 2.88 mmol) and pyridine (684 mg, 8.65 mL) in DCM (10 mL) in an ice bath and the reaction mixture stirred at rt for 30 mins. The mixture was concentrated in vacuo and the residue partitioned between water and DCM. The organic layer was dried ($Na_2SO_4$), filtered and evaporated under reduced pressure to afford the title compound as a tan colored solid, 806 mg, 84%. LCMS m/z=333 $[M+H]^+$ Step 2: Synthesis of ethyl 3-(5-(3-amino-4-methylphenyl)-2H-tetrazol-2-yl)azetidine-1-carboxylate A mixture of ethyl 3-(5-(4-methyl-3-nitrophenyl)-2H-tetrazol-2-yl)azetidine-1-carboxylate (806 mg, 2.53 mmol) and 80 mg of 1% Pt/2% V on carbon in MeOH (25 mL) was hydrogenated under balloon pressure for 2 h. The mixture was filtered through Celite® and evaporated to give the title compound, 700 mg, 95% as an off-white foam.

Step 3: Synthesis of ethyl 3-(5-(3-(5-bromopyrazolo[1,5-a]pyridine-3-carboxamido)-4-methylphenyl)-2H-tetrazol-2-yl)azetidine-1-carboxylate 5-Bromopyrazolo[1,5-a]pyridine-3-carbonyl chloride (600 mg, 2.31 mmol) was added in portions to a solution of ethyl 3-(5-(3-amino-4-methylphenyl)-2H-tetrazol-2-yl)azetidine-1-carboxylate (699 mg, 2.31 mmol) and pyridine (183 mg, 2.31 mmol) in DCM (12 mL) in an ice bath and the reaction then stirred at rt for 30 mins. The mixture was diluted with DCM and washed with water. The organic layer was dried over $Na_2SO_4$, filtered and evaporated to give the crude product. This was purified by ISCO chromatography (0 to 8% MeOH/DCM) to give the title compound, 1.14 g, 94% as an off-white solid. LCMS m/z=526 $[M+H]^+$ Intermediate 15

N-(5-(2-(azetidin-3-yl)-2H-tetrazol-5-yl)-2-methylphenyl)pyrazolo[1,5-a]pyridine-3-carboxamide

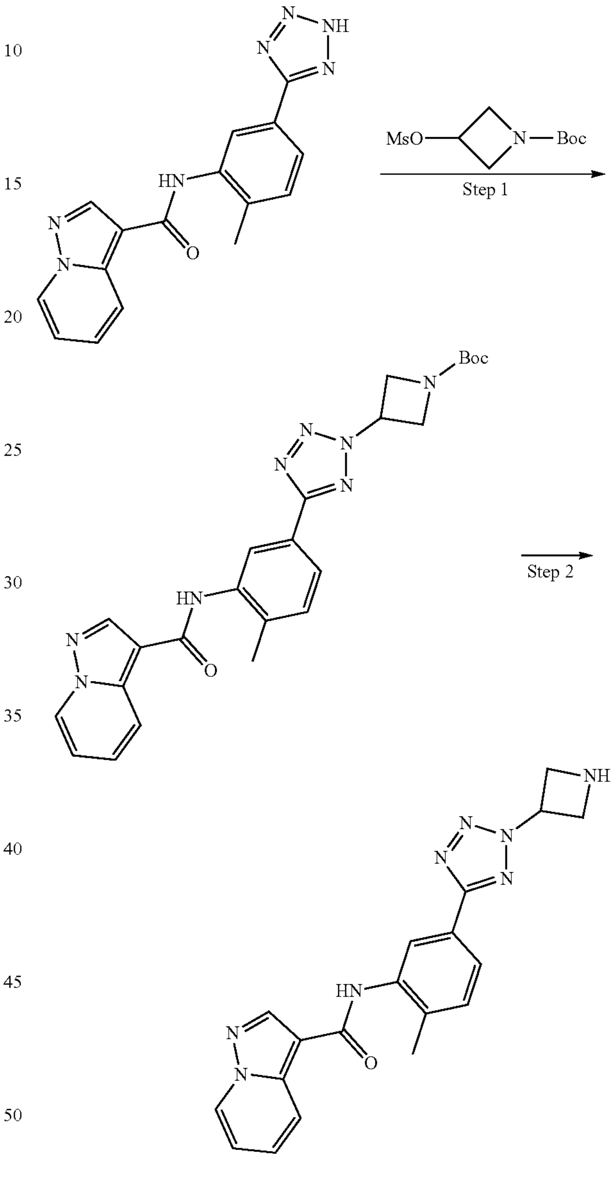

Step 1: Synthesis of tert-butyl 3-(5-(4-methyl-3-(pyrazolo[1,5-a]pyridine-3-carboxamido)phenyl)-2H-tetrazol-2-yl)azetidine-1-carboxylate To a stirred solution of Intermediate 1, (2.5 g, 7.82 mmol) and DIPEA (2.01 g, 15.6 mmol) in DMF (10 mL) was added tert-butyl 3-(methanesulfonyloxy)azetidine-1-carboxylate (2.94 g, 11.7 mmol) at rt under $N_2$. The mixture was stirred at 120° C. for 2 h and then cooled to rt. Water (10 mL) was added and the resulting solution was extracted with DCM (3x30 mL). The organic layer was dried over $Na_2SO_4$ and concentrated under vacuum. The crude product was purified by silica gel column with DCM:MeOH=10:1 to give the title compound (3.4 g; 92%) as a white solid. LCMS: m/z=475 [M+H]$^+$ Step 2: Synthesis of N-(5-(2-(azetidin-3-yl)-2H-tetrazol-5-yl)-2-methylphenyl)pyrazolo[1,5-a]pyridine-3-carboxamide To a stirred solution of tert-butyl 3-(5-(4-methyl-3-(pyrazolo[1,5-a]pyridine-3-carboxamido)phenyl)-2H-tetrazol-2-yl)azetidine-1-carboxylate (3.2 g, 6.74 mmol) in DCM (20 mL) was added TFA (5 mL). The mixture was stirred at rt for 2 h and concentrated. The mixture was adjusted pH to 7 with sat. $NaHCO_3$ solution. The mixture was filtered and the filter cake was washed with water (10 mL), then dried in vacuum to give the title compound (2.1 g; 83%) as a white solid. LCMS m/z=475 [M+H]$^+$ Intermediate 16

N-(5-(4-(azetidin-3-yl)-2H-1,2,3-triazol-2-yl)-2-chlorophenyl)pyrazolo[1,5-a]pyridine-3-carboxamide

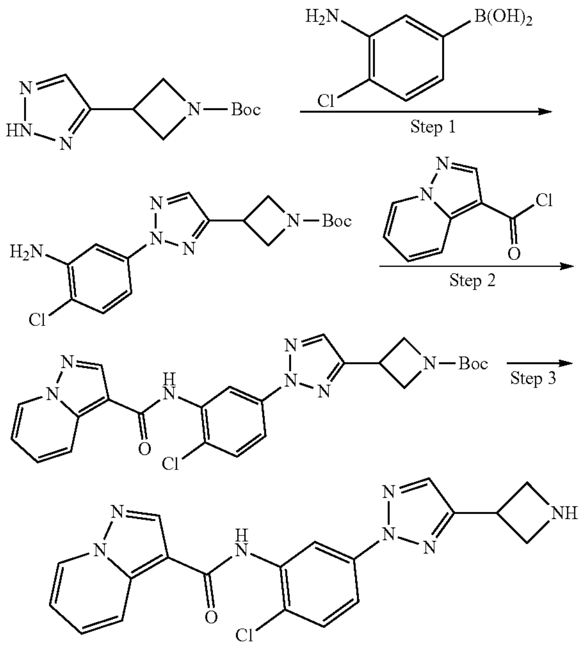

Step 1: Synthesis of tert-butyl 3-(2-(3-amino-4-chlorophenyl)-2H-1,2,3-triazol-4-yl)azetidine-1-carboxylate To a solution of tert-butyl 3-(2H-1,2,3-triazol-4-yl)azetidine-1-carboxylate (190 mg, 0.85 mmol) and (3-amino-4-chlorophenyl)boronic acid (289 mg, 1.69 mmol) in DCE (5 mL) were added $Cu(OAc)_2$ (153 mg, 0.85 mmol), $Na_2CO_3$ (179 mg, 1.69 mmol) and 2,2'-bipyridine (132 mg, 0.85 mmol) at rt and the reaction mixture heated at 60° C. for 3 h under $O_2$. The mixture was filtered and the filter cake was washed with DCM (10 mL). Water was added to the filtrate and the resulting solution extracted with DCM (3×20 mL). The organic layer was dried with $Na_2SO_4$ and concentrated under vacuum. The crude product was purified by silica gel column with PE:EtOAc=1:1 to give the title compound (248 mg, 84%) as a pink oil. LCMS: m/z=348 [M−H]

Step 2: Synthesis of tert-butyl 3-(2-(4-chloro-3-(pyrazolo[1,5-a]pyridine-3-carboxamido)phenyl)-2H-1,2,3-triazol-4-yl)azetidine-1-carboxylate The title compound was obtained as a yellow oil, 324 mg, 98%, from tert-butyl 3-(2-(3-amino-4-chlorophenyl)-2H-1,2,3-triazol-4-yl)azetidine-1-carboxylate and pyrazolo[1,5-a]pyridine-3-carbonyl chloride, following a similar procedure to that described in Intermediate 14, step 3. LCMS: m/z=492 [M−1]

Step 3: Synthesis of N-(5-(4-(azetidin-3-yl)-2H-1,2,3-triazol-2-yl)-2-chlorophenyl)pyrazolo[1,5-a]pyridine-3-carboxamide The title compound was obtained as an off-white solid, 320 mg, crude, from tert-butyl 3-(2-(4-chloro-3-(pyrazolo[1,5-a]pyridine-3-carboxamido)phenyl)-2H-1,2,3-triazol-4-yl)azetidine-1-carboxylate following the procedure described in Intermediate 10, step 3. LCMS: m/z=394 [M+H]$^+$ Intermediate 17

N-(5-(5-(azetidin-3-yl)-2H-tetrazol-2-yl)-2-methylphenyl)pyrazolo[1,5-a]pyridine-3-carboxamide

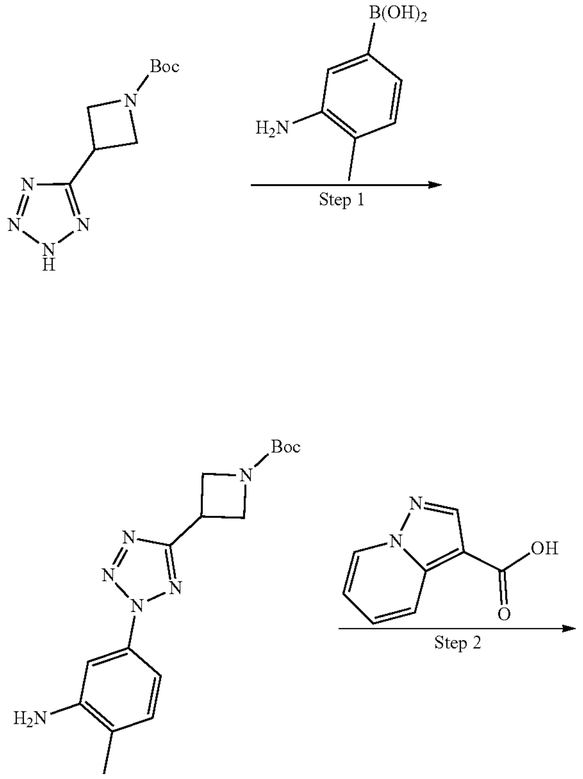

-continued

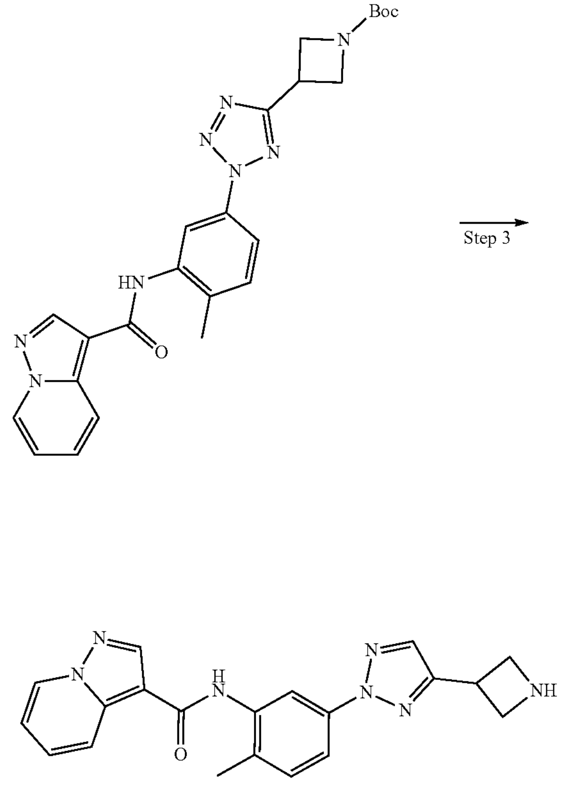

Step 1: Synthesis of tert-butyl 3-(2-(3-amino-4-methylphenyl)-2H-tetrazol-5-yl)azetidine-1-carboxylate The title compound was obtained as a yellow oil, 1 g, 22%, from tert-butyl 3-(2H-1,2,3,4-tetrazol-5-yl)azetidine-1-carboxylate and (3-amino-4-methylphenyl)boronic acid, following the procedure described in Intermediate 16, step 1. LCMS m/z=331 [M+1-56]

Step 2: Synthesis of tert-butyl 3-(2-(4-methyl-3-(pyrazolo[1,5-a]pyridine-3-carboxamido)phenyl)-2H-tetrazol-5-yl)azetidine-1-carboxylate The title compound was obtained as a yellow solid, 280 mg, 65%, from tert-butyl 3-(2-(3-amino-4-methylphenyl)-2H-1,2,3,4-tetrazol-5-yl)azetidine-1-carboxylate and pyrazolo[1,5-a]pyridine-3-carboxylic acid, following the procedure described in Intermediate 7, step 3. LCMS m/z=419 $[M+H]^+$ Step 3: N-(5-(5-(azetidin-3-yl)-2H-tetrazol-2-yl)-2-methylphenyl)pyrazolo[1,5-a]pyridine-3-carboxamide The title compound was obtained as a white solid, 70 mg, 89%, from tert-butyl 3-(2-(4-methyl-3-(pyrazolo[1,5-a]pyridine-3-carboxamido)phenyl)-2H-tetrazol-5-yl)azetidine-1-carboxylate, following the procedure described in Intermediate 10, step 3. LCMS m/z=375 $[M+H]^+$ Intermediate 18 methyl 3-(2-(3-(5-bromopyrazolo[1,5-a]pyridine-3-carboxamido)-4-methylphenyl)-2H-1,2,3-triazol-4-yl)azetidine-1-carboxylate

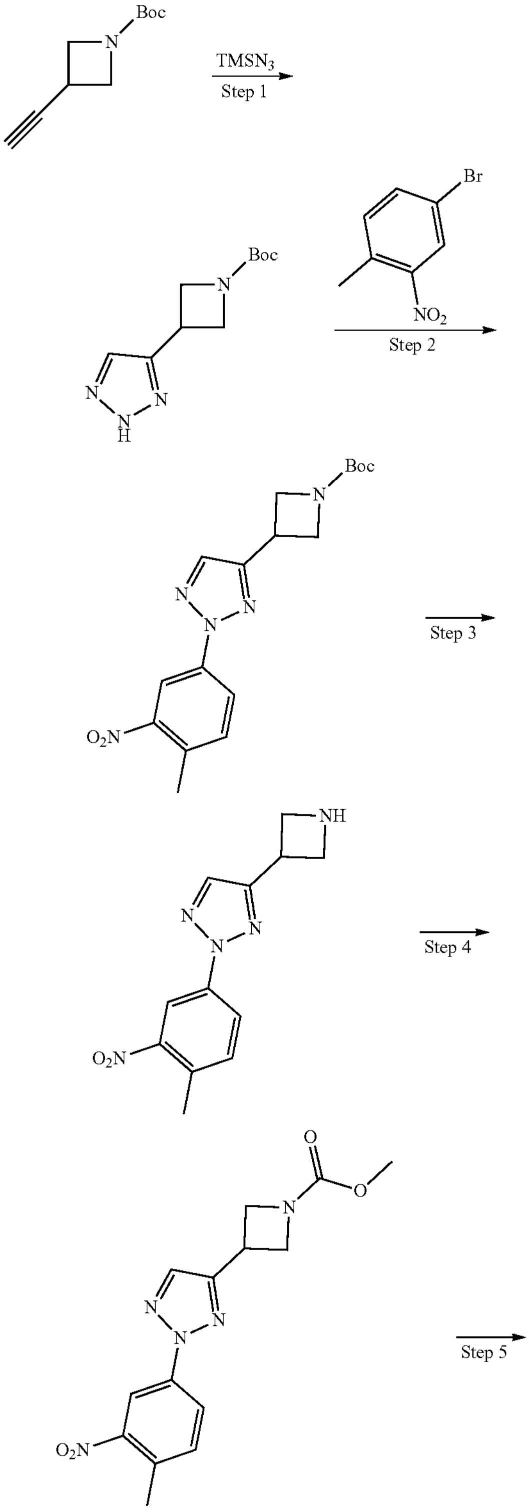

-continued

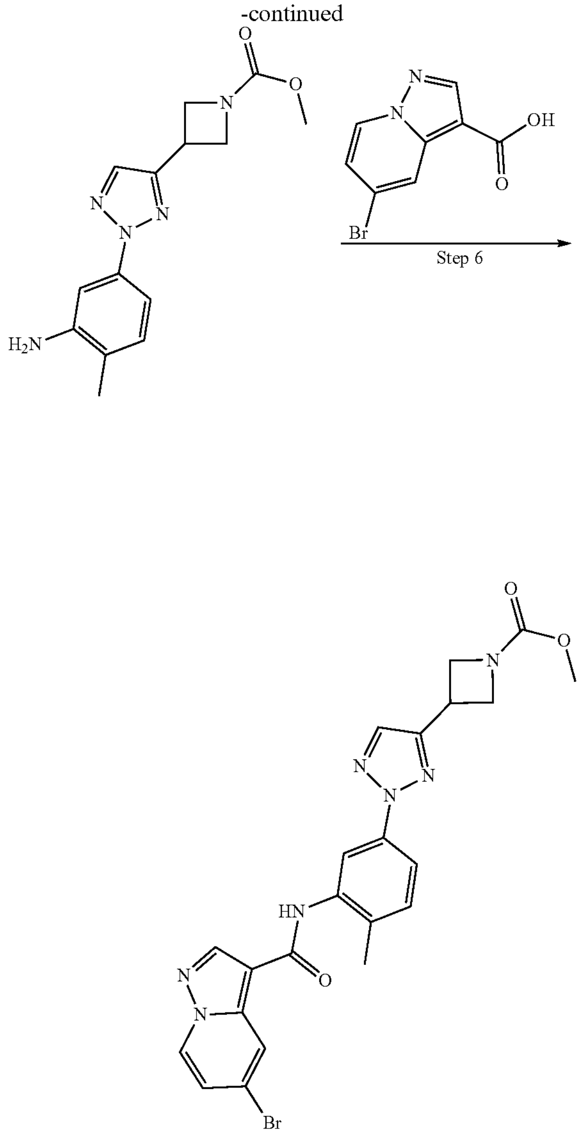

Step 1: Synthesis of tert-butyl 3-(2H-1,2,3-triazol-4-yl)azetidine-1-carboxylate A mixture of tert-butyl 3-ethynylazetidine-1-carboxylate (2.5 g, 13.8 mmol), $TMSN_3$ (2.38 g, 20.7 mmol) and CuI (131 mg, 0.69 mmol) in DMF (20 mL) and MeOH (5 mL) was heated at 100° C. overnight. The cooled reaction mixture was poured into water (125 mL), EtOAc (75 mL) was added and the mixture stirred vigorously. The biphasic mixture was filtered through Celite® and then washed with EtOAc. The layers were separated, the organic layer washed with water, brine and dried over $Na_2SO_4$, filtered and evaporated to give the title compound, 2.22 g, 71.7% as a pale yellow/green semi-solid.

Step 2: Synthesis of tert-butyl 3-(2-(4-methyl-3-nitrophenyl)-2H-1,2,3-triazol-4-yl)azetidine-1-carboxylate A large pressure vessel was purged with $N_2$ and tert-butyl 3-(2H-1,2,3-triazol-4-yl)azetidine-1-carboxylate (2.20 g, 9.81 mmol), 4-bromo-1-methyl-2-nitrobenzene (2.12 g, 9.81 mmol), $K_3PO_4$ (4.17 g, 19.6 mmol) and toluene (15 mL) added. $Pd_2(dba)_3$ (79 mg, 0.1 mmol) and $Me_4$-t-butylxphos (94 mg, 0.2 mmol) were charged in a septum capped vial, purged with $N_2$, toluene (5 mL) added and the mixture stirred at 120° C. for 5 min. The cooled mixture was transferred by syringe into the pressure vessel under $N_2$ and the reaction mixture stirred at 120° C. overnight. The mixture was diluted with EtOAc, filtered through Celite® and evaporated. The crude product was purified by silica gel ISCO chromatography (0 to 60% EtOAc/Hex) to give the title compound, 2.79 g, as yellow foam.

Step 3: Synthesis of 4-(azetidin-3-yl)-2-(4-methyl-3-nitrophenyl)-2H-1,2,3-triazole A solution of tert-butyl 3-(2-(4-methyl-3-nitrophenyl)-2H-1,2,3-triazol-4-yl)azetidine-1-carboxylate (306 mg, 0.85 mmol) in DCM (4 mL) and TFA (0.66 mL) was stirred at rt overnight. The solution was evaporated, the residue partitioned between 5% MeOH/DCM and $NaHCO_3$ (aq) and the organic layer dried over $Na_2SO_4$, filtered and evaporated to give the title compound, as an off-white foam. 771 mg, 91% yield.

Step 4: Synthesis of methyl 3-(2-(4-methyl-3-nitrophenyl)-2H-1,2,3-triazol-4-yl)azetidine-1-carboxylate Methyl chloroformate (0.09 mL, 1.16 mmol) was added to a solution of 4-(azetidin-3-yl)-2-(4-methyl-3-nitrophenyl)-2H-1,2,3-triazole (200 mg, 0.77 mmol) in DCM (3 mL) and pyridine (0.31 mL) and the reaction mixture stirred at rt for 45 mins. The reaction was diluted with DCM and washed with water. The organic layer was dried over $Na_2SO_4$, filtered and evaporated to give the crude product. This was purified by silica gel ISCO chromatography (0 to 75% EtOAc/Hex) to give the title compound, 233 mg as viscous pale-yellow oil. LCMS m/z=318 $[M+H]^+$

Step 5: Synthesis of methyl 3-(2-(3-amino-4-methylphenyl)-2H-1,2,3-triazol-4-yl)azetidine-1-carboxylate The title compound was obtained as a white semi-solid, from methyl 3-(2-(4-methyl-3-nitrophenyl)-2H-1,2,3-triazol-4-yl)azetidine-1-carboxylate, following the procedure described in Intermediate 14, step 2. LCMS m/z=288 $[M+H]^+$

Step 6: Synthesis of methyl 3-(2-(3-(5-bromopyrazolo[1,5-a]pyridine-3-carboxamido)-4-methylphenyl)-2H-1,2,3-triazol-4-yl)azetidine-1-carboxylate The title compound was obtained as a white foam, 415 mg, 85%, from methyl 3-(2-(3-amino-4-methylphenyl)-2H-1,2,3-triazol-4-yl)azetidine-1-carboxylate and 5-bromopyrazolo[1,5-a]pyridine-3-carbonyl chloride, following the procedure described in Intermediate 14, step 3. LCMS m/z=512 $[M+H]^+$ Intermediate 19 methyl 3-(2-(3-(5-bromopyrazolo[1,5-a]pyridine-3-carboxamido)-4-chlorophenyl)-2H-1,2,3-triazol-4-yl)azetidine-1-carboxylate

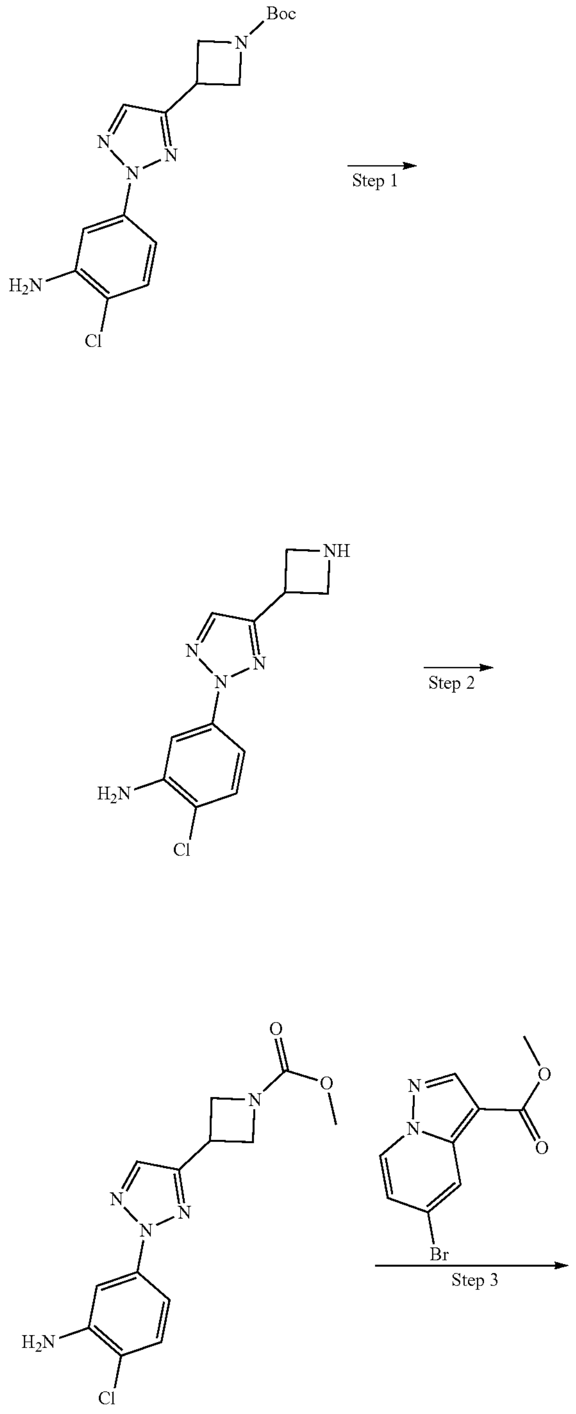

-continued

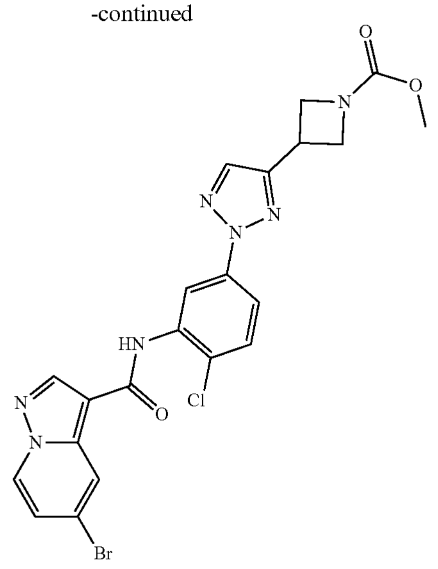

Step 1: Synthesis of 5-(4-(azetidin-3-yl)-2H-1,2,3-triazol-2-yl)-2-chloroaniline trifluoroacetate To a stirred solution of Intermediate 16, step 1, (300 mg, 0.86 mmol) in DCM (4 mL) was added TFA (2 mL) dropwise at 0° C. The reaction was stirred for 2 h at 0° C. and was then evaporated under reduced pressure to give the title compound (185 mg, 86.4%), as a light-yellow solid. LCMS: m/z=249 $[M+H]^+$ Step 2: Synthesis of methyl 3-(2-(3-amino-4-chlorophenyl)-2H-1,2,3-triazol-4-yl)azetidine-1-carboxylate Dimethyl dicarbonate (150.4 mg, 1.12 mmol) was added dropwise to 5-(4-(azetidin-3-yl)-2H-1,2,3-triazol-2-yl)-2-chloroaniline trifluoroacetate (280 mg, 1.12 mmol) and TEA (567.4 mg, 5.61 mmol) in DCM (3 mL) and the reaction was stirred for 2 h at 0° C. The resulting mixture was extracted with EtOAc (20 mL), the organic layer was washed with $H_2O$ (3×10 mL) and dried over $Na_2SO_4$. After filtration, the filtrate was concentrated under reduced pressure and the residue was purified by prep-TLC (DCM:MeOH=20:1) to afford the title compound (215 mg, 62.3%) as a light-yellow solid. LCMS: m/z=308 $[M+H]^+$ Step 3: methyl 3-(2-(3-(5-bromopyrazolo[1,5-a]pyridine-3-carboxamido)-4-chlorophenyl)-2H-1,2,3-triazol-4-yl)azetidine-1-carboxylate To a mixture of methyl 3-(2-(3-amino-4-chlorophenyl)-2H-1,2,3-triazol-4-yl)azetidine-1-carboxylate (140 mg, 0.46 mmol) and methyl 5-bromopyrazolo[1,5-a]pyridine-3-carboxylate (139.3 mg, 0.55 mmol) in toluene (2 mL) was added $AlMe_3$ (65.6 mg, 0.91 mmol) dropwise at 0° C. and the reaction was stirred for 2 h at 100° C. under $N_2$. The reaction mixture was extracted with EtOAc (25 mL), the organic layer was washed with $H_2O$ (3×10 mL) and dried over $Na_2SO_4$. After filtration, the filtrate was concentrated under reduced pressure. The residue was purified by prep-TLC (DCM:MeOH=20:1) to afford the title compound (150 mg, 62.1%) as a light-yellow solid. LCMS m/z=532 $[M+H]^+$ Intermediate 20 methyl 3-(2-(3-(5-bromopyrazolo[1,5-a]pyridine-3-carboxamido)-4-methylphenyl)-2H-tetrazol-5-yl)azetidine-1-carboxylate

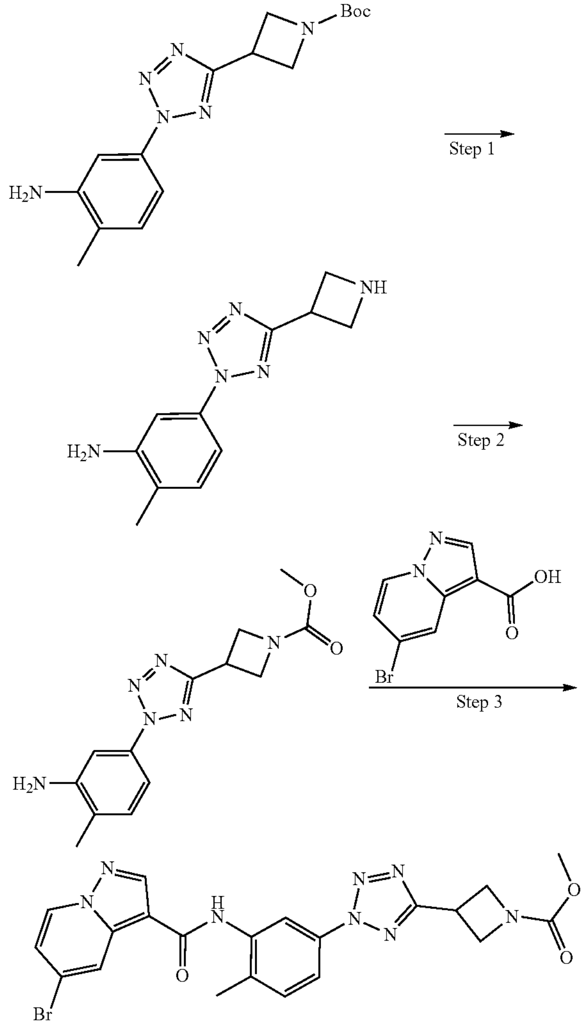

Step 1: Synthesis of 5-(5-(azetidin-3-yl)-2H-tetrazol-2-yl)-2-methylaniline

To a solution of Intermediate 17, step 1, (1.0 g, 3.02 mmol) in DCM (8 mL) was added TFA (4 mL) at rt. The reaction was stirred for 2 h at rt and concentrated. The residue was dissolved in DCM (10 mL), washed with sat. $NaHCO_3$ solution and concentrated. The crude product was purified by prep-TLC with DCM:MeOH=10:1 to give the title compound (0.6 g; 86%) as a yellow oil. LCMS: m/z=231 $[M+H]^+$.

Step 2: Synthesis of methyl 3-(2-(3-amino-4-methylphenyl)-2H-tetrazol-5-yl)azetidine-1-carboxylate To a solution of 5-(5-(azetidin-3-yl)-2H-tetrazol-2-yl)-2-methylaniline (0.4 g, 1.73 mmol) and TEA (349 mg, 3.46 mmol) in DCM (5 mL) was added dimethyl dicarbonate (231 mg, 1.73 mmol) at 0° C. under $N_2$ and the reaction mixture stirred for 1 h at rt. The mixture was quenched with ice water and extracted with DCM (3×20 mL). The organic layer was concentrated and purified by prep-TLC with DCM:MeOH=10:1 to give the title compound (0.4 g, 80%) as a white solid. LCMS: m/z=289 $[M+H]^+$.

Step 3: Synthesis of methyl 3-(2-(3-(5-bromopyrazolo[1,5-a]pyridine-3-carboxamido)-4-methylphenyl)-2H-tetrazol-5-yl)azetidine-1-carboxylate The title compound was obtained as a yellow solid, 190 mg, 53% from methyl 3-(2-(3-amino-4-methylphenyl)-2H-tetrazol-5-yl)azetidine-1-carboxylate and 5-bromopyrazolo[1,5-a]pyridine-3-carboxylic acid, following the procedure described in Intermediate 7, step 3. LCMS: m/z=511 $[M+H]^+$.

Intermediate 21

N-(5-(5-(azetidin-3-yl)-2H-tetrazol-2-yl)-2-chlorophenyl)pyrazolo[1,5-a]pyridine-3-carboxamide

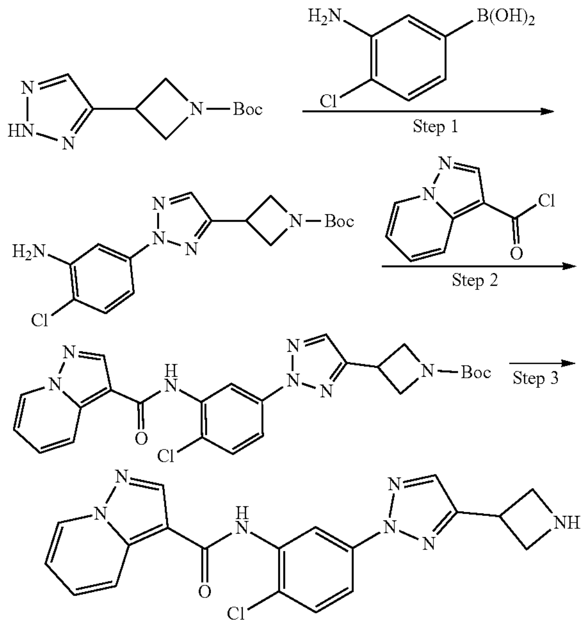

Step 1: Synthesis of tert-butyl 3-(2-(3-amino-4-chlorophenyl)-2H-tetrazol-5-yl)azetidine-1-carboxylate The title compound was obtained as a yellow solid, 270 mg, 17% from tert-butyl 3-(2H-1,2,3,4-tetrazol-5-yl)azetidine-1-carboxylate and (3-amino-4-chlorophenyl)boronic acid following the procedure described in Intermediate 16, step 1. LCMS: m/z=295 [M+1-56].

Step 2; Synthesis of tert-butyl 3-(2-(4-chloro-3-(pyrazolo[1,5-a]pyridine-3-carboxamido)phenyl)-2H-tetrazol-5-yl)azetidine-1-carboxylate To a solution of tert-butyl 3-(2-(3-amino-4-chlorophenyl)-2H-tetrazol-5-yl)azetidine-1-carboxylate (400 mg, 1.14 mmol) in pyridine (2 mL) was added pyrazolo[1,5-a]pyridine-3-carbonyl chloride (308 mg, 1.71 mmol) under $N_2$ at 0° C. The reaction was stirred for 1 h at rt and concentrated under vacuum. The residue was purified by prep-TLC with DCM:MeOH=10:1 to give the title compound (300 mg, 53%) as a white solid. LCMS: m/z=439 [M+1-56].

Step 3: Synthesis of N-(5-(5-(azetidin-3-yl)-2H-tetrazol-2-yl)-2-chlorophenyl)pyrazolo[1,5-a]pyridine-3-carboxamide To a solution of tert-butyl 3-(2-(4-chloro-3-(pyrazolo[1,5-a]pyridine-3-carboxamido)phenyl)-2H-tetrazol-5-yl)azetidine-1-carboxylate (20 mg, 0.04 mmol) in DCM (1.5 mL) was added TFA (0.5 mL) and the reaction was stirred for 2 h at rt and concentrated under vacuum. The residue was dissolved in DCM (20 mL), washed with sat. $NaHCO_3$ solution (3×10 mL) and concentrated. The crude product was purified by Prep-HPLC, Method C, 17% to 42% gradient to give the title compound (9.7 mg, 61%) as a white solid. LCMS: m/z=395 $[M+H]^+$, Intermediate 22 methyl 3-(2-(3-(5-bromopyrazolo[1,5-a]pyridine-3-carboxamido)-4-chlorophenyl)-2H-tetrazol-5-yl)azetidine-1-carboxylate

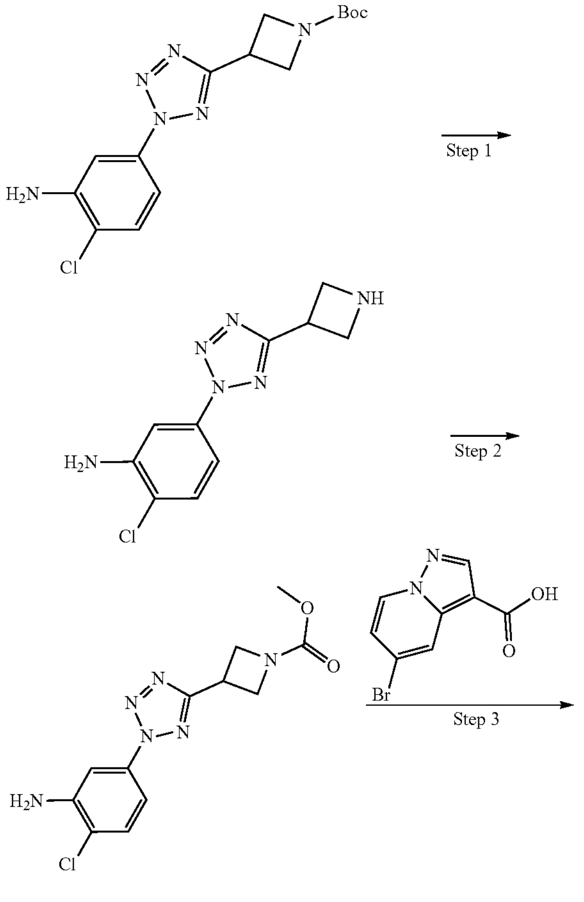

-continued

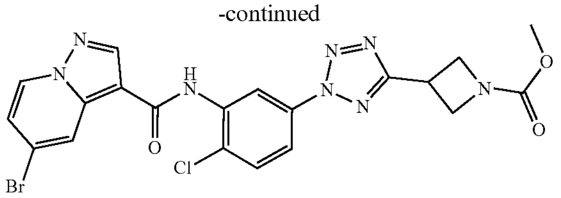

Steps 1 and 2: Synthesis of methyl 3-(2-(3-amino-4-chlorophenyl)-2H-tetrazol-5-yl)azetidine-1-carboxylate The title compound was obtained as a yellow solid, 90 mg, from Intermediate 21, step 2, following the same 2 step procedure to that described in Intermediate 20, steps 1 and 2. LCMS m/z=309 $[M+H]^+$ Step 3: Synthesis of methyl 3-(2-(3-(5-bromopyrazolo[1,5-a]pyridine-3-carboxamido)-4-chlorophenyl)-2H-tetrazol-5-yl)azetidine-1-carboxylate The title compound was obtained as a white solid, 100 mg, 54% from 1-(3-(2-(3-amino-4-chlorophenyl)-2H-tetrazol-5-yl)azetidin-1-yl)ethan-1-one and 5-bromopyrazolo[1,5-a]pyridine-3-carbonyl chloride following a similar procedure to that described in Intermediate 14, step 3. LCMS: m/z=531 $[M+H]^+$.

Intermediate 23

5-((2-methoxyethyl)amino)pyrazolo[1,5-a]pyridine-3-carboxylic acid

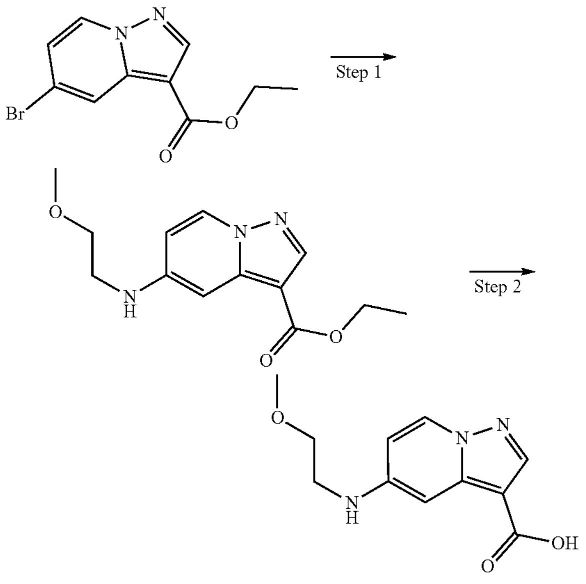

Step 1: Synthesis of ethyl 5-((2-methoxyethyl)amino)pyrazolo[1,5-a]pyridine-3-carboxylate A mixture of ethyl 5-bromopyrazolo[1,5-a]pyridine-3-carboxylate (1 g, 3.71 mmol), 2-methoxyethan-1-amine (833 mg, 11.1 mmol), $Pd_2(dba)_3$ (68 mg, 74 μmol), Xant- Phos (43 mg, 74 μmol) and $Cs_2CO_3$ (2.41 g, 7.42 mmol) in dioxane (30 mL) was stirred at 100° C. for 2 h. The resulting mixture was concentrated to dryness and purified on prep-TLC (PE:EtOAc=1:1) to afford the title compound (850 mg, 87%) as a light brown solid. LCMS: m/z=264 $[M+H]^+$ Step 2: Synthesis of 5-((2-methoxyethyl)amino) pyrazolo[1,5-a]pyridine-3-carboxylic acid A mixture of ethyl 5-((2-methoxyethyl)amino)pyrazolo[1,5-a]pyridine-3-carboxylate (1.1 g, 4.17 mmol) and NaOH (333 mg, 8.34 mmol) in EtOH (15 mL) and $H_2O$ (5 mL) was stirred at 70° C. for 3 h. The resulting mixture was diluted with $H_2O$ (50 mL) and acidified to pH=3. The resulting mixture was extracted with EtOAc (50 mL×2), the combined organic layers were dried over $Na_2SO_4$ and concentrated to afford the title compound (600 mg, 61%) as a light brown solid. LCMS m/z=236 $[M+H]^+$ Intermediate 24

6-((2-methoxyethyl)amino)pyrazolo[1,5-a]pyridine-3-carboxylic acid

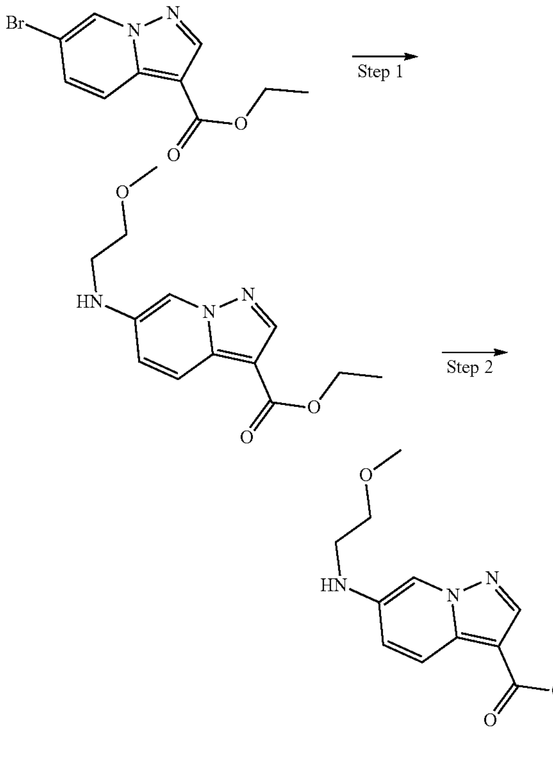

The title compound was obtained as a light brown solid, 600 mg, from ethyl 5-bromopyrazolo[1,5-a]pyridine-3-carboxylate and 2-methoxyethan-1-amine, following the 2-step procedure described in Intermediate 23. LCMS: m/z=236 $[M+H]^+$ Intermediate 25

5-morpholinopyrazolo[1,5-a]pyridine-3-carboxylic acid

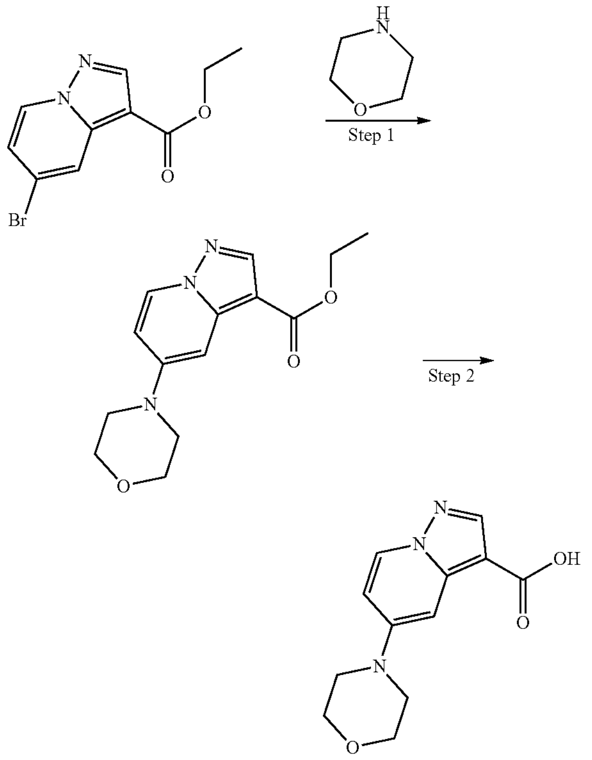

Step 1: Synthesis of ethyl 5-morpholinopyrazolo[1,5-a]pyridine-3-carboxylate

A mixture of ethyl 5-bromopyrazolo[1,5-a]pyridine-3-carboxylate (3 g, 11.1 mmol), morpholine (2.90 g, 33.3 mmol), $Cs_2CO_3$(7.23 g, 22.2 mmol), $Pd_2(dba)_3$ (508 mg, 0.55 mmol) and BINAP (691 mg, 1.11 mmol) in toluene (50 mL) was heated at 100° C. for 4 h. The cooled mixture was concentrated under vacuum and the residue purified by silica gel column with DCM:MeOH=10:1 to give the title compound (3 g, 98.3%) as a yellow solid, LCMS: m/z=276 $[M+H]^+$ Step 2: Synthesis of 5-morpholinopyrazolo[1,5-a] pyridine-3-carboxylic acid KOH (2.42 g, 43.2 mmol) was added to ethyl 5-morpholinopyrazolo[1,5-a]pyridine-3-carboxylate (3 g, 10.8 mmol) in EtOH (24 mL) and $H_2O$ (6 mL) and the reaction mixture stirred at 80° C. for 3 h. The mixture was concentrated and then diluted with water (50 mL) and EtOAc (50 mL) and the layers separated. The pH of the aqueous phase was adjusted to 6.0 with HCl (1M) and was then extracted with EtOAc. The organic layer was dried with $Na_2SO_4$ and concentrated under reduced pressure to give title compound (2 g, 74.9%) as a yellow solid. LCMS: m/z=248 $[M+H]^+$ Intermediate 26 methyl 5-morpholinopyrazolo[1,5-a]pyridine-3-carboxylate

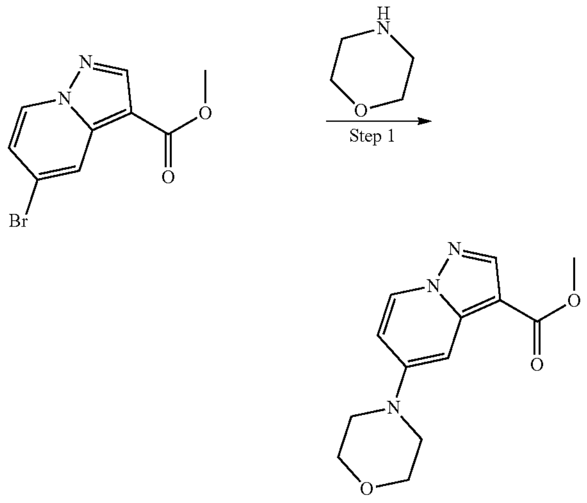

The title compound was obtained as an off-white solid, 200 mg, 66% yield from 5-bromopyrazolo[1,5-a]pyridine-3-carboxylate and morpholine, following the procedure described in Intermediate 25, step 2. LCMS: m/z=302 $[M+H]^+$.

Intermediate 27

6-morpholinopyrazolo[1,5-a]pyridine-3-carbonyl chloride hydrochloride

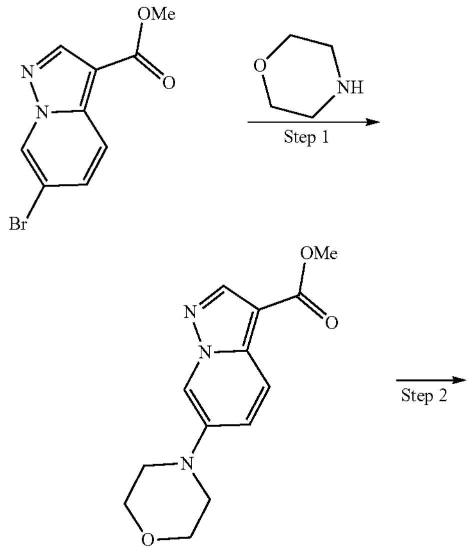

-continued

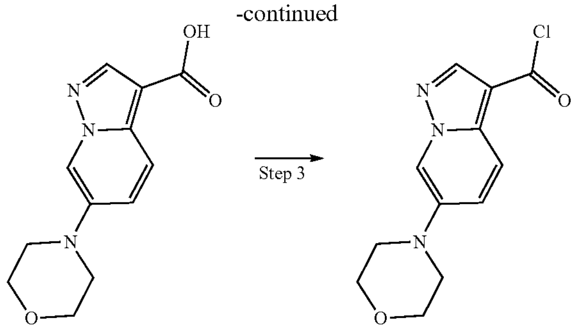

Step 1: Synthesis of methyl 6-morpholinopyrazolo[1,5-a]pyridine-3-carboxylate

A mixture of methyl 6-bromopyrazolo[1,5-a]pyridine-3-carboxylate (400 mg, 1.57 mmol), morpholine (164 mg, 1.88 mmol), $Pd(OAc)_2$ (18 mg, 0.08 mmol), NaOtBu (226 mg, 2.35 mmol) and [1,1'-biphenyl]-2-ylditert-butylphosphane (47 mg, 0.16 mmol) in toluene (3 mL) was heated to 90° C. for 4 h. The mixture was diluted with EtOAc, filtered through Celite® and evaporated to give the crude product. This was purified by silica gel ISCO chromatography (10 to 100% EtOAc/Hex) to give the title compound, 93 mg of yellow solid. LCMS m/z=262 $[M+H]^+$ Step 2: Synthesis of 6-morpholinopyrazolo[1,5-a]pyridine-3-carboxylic acid A mixture of methyl 6-morpholinopyrazolo[1,5-a]pyridine-3-carboxylate (93 mg, 0.36 mmol) and LiOH (60 mg, 1.42 mmol) in THF (1.5 mL) and water (0.5 mL) was stirred at 70° C. for 6 h. The mixture was concentrated in vacuo, the residue diluted with water and the pH adjusted to 2 using 1N HCl. The resulting solid was filtered off and washed with water to give the title compound, as a yellow solid, 70 mg, 80%.

Step 3: Synthesis of 6-morpholinopyrazolo[1,5-a]pyridine-3-carbonyl chloride hydrochloride A drop of DMF was added to a mixture of 6-morpholinopyrazolo[1,5-a]pyridine-3-carboxylic acid (70 mg, 0.28 mmol) in DCM (3 mL) and oxalyl chloride (2M, 0.71 mL, 1.42 mmol) and the reaction mixture stirred at rt overnight. The mixture was evaporated under reduced pressure and azeotroped with DCM to give the title compound, 94 mg of brown solid. LCMS m/z=262 $[M-Cl+OMe]^+$ Intermediate 28

2-(methoxy-d3)ethan-1-amine trifluoroacetate

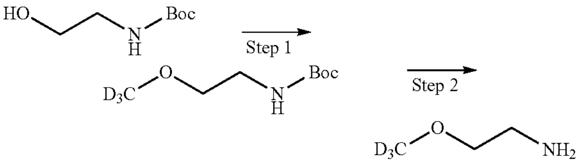

Step 1: Synthesis of tert-butyl(2-(methoxy-d3)ethyl)carbamate

NaH (991 mg, 24.8 mmol, 60%) was added batchwise to tert-butyl N-(2-hydroxyethyl)carbamate (2.0 g, 12.4 mmol) in DMF (20 mL) at 0° C. and the mixture stirred at 0° C. for 30 min. Iodo($D_3$)methane (5.39 g, 37.2 mmol) was added and the reaction mixture stirred at rt for 16 h. The mixture was quenched with ice water (10 mL), diluted with EtOAc (100 mL) and the layers separated. The organic layer was washed with brine (50 mL×2), dried with $Na_2SO_4$ and concentrated under vacuum. The residue was purified by silica gel column with PE:EtOAc=5:1 to afford the title compound (500 mg) as a colorless oil. LCMS: m/z=123 [M−56]

Step 2: Synthesis of 2-(methoxy-d3)ethan-1-amine trifluoroacetate

TFA (3 mL) was added dropwise to tert-butyl(2-(methoxy-d3)ethyl)carbamate (500 mg, 2.80 mmol) in DCM (10 mL) and the reaction was stirred at rt for 2 h. The mixture was evaporated under reduced pressure to afford the title compound, 200 mg, as a yellow solid. LCMS: m/z=79 $[M+H]^+$ Intermediate 29

5-bromo-N-(5-(2-isopropyl-2H-tetrazol-5-yl)-2-methylphenyl)pyrazolo[1,5-a]pyridine-3-carboxamide

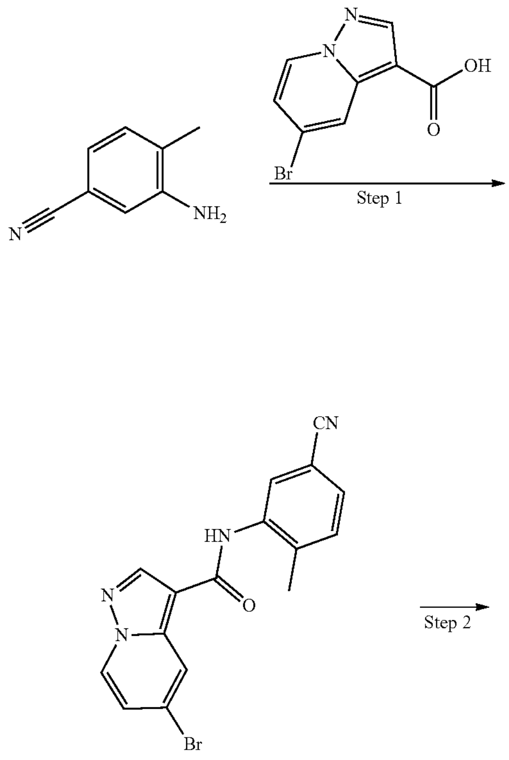

-continued

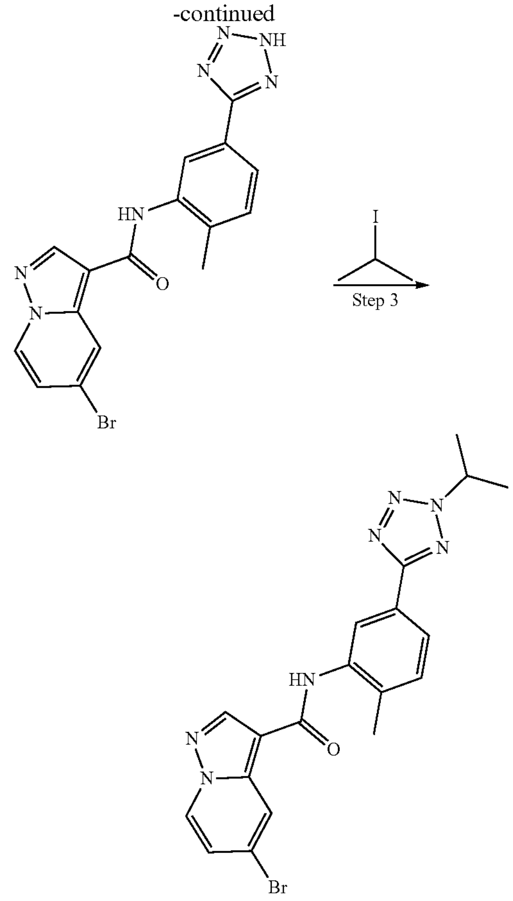

Step 1: Synthesis of 5-bromo-N-(5-cyano-2-methylphenyl)pyrazolo[1,5-a]pyridine-3-carboxamide To a solution of 3-amino-4-methylbenzonitrile (1 g, 7.56 mmol) and 5-bromopyrazolo[1,5-a]pyridine-3-carboxylic acid (1.82 g, 7.56 mmol) in THF (10 mL) was added pyridine (1.19 g, 15.1 mmol) and $T_3P$® (3.70 g, 11.3 mmol) at rt under $N_2$ and the reaction was stirred for 2 h at 60° C. The mixture was concentrated, MeOH (10 mL) was added, the resulting precipitate filtered and dried to afford the title compound, as a white solid, (1.7 g; 63%). LCMS: m/z=355 $[M+H]^+$.

Step 2: Synthesis of 5-bromo-N-(2-methyl-5-(2H-tetrazol-5-yl)phenyl)pyrazolo[1,5-a]pyridine-3-carboxamide The title compound was obtained as a yellow solid, 1.4 g, 83% from 5-bromo-N-(5-cyano-2-methylphenyl)pyrazolo[1,5-a]pyridine-3-carboxamide, following the procedure described in Intermediate 8, step 1. LCMS: m/z=398 $[M+H]^+$ Step 3: Synthesis of 5-bromo-N-(5-(2-isopropyl-2H-tetrazol-5-yl)-2-methylphenyl)pyrazolo[1,5-a]pyridine-3-carboxamide 2-Iodopropane (102 mg, 0.60 mmol) was added to 5-bromo-N-(2-methyl-5-(2H-tetrazol-5-yl)phenyl)pyrazolo[1,5-a]pyridine-3-carboxamide (200 mg, 0.50 mmol) and $K_2CO_3$ (138 mg, 1.0 mmol) in DMF (4 mL) at rt and the reaction was stirred for 2 h at 100° C. The mixture was diluted with water (50 mL) then extracted with DCM (3×20 mL) and the combined organic extracts concentrated in vacuo. The crude was purified by prep-TLC with DCM/MeOH=10:1 to give the title compound (120 mg, 54%) as a white solid. LCMS: m/z=440 $[M+H]^+$.

Intermediate 30

5-bromo-N-(5-(2-cyclopropyl-1,2,3,4-tetrazol-5-yl)-2-methylphenyl)pyrazolo[1,5-a]pyridine-3-carboxamide

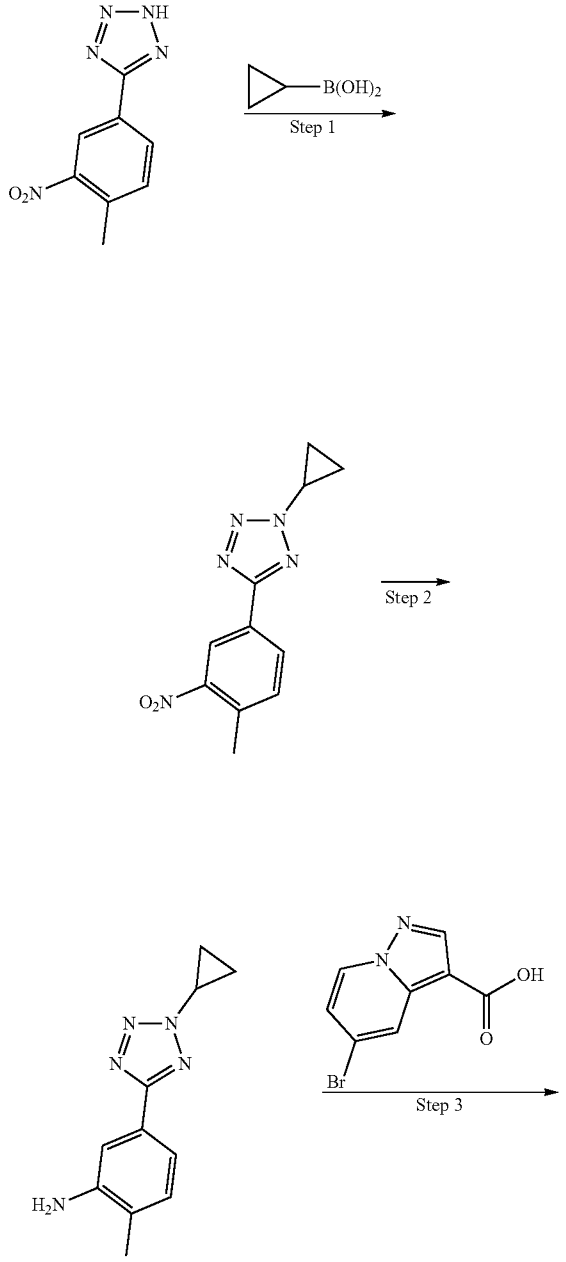

-continued

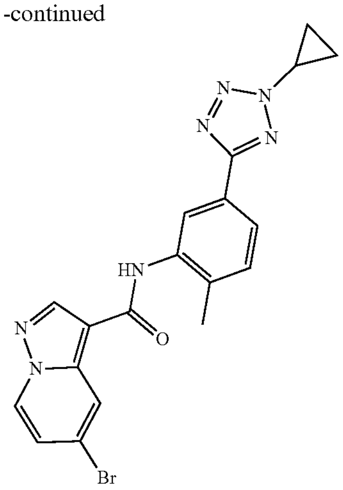

Step 1: Synthesis of 2-cyclopropyl-5-(4-methyl-3-nitrophenyl)-1,2,3,4-tetrazole

The title compound was obtained as a yellow solid, 300 mg, 50.2% from 5-(4-methyl-3-nitrophenyl)-2H-tetrazole and cyclopropylboronic acid following a similar procedure to that described in Intermediate 16, step 1. LCMS: m/z=246 $[M+H]^+$ Step 2: Synthesis of 5-(2-cyclopropyl-1,2,3,4-tetrazol-5-yl)-2-methylaniline The title compound was obtained as a yellow solid, 250 mg, 95%, from 2-cyclopropyl-5-(4-methyl-3-nitrophenyl)-1,2,3,4-tetrazole, following the procedure described in Intermediate 12, step 2. LCMS: m/z=216 $[M+H]^+$ Step 3: Synthesis of 5-bromo-N-(5-(2-cyclopropyl-1,2,3,4-tetrazol-5-yl)-2-methylphenyl)pyrazolo[1,5-a]pyridine-3-carboxamide The title compound was obtained as a yellow solid, 240 mg, 65.5%, from 5-(2-cyclopropyl-1,2,3,4-tetrazol-5-yl)-2-methylaniline and 5-bromopyrazolo[1,5-a]pyridine-3-carboxylic acid following a similar procedure to that described in Intermediate 12, step 3. LCMS: m/z=438 $[M+H]^+$

Intermediate 31

4-amino-2-(2-(3,3-difluorocyclobutyl)-2H-tetrazol-5-yl)-5-methylbenzonitrile

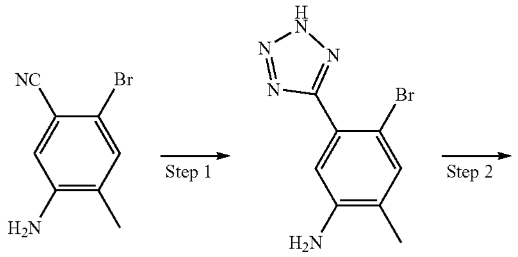

-continued

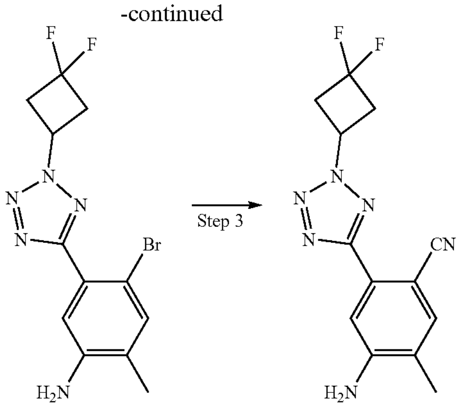

Steps 1 and 2: Synthesis of 4-bromo-5-(2-(3,3-difluorocyclobutyl)-2H-tetrazol-5-yl)-2-methylaniline The title compound was obtained as a light yellow solid, 210 mg, from 5-amino-2-bromo-4-methylbenzonitrile and 3,3-difluorocyclobutan-1-ol following a similar procedure to that described in Intermediate 10, steps 1 and 2. LCMS: m/z=344 $[M+H]^+$.

Step 3: Synthesis of 4-amino-2-(2-(3,3-difluorocyclobutyl)-2H-tetrazol-5-yl)-5-methylbenzonitrile A mixture of 4-bromo-5-(2-(3,3-difluorocyclobutyl)-2H-tetrazol-5-yl)-2-methylaniline (210 mg, 0.61 mmol), $Zn(CN)_2$ (215 mg, 1.83 mmol), $Pd(dppf)Cl_2$ (49.7 mg, 0.06 mmol) and TEA (186 mg, 1.83 mmol) in DMF (5 mL) was stirred at 80° C. for 2 h under $N_2$. The mixture was diluted with EtOAc (100 mL), washed with brine (50 mL×2), the organic layer was dried over ($Na_2SO_4$) and concentrated under vacuum. The residue was purified by a silica gel column with PE:EtOAc=18:1 to afford the title compound (110 mg, 52%) as an off-white solid. LCMS: m/z=291 $[M+H]^+$.

Intermediate 32

4-cyclopropyl-5-(2-(3,3-difluorocyclobutyl)-2H-tetrazol-5-yl)-2-methylaniline

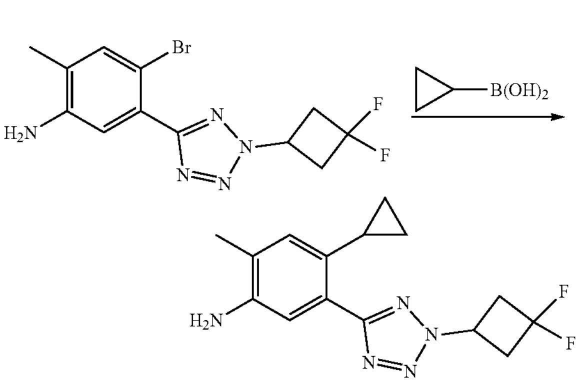

The title compound was obtained as an off-white solid, from Intermediate 31, step 2, and cyclopropylboronic acid, following a similar procedure to that described in Example 117, step 3. LCMS: m/z=306 $[M+H]^+$.

Intermediate 33

2,4-dichloro-5-(2-(3,3-difluorocyclobutyl)-2H-tetrazol-5-yl)aniline

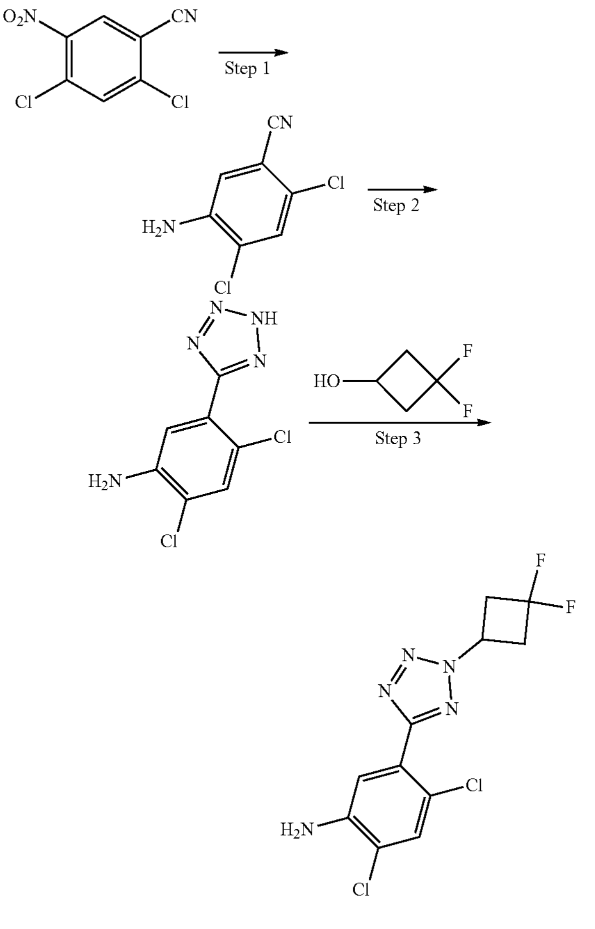

Step 1: Synthesis of 5-amino-2,4-dichlorobenzonitrile

A mixture of 2,4-dichloro-5-nitrobenzonitrile (WO 03086371, 1.4 g, 6.45 mmol) and Fe powder (1.80 g, 32.2 mmol) in EtOH (15 mL) and AcOH (1 mL) was heated at 50° C. for 2 h. The solvent was removed under vacuum and water (500 mL) was added to the residue. The solution was adjusted to pH 6 by addition of $Na_2CO_3$ and extracted with DCM (2×80 mL). The organic layers were combined, dried over $Na_2SO_4$, filtered and evaporated under reduced pressure to afford the title compound, 800 mg, 66.6%. $^1H$ NMR (400 MHz, DMSO-$d_6$) δ 7.66 (s, 1H), 7.19 (s, 1H), 6.05 (s, 2H).

Step 2: Synthesis of 2,4-dichloro-5-(2H-tetrazol-5-yl)aniline

To a solution of 5-amino-2,4-dichlorobenzonitrile (700 mg, 3.74 mmol) in toluene were added $TMSN_3$ (1.28 g, 11.2 mmol) and $Bu_2SnO$ (931 mg, 3.73 mmol) at rt. The mixture was stirred at 100° C. for 16 h then cooled to rt. The mixture was concentrated under vacuum and the residue was purified by column chromatography to give the title compound (500 mg, yield: 58.1%) as a white solid. LCMS: m/z=230 $[M+H]^+$ Step 3: Synthesis of 2,4-dichloro-5-(2-(3,3-difluorocyclobutyl)-2H-tetrazol-5-yl)aniline The title compound was obtained as a white solid, 300 mg, 43%, from 2,4-dichloro-5-(2H-tetrazol-5-yl)aniline 3,3-difluorocyclobutan-1-ol, following the procedure described in Intermediate 7, step 2. LCMS: m/z=320 $[M+H]^+$ Intermediate 34

4-chloro-5-(2-(3,3-difluorocyclobutyl)-2H-tetrazol-5-yl)-2-methylaniline

N-(4-chloro-5-(2-(3,3-difluorocyclobutyl)-2H-tetrazol-5-yl)-2-methylphenyl)-5-morpholinopyrazolo[1,5-a]pyridine-3-carboxamide

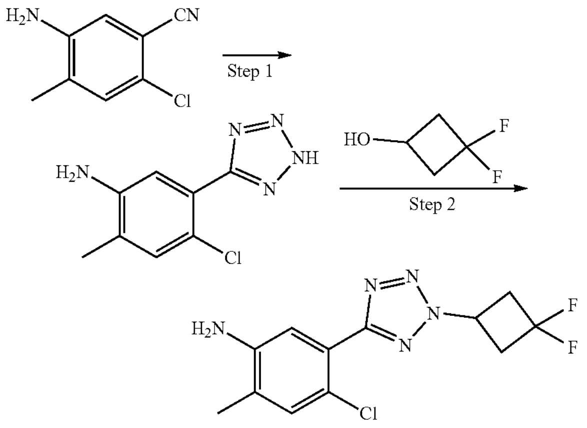

Step 1: Synthesis of 4-chloro-2-methyl-5-(2H-tetrazol-5-yl)aniline

To a mixture of 5-amino-2-chloro-4-methylbenzonitrile (400 mg, 2.40 mmol), $Bu_2SnO$ (1.19 g, 4.80 mmol) in toluene (25 mL) was added $TMSN_3$ (553 mg, 4.80 mmol) at rt and the reaction mixture stirred at 100° C. for 16 h. The cooled mixture was concentrated to dryness and the residue was purified on prep-TLC with DCM:MeOH=30:1 to afford the title compound (220 mg, yield: 43.7%) as an off-white solid. LCMS: m/z=210 $[M+H]^+$.

Step 2: Synthesis of 4-chloro-5-(2-(3,3-difluorocyclobutyl)-2H-tetrazol-5-yl)-2-methylaniline The title compound was obtained, 120 mg, 60%, from 4-chloro-2-methyl-5-(2H-tetrazol-5-yl)aniline and 3,3-difluorocyclobutan-1-ol, following a similar procedure to that described in Intermediate 7, step 2. LCMS: m/z=300 $[M+H]^+$ Intermediate 35

2-chloro-5-(2-(3,3-difluorocyclobutyl)-2H-tetrazol-5-yl)aniline

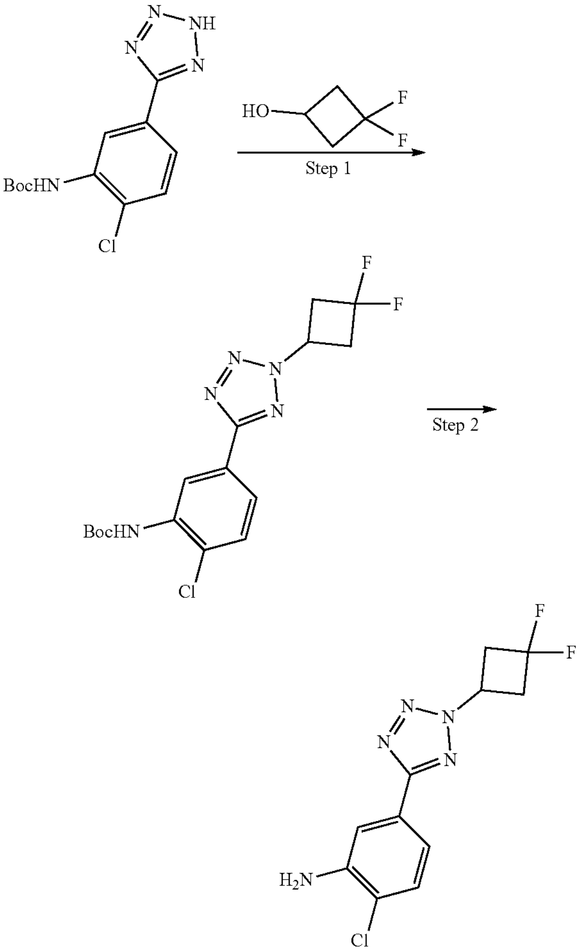

Step 1: Synthesis of tert-butyl(2-chloro-5-(2-(3,3-difluorocyclobutyl)-2H-tetrazol-5-yl)phenyl)carbamate The title compound was obtained as a white solid, 300 mg, 46% from Intermediate 10, Step 1 and 3,3-difluorocyclobutan-1-ol following a similar procedure to that described in Intermediate 4, step 1. LCMS: m/z=386 $[M+H]^+$ Step 2: Synthesis of 2-chloro-5-(2-(3,3-difluorocyclobutyl)-2H-tetrazol-5-yl)aniline The title compound was obtained, 120 mg, 54%, from tert-butyl(2-chloro-5-(2-(3,3-difluorocyclobutyl)-2H-tetrazol-5-yl)phenyl)carbamate, following a similar procedure to that described in Intermediate 18, step 3. LCMS: m/z=286 $[M+H]^+$.

Intermediate 36

2-chloro-5-(2-(3,3-difluorocyclobutyl)-2H-tetrazol-5-yl)-4-methylaniline

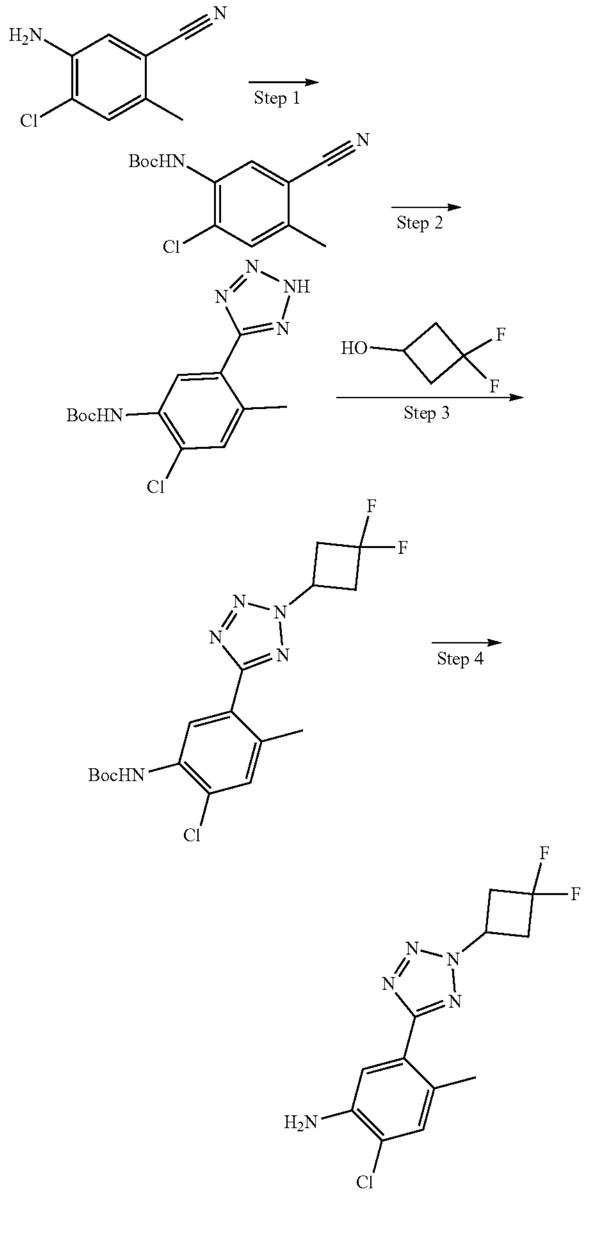

Step 1: tert-butyl(2-chloro-5-cyano-4-methylphenyl) carbamate

A mixture of 5-amino-4-chloro-2-methylbenzonitrile (1.2 g, 7.20 mmol), DMAP (1.31 g, 10.8 mmol), $(Boc)_2O$ (4.71 g, 21.6 mmol) and TEA (1.09 g, 10.8 mmol) in toluene (15 mL) was stirred at 100° C. for 16 h. The solvent was evaporated and the residue was purified by a silica gel column eluting with 1% MeOH in DCM to afford the title compound (1.2 g, 78.1%) as a yellow solid. LCMS: m/z=267 $[M+H]^+$.

Step 2: Synthesis of tert-butyl(2-chloro-4-methyl-5-(2H-tetrazol-5-yl)phenyl)carbamate A mixture of tert-butyl N-(2-chloro-5-cyano-4-methylphenyl)carbamate (1.2 g, 4.49 mmol), $TMSN_3$ (1.03 g, 8.98 mmol) and $Bu_2SnO$ (2.23 g, 8.98 mmol) in toluene (20 mL) was stirred at 100° C. for 16 h. The solvent was evaporated and the residue was purified by silica gel column eluting with 10% MeOH in DCM to afford the title compound (700 mg, 50.3%) as a yellow solid. LCMS: m/z=310 $[M+H]^+$.

Step 3 and Step 4: Synthesis of 2-chloro-5-(2-(3,3-difluorocyclobutyl)-2H-tetrazol-5-yl)-4-methylaniline The title compound was obtained as a white solid, from tert-butyl(2-chloro-4-methyl-5-(2H-tetrazol-5-yl)phenyl) carbamate and 3,3-difluorocyclobutan-1-ol, following a similar 2 step procedure to that described in Intermediate 35.

Intermediate 37

5-bromo-N-(2-methyl-5-(5-methyl-2H-tetrazol-2-yl) phenyl)pyrazolo[1,5-a]pyridine-3-carboxamide

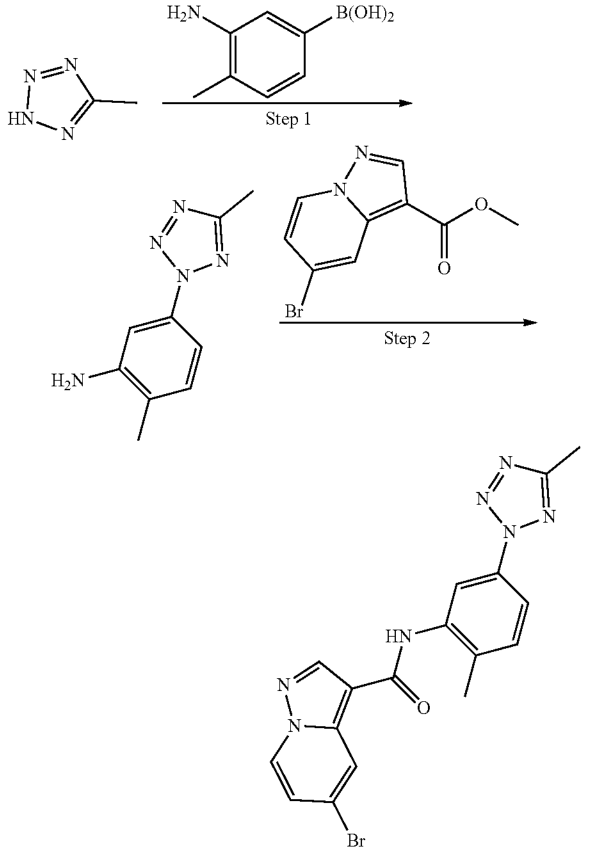

Step 1: Synthesis of 2-methyl-5-(5-methyl-2H-tetrazol-2-yl)aniline

The title compound was obtained as a white solid, 850 mg, 24%, from 5-methyl-2H-tetrazole and (3-amino-4-methylphenyl)boronic acid, following a similar procedure to that described in Intermediate 16, step 1. LCMS: m/z=190 [M+H]$^+$.

Step 2: Synthesis of 5-bromo-N-(2-methyl-5-(5-methyl-2H-tetrazol-2-yl)phenyl)pyrazolo[1,5-a]pyridine-3-carboxamide The title compound was obtained as a white solid, 469 mg, 72%, from 2-methyl-5-(5-methyl-2H-1,2,3,4-tetrazol-2-yl)aniline and methyl 5-bromopyrazolo[1,5-a]pyridine-3-carboxylate, following the procedure described in Intermediate 19, step 3. LCMS: m/z=412 [M+H]$^+$.

Intermediate 38

5-bromo-N-(5-(5-cyclopropyl-2H-tetrazol-2-yl)-2-methylphenyl)pyrazolo[1,5-a]pyridine-3-carboxamide

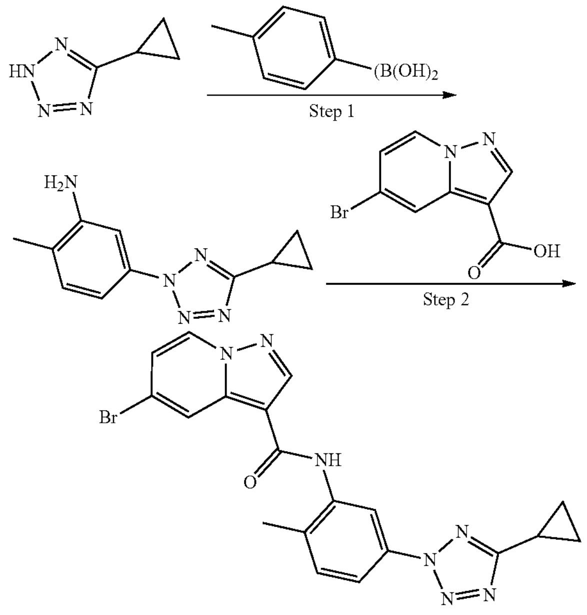

Step 1: Synthesis of 5-(5-cyclopropyl-2H-tetrazol-2-yl)-2-methylaniline

The title compound was obtained as a red solid, 276 mg, 28%, from 5-cyclopropyl-2H-1,2,3,4-tetrazole and (3-amino-4-methylphenyl)boronic acid, following the procedure described in Intermediate 16, step 1. LCMS: m/z=216 [M+H]$^+$.

Step 2: Synthesis of 5-bromo-N-(5-(5-cyclopropyl-2H-tetrazol-2-yl)-2-methylphenyl)pyrazolo[1,5-a]pyridine-3-carboxamide The reaction mixture was obtained as a white solid, 80 mg, 31.8%, from 5-(5-cyclopropyl-2H-tetrazol-2-yl)-2-methylaniline and 5-bromopyrazolo[1,5-a]pyridine-3-carboxylic acid, following a similar procedure to that described in Intermediate 5, step 3. LCMS: m/z=438 [M+H]$^+$.

Intermediate 39

5-bromo-N-(2-methyl-5-(2-(1-(methylsulfonyl)azetidin-3-yl)-2H-tetrazol-5-yl)phenyl)pyrazolo[1,5-a]pyridine-3-carboxamide

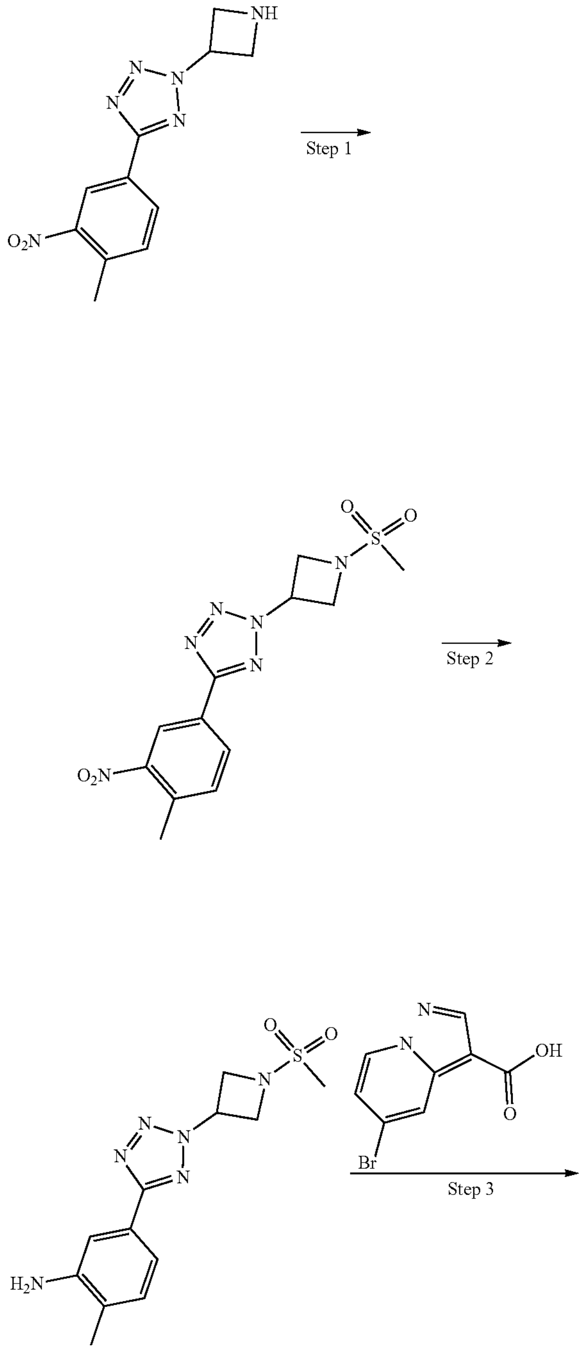

-continued

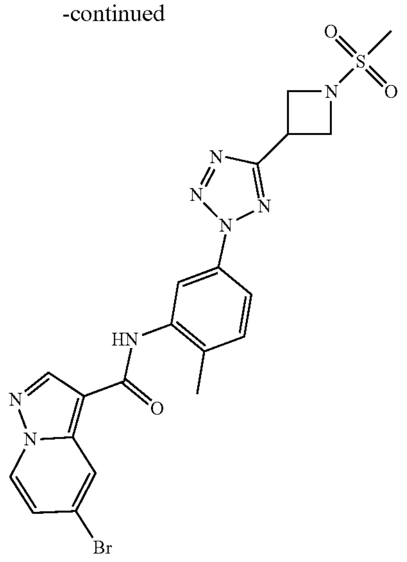

Step 1: Synthesis of 5-(4-methyl-3-nitrophenyl)-2-(1-(methylsulfonyl)azetidin-3-yl)-2H-tetrazole To a stirred solution of Intermediate 11, step 2, (5.5 g, 21.1 mmol) and TEA (6.42 g, 63.4 mmol) in DCM (55 mL) was added methane sulfonic anhydride (4.79 g, 27.4 mmol) in portions at 0° C. and the reaction then stirred at rt for 2 h. The resulting mixture was washed with $NaHCO_3$ and extracted with DCM (3×80 mL). The combined organic layers were washed with brine (2×100 mL), dried over anhydrous $Na_2SO_4$ and filtered. The filtrate was concentrated under reduced pressure to afford the title compound (5.2 g, 72.7%) as a light brown solid. LCMS m/z=339 $[M+H]^+$ Step 2: Synthesis of 2-methyl-5-(2-(1-(methylsulfonyl)azetidin-3-yl)-2H-tetrazol-5-yl)aniline Pd/C (1 g, 9.4 mmol) was added to 2-(1-methanesulfonylazetidin-3-yl)-5-(4-methyl-3-nitrophenyl)-1,2,3,4-tetrazole (5.2 g, 15.4 mmol) in EtOAc (60 mL) at rt. The flask was evacuated and flushed three times with $N_2$, then $H_2$. The mixture was stirred for 2 h at rt under an atmosphere of $H_2$ (balloon). The reaction mixture was filtered, the filter cake was washed with $MeOH:EtOAc:NH_3H_2O$=(50:10:1) (3×15 mL) and the filtrate was evaporated under reduced pressure to give the title compound (2.61 g, 55.0%) as a light brown solid. LCMS m/z=309 $[M+H]^+$ Step 3: Synthesis of 5-bromo-N-(2-methyl-5-(2-(1-(methylsulfonyl)azetidin-3-yl)-2H-tetrazol-5-yl)phenyl)pyrazolo[1,5-a]pyridine-3-carboxamide A mixture of T3P® (2 mL, 1.62 mmol), pyridine (2 mL, 1.62 mmol), 2-methyl-5-(2-(1-(methylsulfonyl)azetidin-3-yl)-2H-tetrazol-5-yl)aniline (500 mg, 1.62 mmol) and 5-bromopyrazolo[1,5-a]pyridine-3-carboxylic acid (390 mg, 1.62 mmol) in THF (4 mL) was heated at 50° C. for 16 h under $N_2$. The reaction mixture was diluted with EtOAc (120 mL) and washed with water (60 mL). The organic layer was dried over $Na_2SO_4$, filtered and concentrated under vacuum. The crude product was purified by Prep-TLC eluting with DCM: MeOH=20:1 to give the title compound (219 mg) as a white solid. LCMS: m/z=531 $[M+H]^+$, Intermediate 40

N-(5-(2-(azetidin-3-yl)-2H-tetrazol-5-yl)-2-chlorophenyl)pyrazolo[1,5-a]pyridine-3-carboxamide

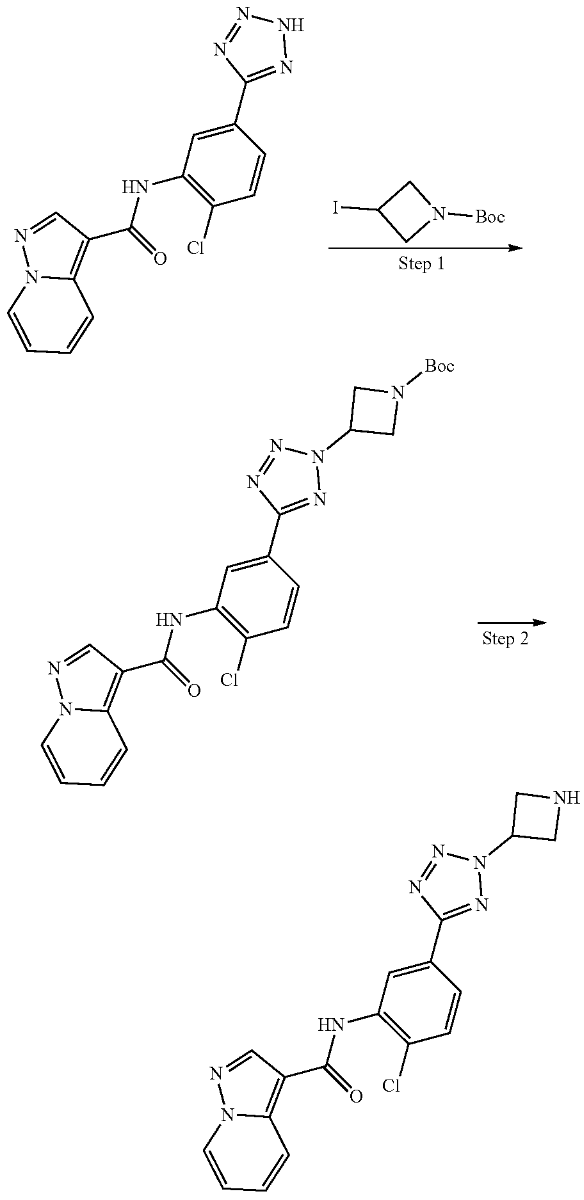

Step 1: Synthesis of tert-butyl 3-(5-(4-chloro-3-(pyrazolo[1,5-a]pyridine-3-carboxamido)phenyl)-2H-tetrazol-2-yl)azetidine-1-carboxylate A mixture of Intermediate 2, (250 mg, 0.74 mmol), tert-butyl 3-iodoazetidine-1-carboxylate (250 mg, 0.88 mmol) and $K_2CO_3$ (153 mg, 1.1 mmol) in DMF was heated at 90° C. overnight. The mixture was concentrated in vacuo and the residue partitioned between 5% MeOH/DCM and water and the layers separated. The organic layer was dried over $Na_2SO_4$, filtered and evaporated to give the crude product. This was purified by ISCO chromatography (0 to 100% EtOAc/Hex) to give the title compound, 253 mg, 69.5% as white foam. LCMS m/z=495 $[M+H]^+$ Step 2: Synthesis of N-(5-(2-(azetidin-3-yl)-2H-tetrazol-5-yl)-2-chlorophenyl)pyrazolo[1,5-a]pyridine-3-carboxamide A solution of tert-butyl 3-(5-(4-chloro-3-(pyrazolo[1,5-a]pyridine-3-carboxamido)phenyl)-2H-tetrazol-2-yl)azetidine-1-carboxylate (253 mg, 0.51 mmol) and TFA (583 mg, 5.1 mmol) in DCM (2 mL) was stirred a rt for 3 h. The solution was evaporated under reduced pressure, the residue diluted with water and the pH adjusted to 10 using 1N NaOH solution. The resulting solid was filtered off, washed with water and dried to give the title compound as an off white solid, 206 mg. LCMS m/z=395 $[M+H]^+$ Intermediate 41 ethyl 5-((tert-butoxycarbonyl)amino)-4-chloropyrazolo[1,5-a]pyridine-3-carboxylate

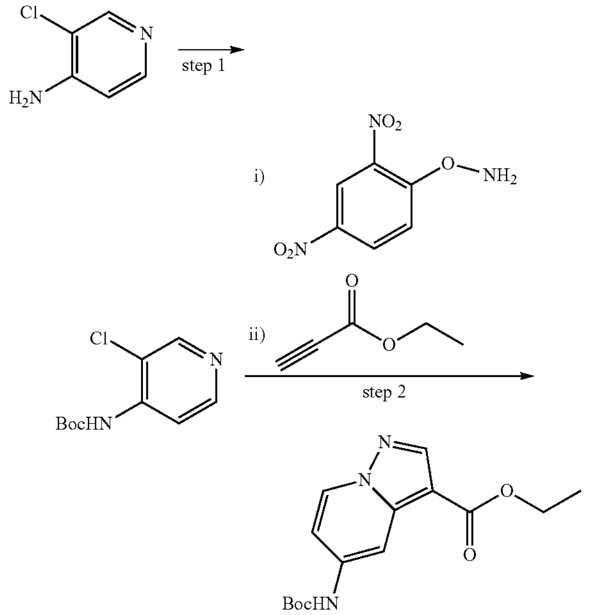

Step 1: Synthesis of tert-butyl N-(3-chloropyridin-4-yl)carbamate $Na_2CO_3$ (8.22 g, 77.6 mmol) was added to di-tert-butyl dicarbonate (8.46 g, 38.8 mmol) and 3-chloropyridin-4-amine (5 g, 38.8 mmol) in dioxane/$H_2O$ (160 mL/40 mL) and the reaction was stirred at rt for 16 h. The reaction mixture was diluted with EtOAc (300 mL), washed with water (200 mL×3) and brine (200 mL). The organic layer was dried over $Na_2SO_4$, filtered and evaporated to afford crude product. This was purified by prep-TLC with PE:EtOAc=5:1 to afford the title compound (8.5 g, 95.8%) as an off-white solid. LCMS: m/z=229 $[M+H]^+$, Step 2: Synthesis of ethyl 5-((tert-butoxycarbonyl)amino)-4-chloropyrazolo[1,5-a]pyridine-3-carboxylate A solution of tert-butyl N-(3-chloropyridin-4-yl)carbamate (8.5 g, 37.1 mmol) and 0-(2,4-dinitrophenyl)hydroxylamine (14.7 g, 74.2 mmol) in MeCN (200 mL) was stirred at 50° C. for 40 h. The mixture was evaporated under reduced pressure to afford crude 1-amino-4-(((tert-butoxy)carbonyl)amino)-3-chloropyridin-1-ium 2,4-dinitrobenzen-1-olate which was dissolved in DMF (200 mL) and $K_2CO_3$ (27.0 g, 196 mmol) added. The mixture was stirred at rt for 1 h, ethyl prop-2-ynoate (9.61 g, 98.0 mmol) was added and the reaction was stirred at rt for 18 h. The reaction mixture was diluted with EtOAc (400 mL) and washed with water (300 mL×3) and brine (300 mL). The organic layer was dried over $Na_2SO_4$, filtered and evaporated to afford crude product which was purified by silica gel column with PE:EtOAc=4:1 to give ethyl 5-(((tert-butoxy)carbonyl)amino)-6-chloropyrazolo[1,5-a]pyridine-3-carboxylate as a yellow solid and ethyl 5-((tert-butoxycarbonyl)amino)-4-chloropyrazolo[1,5-a]pyridine-3-carboxylate as a yellow solid. LCMS m/z=340 $[M+H]^+$ Intermediate 42 methyl 6-((2-methoxyethyl)amino)pyrazolo[1,5-a]pyridine-3-carboxylate

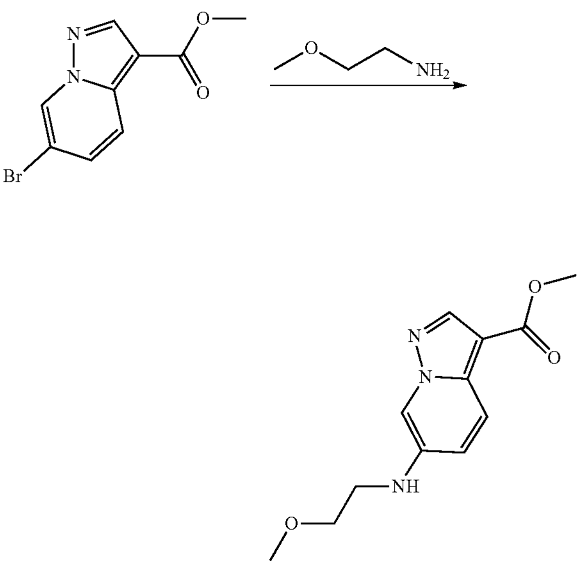

A mixture of methyl 6-bromopyrazolo[1,5-a]pyridine-3-carboxylate (200 mg, 0.78 mmol), $Cs_2CO_3$ (508 mg, 1.56 mmol), BrettPhos Pd G3 (71.0 mg, 0.08 mmol), BrettPhos (83.7 mg, 0.16 mmol) and 2-methoxyethan-1-amine (117 mg, 1.56 mmol) in dioxane (3 mL) was stirred for 4 h at 80° C. under $N_2$ and then cooled to rt. Water (10 mL) was added and the resulting solution was extracted with DCM (3×20 mL). The combined organic phase was dried with $Na_2SO_4$ and concentrated under vacuum. The crude product was purified by a silica gel column with PE:EtOAc=1:1 to give the title compound (150 mg, 77%) as an off-white solid. LCMS: m/z=250 $[M+H]^+$ Intermediate 43

2-chloro-5-(2-cyclopropyl-2H-tetrazol-5-yl)-4-methylaniline

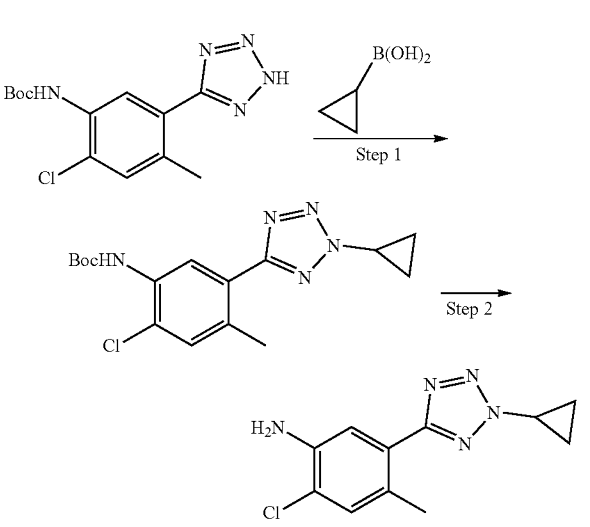

Step 1: Synthesis of tert-butyl(2-chloro-5-(2-cyclopropyl-2H-tetrazol-5-yl-4-methylphenyl)carbamate The title compound was obtained as a light yellow solid, 200 mg, 66%, from tert-butyl(2-chloro-4-methyl-5-(2H-tetrazol-5-yl)phenyl)carbamate and cyclopropylboronic acid following a similar procedure to that described in Intermediate 16, step 1. LCMS: m/z=350 $[M+H]^+$ Step 2: Synthesis of 2-chloro-5-(2-cyclopropyl-2H-tetrazol-5-yl)-4-methylaniline TFA (3 mL) was added to tert-butyl(2-chloro-5-(2-cyclopropyl-2H-tetrazol-5-yl)-4-methylphenyl)carbamate (200 mg, 0.595 mmol) in DCM (10 mL) at rt. The resulting mixture was stirred for 2 h. The mixture was diluted with DCM (100 mL) and washed with aq. sodium bicarbonate (2×50 mL). The organic layer was dried with $Na_2SO_4$ and concentrated under vacuum. The residue was purified by a silica gel column with DCM:EtOAc=25:1 to give the title compound (130 mg, 65%) as a white solid. LCMS: m/z=250 $[M+H]^+$.

Intermediate 44 methyl 5-(1-(2-hydroxy-2-methylpropyl)-1H-pyrazol-4-yl)pyrazolo[1,5-a]pyridine-3-carboxylate

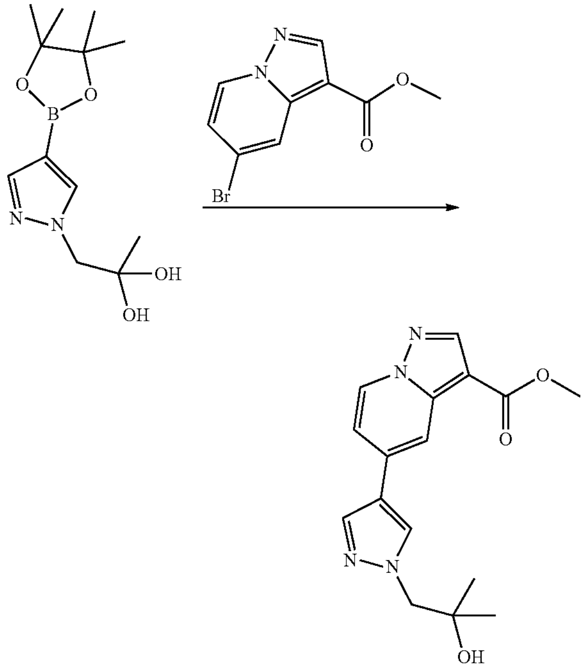

$Pd(dppt)Cl_2$ (159 mg, 0.196 mmol) was added to methyl 5-bromopyrazolo[1,5-a]pyridine-3-carboxylate (500 mg, 1.96 mmol), 2-methyl-1-(4-(4,4,5,5-tetramethyl-1,3,2-dioxaborolan-2-yl)-1H-pyrazol-1-yl)propan-2-ol (521 mg, 1.96 mmol) and $K_2CO_3$ (407 mg, 2.94 mmol) in $H_2O$ (4 mL) and dioxane (16 mL) at rt. The resulting mixture was stirred at 80° C. for 2 h under $N_2$. The mixture was diluted with DCM (100 mL) and washed with water (2×50 mL). The organic layer was dried with $Na_2SO_4$ and concentrated under vacuum. The residue was purified by a silica gel column with DCM:MeOH=20:1 to give the title compound (400 mg, 80%) as a white solid. LCMS: m/z=315 $[M+H]^+$.

Intermediate 45

Methyl 5-(1-((4-hydroxytetrahydro-2H-pyran-4-yl)methyl)-3-methyl-1H-pyrazol-4-yl)pyrazolo[1,5-a]pyridine-3-carboxylate and methyl 5-(1-((4-hydroxytetrahydro-2H-pyran-4-yl)methyl)-5-methyl-1H-pyrazol-4-yl)pyrazolo[1,5-a]pyridine-3-carboxylate (Intermediate 45-1)

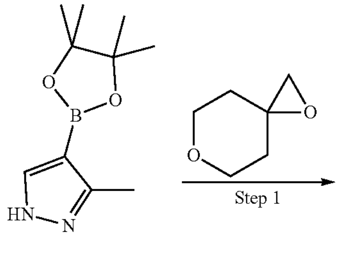

-continued

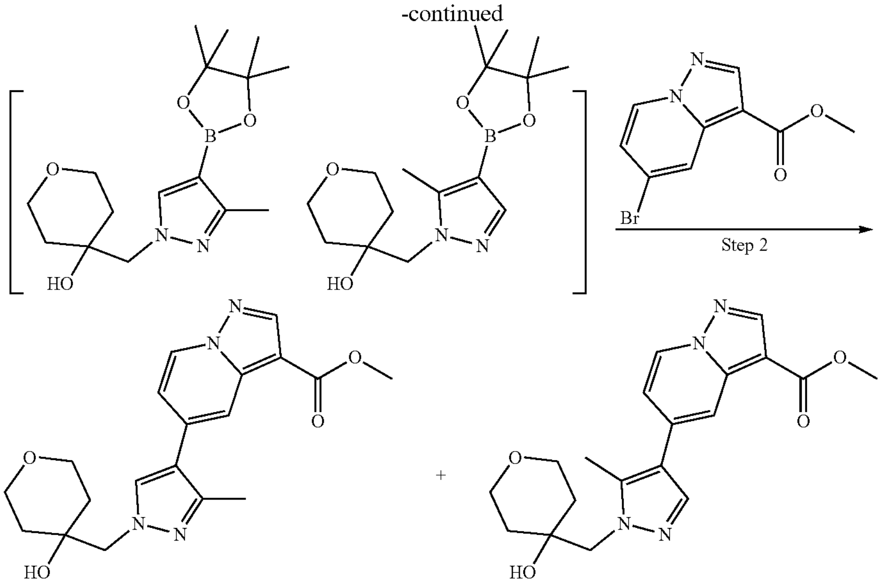

Intermediate 45 Intermediate 45-1

Step 1: Synthesis of mixture of 4-((3-methyl-4-(4,4,5,5-tetramethyl-1,3,2-dioxaborolan-2-yl)-1H-pyrazol-1-yl)methyl)tetrahydro-2H-pyran-4-ol and 4-((5-methyl-4-(4,4,5,5-tetramethyl-1,3,2-dioxaborolan-2-yl)-1H-pyrazol-1-yl)methyl)tetrahydro-2H-pyran-4-ol A mixture of 3-methyl-4-(4,4,5,5-tetramethyl-1,3,2-dioxaborolan-2-yl)-1H-pyrazole (500 mg, 2.40 mmol), 1,6-dioxaspiro[2.5]octane (547 mg, 4.80 mmol) and $Cs_2CO_3$ (1.16 g, 3.59 mmol) in DMF (20 mL) was stirred at 80° C. for 2 h under $N_2$. The solvent was evaporated and the residue was purified on silica gel column eluting with 5% MeOH in DCM to afford the title compounds as a mixture (600 mg, 77.6%) as a colorless oil. LCMS: m/z=323 $[M+H]^+$.

Step 2: Synthesis of Intermediate 45 methyl 5-(1-((4-hydroxytetrahydro-2H-pyran-4-yl)methyl)-3-methyl-1H-pyrazol-4-yl)pyrazolo[1,5-a]pyridine-3-carboxylate and Intermediate 45-1 methyl 5-(1-((4-hydroxytetrahydro-2H-pyran-4-yl)methyl)-5-methyl-1H-pyrazol-4-yl)pyrazolo[1,5-a]pyridine-3-carboxylate A mixture of 4-((3-methyl-4-(4,4,5,5-tetramethyl-1,3,2-dioxaborolan-2-yl)-1H-pyrazol-1-yl)methyl)tetrahydro-2H-pyran-4-ol and 4-((5-methyl-4-(4,4,5,5-tetramethyl-1,3,2-dioxaborolan-2-yl)-1H-pyrazol-1-yl)methyl)tetrahydro-2H-pyran-4-ol (600 mg, 1.86 mmol), methyl 5-bromopyrazolo[1,5-a]pyridine-3-carboxylate (568 mg, 2.23 mmol), $Pd(dppf)Cl_2$ (60 mg, 73.4 μmol) and $Cs_2CO_3$ (1.21 g, 3.72 mmol) in dioxane (25 mL) and $H_2O$ (5 mL) was stirred at 100° C. for 2 h under $N_2$. The solvent was evaporated and the residue was purified on silica gel column eluting with PE/EtOAc (40/60) to initially afford Intermediate 45-1 (250 mg, 36.2%) as a brown solid. LCMS: m/z=371 $[M+H]^+$. And then Intermediate 45 (300 mg, 43.5%) was eluted as an off-white solid. LCMS: m/z=371 $[M+H]^+$.

Intermediate 46

2-chloro-5-(2-cyclopropyl-2H-tetrazol-5-yl)aniline

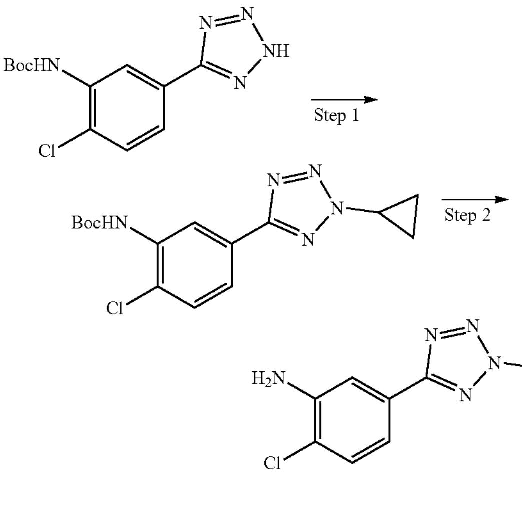

Step 1: Synthesis of tert-butyl(2-chloro-5-(2-cyclopropyl-2H-tetrazol-5-yl)phenyl)carbamate The title compound was obtained as a light yellow solid, 200 mg, 66%, from Intermediate 10, Step 1, and cyclopropylboronic acid following a similar procedure to that described in Intermediate 16, step 1. LCMS: m/z=336 $[M+H]^+$.

Step 2: Synthesis of 2-chloro-5-(2-cyclopropyl-2H-tetrazol-5-yl)aniline

The title compound was obtained as a yellow solid, 100 mg, 50% from tert-butyl(2-chloro-5-(2-cyclopropyl-2H-tetrazol-5-yl)phenyl)carbamate following a similar procedure to that described in Intermediate 43, step 2. LCMS: m/z=236 [M+H]$^+$.

Intermediate 47

5-bromo-N-(2-chloro-5-(2-cyclopropyl-2H-tetrazol-5-yl)phenyl)pyrazolo[1,5-a]pyridine-3-carboxamide

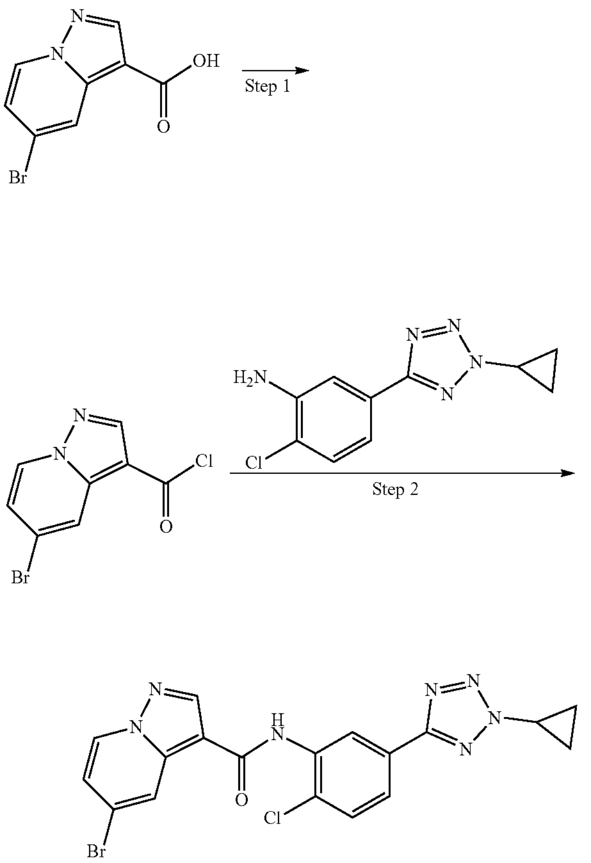

Step 1: Synthesis of 5-bromopyrazolo[1,5-a]pyridine-3-carbonyl chloride $SOCl_2$(10 mL) was added to 5-bromopyrazolo[1,5-a]pyridine-3-carboxylic acid (10 g, 29.88 mmol) at rt. The resulting mixture was stirred at 60° C. for 2 h. The mixture was concentrated under vacuum to afford the title compound (9.5 g, 95%) as a brown solid. LCMS: m/z=259 [M+H]$^+$.

Step 2: Synthesis of 5-bromo-N-(2-chloro-5-(2-cyclopropyl-2H-tetrazol-5-yl)phenyl)pyrazolo[1,5-a]pyridine-3-carboxamide 5-Bromopyrazolo[1,5-a]pyridine-3-carbonyl chloride (8.25 g, 31.8 mmol) was added to Intermediate 46, (5 g, 21.2 mmol) in pyridine (35 mL) at rt and the reaction mixture was stirred for 3 h. The mixture was concentrated under vacuum. The residue was purified by a silica gel column with DCM:EtOAc=18:1 to yield the title compound (6.8 g) as an off-white solid. LCMS: m/z=459 [M+H]$^+$.

Intermediate 48

(S)-1-methoxy-3-(4-(4,4,5,5-tetramethyl-1,3,2-dioxaborolan-2-yl)-1H-pyrazol-1-yl)propan-2-ol

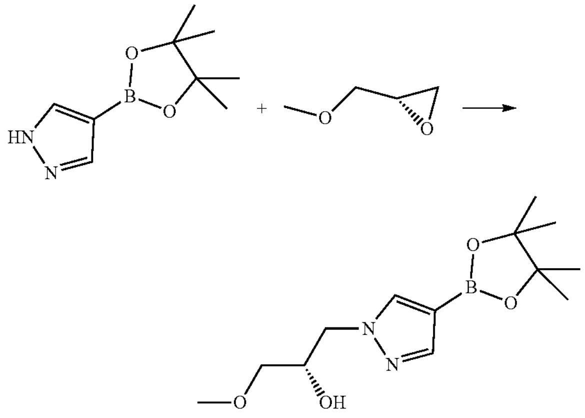

A mixture of 4-(4,4,5,5-tetramethyl-1,3,2-dioxaborolan-2-yl)-1H-pyrazole (3 g, 15.5 mmol), (S)-2-(methoxymethyl)oxirane (1.63 g, 18.5 mmol) and $Cs_2CO_3$ (5.04 g, 15.5 mmol) in DMF (30 mL) was stirred at 100° C. for 3 h under $N_2$. The solvent was evaporated and the residue was purified by silica gel column eluting with 5% MeOH in DCM to afford the title compound (4 g, 91.8%) as a yellow solid. LCMS: m/z=282 [M+H]$^+$.

Intermediate 49

5-(2-cyclopropyl-2H-tetrazol-5-yl)-4-fluoro-2-methylaniline

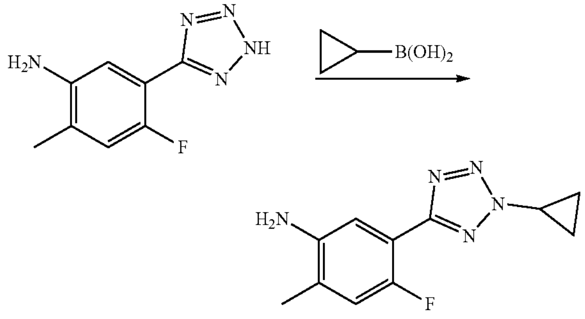

A mixture of Intermediate 7, Step 1 (300 mg, 1.55 mmol), $K_2CO_3$ (641 mg, 4.65 mmol), $[CuOH(TMEDA)]_2Cl_2$ (143 mg, 0.310 mmol) and cyclopropylboronic acid (266 mg, 3.10 µmol) in DCE (10 mL) was stirred at 60° C. for 24 h under $O_2$ and then cooled to rt. The mixture was filtered and the residue was washed with a solution of DCM:MeOH=10:1. The filtrate was concentrated under vacuum. The crude product was purified by silica gel column with PE:EtOAc (2:1) to give the title compound (60 mg, 17%) as a yellow solid. LCMS: m/z=234 [M+H]$^+$.

Intermediate 50

2-methyl-1-(3-methyl-4-(4,4,5,5-tetramethyl-1,3,2-dioxaborolan-2-yl)-1H-pyrazol-1-yl)propan-2-ol and 2-methyl-1-(5-methyl-4-(4,4,5,5-tetramethyl-1,3,2-dioxaborolan-2-yl)-1H-pyrazol-1-yl)propan-2-ol

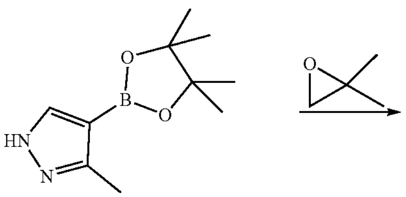

-continued

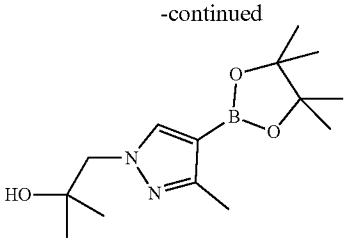

and

50B

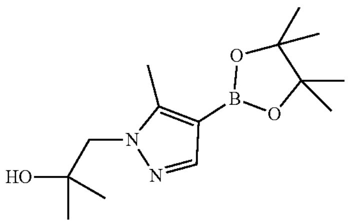

50A

A mixture of 3-methyl-4-(4,4,5,5-tetramethyl-1,3,2-dioxaborolan-2-yl)-1H-pyrazole (7 g, 33.6 mmol), 2,2-dimethyloxirane (2.90 g, 40.3 mmol) and $Cs_2CO_3$ (10.9 g, 33.6 mmol) in DMF (100 mL) was stirred at 100° C. for 3 h under $N_2$. The solvent was evaporated and the residue was purified by silica gel column with 5% MeOH in DCM to afford the title compound (7.5 g, 89.6%) as a yellow solid. LCMS: m/z=281 $[M+H]^+$.

Intermediate 51

Intermediate 51A

Methyl 5-(1-(2-hydroxy-2-methylpropyl)-5-methyl-1H-pyrazol-4-yl)pyrazolo[1,5-a]pyridine-3-carboxylate Intermediate 51B Methyl 5-(1-(2-hydroxy-2-methylpropyl)-3-methyl-1H-pyrazol-4-yl)pyrazolo[1,5-a]pyridine-3-carboxylate

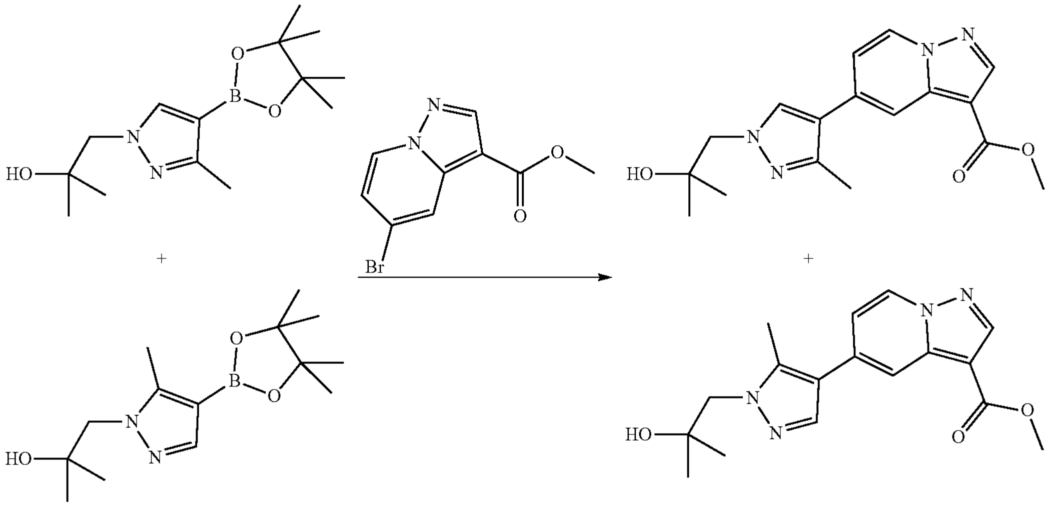

A mixture of Intermediate 50, (6 g, 21 mmol), methyl 5-bromopyrazolo[1,5-a]pyridine-3-carboxylate (5.5 g, 21 mmol), $Cs_2CO_3$ (13.9 g, 42 mmol) and Pd(pddf)$Cl_2$ (171 mg, 2 mmol) in dioxane (50 mL) and water (5 mL) was stirred at 100° C. for 3 h under $N_2$. The solvent was evaporated and the residue was purified on silica gel column with 5% MeOH in DCM to give Intermediate 51, a mixture of the title compounds (51A and 51B). LCMS m/z=329 [M+H]+. The regioisomeric mixture was separated by SFC (Column: Green Sep Basic, 4.6*100 mm, 3 m; Mobile Phase B: MeCN:MeOH=80:20 (1% 2M $NH_3$-MeOH)) to yield Peak 1 Intermediate 51A (0.9 g) as a solid. 1H NMR (400 MHz, DMSO-d6) δ 8.87-8.81 (m, 1H), 8.41 (s, 1H), 8.04-7.99 (m, 1H), 7.89 (s, 1H), 7.29 (dd, 1H), 4.70 (s, 1H), 4.07 (s, 2H), 3.84 (s, 3H), 2.54 (s, 3H), 1.17 (s, 6H).

Further elution provided Peak 2 Intermediate 51B, (2.3 g, 33%) as a yellow solid. 1H NMR (400 MHz, DMSO-d6) δ 8.82 (dd, 1H), 8.40 (s, 1H), 8.19 (s, 1H), 8.08 (d, 1H), 7.30 (dd, 1H), 4.73 (s, 1H), 4.00 (s, 2H), 3.84 (s, 3H), 2.44 (s, 3H), 1.12 (s, 6H).

Intermediate 52

1-(4-bromo-3-cyclopropyl-1H-pyrazol-1-yl)-2-methylpropan-2-ol and 1-(4-bromo-5-cyclopropyl-1H-pyrazol-1-yl)-2-methylpropan-2-ol

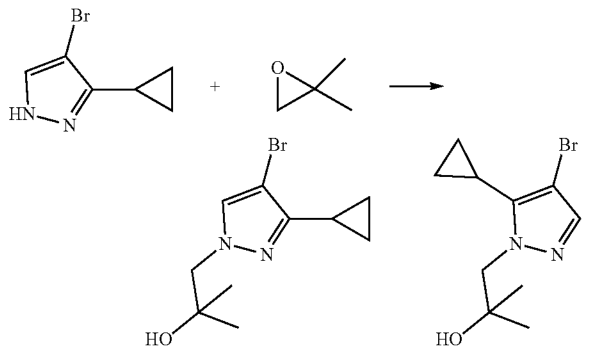

To a solution of 4-bromo-3-cyclopropyl-1H-pyrazole (2 g, 10.7 mmol) in DMF (30 mL) was added $Cs_2CO_3$ (3.48 g, 10.7 mmol), then 2,2-dimethyloxirane (0.92 g, 12.8 mmol) and the reaction mixture was stirred at 80° C. for 3 h. The solvent was evaporated and the residue was purified by silica gel column eluting with 5% MeOH in DCM to afford title compounds (2.5 g, 90.2%) as a yellow solid. The ratio of the two isomers was 4:1 (1-(4-bromo-3-cyclopropyl-1H-pyrazol-1-yl)-2-methylpropan-2-ol/1-(4-bromo-5-cyclopropyl-1H-pyrazol-1-yl)-2-methylpropan-2-ol). LCMS: m/z=259, 261 $[M+H]^+$.

Intermediate 53 methyl 5-(4,4,5,5-tetramethyl-1,3,2-dioxaborolan-2-yl)pyrazolo[1,5-a]pyridine-3-carboxylate

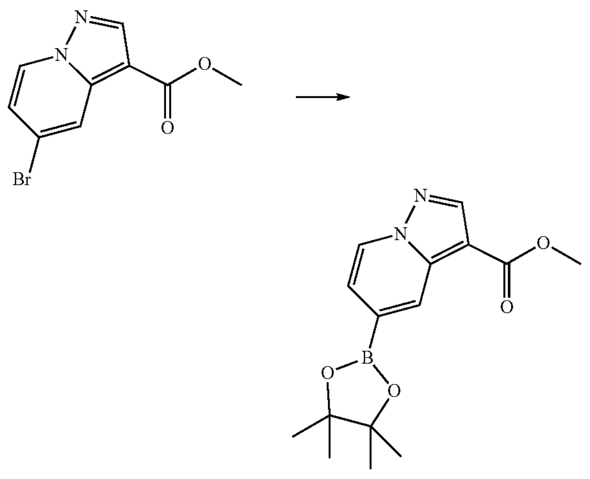

A mixture of methyl 5-bromopyrazolo[1,5-a]pyridine-3-carboxylate (3.2 g, 11.6 mmol), $(BPin)_2$ (3.8 g, 11.6 mmol), $Pd(dppf)Cl_2$ (170 mg, 232 μmol) and $Cs_2CO_3$ (2.7 g, 11.6 mmol) in dioxane (50 mL) and $H_2O$ (10 mL) was stirred at 100° C. for 16 h. The solvent was evaporated and the residue was purified on a silica gel column with EtOAc/PE (60/40) to afford title compound (3.2 g, 40.9%) as a yellow oil. LCMS: m/z=371 $[M+H]^+$.

Intermediate 54 methyl 5-(3-cyclopropyl-1-(2-hydroxy-2-methylpropyl)-1H-pyrazol-4-yl)pyrazolo[1,5-a]pyridine-3-carboxylate and methyl 5-(5-cyclopropyl-1-(2-hydroxy-2-methylpropyl)-1H-pyrazol-4-yl)pyrazolo[1,5-a]pyridine-3-carboxylate

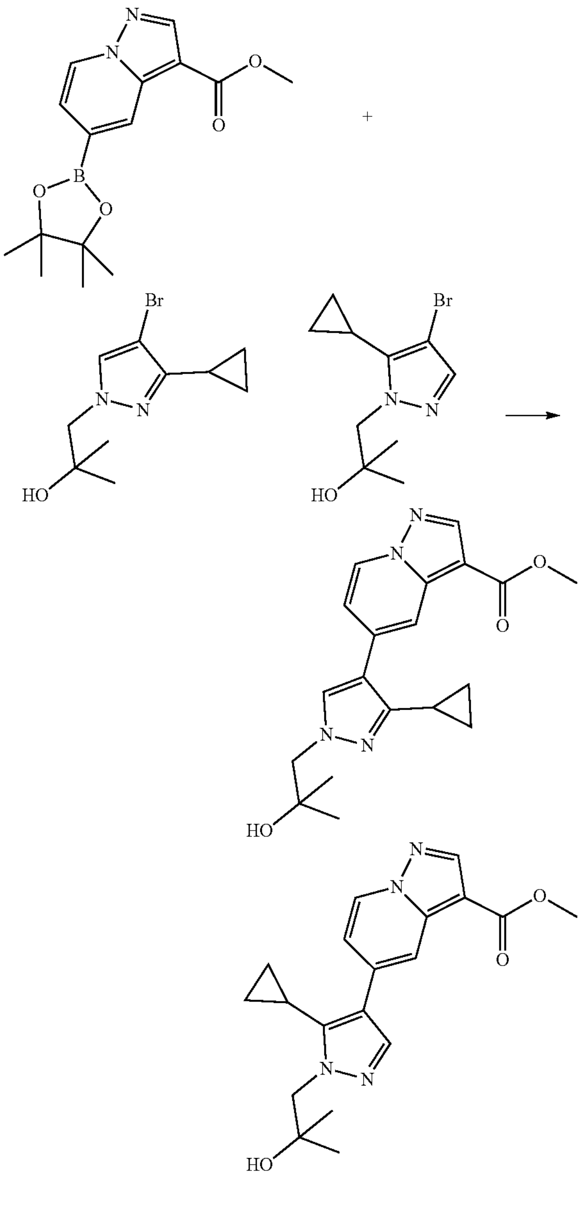

A mixture of Intermediate 52, (2.1 g, 8.28 mmol), Intermediate 53, (2.5 g, 8.28 mmol), $Pd(dppf)Cl_2$ (121 mg, 0.166 mmol) and $Cs_2CO_3$ (2.7 g, 8.28 mmol) in dioxane (50 mL) and $H_2O$ (10 mL) was stirred at 100° C. for 16 h. The solvent was evaporated and the residue was purified on a silica gel column with EtOAc/PE (60/40) to afford title compound (1.2 g, 40.9%) as a yellow oil. LCMS: m/z=355 $[M+H]^+$.

Intermediate 55

5-(2-cyclopropyl-2H-tetrazol-5-yl)-2-methylaniline

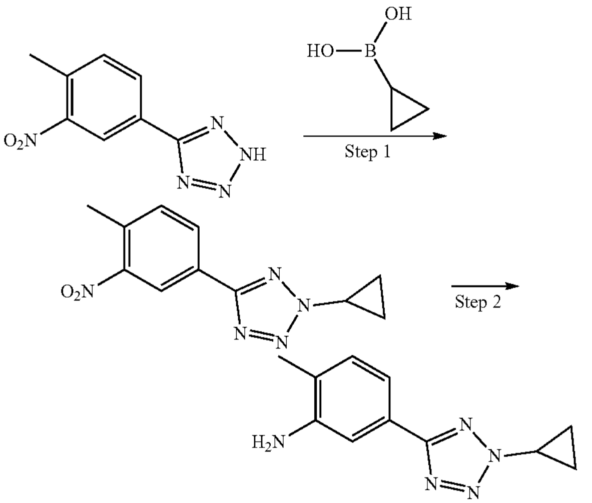

Step 1: Synthesis of 2-cyclopropyl-5-(4-methyl-3-nitrophenyl)-2H-tetrazole

A mixture of Intermediate 13, Step 1, (20 g, 97.4 mmol), cyclopropylboronic acid (16.6 g, 194 mmol), $Cu(OAc)_2$ (17.7 g, 97.4 mmol), 2,2'-bipyridine (15.2 g, 97.4 mmol) and $Na_2CO_3$ (20.5 g, 194 mmol) in DCE (1000 mL) was heated at 60° C. for 16 h. The mixture was extracted with EtOAc (3×500 mL). The organic layer was dried with $Na_2SO_4$ and concentrated under vacuum. The crude product was purified by a silica gel column with PE:EtOAc=8:1 to give the title compound (11.5 g, 48%) as a yellow solid. LCMS: m/z=246 $[M+H]^+$.

Step 2: Synthesis of 5-(2-cyclopropyl-2H-tetrazol-5-yl)-2-methylaniline

A mixture of 2-cyclopropyl-5-(4-methyl-3-nitrophenyl)-2H-tetrazole (11.5 g, 46.8 mmol), Fe (26.2 g, 468 mmol) and $NH_4Cl$ (25.2 g, 468 mmol) in EtOH/$H_2O$ (500 mL/100 mL) was heated to 80° C. for 2 h. The mixture was extracted with EtOAc (3×300 mL), the combined organic layer was dried with $Na_2SO_4$ and concentrated under vacuum to give the title compound (9 g, 90%) as a yellow solid. LCMS: m/z=216 $[M+H]^+$.

Intermediate 56

5-bromo-N-(5-(2-cyclopropyl-2H-tetrazol-5-yl)-2-methylphenyl)pyrazolo[1,5-a]pyridine-3-carboxamide

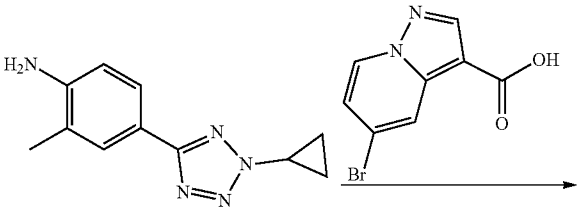

-continued

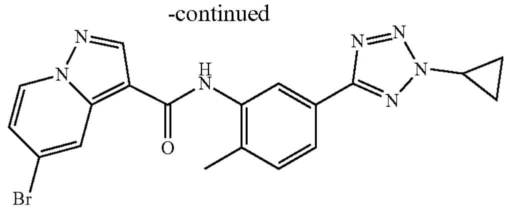

A mixture of pyridine (25 mL) and $PPh_3$ (25 mL), 5-bromopyrazolo[1,5-a]pyridine-3-carboxylic acid (8 g, 33.1 mmol) and Intermediate 55, (10.6 g, 49.6 mmol) in THF (30 mL) was stirred at 50° C. for 3 h. The mixture was concentrated under vacuum. The residue was purified by a silica gel column with DCM:EtOAc=18:1 to provide the title compound (7.8 g, 97.5%) as an off-white solid. LCMS: m/z=438 $[M+H]^+$.

Intermediate 57

5-(3-cyclopropyl-1H-pyrazol-4-yl)-N-(5-(2-cyclopropyl-2H-tetrazol-5-yl)-2-methylphenyl)pyrazolo[1,5-a]pyridine-3-carboxamide

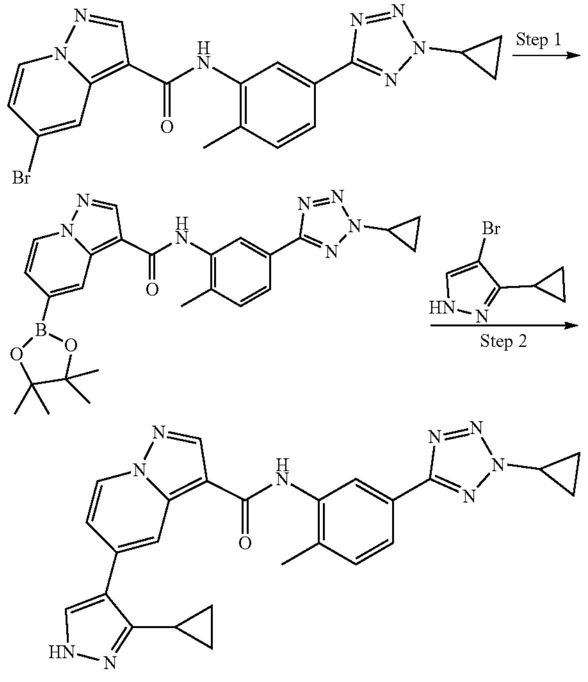

Step 1: Synthesis of N-(5-(2-cyclopropyl-2H-tetrazol-5-yl)-2-methylphenyl)-5-(4,4,5,5-tetramethyl-1,3,2-dioxaborolan-2-yl)pyrazolo[1,5-a]pyridine-3-carboxamide A mixture of Intermediate 56, (1 g, 2.28 mmol), KOAc (447 mg, 4.56 mmol), $Pd(dppf)Cl_2$ (186 mg, 228 μmol) and $(BPin)_2$ (1.15 g, 4.56 mmol) in dioxane (10 mL) was stirred at 80° C. for 2 h under $N_2$. The crude was used to next step directly without further purification. LCMS: m/z=486 $[M+H]^+$.

Step 2: Synthesis of 5-(3-cyclopropyl-1H-pyrazol-4-yl)-N-(5-(2-cyclopropyl-2H-tetrazol-5-yl)-2-methylphenyl)pyrazolo[1,5-a]pyridine-3-carboxamide A mixture of N-(5-(2-cyclopropyl-2H-tetrazol-5-yl)-2-methylphenyl)-5-(4,4,5,5-tetramethyl-1,3,2-dioxaborolan-2-yl)pyrazolo[1,5-a]pyridine-3-carboxamide (Step 1, 1.10 g, 2.26 mmol), Pd(dppf)$Cl_2$ (369 mg, 0.452 mmol), $Cs_2CO_3$ (1.47 g, 4.52 mmol) and 4-bromo-3-cyclopropyl-1H-pyrazole (632 mg, 3.38 mmol) in dioxane (9 mL) and $H_2O$ (3 mL) was stirred at 100° C. for 12 h under $N_2$. The mixture was cooled to rt, water was added and the resulting solution was extracted with DCM (3×100 mL). The organic layer was dried with $Na_2SO_4$ and concentrated under vacuum. The crude product was purified by a silica gel column with DCM:MeOH=20:1 to yield the title compound (500 mg, 48%) as a reddish brown solid. LCMS: m/z=466 $[M+H]^+$.

Intermediate 58

1-(3,5-dimethyl-4-(4,4,5,5-tetramethyl-1,3,2-dioxaborolan-2-yl)-1H-pyrazol-1-yl)-2-methylpropan-2-ol

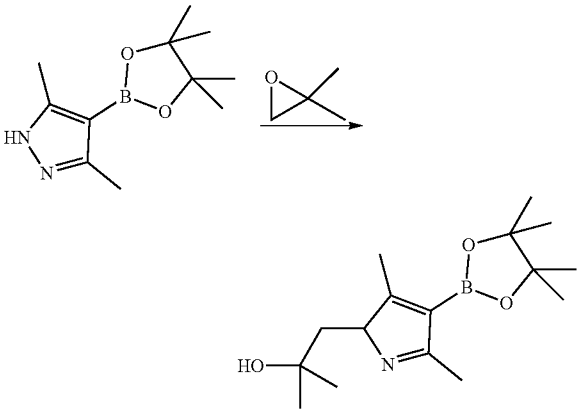

A mixture of 3,5-dimethyl-4-(4,4,5,5-tetramethyl-1,3,2-dioxaborolan-2-yl)-1H-pyrazole (1 g, 4.50 mmol), 2,2-dimethyloxirane (486 mg, 6.75 mmol) and $Cs_2CO_3$ (2.19 g, 6.75 mmol) in DMF (20 mL) was stirred at 100° C. for 3 h under $N_2$. The solvent was evaporated and the residue was purified by silica gel column with 5% MeOH in DCM to afford the title compound (1.2 g, 90.9%) as a yellow solid. LCMS: m/z=295 $[M+H]^+$.

Intermediate 59 methyl 5-(1-(2-hydroxy-2-methylpropyl)-3,5-dimethyl-1H-pyrazol-4-yl)pyrazolo[1,5-a]pyridine-3-carboxylate

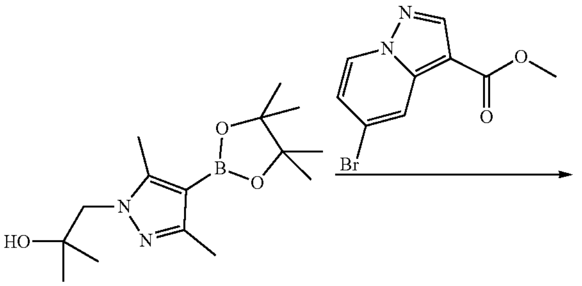

-continued

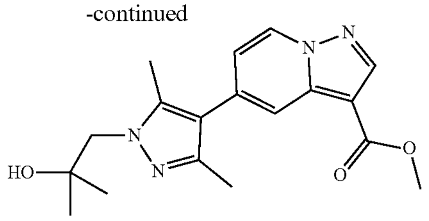

A mixture of Intermediate 58, (300 mg, 1.01 mmol), methyl 5-bromopyrazolo[1,5-a]pyridine-3-carboxylate (385 mg, 1.51 mmol), $Cs_2CO_3$ (491 mg, 1.51 mmol) and Pd(pddf)$Cl_2$ (41.7 mg, 50 μmol) in dioxane (9 mL) and water (3 mL) was stirred at 100° C. for 3 h. The solvent was evaporated and the residue was purified on Prep-TLC with DCM: MeOH=20:1 to afford the title compound (240 mg, 69.5%) as a yellow solid. LCMS: m/z=343 $[M+H]^+$.

Intermediate 60

(S)-1-(4-bromo-3-cyclopropyl-1H-pyrazol-1-yl)-3-methoxypropan-2-ol and (S)-1-(4-bromo-5-cyclopropyl-1H-pyrazol-1-yl)-3-methoxypropan-2-ol

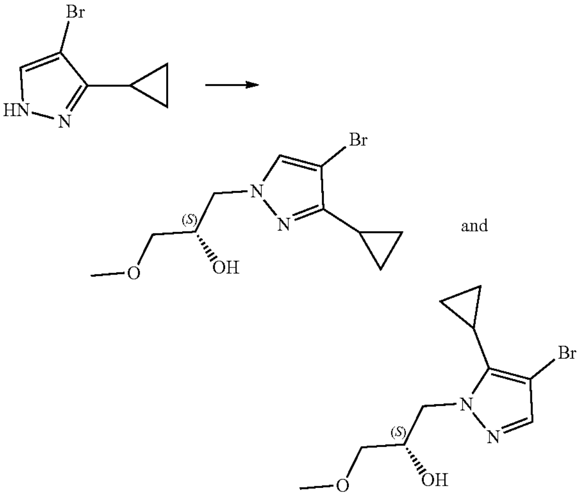

and

The title compounds were obtained in the ratio 3:1, 3.5 g, 79%, from 4-bromo-3-cyclopropyl-1H-pyrazole and (S)-2-(methoxymethyl)oxirane, following the procedure described in Intermediate 48. LCMS: m/z=275, 277 $[M+H]^+$ Intermediates 61 to 64

The compounds in the following table were prepared from the appropriate 4-(4,4,5,5-tetramethyl-1,3,2-dioxaborolan-2-yl)-1H-pyrazole and oxirane, following the procedure described in Intermediate 48.

| Int. no | Name, Structure | Starting Materials (SM) Data |
|---|---|---|
| 61 | (S)-1-(3,5-dimethyl-4-(4,4,5,5-tetramethyl-1,3,2-dioxaborolan-2-yl)-1H-pyrazol-1-yl)-3-methoxypropan-2-ol 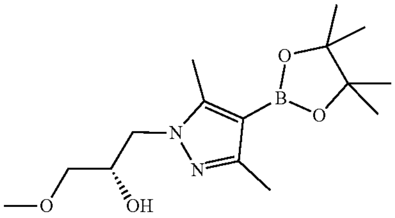 | SM: 3,5-dimethyl-4-(4,4,5,5-tetramethyl-1,3,2-dioxaborolan-2-yl)-1H-pyrazole (Intermediate 58, step 1) and (S)-2-(methoxymethyl)oxirane LCMS: m/z = 311 [M + H]+. |
| 62 | (S)-1-(3,5-dimethyl-4-(4,4,5,5-tetramethyl-1,3,2-dioxaborolan-2-yl)-1H-pyrazol-1-yl)propan-2-ol 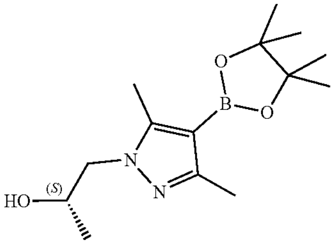 | SM: 3,5-dimethyl-4-(4,4,5,5-tetramethyl-1,3,2-dioxaborolan-2-yl)-1H-pyrazole (Intermediate 58, step 1) and (2S)-2-(methoxymethyl)oxirane LCMS: m/z =281 [M + H]+. |
| 63 | (R)-1-(5-methyl-4-(4,4,5,5-tetramethyl-1,3,2-dioxaborolan-2-yl)-1H-pyrazol-1-yl)propan-2-ol and (R)-1-(3-methyl-4-(4,4,5,5-tetramethyl-1,3,2-dioxaborolan-2-yl)-1H-pyrazol-1-yl)propan-2-ol 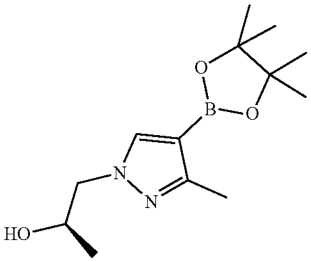 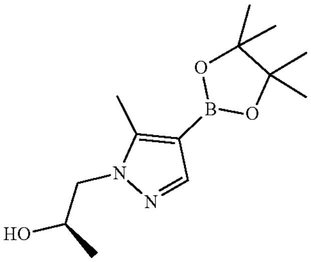 | SM: 3-methyl-4-(4,4,5,5-tetramethyl-1,3,2-dioxaborolan-2-yl)-1H-pyrazole and (2R)-2-methyloxirane LCMS m/z = 267 [M + H]+ |
| 64 | (S)-1-methoxy-3-(3-methyl-4-(4,4,5,5-tetramethyl-1,3,2-dioxaborolan-2-yl)-1H-pyrazol-1-yl)propan-2-ol and (S)-1-methoxy-3-(5-methyl-4-(4,4,5,5-tetramethyl-1,3,2-dioxaborolan-2-yl)-1H-pyrazol-1-yl)propan-2-ol 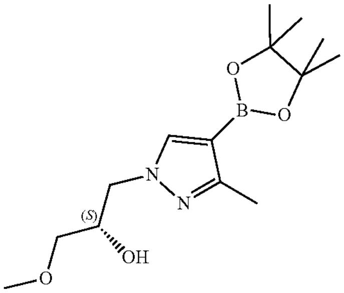 and 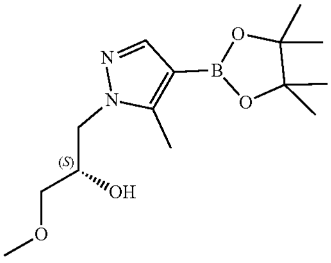 | SM: 3-methyl-4-(4,4,5,5-tetramethyl-1,3,2-dioxaborolan-2-yl)-1H-pyrazole and (S)-2-(methoxymethyl)oxirane LCMS: m/z = 297 [M + H]+. |
| 65 | (S)-1-(3-methyl-4-(4,4,5,5-tetramethyl-1,3,2-dioxaborolan-2-yl)-1H-pyrazol-1-yl)propan-2-ol and (S)-1-(5-methyl-4-(4,4,5,5-tetramethyl-1,3,2-dioxaborolan-2-yl)-1H-pyrazol-1-yl)propan-2-ol | SM: 3-methyl-4-(4,4,5,5-tetramethyl-1,3,2-dioxaborolan-2-yl)-1H-pyrazole and (2S)-2-methyloxirane LCMS: m/z = 267 [M + H]+. |

-continued

| Int. no | Name, Structure | Starting Materials (SM) Data |
| --- | --- | --- |
| | 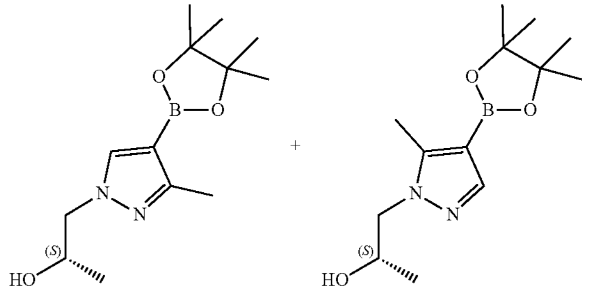 | |
| 66 | (R)-1-methoxy-3-(3-methyl-4-(4,4,5,5-tetramethyl-1,3,2-dioxaborolan-2-yl)-1H-pyrazol-1-yl)propan-2-ol and (R)-1-methoxy-3-(5-methyl-4-(4,4,5,5-tetramethyl-1,3,2-dioxaborolan-2-yl)-1H-pyrazol-1-yl)propan-2-ol 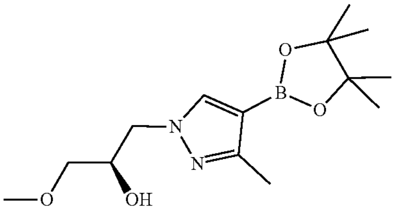 and 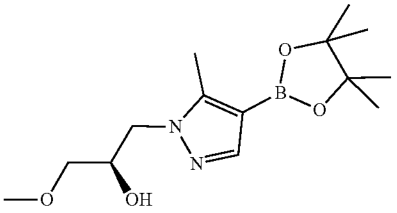 | SM: 3-methyl-4-(4,4,5,5-tetramethyl-1,3,2-dioxaborolan-2-yl)-1H-pyrazole and (R)-2-(methoxymethyl)oxirane, LCMS: m/z = 297 [M + H]$^+$. |

Intermediate 67

1-methoxy-2-methyl-3-(3-methyl-4-(4,4,5,5-tetramethyl-1,3,2-dioxaborolan-2-yl)-1H-pyrazol-1-yl)propan-2-ol and 1-methoxy-2-methyl-3-(5-methyl-4-(4,4,5,5-tetramethyl-1,3,2-dioxaborolan-2-yl)-1H-pyrazol-1-yl)propan-2-ol

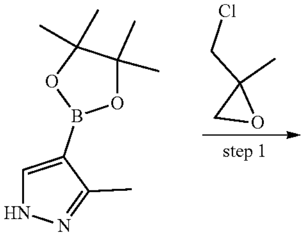

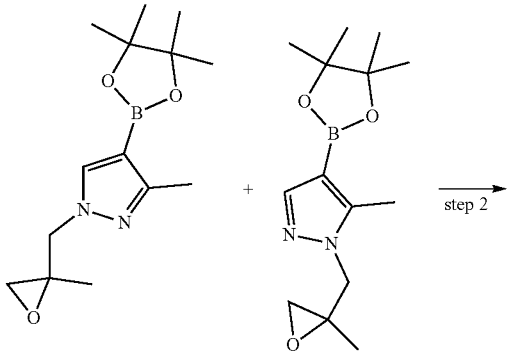

-continued

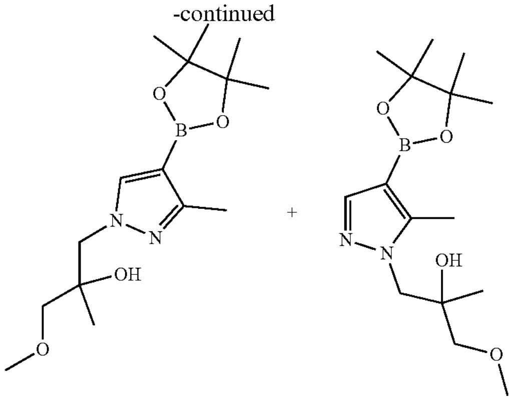

Step 1: Synthesis of 3-methyl-1-((2-methyloxiran-2-yl)methyl)-4-(4,4,5,5-tetramethyl-1,3,2-dioxaborolan-2-yl)-1H-pyrazole and 5-methyl-1-(2-methyloxiran-2-yl)-4-(4,4,5,5-tetramethyl-1,3,2-dioxaborolan-2-yl)-1H-pyrazole A mixture of 3-methyl-4-(4,4,5,5-tetramethyl-1,3,2-dioxaborolan-2-yl)-1H-pyrazole (4 g, 19.2 mmol), 2-(chloromethyl)-2-methyloxirane (3.05 g, 28.7 mmol) and $Cs_2CO_3$ (6.25 g, 19.2 mmol) in DMF (40 mL) was stirred for 3 h at 100° C. The cooled reaction was quenched with water and extracted with EtOAc (3×50 mL), the organic layer was dried with $Na_2SO_4$ and concentrated in vacuo. The crude product was purified by a Prep-TLC with PE:EtOAc=30:1, to give a mixture of the title compounds (5 g, 93.6%). LCMS: m/z=279 [M+H]$^+$.

Step 2: Synthesis of 1-methoxy-2-methyl-3-(3-methyl-4-(4,4,5,5-tetramethyl-1,3,2-dioxaborolan-2-yl)-1H-pyrazol-1-yl)propan-2-ol and 1-methoxy-2-methyl-3-(5-methyl-4-(4,4,5,5-tetramethyl-1,3,2-dioxaborolan-2-yl)-1H-pyrazol-1-yl)propan-2-ol A mixture of the compounds from step 1 (5 g, 17.9 mmol), MeONa (966 mg, 17.9 mmol) in MeOH (80 mL) was stirred at 100° C. for 16 h under $N_2$. The cooled reaction mixture was diluted with water (8 mL), extracted with EtOAc (2×50 mL) and the combined organic extracts washed with brine. The organic layer was dried over $Na_2SO_4$ and concentrated in vacuo. The product was purified by Prep-TLC with DCM:MeOH=30:1 to give a mixture of title compounds (3.0 g, 54%). LCMS: m/z=311 $[M+H]^+$.

Intermediate 68

(S)-1-(2-methoxyethoxy)-3-(4-(4,4,5,5-tetramethyl-1,3,2-dioxaborolan-2-yl)-1H-pyrazol-1-yl)propan-2-ol

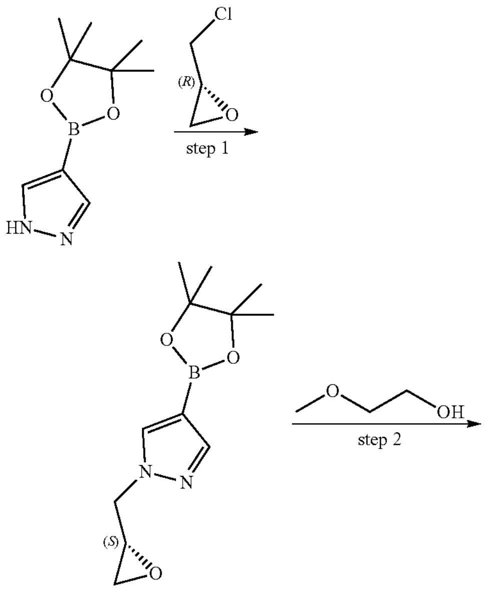

-continued

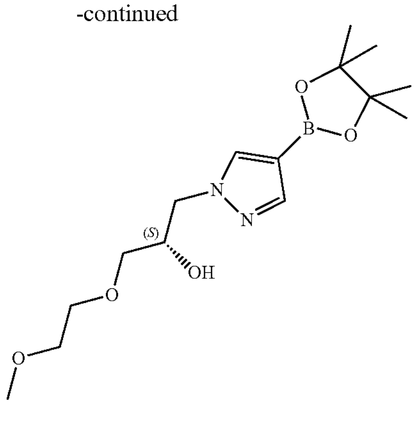

Step 1: Synthesis of(S)-1-(oxiran-2-ylmethyl)-4-(4,4,5,5-tetramethyl-1,3,2-dioxaborolan-2-yl)-1H-pyrazole The title compound was obtained as a white solid, 2.5 g, 64.9%, from 4-(4,4,5,5-tetramethyl-1,3,2-dioxaborolan-2-yl)-1H-pyrazole and 2-(chloromethyl)oxirane, following the procedure described in Intermediate 48. LCMS m/z=251 $[M+H]^+$ Step 2: Synthesis of(S)-1-(2-methoxyethoxy)-3-(4-(4,4,5,5-tetramethyl-1,3,2-dioxaborolan-2-yl)-1H-pyrazol-1-yl)propan-2-ol To a mixture of (S)-1-(oxiran-2-ylmethyl)-4-(4,4,5,5-tetramethyl-1,3,2-dioxaborolan-2-yl)-1H-pyrazole (1.1 g, 4.39 mmol), 2-methoxyethan-1-ol (668 mg, 8.78 mmol) in DMF (25 mL) was added NaH (60%, 349 mg, 8.78 mmol) and the reaction mixture stirred at 60° C. for 2 h. The reaction was quenched with water (10 mL) then the mixture evaporated under reduced pressure. The residue was purified on silica gel column with 5% MeOH in DCM to afford title compound (800 mg, 55.9%) as a yellow oil. LCMS: m/z=327 $[M+H]^+$.

Intermediate 69 methyl (R)-5-(1-(2-hydroxy-3-(2-methoxyethoxy)propyl)-3-methyl-1H-pyrazol-4-yl)pyrazolo[1,5-a]pyridine-3-carboxylate and methyl (R)-5-(1-(2-hydroxy-3-(2-methoxyethoxy)propyl)-5-methyl-1H-pyrazol-4-yl)pyrazolo[1,5-a]pyridine-3-carboxylate and methyl (S)-5-(1-(2-hydroxy-3-(2-methoxyethoxy)propyl)-3-methyl-1H-pyrazol-4-yl)pyrazolo[1,5-a]pyridine-3-carboxylate and methyl (S)-5-(1-(2-hydroxy-3-(2-methoxyethoxy)propyl)-5-methyl-1H-pyrazol-4-yl)pyrazolo[1,5-a]pyridine-3-carboxylate

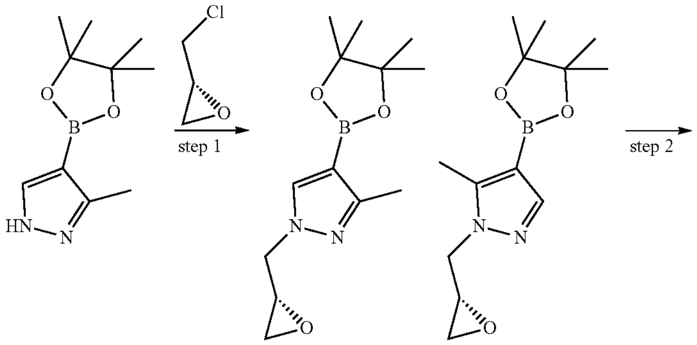

-continued

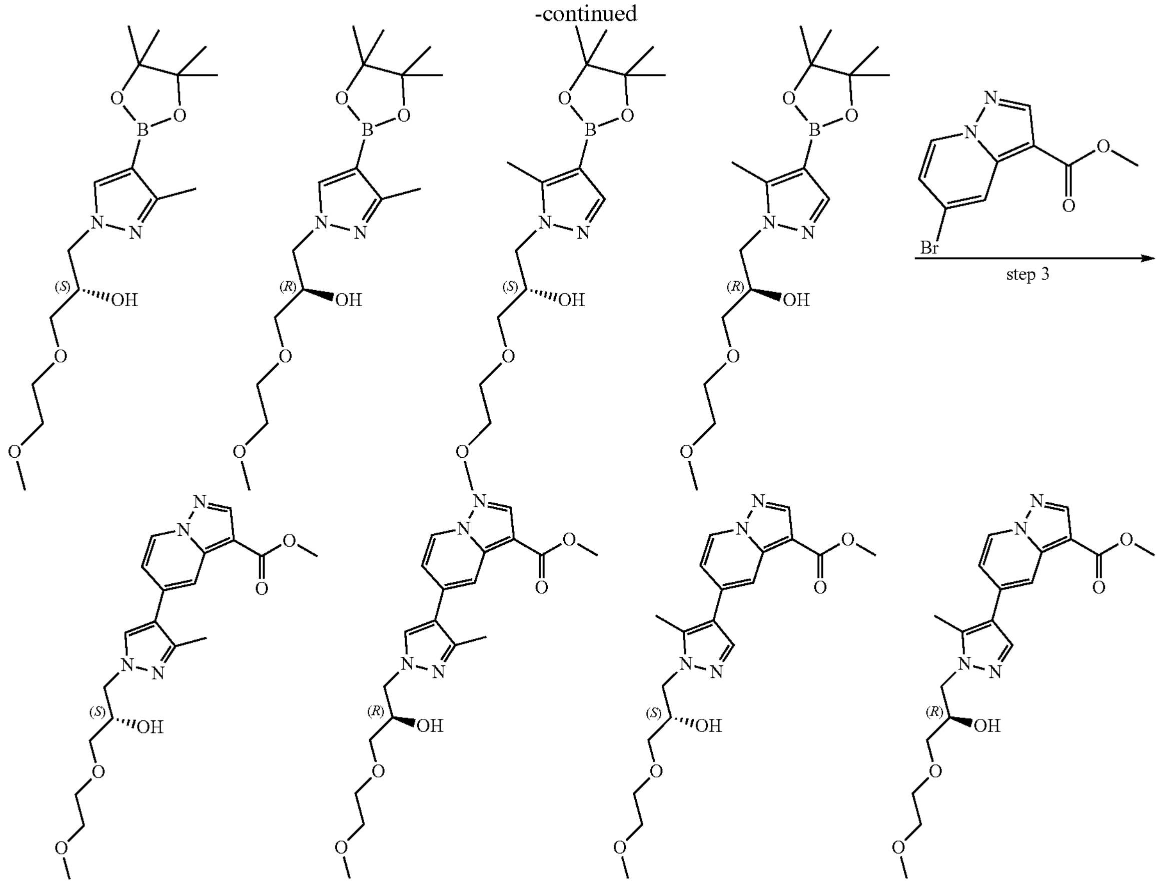

Steps 1 and 2: Synthesis of (S)-1-(2-methoxyethoxy)-3-(3-methyl-4-(4,4,5,5-tetramethyl-1,3,2-dioxaborolan-2-yl)-1H-pyrazol-1-yl)propan-2-ol, (R)-1-(2-methoxyethoxy)-3-(3-methyl-4-(4,4,5,5-tetramethyl-1,3,2-dioxaborolan-2-yl)-1H-pyrazol-1-yl)propan-2-ol, (S)-1-(2-methoxyethoxy)-3-(5-methyl-4-(4,4,5,5-tetramethyl-1,3,2-dioxaborolan-2-yl)-1H-pyrazol-1-yl)propan-2-ol and (R)-1-(2-methoxyethoxy)-3-(5-methyl-4-(4,4,5,5-tetramethyl-1,3,2-dioxaborolan-2-yl)-1H-pyrazol-1-yl)propan-2-ol The title compounds were obtained from 3-methyl-4-(4,4,5,5-tetramethyl-1,3,2-dioxaborolan-2-yl)-1H-pyrazole and (2R)-2-(chloromethyl)oxirane, following the 2 step procedure described in Intermediate 68. LCMS m/z=341 $[M+H]^+$ Step 3: Synthesis of methyl (S)-5-(1-(2-hydroxy-3-(2-methoxyethoxy)propyl)-3-methyl-1H-pyrazol-4-yl)pyrazolo[1,5-a]pyridine-3-carboxylate, methyl (R)-5-(1-(2-hydroxy-3-(2-methoxyethoxy)propyl)-3-methyl-1H-pyrazol-4-yl)pyrazolo[1,5-a]pyridine-3-carboxylate, methyl (S)-5-(1-(2-hydroxy-3-(2-methoxyethoxy)propyl)-5-methyl-1H-pyrazol-4-yl) pyrazolo[1,5-a]pyridine-3-carboxylate and methyl (R)-5-(1-(2-hydroxy-3-(2-methoxyethoxy)propyl)-5-methyl-1H-pyrazol-4-yl)pyrazolo[1,5-a]pyridine-3-carboxylate A mixture of the compound mixture of step 2 (100 mg, 306 μmol), methyl 5-bromopyrazolo[1,5-a]pyridine-3-carboxylate (78.0 mg, 306 μmol), $Pd(dppf)Cl_2$ (15 mg, 18.3 μmol) and $Cs_2CO_3$ (199 mg, 612 μmol) in dioxane (8 mL) and $H_2O$ (2 mL) was stirred at 100° C. for 3 h. The reaction was evaporated under reduced pressure and the residue was purified by prep-TLC with DCM:MeOH=20:1 to afford the mixture of title compounds (70 mg, 61.4%). LCMS m/z=389 $[M+H]^+$.

Intermediate 70 methyl 6-(1-(2-hydroxy-2-methylpropyl)-3-methyl-1H-pyrazol-4-yl)pyrazolo[1,5-a]pyridine-3-carboxylate and methyl 6-(1-(2-hydroxy-2-methylpropyl)-5-methyl-1H-pyrazol-4-yl)pyrazolo[1,5-a]pyridine-3-carboxylate

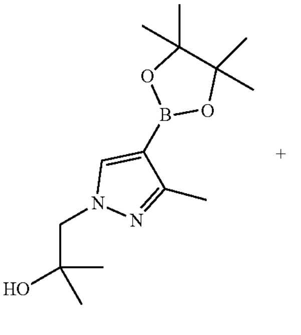

-continued

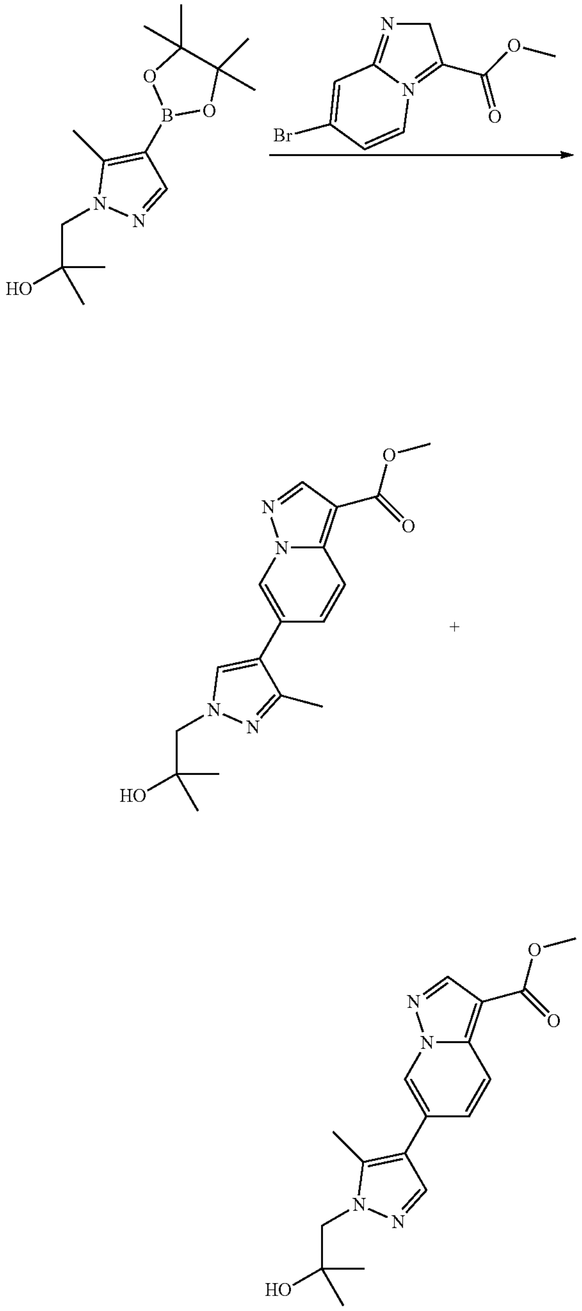

Into a 20-mL pressure tank reactor purged and maintained under $N_2$, was placed Intermediate 50 (280 mg, 1 mmol), methyl 6-bromopyrazolo[1,5-a]pyridine-3-carboxylate (254 mg, 1 mmol), $K_2CO_3$ (276 mg, 2 mmol) and Pd(dppf)$Cl_2$ (75 mg, 0.1 mmol) in dioxane (4 mL) and $H_2O$ (1 mL) and the reaction mixture was stirred for 1 h at 80° C. under $N_2$. The reaction was quenched with water/ice (10 mL) and the solids were filtered off. The resulting solution was extracted with EtOAc (3×10 mL) and the combined organic extracts concentrated under vacuum. The residue was purified by silica gel column (DCM/MeOH (20/1)) to give a mixture of the title compounds (150 mg, 45.7%) as a solid. LCMS: m/z=329 $[M+H]^+$.

Intermediate 71

Rac-2-chloro-5-(5-((1R,2S)-2-fluorocyclopropyl)-2H-tetrazol-2-yl)aniline

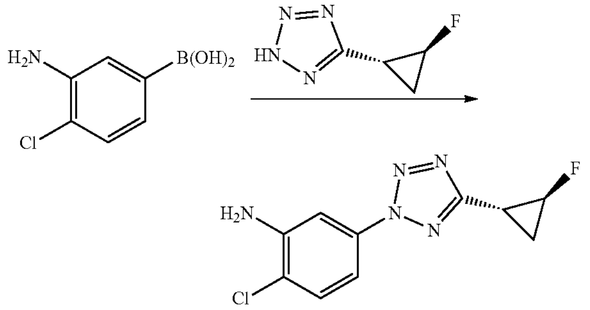

The title compound was obtained as a brown solid, 300 mg, 15%, from rac-5-((1R,2S)-2-fluorocyclopropyl)-2H-tetrazole and (3-amino-4-chlorophenyl)boronic acid, following the procedure described in Intermediate 16, step 1. LCMS: m/z=254 $[M+H]^+$.

Intermediate 72

4-fluoro-2-methyl-5-(4,4,5,5-tetramethyl-1,3,2-dioxaborolan-2-yl)aniline

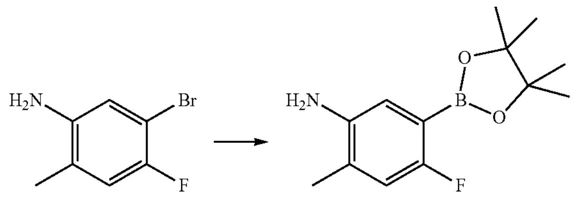

A mixture of 5-bromo-4-fluoro-2-methylaniline (200 mg, 0.98 mmol), $(BPin)_2$ (496 mg, 1.96 mmol), Pd(dppf)$Cl_2$ (71.8 mg, 0.098 mmol) and KOAc (96 mg, 0.98 mmol) in dioxane (5 mL) was stirred at 100° C. for 12 h under $N_2$. The mixture was diluted with EtOAc (30 mL) and water (30 mL), the layers separated and the aqueous phase extracted with EtOAc (3×15 mL). The combined organic phase was washed with brine, dried over $Na_2SO_4$ and concentrated under vacuum. The residue was purified by silica gel column with DCM:MeOH=5:1 to give the title compound (100 mg, 41%) as a yellow solid. LCMS: m/z=252 $[M+H]^+$.

Intermediate 73

2-chloro-5-(2-cyclopropyl-2H-tetrazol-5-yl)-4-fluoroaniline

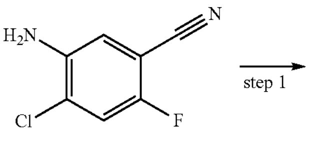

-continued

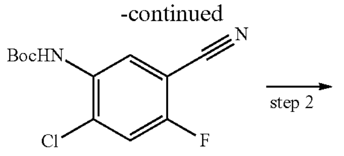

3

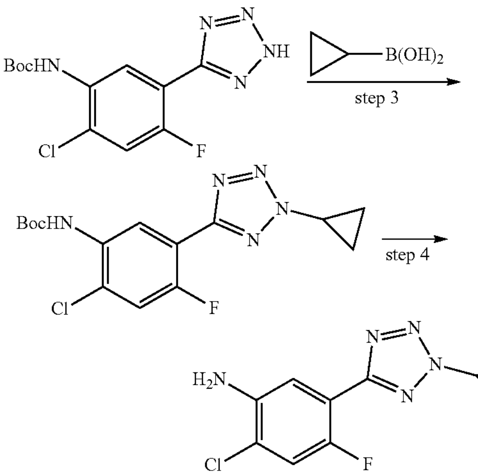

Step 1: tert-butyl(2-chloro-5-cyano-4-fluorophenyl) carbamate $(Boc)_2O$ (7.63 g, 35.0 mmol) was added to a solution of 5-amino-4-chloro-2-fluorobenzonitrile (3 g, 17.5 mmol), TEA (3.54 g, 35.0 mmol) and DMAP (427 mg, 3.50 mmol) in toluene (50 mL) at 0° C. under $N_2$ and the reaction mixture heated at 100° C. for 4 h. The mixture was extracted with EtOAc (3×50 mL), the combined organic layers were washed with saturated $NaHCO_3$ (2×50 mL), dried over anhydrous $Na_2SO_4$ and concentrated in vacuo. The solution was purified by silica gel column (PE:EtOAc, 100/0 to 0/100) to give the title compound (3 g, 63.4%) as a brown oil. LCMS: m/z=269 [M−H].

Step 2: Synthesis of tert-butyl(2-chloro-4-fluoro-5-(2H-tetrazol-5-yl)phenyl)carbamate To a mixture of tert-butyl N-(2-chloro-5-cyano-4-fluorophenyl) carbamate (2 g, 7.38 mmol) and $K_2CO_3$ (3.04 g, 22.0 mmol) in toluene (30 mL) were added $Bu_2SnO$ (2.3 g, 7.38 mmol) and $TMSN_3$ (1.7 g, 14.76 mmol) at rt under $N_2$ and the reaction mixture was heated at 100° C. overnight. The mixture was extracted with EtOAc (3×50 mL), the combined organic layers were washed with saturated aq. $NaHCO_3$ (2×50 mL), dried over anhydrous $Na_2SO_4$, and concentrated in vacuo. The mixture was purified by silica gel column (EtOAc/PE 0 to 100%) to give the title compound (2 g, 86.9%) as a yellow oil. LCMS: m/z=314 $[M+H]^+$.

Step 3: Synthesis of tert-butyl(2-chloro-5-(2-cyclopropyl-2H-tetrazol-5-yl)-4-fluorophenyl)carbamate The title compound was obtained, 1 g, 59.1%, from tert-butyl(2-chloro-4-fluoro-5-(2H-tetrazol-5-yl)phenyl)carbamate and cyclopropylboronic following the procedure described in Intermediate 16, step 1. LCMS: m/z=354 $[M+H]^+$.

Step 4: Synthesis of 2-chloro-5-(2-cyclopropyl-2H-tetrazol-5-yl)-4-fluoroaniline The title compound was obtained as a yellow oil, 450 mg, 63%, from tert-butyl(2-chloro-5-(2-cyclopropyl-2H-tetrazol-5-yl)-4-fluorophenyl)carbamate, following the procedure described in Intermediate 10, step 3. LCMS: m/z=254 $[M+H]^+$.

Intermediate 74

2-chloro-5-(2-ethyl-2H-tetrazol-5-yl)aniline

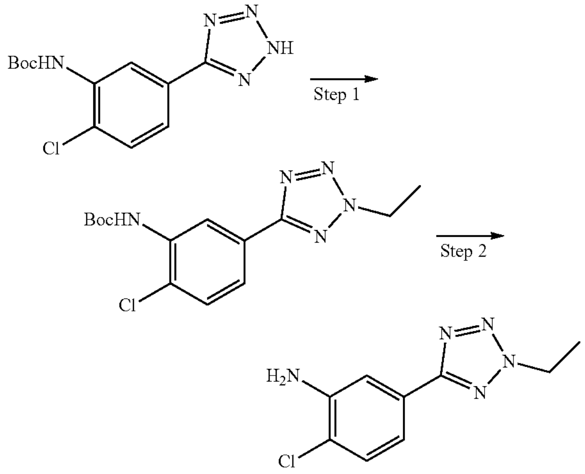

Step 1: Synthesis of tert-butyl(2-chloro-5-(2-ethyl-2H-tetrazol-5-yl)phenyl)carbamate A mixture of tert-butyl(2-chloro-5-(2H-tetrazol-5-yl)phenyl)carbamate (5 g, 16.9 mmol), $Cs_2CO_3$ (11.0 g, 33.8 mmol) and iodoethane (5.27 g, 33.8 mmol) in MeCN (150 mL) was stirred at 80° C. for 3 h. The cooled reaction was concentrated to dryness and the residue was purified on silica gel column with 40% EtOAc in PE to afford the title compound (3 g, 54.8%) as an off-white solid. LCMS: m/z=324 $[M+H]^+$.

Step 2: Synthesis of 2-chloro-5-(2-ethyl-2H-tetrazol-5-yl)aniline

The title compound was obtained as an off-white solid, 1.6 g, 86%, from tert-butyl(2-chloro-5-(2-ethyl-2H-tetrazol-5-yl)phenyl)carbamate, following the procedure described in Intermediate 10, step 3. LCMS m/z=224 $[M+H]^+$ Intermediate 75

2-chloro-5-(2-ethyl-2H-tetrazol-5-yl)-4-fluoroaniline

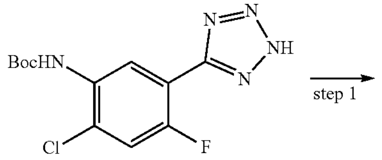

-continued

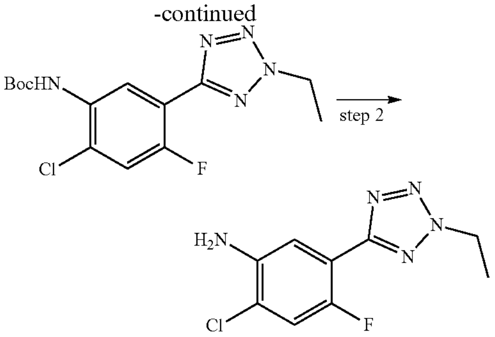

Step 1: Synthesis of tert-butyl(2-chloro-5-(2-ethyl-2H-tetrazol-5-yl)-4-fluorophenyl)carbamate A mixture of Intermediate 73, step 2 (2.06 g, 6.88 mmol), iodoethane (1.60 g, 10.3 mmol) and $K_2CO_3$ (1.13 g, 8.25 mmol) in DMF (20 mL) was stirred at rt for 16 h under $N_2$. The reaction mixture was diluted with EtOAc (120 mL) and washed with water (60 mL). The organic phase was concentrated in vacuo and the residue was purified by silica gel column (DCM:MeOH=100:1) to give the title compound (1.38 g) as an off-white solid. LCMS: m/z=342 $[M+H]^+$.

Step 2: Synthesis of 2-chloro-5-(2-ethyl-2H-tetrazol-5-yl)-4-fluoroaniline

The title compound was obtained as a white solid, 1.12 g, from tert-butyl(2-chloro-5-(2-ethyl-2H-tetrazol-5-yl)-4-fluorophenyl)carbamate, following the procedure described in Intermediate 10, step 3. LCMS: m/z=242 $[M+H]^+$.

Intermediate 76

5-bromo-N-(5-(2-cyclopropyl-2H-tetrazol-5-yl)-4-fluoro-2-methylphenyl)-6-fluoropyrazolo[1,5-a]pyridine-3-carboxamide

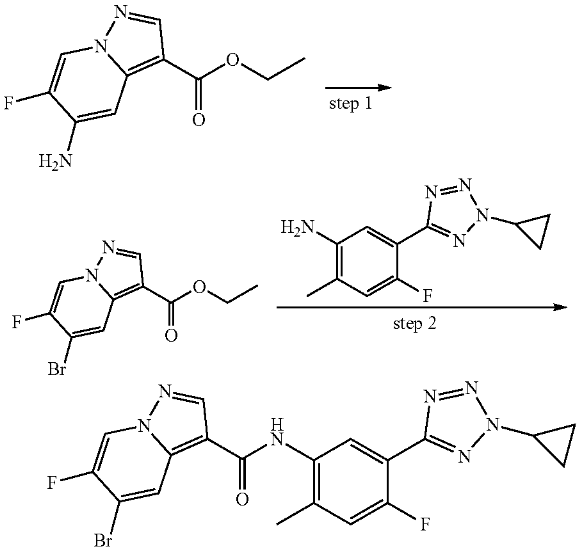

Step 1: Synthesis of ethyl 5-bromo-6-fluoropyrazolo[1,5-a]pyridine-3-carboxylate A solution of $NaNO_2$ (4.16 g, 60.4 mmol) in water (67 mL) was added dropwise to a solution of Example 171, step 3 (9 g, 40.3 mmol) in concentrated HBr (45 mL) at 0° C. After 10 min, a solution of CuBr (11.5 g, 80.6 mmol) in concentrated HBr (45 mL) was added and the reaction mixture heated at 50° C. for 15 min until gas evolution ceased. The reaction mixture was diluted with water (300 mL) and extracted with EtOAc (2×400 mL). The combined organic extracts were dried ($Na_2SO_4$) and the solvent was concentrated in vacuo. The crude product was purified by a silica gel column (PE:EtOAc=3:1), to afford the title compound (3 g, 26%) as a yellow solid. LCMS: m/z=287 $[M+H]^+$.

Step 2: Synthesis of 5-bromo-N-(5-(2-cyclopropyl-2H-tetrazol-5-yl)-4-fluoro-2-methylphenyl)-6-fluoropyrazolo[1,5-a]pyridine-3-carboxamide The title compound was obtained as a solid, 600 mg, 72.7%, from ethyl 5-bromo-6-fluoropyrazolo[1,5-a]pyridine-3-carboxylate and Intermediate 49, following the method described in Example 45, step 3. LCMS: m/z=474 $[M+H]^+$.

Intermediate 77

5-bromo-N-(5-(2-ethyl-2H-tetrazol-5-yl)-4-fluoro-2-methylphenyl)pyrazolo[1,5-a]pyridine-3-carboxamide

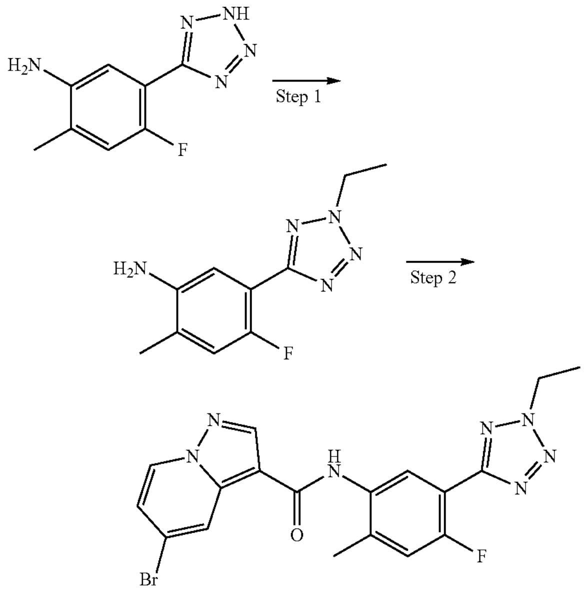

Step 1: Synthesis of 5-(2-ethyl-2H-tetrazol-5-yl)-4-fluoro-2-methylaniline

The title compound was obtained, 410 mg, 89%, from Intermediate 7, step 1 and ethyl iodide, following the procedure described in Intermediate 29, step 3. LCMS: m/z=222 [M+1].

Step 2: Synthesis of 5-bromo-N-(5-(2-ethyl-2H-tetrazol-5-yl)-4-fluoro-2-methylphenyl) pyrazolo[1,5-a]pyridine-3-carboxamide The title compound was obtained, 230 mg, 57%, from 5-(2-ethyl-2H-1,2,3,4-tetrazol-5-yl)-4-fluoro-2-methylaniline and methyl 5-bromopyrazolo[1,5-a]pyridine-3-carboxylate, following the procedure described in Example 207, step 2. LCMS: m/z=444 $[M+H]^+$.

Example 1

N-(2-methyl-5-(2-(4,4,4-trifluorobutyl)-2H-tetrazol-5-yl)phenyl)pyrazolo[1,5-a]pyridine-3-carboxamide

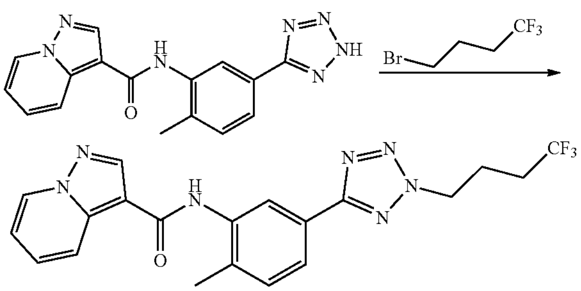

To a solution of Intermediate 1 (45 mg, 0.14 mmol) and $K_2CO_3$ (29 mg, 0.21 mmol) in DMF (0.5 mL), was added 4-bromo-1,1,1-trifluorobutane (32 mg, 0.17 mmol) and the reaction mixture stirred at 90° C. for 1 h. The mixture was partitioned between water and 5% MeOH/DCM, the layers separated and the organic phase dried over $Na_2SO_4$ and concentrated in vacuo. The crude product was purified by reverse phase ISCO (5 to 100% MeCN/water containing 0.1% TFA). The product containing fractions were concentrated in vacuo, and the residue triturated with aq. $NaHCO_3$. The mixture was filtered and the resulting solid dried under vacuum to give the title compound as an off-white solid, 27.7 mg, 45.8%. LCMS m/z=430 $[M+H]^+$; 1H NMR (500 MHz, DMSO-$d_6$) δ 9.73 (s, 1H), 8.86 (d, 1H), 8.79 (s, 1H), 8.25 (d, 1H), 8.17 (d, 1H), 7.85 (dd, 1H), 7.54 (dd, 1H), 7.48 (d, 1H), 7.13 (t, 1H), 4.84 (t, 2H), 2.48-2.34 (m, 5H), 2.23 (p, 2H)

Example 2

N-(2-methyl-5-(2-methyl-2H-tetrazol-5-yl)phenyl) pyrazolo[1,5-a]pyridine-3-carboxamide (X)

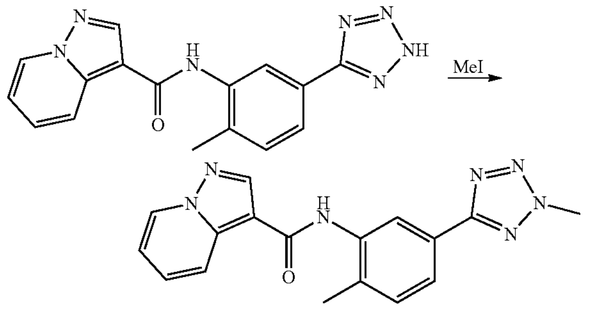

To a solution of Intermediate 1 (50 mg, 0.16 mmol) and $K_2CO_3$ (64.9 mg, 0.47 mmol) in DMF (1 mL), was added iodomethane (66.7 mg, 0.47 mmol) and the reaction mixture was stirred at 90° C. overnight. The reaction was quenched with $NH_4Cl$ aq. and extracted with EtOAc. The combined organic extracts were evaporated under reduced pressure. The residue was purified by reverse phase HPLC (water/0.1% TFA/MeCN/0.1% TFA) to give the title compound (8.9 mg, 17%). LCMS m/z=334 $[M+H]^+$; 1H NMR (500 MHz, DMSO-$d_6$) δ 9.63 (s, 1H), 8.78 (d, 1H), 8.71 (d, 1H), 8.10 (s, 1H), 7.76 (d, 1H), 7.46 (t, 1H), 7.40 (d, 1H), 7.05 (t, 1H), 4.36 (d, 3H), 2.29 (s, 3H).

Examples 3 to 21

The compounds in the following table were prepared using an analogous method to that described in Example 2 from Intermediate 1, Intermediate 2 and Intermediate 3 and the appropriate alkylating agent and the purification conditions listed in the table below.

| Compound No | Name, Starting Materials (SM), Purification, Yield | Data |
|---|---|---|
| 3 | N-(2-methyl-5-(2-((tetrahydro-2H-pyran-4-yl)methyl)-2H-tetrazol-5-yl)phenyl)pyrazolo[1,5-a]pyridine-3-carboxamide<br>SM: Intermediate 1 and 4-(bromomethyl)oxane<br>Prep-HPLC: Method-A, gradient 29% to 53%<br>13.7 mg, 35% as a white solid. | LCMS: m/z = 418 $[M + H]^+$, 1H NMR (300 MHz, DMSO-$d_6$) δ 9.74 (s, 1H), 8.86 (d, 1H), 8.80 (s, 1H), 8.25 (d, 1H), 8.16 (s, 1H), 7.85 (d, 1H), 7.60-7.44 (m, 2H), 7.14 (t, 1H), 4.68 (d, 2H), 3.85 (d, 2H), 2.37 (s, 3H), 2.28 (s, 2H), 1.48 (d, 2H), 1.40-1.29 (m, 1H). |
| 4 | N-(2-methyl-5-(2-(spiro[3.3]heptan-2-yl)-2H-tetrazol-5-yl)phenyl)pyrazolo[1,5-a]pyridine-3-carboxamide<br>SM: Intermediate 1 and spiro[3.3]heptan-2-yl methanesulfonate<br>Prep-HPLC: Method C, gradient 45% to 70% organic<br>42.3 mg, 33% as a white solid | LCMS: m/z = 414 $[M + H]^+$, 1H NMR (400 MHz, DMSO-$d_6$) δ 9.75 (s, 1H), 8.86 (dt, 1H), 8.79 (s, 1H), 8.24 (dt, 1H), 8.13 (d, 1H), 7.85 (dd, 1H), 7.58-7.49 (m, 1H), 7.47 (d, 1H), 7.13 (td, 1H), 5.39 (p, 1H), 2.77-2.59 (m, 4H), 2.35 (s, 3H), 2.16 (t, 2H), 2.05 (t, 2H), 1.91-1.79 (m, 2H). |
| 5 | N-(5-(2-(3,3-difluorocyclobutyl)-2H-tetrazol-5-yl)-2-methylphenyl)pyrazolo[1,5- | LCMS: m/z = 410 $[M + H]^+$, 1H NMR (500 MHz, DMSO-$d_6$) δ 9.75 (s, 1H), 8.86 (d, 1H), 8.79 (d, 1H), 8.25 (d, |

-continued

| Compound No | Name, Starting Materials (SM), Purification, Yield | Data |
|---|---|---|
| | a]pyridine-3-carboxamide SM: Intermediate 1 and 3,3-difluorocyclobutyl 4-methylbenzenesulfonate 27.5 mg, 35.7% yield as an off-white solid | 1H), 8.18 (s, 1H), 7.88 (dd, 1H), 7.58-7.46 (m, 2H), 7.13 (t, 1H), 5.61 (h, 1H), 3.52-3.36 (m, 4H), 2.37 (s, 3H). |
| 6 | N-(5-(2-((2,2-difluorocyclopropyl)methyl)-2H-tetrazol-5-yl)-2-methylphenyl)pyrazolo[1,5-a]pyridine-3-carboxamide SM: Intermediate 1 and 2-(bromomethyl)-1,1-difluorocyclopropane Prep-HPLC: Method-A, gradient 36% to 57% white solid, 34.6 mg, 34% | LCMS: m/z = 410 $[M + H]^+$. 1H NMR (300 MHz, DMSO-$d_6$) δ 9.74 (s, 1H), 8.86 (dt, 1H), 8.79 (s, 1H), 8.25 (dt, 1H), 8.17 (d, 1H), 7.86 (dd, 1H), 7.59-7.45 (m, 2H), 7.13 (td, 1H), 4.97-4.89 (m, 1H), 4.94-4.81 (m, 1H), 2.58-2.40 (m, 1H), 2.37 (s, 3H), 1.84 (tdd, 1H), 1.67 (dtd, 1H). |
| 7 | N-(5-(2-(cyclopropylmethyl)-2H-tetrazol-5-yl)-2-methylphenyl)pyrazolo[1,5-a]pyridine-3-carboxamide SM: Intermediate 1 and (bromomethyl)cyclopropane Reverse phase HPLC 17 mg, 29.1% | LCMS m/z = 374 $[M + H]^+$; 1H NMR (500 MHz, DMSO-$d_6$) δ 9.66 (s, 1H), 8.78 (d, 1H), 8.72 (d, 1H), 8.18 (d, 1H), 8.09 (d, 1H), 7.78 (dt, 1H), 7.49-7.38 (m, 2H), 7.09-7.02 (m, 1H), 4.55 (dd, 2H), 2.29 (s, 3H), 1.36 (ddt, 1H), 0.56 (qt, 2H), 0.48-0.40 (m, 2H). |
| 9 | N-(5-(2-cyclobutyl-2H-tetrazol-5-yl)-2-methylphenyl)pyrazolo[1,5-a]pyridine-3-carboxamide SM: Intermediate 1 and bromocyclobutane HPLC Method-E, 50% to 60% organic gradient 31.8 mg; 27% as a white solid. | LCMS: m/z = 374 $[M + H]^+$, $^1H$ NMR (400 MHz, DMSO-$d_6$) δ 9.75 (s, 1H), 8.86 (dt, 1H), 8.79 (s, 1H), 8.25 (dt, 1H), 8.16 (d, 1H), 7.86 (dd, 1H), 7.53 (ddd, 1H), 7.47 (d, 1H), 7.13 (td, 1H), 5.52 (p, 1H), 2.76-2.54 (m, 4H), 2.36 (s, 3H), 2.02-1.89 (m, 2H). |
| 9 | N-(5-(2-((6-oxaspiro[3.4]octan-7-yl)methyl)-2H-tetrazol-5-yl)-2-methylphenyl)pyrazolo[1,5-a]pyridine-3-carboxamide SM: Intermediate 1 and 7-(iodomethyl)-6-oxaspiro[3.4]octane 8.32 mg, 9.4% | LCMS m/z = 444 $[M + H]^+$ |
| 10 | N-(5-(2-((5-oxaspiro[2.4]heptan-6-yl)methyl)-2H-tetrazol-5-yl)-2-methylphenyl)pyrazolo[1,5-a]pyridine-3-carboxamide SM: Intermediate 1 and 6-(iodomethyl)-5-oxaspiro[2.4]heptane 5.88 mg, 6.8% | LCMS m/z = 430 $[M + H]^+$ |
| 11 | N-(5-(2-(2-isopropoxyethyl)-2H-tetrazol-5-yl)-2-methylphenyl)pyrazolo[1,5-a]pyridine-3-carboxamide SM: Intermediate 1 and 2-isopropoxyethanol 23.5 mg, 10% | LCMS m/z = 406 $[M + H]^+$ |
| 12 | N-(5-(2-(2-cyclobutoxyethyl)-2H-tetrazol-5-yl)-2-methylphenyl)pyrazolo[1,5-a]pyridine-3-carboxamide SM: Intermediate 1 and 2-bromoethoxycyclobutane 10.3 mg, 12.3% | LCMS m/z = 418 $[M + H]^+$ |
| 13 | N-(5-(2-(2-fluorobenzyl)-2H-tetrazol-5-yl)-2-methylphenyl)pyrazolo[1,5-a]pyridine-3-carboxamide SM: Intermediate 1 and 1-(bromomethyl)-2-fluorobenzene HPLC Method-E, 46% to 66% organic gradient white solid, 30 mg, 28% yield | LCMS: m/z = 428 $[M + H]^+$, $^1H$ NMR (300 MHz, DMSO-$d_6$) δ 9.74 (s, 1H), 8.86 (dt, 1H), 8.78 (s, 1H), 8.24 (dt, 1H), 8.12 (d, 1H), 7.82 (dd, 1H), 7.59 -7.42 (m, 4H), 7.37-7.22 (m, 2H), 7.13 (td, 1H), 6.06 (s, 2H), 2.35 (s, 3H). |
| 14 | N-(5-(2-ethyl-2H-tetrazol-5-yl)-2-methylphenyl)pyrazolo[1,5-a]pyridine-3-carboxamide SM; Intermediate 1 and Iodoethane White solid, 23 mg, 42% | LCMS m/z = 348 $[M + H]^+$; 1H NMR (500 MHz, $CDCl_3$) δ 8.60 (d, 1H), 8.52 (d, 1H), 8.36 (d, 1H), 8.29 (s, 1H), 7.89 (d, 1H), 7.64 (s, 1H), 7.39 (dd, 1H), 7.33 (d, 1H), 6.96 (t, 1H), 4.68 (q, 2H), 1.67 (t, 3H) |

-continued

| Compound No | Name, Starting Materials (SM), Purification, Yield | Data |
|---|---|---|
| 15 | N-(2-chloro-5-(2-(cyclopropylmethyl)-2H-tetrazol-5-yl)phenyl)pyrazolo[1,5-a]pyridine-3-carboxamide<br>SM: Intermediate 2 and (bromomethyl)cyclopropane<br>Reverse phase HPLC<br>24.6 mg, 38.6% yield | LCMS m/z = 394 $[M + H]^+$; 1H NMR (500 MHz, DMSO-$d_6$) δ 9.82 (d, 1H), 8.80 (d, 1H), 8.75 (d, 1H), 8.35 (d, 1H), 8.18 (d, 1H), 7.87 (dd, 1H), 7.69 (dd, 1H), 7.49 (t, 1H), 7.08 (t, 1H), 4.58 (dd, 2H), 1.37 (ddt, 1H), 0.56 (d, 2H), 0.44 (d, 2H). |
| 16 | N-(2-chloro-5-(2-((2,2-difluorocyclopropyl)methyl)-2H-tetrazol-5-yl)phenyl)pyrazolo[1,5-a]pyridine-3-carboxamide<br>SM: Intermediate 2 and 2-(bromomethyl)-1,1-difluorocyclopropane<br>23 mg, 33% | LCMS m/z = 430 $[M + H]^+$; 1H NMR (500 MHz, MeOD-$d_4$) δ 8.60 (d, 1H), 8.58-8.51 (m, 2H), 8.22 (d, 1H), 7.90 (dd, 1H), 7.59 (dd, 1H), 7.45 (t, 1H), 7.03 (t, 1H), 4.82 (dd, 2H), 2.33 (tt, 1H), 1.63 (tq, 1H), 1.51-1.40 (m, 1H) |
| 17 | N-(2-chloro-5-(2-(3,3-difluorocyclobutyl)-2H-tetrazol-5-yl)phenyl)pyrazolo[1,5-a]pyridine-3-carboxamide<br>SM: Intermediate 2 and 3,3-difluorocyclobutyl 4-methylbenzenesufonate<br>Reverse phase HPLC<br>31.3 mg, 30.9%, as a tan colored solid | LCMS m/z = 430 $[M + H]^+$; 1H NMR (500 MHz, DMSO-$d_6$) δ 9.91 (s, 1H), 8.87 (d, 1H), 8.83 (s, 1H), 8.43 (s, 1H), 8.25 (d, 1H), 7.96 (d, 1H), 7.78 (d, 1H), 7.57 (t, 1H), 7.16 (t, 1H), 5.68-5.57 (m, 1H), 3.53-3.34 (m, 4H). |
| 18 | N-(5-(2-((2-oxabicyclo[2.1.1]hexan-4-yl)methyl)-2H-tetrazol-5-yl)-2-chlorophenyl)pyrazolo[1,5-a]pyridine-3-carboxamide<br>SM: Intermediate 2 and 4-(bromomethyl)-2-oxabicyclo[2.1.1 ]hexane | LCMS m/z = 436 $[M + H]^+$; 1H NMR (500 MHz, DMSO-$d_6$) δ 9.83 (d, 1H), 8.77 (dd, 2H), 8.34 (d, 1H), 8.18 (d, 1H), 7.90-7.83 (m, 1H), 7.70 (dd, 1H), 7.49 (t, 1H), 7.08 (t, 1H), 5.13 (d, 2H), 4.41 (s, 1H), 3.50 (d, 2H), 1.69 (d, 2H), 1.43 (d, 2H) |
| 19 | N-(2-chloro-5-(2-((3,3-difluorocyclobutyl)methyl)-2H-tetrazol-5-yl)phenyl)pyrazolo[1,5-a]pyridine-3-carboxamide<br>SM: Intermediate 2 and 3-(bromomethyl)-1,1-difluorocyclobutane | LCMS m/z = 444 $[M + H]^+$; 1H NMR (500 MHz, DMSO-$d_6$) δ 9.82 (s, 1H), 8.80 (d, 1H), 8.75 (d, 1H), 8.34 (d, 1H), 8.18 (d, 1H), 7.89-7.80 (m, 1H), 7.70 (dd, 1H), 7.49 (t, 1H), 7.08 (t, 1H), 4.86 (d, 2H), 2.83-2.63 (m, 3H), 2.51 (ddd, 2H). |
| 20 | N-(5-(2-((2-oxabicyclo[2.1.1]hexan-4-yl)methyl)-2H-tetrazol-5-yl)-2,4-dimethylphenyl)pyrazolo[1,5-a]pyridine-3-carboxamide<br>SM: Intermediate 3 and 4-(bromomethyl)-2-oxabicyclo[2.1.1]hexane<br>53 mg, 43.7% yield. | LCMS m/z = 430 $[M + H]^+$; 1H NMR (500 MHz, DMSO-$d_6$) δ 9.63 (s, 1H), 8.76 (d, 1H), 8.69 (d, 1H), 8.16 (d, 1H), 7.91 (d, 1H), 7.48-7.41 (m, 1H), 7.24 (s, 1H), 7.07-7.01 (m, 1H), 5.12 (d, 2H), 4.41 (s, 1H), 3.50 (d, 2H), 2.48 (d, 3H), 2.24 (d, 3H), 1.69 (d, 2H), 1.43 (dd, 2H). |
| 21 | N-(5-(2-((2,2-difluorocyclopropyl)methyl)-2H-tetrazol-5-yl)-2,4-dimethylphenyl)pyrazolo[1,5-a]pyridine-3-carboxamide<br>SM: Intermediate 3 and 2-(bromomethyl)-1,1-difluorocyclopropane<br>Reverse phase HPLC<br>32.3 mg, 50.9% yield | LCMS m/z = 424 $[M + H]^+$; 1H NMR (500 MHz, DMSO-$d_6$) δ 9.63 (s, 1H), 8.76 (d, 1H), 8.72-8.68 (m, 1H), 8.16 (d, 1H), 7.92 (d, 1H), 7.44 (t, 1H), 7.25 (s, 1H), 7.04 (t, 1H), 4.93-4.77 (m, 2H), 2.51 (d, 3H), 2.24 (d, 3H), 1.76 (dq, 1H), 1.60 (dp, 1H). One proton was buried in the solvent peak |

Example 22

N-(2-chloro-5-(2-(2-(2,2,2-trifluoroethoxy)ethyl)-2H-tetrazol-5-yl)phenyl)pyrazolo[1,5-a]pyridine-3-carboxamide

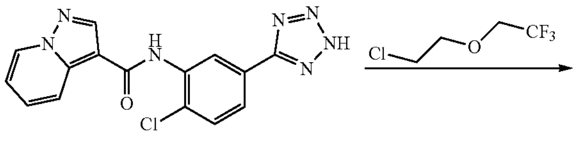

-continued

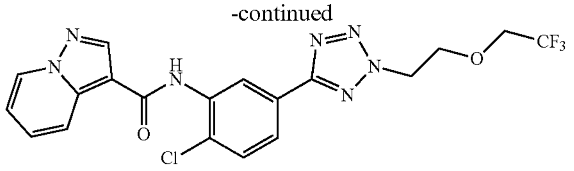

A mixture of Intermediate 2 (47 mg, 0.14 mmol), $K_2CO_3$ (29 mg, 0.21 mmol) and 2-(2-chloroethoxy)-1,1,1-trifluoroethane (27 mg, 0.17 mmol) in DMF (0.5 mL) was heated at 90° C. for 4 h. Further 2-(2-chloroethoxy)-1,1,1-trifluoroethane (27 mg, 0.17 mmol) was added, the reaction mixture heated at 90° C. for 90 min, then at rt for 3 days. The mixture was diluted with water, stirred for 1 h, then filtered and the solid dried under vacuum. This was re-crystallized from EtOH to provide the title compound as a light brown solid, 32 mg, 49.7%. LCMS m/z=466 $[M+H]^+$; 1H NMR (500 MHz, DMSO-$d_6$) δ 9.89 (s, 1H), 8.88 (d, 1H), 8.83 (s, 1H), 8.43 (d, 1H), 8.26 (d, 1H), 7.94 (dt, 1H), 7.78 (d, 1H), 7.57 (dd, 1H), 7.16 (t, 1H), 5.00 (t, 2H), 4.21 (t, 2H), 4.13 (q, 2H).

Example 23 and 24

N-(2-methyl-5-(2-((1s,3s)-3-(trifluoromethyl)cyclobutyl)-2H-tetrazol-5-yl)phenyl)pyrazolo[1,5-a]pyridine-3-carboxamide and N-(2-methyl-5-(2-((1r,3r)-3-(trifluoromethyl)cyclobutyl)-2H-tetrazol-5-yl)phenyl)pyrazolo[1,5-a]pyridine-3-carboxamide

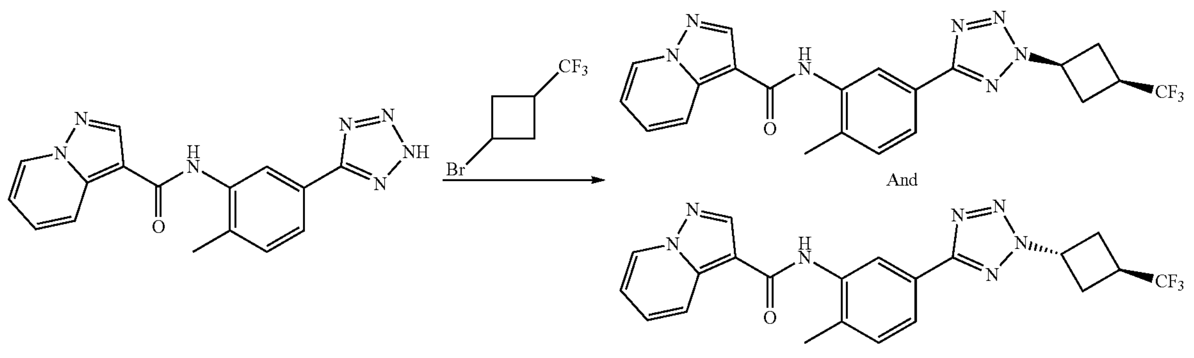

To a stirred solution of Intermediate 1 (200 mg, 0.63 mmol) in DMF (2 mL) was added $K_2CO_3$ (258 mg, 1.87 mmol) and 1-bromo-3-(trifluoromethyl)cyclobutane (253 mg, 1.25 mmol) at rt. The mixture was heated at 100° C. for 6 h, then cooled to rt and diluted with water (10 mL). The resulting solution was extracted with EtOAc (3×20 mL) and the combined organic phase washed with brine (3×10 mL). The organic layer was dried over $Na_2SO_4$ and concentrated in vacuo. The crude product was purified by silica gel column with PE:EtOAc=3:2 to initially afford Isomer 1 and Isomer 2 eluted second.

Isomer 1 was further purified by Prep-HPLC, Method B, 40% to 65% gradient, to give N-(2-methyl-5-(2-((1s,3s)-3-(trifluoromethyl)cyclobutyl)-2H-tetrazol-5-yl)phenyl)pyrazolo[1,5-a]pyridine-3-carboxamide or N-(2-methyl-5-(2-((1r,3r)-3-(trifluoromethyl)cyclobutyl)-2H-tetrazol-5-yl)phenyl)pyrazolo[1,5-a]pyridine-3-carboxamide (73.2 mg, yield: 26%) as a white solid. LCMS: m/z=442 $[M+H]^+$, 1H NMR (400 MHz, DMSO-$d_6$) δ 9.76 (s, 1H), 8.86 (dt, 1H), 8.79 (s, 1H), 8.24 (dt, 1H), 8.18 (d, 1H), 7.88 (dd, 1H), 7.58-7.45 (m, 2H), 7.13 (td, 1H), 5.64 (p, 1H), 3.49 (ddd, 1H), 3.03 (ddd, 2H), 2.87 (ddd, 2H), 2.36 (s, 3H).

Isomer 2 was further purified by Prep-HPLC, Method B, 40% to 65% gradient, to give N-(2-methyl-5-(2-((1r,3r)-3-(trifluoromethyl)cyclobutyl)-2H-tetrazol-5-yl)phenyl)pyrazolo[1,5-a]pyridine-3-carboxamide or N-(2-methyl-5-(2-((1s,3s)-3-(trifluoromethyl)cyclobutyl)-2H-tetrazol-5-yl)phenyl)pyrazolo[1,5-a]pyridine-3-carboxamide (63.9 mg; yield: 23%) as a white solid. LCMS: m/z=442 $[M+H]^+$, 1H NMR (400 MHz, DMSO-$d_6$) δ 9.76 (s, 1H), 8.85 (d, 1H), 8.78 (s, 1H), 8.24 (dd, 1H), 8.15 (d, 1H), 7.86 (dd, 1H), 7.57-7.49 (m, 1H), 7.48 (d, 1H), 7.12 (td, 1H), 5.57 (p, 1H), 3.25 (dd, 1H), 2.96-2.73 (m, 4H), 2.36 (s, 3H).

Example 25 and 26

(S)—N-(5-(2-((2,2-difluorocyclopropyl)methyl)-2H-tetrazol-5-yl)-2-methylphenyl)pyrazolo[1,5-a]pyridine-3-carboxamide and (R)—N-(5-(2-((2,2-difluorocyclopropyl)methyl)-2H-tetrazol-5-yl)-2-methylphenyl)pyrazolo[1,5-a]pyridine-3-carboxamide

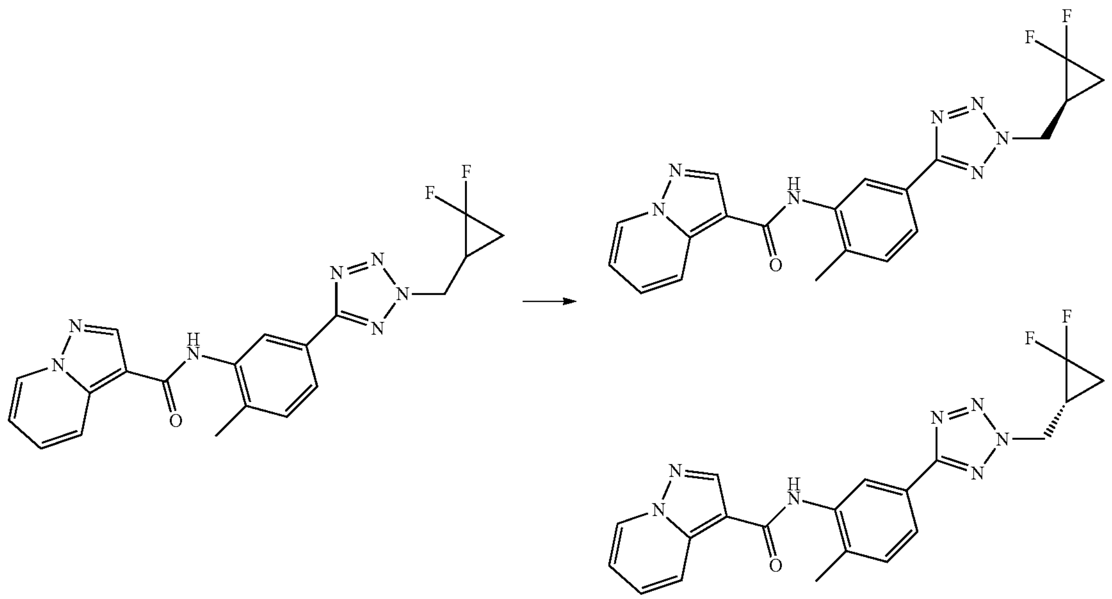 [SMILES: Cc1ccc(-c2nnn(CC3CC3(F)F)n2)cc1NC(=O)c1cnn2ccccc12 ; Cc1ccc(-c2nnn(C[C@@H]3CC3(F)F)n2)cc1NC(=O)c1cnn2ccccc12 ; Cc1ccc(-c2nnn(C[C@H]3CC3(F)F)n2)cc1NC(=O)c1cnn2ccccc12]

Example 6 (28 mg, 0.07 mmol) was purified by chiral-HPLC: Column: CHIRALPAK IF, 2*25 cm, 5 μm; Mobile Phase A: Hex (0.2% DEA), Mobile Phase B: MeOH: DCM=2:1; Flow rate: 20 mL/min; isocratic gradient: 35% B; to give Peak 1 (Isomer 1), (S)—N-(5-(2-((2,2-difluorocyclopropyl)methyl)-2H-tetrazol-5-yl)-2-methylphenyl)pyrazolo[1,5-a]pyridine-3-carboxamide or (R)—N-(5-(2-((2,2-difluorocyclopropyl)methyl)-2H-tetrazol-5-yl)-2-methylphenyl)pyrazolo[1,5-a]pyridine-3-carboxamide (7.3 mg, 26%) as a white solid. LCMS: m/z=410 $[M+H]^+$, 1H NMR (400 MHz, DMSO-$d_6$) δ 9.75 (s, 1H), 8.85 (dt, 1H), 8.79 (s, 1H), 8.24 (dt, 1H), 8.16 (d, 1H), 7.86 (dd, 1H), 7.53 (ddd, 1H), 7.48 (d, 1H), 7.13 (td, 1H), 4.99-4.83 (m, 2H), 2.36 (s, 3H), 1.90-1.76 (m, 1H), 1.73-1.60 (m, 1H).

and Peak 2 (Isomer 2), (R)—N-(5-(2-((2,2-difluorocyclopropyl)methyl)-2H-tetrazol-5-yl)-2-methylphenyl)pyrazolo[1,5-a]pyridine-3-carboxamide or (S)—N-(5-(2-((2,2-difluorocyclopropyl)methyl)-2H-tetrazol-5-yl)-2-methylphenyl)pyrazolo[1,5-a]pyridine-3-carboxamide (8.2 mg, 29%) as a white solid. LCMS: m/z=410 $[M+H]^+$, $^1H$ NMR (400 MHz, DMSO-$d_6$) δ 9.75 (s, 1H), 8.85 (dt, 1H), 8.79 (s, 1H), 8.24 (dt, 1H), 8.16 (d, 1H), 7.86 (dd, 1H), 7.53 (ddd, 1H), 7.48 (d, 1H), 7.13 (td, 1H), 4.99-4.83 (m, 2H), 2.36 (s, 3H), 1.90-1.76 (m, 1H), 1.73-1.62 (m, 1H).

Example 27

5-amino-N-(2-chloro-5-(2-((2,2-difluorocyclopropyl)methyl)-2H-tetrazol-5-yl)phenyl)pyrazolo[1,5-a]pyridine-3-carboxamide

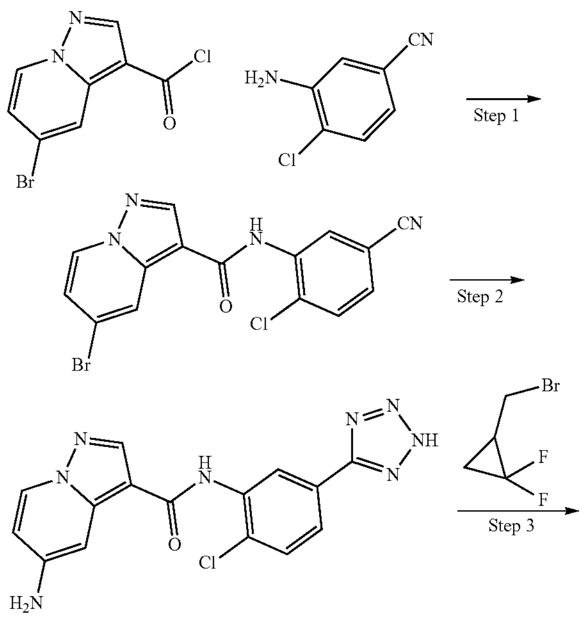

-continued

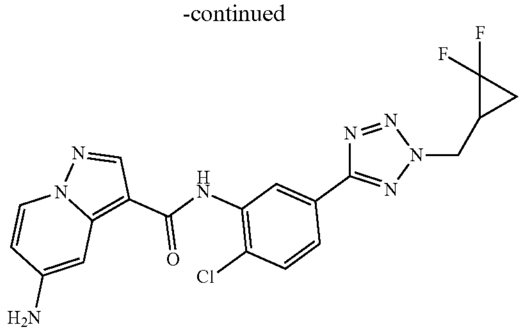

Step 1: Synthesis of 5-bromo-N-(2-chloro-5-cyano-phenyl)pyrazolo[1,5-a]pyridine-3-carboxamide To a solution of 3-amino-4-chlorobenzonitrile (250 mg, 1.64 mmol) in pyridine (8 mL) was added 5-bromopyrazolo[1,5-a]pyridine-3-carbonyl chloride (425 mg, 1.64 mmol) and the reaction mixture stirred for 30 mins. The reaction was quenched with water and the resulting solid filtered off and dried to give the title compound, 507 mg, 82%. LCMS m/z=377 $[M+H]^+$ Step 2: Synthesis of 5-amino-N-(2-chloro-5-(2H-tetrazol-5-yl)phenyl)pyrazolo[1,5-a]pyridine-3-carboxamide To a solution of 5-bromo-N-(2-chloro-5-cyanophenyl)pyrazolo[1,5-a]pyridine-3-carboxamide (589 mg, 1.57 mmol) and ammonium chloride (252 mg, 4.70 mmol) in DMF (7.84 mL), was added sodium azide (306 mg, 4.70 mmol) at rt. The mixture was heated at 150° C. under microwave irradiation for 1 h. The mixture was quenched with water and acidified with HCl until pH=2. The solid was filtered off and purified by reverse phase HPLC to give the title compound (35 mg, 6.29%). LCMS m/z=355 $[M+H]^+$ Step 3: Synthesis of 5-amino-N-(2-chloro-5-(2-((2,2-difluorocyclopropyl)methyl)-2H-tetrazol-5-yl)phenyl)pyrazolo[1,5-a]pyridine-3-carboxamide The title compound was obtained, 6.3 mg, 14.4% yield, from 5-amino-N-(2-chloro-5-(2H-tetrazol-5-yl)phenyl)pyrazolo[1,5-a]pyridine-3-carboxamide and 2-(bromomethyl)-1,1-difluorocyclopropane, following the procedure described in Example 2. LCMS m/z=445 [M+H]; 1H NMR (500 MHz, DMSO-$d_6$) δ 9.38 (s, 1H), 8.51 (q, 2H), 8.41 (dd, 1H), 7.88 (d, 1H), 7.74 (dd, 1H), 7.15 (d, 1H), 6.57-6.48 (m, 2H), 6.22 (s, 2H), 5.00-4.87 (m, 2H), 1.84 (dq, 1H), 1.67 (dt, 1H)

Example 28

N-(5-(2-cyclopropyl-2H-tetrazol-5-yl)-2-methylphenyl)pyrazolo[1,5-a]pyridine-3-carboxamide

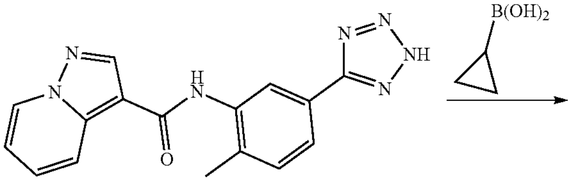

-continued

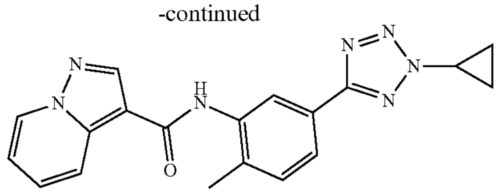

To a stirred solution of Intermediate 1 (100 mg, 0.31 mmol) in DCE (2 mL) were added $Cu(OAc)_2$ (56.8 mg, 0.31 mmol), $Na_2CO_3$ (66.3 mg, 0.63 mmol), 2,2'-dipyridine (48.8 mg, 0.31 mmol) and cyclopropylboronic acid (53.7 mg, 0.63 mmol) and the reaction was heated to 60° C. under $O_2$ and stirred for 12 h. The mixture was cooled to rt and filtered. The filter cake was washed with DCM (20 mL) and the filtrate was concentrated under vacuum. Water (20 mL) was added and the resulting solution was extracted with DCM (3×20 mL). The organic layer was dried over $Na_2SO_4$ and concentrated under vacuum. The crude product was purified by Prep-HPLC Method E, Gradient: 38% B to 55% B in 8 min, to give the title compound (29.4 mg, 26%) as a white solid. LCMS: m/z=360 $[M+H]^+$, 1H NMR (400 MHz, DMSO-$d_6$) δ 9.74 (s, 1H), 8.85 (dt, 1H), 8.78 (s, 1H), 8.24 (dt, 1H), 8.13 (d, 1H), 7.83 (dd, 1H), 7.53 (ddd, 1H), 7.46 (d, 1H), 7.13 (td, 1H), 4.47 (tt, 1H), 2.35 (s, 3H), 1.45-1.30 (m, 2H), 1.33-1.21 (m, 2H).

Example 29

N-(5-(2-cyclopropyl-2H-1,2,3-triazol-4-yl)-2-methylphenyl)pyrazolo[1,5-a]pyridine-3-carboxamide

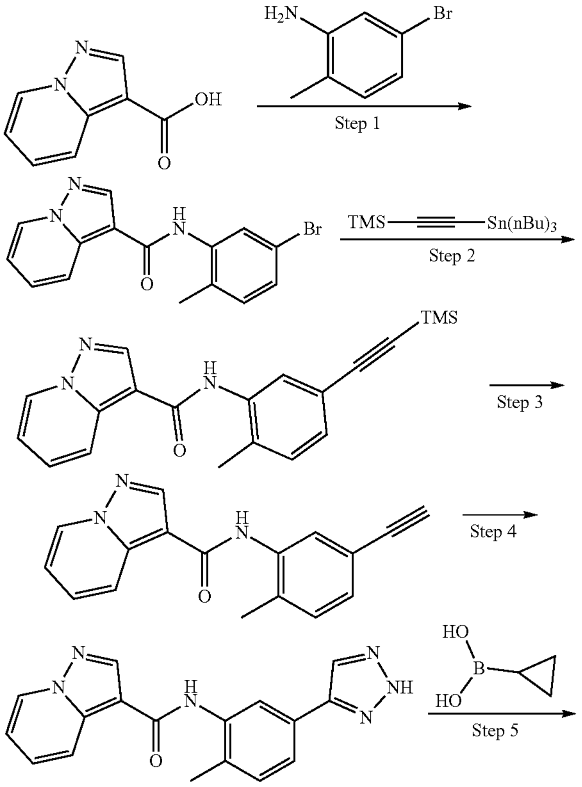

-continued

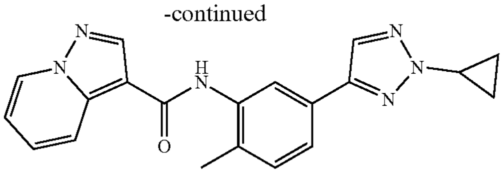

Step 1: Synthesis of N-(5-bromo-2-methylphenyl) pyrazolo[1,5-a]pyridine-3-carboxamide A mixture of pyrazolo[1,5-a]pyridine-3-carboxylic acid (500 mg, 3.08 mmol), 5-bromo-2-methylaniline (573 mg, 3.08 mmol), DMAP (564 mg, 4.62 mmol) and EDCI (885 mg, 4.62 mmol) in DMF (10 mL) was stirred at 50° C. for 3 h. The reaction mixture was concentrated to dryness. The residue was purified on silica gel column with 5% MeOH in DCM to give the title compound (300 mg, 29.7%) as a yellow solid. LCMS: m/z=330 $[M+H]^+$.

Step 2: Synthesis of N-(2-methyl-5-((trimethylsilyl) ethynyl)phenyl)pyrazolo[1,5-a]pyridine-3-carboxamide To a solution of N-(5-bromo-2-methylphenyl)pyrazolo[1,5-a]pyridine-3-carboxamide (300 mg, 0.91 mmol) and $Pd(PPh_3)_2Cl_2$ (64 mg, 0.91 mmol) in DMF (10 mL) was added trimethyl(2-(tributylstannyl)ethynyl)silane (1.05 g, 2.72 mmol) at 0° C. and the reaction mixture stirred at 100° C. for 2 h. The cooled mixture was concentrated to dryness and the residue purified by silica gel column with PE:EtOAc=3:1 to give the title compound (200 mg, 63.4%) as a yellow solid. LCMS: m/z=348 $[M+H]^+$.

Step 3: Synthesis of N-(5-ethynyl-2-methylphenyl) pyrazolo[1,5-a]pyridine-3-carboxamide A mixture of N-(2-methyl-5-((trimethylsilyl)ethynyl)phenyl)pyrazolo[1,5-a]pyridine-3-carboxamide (200 mg, 0.58 mmol) and TBAF (449 mg, 1.72 mmol) in THF (10 mL) was stirred at rt for 2 h. The reaction mixture was concentrated to dryness and the residue was purified on a silica gel column with 5% MeOH in DCM to give the title compound (120 mg, 75.9%) as a yellow solid. LCMS: m/z=276 $[M+H]^+$.

Step 4: Synthesis of N-(2-methyl-5-(2H-1,2,3-triazol-4-yl)phenyl)pyrazolo[1,5-a]pyridine-3-carboxamide To a stirred solution of N-(5-ethynyl-2-methylphenyl) pyrazolo[1,5-a]pyridine-3-carboxamide (120 mg, 0.44 mmol), $CuSO_4 \cdot 5H_2O$ (22 mg, 0.09 mmol) and sodium ascorbate (5 mg, 21 μmol) in t-BuOH/$H_2O$ (1.5 mL/1.5 mL) was added $TMSN_3$ (250 mg, 2.18 mmol) dropwise and the reaction mixture heated at 80° C. for 16 h. The mixture was cooled to rt, diluted with DCM/$H_2O$ (10 mL/2 mL), the phases were separated and the aqueous phase extracted with DCM (10 mL). The combined organic extracts were dried and concentrated. The residue was purified by reverse chromatography (MeCN/$H_2O$=30%) to give the title compound (70 mg, 50%) as a yellow oil. LCMS: m/z=319 $[M-56+H]^+$ Step 5: Synthesis of N-(5-(2-cyclopropyl-2H-1,2,3-triazol-4-yl)-2-methylphenyl)pyrazolo[1,5-a]pyridine-3-carboxamide The title compound was obtained as an off-white solid, 6.8 mg, 8.7% from N-(2-methyl-5-(2H-1,2,3-triazol-4-yl) phenyl)pyrazolo[1,5-a]pyridine-3-carboxamide and cyclopropylboronic acid following a similar method to that described in Example 28. The crude product was purified by HPLC Method C, 31% to 59% gradient. LCMS: m/z=359 $[M+H]^+$, 1H NMR (400 MHz, DMSO-$d_6$) δ 9.70 (s, 1H), 8.84 (d, 1H), 8.77 (s, 1H), 8.27-8.18 (m, 2H), 7.85 (d, 1H), 7.62 (dd, 1H), 7.56-7.48 (m, 1H), 7.36 (d, 1H), 7.15-7.08 (m, 1H), 4.15 (tt, 1H), 2.29 (s, 3H), 1.24 (s, 2H), 1.11 (td, 2H).

Example 30

N-(5-(2-((3-fluorobicyclo[1.1.1]pentan-1-yl)methyl)-2H-tetrazol-5-yl)-2-methylphenyl)pyrazolo[1,5-a]pyridine-3-carboxamide

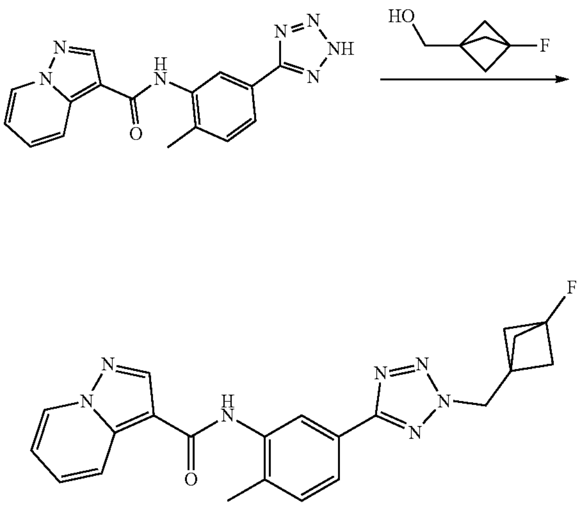

To a solution of Intermediate 1 (80 mg, 0.25 mmol), $PPh_3$ (131 mg, 0.50 mmol) and (3-fluorobicyclo[1.1.1]pentan-1-yl)methanol (58.0 mg, 0.50 mmol) in THF (5 mL) was added DIAD (101 mg, 0.50 mmol) at 0° C. and the reaction mixture stirred at rt for 2 h. The resulting solution was washed with water and extracted with EtOAc (3×50 mL), the combined organic phase dried over $Na_2SO_4$ and concentrated under vacuum. The crude product was purified by prep-TLC with EtOAc:PE=2:1 and further purified by Prep-HPLC Method B, 35% to 68% gradient, to give the title compound (37.0 mg, 35%) as a white solid. LCMS: m/z=418 $[M+H]^+$, 1H NMR (300 MHz, DMSO-$d_6$) δ 9.76 (s, 1H), 8.86 (d, 1H), 8.80 (s, 1H), 8.25 (d, 1H), 8.15 (d, 1H), 7.85 (dd, 1H), 7.60-7.48 (m, 1H), 7.48 (d, 1H), 7.13 (td, 1H), 5.14 (s, 2H), 2.37 (s, 3H), 2.08 (d, 6H).

Examples 31 to 35

The compounds in the following table were prepared from Intermediate 1 and the appropriate alcohol, following similar conditions to those described in Example 30.

| Compound No | Name, Starting material (SM), Purification, Yield | Data |
|---|---|---|
| 31 | N-(2-methyl-5-(2-(tetrahydro-2H-pyran-4-yl)-2H-tetrazol-5-yl)phenyl)pyrazolo[1,5-a]pyridine-3-carboxamide<br>SM: tetrahydro-2H-pyran-4-ol.<br>HPLC Method L, Gradient: 33% B to 43% B.<br>32.7 mg; 26% as a white solid. | LCMS: m/z = 404 [M + H]$^+$, 1H NMR (400 MHz, DMSO-$d_6$) δ 9.76 (s, 1H), 8.86 (dt, 1H), 8.79 (s, 1H), 8.25 (dt, 1H), 8.15 (d, 1H), 7.85 (dd, 1H), 7.53 (ddd, 1H), 7.48 (d, 1H), 7.13 (td, 1H), 5.18 (tt, 1H), 3.99 (ddd, 2H), 3.57 (td, 2H), 2.36 (s, 3H), 2.24 (ddd, 2H), 2.19-2.05 (m, 2H). |
| 32 | N-(5-(2-(3-fluorocyclobutyl)-2H-tetrazol-5-yl)-2-methylphenyl)pyrazolo[1,5-a]pyridine-3-carboxamide<br>SM: 3-fluorocyclobutan-1-ol<br>Prep HPLC Method B, 40% to 46% gradient<br>48.5 mg; 39% as a white solid | LCMS: m/z = 392 [M + H]$^+$, $^1$H NMR (300 MHz, DMSO-$d_6$) δ 9.77 (s, 1H), 8.86 (dt, 1H), 8.80 (s, 1H), 8.26 (dt, 1H), 8.18 (d, 1H), 7.88 (dd, 1H), 7.60-7.44 (m, 2H), 7.13 (td, 1H), 5.27-4.85 (m, 2H), 3.17 (dt, 2H), 3.00-2.77 (m, 2H), 2.37 (s, 3H). |
| 33 | (S)-N-(5-(2-(1-(2-fluorophenyl)ethyl)-2H-tetrazol-5-yl)-2-methylphenyl)pyrazolo[1,5-a]pyridine-3-carboxamide<br>SM: (1R)-1-(2-fluorophenyl)ethan-1-ol<br>HPLC Method J, 40% to 60% gradient.<br>(14.1 mg; 5%) as a white solid | LCMS: m/z = 442 [M + H]$^+$, 1H NMR (400 MHz, DMSO-$d_6$) δ 9.74 (s, 1H), 8.85 (dt, 1H), 8.77 (s, 1H), 8.23 (dt, 1H), 8.10 (d,), 7.83 (dd, 1H), 7.57-7.40 (m, 4H), 7.27 (td, 2H), 7.12 (td, 1H), 6.52 (q, 1H), 2.34 (s, 3H), 2.04 (d, 3H). |
| 34 | N-(2-methyl-5-(2-((tetrahydro-2H-pyran-2-yl)methyl)-2H-tetrazol-5-yl)phenyl)pyrazolo[1,5-a]pyridine-3-carboxamide<br>SM: (oxan-2-yl)methanol<br>HPLC Method E, 46% to 61% gradient<br>14.9 mg; 14.3% as a white solid | LCMS: m/z = 418 [M + H]$^+$, $^1$H NMR (300 MHz, DMSO-$d_6$) δ 9.74 (s, 1H), 8.90-8.77 (m, 2H), 8.26 (d, 1H), 8.16 (d, 1H), 7.85 (d, 1H), 7.60-7.44 (m, 2H), 7.19-7.08 (m, 1H), 4.77 (d, 2H), 3.92 (s, 1H), 3.82 (d, 1H), 2.37 (s, 3H), 1.81 (s, 2H), 1.73 (d, 1H), 1.47 (s, 4H), 1.33 (d, 1H). |
| 35 | N-(5-(2-((1s,3s)-3-methoxycyclobutyl)-2H-tetrazol-5-yl)-2-methylphenyl)pyrazolo[1,5-a]pyridine-3-carboxamide<br>SM: (1r,3r)-3-methoxycyclobutan-1-ol<br>HPLC Method B, 32% to 53% gradient<br>62.4 mg, 49% as a white solid | LCMS m/z = 404 [M + H]$^+$; $^1$H NMR (400 MHz, DMSO-$d_6$) δ 9.74 (s, 1H), 8.85 (d, 1H), 8.78 (s, 1H), 8.25 (d, 1H), 8.16 (d, 1H), 7.86 (dd, 1H), 7.57-7.49 (m, 1H), 7.47 (d, 1H), 7.17-7.08 (m, 1H), 5.21 (p, 1H), 3.88 (p, 1H), 3.22 (s, 3H), 3.00 (ddd, 2H), 2.57 (d, 2H), 2.36 (s, 3H). |

Example 36

N-(2,4-dimethyl-5-(2-(4,4,4-trifluoro-3-hydroxy-3-methylbutyl)-2H-tetrazol-5-yl)phenyl)pyrazolo[1,5-a]pyridine-3-carboxamide

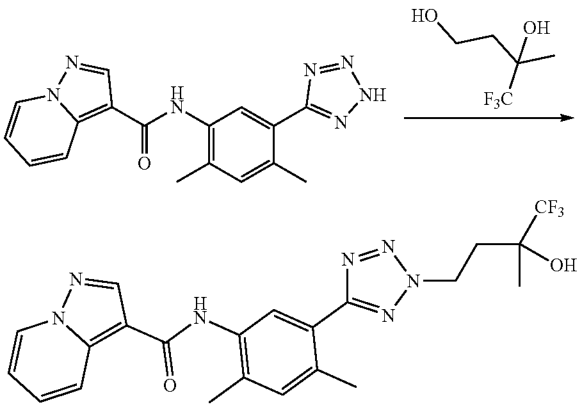

To the solution of Intermediate 3 (50 mg, 0.15 mmol) and 4,4,4-trifluoro-3-methylbutane-1,3-diol (WO 2018215801, 23.7 mg, 0.15 mmol) in THF (1 mL), was added DIAD (35.0 μL, 0.18 mmol) and $PPh_3$ (47.2 mg, 0.18 mmol) and the reaction mixture stirred for 4 h. The mixture was filtered and purified by reverse HPLC to yield the title compound (13.3 mg, 18.7%). LCMS m/z=474 [M+H]$^+$; 1H NMR (500 MHz, DMSO-$d_6$) δ 9.62 (s, 1H), 8.77 (d, 1H), 8.69 (d, 1H), 8.16 (d, 1H), 7.91 (d, 1H), 7.44 (t, 1H), 7.24 (s, 1H), 7.04 (t, 1H), 6.18 (s, 1H), 4.92-4.82 (m, 1H), 4.82-4.74 (m, 1H), 2.50 (d, 3H), 2.37-2.29 (m, 1H), 2.24 (d, 4H), 1.26 (s, 3H)

Examples 37 to 42

The compounds in the following table were obtained from Intermediate 1 and the appropriate alcohol, following a similar procedure to that described in Example 30. The resulting racemic compounds were separated by chiral HPLC as detailed in the table, to afford the desired compounds.

| Compound No | Compound Name | Starting Material (SM), Purification details, Yield | Data |
|---|---|---|---|
| 37 | (R)-N-(5-(2-(1-cyclopropylethyl)-2H-tetrazol-5-yl)-2-methylphenyl)pyrazolo[1,5-a]pyridine-3-carboxamide or (S)-N-(5-(2-(1-cyclopropylethyl)-2H-tetrazol-5-yl)-2-methylphenyl)pyrazolo[1,5-a]pyridine-3-carboxamide, | 1-cyclopropylethan-1-ol Prep-CHIRAL HPLC: Column: CHIRAL ART Amylose-SA, 2*25 cm, 5 μm; Mobile Phase A: Hex (0.5% 2M $NH_3$—MeOH), Mobile Phase B: EtOH; Flow rate: 20 mL/min; isocratic gradient: 15% B 13.4 mg; 11% as a white solid | Peak 1 LCMS: m/z = 388 $[M + H]^+$, $^1$H NMR (300 MHz, DMSO-$d_6$) δ 9.77 (s, 1H), 8.86 (dt, 1H), 8.80 (s, 1H), 8.25 (dt, 1H), 8.15 (d, 1H), 7.87 (dd, 1H), 7.54 (ddd, 1H), 7.48 (d, 1H), 7.13 (td, 1H), 4.43 (dq, 1H), 2.37 (s, 3H), 1.71 (d, 3H), 1.49-1.33 (m, 1H), 0.76-0.62 (m, 1H), 0.68-0.45 (m, 2H), 0.42 (ddd, 1H). |
| 38 | (S)-N-(5-(2-(1-cyclopropylethyl)-2H-tetrazol-5-yl)-2-methylphenyl) pyrazolo[1,5-a]pyridine-3-carboxamide or (R)-N-(5-(2-(1-cyclopropylethyl)-2H-tetrazol-5-yl)-2-methylphenyl) pyrazolo[1,5-a]pyridine-3-carboxamide | 1-cyclopropylethan-1-ol Prep-CHIRAL HPLC: Column: CHIRAL ART Amylose-SA, 2*25 cm, 5 μm; Mobile Phase A: Hex (0.5% 2M $NH_3$—MeOH), Mobile Phase B: EtOH; Flow rate: 20 mL/min; isocratic gradient: 15% B 5.2 mg; 4% as a white solid | Peak 2 LCMS: m/z = 388 $[M + H]^+$, $^1$H NMR (300 MHz, DMSO-$d_6$) δ 9.77 (s, 1H), 8.86 (dt, 1H), 8.80 (s, 1H), 8.25 (dt, 1H), 8.15 (d, 1H), 7.87 (dd, 1H), 7.54 (ddd, 1H), 7.48 (d, 1H), 7.13 (td, 1H), 4.43 (dq, 1H), 2.37 (s, 3H), 1.71 (d, 3H), 1.49-1.33 (m, 1H), 0.68 (tdd, 1H), 0.61-0.45 (m, 2H), 0.42 (ddd, 1H). |
| 39 | (R)-N-(2-methyl-5-(2-(1-(tetrahydro-2H-pyran-4-yl)ethyl)-2H-tetrazol-5-yl)phenyl)pyrazolo[1,5-a]pyridine-3-carboxamide or (S)-N-(2-methyl-5-(2-(1-(tetrahydro-2H-pyran-4-yl)ethyl)-2H-tetrazol-5-yl)phenyl)pyrazolo[1,5-a]pyridine-3-carboxamide | 1-(oxan-4-yl)ethan-1-ol, Prep-Chiral-HPLC: Column: CHIRALPAK IF, 2*25 cm, 5 μm; Mobile Phase A: Hex: DCM = 3:1(0.5% 2M $NH_3$—MeOH), Mobile Phase B: IPA; Flow rate: 20 mL/min; 30% B isocratic gradient (14.4 mg; 25%) as a white solid | Peak 1: LCMS: m/z = 432 $[M + H]^+$, $^1$H NMR (300 MHz, DMSO-$d_6$) δ 9.77 (s, 1H), 8.87 (dt, 1H), 8.80 (s, 1H), 8.29-8.20 (m, 1H), 8.13 (d, 1H), 7.86 (dd, 1H), 7.60-7.44 (m, 2H), 7.14 (td, 1H), 4.94 (q, 1H), 3.89 (d, 1H), 3.79 (d, 1H), 3.30-3.14 (m, 2H), 2.36 (s, 3H), 2.14 (s, 1H), 1.68 (d, , 1H), 1.61 (d, 3H), 1.29 (dtd, 2H), 1.01 (d, 1H). |
| 40 | (S)-N-(2-methyl-5-(2-((tetrahydro-2H-pyran-2-yl)methyl)-2H-tetrazol-5-yl)phenyl)pyrazolo[1,5-a]pyridine-3-carboxamide or (R)-N-(2-methyl-5-(2-((tetrahydro-2H-pyran-2-yl)methyl)-2H-tetrazol-5-yl)phenyl)pyrazolo[1,5-a]pyridine-3-carboxamide | (Oxan-2-yl)methanol Column: DZ-CHIRALPAK IC-3, 4.6*50 mm, 3.0 μm; Mobile Phase A: Hex (0.2% DEA): (EtOH: DCM = 1:1) = 60:40; Flow rate: 1 mL/min; isocratic gradient: 0% B (2.2 mg; 21%) as a white solid | Peak 2: LCMS: m/z = 418 $[M + H]^+$, $^1$H NMR (400 MHz, DMSO-$d_6$) δ 9.72 (s, 1H), 8.85 (d, 1H), 8.79 (s, 1H), 8.25 (d, 1H), 8.15 (s, 1H), 7.84 (d, 1H), 7.57-7.50 (m, 1H), 7.47 (d, 1H), 7.12 (t, 1H), 4.81-4.69 (m, 2H), 3.91 (s, 1H), 3.81 (d, 1H), 2.36 (s, 3H), 1.81 (d, 1H), 1.72 (d, 1H), 1.52 (d, 1H), 1.45 (s, 2H), 1.33 (q, 1H). |
| 41 | (R)-N-(2-methyl-5-(2-(4,4,4-trifluoro-3-hydroxy-3-methylbutyl)-2H-tetrazol-5-yl)phenyl)pyrazolo[1,5-a]pyridine-3-carboxamide or (S)-N-(2-methyl-5-(2-(4,4,4-trifluoro-3-hydroxy-3-methylbutyl)-2H-tetrazol-5-yl)phenyl)pyrazolo[1,5-a]pyridine-3-carboxamide | 4,4,4-trifluoro-3-methylbutane-1,3-diol (WO 2018215801) prep-Chiral-HPLC with Column: CHIRALPAK IE, 2*25 cm, 5 μm; Mobile Phase A: Hex (0.2% DEA), Mobile Phase B: EtOH: DCM = 1: 1; Flow rate: 20 mL/min; | Peak 1: LCMS: m/z = 460 $[M + H]^+$; 1H NMR (400 MHz, DMSO-$d_6$) δ 9.73 (s, 1H), 8.89-8.82 (m, 1H), 8.79 (s, 1H), 8.28-8.21 (m, 1H), 8.17 (d, 1H), 7.85 (dd, 1H), 7.58-7.50 (m, 1H), 7.47 (d, 1H), |

-continued

| Compound No | Compound Name | Starting Material (SM), Purification details, Yield | Data |
|---|---|---|---|
| | | 50% B isocratic gradient 3.9 mg, 26.1% as a white solid | 7.13 (td, 1H), 6.27 (s, 1H), 4.98-4.79 (m, 2H), 2.42-2.24 (m, 5H), 1.33 (s, 3H). |
| 42 | N-(5-(2-((3r,5r)-1,1-difluorospiro [2.3]hexan-5-yl)-2H-tetrazol-5-yl)-2-methylphenyl)pyrazolo[1,5-a]pyridine-3-carboxamide or N-(5-(2-((3s,5s)-1,1-difluorospiro[2.3]hexan-5-yl)-2H-tetrazol-5-yl)-2-methylphenyl)pyrazolo[1,5-a]pyridine-3-carboxamide | 1,1-difluorospiro [2.3]hexan-5-ol Prep-HPLC, Method K, 50% to 60% gradient 23.8 mg, 8.7% as white solid | Peak 2, LCMS: m/z = 436 $[M + H]^+$, 1H NMR (400 MHz, DMSO-$d_6$) δ 9.75 (s, 1H), 8.86 (d, 1H), 8.79 (s, 1H), 8.29-8.22 (m, 1H), 8.18 (d, 1H), 7.88 (dd, 1H), 7.58-7.50 (m, 1H), 7.49 (d, 1H), 7.13 (td, 1H), 5.82-5.70 (m, 1H), 2.93 (q, 4H), 2.37 (s, 3H), 1.61 (t, 2H). |

Example 43

N-(2-methyl-5-(2-methyl-2H-tetrazol-5-yl)phenyl)-5-(1H-pyrazol-4-yl)pyrazolo[1,5-a]pyridine-3-carboxamide

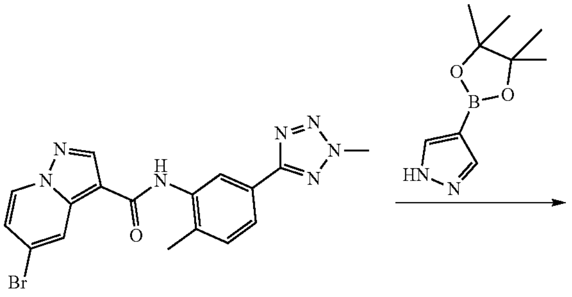

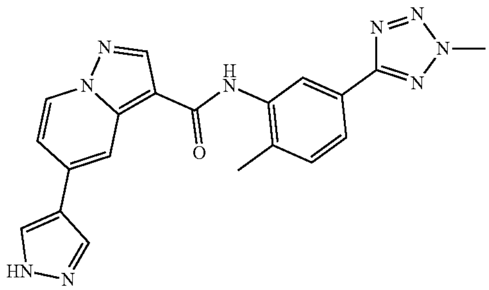

A mixture of Intermediate 13 (100 mg, 0.24 mmol), 4-(4,4,5,5-tetramethyl-1,3,2-dioxaborolan-2-yl)-1H-pyrazole (70.4 mg, 0.36 mmol), XPhos (15 mg, 0.03 mmol), XPhos Pd G3 (15 mg, 0.02 mmol) and $Cs_2CO_3$ (118 mg, 0.36 mmol) in dioxane (9 mL) and $H_2O$ (3 mL) was stirred at 100° C. for 3 h. The reaction was concentrated to dryness and the residue was purified by prep-TLC with DCM: MeOH=20:1. The product was purified by prep-HPLC, Method B, 20% to 44% gradient, to afford the title compound (33.6 mg, 34.7%) as a white solid. LCMS: m/z=400 $[M+H]^+$; 1H NMR (400 MHz, DMSO-$d_6$) δ 13.19 (s, 1H), 9.62 (s, 1H), 8.82 (dd, 1H), 8.73 (s, 1H), 8.51-8.33 (m, 2H), 8.23 (d, 1H), 8.09 (s, 1H), 7.82 (dd, 1H), 7.50-7.38 (m, 2H), 4.43 (s, 3H), 2.38 (s, 3H).

Example 44

N-(2-methyl-5-(2-((1r,3r)-3-(trifluoromethyl)cyclobutyl)-2H-tetrazol-5-yl)phenyl)-5-(1H-pyrazol-4-yl)pyrazolo[1,5-a]pyridine-3-carboxamide or N-(2-methyl-5-(2-((1s,3s)-3-(trifluoromethyl)cyclobutyl)-2H-tetrazol-5-yl)phenyl)-5-(1H-pyrazol-4-yl) pyrazolo[1,5-a]pyridine-3-carboxamide

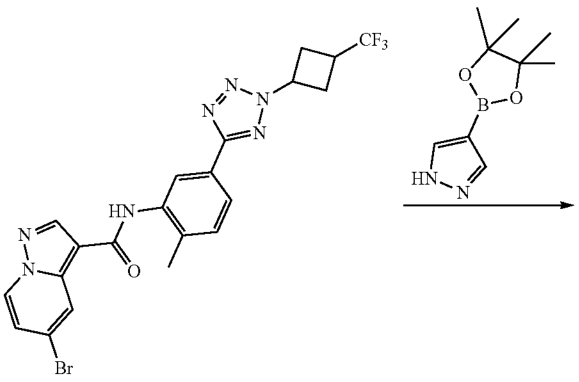

-continued

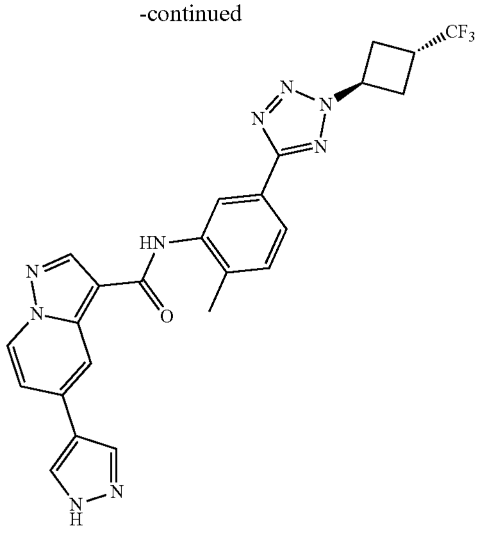

OR

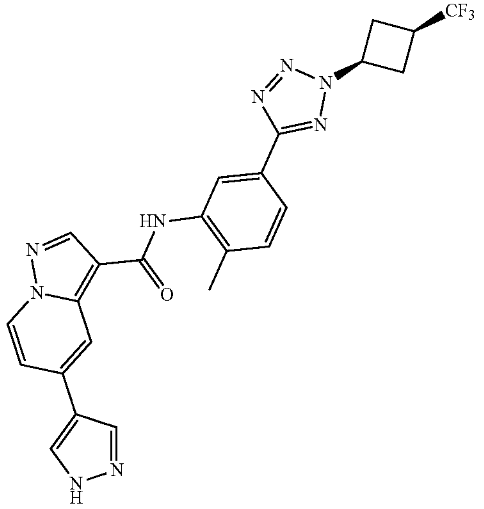

A mixture of Intermediate 12 (130 mg, 0.25 mmol), 4-(4,4,5,5-tetramethyl-1,3,2-dioxaborolan-2-yl)-1H-pyrazole (72.7 mg, 0.38 mmol), XPhos Pd G3 (31.72 mg, 0.04 mmol) and $K_2CO_3$ (69.06 mg, 0.50 mmol) in THF (2 mL) and $H_2O$ (0.4 mL) was stirred at 80° C. for 16 h under $N_2$ and the reaction was concentrated under reduced pressure. The residue was purified by prep-TLC (PE:EtOAc=2:1) and the product was further purified by prep-SFC: Column: Lux 3 um Cellulose-4, 4.6*100 mm, 3 um; Mobile Phase B: MeOH (0.5% 2M $NH_3$-MeOH); Flow rate: 4 mL/min; Gradient: isocratic 50% B; to give Peak 1, N-(2-methyl-5-(2-((1r,3r)-3-(trifluoromethyl)cyclobutyl)-2H-tetrazol-5-yl)phenyl)-5-(1H-pyrazol-4-yl)pyrazolo[1,5-a]pyridine-3-carboxamide or N-(2-methyl-5-(2-((1s,3s)-3-(trifluoromethyl)cyclobutyl)-2H-tetrazol-5-yl)phenyl)-5-(1H-pyrazol-4-yl)pyrazolo[1,5-a]pyridine-3-carboxamide (27.8 mg, 9.5%) as a white solid. LCMS: m/z=508 $[M+H]^+$; 1H NMR (400 MHz, DMSO-$d_6$) δ 13.20 (s, 1H), 9.69 (s, 1H), 8.87-8.80 (m, 1H), 8.74 (s, 1H), 8.46 (s, 1H), 8.39-8.33 (m, 1H), 8.21 (d, 1H), 8.10 (s, 1H), 7.87 (dd, 1H), 7.53-7.40 (m, 2H), 5.58 (p, 1H), 3.30-3.18 (m, 1H), 2.94-2.88 (m, 2H), 2.81 (dt, 2H), 2.39 (s, 3H).

Example 45 methyl 3-(5-(3-(5-((2-methoxyethyl)amino)-4-methylpyrazolo[1,5-a]pyridine-3-carboxamido)-4-methylphenyl)-2H-tetrazol-2-yl)azetidine-1-carboxylate

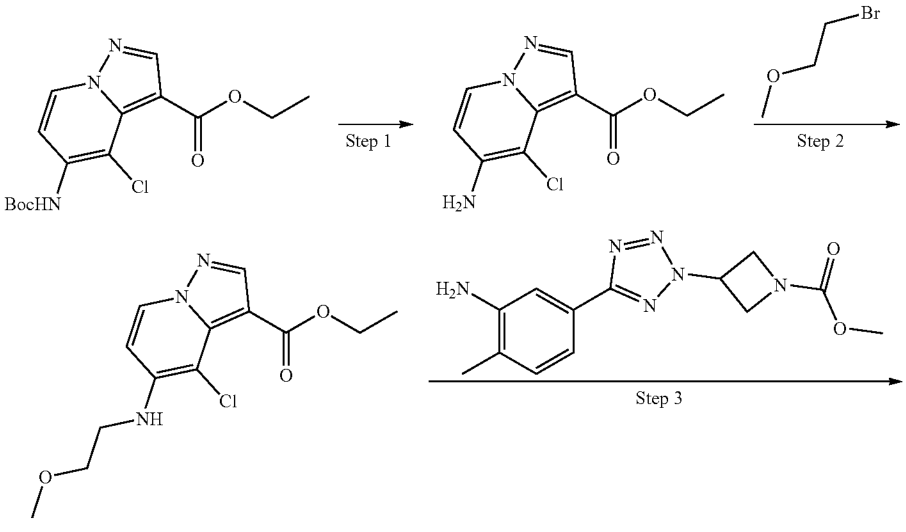

-continued

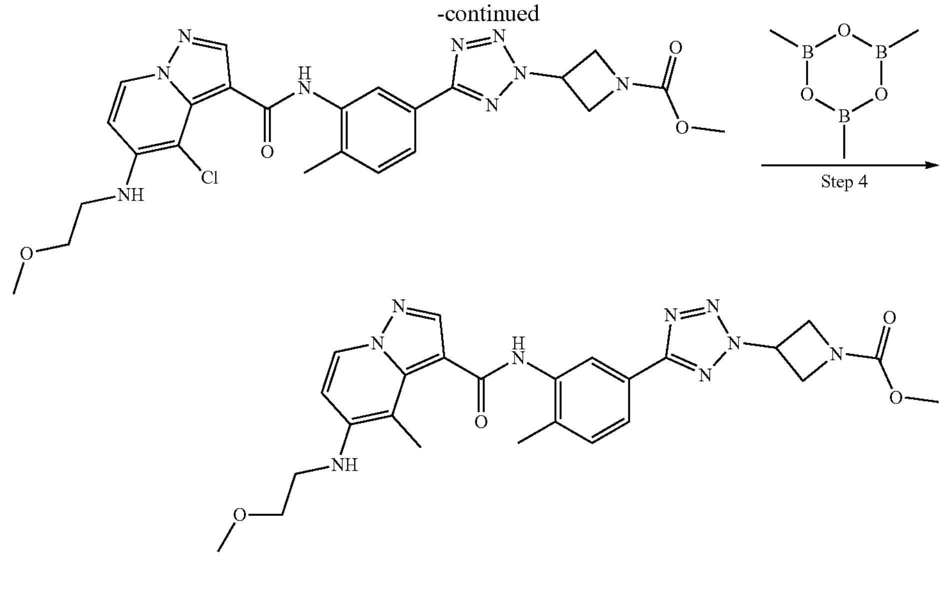

Step 1: Synthesis of ethyl 5-amino-4-chloropyrazolo[1,5-a]pyridine-3-carboxylate TFA (3 mL) was added to Intermediate 41 (600 mg, 1.76 mmol) in DCM (8 mL) and the reaction was stirred at rt for 2 h. The reaction mixture was diluted with EtOAc (100 mL), washed with saturated aqueous $NaHCO_3$ (100 mL×3) and saturated brine (100 mL). The organic layer was dried over $Na_2SO_4$, filtered and evaporated to afford the title compound (300 mg, 71.2%) as a yellow solid. LCMS: m/z=239.0 $[M+H]^+$.

Step 2: Synthesis of ethyl 4-chloro-5-((2-methoxyethyl)amino)pyrazolo[1,5-a]pyridine-3-carboxylate The title compound was obtained as a brown solid, 300 mg, 80.6% from ethyl 5-amino-4-chloropyrazolo[1,5-a]pyridine-3-carboxylate and 1-bromo-2-methoxyethane, following the procedure described in Intermediate 28. LCMS: m/z=298 $[M+H]^+$.

Step 3: Synthesis of methyl 3-(5-(3-(4-chloro-5-((2-methoxyethyl)amino)pyrazolo[1,5-a]pyridine-3-carboxamido)-4-methylphenyl)-2H-tetrazol-2-yl)azetidine-1-carboxylate $Me_3Al$ (2M in toluene, 1 mL) was added dropwise to ethyl 4-chloro-5-((2-methoxyethyl)amino)pyrazolo[1,5-a]pyridine-3-carboxylate (300 mg, 1.0 mmol) and methyl 3-(5-(3-amino-4-methylphenyl)-2H-tetrazol-2-yl)azetidine-1-carboxylate (Intermediate 11, Step 4, 288 mg, 1 mmol) in toluene (10 mL) at 0° C. and the reaction was heated to 100° C. for 16 h. The reaction mixture was diluted with EtOAc (100 mL), washed with water (100 mL×3) and saturated brine (100 mL). The organic layer was dried over $Na_2SO_4$, filtered and evaporated. The residue was purified by prep-TLC with DCM:MeOH=30:1 to afford the title compound (110 mg, 20.4%) as a brown solid. LCMS: m/z=540 $[M+H]^+$.

Step 4: Synthesis of methyl 3-(5-(3-(5-((2-methoxyethyl)amino)-4-methylpyrazolo[1,5-a]pyridine-3-carboxamido)-4-methylphenyl)-2H-tetrazol-2-yl)azetidine-1-carboxylate The title compound was obtained as a white solid, 3.6 mg, from methyl 3-(5-(3-(4-chloro-5-((2-methoxyethyl)amino)pyrazolo[1,5-a]pyridine-3-carboxamido)-4-methylphenyl)-2H-tetrazol-2-yl)azetidine-1-carboxylate and 2,4,6-trimethyl-1,3,5,2,4,6-trioxatriborinane, following a similar procedure to that described in Example 44. The residue was purified by Prep-HPLC, method O, 25% to 45% gradient. LCMS: m/z=520 $[M+H]^+$; $^1H$ NMR (400 MHz, DMSO-$d_6$) δ 9.53 (s, 1H), 8.46 (d, 1H), 8.31 (s, 1H), 8.21 (d, 1H), 7.83 (dd, 1H), 7.44 (d, 1H), 6.73 (d, 1H), 5.91 (tt, 1H), 5.68 (s, 1H), 4.56 (t, 2H), 4.39 (s, 2H), 3.63 (s, 3H), 3.50 (d, 2H), 3.43 (s, 2H), 3.21-3.31 (m, 3H), 2.40 (s, 3H), 2.35 (s, 3H).

Example 46

N-(5-(2-(3,3-difluorocyclobutyl)-2H-tetrazol-5-yl)-2-methylphenyl)-5-(1-(2-hydroxyethyl)-1H-pyrazol-4-yl)pyrazolo[1,5-a]pyridine-3-carboxamide

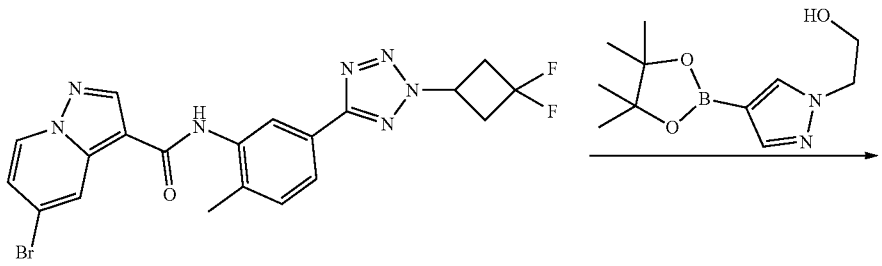

-continued

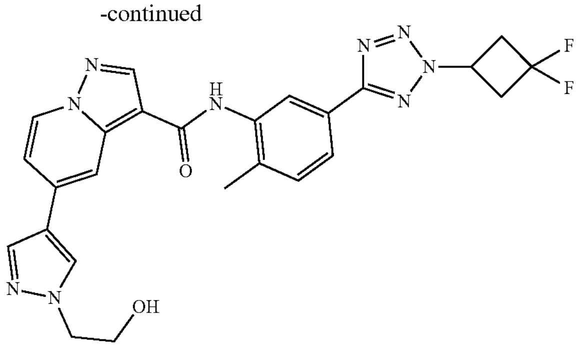

A mixture of Intermediate 4 (150 mg, 0.31 mmol), 2-(4-(4,4,5,5-tetramethyl-1,3,2-dioxaborolan-2-yl)-1H-pyrazol-1-yl)ethan-1-ol (73.1 mg, 0.31 mmol), Pd(dppf)$Cl_2$ (22.4 mg, 0.031 mmol) and $Na_2CO_3$ (65.1 mg, 0.61 mmol) in dioxane (8 mL) and $H_2O$ (2 mL) was stirred at 100° C. for 3 h under $N_2$. The reaction mixture was cooled to rt, then diluted with water (25 mL). The resulting solution was extracted with EtOAc (2×40 mL), the combined organic layers washed with brine (20 mL), dried over anhydrous $Na_2SO_4$ and concentrated under vacuum. The product was purified by HPLC, Method E, 38% to 58% gradient, to give the title compound (55.1 mg 34.6%) as a white solid. LCMS: m/z=520 $[M+H]^+$. 1H NMR (300 MHz, DMSO-$d_6$) δ 9.66 (s, 1H), 8.81 (dd, 1H), 8.73 (s, 1H), 8.40 (d, 1H), 8.32 (dd, 1H), 8.21 (d, 1H), 8.05 (d, 1H), 7.85 (dd, 1H), 7.47 (d, 1H), 7.37 (dd, 1H), 5.67-5.50 (m, 1H), 5.02-4.87 (m, 1H), 4.18 (t, 2H), 3.77 (d, 2H), 3.63-3.35 (m, 4H), 2.37 (s, 3H).

Example 47

5-(1-(2-hydroxyethyl)-1H-pyrazol-4-yl)-N-(2-methyl-5-(2-methyl-2H-tetrazol-5-yl)phenyl)pyrazolo[1,5-a]pyridine-3-carboxamide

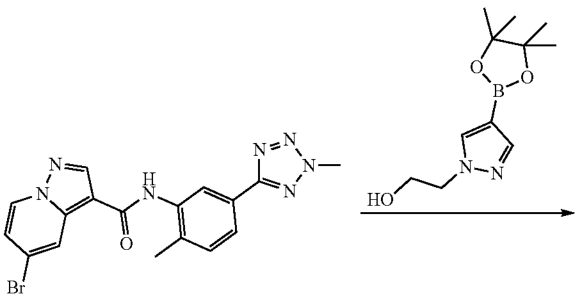

-continued

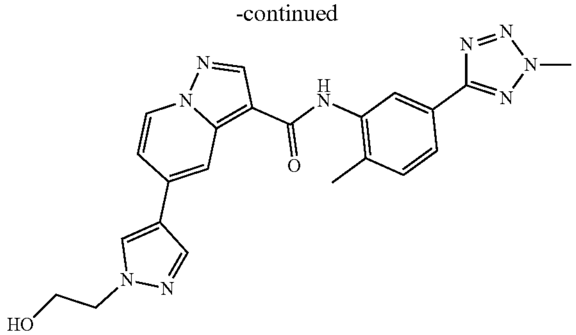

To a solution of Intermediate 13 (80 mg, 0.19 mmol) and 2-(4-(4,4,5,5-tetramethyl-1,3,2-dioxaborolan-2-yl)-1H-pyrazol-1-yl)ethan-1-ol (46.1 mg, 0.19 mmol) in dioxane (2 mL) and $H_2O$ (0.5 mL) were added $K_2CO_3$ (26.7 mg, 0.19 mmol) and Pd(dppf)$Cl_2$ (158 mg, 0.19 mmol) at rt under $N_2$ and the reaction mixture stirred for 2 h at 80° C. The mixture was quenched with water (10 mL) and extracted with EtOAc (3×20 mL). The combined organic layer was concentrated under vacuum and purified by Prep-HPLC, Method C, 13% to 43% gradient, to give the title compound (5.6 mg, 6%) as a white solid. LCMS: m/z=444 $[M+H]^+$, $^1H$ NMR (400 MHz, DMSO-$d_6$) δ 9.64 (s, 1H), 8.86-8.70 (m, 2H), 8.43 (d, 1H), 8.34 (dd, 1H), 8.24 (d, 1H), 8.07 (d, 1H), 7.82 (dd, 1H), 7.50-7.34 (m, 2H), 4.97 (t, 1H), 4.43 (s, 3H), 4.19 (t, 2H), 3.78 (q, 2H), 2.38 (s, 3H).

Examples 48 to 52

The compounds in the following table were prepared from the appropriate bromopyrazolo[1,5-a]pyridine and boronic acid ester, following a similar procedure to that described in Example 47.

| Compound No | Name, Starting Materials (SM), Purification, Yield | Data |
|---|---|---|
| 48 | 5-(1-(2-hydroxy-2-methylpropyl)-1H-pyrazol-4-yl)-N-(2-methyl-5-(2-methyl-2H-tetrazol-5-yl)phenyl)pyrazolo[1,5-a]pyridine-3-carboxamide<br>SM: Intermediate 13 and 2-methyl-1-(4-(4,4,5,5-tetramethyl-1,3,2-dioxaborolan-2-yl)-1H-pyrazol-1-yl)propan-2-ol<br>prep-HPLC, Method B, 25% to 45% gradient.<br>off-white solid, 18.9 mg, 16.5% | LCMS: m/z = 472 $[M + H]^+$. $^1$HNMR (400 MHz, DMSO-$d_6$) δ 9.63 (s, 1H), 8.82 (d, 1H), 8.74 (s, 1H), 8.34 (d, 2H), 8.23 (d, 1H), 8.05 (s, 1H), 7.82 (dd, 1H), 7.47 (d, 1H), 7.39 (dd, 1H), 4.77 (s, 1H), 4.43 (s, 3H), 4.07 (s, 2H), 2.38 (s, 3H), 1.10 (s, 6H). |

-continued

| Compound No | Name, Starting Materials (SM), Purification, Yield | Data |
|---|---|---|
| 49 | 5-(1-(2-hydroxyethyl)-1H-pyrazol-4-yl)-N-(5-(2-isopropyl-2H-tetrazol-5-yl)-2-methylphenyl)pyrazolo[1,5-a]pyridine-3-carboxamide<br>SM: Intermediate 29 and 2-(4-(4,4,5,5-tetramethyl-1,3,2-dioxaborolan-2-yl)-1H-pyrazol-1-yl)ethan-1-ol,<br>Prep-HPLC Method A, 21% to 50% gradient.<br>white solid, 58.8 mg, 36% | LCMS: m/z = 472 $[M + H]^+$; $^1H$ NMR (400 MHz, DMSO-$d_6$) δ 9.66 (s, 1H), 8.82 (d, 1H), 8.74 (s, 1H), 8.42 (s, 1H), 8.36-8.31 (m, 1H), 8.20 (d, 1H), 8.06 (s, 1H), 7.84 (dd, 1H), 7.47 (d, 1H), 7.38 (dd, 1H), 5.18 (h, 1H), 4.95 (t, 1H), 4.19 (t, 2H), 3.78 (q, 2H), 2.38 (s, 3H), 1.63 (d, 6H). |
| 50 | 5-cyclopropyl-N-(2-methyl-5-(2-(1-(methylsulfonyl)azetidin-3-yl)-2H-tetrazol-5-yl)phenyl)pyrazolo[1,5-a]pyridine-3-carboxamide<br>SM: Intermediate 39 and 2-cyclopropyl-4,4,5,5-tetramethyl-1,3,2-dioxaborolane<br>Prep-HPLC Method D, 35% to 60% gradient<br>off-white solid, 25.6 mg, 27% | LCMS: m/z = 493 $[M + H]^+$, $^1H$ NMR (400 MHz, $CDCl_3$) δ 8.74 (d, 1H), 8.43 (d, 1H), 8.23 (s, 1H), 8.07 (d, 1H), 7.95 (dd, 1H), 7.53 (s, 1H), 7.41 (d, 1H), 6.71 (dd, 1H), 5.80-5.69 (m, 1H), 4.67-4.56 (m, 4H), 3.51 (s, 1H), 3.10 (s, 3H), 2.46 (s, 3H), 2.02 (tt, 1H), 1.19-1.08 (m, 2H), 0.89 (dt, 2H). |
| 51 | 5-(1-(2-hydroxyethyl)-1H-pyrazol-4-yl)-N-(2-methyl-5-(5-methyl-2H-tetrazol-2-yl)phenyl)pyrazolo[1,5-a]pyridine-3-carboxamide<br>SM: Intermediate 37 and 2-(4-(4,4,5,5-tetramethyl-1,3,2-dioxaborolan-2-yl)-1H-pyrazol-1-yl)ethan-1-ol,<br>Prep-HPLC, method A, 16% to 45% gradient<br>white solid, 23.5 mg, 14.5% | LCMS: m/z = 444 $[M + H]^+$; $^1H$ NMR (400 MHz, DMSO-$d_6$) δ 9.65 (s, 1H), 8.83 (d, 2H), 8.44 (s, 3H), 8.07 (s, 1H), 7.83 (dd, 1H), 7.55 (d, 1H), 7.40 (dd, , 1H), 4.96 (t, 1H), 4.19 (t, 2H), 3.78 (q, 2H), 2.60 (s, 3H), 2.42 (s, 3H). |
| 52 | N-(5-(5-cyclopropyl-2H-tetrazol-2-yl)-2-methylphenyl)-5-(1-(2-hydroxyethyl)-1H-pyrazol-4-yl)pyrazolo[1,5-a]pyridine-3-carboxamide<br>SM: Intermediate 38 and 2-(4-(4,4,5,5-tetramethyl-1,3,2-dioxaborolan-2-yl)-1H-pyrazol-1-yl)ethan-1-ol,<br>Prep-HPLC, Method B, 28% to 53% gradient<br>white solid, 25.3 mg, 39.4% | LCMS: m/z = 470 $[M + H]^+$; $^1H$ NMR (400 MHz, DMSO-$d_6$) δ 9.68 (s, 1H), 8.83 (dd, 1H), 8.75 (s, 1H), 8.43 (d, 1H), 8.33 (dd, 1H), 8.27 (d, 1H), 8.07 (d, 1H), 7.81 (dd, 1H), 7.54 (d, 1H), 7.39 (dd, 1H), 4.96 (t, 1H), 4.19 (t, 2H), 3.78 (q, 2H), 2.41 (s, 3H), 2.39-2.28 (m, 1H), 1.26-1.15 (m, 1H), 1.19-1.12 (m, 1H), 1.12-1.00 (m, 2H). |

Examples 53 and 54

(R)-5-(1-(2-hydroxypropyl)-1H-pyrazol-4-yl)-N-(2-methyl-5-(2-methyl-2H-tetrazol-5-yl)phenyl)pyrazolo[1,5-a]pyridine-3-carboxamide and (S)-5-(1-(2-hydroxypropyl)-1H-pyrazol-4-yl)-N-(2-methyl-5-(2-methyl-2H-tetrazol-5-yl)phenyl)pyrazolo[1,5-a]pyridine-3-carboxamide

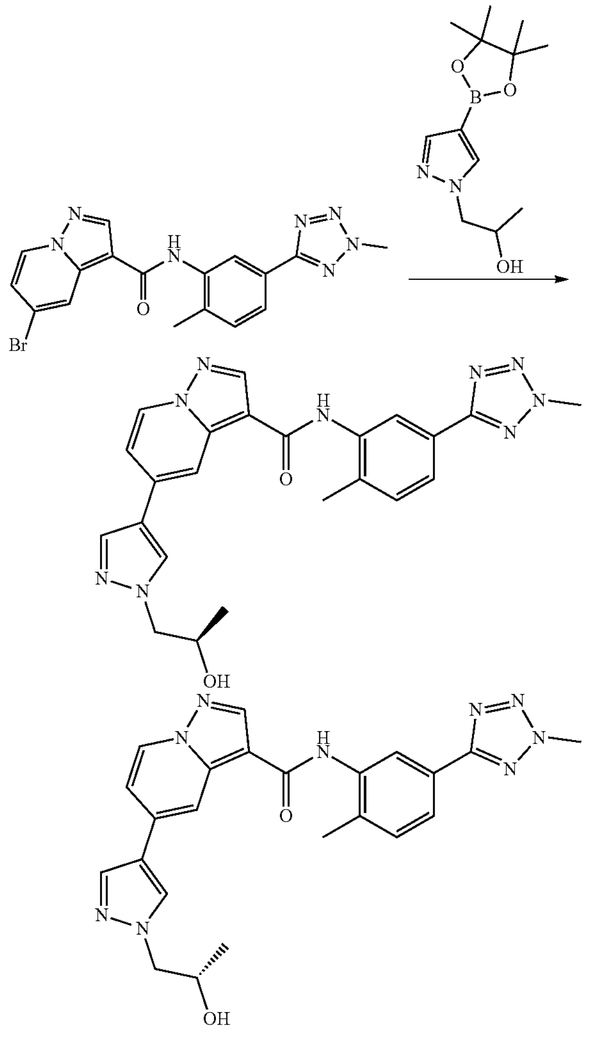

A mixture of Intermediate 13 (200 mg, 0.49 mmol), 1-(4-(4,4,5,5-tetramethyl-1,3,2-dioxaborolan-2-yl)-1H-pyrazol-1-yl)propan-2-ol (244 mg, 0.97 mmol), Pd(dppf)$Cl_2$ (20 mg, 24.4 μmol) and $Cs_2CO_3$ (316 mg, 0.97 mmol) in dioxane (10 mL) and $H_2O$ (3 mL) was stirred at 100° C. for 2 h under $N_2$. The mixture was concentrated to dryness and the residue purified by prep-TLC with DCM:MeOH=20:1. The product was further purified by HPLC using: CHIRALPAK ID, 2*25 cm, 5 μm; Mobile Phase A: Hex (0.5% 2M $NH_3$-MeOH), Mobile Phase B: EtOH:DCM=1:1; Flow rate: 20 mL/min; isocratic Gradient: 70% B, to afford peak 1 (Isomer 1), (R)-5-(1-(2-hydroxypropyl)-1H-pyrazol-4-yl)-N-(2-methyl-5-(2-methyl-2H-tetrazol-5-yl)phenyl)pyrazolo[1,5-a]pyridine-3-carboxamide and (S)-5-(1-(2-hydroxypropyl)-1H-pyrazol-4-yl)-N-(2-methyl-5-(2-methyl-2H-tetrazol-5-yl)phenyl)pyrazolo[1,5-a]pyridine-3-carboxamide, 54.4 mg, as a white solid. LCMS: m/z=458 $[M+H]^+$, 1H NMR (400 MHz, DMSO-$d_6$) δ 9.63 (s, 1H), 8.82 (d, 1H), 8.74 (s, 1H), 8.39 (s, 1H), 8.34 (d, 1H), 8.24 (d, 1H), 8.06 (s, 1H), 7.82 (dd, 1H), 7.47 (d, 1H), 7.38 (dd, 1H), 4.97 (d, 1H), 4.43 (s, 3H), 4.08-4.00 (m, 3H), 2.38 (s, 3H), 1.07 (d, 3H) and Peak 2 (Isomer 2), (S)-5-(1-(2-hydroxypropyl)-1H-pyrazol-4-yl)-N-(2-methyl-5-(2-methyl-2H-tetrazol-5-yl)phenyl)pyrazolo[1,5-a]pyridine-3-carboxamide or (R)-5-(1-(2-hydroxypropyl)-1H-pyrazol-4-yl)-N-(2-methyl-5-(2-methyl-2H-tetrazol-5-yl)phenyl)pyrazolo[1,5-a]pyridine-3-carboxamide (54.9 mg, as a white solid. LCMS: m/z=458 $[M+H]^+$, 1H NMR (400 MHz, DMSO-$d_6$) δ 9.62 (s, 1H), 8.82 (d,), 8.73 (s, 1H), 8.39 (s, 1H), 8.36-8.31 (m, 1H), 8.23 (d, 1H), 8.05 (s, 1H), 7.82 (dd, 1H), 7.47 (d, 1H), 7.38 (dd, 1H), 4.97 (d, 1H), 4.43 (s, 3H), 4.08-4.00 (m, 3H), 2.38 (s, 3H), 1.07 (d, 3H).

Examples 55 and 56

(R)—N-(5-(2-((2,2-difluorocyclopropyl)methyl)-2H-tetrazol-5-yl)-2-methylphenyl)-5-(1H-pyrazol-4-yl)pyrazolo[1,5-a]pyridine-3-carboxamide and (S)—N-(5-(2-((2,2-difluorocyclopropyl)methyl)-2H-tetrazol-5-yl)-2-methylphenyl)-5-(1H-pyrazol-4-yl)pyrazolo[1,5-a]pyridine-3-carboxamide

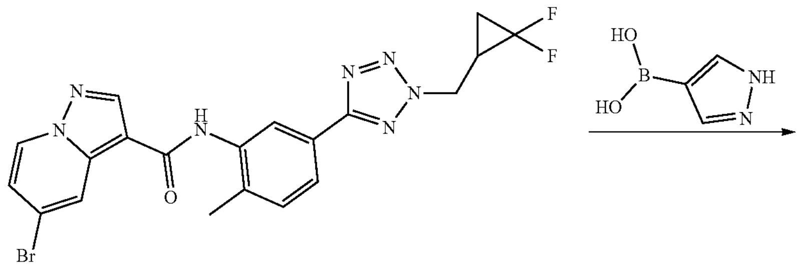

-continued

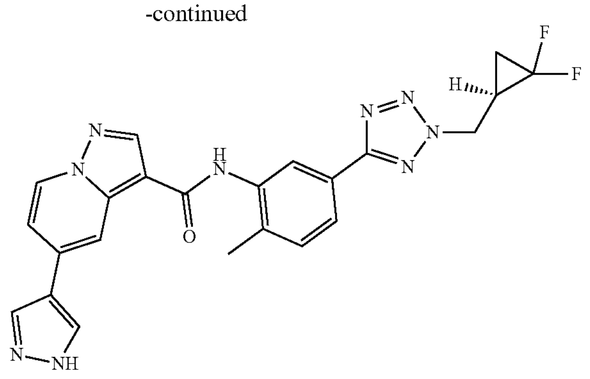

And

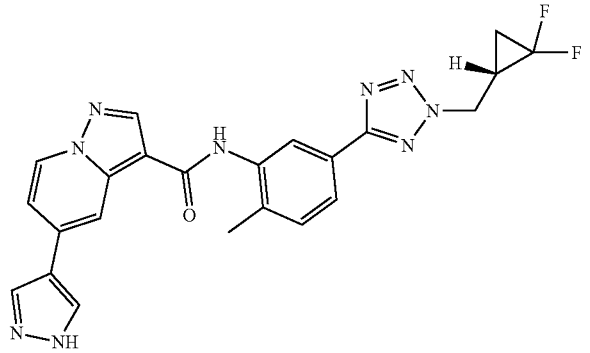

To a solution of Intermediate 5 (100 mg, 0.20 mmol) in dioxane (1 mL) and $H_2O$ (0.3 mL) were added Pd(dppf)$Cl_2$ (14.8 mg, 0.02 mmol), $K_2CO_3$ (56.3 mg, 0.41 mmol), (1H-pyrazol-4-yl)boronic acid (45.6 mg, 0.41 mmol) and the reaction was stirred for 2 h at 100° C. under $N_2$ and then cooled to rt. Water (10 mL) was added and the resulting solution was extracted with DCM (3x20 mL). The organic layer was dried over $Na_2SO_4$ and concentrated under vacuum. The crude product was purified by silica gel column with PE:EtOAc=1:3 to give N-(5-(2-((2,2-difluoro-cyclopropyl)methyl)-2H-tetrazol-5-yl)-2-methylphenyl)-5-(1H-pyrazol-4-yl)pyrazolo[1,5-a]pyridine-3-carboxamide (85 mg; 88%) as a light-yellow solid.

This was further purified by Prep-chiral-HPLC: Column: CHIRALPAK ID, 2*25 cm, 5 μm; Mobile Phase A: Hex (0.2% DEA), Mobile Phase B: EtOH:MeOH=2:1; Flow rate: 20 mL/min; isocratic gradient: 50% B; to give Peak 1 (Isomer 1): (R)—N-(5-(2-((2,2-difluorocyclopropyl) methyl)-2H-tetrazol-5-yl)-2-methylphenyl)-5-(1H-pyrazol-4-yl)pyrazolo[1,5-a]pyridine-3-carboxamide or (S)—N-(5-(2-((2,2-difluorocyclopropyl)methyl)-2H-tetrazol-5-yl)-2-methylphenyl)-5-(1H-pyrazol-4-yl)pyrazolo[1,5-a] pyridine-3-carboxamide (23.3 mg; 28%) as a white solid. LCMS: m/z=476 $[M+H]^+$, 1H NMR (400 MHz, DMSO-$d_6$) δ 13.19 (s, 1H), 9.65 (s, 1H), 8.82 (dd, 1H), 8.73 (s, 1H), 8.46 (s, 1H), 8.35 (dd, 1H), 8.21 (d, 1H), 8.08 (s, 1H), 7.85 (dd, 1H), 7.48 (d, 1H), 7.42 (dd, 1H), 4.99-4.83 (m, 2H), 2.56-2.54 (m, 1H), 2.38 (s, 3H), 1.90-1.76 (m, 1H), 1.71-1.64 (m, 1H).

And Peak 2 (Isomer 2): (S)—N-(5-(2-((2,2-difluorocyclopropyl)methyl)-2H-tetrazol-5-yl)-2-methylphenyl)-5-(1H-pyrazol-4-yl)pyrazolo[1,5-a]pyridine-3-carboxamide or (R)—N-(5-(2-((2,2-difluorocyclopropyl)methyl)-2H-tetrazol-5-yl)-2-methylphenyl)-5-(1H-pyrazol-4-yl)pyrazolo [1,5-a]pyridine-3-carboxamide (27.2 mg; 32%) as a white solid. LCMS: m/z=476 $[M+H^+]$, 1H NMR (400 MHz, DMSO-$d_6$) δ 13.19 (s, 1H), 9.65 (s, 1H), 8.82 (dd, 1H), 8.73 (s, 1H), 8.45 (s, 1H), 8.36 (dd, 1H), 8.21 (d, 1H), 8.09 (s, 1H), 7.85 (dd, 1H), 7.48 (d, 1H), 7.42 (dd, 1H), 4.99-4.89 (m, 1H), 4.88 (dd, 1H), 2.54-2.52 (m, 1H), (2.38 (s, 3H), 1.85-1.82 (m, 1H), 1.73-1.60 (m, 1H).

Example 57

5-(1-(2-hydroxyethyl)-1H-pyrazol-4-yl)-N-(2-methyl-5-(4-methyl-2H-1,2,3-triazol-2-yl)phenyl) pyrazolo[1,5-a]pyridine-3-carboxamide

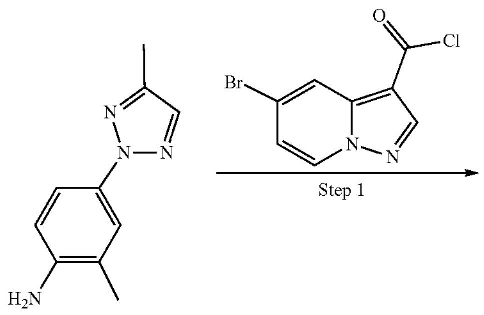

-continued

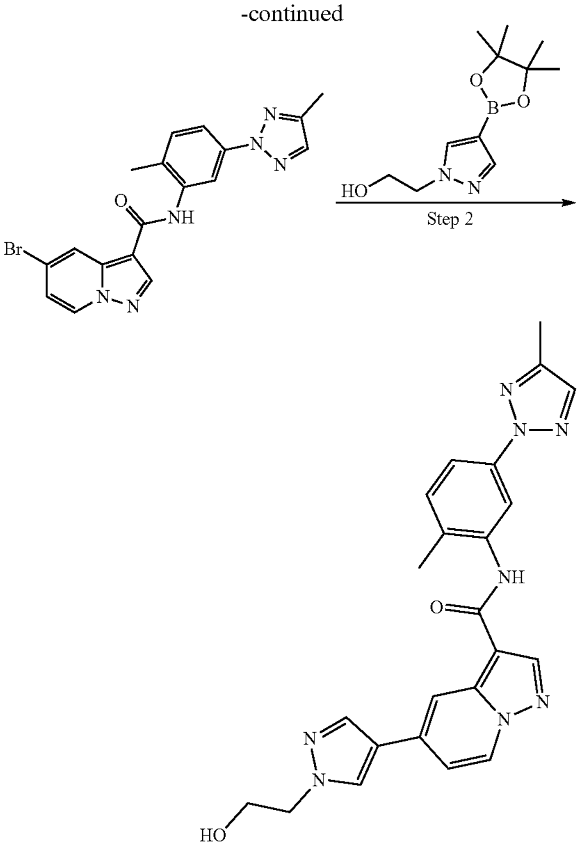

Step 2: Synthesis of 5-(1-(2-hydroxyethyl)-1H-pyrazol-4-yl)-N-(2-methyl-5-(4-methyl-2H-1,2,3-triazol-2-yl)phenyl)pyrazolo[1,5-a]pyridine-3-carboxamide A mixture of 5-bromo-N-(2-methyl-5-(4-methyl-2H-1,2,3-triazol-2-yl)phenyl)pyrazolo[1,5-a]pyridine-3-carboxamide (50 mg, 0.12 mmol), 2-(4-(4,4,5,5-tetramethyl-1,3,2-dioxaborolan-2-yl)-1Hpyrazol-1-yl)ethan-1-ol (35 mg, 0.15 mmol), $Pd(dppf)Cl_2$ (4.45 mg, 0.006 mmol) and $Na_2CO_3$ (39 mg, 0.37 mmol) were combined under $N_2$ in dioxane (0.75 mL) and water (0.25 mL) and heated to 90° C. for 5 h. The mixture was concentrated in vacuo and purified by reverse phase ISCO (5 to 100% MeCN/water containing 0.1% TFA) to give the title compound, 26.8 mg as off-white solid. LCMS: m/z=443 $[M+H]^+$ $^1H$ NMR (500 MHz, DMSO-$d_6$) δ 9.59 (s, 1H), 8.82 (dd, 1H), 8.74 (d, 1H), 8.43 (d, 1H), 8.34 (s, 1H), 8.21 (d, 1H), 8.07 (d, 1H), 7.88 (d, 1H), 7.74 (d, 1H), 7.43 (d, 1H), 7.39 (d, 1H), 4.95 (dt, 1H), 4.20 (t, 2H), 3.79 (q, 2H), 2.37 (d, 6H).

Example 58 methyl 3-(5-(3-(5-(3-methoxypropyl)pyrazolo[1,5-a]pyridine-3-carboxamido)-4-methylphenyl)-2H-tetrazol-2-yl)azetidine-1-carboxylate

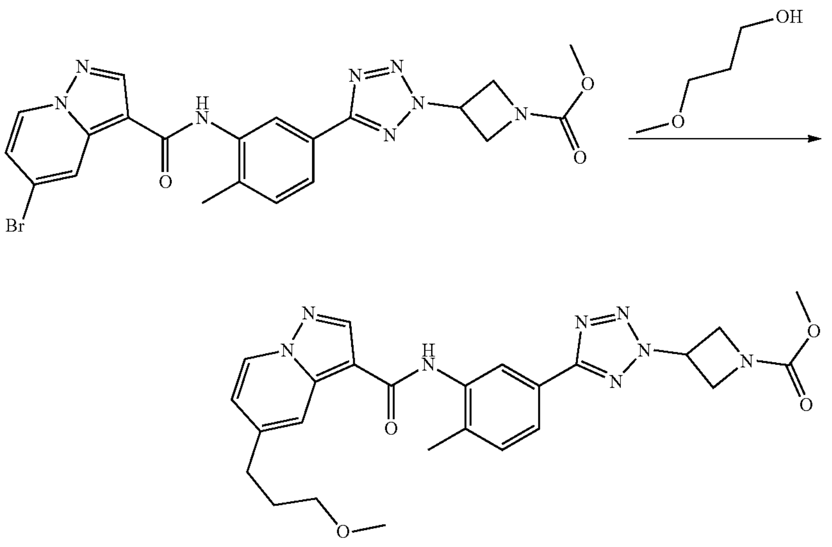

Step 1: Synthesis of 5-bromo-N-(2-methyl-5-(4-methyl-2H-1,2,3-triazol-2-yl)phenyl)pyrazolo[1,5-a]pyridine-3-carboxamide The title compound was obtained as an off-white solid, 199 mg, 90% yield from 2-methyl-4-(4-methyl-2H-1,2,3-triazol-2-yl)aniline and 5-bromopyrazolo[1,5-a]pyridine-3-carbonyl chloride following the procedure described in Example 27, step 1. LCMS m/z=411 $[M+H]^+$ NHC-1 (85.7 mg, 0.217 mmol) was added to 3-methoxypropan-1-ol (24.5 mg, 0.27 mmol) in t-BuOMe (4 mL) at rt, the mixture flushed with $N_2$, then pyridine (16.0 mg, 0.27 mmol) in t-BuOMe (4 mL) were added and the reaction mixture stirred for 10 mins to give Solution 1.

A mixture of Intermediate 11 (70 mg, 0.14 mmol), $Ir(ppy)_2(dtbbpy)PF_6$ (12.4 mg, 0.27 mmol), $NiBr_2(dtbbpy)$ (15 mg, 0.32 mmol) and quinuclidine (30.1 mg, 0.27 mmol) in DMA (5 mL) was purged with $N_2$ at rt. Solution 1 was filtered and then added and the reaction mixture stirred under blue LED lights for 2 h. The mixture was diluted with EtOAc (100 mL) and washed with brine (50 mL×2), the organic layer was dried over $Na_2SO_4$ and concentrated under vacuum. The residue was purified by prep-TLC with DCM: MeOH=25:1. The product was further purified by prep-HPLC, Method B 27% to 47% gradient, to give the title compound (3.4 mg) as an off-white solid. LCMS: m/z=505 $[M+H]^+$; 1H NMR (400 MHz, DMSO-$d_6$) δ 9.69 (s, 1H), 8.78-8.71 (m, 2H), 8.19 (d, 1H), 8.04 (dd, 1H), 7.87 (dd, 1H), 7.48 (d, 1H), 7.01 (dd, 1H), 5.91 (tt, 1H), 4.57 (s, 2H), 4.38 (s, 2H), 3.63 (s, 3H), 3.34 (s, 2H), 3.24 (s, 3H), 2.79-2.71 (m, 2H), 2.36 (s, 3H), 1.93-1.81 (m, 2H).

Example 59

N-(5-(2-(3,3-difluorocyclobutyl)-2H-tetrazol-5-yl)-4-fluoro-2-methylphenyl)-5-morpholinopyrazolo[1,5-a]pyridine-3-carboxamide

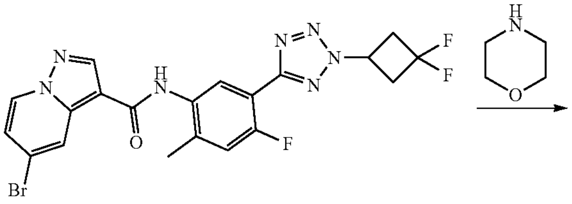

-continued

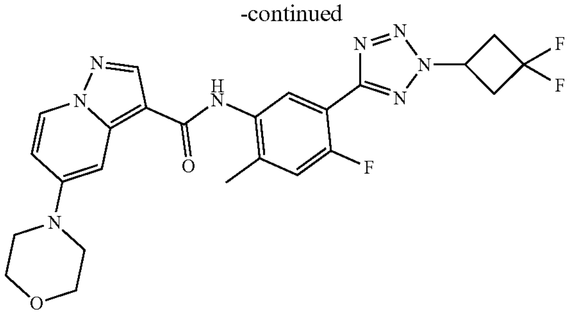

To a stirred solution of Intermediate 7 (200 mg, 0.40 mmol) in dioxane (5 mL) were added morpholine (68.8 mg, 0.79 mmol), $Cs_2CO_3$ (257 mg, 0.79 mmol), RuPhos (36.8 mg, 0.08 mmol) and RuPhos Pd G3 (33 mg, 0.04 mmol) and the reaction was stirred at 80° C. for 3 h under $N_2$. The mixture was diluted with EtOAc (50 mL) and water (50 mL), the aqueous phase was extracted with EtOAc (3×40 mL) and the combined organic phase was washed with brine (50 mL). The organic layer was dried over $Na_2SO_4$ and concentrated under vacuum. The crude product was purified by Prep-HPLC Method F, 43% to 58% gradient, to give the title compound (33 mg, 16%) as a white solid. LCMS: m/z=513 $[M+H]^+$. $^1H$ NMR (400 MHz, DMSO-$d_6$) δ 9.52 (s, 1H), 8.63-8.56 (m, 2H), 8.10 (d, 1H), 7.43-7.33 (m, 2H), 6.99 (dd, 1H), 5.62 (dd, 1H), 3.76 (t, 4H), 3.50-3.42 (m, 4H), 3.29 (t, 4H), 2.35 (s, 3H).

Examples 60 to 64

The compounds in the following table were prepared from the appropriate 5-bromopyrazolo[1,5-a]pyridine and amine following a similar procedure to that described in Example 59.

| Compound No | Name, Structure, Starting materials (SM), HPLC, Yield | Data |
|---|---|---|
| 60 | N-(5-(2-(3,3-difluorocyclobutyl)-2H-tetrazol-5-yl)-2-methylphenyl)-5-(3-hydroxyazetidin-1-yl)pyrazolo[1,5-a]pyridine-3-carboxamide<br>SM: Intermediate 4 and azetidin-3-ol<br>HPLC Method C, 25% to 55% gradient. 16.6 mg, 28% as a white solid. | LCMS: m/z = 481 $[M + H]^+$. $^1H$ NMR (400 MHz, DMSO-$d_6$) δ 9.38 (s, 1H), 8.58-8.51 (m, 2H), 8.19 (d, 1H), 7.83 (dd, 1H), 7.45 (d, 1H), 6.85 (d, 1H), 6.42 (dd, 1H), 5.78 (d, 1H), 5.60 (ddt, 1H), 4.61 (ddd, 1H), 4.21 (dd, 2H), 3.69 (dd, 2H), 3.44 (tdt, 4H), 2.42 (s, 1H), 2.35 (s, 3H). |
| 61 | N-(5-(2-(3,3-difluorocyclobutyl)-2H-tetrazol-5-yl)-2-methylphenyl)-5-(4-hydroxy-4-methylpiperidin-1-yl)pyrazolo[1,5-a]pyridine-3-carboxamide<br>SM: Intermediate 4 and 4-methylpiperidin-4-ol.<br>HPLC Method C, 25% to 55% gradient. White solid, 14.4 mg, 22% yield | LCMS: m/z = 523 $[M + H]^+$. $^1H$ NMR (400 MHz, DMSO-$d_6$) δ 9.42 (s, 1H), 8.57 (s, 1H), 8.52 (d, 1H), 8.18 (d, 1H), 7.83 (dd, 1H), 7.46 (d, 1H), 7.34 (d, 1H), 6.96 (dd, 1H), 5.65-5.55 (m, 1H), 4.42 (s, 1H), 3.60-3.36 (m, 6H), 3.33-3.24 (m, 2H), 2.35 (s, 3H), 1.57 (d, 4H), 1.15 (s, 3H). |
| 62 | (S)-N-(5-(2-(3,3-difluorocyclobutyl)-2H-tetrazol-5-yl)-2-methylphenyl)-5-(3-hydroxypyrrolidin-1-yl)pyrazolo[1,5-a]pyridine-3-carboxamide<br>SM: Intermediate 4 and (3S)-pyrrolidin-3-ol.<br>HPLC method C, 27% to 55% gradient White solid, 42.9 mg, 42.4%. | LCMS: m/z = 495 $[M + H]^+$, $^1H$ NMR (400 MHz, DMSO-$d_6$) δ 9.34 (s, 1H), 8.56-8.49 (m, 2H), 8.20 (d, 1H), 7.83 (dd, 1H), 7.45 (d, 1H), 6.94 (d, 1H), 6.61 (dd, 1H), 5.65-5.55 (m, 1H), 5.07 (d, 1H), 4.44 (s, 1H), 3.51 (dd, 1H), 3.46-3.35 (m, 1H), 3.21 (d, 1H), 2.36 (s, 3H), 2.14-2.01 (m, 1H), 1.98-1.92 (m, 1H). |
| 63 | N-(2-chloro-5-(2-(3,3-difluorocyclobutyl)-2H-tetrazol-5-yl)-4-fluorophenyl)-5- | LCMS: m/z = 533 $[M + H]^+$, $^1H$ NMR (400 MHz, DMSO-$d_6$) δ |

-continued

| Compound No | Name, Structure, Starting materials (SM), HPLC, Yield | Data |
|---|---|---|
| | morpholinopyrazolo[1,5-a]pyridine-3-carboxamide<br>SM: Intermediate 8 and morpholine<br>Prep-HPLC Method B, 35% to 65% gradient<br>35.9 mg, 35% as a white solid. | 9.69 (s, 1H), 8.64-8.58 (m, 2H), 8.36 (d, 1H), 7.84 (d, 1H), 7.35 (d, 1H), 7.01 (dd, 1H), 5.68-5.60 (m, 1H), 3.76 (t, 4H), 3.44 (ddd, 4H), 3.32-3.25 (m, 4H). |
| 64 | N-(4-fluoro-2-methyl-5-(2-((1s,3s)-3-(trifluoromethyl)cyclobutyl)-2H-tetrazol-5-yl)phenyl)-5-(3-hydroxy-3-methylazetidin-1-yl)pyrazolo[1,5-a]pyridine-3-carboxamide<br>SM: Intermediate 9 and 3-methylazetidin-3-ol<br>HPLC Method C, 36% to 61% gradient<br>7 mg; 14% as a white solid. | LCMS: m/z = 545 [M + H]$^+$, $^1$H NMR (400 MHz, DMSO-$d_6$) δ 9.43 (s, 1H), 8.57-8.51 (m, 2H), 8.07 (d, 1H), 7.38 (d, 1H), 6.84 (d, 1H), 6.43 (dd, 1H), 5.69 (s, 1H), 5.59 (p, 1H), 3.88 (d, 2H), 3.78 (d, 2H), 3.31-3.22 (m, 1H), 2.97-2.74 (m, 4H), 2.34 (s, 3H), 1.46 (s, 3H). |

Example 65 methyl 3-(5-(3-(5-(3-hydroxy-3-methylbutoxy)pyrazolo[1,5-a]pyridine-3-carboxamido)-4-methylphenyl)-2H-tetrazol-2-yl)azetidine-1-carboxylate

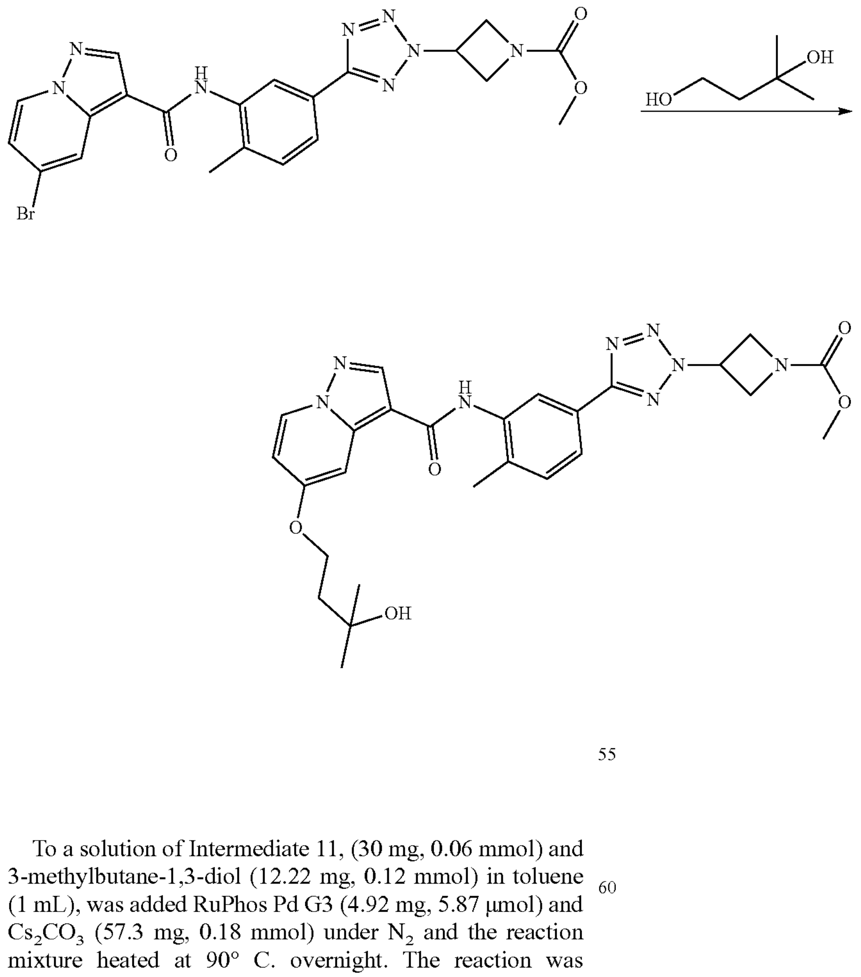

To a solution of Intermediate 11, (30 mg, 0.06 mmol) and 3-methylbutane-1,3-diol (12.22 mg, 0.12 mmol) in toluene (1 mL), was added RuPhos Pd G3 (4.92 mg, 5.87 μmol) and $Cs_2CO_3$ (57.3 mg, 0.18 mmol) under $N_2$ and the reaction mixture heated at 90° C. overnight. The reaction was quenched with water and extracted with EtOAc. The residue was purified by reverse phase HPLC and then prep-TLC to yield the title compound (2.2 mg, 7.0%). LCMS m/z=535 [M+H]$^+$

Example 66 methyl 3-(5-(4-methyl-3-(5-(4-methylpiperazin-1-yl)pyrazolo[1,5-a]pyridine-3-carboxamido)phenyl)-2H-tetrazol-2-yl)azetidine-1-carboxylate

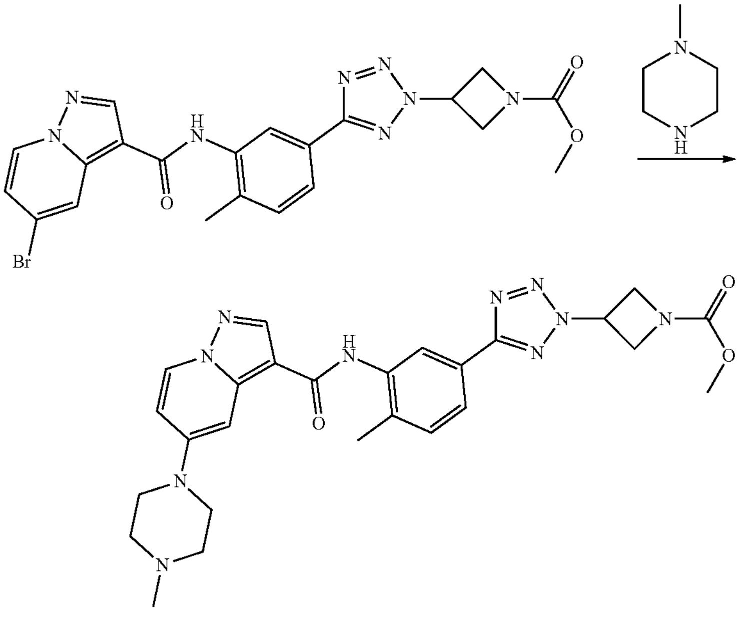

A mixture of Intermediate 11, (70 mg, 0.14 mmol), 1-methylpiperidine (21 mg, 0.21 mol), RuPhos Pd G3 (5.73 mg, 0.07 mmol) and $Cs_2CO_3$ (134 mg, 0.41 mmol) in dioxane (1 mL) was stirred under $N_2$ at 90° C. for 1 h. The reaction was diluted with EtOAc, the mixture filtered through Celite® and the filtrate evaporated under reduced pressure. The crude product was purified by reverse phase chromatography using ISCO (5 to 100% MeCN/water containing 0.1% TFA) and the product partitioned between 10% MeOH/DCM and aq. $NaHCO_3$. The organic layer was dried over $Na_2SO_4$, filtered and evaporated under reduced pressure to give the title compound, 45.8 mg as a white foam. LCMS m/z=531 $[M+H]^+$ 1H NMR (500 MHz, DMSO-$d_6$) δ 9.44 (s, 1H), 8.59 (d, 1H), 8.58-8.55 (m, 1H), 8.22 (d, 1H), 7.88-7.81 (m, 1H), 7.50-7.44 (m, 1H), 7.37 (t, 1H), 6.99 (dt, 1H), 5.92 (tp, 1H), 4.57 (t, 2H), 4.39 (d, 2H), 3.64 (d, 3H), 2.47 (t, 4H), 2.37 (s, 3H), 2.24 (s, 3H). 4 piperazine protons buried under the DMSO peak

Examples 67 to 84

The compounds in the following table were prepared from the appropriate bromopyrazolo[1,5-a]pyridine, Intermediates 4, 11, 14, or 18 and amine, following a similar procedure, to that described in Example 66 with alternative purification conditions described in the table below.

| Compound No | Name, Structure, Starting materials, Yield | Data |
|---|---|---|
| 67 | methyl 3-(5-(3-(5-(3,3-difluoropyrrolidin-1-yl)pyrazolo[1,5-a]pyridine-3-carboxamido)-4-methylphenyl)-2H-tetrazol-2-yl)azetidine-1-carboxylate<br>SM: Intermediate 11 and 3,3-difluoropyrrolidine<br>HPLC Method B, 35% to 55% gradient.<br>8.6 mg, 8.3% as a white solid. | LCMS: m/z = 538 $[M + H]^+$; 1H NMR (400 MHz, DMSO-$d_6$) δ 9.40 (s, 1H), 8.66-8.56 (m, 2H), 8.22 (d, 1H), 7.84 (dd, 1H), 7.46 (d, 1H), 7.05 (d, 1H), 6.68 (dd, 1H), 5.97-5.86 (m, 1H), 4.56 (s, 2H), 4.38 (s, 2H), 3.87 (t, 2H), 3.67-3.58 (m, 5H), 2.59 (tt, 2H), 2.36 (s, 3H). |
| 68 | methyl (S)-3-(5-(3-(5-(2-(hydroxymethyl)morpholino)pyrazolo[1,5-a]pyridine-3-carboxamido)-4-methylphenyl)-2H-tetrazol-2-yl)azetidine-1-carboxylate<br>SM: Intermediate 11 and ((2S)-morpholin-2-yl)methanol<br>prep-TLC with DCM:MeOH = 20:1<br>9.9 mg, 9.33% as a white solid | LCMS: m/z = 548 $[M + H]^+$; 1H NMR (400 MHz, DMSO-$d_6$) δ 9.49 (s, 1H), 8.64-8.57 (m, 2H), 8.20 (d, 1H), 7.88-7.82 (m, 1H), 7.46 (d, 1H), 7.39 (d, 1H), 7.00 (dd, 1H), 5.91 (m, 1H), 4.88 (t, 1H), 4.56 (s, 2H), 4.38 (s, 2H), 3.98 (d, 1H), 3.72 (m, 3H), 3.63 (s, 3H), 3.57-3.42 (m, 3H), 2.88-2.78 (m, 1H), 2.61 (t, 1H), 2.36 (s, 3H). |

-continued

| Compound No | Name, Structure, Starting materials, Yield | Data |
|---|---|---|
| 69 | methyl 3-(5-(4-methyl-3-(5-morpholinopyrazolo[1,5-a]pyridine-3-carboxamido)phenyl)-2H-tetrazol-2-yl)azetidine-1-carboxylate<br>SM: Intermediate 11 and morpholine<br>53.5 mg, 70.3% of white foam | LCMS m/z = 518 $[M + H]^+$ 1H NMR (500 MHz, DMSO-$d_6$) δ 9.45 (s, 1H), 8.60 (dd, 2H), 8.22 (s, 1H), 7.88-7.82 (m, 1H), 7.47 (d, 1H), 7.39 (t, 1H), 7.00 (dt, 1H), 5.92 (ttd, 1H), 4.57 (t, 2H), 4.45-4.33 (m, 2H), 3.77 (t, 4H), 3.64 (d, 3H), 3.29 (t, 4H), 2.37 (d, 3H) |
| 70 | methyl (S)-3-(5-(3-(5-(3-hydroxypiperidin-1-yl)pyrazolo[1,5-a]pyridine-3-carboxamido)-4-methylphenyl)-2H-tetrazol-2-yl)azetidine-1-carboxylate<br>SM: Intermediate 11 and (S)-piperidin-3-ol hydrochloride<br>30.7 mg, 39.3% yield as off-white solid. | LCMS m/z = 532 $[M + H]^+$<br>1H NMR (500 MHz, DMSO-$d_6$) δ 9.41 (s, 1H), 8.57 (d, 1H), 8.52 (d, 1H), 8.21 (s, 1H), 7.85 (d, 1H), 7.46 (d, 1H), 7.35 (d, 1H), 6.93 (d, 1H), 5.91 (dt, 1H), 4.96-4.88 (m, 1H), 4.57 (t, 2H), 4.39 (t, 2H), 3.77-3.68 (m, 1H), 3.68-3.56 (m, 5H), 2.95 (t, 1H), 2.85-2.77 (m, 1H), 2.37 (s, 3H), 1.91 (dd, 1H), 1.79 (d, 1H), 1.53 (q, 1H), 1.46-1.34 (m, 1H). |
| 71 | methyl (R)-3-(5-(3-(5-(3-hydroxypiperidin-1-yl)pyrazolo[1,5-a]pyridine-3-carboxamido)-4-methylphenyl)-2H-tetrazol-2-yl)azetidine-1-carboxylate<br>SM: Intermediate 11 and (R)-piperidin-3-ol hydrochloride<br>off-white solid, 32.8 mg, 42.1% yield | LCMS m/z = 532 $[M + H]^+$<br>1H NMR (500 MHz, DMSO-$d_6$) δ 9.41 (s, 1H), 8.57 (d, 1H), 8.52 (dd, 1H), 8.21 (s, 1H), 7.85 (d, 1H), 7.46 (d, 1H), 7.35 (d, 1H), 6.93 (d, 1H), 5.92 (dt, 1H), 4.97-4.88 (m, 1H), 4.57 (t, 2H), 4.39 (d, 2H), 3.72 (d, 1H), 3.64 (d, 5H), 3.01-2.91 (m, 1H), 2.86-2.77 (m, 1H), 2.37 (s, 3H), 1.95-1.86 (m, 1H), 1.79 (d, 1H), 1.53 (q, 1H), 1.39 (q, 1H). |
| 72 | methyl 3-(5-(4-methyl-3-(5-(4-(methyl-d3)piperazin-1-yl)pyrazolo[1,5-a]pyridine-3-carboxamido)phenyl)-2H-tetrazol-2-yl)azetidine-1-carboxylate<br>SM: Intermediate 11 and 1-(methyl-$d_3$)piperazine<br>white solid 19.4 mg, 25%. | LCMS m/z = 534 $[M + H]^+$, $^1H$ NMR (500 MHz, DMSO-$d_6$) δ 9.44 (s, 1H), 8.59 (s, 1H), 8.56 (d, 1H), 8.22 (s, 1H), 7.85 (d, 1H), 7.47 (d, 1H), 7.37 (d, 1H), 6.99 (d, 1H), 5.92 (td, 1H), 4.57 (d, 2H), 4.39 (t, 2H), 3.63 (s, 3H), 2.47 (t, 4H), 2.37 (s, 3H). 4 piperazine protons buried under the water peak. |
| 73 | methyl 3-(5-(3-(5-(4-(2,2-difluoroethyl)piperazin-1-yl)pyrazolo[1,5-a]pyridine-3-carboxamido)-4-methylphenyl)-2H-tetrazol-2-yl)azetidine-1-carboxylate<br>SM; Intermediate 11 and 1-(2,2-difluoromethyl)piperazine<br>6.3 mg, 11.1% yield | LCMS m/z = 581.2 $[M + H]^+$ $^1H$ NMR (500 MHz, DMSO) δ 9.37 (s, 1H), 8.54-8.44 (m, 2H), 8.13 (s, 1H), 7.78 (d, J = 7.9 Hz, 1H), 7.39 (d, J = 7.9 Hz, 1H), 7.29 (d, J = 3.3 Hz, 1H), 6.91 (d, J = 7.8 Hz, 1H), 6.31-5.96 (m, 1H), 5.84 (d, J = 9.9 Hz, 1H), 4.49 (d, J = 9.1 Hz, 2H), 4.32 (d, J = 8.2 Hz, 2H), 3.56 (d, J = 2.5 Hz, 3H), 2.74 (t, J = 15.6 Hz, 2H), 2.62 (s, 4H), 2.29 (d, J = 2.5 Hz, 3H). A peaks was buried in solvent peak. |
| 74 | methyl 3-(5-(4-methyl-3-(5-(4-(oxetan-3-yl)piperazin-1-yl)pyrazolo[1,5-a]pyridine-3-carboxamido)phenyl)-2H-tetrazol-2-yl)azetidine-1-carboxylate<br>SM: Intermediate 11 and 1-(oxetan-3-yl)piperazine | LCMS m/z = 573.1 $[M + H]^+$. $^1H$ NMR (500 MHz, DMSO-$d_6$) δ 9.37 (s, 1H), 8.54-8.47 (m, 2H), 8.13 (s, 1H), 7.78 (d, 1H), 7.39 (d, 1H), 7.30 (d, 1H), 6.92 (d, 1H), 5.84 (t, 1H), 4.53-4.44 (m, 4H), 4.44-4.38 (m, 2H), 4.32 (s, 2H), 3.56 (t, 3H), 3.40 (h, 1H), 3.28 (t, 4H), 2.36 (t, 4H), 2.29 (d, 3H). |
| 75 | methyl (R)-3-(5-(3-(5-(hexahydropyrrolo[1,2-a]pyrazin-2(1H)-yl)pyrazolo[1,5-a]pyridine-3-carboxamido)-4-methylphenyl)-2H-tetrazol-2-yl)azetidine-1-carboxylate<br>SM: Intermediate 11 and (R)-octahydropyrrolo[1,2-a]pyrazine<br>17.1 mg, 31.4%. | LCMS m/z = 557 $[M + H]^+$. $^1H$ NMR (500 MHz, DMSO-$d_6$) δ 9.38-9.34 (m, 1H), 8.54-8.45 (m, 2H), 8.14 (s, 1H), 7.78 (d, 1H), 7.42-7.36 (m, 1H), 7.30 (d, 1H), 6.93 (dd, 1H), 5.84 (d, 1H), 4.50 (t, 2H), 4.35-4.28 (m, 2H), 3.89 (d, 1H), 3.75 (d, 1H), 3.56 (t, 3H), 3.05-2.92 (m, 2H), 2.82 (t, 1H), 2.49 (t, 1H), 2.29 (d, 3H), 2.20-2.11 (m, 1H), 1.99 (dq, 2H), 1.86-1.75 (m, 1H), 1.70-1.56 (m, 2H), 1.32 (h, 1H). |
| 76 | ethyl 3-(5-(4-methyl-3-(5-(4-methylpiperazin-1-yl)pyrazolo[1,5-a]pyridine-3-carboxamido)phenyl)-2H-tetrazol-2-yl)azetidine-1-carboxylate | LCMS m/z = 545 $[M + H]^+$; 1H NMR (500 MHz, DMSO-$d_6$) δ 9.43 (s, 1H), 8.63-8.54 (m, 2H), 8.22 (s, 1H), 7.85 (d, 1H), 7.47 (d, 1H), 7.37 |

-continued

| Compound No | Name, Structure, Starting materials, Yield | Data |
|---|---|---|
| | SM: Intermediate 14 and 1-methylpiperazine<br>55.1 mg, 66.4% yield as a white foam | (d, 1H), 6.99 (d, 1H), 5.96-5.86 (m, 1H), 4.57 (t, 2H), 4.39 (d, 2H), 4.15-4.04 (m, 2H), 2.48 (d, 4H), 2.37 (s, 3H), 2.24 (s, 3H), 1.21 (t, 3H) |
| 77 | ethyl 3-(5-(4-methyl-3-(5-morpholinopyrazolo[1,5-a]pyridine-3-carboxamido)phenyl)-2H-tetrazol-2-yl)azetidine-1-carboxylate<br>SM: Intermediate 14 and morpholine<br>ISCO chromatography (0 to 8% MeOH/DCM)<br>61.4 mg, 76.9% of pale-yellow foam | LCMS m/z = 532 $[M + H]^+$;<br>1H NMR (500 MHz, DMSO-$d_6$) δ 9.45 (d, 1H), 8.60 (dd, 2H), 8.22 (s, 1H), 7.85 (d, 1H), 7.47 (dd, 1H), 7.39 (d, 1H), 7.03-6.97 (m, 1H), 5.91 (td, 1H), 4.56 (d, 2H), 4.38 (s, 2H), 4.08 (dt, 2H), 3.77 (s, 4H), 3.29 (p, 4H), 2.37 (s, 3H), 1.21 (tt, 3H) |
| 78 | (R)-N-(5-(2-(3,3-difluorocyclobutyl)-2H-tetrazol-5-yl)-2-methylphenyl)-5-(3-hydroxypyrrolidin-1-yl)pyrazolo[1,5-a]pyridine-3-carboxamide<br>SM: Intermediate 4 and (3R)-pyrrolidin-3-ol<br>HPLC Method F, 37% to 52% gradient.<br>47.9 mg, 47.4% as a white solid | LCMS: m/z = 495 $[M + H]^+$, 1H NMR (400 MHz, DMSO-$d_6$) δ 9.34 (s, 1H), 8.56-8.49 (m, 2H), 8.20 (d, 1H), 7.83 (dd, 1H), 7.45 (d, 1H), 6.94 (d, 1H), 6.61 (dd, 1H), 5.60 (q, 1H), 5.07 (d, 1H), 4.43 (s, 1H), 3.55-3.35 (m, 4H), 3.21 (d, 1H), 2.36 (s, 3H), 2.14-2.01 (m, 2H). |
| 79 | N-(5-(2-(3,3-difluorocyclobutyl)-2H-tetrazol-5-yl)-2-methylphenyl)-5-morpholinopyrazolo[1,5-a]pyridine-3-carboxamide<br>SM: Intermediate 4 and morpholine<br>HPLC Method J, 30% to 65% gradient,<br>30.1 mg, 30.0% as a white solid. | LCMS: m/z = 495 $[M + H]^+$, $^1$H NMR (300 MHz, DMSO-$d_6$) δ 9.45 (s, 1H), 8.59 (d, 2H), 8.18 (d, 1H), 7.82 (dd, 1H), 7.45 (d, 1H), 7.37 (d, 1H), 6.98 (dd, 1H), 5.59 (q, 1H), 3.75 (t, 4H), 3.49-3.34 (m, 4H), 3.27 (d, 4H), 2.35 (s, 3H). |
| 80 | methyl 3-(2-(4-methyl-3-(5-morpholinopyrazolo[1,5-a]pyridine-3-carboxamido)phenyl)-2H-1,2,3-triazol-4-yl)azetidine-1-carboxylate<br>SM: Intermediate 18 and morpholine<br>ISCO column (0 to 100% EtOAc/hexane)<br>61.2 mg, 67%, as off-white foam | LCMS m/z = 517 $[M + H]^+$; 1H NMR (500 MHz, DMSO-$d_6$) δ 9.42 (s, 1H), 8.60 (dd, 2H), 8.19 (s, 1H), 8.15 (s, 1H), 7.74 (d, 1H), 7.43 (d, 1H), 7.39 (d, 1H), 7.00 (d, 1H), 4.35 (br. s, 2H), 4.08 (br. s, 3H), 3.77 (t, 4H), 3.60 (s, 3H), 3.31-3.26 (m, 4H), 2.34 (s, 3H) |
| 81 | methyl 3-(2-(4-methyl-3-(5-(4-methylpiperazin-1-yl)pyrazolo[1,5-a]pyridine-3-carboxamido)phenyl)-2H-1,2,3-triazol-4-yl)azetidine-1-carboxylate<br>SM: Intermediate 18 and 1-methylpiperazine<br>reverse phase ISCO (5 to 100% MeCN/water containing 0.1% TFA) then basify<br>53 mg as a white foam | LCMS m/z = 530 $[M + H]^+$ 1H NMR (500 MHz, DMSO-$d_6$) δ 9.40 (d, 1H), 8.61-8.54 (m, 2H), 8.19 (d, 1H), 8.15 (d, 1H), 7.74 (d, 1H), 7.46-7.40 (m, 1H), 7.37 (d, 1H), 6.99 (d, 1H), 4.35 (br s, 2H), 4.08 (br s, 3H), 3.60 (s, 3H), 2.48 (d, 4H), 2.34 (s, 3H), 2.24 (s, 3H). |
| 82 | methyl 3-(2-(4-methyl-3-(5-(4-(methyl-d3)piperazin-1-yl)pyrazolo[1,5-a]pyridine-3-carboxamido)phenyl)-2H-1,2,3-triazol-4-yl)azetidine-1-carboxylate<br>SM: Intermediate 18 and 1-(methyl-$d_3$)piperazine<br>Off-white solid, 44.5 mg, 57% | LCMS m/z = 533 $[M + H]^+$; $^1$H NMR (500 MHz, DMSO-$d_6$) δ 9.40 (s, 1H), 8.64-8.53 (m, 2H), 8.18 (s, 1H), 8.15 (s, 1H), 7.74 (d, 1H), 7.43 (d, 1H), 7.37 (s, 1H), 6.99 (d, 1H), 4.35 (s, 2H), 4.15-4.00 (m, 3H), 3.60 (s, 3H), 2.34 (s, 3H). Piperazine protons obscured by DMSO and water peaks. |
| 83 | methyl 3-(2-(4-methyl-3-(5-(4-(oxetan-3-yl)piperazin-1-yl)pyrazolo[1,5-a]pyridine-3-carboxamido)phenyl)-2H-1,2,3-triazol-4-yl)azetidine-1-carboxylate<br>SM: Intermediate 18 and 1-(oxetan-3-yl)piperazine<br>40.1 mg, 59.7% yield as a white solid. | LCMS m/z = 572 $[M + H]^+$<br>1H NMR (500 MHz, DMSO-$d_6$) δ 9.41 (s, 1H), 8.62-8.56 (m, 2H), 8.18 (d, 1H), 8.15 (s, 1H), 7.74 (d, 1H), 7.43 (d, 1H), 7.37 (d,), 7.00 (d, 1H), 4.58 (t, 2H), 4.49 (t, 2H), 4.35 (s, 2H), 4.08 (q, 3H), 3.60 (s, 3H), 3.47 (p, 1H), 3.36 (t, 4H), 3.19-3.17 (m, 1H), 2.44 (t, 4H), 2.34 (s, 3H) |
| 84 | methyl 3-(2-(3-(5-((2-hydroxyethyl)(methyl)amino)pyrazolo[1,5-a]pyridine-3-carboxamido)-4-methylphenyl)-2H-1,2,3-triazol-4-yl)azetidine-1-carboxylate<br>SM: Intermediate 18 and 2-(methylamino)ethan-1-ol<br>reverse phase ISCO (5 to 100% MeCN/water containing 0.1% TFA) then basify<br>yellow solid, 8.8 mg 9.9% yield | LCMS m/z = 505 $[M + H]^+$; 1H NMR (500 MHz, DMSO-$d_6$) δ 9.29 (s, 1H), 8.54 (s, 1H), 8.50 (d, 1H), 8.19 (s, 1H), 8.15 (d, 1H), 7.73 (d, 1H), 7.42 (d, 1H), 7.11 (s, 1H), 6.80 (d, 1H), 4.82-4.75 (m, 1H), 4.35 (br.s, 2H), 4.08 (br.s, 3H), 3.60 (t,), 3.54 (d, 2H), 3.05 (s, 3H), 2.34 (s, 3H) |

Example 85 methyl (S)-3-(5-(3-(5-(2-(methoxymethyl)azetidin-1-yl)pyrazolo[1,5-a]pyridine-3-carboxamido)-4-methylphenyl)-2H-tetrazol-2-yl)azetidine-1-carboxylate or methyl (R)-3-(5-(3-(5-(2-(methoxymethyl)azetidin-1-yl)pyrazolo[1,5-a]pyridine-3-carboxamido)-4-methylphenyl)-2H-tetrazol-2-yl)azetidine-1-carboxylate

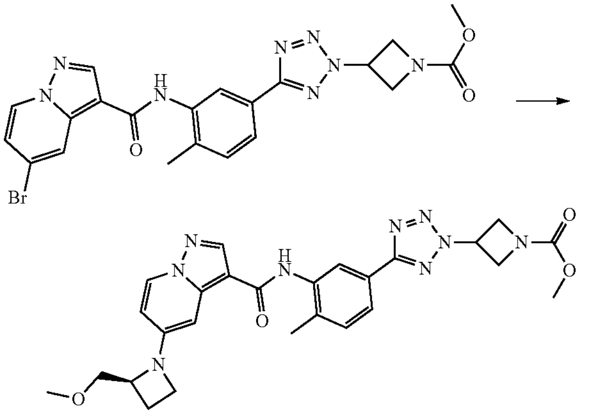

or

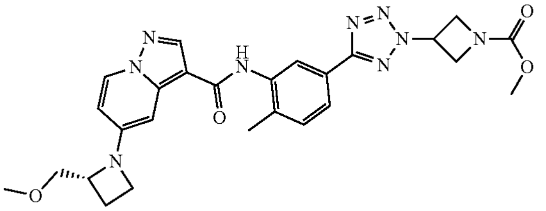

A mixture of Intermediate 11, (100 mg, 0.20 mmol), 2-(methoxymethyl)azetidine (29.5 mg, 0.29 mmol), RuPhos Pd G3 (94.4 mg, 0.29 mmol) and $Cs_2CO_3$ (17.1 mg, 0.20 mmol) in dioxane (10 mL) was stirred at 100° C. for 16 h under $N_2$. The reaction was concentrated to dryness and the residue purified by prep-TLC with DCM:MeOH=20:1. The product was separated on prep-CHIRAL-HPLC, Column: DZ-CHIRALPAK IH-3, 4.6*50 mm, 3.0 m; Mobile Phase A: Hex (0.2% DEA): (EtOH:DCM=1:1)=75:25, to afford Peak 1 (Isomer 1), methyl (S)-3-(5-(3-(5-(2-(methoxymethyl)azetidin-1-yl)pyrazolo[1,5-a]pyridine-3-carboxamido)-4-methylphenyl)-2H-tetrazol-2-yl)azetidine-1-carboxylate or methyl (R)-3-(5-(3-(5-(2-(methoxymethyl)azetidin-1-yl)pyrazolo[1,5-a]pyridine-3-carboxamido)-4-methylphenyl)-2H-tetrazol-2-yl)azetidine-1-carboxylate (12.1 mg) as a white solid. LCMS: m/z=532 $[M+H]^+$; 1H NMR (400 MHz, DMSO-$d_6$) δ 9.39 (s, 1H), 8.58-8.50 (m, 2H), 8.23-8.18 (m, 1H), 7.87-7.80 (m, 1H), 7.45 (d, 1H), 7.01 (d, 1H), 6.62 (dd, 1H), 5.92 (td, 1H), 4.56 (s, 2H), 4.38 (s, 3H), 3.97 (s, 1H), 3.73 (d, 1H), 3.63 (d, 5H), 3.36 (s, 3H), 2.35 (s, 4H), 2.17 (d, 1H).

Example 86

(S)—N-(5-(2-(3,3-difluorocyclobutyl)-2H-tetrazol-5-yl)-2-methylphenyl)-5-(3-hydroxy-3-methylpyrrolidin-1-yl)pyrazolo[1,5-a]pyridine-3-carboxamide or (R)—N-(5-(2-(3,3-difluorocyclobutyl)-2H-tetrazol-5-yl)-2-methylphenyl)-5-(3-hydroxy-3-methylpyrrolidin-1-yl)pyrazolo[1,5-a]pyridine-3-carboxamide

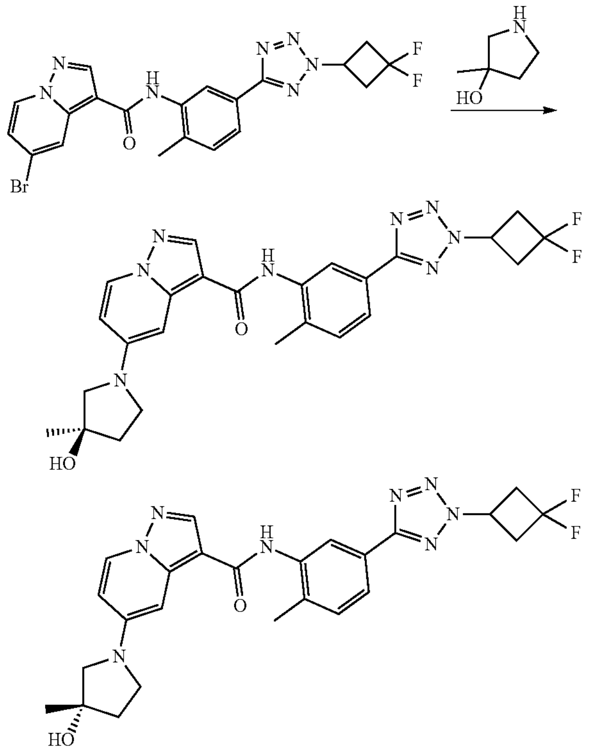

N-(5-(2-(3,3-Difluorocyclobutyl)-2H-tetrazol-5-yl)-2-methylphenyl)-5-(3-hydroxy-3-methylpyrrolidin-1-yl)pyrazolo[1,5-a]pyridine-3-carboxamide was obtained as a yellow solid, 80 mg, from Intermediate 4 and 3-methylpyrrolidin-3-ol following the procedure described in Example 85.

This was further purified by Chiral-Prep HPLC: Column: CHIRALPAK IG, 2*25 cm, 5 μm; Mobile Phase A: Hex (0.2% DEA), Mobile Phase B: EtOH:DCM=1:1; Flow rate: 20 mL/min; isocratic gradient: 50% B to afford Peak 1 (Isomer 1), 20.7 mg, as a white solid and Peak 2 (Isomer 2): (S)—N-(5-(2-(3,3-difluorocyclobutyl)-2H-tetrazol-5-yl)-2-methylphenyl)-5-(3-hydroxy-3-methylpyrrolidin-1-yl)pyrazolo[1,5-a]pyridine-3-carboxamide or (R)—N-(5-(2-(3,3-difluorocyclobutyl)-2H-tetrazol-5-yl)-2-methylphenyl)-5-(3-hydroxy-3-methylpyrrolidin-1-yl)pyrazolo[1,5-a]pyridine-3-carboxamide (21.3 mg) as a white solid. LCMS: m/z=509 $[M+H]^+$, 1H NMR (400 MHz, DMSO-$d_6$) δ 9.32 (s, 1H), 8.55-8.48 (m, 2H), 8.20 (d, 1H), 7.82 (dd, 1H), 7.45 (d, 1H), 6.91 (d, 1H), 6.58 (dd, 1H), 5.60 (ddd, 1H), 4.90 (s, 1H), 3.48-3.38 (m, 2H), 3.32 (s, 6H), 3.28 (d, 2H), 2.36 (s, 3H), 1.95 (t, 2H), 1.37 (s, 3H).

Example 87

5-((2-methoxyethyl)amino)-N-(2-methyl-5-(2-methyl-2H-tetrazol-5-yl)phenyl)pyrazolo[1,5-a]pyridine-3-carboxamide

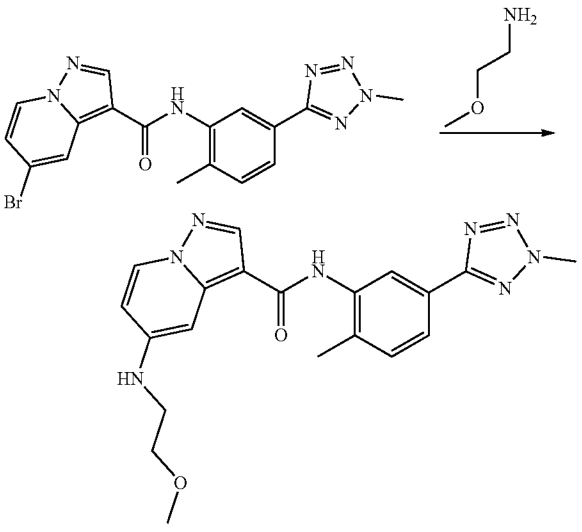

To a solution of Intermediate 13 (80 mg, 0.194 mmol) and 2-methoxyethan-1-amine (17.4 mg, 0.39 mmol) in dioxane (2 mL) were added $Cs_2CO_3$ (127 mg, 0.39 mmol), Xantphos (11.2 mg, 19.4 μmol) and $Pd_2(dba)_3$ (177 mg, 0.19 mmol) under $N_2$ and the reaction mixture stirred for 2 h at 80° C. The reaction was washed with water (50 mL) and extracted with EtOAc (3×50 mL). The organic layer was concentrated under vacuum and purified by prep-HPLC, Method C, 58% to 75% gradient, to give the title compound (36.0 mg, 45%) as a white solid. LCMS m/z=407 $[M+H]^+$, $^1H$ NMR (400 MHz, DMSO-$d_6$) δ 9.28 (s, 1H), 8.49 (s, 1H), 8.39 (d, 1H), 8.21 (d, 1H), 7.78 (dd, 1H), 7.43 (d, 1H), 6.97 (d, 1H), 6.78 (t, 1H), 6.60 (dd, 1H), 4.43 (s, 3H), 3.55 (t, 2H), 3.33-3.23 (m, 5H), 2.35 (s, 3H).

Example 88

N-(5-(2-cyclopropyl-2H-tetrazol-5-yl)-2-methylphenyl)-5-((2-methoxyethyl)amino)pyrazolo[1,5-a]pyridine-3-carboxamide

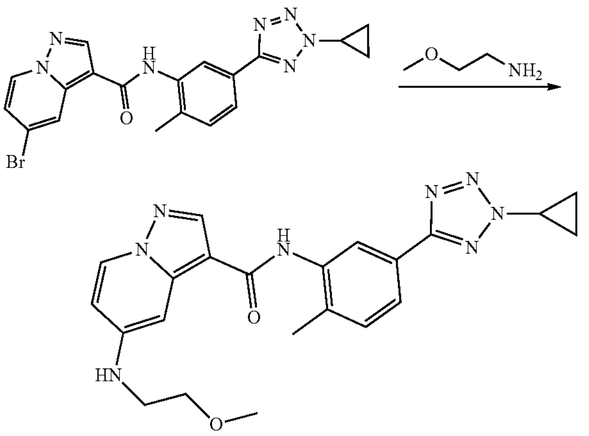

The title compound was obtained as a white solid, 45.7 mg, 30.9% from Intermediate 30 and 2-methoxyethanamine, following a similar method to that described in Example 87. The crude was purified by reverse phase HPLC Method-F, 37% to 56% gradient. LCMS: m/z=433 $[M+H]^+$ 1H NMR (400 MHz, DMSO-$d_6$) δ 9.30 (s, 1H), 8.49 (s, 1H), 8.39 (d, 1H), 8.16 (d, 1H), 7.78 (dd, 1H), 7.43 (d, 1H), 6.97 (d, 1H), 6.78 (t, 1H), 6.60 (dd, 1H), 4.47 (tt, 1H), 3.55 (t, 2H), 3.29-3.22 (m, 2H), 2.34 (s, 3H), 1.47-1.36 (m, 2H), 1.35-1.19 (m, 2H).

Example 89 methyl 3-(5-(3-(5-((2-hydroxy-2-methylpropyl)amino)pyrazolo[1,5-a]pyridine-3-carboxamido)-4-methylphenyl)-2H-tetrazol-2-yl)azetidine-1-carboxylate

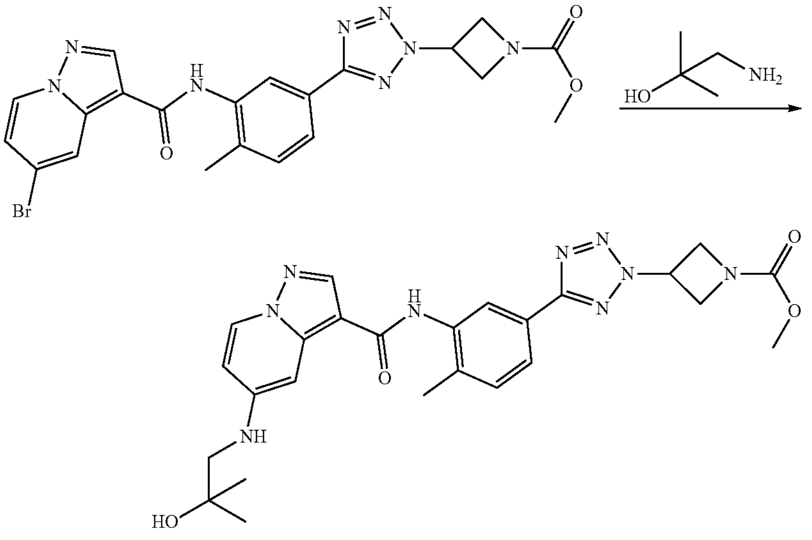

A mixture of Intermediate 11 (100 mg, 0.20 mmol), 1-amino-2-methylpropan-2-ol (52.1 mg, 0.59 mmol), $Pd_2(dba)_3$ (35.7 mg, 0.04 mmol), XantPhos (45.1 mg, 0.08 mmol) and $Cs_2CO_3$ (127 mg, 0.39 mmol) in dioxane (4 mL) was stirred at 100° C. for 2 h under $N_2$ atmosphere. The reaction was concentrated in vacuo and the residue purified by prep-TLC (EtOAc). The product was further purified by Prep-HPLC-Method C, 28% to 47% gradient, to afford the title compound (23.6 mg, 22.7%) as a white solid. LCMS: m/z=520 [M+H$^+$], 1H NMR (400 MHz, DMSO-$d_6$) δ 9.30 (s, 1H), 8.48 (s, 1H), 8.37 (d, 1H), 8.22 (d, 1H), 7.83 (dd, 1H), 7.45 (d, 1H), 7.00 (d, 1H), 6.74 (dd, 1H), 6.51 (t, 1H), 5.91 (m, 1H), 4.61 (s, 1H), 4.57 (m, 2H), 4.39 (m, 2H), 3.63 (s, 3H), 3.01 (d, 2H), 2.35 (s, 3H), 1.19 (s, 6H).

Example 90 methyl (S)-3-(5-(3-(5-(2-(hydroxymethyl)azetidin-1-yl)pyrazolo[1,5-a]pyridine-3-carboxamido)-4-methylphenyl)-2H-tetrazol-2-yl)azetidine-1-carboxylate

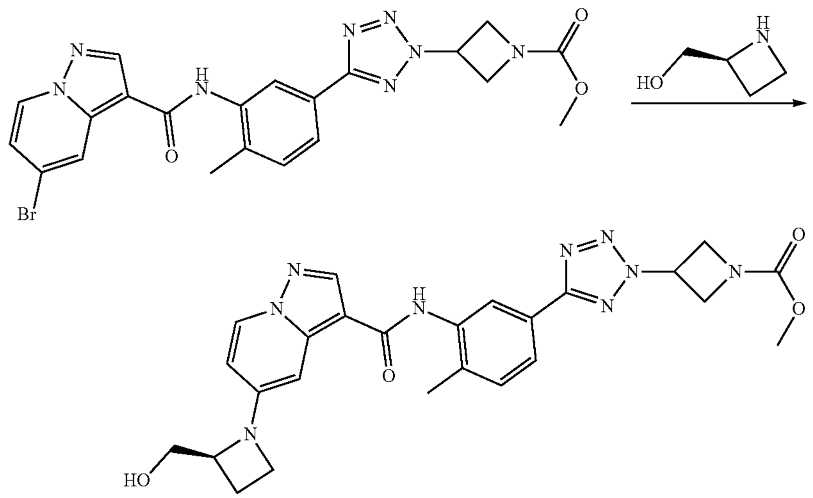

A mixture of Intermediate 11 (100 mg, 0.2 mmol), ((2S)-azetidin-2-yl)methanol (50.9 mg, 0.59 mmol), $Pd_2(dba)_3$ (35.7 mg, 0.4 mmol), XantPhos (45.1 mg, 0.08 mmol) and $Cs_2CO_3$ (127 mg, 0.39 mmol) in dioxane (4 mL) was stirred at 100)C for 2 h under $N_2$. The reaction was concentrated in vacuo and the residue purified by prep-TLC (EtOAc). The crude product was purified by Prep-HPLC-Method C, 19% to 49% gradient, to afford the title compound (32.3 mg, 31.1%) as an off-white solid. LCMS: m/z=518 [M+H]$^+$, 1H NMR (400 μMHz, DMSO-$d_6$) δ 9.36 (s, 1H), 8.57-8.49 (m, 2H), 8.20 (d, 1H), 7.83 (dd, 1H), 7.45 (d, 1H), 6.98 (d, 1H), 6.67 (dd, 1H), 5.93-5.89 (m, 1H), 5.11 (t, 1H), 4.56 (s, 2H), 4.38 (s, 2H), 4.25 (s, 1H), 4.01-3.91 (m, 1H), 3.73-3.67 (3, 3H), 3.63 (s, 3H), 2.35 (s, 4H), 2.18-2.16 (2, 1H).

Examples 91 to 113

The compounds in the following table were prepared from the appropriate Intermediates and amine, following a similar procedure to that described in Example 90. Alternative purification conditions are highlighted in the table below.

| Compound No | Name, Starting materials (SM), HPLC Conditions, Yield | Data |
|---|---|---|
| 91 | methyl (R)-3-(5-(3-(5-(2-(hydroxymethyl)morpholino)pyrazolo[1,5-a]pyridine-3-carboxamido)-4-methylphenyl)-2H-tetrazol-2-yl)azetidine-1-carboxylate<br>SM: Intermediate 11 and (2R)-morpholin-2-yl)methanol<br>Prep-HPLC Method-A, 22% to 42% gradient<br>8.5 mg, 7.9% as a white solid | LCMS: m/z = 548 [M + H]$^+$, 1H NMR (400 MHz, DMSO-$d_6$) δ 9.48 (s, 1H), 8.60 (d, 2H), 8.20 (d, 1H), 7.85 (dd, 1H), 7.46 (d, 1H), 7.39 (d, 1H), 6.99 (dd, 1H), 5.94-5.88 (m, 1H), 4.87 (t, 1H), 4.56 (s, 2H), 4.38 (s, 2H), 3.98 (d, 1H), 3.73 (m, 2H), 3.63 (s, 4H), 3.58-3.42 (m, |

-continued

| Compound No | Name, Starting materials (SM), HPLC Conditions, Yield | Data |
|---|---|---|
| | | 3H), 2.89-2.79 (m, 1H), 2.64-2.61 (m, 1H), 2.36 (s, 3H). |
| 92 | methyl 3-(5-(3-(5-((2,2-difluoropropyl)amino)pyrazolo[1,5-a]pyridine-3-carboxamido)-4-methylphenyl)-2H-tetrazol-2-yl)azetidine-1-carboxylate<br>SM: Intermediate 11 and 2,2-difluoropropan-1-amine<br>Prep HPLC Method-F, 35% to 57% gradient<br>37.2 mg, 45.4% as a white solid | LCMS: m/z = 526 $[M + H]^+$ 1H NMR (400 MHz, DMSO-$d_6$) δ 9.35 (s, 1H), 8.53-8.43 (m, 2H), 8.21 (d, 1H), 7.84 (dd, 1H), 7.45 (d, 1H), 7.16 (d, 1H), 7.02 (t, 1H), 6.68 (dd, 1H), 5.97-5.86 (m, 1H), 4.57 (s, 2H), 4.39 (s, 2H), 3.63 (s, 5H), 2.35 (s, 3H), 1.68 (t, 3H). |
| 93 | methyl 3-(5-(3-(5-((2-(tert-butoxy)ethyl)amino)pyrazolo[1,5-a]pyridine-3-carboxamido)-4-methylphenyl)-2H-tetrazol-2-yl)azetidine-1-carboxylate<br>SM: Intermediate 11 and 2-(tert-butoxy)ethan-1-amine<br>Prep-HPLC Method-F, 38 to 58% gradient<br>White solid, 3.5 mg, 3.3% as a white solid | LCMS: m/z = 548 $[M + H]^+$ 1H NMR (400 MHz, DMSO-$d_6$) δ 9.32 (s, 1H), 8.52-8.36 (m, 2H), 8.21 (d, 1H), 7.83 (dd, 1H), 7.45 (d, 1H), 7.00 (d, 1H), 6.70-6.57 (m, 2H), 5.91 (ddd, 1H), 4.56 (s, 2H), 4.38 (s, 2H), 3.63 (s, 3H), 3.50 (t, 2H), 3.21 (q, 2H), 2.35 (s, 3H), 1.15 (s, 9H). |
| 94 | methyl (S)-3-(5-(3-(5-((2-hydroxypropyl)amino)pyrazolo[1,5-a]pyridine-3-carboxamido)-4-methylphenyl)-2H-tetrazol-2-yl)azetidine-1-carboxylate<br>SM: Intermediate 1 and (2S)-1-aminopropan-2-ol<br>Prep-HPLC-Method C, 25% to 46% gradient<br>18.9 mg, 16.1% as a white solid | LCMS: m/z = 506 $[M + H]^+$; 1H NMR (400 MHz, DMSO-$d_6$) δ 9.32 (s, 1H), 8.48 (s, 1H), 8.38 (d, 1H), 8.21 (d, 1H), 7.83 (dd, 1H), 7.45 (d, 1H), 6.96 (d, 1H), 6.68 (t, 1H), 6.63 (dd, 1H), 5.93-5.89 (m, 1H), 4.83 (d, 1H), 4.56 (s, 2H), 4.39 (s, 2H), 3.88-3.85 (m, 1H), 3.63 (s, 3H), 3.01 (t, 2H), 2.35 (s, 3H), 1.14 (d, 3H). |
| 95 | methyl 3-(5-(4-methyl-3-(5-((oxetan-2-ylmethyl)amino)pyrazolo[1,5-a]pyridine-3-carboxamido)phenyl)-2H-tetrazol-2-yl)azetidine-1-carboxylate<br>SM: Intermediate 11 and 1-(oxetan-2-yl)methanamine<br>HPLC Method J, 33% to 45% gradient<br>54.8 mg, 45.2% as an off-white solid. | LCMS: m/z = 518 $[M + H]^+$ 1H NMR (400 MHz, DMSO-$d_6$) δ 9.32 (s, 1H), 8.50 (s, 1H), 8.40 (d, 1H), 8.21 (d, 1H), 7.83 (dd, 1H), 7.45 (d, 1H), 7.03 (d, 1H), 6.88 (t, 1H), 6.64 (dd, 1H), 5.91 (tt, 1H), 4.97-4.88 (m, 1H), 4.61-4.33 (m, 6H), 3.63 (s, 3H), 3.45-3.27 (m, 2H), 2.67-2.64 (m, 1H), 2.50-2.38 (m, 1H), 2.35 (s, 3H). |
| 96 | methyl 3-(5-(3-(5-((2-methoxy-2-methylpropyl)amino)pyrazolo[1,5-a]pyridine-3-carboxamido)-4-methylphenyl)-2H-tetrazol-2-yl)azetidine-1-carboxylate<br>SM: Intermediate 11 and 2-methoxy-2-methylpropan-1-amine<br>Prep-HPLC Method A, 29% to 56% gradient<br>17.8 mg, 17.1% as a white solid. | LCMS: m/z = 534 $[M + H]^+$; 1H NMR (400 MHz, DMSO-$d_6$) δ 9.31 (s, 1H), 8.48 (s, 1H), 8.38 (d, 1H), 8.21 (d, 1H), 7.83 (dd, 1H), 7.45 (d, 1H), 7.00 (d, 1H), 6.77 (dd, 1H), 6.48 (t, 1H), 5.91 (ddd, 1H), 4.57 (s, 2H), 4.39 (s, 2H), 3.63 (s, 3H), 3.14 (s, 3H), 3.09 (d, 2H), 2.35 (s, 3H), 1.20 (s, 6H). |
| 97 | methyl (R)-3-(5-(3-(5-(3-(dimethylamino)pyrrolidin-1-yl)pyrazolo[1,5-a]pyridine-3-carboxamido)-4-methylphenyl)-2H-tetrazol-2-yl)azetidine-1-carboxylate<br>SM: Intermediate 11 and (3R)-N,N-dimethylpyrrolidin-3-amine<br>HPLC Method A, 21% to 50% gradient<br>23.6 mg, 22.2% as a white solid | LCMS: m/z = 545 $[M + H]^+$; 1H NMR (400 MHz, DMSO-$d_6$) δ 9.34 (s, 1H), 8.57-8.50 (m, 2H), 8.22 (d, 1H), 7.83 (dd, 1H), 7.45 (d, 1H), 6.95 (d, 1H), 6.64 (dd, 1H), 5.91 (m, 1H), 4.56 (s, 2H), 4.38 (s, 2H), 3.63 (s, 3H), 3.55 (m, 2H), 3.36 (s, 1H), 3.14 (t, 1H), 2.87-2.79 (m, 1H), 2.36 (s, 3H), 2.21 (s, 6H), 1.86 (m, 1H). |
| 98 | methyl 3-(5-(3-(5-(2-oxa-6-azaspiro[3.3]heptan-6-yl)pyrazolo[1,5-a]pyridine-3-carboxamido)-4-methylphenyl)-2H-tetrazol-2-yl)azetidine-1-carboxylate<br>SM: Intermediate 11 and 2-oxa-6- | LCMS: m/z = 530 $[M + H]^+$; 1H NMR (400 MHz, DMSO-$d_6$) δ 9.40 (s, 1H), 8.55 (d, 2H), 8.19 (d, 1H), 7.84 (dd, 1H), 7.46 (d, 1H), 6.87 (d, 1H), 6.42 (dd, 1H), 5.92 (td, |

-continued

| Compound No | Name, Starting materials (SM), HPLC Conditions, Yield | Data |
|---|---|---|
| | azaspiro[3.3]heptane 42.3 mg, 51.2% as a white solid | 1H), 4.74 (s, 4H), 4.56 (d, 2H), 4.39 (s, 2H), 4.16 (s, 4H), 3.63 (s, 3H), 2.35 (s, 3H). |
| 99 | Methyl 3-(5-(4-methyl-3-(5-(3-(methylsulfonyl)azetidin-1-yl)pyrazolo[1,5-a]pyridine-3-carboxamido)phenyl)-2H-tetrazol-2-yl)azetidine-1-carboxylate SM: Intermediate 11 and 3-methanesulfonylazetidine HPLC Method B, 21% to 46% gradient 14.1 mg, 12.8% as a white solid. | LCMS: m/z = 566 $[M + H]^+$; 1H NMR (400 MHz, DMSO-$d_6$) δ 9.43 (s, 1H), 8.65-8.57 (m, 2H), 8.22 (d, 1H), 7.84 (dd, 1H), 7.46 (d, 1H), 6.95 (d, 1H), 6.51 (dd, 1H), 5.91 (ddd, 1H), 4.56 (s, 2H), 4.46 (d, 1H), 4.38 (s, 2H), 4.31 (t, 2H), 4.21 (dd, 2H), 3.63 (s, 3H), 3.08 (s, 3H), 2.36 (s, 3H). |
| 100 | methyl 3-(5-(3-(5-((2-(methoxy-d3)ethyl)amino)pyrazolo[1,5-a]pyridine-3-carboxamido)-4-methylphenyl)-2H-tetrazol-2-yl)azetidine-1-carboxylate SM: Intermediate 11 and 2-(methoxy-$d_3$)ethan-1-amine (Intermediate 28) HPLC Method B, 27% to 45% gradient 4.3 mg, 4.8% as a white solid | LCMS: m/z = 509 $[M + H]^+$; 1H NMR (400 MHz, DMSO-$d_6$) δ 9.33 (s, 1H), 8.49 (s, 1H), 8.39 (d, 1H), 8.21 (d, 1H), 7.83 (dd, 1H), 7.45 (d, 1H), 6.97 (d, 1H), 6.77 (t, 1H), 6.60 (dd, 1H), 5.91 (tt, 1H), 4.56 (d, 2H), 4.39 (s, 2H), 3.63 (s, 3H), 3.54 (t, 2H), 3.26 (d, 2H), 2.35 (s, 3H). |
| 101 | N-(5-(2-(3,3-difluorocyclobutyl)-2H-tetrazol-5-yl)-2-methylphenyl)-5-((2-hydroxyethyl)amino)pyrazolo[1,5-a]pyridine-3-carboxamide SM: Intermediate 4 and 2-aminoethan-1-ol Prep-HPLC Method G-35% to 50% gradient 40.5 mg, 28%, as a white solid | LCMS: m/z = 469 $[M + H]^+$, 1H NMR (400 MHz, DMSO-$d_6$) δ 9.33 (s, 1H), 8.49 (s, 1H), 8.39 (d, 1H), 8.20 (d, 1H), 7.83 (dd, 1H), 7.45 (d, 1H), 6.97 (d, 1H), 6.73 (t, 1H), 6.60 (dd, 1H), 5.65-5.55 (m, 1H), 4.84 (t, 1H), 3.61 (q, 2H), 3.50-3.38 (m, 4H), 3.16 (q, 2H), 2.35 (s, 3H). |
| 102 | 5-((2,2-difluoro-3-hydroxypropyl)amino)-N-(5-(2-(3,3-difluorocyclobutyl)-2H-tetrazol-5-yl)-2-methylphenyl)pyrazolo[1,5-a]pyridine-3-carboxamide SM: Intermediate 4 and 3-amino-2,2-difluoropropan-1-ol HPLC-Method H, 33 to 53% gradient 37.4 mg, 35.2% as a white solid | LCMS: m/z = 519 $[M + H]^+$, 1H NMR (400 MHz, DMSO-$d_6$) δ 9.35 (s, 1H), 8.52 (s, 1H), 8.45 (d, 1H), 8.18 (d, 1H), 7.83 (dd,1H), 7.45 (d, 1H), 7.17 (d, 1H), 6.97 (t, 1H), 6.67 (dd, , 1H), 5.67-5.53 (m, 2H), 3.70 (d, 4H), 3.53-3.35 (m, 4H), 2.35 (s, 3H). |
| 103 | N-(5-(2-(3,3-difluorocyclobutyl)-2H-tetrazol-5-yl)-2-methylphenyl)-5-(3-(hydroxymethyl)azetidin-1-yl)pyrazolo[1,5-a]pyridine-3-carboxamide SM: Intermediate 4 and (azetidin-3-yl)methanol HPLC Method F, 12% to 33% gradient 47.5 mg 47% as an off-white solid. | LCMS: m/z = 495 $[M + H]^+$, 1H NMR (400 MHz, DMSO-$d_6$) δ 9.38 (s, 1H), 8.57-8.50 (m, 2H), 8.18 (d, 1H), 7.83 (dd, 1H), 7.45 (d, 1H), 6.82 (d, 1H), 6.40 (dd, 1H), 5.60 (q, 1H), 4.84 (t, 1H), 3.99 (t, 2H), 3.71 (dd, 2H), 3.59 (t, 2H), 3.46-3.34 (m, 4H), 2.88-2.80 (m, 1H), 2.35 (s, 3H). |
| 104 | (S)-N-(5-(2-(3,3-difluorocyclobutyl)-2H-tetrazol-5-yl)-2-methylphenyl)-5-(2-(hydroxymethyl)azetidin-1-yl)pyrazolo[1,5-a]pyridine-3-carboxamide SM: Intermediate 4 and (S)-azetidin-2-ylmethanol HPLC-Method-H, 32% to 58% gradient 20.8 mg, 20.4% as a white solid. | LCMS: m/z = 395 $[M + H]^+$; $^1$H NMR (400 MHz, DMSO-$d_6$) δ 9.36 (s, 1H), 8.57-8.49 (m, 2H), 8.19 (d, 1H), 7.82 (dd, 1H), 7.45 (d, 1H), 6.98 (d, 1H), 6.67 (dd, 1H), 5.60 (ddt, 1H), 5.11 (t, 1H), 4.25 (t, 1H), 3.96 (td, 1H), 3.69 (dp, 3H), 3.53-3.34 (m, 4H), 2.35 (s, 3H), 2.18 (q, 1H). |
| 105 | N-(5-(2-(3,3-difluorocyclobutyl)-2H-tetrazol-5-yl)-4-fluoro-2-methylphenyl)-5-((2-methoxyethyl)amino)pyrazolo[1,5-a]pyridine-3-carboxamide SM: Intermediate 7 and 2-methoxyethan-1-amine HPLC-Method-B-27% to 57% gradient | LCMS: m/z = 501 $[M + H]^+$, 1H NMR (400 MHz, DMSO-$d_6$) δ 9.38 (s, 1H), 8.47 (s, 1H), 8.39 (d, 1H), 8.09 (d, 1H), 7.39 (d, 1H), 6.95 (d, 1H), 6.78 (t, 1H), 6.60 (dd, 1H), 5.62 (dd, 1H), 3.54 (t, |

-continued

| Compound No | Name, Starting materials (SM), HPLC Conditions, Yield | Data |
| --- | --- | --- |
| | 4.9 mg; 16% as a white solid | 2H), 3.50-3.43 (m, 4H), 3.47-3.34 (m, 3H), 3.25 (q, 2H), 2.34 (s, 3H). |
| 106 | 5-(4-(2-hydroxyethyl)piperazin-1-yl)-N-(2-methyl-5-(2-((1s,3s)-3-(trifluoromethyl)cyclobutyl)-2H-tetrazol-5-yl)phenyl)pyrazolo[1,5-a]pyridine-3-carboxamide<br>SM: Intermediate 6 and 2-(piperazin-1-yl)ethan-1-ol<br>HPLC-Method-A, 27% to 56% gradient<br>67.3 mg, 61.7% as a white solid. | LCMS: m/z = 570 [M + H]$^+$; 1H NMR (400 MHz, DMSO-$d_6$) δ 9.46 (s, 1H), 8.61-8.53 (m, 2H), 8.17 (d, 1H), 7.83 (dd, 1H), 7.46 (d, 1H), 7.34 (d, 1H), 6.98 (dd, 1H), 5.59-5.54 (m, 1H), 4.48-4.45 (m, 1H), 3.56-3.53 (m, 2H), 3.35-3.27 (m, 5H), 2.96-2.74 (m, 4H), 2.58-2.56 (m, 4H), 2.44 (t, 2H), 2.35 (s, 3H). |
| 107 | 5-(3-hydroxy-3-methylazetidin-1-yl)-N-(2-methyl-5-(2-((1s,3s)-3-(trifluoromethyl)cyclobutyl)-2H-tetrazol-5-yl)phenyl)pyrazolo[1,5-a]pyridine-3-carboxamide<br>SM: Intermediate 6 and 3-methylazetidin-3-ol<br>17.6 mg, yield: 21.8% as a white solid | LCMS: m/z = 527 [M + H]$^+$; 1H NMR (400 MHz, DMSO-$d_6$) δ 9.40 (s, 1H), 8.54 (d, 2H), 8.16 (d, 1H), 7.82 (dd,), 7.45 (d, 1H), 6.86 (d, 1H), 6.43 (dd, 1H), 5.69 (s, 1H), 5.57 (m, 1H), 3.89 (d, 2H), 3.79 (d, 2H), 3.26 (m, 1H), 2.96-2.85 (m, 2H), 2.85-2.74 (m, 2H), 2.35 (s, 3H), 1.46 (s, 3H). |
| 108 | N-(4-fluoro-2-methyl-5-(2-((1s,3s)-3-(trifluoromethyl)cyclobutyl)-2H-tetrazol-5-yl)phenyl)-5-((2-methoxyethyl)amino)pyrazolo[1,5-a]pyridine-3-carboxamide<br>SM: Intermediate 9 and 2-methoxyethan-1-amine<br>HPLC-Method-C 48% to 58% gradient<br>22.2 mg, 45% as a white solid | LCMS: m/z = 533 [M + H]$^+$, 1H NMR (400 MHz, DMSO-$d_6$) δ 9.37 (s, 1H), 8.47 (s, 1H), 8.39 (d, 1H), 8.07 (d, 1H), 7.38 (d,), 6.95 (d, 1H), 6.77 (t, 1H), 6.60 (dd, 1H), 5.59 (p, 1H), 3.54 (t, 2H), 3.27 (d, 6H), 2.97-2.86 (m, 2H), 2.80 (qd, 2H), 2.34 (s, 3H). |
| 109 | N-(4-fluoro-2-methyl-5-(2-((1s,3s)-3-(trifluoromethyl)cyclobutyl)-2H-tetrazol-5-yl)phenyl)-5-(4-hydroxy-4-methylpiperidin-1-yl)pyrazolo[1,5-a]pyridine-3-carboxamide<br>SM: Intermediate 9 and 4-methylpiperidin-4-ol<br>HPLC Method A 30% to 60% gradient<br>10.8 mg; 20% as a white solid. | LCMS: m/z = 573 [M + H]$^+$, 1H NMR (400 MHz, DMSO-$d_6$) δ 9.46 (s, 1H), 8.56-8.48 (m, 2H), 8.07 (d, 1H), 7.38 (d, 1H), 7.33 (d, 1H), 6.96 (dd, 1H), 5.59 (p, 1H), 4.41 (s, 1H), 3.52 (dd, 2H), 3.33-3.22 (m, 3H), 2.97-2.86 (m, 2H), 2.80 (dt, 2H), 2.34 (s, 3H), 1.56 (t, 4H), 1.15 (s, 3H). |
| 110 | methyl 3-(2-(3-(5-((2-methoxyethyl)amino)pyrazolo[1,5-a]pyridine-3-carboxamido)-4-methylphenyl)-2H-1,2,3-triazol-4-yl)azetidine-1-carboxylate<br>SM: Intermediate 18 and 2-methoxyethanamine<br>HPLC method C, 30% to 50% gradient<br>16.2 mg, 32% yield | LCMS: m/z = 505 [M + H]$^+$, 1H NMR (400 MHz, DMSO-$d_6$) δ 9.28 (s, 1H), 8.49 (s, 1H), 8.39 (d, 1H), 8.20-8.12 (m, 2H), 7.72 (dd, 1H), 7.41 (d, 1H), 6.97 (d, 1H), 6.78 (t, 1H), 6.61 (dd, 1H), 4.34 (s, 2H), 4.08 (q, 3H), 3.59 (s, 3H), 3.54 (d, 2H), 3.30 (s, 3H), 3.26 (d, 2H), 2.33 (s, 3H). |
| 111 | methyl 3-(2-(4-chloro-3-(5-((2-methoxyethyl)amino)pyrazolo[1,5-a]pyridine-3-carboxamido)phenyl)-2H-1,2,3-triazol-4-yl)azetidine-1-carboxylate<br>SM: Intermediate 19 and 2-methoxyethanamine<br>HPLC-Method-A, 30% to 60% gradient<br>81.5 mg, 45.8% as a white solid | LCMS: m/z = 525 [M + H]$^+$ 1H NMR (400 MHz, DMSO-$d_6$) δ 9.38 (s, 1H), 8.53-8.48 (m, 2H), 8.41 (d, 1H), 8.22 (s, 1H), 7.81 (dd, 1H), 7.70 (d, 1H), 6.97 (d, 1H), 6.84 (t, 1H), 6.62 (dd, 1H), 4.34 (s, 2H), 4.10 (d, 3H), 3.59 (s, 3H), 3.55 (t, 2H), 3.30-3.25 (m, 5H). |
| 112 | methyl 3-(2-(4-methyl-3-(5-(4-methylpiperazin-1-yl)pyrazolo[1,5-a]pyridine-3-carboxamido)phenyl)-2H-tetrazol-5-yl)azetidine-1-carboxylate<br>SM: Intermediate 20 and 1-methyl piperazine<br>HLC Method A, 20% to 49% gradient<br>35.6 mg, 34% as a white solid | LCMS: m/z = 531 [M + H]$^+$, $^1$H NMR (400 MHz, DMSO-$d_6$) δ 9.45 (s, 1H), 8.63-8.54 (m, 2H), 8.30 (d, 1H), 7.82 (dd, 1H), 7.53 (d, 1H), 7.35 (d, 1H), 7.00 (dd, 1H), 4.41 (s, 2H), 4.28 (tt, 1H), 4.18 (s, 2H), 3.60 (s, 3H), 3.32 (s, |

-continued

| Compound No | Name, Starting materials (SM), HPLC Conditions, Yield | Data |
|---|---|---|
| | | 3H), 2.46 (t, 5H), 2.39 (s, 3H), 2.23 (s, 3H). |
| 113 | methyl 3-(2-(4-chloro-3-(5-((2-methoxyethyl)amino)pyrazolo[1,5-a]pyridine-3-carboxamido)phenyl)-2H-tetrazol-5-yl)azetidine-1-carboxylate<br>SM: Intermediate 22 and 2-methoxyethan-1-amine<br>HPLC Method B, 35% to 60% gradient<br>6.7 mg, 22% as a white solid | LCMS: m/z = 526 [M + H]$^+$, 1H NMR (400 MHz, DMSO-$d_6$) δ 9.48 (s, 1H), 8.62 (d, 1H), 8.53 (s, 1H), 8.42 (d, 1H), 7.92 (dd, 1H), 7.83 (d, 1H), 6.97 (d, 1H), 6.88 (t, 1H), 6.63 (dd, 1H), 4.42 (s, 2H), 4.36-4.24 (m, 1H), 4.19 (s, 2H), 3.60 (s, 3H), 3.55 (t, 2H), 3.31-3.23 (m, 6H). |

Example 114 methyl 3-(5-(2-fluoro-5-(5-((2-methoxyethyl)amino)pyrazolo[1,5-a]pyridine-3-carboxamido)-4-methylphenyl)-2H-tetrazol-2-yl)azetidine-1-carboxylate

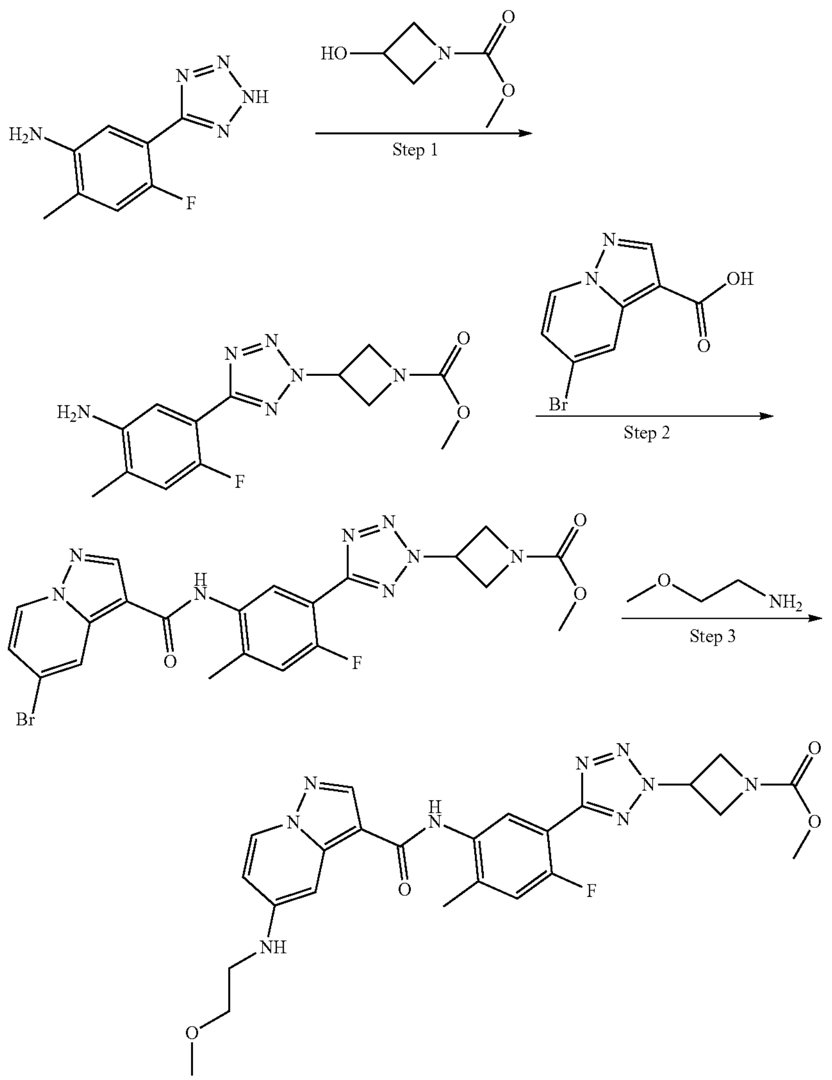

Step 1: Synthesis of methyl 3-(5-(5-amino-2-fluoro-4-methylphenyl)-2H-tetrazol-2-yl)azetidine-1-carboxylate To a solution of Intermediate 7, step 1 (150 mg, 0.78 mmol), methyl 3-hydroxyazetidine-1-carboxylate (152 mg, 1.16 mmol) and $PPh_3$ (607 mg, 2.32 mmol) in THF (5 mL) was added DIAD (313 mg, 1.55 mmol) at 0° C. under $N_2$ and the reaction mixture was stirred at rt for 2 h. Water (30 mL) and EtOAc (50 mL) were added, the organic phase was separated and the aqueous layer extracted with EtOAc (3×30 mL). The combined organic phase was dried over anhydrous $Na_2SO_4$ and concentrated to give crude product. This was purified by Prep-TLC with DCM:MeOH=10:1 to give the title compound (120 mg, 51%) as a white solid. LCMS: m/z=307 $[M+H]^+$.

Step 2: Synthesis of methyl 3-(5-(5-(5-bromopyrazolo[1,5-a]pyridine-3-carboxamido)-2-fluoro-4-methylphenyl)-2H-tetrazol-2-yl)azetidine-1-carboxylate A mixture of methyl 3-(5-(5-amino-2-fluoro-4-methylphenyl)-2H-tetrazol-2-yl)azetidine-1-carboxylate (50 mg, 0.16 mmol), pyridine (25.7 mg, 0.33 mmol), 5-bromopyrazolo[1,5-a]pyridine-3-carboxylic acid (58.8 mg, 0.24 mmol) and T3P® (155 mg, 0.49 mmol) in THF (3 mL) was stirred at 60° C. for 2 h and cooled to rt. Water (30 mL) and EtOAc (50 mL) were added, the organic phase was separated and the aqueous layer was extracted with EtOAc (3×30 mL). The combined organic phase was dried over anhydrous $Na_2SO_4$ and concentrated. The crude product was purified by Prep-TLC with EtOAc to give the title compound (60 mg, 69%) as a white solid. LCMS m/z=529 [M+H]+

Step 3: Synthesis of methyl 3-(5-(2-fluoro-5-(5-((2-methoxyethyl)amino)pyrazolo[1,5-a]pyridine-3-carboxamido)-4-methylphenyl)-2H-tetrazol-2-yl)azetidine-1-carboxylate To a stirred solution of methyl 3-(5-(5-(5-bromopyrazolo[1,5-a]pyridine-3-carboxamido)-2-fluoro-4-methylphenyl)-2H-tetrazol-2-yl)azetidine-1-carboxylate (50 mg, 0.09 mmol), XantPhos (5.45 mg, 0.09 mmol), $Pd_2(dba)_3$ (8.63 mg, 0.09 mmol) and $Cs_2CO_3$ (61.0 mg, 0.19 mmol) in dioxane (4 mL) was added 2-methoxyethan-1-amine (10.5 mg, 0.14 mmol) under $N_2$. The mixture was stirred at 80° C. for 2 h and cooled to rt. Water (30 mL) and EtOAc (50 mL) were added, the organic phase was separated and the aqueous phase was extracted with EtOAc (3×20 mL). The combined organic extracts were dried over anhydrous $Na_2SO_4$ and concentrated. The crude product was purified by Prep-TLC with EtOAc and then by Prep-HPLC-Method B, 23% to 47% gradient, to give the title compound, (12.9 mg; 26%) as a white solid. LCMS: m/z=524 $[M+H]^+$, 1H NMR (400 MHz, DMSO-$d_6$) δ 9.37 (s, 1H), 8.47 (s, 1H), 8.39 (d, 1H), 8.11 (d, 1H), 7.39 (d, 1H), 6.95 (d, 1H), 6.77 (t, 1H), 6.60 (dd, 1H), 5.93 (tt, 1H), 4.56 (d, 2H), 4.39 (s, 2H), 3.62 (s, 3H), 3.54 (t, 2H), 3.29 (s, 3H), 3.25 (q, 2H), 2.35 (s, 3H).

Example 115

Methyl 3-(5-(4-fluoro-3-(5-((2-methoxyethyl)amino)pyrazolo[1,5-a]pyridine-3-carboxamido)phenyl)-2H-tetrazol-2-yl)azetidine-1-carboxylate

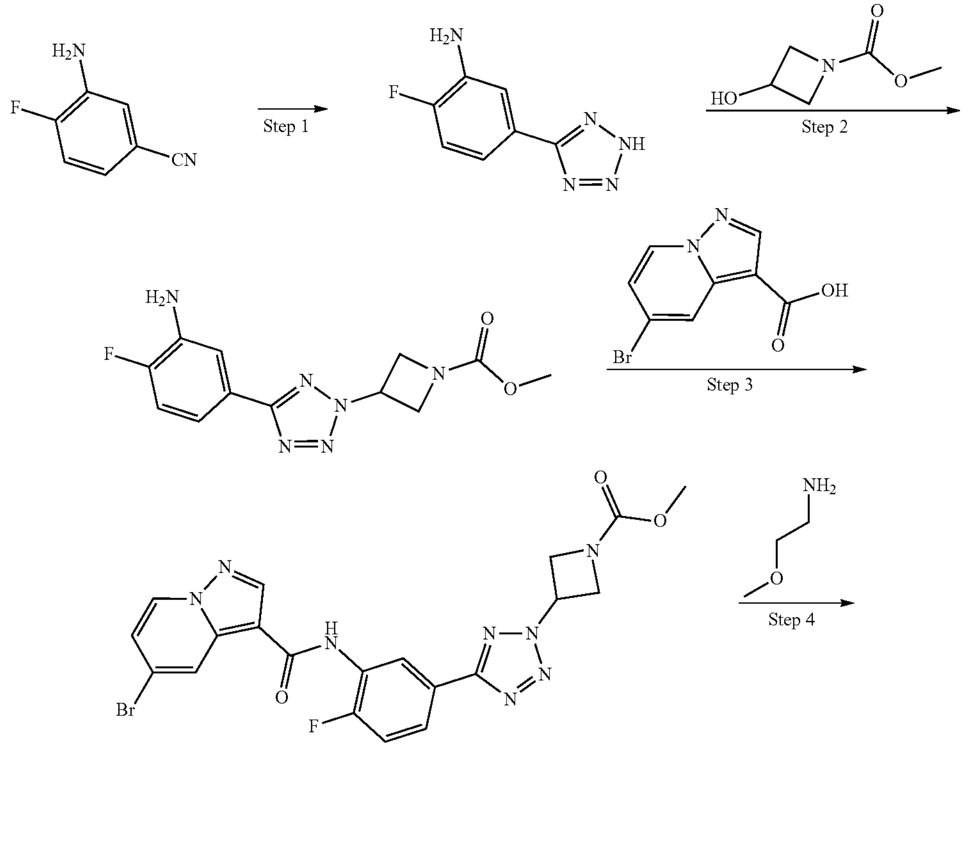

-continued

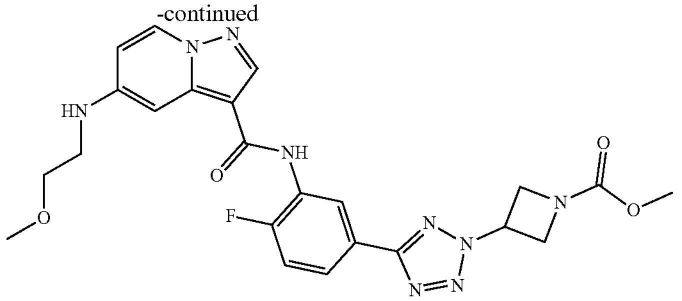

Steps 1 to 3: Synthesis of methyl 3-(5-(3-(5-bromopyrazolo[1,5-a]pyridine-3-carboxamido)-4-fluorophenyl)-2H-tetrazol-2-yl)azetidine-1-carboxylate The title compound was obtained as a yellow solid, 35 mg, from 3-amino-4-fluorobenzonitrile, methyl 3-hydroxyazetidine-1-carboxylate and 5-bromopyrazolo[1,5-a]pyridine-3-carboxylic acid, following a similar 3 step procedure to that described in Intermediate 7. LCMS: m/z=516 $[M+H]^+$.

Step 4: Synthesis of methyl 3-(5-(4-fluoro-3-(5-((2-methoxyethyl)amino)pyrazolo[1,5-a]pyridine-3-carboxamido)phenyl)-2H-tetrazol-2-yl)azetidine-1-carboxylate The title compound was obtained as a white solid, 3.4 mg, 11.4% yield, from methyl 3-(5-(3-(5-bromopyrazolo[1,5-a]pyridine-3-carboxamido)-4-fluorophenyl)-2H-tetrazol-2-yl)azetidine-1-carboxylate and 2-methoxyethan-1-amine, following the procedure described in Example 114, step 3. LCMS: m/z=510 $[M+H]^+$; $^1H$ NMR (400 MHz, DMSO-$d_6$) δ 9.61 (s, 1H), 8.58-8.51 (m, 1H), 8.53 (s, 1H), 8.40 (d, 1H), 7.90 (ddd, 1H), 7.49 (dd, 1H), 6.99 (d, 1H), 6.82 (t, 1H), 6.62 (dd, 1H), 5.92 (td, 1H), 4.57 (s, 2H), 4.39 (s, 2H), 3.63 (s, 3H), 3.55 (t, 2H), 3.32 (s, 3H), 3.28 (s, 2H).

Example 116

5-((2-methoxyethyl)amino)-N-(2-methyl-5-(2-(4,4,4-trifluorobutyl)-2H-tetrazol-5-yl)phenyl)pyrazolo[1,5-a]pyridine-3-carboxamide

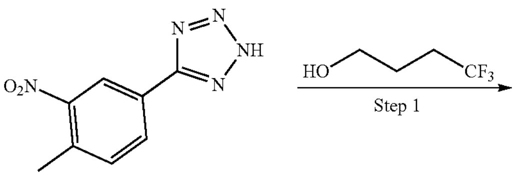

-continued

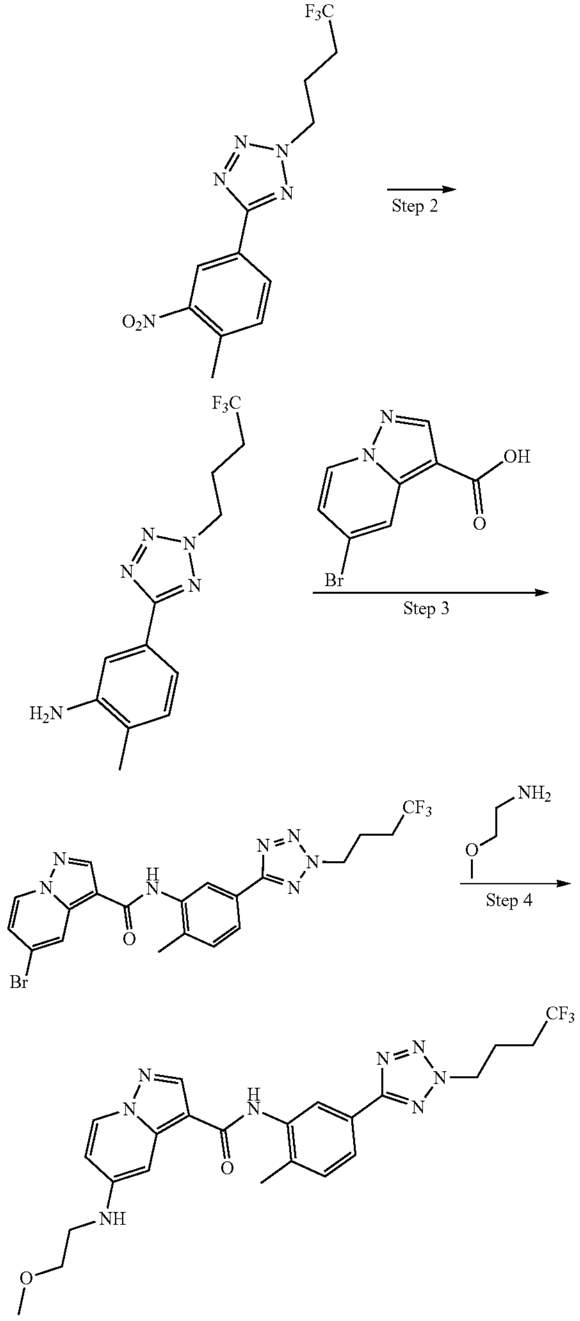

Step 1: Synthesis of 5-(4-methyl-3-nitrophenyl)-2-(4,4,4-trifluorobutyl)-2H-tetrazole DIAD (590 mg, 2.92 mmol) was added dropwise to 5-(4-methyl-3-nitrophenyl)-2H-tetrazole (J. Med. Chem. 54(6), 1599-1612, 300 mg, 1.46 mmol), 4,4,4-trifluorobutan-1-ol (280 mg, 2.19 mmol) and $PPh_3$ (574 mg, 2.19 mmol) in THF (20 mL) at 0° C. The resulting mixture was stirred at 60° C. for 2 h then concentrated to dryness. The residue was purified on prep-TLC with PE:EtOAc=8:1 to afford the title compound (400 mg, 86.9%) as a colorless oil. LCMS: m/z=316 $[M+H]^+$ Step 2: Synthesis of 2-methyl-5-(2-(4,4,4-trifluorobutyl)-2H-tetrazol-5-yl)aniline A mixture of 5-(4-methyl-3-nitrophenyl)-2-(4,4,4-trifluorobutyl)-2H-1,2,3,4-tetrazole (400 mg, 1.26 mmol) and $SnCl_2$ (955 mg, 5.04 mmol) in EtOH (25 mL) was stirred at 80° C. for 2 h and concentrated to dryness. The residue was purified on a silica gel column to afford the title compound (300 mg, 83.5%) as a yellow solid. LCMS: m/z=286 $[M+H]^+$ Step 3: Synthesis of 5-bromo-N-(2-methyl-5-(2-(4,4,4-trifluorobutyl)-2H-tetrazol-5-yl)phenyl)pyrazolo[1,5-a]pyridine-3-carboxamide The title compound was obtained as a yellow solid, 120 mg, 45.1%, from 2-methyl-5-(2-(4,4,4-trifluorobutyl)-2H-tetrazol-5-yl)aniline and 5-bromopyrazolo[1,5-a]pyridine-3-carboxylic acid, following a similar procedure to that described in Example 114, step 2. LCMS: m/z=510 $[M+H]^+$ Step 4: Synthesis of 5-((2-methoxyethyl)amino)-N-(2-methyl-5-(2-(4,4,4-trifluorobutyl)-2H-tetrazol-5-yl)phenyl)pyrazolo[1,5-a]pyridine-3-carboxamide The title compound was obtained as a white solid, 71.1 mg, 56.4% from 5-bromo-N-(2-methyl-5-(2-(4,4,4-trifluorobutyl)-2H-tetrazol-5-yl)phenyl)pyrazolo[1,5-a]pyridine-3-carboxamide and 2-methoxyethan-1-amine, following a similar procedure to that described in Example 114, step 3. LCMS: m/z=503 $[M+H]^+$ 1H NMR (400 MHz, DMSO-$d_6$) δ 9.30 (s, 1H), 8.49 (s, 1H), 8.39 (d, 1H), 8.20 (d, 1H), 7.80 (dd, 1H), 7.44 (d, 1H), 6.97 (d, 1H), 6.77 (t, 1H), 6.60 (dd, 1H), 4.84 (t, 2H), 3.55 (t, 2H), 3.32-3.22 (m, 5H), 2.48-2.37 (m, 2H), 2.35 (s, 3H), 2.22 (p, 2H).

Example 117

N-(2-chloro-4-cyclopropyl-5-(2-(3,3-difluorocyclobutyl)-2H-tetrazol-5-yl)phenyl)-5-morpholinopyrazolo[1,5-a]pyridine-3-carboxamide

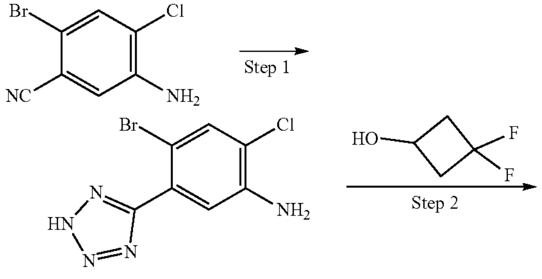

-continued

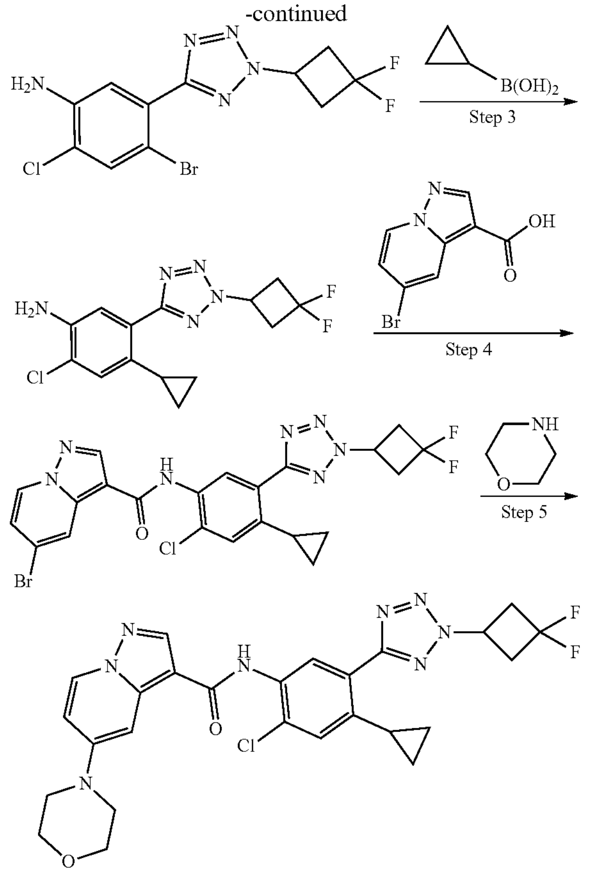

Step 1: Synthesis of 4-bromo-2-chloro-5-(2H-tetrazol-5-yl)aniline

The title compound was obtained as a yellow solid, 300 mg, 50%, from 5-amino-2-bromo-4-chlorobenzonitrile, following the procedure described in Intermediate 8, step 1. LCMS: m/z=274 $[M+H]^+$.

Step 2: Synthesis of 4-bromo-2-chloro-5-(2-(3,3-difluorocyclobutyl)-2H-tetrazol-5-yl)aniline The title compound was obtained as a white solid, 250 mg, 63%, from 4-bromo-2-chloro-5-(2H-tetrazol-5-yl)aniline and 3,3-difluorocyclobutan-1-ol following the procedure described in Intermediate 7, step 2. LCMS: m/z=364 $[M+H]^+$.

Step 3: Synthesis of 2-chloro-4-cyclopropyl-5-(2-(3,3-difluorocyclobutyl)-2H-tetrazol-5-yl)aniline To a stirred solution of 4-bromo-2-chloro-5-(2-(3,3-difluorocyclobutyl)-2H-tetrazol-5-yl)aniline (100 mg, 0.27 mmol) and cyclopropylboronic acid (28.1 mg, 0.33 mmol) in dioxane (2 mL) and $H_2O$ (0.5 mL) were added $K_2CO_3$ (75.6 mg, 0.55 mmol) and $Pd(dppf)Cl_2$ (22.3 mg, 27.4 μmol) at rt under $N_2$. The reaction was stirred for 2 h at 100° C. and then cooled to rt. The mixture was diluted with water and the mixture was extracted with DCM (2×30 mL). The organic layer was concentrated and purified by prep-TLC with PE:EtOAc=1:1 to give the title compound (80 mg; 89%) as a yellow solid. LCMS: m/z=326 $[M+H]^+$.

Step 4: Synthesis of 5-bromo-N-(2-chloro-4-cyclopropyl-5-(2-(3,3-difluorocyclobutyl)-2H-tetrazol-5-yl)phenyl)pyrazolo[1,5-a]pyridine-3-carboxamide To a stirred solution of 2-chloro-4-cyclopropyl-5-(2-(3,3-difluorocyclobutyl)-2H-tetrazol-5-yl)aniline (80 mg, 0.25 mmol) in pyridine (2 mL) was added 5-bromopyrazolo[1,5-a]pyridine-3-carbonyl chloride (127 mg, 0.49 mmol) and the reaction was stirred for 1 h at rt and concentrated. The crude product was purified by prep-TLC with DCM:MeOH=10:1 to give the title compound (90 mg; 67%) as a white solid. LCMS: m/z=548 $[M+H]^+$.

Step 5: Synthesis of N-(2-chloro-4-cyclopropyl-5-(2-(3,3-difluorocyclobutyl)-2H-tetrazol-5-yl)phenyl)-5-morpholinopyrazolo[1,5-a]pyridine-3-carboxamide The title compound was obtained as a gray solid, 12.2 mg, 30% from 5-bromo-N-(2-chloro-4-cyclopropyl-5-(2-(3,3-difluorocyclobutyl)-2H-tetrazol-5-yl)phenyl)pyrazolo[1,5-a]pyridine-3-carboxamide and morpholine, following a similar procedure to that described in Example 114, step 3. The crude product was purified by Prep-HPLC, Method J, 45% to 55% gradient. LCMS: m/z=555 $[M+H]^+$; $^1H$ NMR (400 MHz, DMSO-$d_6$) δ 9.58 (s, 1H), 8.60 (d, 2H), 8.14 (s, 1H), 7.34 (d, 1H), 7.26 (s, 1H), 7.00 (dd, 1H), 5.70-5.56 (m, 1H), 3.75 (t, 4H), 3.44 (dtd, 4H), 3.28 (d, 4H), 2.57 (td, 1H), 1.03-0.94 (m, 2H), 0.82-0.74 (m, 2H).

Example 118 methyl 3-(5-(3-(5-((2-methoxyethyl)amino)pyrazolo[1,5-a]pyridine-3-carboxamido)-4-(methyl-d3)phenyl)-2H-tetrazol-2-yl)azetidine-1-carboxylate

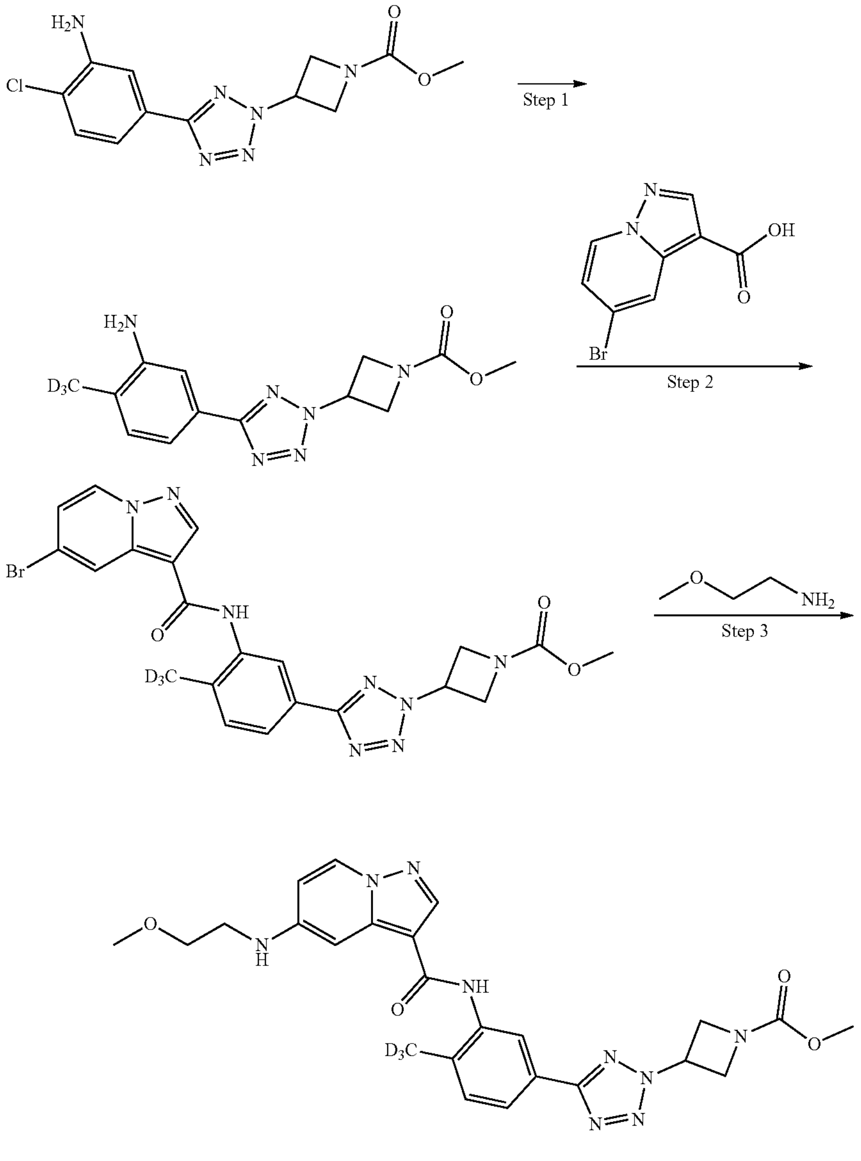

Step 1: Synthesis of methyl 3-(5-(3-amino-4-(methyl-d3)phenyl)-2H-tetrazol-2-yl)cyclobutane-1-carboxylate A mixture of Intermediate 10 (80 mg, 0.26 mmol), 2-(methyl-$d_3$)-4,4,5,5-tetramethyl-1,3,2-dioxaborolane (75.1 mg, 0.52 mmol), XPhos Pd G3 (21.1 mg, 0.03 mmol) and $K_2CO_3$ (71.5 mg, 0.52 mmol) in dioxane/$H_2O$ (2 mL/0.5 mL) was stirred at 80° C. for 16 h under $N_2$. The reaction was extracted with EtOAc (50 mL×3), the combined organic layer was concentrated in vacuo and purified by Prep-TLC (PE:EtOAc=2:1) to afford the title compound (65 mg; 86.2%) as a white solid. LCMS: m/z=292 $[M+H]^+$.

Step 2: Synthesis of methyl 3-(5-(3-(5-bromopyrazolo[1,5-a]pyridine-3-carboxamido)-4-(methyl-d3)phenyl)-2H-tetrazol-2-yl)azetidine-1-carboxylate The title compound was obtained as a light yellow solid, 50 mg, 47.6% from methyl 3-(5-(3-amino-4-(methyl-d3)phenyl)-2H-tetrazol-2-yl)cyclobutane-1-carboxylate and 5-bromopyrazolo[1,5-a]pyridine-3-carboxylic acid following the procedure described in Example 114, step 2. LCMS: m/z=514 $[M+H]^+$.

Step 3: Synthesis of methyl 3-(5-(3-(5-((2-methoxyethyl)amino)pyrazolo[1,5-a]pyridine-3-carboxamido)-4-(methyl-d3)phenyl)-2H-tetrazol-2-yl)azetidine-1-carboxylate The title compound was obtained as a white solid, 9.2 mg, 18.6%, from methyl 3-(5-(3-(5-bromopyrazolo[1,5-a]pyridine-3-carboxamido)-4-(methyl-$d_3$)phenyl)-2H-tetrazol-2-yl)azetidine-1-carboxylate and 2-methoxyethan-1-amine, following a similar procedure to that described in Example 89. The crude compound was further purified by Prep-HPLC, Method A, 27% to 45% gradient. LCMS: m/z=509 $[M+H]^+$, 1H NMR (400 MHz, DMSO-$d_6$) δ 9.32 (s, 1H), 8.49 (s, 1H), 8.39 (d, 1H), 8.21 (d, 1H), 7.83 (dd, 1H), 7.45 (d, 1H), 6.97 (d, 1H), 6.77 (t, 1H), 6.60 (dd, 1H), 5.91 (tt, 1H), 4.56 (t, 2H), 4.39 (s, 2H), 3.63 (s, 3H), 3.54 (t, 21H), 3.32-3.22 (n, 5H).

Examples 119 to 124

The compounds in the following table were prepared from the appropriate 5-bromopyrazolo[1,5-a]pyridine and amine, following a similar procedure to that described in Example 89 and the diasteroisomers separated by HPLC as described in the table below.

| Example No | Name, Starting Materials (SM), | Purification, Yield | Data |
|---|---|---|---|
| 119 | 5-((2-methoxyethyl)amino)-N-(2-methyl-5-(2-((1s,3s)-3-(trifluoromethyl)cyclobutyl)-2H-tetrazol-5-yl)phenyl)pyrazolo[1,5-a]pyridine-3-carboxamide or 5-((2-methoxyethyl)amino)-N-(2-methyl-5-(2-((1r,3r)-3-(trifluoromethyl)cyclobutyl)-2H-tetrazol-5-yl)phenyl)pyrazolo[1,5-a]pyridine-3-carboxamide SM: Intermediate 12 and 2-methoxyethan-1-amine | CHIRAL-HPLC: Column: CHIRALPAK IG, 2*25 cm, 5 μm; Mobile Phase A: Hex (0.2% DEA), Mobile Phase B: EtOH: DCM = 1: 1; Flow rate: 20 mL/min; isocratic gradient: 50% B 52.7 mg, 26.7% as a white solid. | Peak 1, LCMS: m/z = 515 $[M + H]^+$; 1H NMR (400 MHz, DMSO-$d_6$) δ 9.34 (s, 1H), 8.49 (s, 1H), 8.40 (d, 1H), 8.17 (d, 1H), 7.82 (dd, 1H), 7.45 (d, 1H), 6.97 (d, 1H), 6.78 (t, 1H), 6.61 (dd, 1H), 5.57 (p, 1H), 3.54 (t, 2H), 3.31-3.19 (m, 6H), 2.90 (ddd, 2H), 2.80 (q, 2H), 2.35 (s, 3H). |
| 120 | 5-((2-hydroxyethyl)amino)-N-(2-methyl-5-(2-((1s,3s)-3-(trifluoromethyl)cyclobutyl)-2H-tetrazol-5-yl)phenyl)pyrazolo[1,5-a]pyridine-3-carboxamide or 5-((2-hydroxyethyl)amino)-N-(2-methyl-5-(2-((1r,3r)-3-(trifluoromethyl)cyclobutyl)-2H-tetrazol-5-yl)phenyl)pyrazolo[1,5-a]pyridine-3-carboxamide SM: Intermediate 12 and 2-aminoethan-1-ol | prep-HPLC, Method-J, 38% to 48% gradient 35 mg, 24.3% as an off-white solid | Peak 1, LCMS: m/z = 501 $[M + H^+]$; 1H NMR (400 MHz, DMSO-$d_6$) δ 9.33 (s, 1H), 8.49 (s, 1H), 8.39 (d, 1H), 8.17 (d, 1H), 7.81 (dd, 1H), 7.45 (d, 1H), 6.96 (d, 1H), 6.73 (t, 1H), 6.60 (dd, 1H), 5.59-5.54 (m, 1H), 4.82 (t, 1H), 3.61 (q, 2H), 3.26 (m, 1H), 3.30-3.26 (m, 2H), 2.96-2.85 (m, 2H), 2.80 (m, 2H), 2.35 (s, 3H). |
| 121 | 5-((2-hydroxyethyl)amino)-N-(2-methyl-5-(2-((1r,3r)-3-(trifluoromethyl)cyclobutyl)-2H-tetrazol-5-yl)phenyl)pyrazolo[1,5-a]pyridine-3-carboxamide or 5-((2-hydroxyethyl)amino)-N-(2-methyl-5-(2-((1s,3s)-3-(trifluoromethyl)cyclobutyl)-2H-tetrazol-5-yl)phenyl)pyrazolo[1,5-a]pyridine-3-carboxamide. SM: Intermediate 12 and 2-aminoethan-1-ol | prep-HPLC, Method-J, 38% to 48% gradient 14.8 mg, 10.2% as a light pink solid | Peak 2, LCMS: m/z = 501 $[M + H]^+$; 1H NMR (400 MHz, DMSO-$d_6$) δ 9.31 (s, 1H), 8.49 (s, 1H), 8.39 (d, 1H), 8.21 (d, 1H), 7.83 (dd, 1H), 7.45 (d, 1H), 6.96 (d, 1H), 6.73 (t, 1H), 6.60 (dd, 1H), 5.66-5.62 (m, 1H), 4.83 (t, 1H), 3.63-3.59 (m, 2H), 3.55-3.43 (m, 1H), 3.18-3.14 (m, 2H), 3.08-3.01 (m, 2H), 2.93-2.81 (m, 2H), 2.35 (s, 3H). |

-continued

| Example No | Name, Starting Materials (SM), | Purification, Yield | Data |
|---|---|---|---|
| 122 | 5-(4-hydroxy-4-methylpiperidin-1-yl)-N-(2-methyl-5-(2-((1s,3s)-3-(trifluoromethyl)cyclobutyl)-2H-tetrazol-5-yl)phenyl)pyrazolo[1,5-a]pyridine-3-carboxamide or 5-(4-hydroxy-4-methylpiperidin-1-yl)-N-(2-methyl-5-(2-((1r,3r)-3-(trifluoromethyl)cyclobutyl)-2H-tetrazol-5-yl)phenyl)pyrazolo[1,5-a]pyridine-3-carboxamide SM: Intermediate 12 and 4-methylpiperidin-3-ol | prep-HPLC, Method-J, 41% to 51% gradient 32.1 mg, 20.1% as a light pink solid | Peak 1: LCMS: m/z = 555 $[M + H]^+$; 1H NMR (400 MHz, DMSO-$d_6$) δ 9.43 (s, 1H), 8.59-8.49 (m, 2H), 8.16 (d, 1H), 7.82 (dd, 1H), 7.45 (d, 1H), 7.34 (d, 1H), 6.96 (dd, 1H), 5.59-5.55 (m, 1H), 4.42 (s, 1H), 3.54 (d, 2H), 3.31-3.36 (m, 3H), 2.96-2.74 (m, 4H), 2.35 (s, 3H), 1.57 (d, 4H), 1.15 (s, 3H). |
| 123 | (S)-N-(5-(2-((2,2-difluorocyclopropyl)methyl)-2H-tetrazol-5-yl)-2-methylphenyl)-5-((2-methoxyethyl)amino)pyrazolo[1,5-a]pyridine-3-carboxamide or (R)-N-(5-(2-((2,2-difluorocyclopropyl)methyl)-2H-tetrazol-5-yl)-2-methylphenyl)-5-((2-methoxyethyl)amino)pyrazolo[1,5-a]pyridine-3-carboxamide SM: Intermediate 5 and 2-methoxyethan-1-amine | Prep-chiral-HPLC: Column: CHIRAL ART Cellulose-SB, 2*25 cm, 5 μm; Mobile Phase A: Hex (0.5% 2M $NH_3$—MeOH), Mobile Phase B: MeOH: DCM = 1; Flow rate: 20 mL/min; isocratic gradient: 35% B 9.3 mg; 19% as a white solid. | Peak 1: LCMS: m/z = 483 $[M + H]^+$, 1H NMR (400 MHz, DMSO-$d_6$) δ 9.30 (s, 1H), 8.49 (s, 1H), 8.39 (d, 1H), 8.19 (d, 1H), 7.81 (dd, 1H), 7.45 (d, 1H), 6.97 (d, 1H), 6.76 (t, 1H), 6.60 (dd, 1H), 4.98-4.83 (m, 2H), 3.55 (t, 2H), 3.28 (d, 5H), 2.49 (m, 1H) 2.35 (s, 3H), 1.83 (tdd, 1H), 1.73-1.60 (m, 1H). |
| 124 | (R)-N-(5-(2-((2,2-difluorocyclopropyl)methyl)-2H-tetrazol-5-yl)-2-methylphenyl)-5-((2-methoxyethyl)amino)pyrazolo[1,5-a]pyridine-3-carboxamide or (S)-N-(5-(2-((2,2-difluorocyclopropyl)methyl)-2H-tetrazol-5-yl)-2-methylphenyl)-5-((2-methoxyethyl)amino)pyrazolo[1,5-a]pyridine-3-carboxamide SM: Intermediate 5 and 2-methoxyethan-1-amine | Prep-chiral-HPLC: Column: CHIRAL ART Cellulose-SB, 2*25 cm, 5 μm; Mobile Phase A: Hex (0.5% 2M $NH_3$—MeOH), Mobile Phase B: MeOH: DCM = 1; Flow rate: 20 mL/min; isocratic gradient: 35% B 4.8 mg; 10% as a white solid | Peak 2: LCMS: m/z = 483 $[M + H]^+$, 1H NMR (400 MHz, DMSO-$d_6$) δ 9.30 (s, 1H), 8.49 (s, 1H), 8.39 (d, 1H), 8.19 (d, 1H), 7.81 (dd, 1H), 7.45 (d, 1H), 6.97 (d, 1H), 6.76 (t, 1H), 6.60 (dd, 1H), 4.98-4.83 (m, 2H), 3.55 (t, 2H), 3.28 (d, 5H), 2.50-2.48 (m, 1H) 2.35 (s, 3H), 1.85-1.81 (m, 1H), 1.73-1.60 (m, 1H). |

Example 125 methyl 3-(2-(3-(5-((2-methoxyethyl)amino)pyrazolo[1,5-a]pyridine-3-carboxamido)-4-methylphenyl)-2H-tetrazol-5-yl)azetidine-1-carboxylate

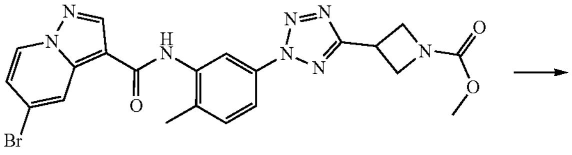

-continued

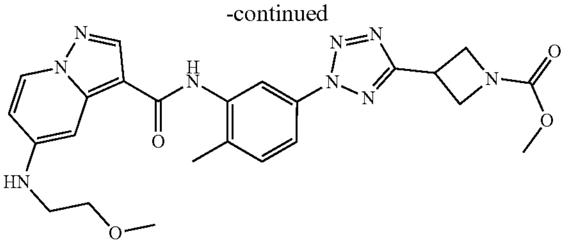

To a solution of 2-methoxyethan-1-amine (17.5 mg, 0.23 mmol) and Intermediate 20 (100 mg, 0.20 mmol) in dioxane (2 mL) were added $Cs_2CO_3$ (127 mg, 0.39 mmol), XantPhos (127 mg, 0.39 mmol) and $Pd_2(dba)_3$ (17.8 mg, 0.02 mmol) under $N_2$ and the reaction was stirred for 2 h at 80° C. The mixture was extracted with EtOAc (3×50 mL) and the combined organic layer was concentrated under vacuum. The crude product was purified by Prep-HPLC, Method B, 25% to 50% gradient, to give the title compound (25 mg, 25%) as a white solid. LCMS: m/z=506 $[M+H]^+$, $^1H$ NMR (400 MHz, DMSO-$d_6$) δ 9.32 (s, 1H), 8.50 (s, 1H), 8.40 (d, 1H), 8.31 (d, 1H), 7.81 (dd, 1H), 7.52 (d, 1H), 6.97 (d, 1H), 6.80 (t, 1H), 6.61 (dd, 1H), 4.44-4.12 (m, 5H), 3.60 (s, 3H), 3.55 (t, 2H), 3.30-3.26 (m, 5H), 2.39 (s, 3H).

Example 126 ethyl 3-(5-(4-methyl-3-(5-(methylamino)pyrazolo[1,5-a]pyridine-3-carboxamido)phenyl)-2H-tetrazol-2-yl)azetidine-1-carboxylate

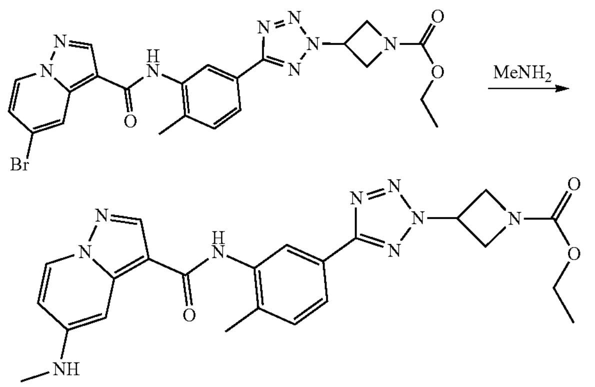

A mixture of BrettPhos Pd G4 (6.76 mg, 7.33 μmol), Intermediate 14 (75 mg, 0.15 mmol), methanamine hydrochloride (15 mg, 0.22 mmol) and $Cs_2CO_3$ (167 mg, 0.51 mmol) in dioxane (1 mL) was stirred under $N_2$ at 90° C. overnight. The mixture was concentrated in vacuo, the residue partitioned between DCM and water and the layers separated. The organic layer was dried over $Na_2SO_4$, filtered and evaporated to give the crude product. This was purified by silica gel ISCO chromatography (0 to 8% MeOH/DCM) to give a yellow glassy solid. This was further purified by reverse phase ISCO (0 to 100% MeCN/water containing 0.1% TFA). The product containing fractions were concentrated in vacuo, the residue was triturated with aq. $NaHCO_3$, the resulting solid filtered, washed with water and dried to give a white solid, 26 mg. This solid was triturated with hot EtOH (1 mL), filtered, washed with EtOH and dried to give the title compound as an off-white solid, 15.7 mg, 22.5% LCMS m/z=476 $[M+H]^+$; 1H NMR (500 MHz, DMSO-$d_6$) δ 9.31 (s, 1H), 8.50 (d, 1H), 8.39 (dd, 1H), 8.22 (s, 1H), 7.84 (d, 1H), 7.49-7.43 (m, 1H), 6.92 (d, 1H), 6.77-6.70 (i, 1H), 6.56-6.48 (m, 1H), 5.91 (dt, 1H), 4.56 (t, 2H), 4.39 (d, 2H), 4.08 (q, 2H), 2.77 (s, 3H), 2.36 (s, 3H), 1.21 (t, 331).

Examples 127 to 130

The compounds in the following table were prepared from the appropriate Intermediate and amine, following a similar procedure to that described in Example 126.

| Compound No | Name, Structure, Starting materials | Data |
|---|---|---|
| 127 | methyl 3-(5-(3-(5-(ethylamino)pyrazolo[1,5-a]pyridine-3-carboxamido)-4-methylphenyl)-2H-tetrazol-2-yl)azetidine-1-carboxylate<br>SM: Intermediate 11 and ethylamine | LCMS m/z = 476 $[M + H]^+$; 1H NMR (500 MHz, DMSO-$d_6$) δ 9.30 (d, 1H), 8.49 (d, 1H), 8.39 (dd,), 8.22 (s, 1H), 7.84 (d, 1H), 7.46 (dd, 1H), 6.95 (d, 1H), 6.70-6.62 (m, 1H), 6.58-6.48 (m, 1H), 5.98-5.85 (m, 1H), 4.57 (d, 2H), 4.40 (d, 2H), 3.63 (s, 3H), 3.11 (p, 2H), 2.36 (s, 3H), 1.26-1.18 (m, 3H). |
| 128 | methyl (S)-3-(5-(3-(5-((1-methoxypropan-2-yl)amino)pyrazolo[1,5-a]pyridine-3-carboxamido)-4-methylphenyl)-2H-tetrazol-2-yl)azetidine-1-carboxylate<br>SM: Intermediate 11 and (S)-1-methoxypropan-2-amine white solid, 33 mg, 40.6% | LCMS m/z = 520 $[M + H]^+$; 1H NMR (500 MHz, DMSO-$d_6$) δ 9.30 (s, 1H), 8.49 (d, 1H), 8.39 (dd, 1H), 8.21 (s, 1H), 7.84 (d, 1H), 7.46 (d, 1H), 7.03 (d, 1H), 6.62-6.53 (m, 2H), 5.98-5.86 (m, 1H), 4.56 (d, 2H), 4.39 (d, 2H), 3.73-3.59 (m, 4H), 3.42 (dd, 1H), 3.29 (s, 3H), 2.36 (s, 3H), 1.18 (d, 3H). |
| 129 | methyl (R)-3-(5-(4-methyl-3-(5-((tetrahydrofuran-3-yl)amino)pyrazolo[1,5-a]pyridine-3-carboxamido)phenyl)-2H-tetrazol-2-yl)azetidine-1-carboxylate<br>SM: Intermediate 11 and (R)-tetrahydrofuran-3-amine<br>46.2 mg of off-white foam. | LCMS m/z = 518 $[M + H]^+$<br>1H NMR (500 MHz, DMSO-$d_6$) δ 9.33 (s, 1H), 8.51 (d, 1H), 8.42 (d, 1H), 8.21 (s, 1H), 7.84 (d, 1H), 7.46 (d, 1H), 6.99 (s, 1H), 6.92 (d, 1H), 6.56 (d, 1H), 5.91 (qd, 1H), 4.56 (d, 2H), 4.39 (d, 2H), 4.05 (s, 1H), 3.91-3.81 (m, 2H), 3.75 (q, 1H), 3.64 (d, 4H), 2.36 (s, 3H), 2.22 (dq, 1H), 1.84 (d, 1H). |
| 130 | ethyl 3-(5-(3-(5-(ethylamino)pyrazolo[1,5-a]pyridine-3-carboxamido)-4-methylphenyl)-2H-tetrazol-2-yl)azetidine-1-carboxylate<br>SM: Intermediate 14 and ethylamine pale yellow solid, 26.9 mg, 35.1% | LCMS m/z = 490 $[M + H]^+$; 1H NMR (500 MHz, DMSO-$d_6$) δ 9.29 (s, 1H), 8.48 (s, 1H), 8.38 (d, 1H), 8.21 (s, 1H), 7.82 (d, 1H), 7.44 (d, 1H), 6.94 (d, 1H), 6.69-6.61 (m, 1H), 6.52 (d, 1H), 5.90 (p, 1H), 4.55 (t, 2H), 4.36 (d, 2H), 4.12-3.97 (m, 3H), 3.10 (p, 2H), 2.35 (s, 3H), 1.24-1.16 (m, 7H). |

Example 131 methyl 3-(5-(3-(5-((2,2-difluoroethyl)amino)pyrazolo[1,5-a]pyridine-3-carboxamido)-4-methylphenyl)-2H-tetrazol-2-yl)azetidine-1-carboxylate

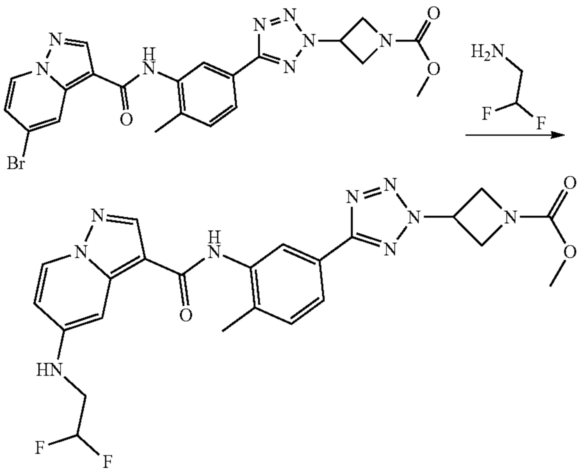

A mixture of Intermediate 11 (85 mg, 0.17 mmol), $Cs_2CO_3$ (162 mg, 0.5 mmol), 2,2-difluoroethane-1-amine (20 mg, 0.25 mmol) and Brettphos Pd G4 (7.66 mg, 8.31 μmol) in dioxane (1 mL) was heated to 90° C. for 1 h. The mixture was concentrated in vacuo and the residue was partitioned between 5% MeOH/DCM and water and the layers separated. The organic layer was dried over $Na_2SO_4$, filtered and evaporated to give the crude product. This was purified by silica gel chromatography on ISCO (0 to 8% MeOH/DCM) to give the title compound as a pale-yellow foam, 6.4 mg, 76%. LCMS m/z=512 $[M+H]^+$; 1H NMR (500 MHz, DMSO-$d_6$) δ 9.75 (d, 1H), 8.86 (d, 1H), 8.79 (d, 1H), 8.26 (d, 1H), 8.20 (s, 1H), 7.90 (d, 1H), 7.58-7.48 (m, 2H), 7.13 (t, 1H), 6.04-5.92 (m, 1H), 4.49 (dt, 4H), 3.79-3.69 (m, 2H), 3.65-3.51 (m, 3H), 3.48-3.39 (m, 1H), 3.23-3.15 (m, 1H), 2.37 (s, 3H), 1.90-1.70 (m, 2H).

Examples 132 to 141

The compounds in the following table were prepared from the appropriate bromopyrazolo[1,5-a]pyridine and amine, following a similar procedure to that described in Example 131. Alternative purification conditions are listed in the table below.

| Compound No | Name, Starting Materials (SM), Purification, Yield | Data |
|---|---|---|
| 132 | methyl 3-(5-(3-(5-(dimethylamino)pyrazolo[1,5-a]pyridine-3-carboxamido)-4-methylphenyl)-2H-tetrazol-2-yl)azetidine-1-carboxylate<br>SM: Intermediate 11 and dimethylamine<br>silica gel ISCO chromatography (0 to 100% EtOAc/Hex<br>pale yellow foam, 60.7 mg, 86% yield | LCMS m/z = 476 $[M + H]^+$; 1H NMR (500 MHz, DMSO-$d_6$) δ 9.35 (s, 1H), 8.59-8.50 (m, 2H), 8.22 (s, 1H), 7.84 (d, 1H), 7.46 (d, 1H), 7.12 (d, 1H), 6.83-6.76 (m, 1H), 5.91 (q, 1H), 4.57 (t, 2H), 4.39 (d, 2H), 3.63 (s, 3H), 3.05 (s, 6H), 2.37 (s, 3H). |
| 133 | methyl 3-(5-(4-methyl-3-(5-(methylamino)pyrazolo[1,5-a]pyridine-3-carboxamido)phenyl)-2H-tetrazol-2-yl)azetidine-1-carboxylate<br>SM: Intermediate 11 and methylamine<br>21.4 mg, 26.3% yield as a pale-yellow solid | LCMS m/z = 462 $[M + H]^+$; 1H NMR (500 MHz, DMSO-$d_6$) δ 9.31 (d, 1H), 8.50 (d, 1H), 8.39 (dd, 1H), 8.22 (s, 1H), 7.84 (d, 1H), 7.46 (dd, 1H), 6.92 (d, 1H), 6.77-6.69 (m, 1H), 6.54-6.49 (m, 1H), 5.91 (p, 1H), 4.57 (t, 2H), 4.39 (d, 2H), 3.64 (s, 3H), 2.76 (d, 3H), 2.37 (s, 3H). |
| 134 | methyl (S)-3-(5-(3-(5-((2-methoxypropyl)amino)pyrazolo[1,5-a]pyridine-3-carboxamido)-4-methylphenyl)-2H-tetrazol-2-yl)azetidine-1-carboxylate<br>SM: Intermediate 11 and (S)-2-methoxypropan-1-amine<br>white foam, 24.7 mg, 30.4% yield, | LCMS m/z = 520 $[M + H]^+$; 1H NMR (500 MHz, DMSO-$d_6$) δ 9.31 (s, 1H), 8.49 (d, 1H), 8.39 (dd, 1H), 8.21 (s, 1H), 7.84 (d, 1H), 7.49-7.42 (m, 1H), 7.00 (s, 1H), 6.73-6.62 (m, 2H), 5.99-5.86 (m, 1H), 4.57 (t, 2H), 4.39 (d, 2H), 3.64 (s, 3H), 3.57 (q, 1H), 3.30 (s, 3H), 3.13 (s, 2H), 2.36 (s, 3H), 1.17 (dd, 3H) |
| 135 | methyl (R)-3-(5-(3-(5-((1-methoxypropan-2-yl)amino)pyrazolo[1,5-a]pyridine-3-carboxamido)-4-methylphenyl)-2H-tetrazol-2-yl)azetidine-1-carboxylate<br>SM: Intermediate 11 and (R)-1-methoxypropan-2-amine<br>26.9 mg, 33.1% yield | LCMS m/z = 520 $[M + H]^+$; 1H NMR (500 MHz, DMSO-$d_6$) δ 9.30 (d, 1H), 8.49 (d, 1H), 8.39 (dd, 1H), 8.21 (s, 1H), 7.84 (d, 1H), 7.46 (dd, 1H), 7.02 (d, 1H), 6.61-6.55 (m, 2H), 5.91 (dt, 1H), 4.57 (t, 2H), 4.40 (d, 2H), 3.64 (d, 4H), 3.46-3.38 (m, 1H), 3.29 (s, 3H), 2.36 (s, 3H), 1.18 (d, 3H). |
| 136 | methyl (S)-3-(5-(4-methyl-3-(5-((tetrahydrofuran-3-yl)amino)pyrazolo[1,5-a]pyridine-3-carboxamido)phenyl)-2H- | LCMS m/z = 518 $[M + H]^+$; 1H NMR (500 MHz, DMSO-$d_6$) δ 9.33 (s, 1H), 8.51 (d, 1H), 8.42 |

-continued

| Compound No | Name, Starting Materials (SM), Purification, Yield | Data |
|---|---|---|
| | tetrazol-2-yl)azetidine-1-carboxylate<br>SM: Intermediate 11 and (S)-tetrahydrofuran-3-amine 58.1 mg of white foam. | (dd, 1H), 8.21 (s, 1H), 7.84 (d, 1H), 7.46 (d, 1H), 6.99 (s, 1H), 6.92 (d, 1H), 6.59-6.52 (m, 1H), 5.92 (dq, 1H), 4.56 (d, 2H), 4.39 (d, 2H), 4.06 (d, 1H), 3.93-3.81 (m, 2H), 3.80-3.71 (m, 1H), 3.64 (d, 4H), 2.36 (s, 3H), 2.22 (dq, 1H), 1.84 (s, 1H). |
| 137[A] | methyl 3-(2-(3-(5-(ethylamino)pyrazolo[1,5-a]pyridine-3-carboxamido)-4-methylphenyl)-2H-1,2,3-triazol-4-yl)azetidine-1-carboxylate<br>SM: Intermediate 18 and ethylamine<br>53.2 mg, 63.6% yield as an off-white solid | LCMS m/z = 475 $[M + H]^+$; 1H NMR (500 MHz, DMSO-$d_6$) δ 9.26 (s, 1H), 8.49 (s, 1H), 8.39 (d, 1H), 8.19 (s, 1H), 8.14 (s, 1H), 7.72 (d, 1H), 7.41 (d, 1H), 6.95 (s, 1H), 6.67 (d, 1H), 6.53 (d, 1H), 4.41-4.28 (m, 2H), 4.12-4.03 (m, 3H), 3.60 (s, 3H), 3.12 (p, 2H), 2.34 (s, 3H), 1.22 (t, 3H). |
| 138 | methyl 3-(2-(4-methyl-3-(5-(methylamino)pyrazolo[1,5-a]pyridine-3-carboxamido)phenyl)-2H-1,2,3-triazol-4-yl)azetidine-1-carboxylate<br>SM: Intermediate 18 and methylamine<br>21.1 mg, 26%, of pale-yellow solid | LCMS m/z = 461 $[M + H]^+$; 1H NMR (500 MHz, DMSO-$d_6$) δ 9.27 (d, 1H), 8.49 (s, 1H), 8.39 (d, 1H), 8.19 (s, 1H), 8.14 (s, 1H), 7.73 (d, 1H), 7.44-7.39 (m, 1H), 6.92 (s, 1H), 6.78-6.70 (m, 1H), 6.52 (d, 1H), 4.35 (br s, 2H), 4.08 (br s, 3H), 3.60 (s, 3H), 2.77 (d, 3H), 2.34 (s, 3H). |
| 139 | methyl 3-(2-(3-(5-((2,2-difluoroethyl)amino)pyrazolo[1,5-a]pyridine-3-carboxamido)-4-methylphenyl)-2H-1,2,3-triazol-4-yl)azetidine-1-carboxylate<br>SM: Intermediate 18 and 2,2-difluoroethan-1-amine<br>61.5 mg, 68.3% yield as an off white solid. | LCMS m/z = 511 $[M + H]^+$; 1H NMR (500 MHz, DMSO-$d_6$) δ 9.31 (s, 1H), 8.53 (s, 1H), 8.46 (d, 1H), 8.19 (s, 1H), 8.14 (s, 1H), 7.73 (d, 1H), 7.42 (d, 1H), 7.15 (s, 1H), 7.00 (t, 1H), 6.66 (d, 1H), 6.20 (t, 1H), 4.35 (br. s, 2H), 4.08 (br. s, 3H), 3.67-3.55 (m, 5H), 2.34 (s, 3H). |
| 140 | methyl 3-(2-(4-methyl-3-(5-((oxetan-3-ylmethyl)amino)pyrazolo[1,5-a]pyridine-3-carboxamido)phenyl)-2H-1,2,3-triazol-4-yl)azetidine-1-carboxylate<br>SM: Intermediate 18 and oxetan-3-ylmethanamine<br>30 mg, 32.9% as white foam. | LCMS m/z = 517 $[M + H]^+$; H NMR (500 MHz, DMSO-$d_6$) δ 9.28 (s, 1H), 8.50 (s, 1H), 8.41 (d, 1H), 8.20 (s, 1H), 8.15 (s, 1H), 7.73 (d, 1H), 7.42 (d, 1H), 7.00 (s, 1H), 6.78 (d, 1H), 6.53 (d, 1H), 4.70 (t, 2H), 4.40-4.29 (m, 4H), 4.14-4.00 (m, 3H), 3.60 (s, 3H), 3.40 (t, 2H), 3.30-3.21 (m, 1H), 2.34 (s, 3H). |
| 141 | methyl 3-(2-(4-methyl-3-(5-(oxetan-3-ylamino)pyrazolo[1,5-a]pyridine-3-carboxamido)phenyl)-2H-1,2,3-triazol-4-yl)azetidine-1-carboxylate<br>SM: Intermediate 18 and oxetan-3-ylamine<br>49.6 mg, 56% of white foam. | LCMS m/z = 503 $[M + H]^+$;<br><br>1H NMR (500 MHz, DMSO-$d_6$) δ 9.32 (s, 1H), 8.52 (d, 1H), 8.47 (d, 1H), 8.15 (s, 2H), 7.74 (d, 1H), 7.42 (d, 2H), 6.80 (s, 1H), 6.55 (d, 1H), 4.89 (t, 2H), 4.61 (p, 1H), 4.47 (t, 2H), 4.35 (br.s, 2H), 4.08 (br.s, 3H), 3.60 (s, 3H), 2.33 (s, 3H) |

A = DMF was used as the reaction solvent

Example 142

Methyl 3-(5-(3-(5-((2-hydroxyethyl)amino)pyrazolo[1,5-a]pyridine-3-carboxamido)-4-methylphenyl)-2H-tetrazol-2-yl)azetidine-1-carboxylate

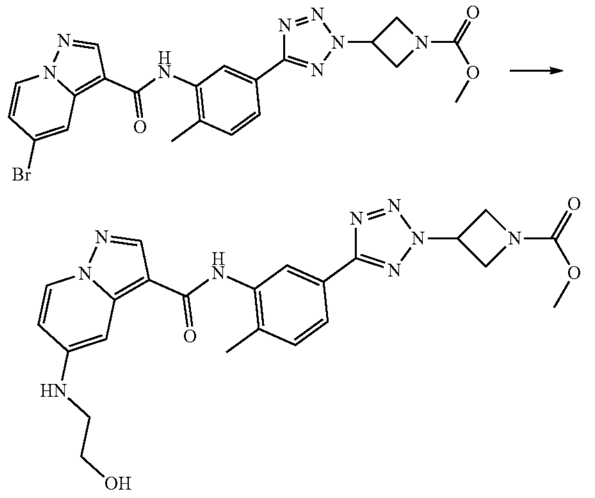

A mixture of Intermediate 11 (100 mg, 0.20 mmol), 2-aminoethan-1-ol (17.8 mg, 0.29 mmol), RockPhos Pd G3 (23 mg, 0.03 mmol) and $Cs_2CO_3$ (95.1 mg, 0.29 mmol) in dioxane (10 mL) was stirred at 100° C. under $N_2$ for 3 h. The mixture was concentrated to dryness and the residue was purified on prep-TLC with DCM:MeOH=20:1. The resulting product was purified by prep-HPLC, Method C, 34% to 63%, (9.1 mg, 9.5%) as a white solid. LCMS: m/z=492 $[M+H]^+$; 1H NMR (400 MHz, DMSO-$d_6$) δ 9.31 (s, 1H), 8.51-8.33 (m, 2H), 8.21 (d, 1H), 7.83 (dd, 1H), 7.45 (d, 1H), 6.97 (d, 1H), 6.72 (t, 1H), 6.59 (dd, 1H), 5.97-5.86 (m, 1H), 4.81 (t, 1H), 4.56 (s, 2H), 4.38 (s, 2H), 3.61 (d, 5H), 3.16 (q, 2H), 2.35 (s, 3H).

Example 143 methyl 3-(5-(3-(6-(2-methoxyethoxy)pyrazolo[1,5-a]pyridine-3-carboxamido)-4-methylphenyl)-2H-tetrazol-2-yl)azetidine-1-carboxylate

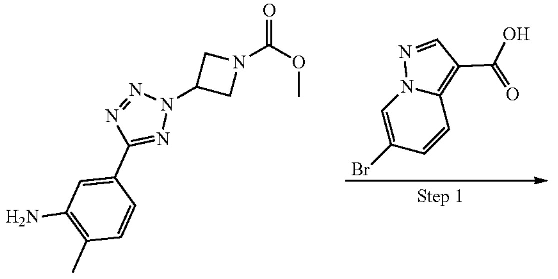

-continued

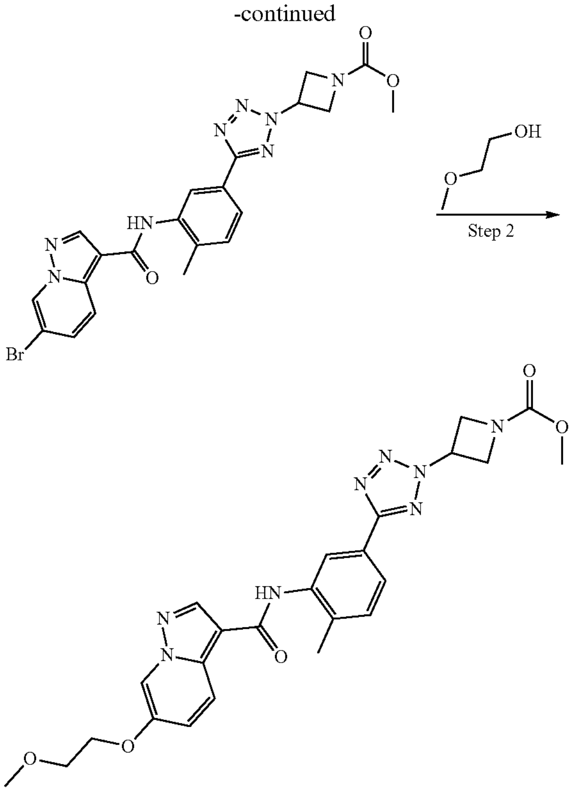

Step 1: Synthesis of methyl 3-(5-(3-(6-bromopyrazolo[1,5-a]pyridine-3-carboxamido)-4-methylphenyl)-2H-tetrazol-2-yl)azetidine-1-carboxylate To a stirred solution of Intermediate 11, step 4, (1.5 g, 5.20 mmol) in THF (15 mL) were added T3PR (4.96 g, 15.6 mmol), pyridine (821 mg, 10.4 mmol) and 6-bromopyrazolo[1,5-a]pyridine-3-carboxylic acid (2.50 g, 10.4 mmol) at rt. The mixture was stirred for 12 h at 80° C. and then cooled to rt. Water (5 mL) was added and the resulting solution was extracted with DCM (3×20 mL). The organic layer was dried with $Na_2SO_4$ and concentrated under vacuum. The crude product was purified by silica gel column with PE:EtOAc=1:2 to give the title compound (1.8 g, 68%) as an off-white solid. LCMS: m/z=511 $[M+H]^+$ Step 2: Synthesis of methyl 3-(5-(3-(6-(2-methoxyethoxy)pyrazolo[1,5-a]pyridine-3-carboxamido)-4-methylphenyl)-2H-tetrazol-2-yl)azetidine-1-carboxylate The title compound was obtained as a white solid, 19.6 mg, 25%, from methyl 3-(5-(3-(6-bromopyrazolo[1,5-a]pyridine-3-carboxamido)-4-methylphenyl)-2H-tetrazol-2-yl)azetidine-1-carboxylate and 2-methoxyethan-1-ol, following a similar procedure to that described in Example 142. The crude product was purified by Prep-HPLC, Method A, 30% to 52% gradient, to give the title compound (19.6 mg, 25%) as a white solid. LCMS: m/z=507 $[M+H]^+$; 1H NMR (400 MHz, DMSO-$d_6$) δ 9.71 (s, 1H), 8.68 (s, 1H), 8.58 (d, 1H), 8.19-8.09 (m, 2H), 7.88 (dd, 1H), 7.48 (d, 1H), 7.34 (dd, 1H), 5.91 (td, 1H), 4.55 (d, 2H), 4.38 (s, 2H), 4.24-4.17 (m, 2H), 3.74-3.67 (m, 2H), 3.63 (s, 3H), 3.34 (s, 3H), 2.36 (s, 3H).

Example 144 methyl 3-(5-(3-(5-((2-methoxyethyl)amino)-6-methylpyrazolo[1,5-a]pyridine-3-carboxamido)-4-methylphenyl)-2H-tetrazol-2-yl)azetidine-1-carboxylate

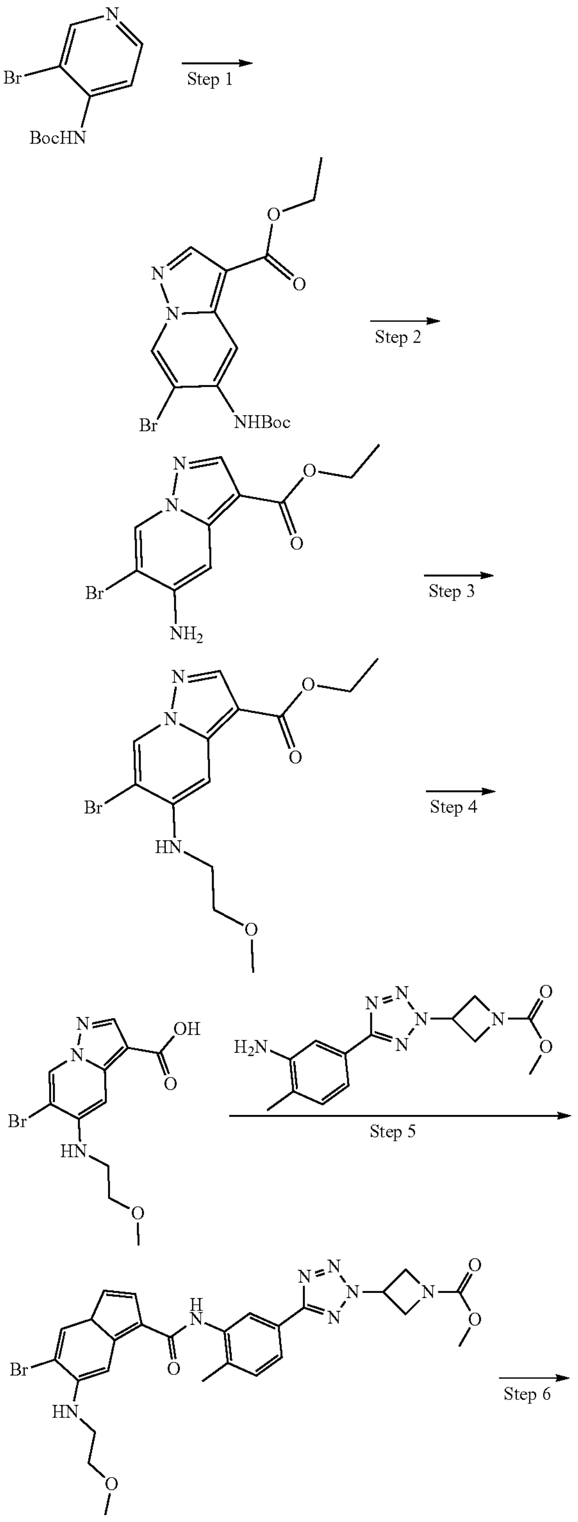

-continued

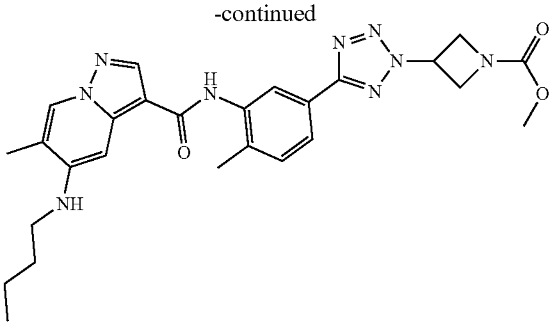

Step 1: Synthesis of ethyl 6-bromo-5-((tert-butoxycarbonyl)amino)pyrazolo[1,5-a]pyridine-3-carboxylate A solution of tert-butyl(3-bromopyridin-4-yl)carbamate (5 g, 18.3 mmol) and O-(2,4-dinitrophenyl)hydroxylamine (9.09 g, 45.7 mmol) in MeCN (100 mL) was stirred at 50° C. for 40 h. The mixture was evaporated under reduced pressure to give 1-amino-3-bromo-4-(((tert-butoxy)carbonyl)amino)pyridin-1-ium 2,4-dinitrobenzen-1-olate (crude), 15 g. This was dissolved in DMF (100 mL), $K_2CO_3$ (21.3 g, 155 mmol) added and the reaction mixture stirred at rt for 1 h. Ethyl prop-2-ynoate (5.08 g, 51.8 mmol) was added and the reaction mixture stirred at rt for 18 h. The mixture was diluted with EtOAc (200 mL), washed with water (200 mL×3) and saturated brine (200 mL). The organic layer was dried over $Na_2SO_4$, filtered and evaporated to afford the crude product. This was purified by silica gel column with PE:EtOAc=5:1 to give the title compound, 580 mg as a yellow solid and ethyl 4-bromo-5-((tert-butoxycarbonyl)amino)pyrazolo[1,5-a]pyridine-3-carboxylate, 880 mg. LCMS m/z=384 $[M+H]^+$ Step 2: Synthesis of ethyl 5-amino-6-bromopyrazolo[1,5-a]pyridine-3-carboxylate TFA (2 mL) was added to ethyl 6-bromo-5-((tert-butoxycarbonyl)amino)pyrazolo[1,5-a]pyridine-3-carboxylate in DCM (8 mL) and the solution stirred at rt for 2 h. The reaction mixture was diluted with EtOAc (100 mL), washed with saturated aq. $NaHCO_3$ (100 mL×3) and brine (100 mL). The organic layer was dried over $Na_2SO_4$, filtered and evaporated to give the title compound (200 mg, 90.4%) as a yellow solid. LCMS m/z=284 $[M+H]^+$ Step 3: Synthesis of ethyl 6-bromo-5-((2-methoxyethyl)amino)pyrazolo[1,5-a]pyridine-3-carboxylate NaH (56.0 mg, 1.40 mmol) was added to ethyl 5-amino-6-bromopyrazolo[1,5-a]pyridine-3-carboxylate (200 mg, 0.70 mmol) in DMF (10 mL) at 0° C., and after stirring for 30 min, 1-bromo-2-methoxyethane (145 mg, 1.05 mmol) was added and the reaction mixture stirred for 16 h. The reaction mixture was diluted with EtOAc (100 mL), washed with water (100 mL×3) and brine (100 mL). The organic layer was dried over $Na_2SO_4$, filtered and evaporated to afford crude product. This was purified by prep-TLC with PE:EtOAc=4:1 to afford the title compound (140 mg, 58.3%) as a brown solid. LCMS m/z=342 $[M+H]^+$ Step 4: Synthesis of 6-bromo-5-((2-methoxyethyl)amino)pyrazolo[1,5-a]pyridine-3-carboxylic acid NaOH (32.7 mg, 0.82 mmol) was added to ethyl 6-bromo-5-((2-methoxyethyl)amino)pyrazolo[1,5-a]pyridine-3-carboxylate (140 mg, 0.41 mmol) in MeOH/$H_2O$ (2 mL/6 mL) at rt and the reaction mixture was heated to 60° C. for 16 h. The residue was diluted with water, then adjusted to pH 3 with HCl (1M). The mixture was extracted with EtOAc (3×100 mL), the organic layers combined, washed with brine, dried over $Na_2SO_4$ and concentrated under vacuum to give the title compound (115 mg, 89.8%) as a yellow solid. LCMS m/z=314 $[M+H]^+$ Step 5: Synthesis of methyl 3-(5-(3-(6-bromo-5-((2-methoxyethyl)amino)pyrazolo[1,5-a]pyridine-3-carboxamido)-4-methylphenyl)-2H-tetrazol-2-yl) azetidine-1-carboxylate The title compound was obtained as a yellow solid, 80 mg, 43.2% from 6-bromo-5-((2-methoxyethyl)amino)pyrazolo[1,5-a]pyridine-3-carboxylic acid and Intermediate 11, step 4, following the procedure described in Example 114, step 2. LCMS m/z=584.4 $[M+H]^+$ Step 6: Synthesis of methyl 3-(5-(3-(5-((2-methoxyethyl)amino)-6-methylpyrazolo[1,5-a]pyridine-3-carboxamido)-4-methylphenyl)-2H-tetrazol-2-yl) azetidine-1-carboxylate A mixture of $Pd(PPh_3)_4$(11.7 mg, 10.2 μmol), $K_2CO_3$ (21.1 mg, 0.15 mmol), methyl 3-(5-(3-(6-bromo-5-((2-methoxyethyl)amino)pyrazolo[1,5-a]pyridine-3-carboxamido)-4-methylphenyl)-2H-tetrazol-2-yl)azetidine-1-carboxylate (60 mg, 0.10 mmol) and trimethyl-1,3,5,2,4,6-trioxatriborinane (15.3 mg, 0.12 mmol) in DMF (5 mL) was stirred at 100° C. under $N_2$ for 16 h. The reaction mixture was diluted with EtOAc (100 mL), washed with water (100 mL×3) and saturated brine (100 mL). The organic layer was dried over $Na_2SO_4$, filtered and evaporated to afford crude product. The crude product was purified by prep-TLC with DCM:MeOH=35:1. The residue was purified by Prep-HPLC, Method C, 22% to 510% gradient, to afford the title compound (6.8 mg, 12.8%) as a white solid. LCMS: m/z=520 $[M+H]^+$, 1H NMR (400 MHz, DMSO-$d_6$) δ 9.31 (s, 1H), 8.46 (s, 1H), 8.40 (d, 1H), 8.21 (d, 1H), 7.83 (dd, 1H), 7.45 (d, 1H), 7.03 (s, 1H), 5.91 (dq, 2H), 4.56 (s, 2H), 4.38 (s, 2H), 3.63 (s, 3H), 3.57 (t, 2H), 3.30-3.33 (m, 1H), 3.34-3.36 (m, 1H), 3.29 (s, 3H), 2.35 (s, 3H), 2.15 (d, 3H).

Example 145 methyl 3-(5-(3-(6-chloro-5-((2-methoxyethyl)amino) pyrazolo[1,5-a]pyridine-3-carboxamido)-4-methylphenyl)-2H-tetrazol-2-yl)azetidine-1-carboxylate

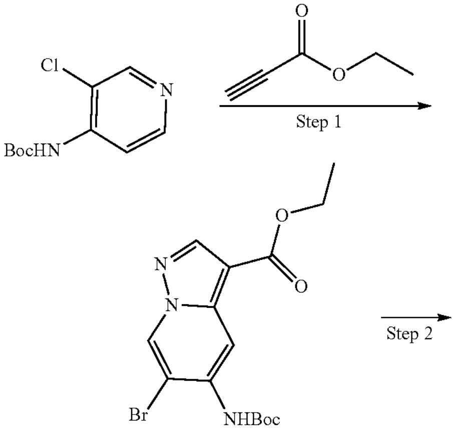

-continued

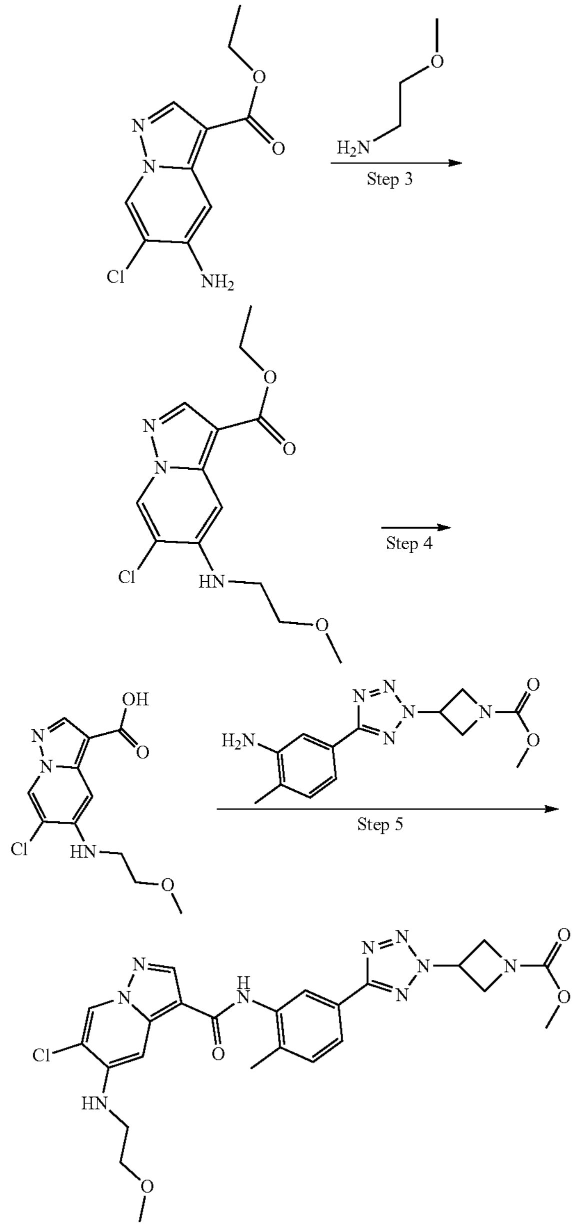

The title compound was obtained as a white solid, from tert-butyl(3-chloropyridin-4-yl)carbamate and Intermediate 11, step 4, following a similar 5 step process to that described in Example 144, step 1 to 5. LCMS: m/z=540.0 $[M+H]^+$, 1H NMR (400 MHz, DMSO-$d_6$) δ 9.45 (s, 1H), 8.99 (s, 1H), 8.58 (s, 1H), 8.19 (d, 1H), 7.85 (dd, 1H), 7.46 (d, 1H), 7.18 (s, 1H), 6.22 (t, 1H), 5.91 (ddd, 1H), 4.56 (t, 2H), 4.38 (s, 2H), 3.63 (s, 3H), 3.58 (t, 2H), 3.39 (q, 2H), 3.29 (s, 3H), 2.35 (s, 3H).

Example 146 methyl 3-(5-(3-(5-((2-(2-methoxyethoxy)ethyl)amino)pyrazolo[1,5-a]pyridine-3-carboxamido)-4-methylphenyl)-2H-tetrazol-2-yl)azetidine-1-carboxylate

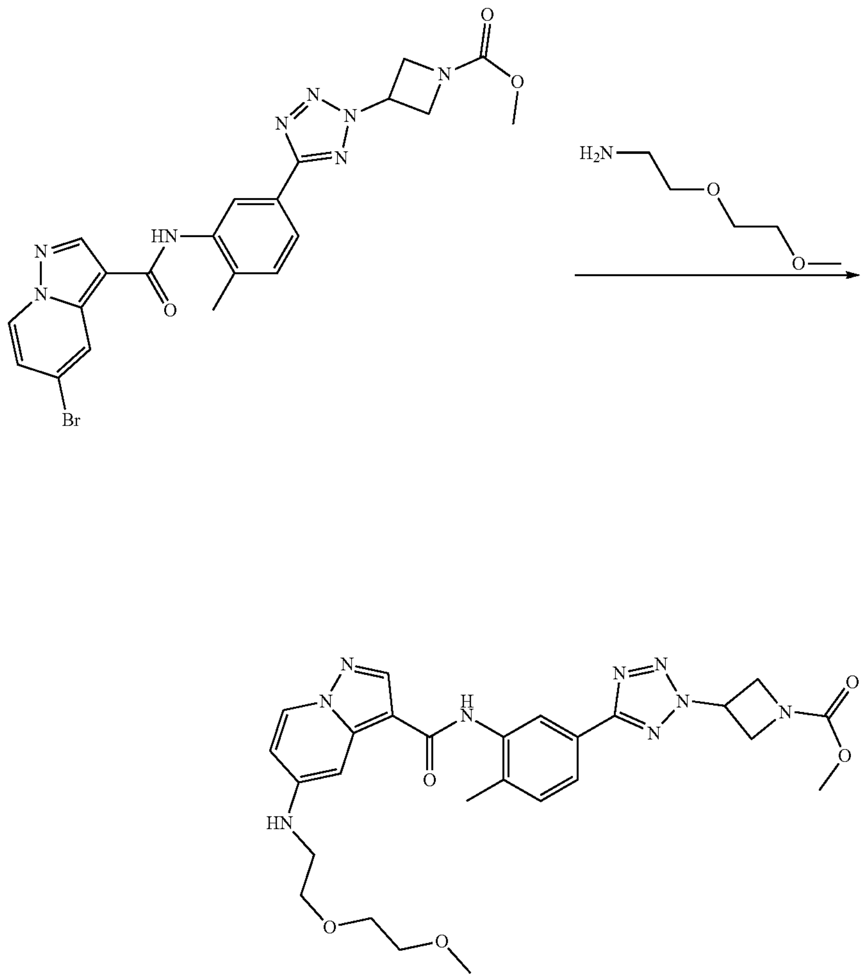

A mixture of Intermediate 11 (100 mg, 0.2 mmol), 1-(2-aminoethoxy)-2-methoxyethane (23.2 mg, 0.2 mmol), Pd-PEPPSI-IPentCl-o-picoline (14 mg, 16.7 μmol) and $Cs_2CO_3$ (95.1 mg, 0.29 mmol) in dioxane (10 mL) was stirred at 100° C. for 3 h. The cooled mixture was concentrated to dryness. The residue was purified by prep-TLC with DCM: MeOH=20:1. The resulting crude product was purified by prep-HPLC, Method B, Gradient: 23% B to 48% to afford the title compound (25.2 mg) as a white solid. LCMS: m/z=550 $[M+H]^+$; 1H NMR (400 MHz, DMSO-$d_6$) δ 9.32 (s, 1H), 8.51-8.34 (m, 2H), 8.21 (d, 1H), 7.83 (dd, 1H), 7.45 (d, 1H), 6.98 (d, 1H), 6.77 (t, 1H), 6.60 (dd, 1H), 5.91 (m, 1H), 4.56 (s, 2H), 4.38 (s, 2H), 3.62 (d, 5H), 3.59-3.52 (m, 2H), 3.49-3.42 (m, 2H), 3.26 (d, 2H), 3.23 (s, 3H), 2.35 (s, 3H).

Example 147 methyl 3-(5-(3-(5-(4,4-difluoropiperidin-1-yl)pyrazolo[1,5-a]pyridine-3-carboxamido)-4-methylphenyl)-2H-tetrazol-2-yl)azetidine-1-carboxylate

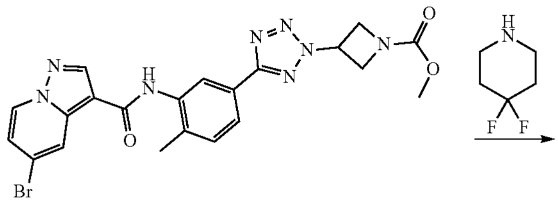

-continued

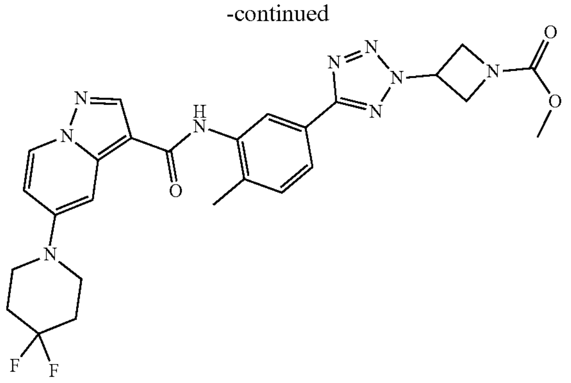

The title compound was obtained as a white solid, 10.6 mg, 9.8%, from Intermediate 11 and 4,4-difluoropiperidine following the method described in Example 146. LCMS: m/z=552 $[M+H]^+$; 1H NMR (400 MHz, DMSO-$d_6$) δ 9.47 (s, 1H), 8.61 (t, 2H), 8.21 (d, 1H), 7.85 (dd, 1H), 7.50-7.41 (m, 2H), 7.04 (dd, 1H), 5.91 (m, 1H), 4.56 (s, 2H), 4.38 (s, 2H), 3.63 (s, 3H), 3.52 (t, 4H), 2.36 (s, 3H), 2.15-2.03 (m, 4H).

Example 148 methyl 3-(5-(3-(5-((2-methoxyethyl)amino)pyrazolo [1,5-a]pyridine-3-carboxamido)-4-methylphenyl)-2H-tetrazol-2-yl)azetidine-1-carboxylate

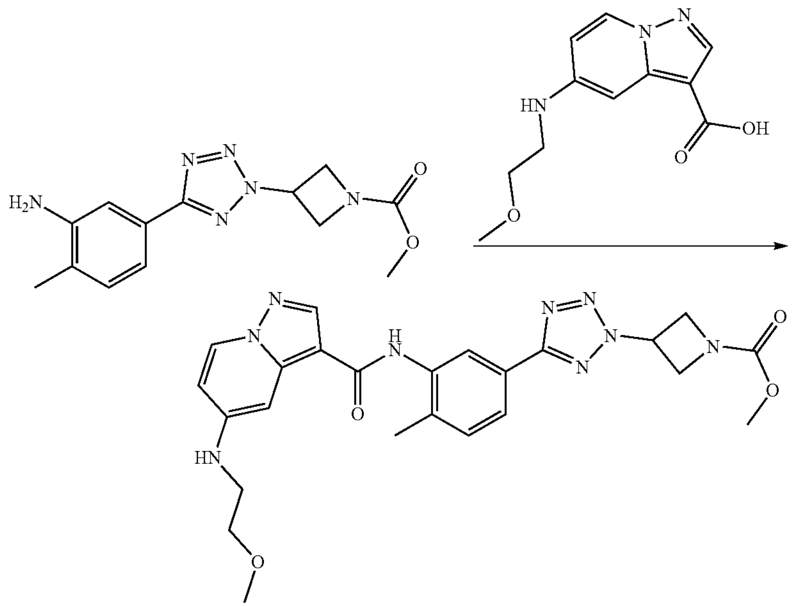

A solution of Intermediate 23 (200 mg, 0.85 mmol), Intermediate 11, step 4 (291 mg, 1.01 mmol), $T_3P$® (1 mL, 50% in EtOAc) and pyridine (1 mL) in THF (5 mL) was stirred for 2 h at 80° C. The resulting mixture was concentrated to dryness. The residue was purified by Prep TLC (EtOAc). The crude product was purified prep-HPLC Method C, 20% to 50% gradient, to afford the title compound, 96.2 mg, 22.3%, as an off-white solid. LCMS: m/z=506 $[M+H]_+$, 1H NMR (400 MHz, DMSO-$d_6$) δ 9.32 (s, 1H), 8.49 (s, 1H), 8.40 (d, 1H), 8.21 (d, 1H), 7.83 (dd, 1H), 7.45 (d, 1H), 6.98 (d, 1H), 6.77 (t, 1H), 6.61 (dd, 1H), 5.91 (m, 1H), 4.57 (m, 4H), 3.63 (s, 3H), 3.54 (t, 2H), 3.32-3.22 (m, 5H), 2.35 (s, 3H).

Example 149 ethyl 3-(5-(3-(5-((2-methoxyethyl)amino)pyrazolo [1,5-a]pyridine-3-carboxamido)-4-methylphenyl)-2H-tetrazol-2-yl)azetidine-1-carboxylate

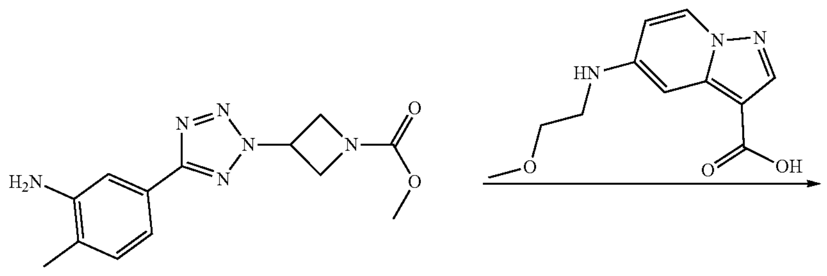

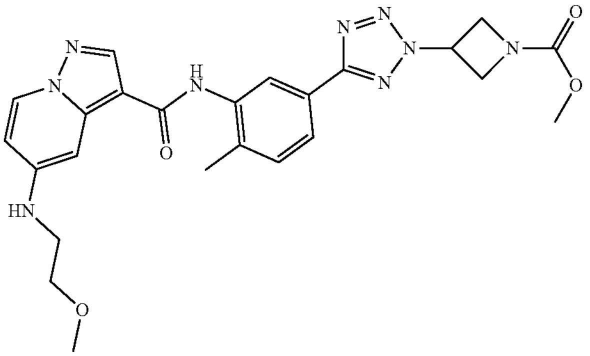

The title compound was obtained as a white solid, 47.1 mg, 27.4%, from Intermediate 14, step 2 and Intermediate 23 following the procedure described in Example 148. LCMS: m/z=520 $[M+H]^+$, 1H NMR (400 MHz, DMSO-$d_6$) δ 9.32 (s, 1H), 8.51-8.36 (m, 2H), 8.21 (d, 1H), 7.83 (dd, 1H), 7.45 (d, 1H), 6.98 (d, 1H), 6.77 (m, 1H), 6.60 (dd, 1H), 5.96-5.85 (m, 1H), 4.56 (m, 4H), 4.07 (m, 2H), 3.54 (m, 2H), 3.29 (s, 3H), 3.26 (m, 2H), 2.35 (s, 3H), 1.20 (t, 3H).

Example 150

5-((2-methoxyethyl)amino)-N-(2-methyl-5-(2-(spiro [3.3]heptan-2-yl)-2H-tetrazol-5-yl)phenyl)pyrazolo [1,5-a]pyridine-3-carboxamide

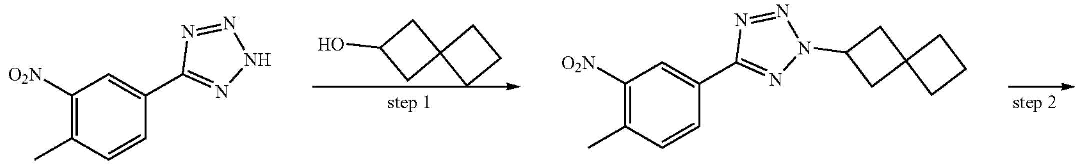

-continued

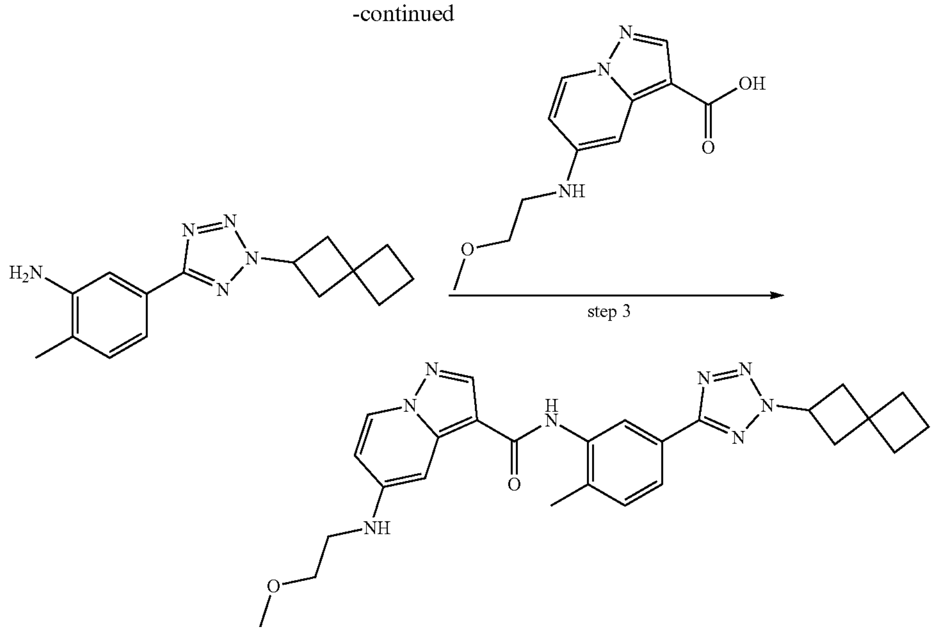

Step 1: Synthesis of 5-(4-methyl-3-nitrophenyl)-2-(spiro[3.3]heptan-2-yl)-2H-tetrazole The title compound was obtained as a white solid, 330 mg, 61.3%, from 5-(4-methyl-3-nitrophenyl)-2H-tetrazole (J. Med. Chem. 54(6), 1599-1612, 370 mg, 1.80 mmol) and spiro[3.3]heptan-2-ol, using a similar procedure to that described in Intermediate 4, step 1. LCMS: m/z=300 $[M+H]^+$ Step 2: Synthesis of 2-methyl-5-(2-(spiro[3.3]heptan-2-yl)-2H-tetrazol-5-yl)aniline The title compound was obtained as a brown solid, 280 mg, 94.5% yield, from 5-(4-methyl-3-nitrophenyl)-2-(spiro[3.3]heptan-2-yl)-2H-tetrazole, following the procedure described in Intermediate 14, step 2. LCMS: m/z=270 $[M+H]^+$ Step 3: Synthesis of 5-((2-methoxyethyl)amino)-N-(2-methyl-5-(2-(spiro[3.3]heptan-2-yl)-2H-tetrazol-5-yl)phenyl)pyrazolo[1,5-a]pyridine-3-carboxamide The title compound was obtained as an off-white solid, 20.3 mg, 9.2%, from 2-methyl-5-(2-(spiro[3.3]heptan-2-yl)-2H-tetrazol-5-yl)aniline and Intermediate 23 following a similar procedure to that described in Example 148. LCMS: m/z=487 $[M+H]^+$, $^1H$ NMR (400 MHz, DMSO-$d_6$) δ 9.31 (s, 1H), 8.49 (s, 1H), 8.39 (d, 1H), 8.16 (d, 1H), 7.80 (dd, 1H), 7.43 (d, 1H), 6.97 (d, 1H), 6.77 (t, 1H), 6.60 (dd, 1H), 5.40-5.36 (m, 1H), 3.54 (t, 2H), 3.29 (s, 3H), 3.29-3.24 (m, 2H), 2.77-2.68 (m, 2H), 2.68-2.59 (m, 2H), 2.34 (s, 3H), 2.16 (t, 2H), 2.05 (dd, 2H), 1.91-1.78 (m, 2H).

Example 151

N-(5-(2-(3-fluorocyclobutyl)-2H-tetrazol-5-yl)-2-methylphenyl)-5-((2-methoxyethyl)amino)pyrazolo[1,5-a]pyridine-3-carboxamide

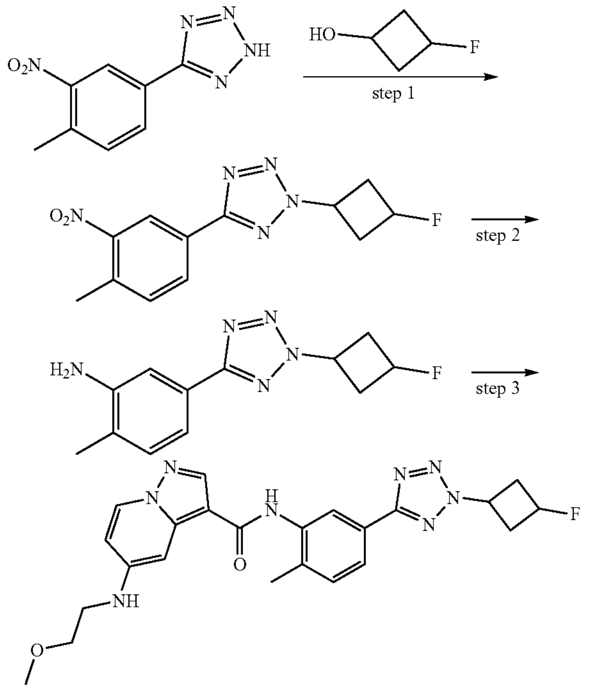

The title compound was obtained as a white solid, from 5-(4-methyl-3-nitrophenyl)-2H-1,2,3,4-tetrazole, 3-fluorocyclobutan-1-ol and Intermediate 23 following a similar 3 step procedure to that described in Example 150. LCMS: m/z=465 $[M+H]^+$; $^1H$ NMR (400 MHz, DMSO-$d_6$) δ 9.32

(s, 1H), 8.49 (s, 1H), 8.39 (d, 1H), 8.19 (d, 1H), 7.82 (dd, 1H), 7.44 (d, 1H), 6.97 (d, 1H), 6.77 (t, 1H), 6.60 (dd, 1H), 5.23-5.01 (m, 2H), 3.54 (t, 2H), 3.29-3.24 (m, 5H), 3.21-3.11 (m, 2H), 2.99-2.81 (m, 2H), 2.35 (s, 3H).

Example 152

N-(5-(5-cyclopropyl-2H-tetrazol-2-yl)-2-methylphenyl)pyrazolo[1,5-a]pyridine-3-carboxamide

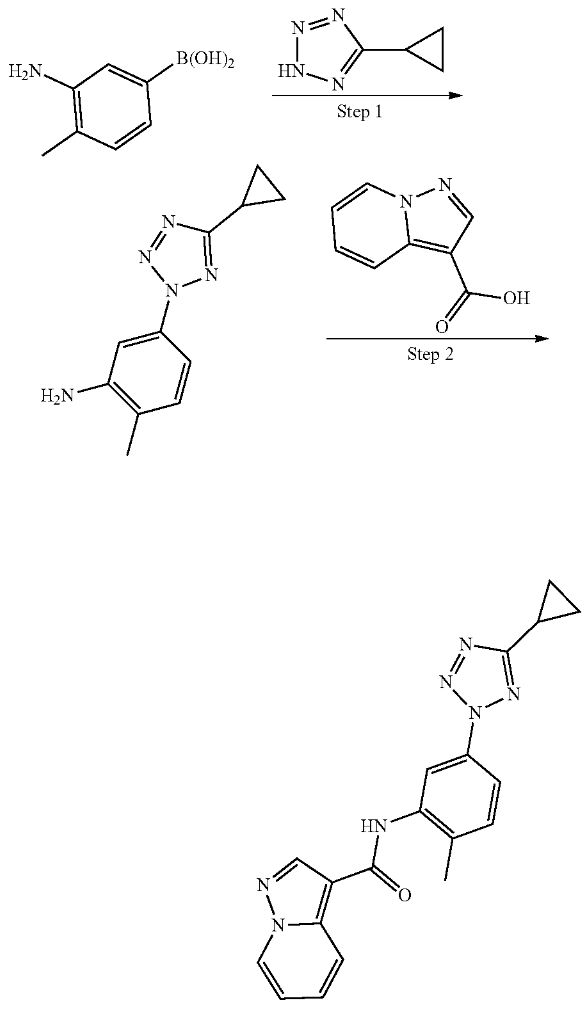

Step 1: Synthesis of 5-(5-cyclopropyl-2H-1,2,3,4-tetrazol-2-yl)-2-methylaniline

The title compound was obtained as a brown solid, 400 mg, 40%, from (3-amino-4-methylphenyl)boronic acid and 5-cyclopropyl-2H-1,2,3,4-tetrazole, following a similar procedure to that described in Intermediate 21, step 1. LCMS: m/z=216 $[M+H]^+$ Step 2: Synthesis of N-(5-(5-cyclopropyl-2H-tetrazol-2-yl)-2-methylphenyl)pyrazolo[1,5-a]pyridine-3-carboxamide The title compound was obtained as a white solid, 6.1 mg, from 5-(5-cyclopropyl-2H-1,2,3,4-tetrazol-2-yl)-2-methylaniline and pyrazolo[1,5-a]pyridine-3-carboxylic acid, following a similar procedure to that described in Example 148. LCMS: m/z=360 $[M+H]^+$, 1H NMR (300 MHz, DMSO-$d_6$) δ 9.78 (s, 1H), 8.87 (d, 1H), 8.80 (s, 1H), 8.30-8.17 (m, 2H), 7.82 (dd, 1H), 7.61-7.49 (m, 2H), 7.16-7.11 (m, 1H), 2.39 (s, 3H), 2.39-2.31 (m, 1H), 1.20-1.16 (m, 2H), 1.12-0.99 (m, 2H).

Example 153

5-methoxy-N-(2-methyl-5-(2-(1-(methylsulfonyl)azetidin-3-yl)-2H-tetrazol-5-yl)phenyl)pyrazolo[1,5-a]pyridine-3-carboxamide

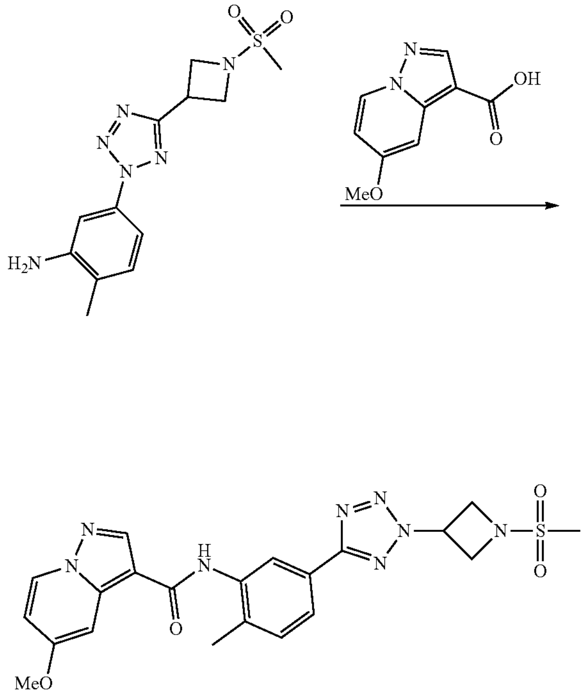

A mixture of 6-methoxypyrazolo[1,5-a] pyridine-3-carboxylic acid (100 mg, 0.52 mmol), Intermediate 39, step 2 (160 mg, 0.52 mmol), HATU (197 mg, 0.52 mmol) and DIPEA (143 mg, 1.03 mmol) in DMF (4 mL) was stirred at 50° C. for 16 h. The mixture was extracted with EtOAc (2×50 mL), the combined organic extracts washed with water (20 mL) then dried over $Na_2SO_4$. The organic layer was concentrated and the residue was purified by Prep-HPLC, Method H, 40% to 50% gradient, to give the title compound (12.2 mg) as a white solid. LCMS: m/z=483 $[M+H]^+$, 1H NMR (400 MHz, DMSO-$d_6$) δ 9.71 (s, 1H), 8.69 (s, 1H), 8.56 (d, 1H), 8.19 (d, 1H), 8.13 (d, 1H), 7.88 (dd, 1H), 7.49 (d, 1H), 7.33 (dd, 1H), 5.93 (td, 1H), 4.55-4.43 (m, 4H), 3.87 (s, 3H), 3.18 (s, 3H), 2.36 (s, 3H).

Example 154

5-((2,2-difluoroethoxy)methyl)-N-(2-methyl-5-(2-(1-(methylsulfonyl)azetidin-3-yl)-2H-tetrazol-5-yl)phenyl)pyrazolo[1,5-a]pyridine-3-carboxamide

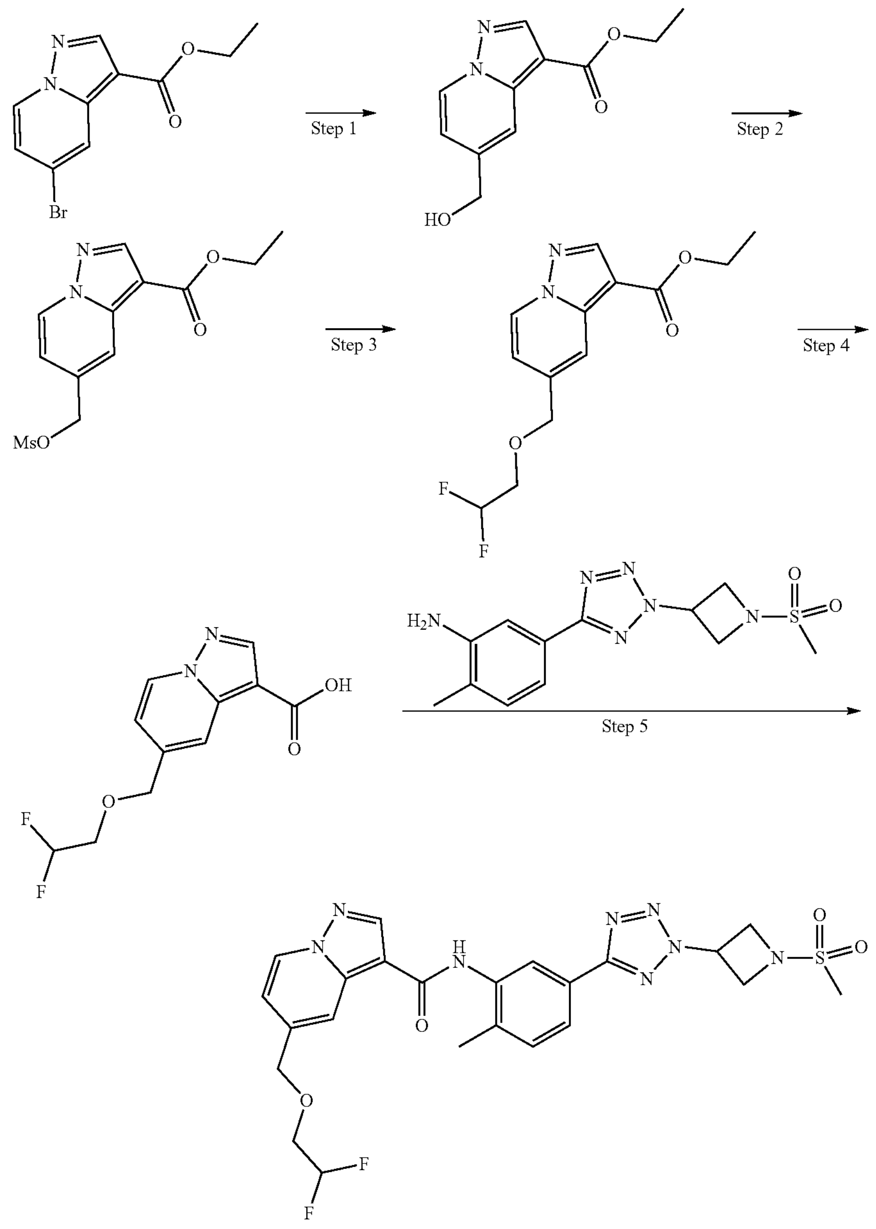

Step 1: Synthesis of ethyl 5-(hydroxymethyl)pyrazolo[1,5-a]pyridine-3-carboxylate (Tributylstannyl)methanol (3.56 g, 11.1 mmol) was added to ethyl 5-bromopyrazolo[1,5-a]pyridine-3-carboxylate (2 g, 7.43 mmol) and $Pd(PPh_3)_4$(858 mg, 0.74 mmol) in DMF (20 mL) at rt and the reaction mixture stirred at 100° C. for 3 h under $N_2$. The mixture was diluted with EtOAc (200 mL) and washed with water (50 mL×2), the organic layer was dried with $Na_2SO_4$ and concentrated under vacuum. The residue was purified by silica gel column with DCM: EtOAc=18:1 to give the title compound (1.5 mg, 75%) as a white solid. LCMS: m/z=221 $[M+H]^+$.

Step 2: Synthesis of ethyl 5-(((methylsulfonyl)oxy)methyl)pyrazolo[1,5-a]pyridine-3-carboxylate Methanesulfonyl methanesulfonate (1.42 g, 8.17 mmol) was added to ethyl 5-(hydroxymethyl)pyrazolo[1,5-a]pyridine-3-carboxylate (1.5 g, 6.81 mmol) and TEA (694 mg, 6.81 mmol) in DCM (30 mL) at 0° C. and the reaction mixture stirred at 25° C. for 1.5 h. The mixture was concentrated in vacuo and the residue was purified by silica gel column with DCM:MeOH=18:1 to give the title compound (850 mg, 56.6%) as a yellow solid. LCMS: m/z=299 $[M+H]^+$.

Step 3: Synthesis of ethyl 5-((2,2-difluoroethoxy)methyl)pyrazolo[1,5-a]pyridine-3-carboxylate NaH (66.8 mg, 1.67 mmol) was added to 2,2-difluoroethan-1-ol (411 mg, 5.01 mmol) in THF (10 mL) at 0° C. and the reaction mixture stirred at 25° C. for 0.5 h. Ethyl 5-(((methylsulfonyl)oxy)methyl)pyrazolo[1,5-a]pyridine-3-carboxylate (500 mg, 1.67 mmol) was added and the reaction mixture stirred at rt for 2 h under $N_2$. The mixture was diluted with EtOAc (100 mL), washed with brine (50 mL×2), the organic layer was dried with $Na_2SO_4$ and concentrated under vacuum. The residue was purified by silica gel column with PE:EtOAc=15:1 to give the title compound (150 mg, 30%) as an off-white solid. LCMS: m/z=285 $[M+H]^+$.

Step 4: Synthesis of 5-((2,2-difluoroethoxy)methyl)pyrazolo[1,5-a]pyridine-3-carboxylic acid NaOH (126 mg, 3.16 mmol) was added to ethyl 5-((2,2-difluoroethoxy)methyl)pyrazolo[1,5-a]pyridine-3-carboxylate (150 mg, 0.53 mmol) in EtOH (8 mL) and $H_2O$ (2 mL) and the reaction was stirred at 100° C. for 10 h. Dilute HCl was added to acidify to pH 6, the mixture was diluted with EtOAc (100 mL), washed with brine (50 mL×2), the organic layer was dried with $Na_2SO_4$ and concentrated under vacuum. The residue was purified by silica gel column with DCM:MeOH=18:1 to give the title compound (850 mg, 42.5%) as a yellow solid. LCMS: m/z=257 $[M+H]^+$.

Step 5: 5-((2,2-difluoroethoxy)methyl)-N-(2-methyl-5-(2-(1-(methylsulfonyl)azetidin-3-yl)-2H-tetrazol-5-yl)phenyl)pyrazolo[1,5-a]pyridine-3-carboxamide 2,4,6-Trichlorobenzoyl chloride (99.7 mg, 0.409 mmol) and TEA (78.4 mg, 0.682 mmol) were added to 5-((2,2-difluoroethoxy)methyl)pyrazolo[1,5-a]pyridine-3-carboxylic acid (70 mg, 0.27 mmol) in THF (6 mL) at 0° C. and the solution stirred for 1 h. Intermediate 39, Step 2 (50 mg, 0.16 mmol) was added and the reaction mixture stirred at 80° C. for 4 h under $N_2$. The mixture was diluted with DCM (100 mL), washed with brine (50 mL×2), the organic layer was dried with $Na_2SO_4$ and concentrated under vacuum. The residue was purified by silica gel column with PE:EtOAc=15:1 to give the title compound (8.2 mg) as a white solid. LCMS: m/z=520 $[M+H]^+$. $^1$H NMR (400 MHz, DMSO-$d_6$) δ 9.76 (s, 1H), 8.83 (dd, 2H), 8.25-8.18 (m, 2H), 7.89 (dd, 1H), 7.49 (d, 1H), 7.05 (dd, 1H), 6.24 (t, 1H), 5.95 (tt, 1H), 4.77-4.72 (m, 2H), 4.57-4.41 (m, 4H), 3.82 (td, 2H), 3.18 (s, 3H), 2.37 (s, 3H).

Example 155

5-(3-hydroxy-3-methylbutyl)-N-(2-methyl-5-(2-(1-(methylsulfonyl)azetidin-3-yl)-2H-tetrazol-5-yl)phenyl)pyrazolo[1,5-a]pyridine-3-carboxamide

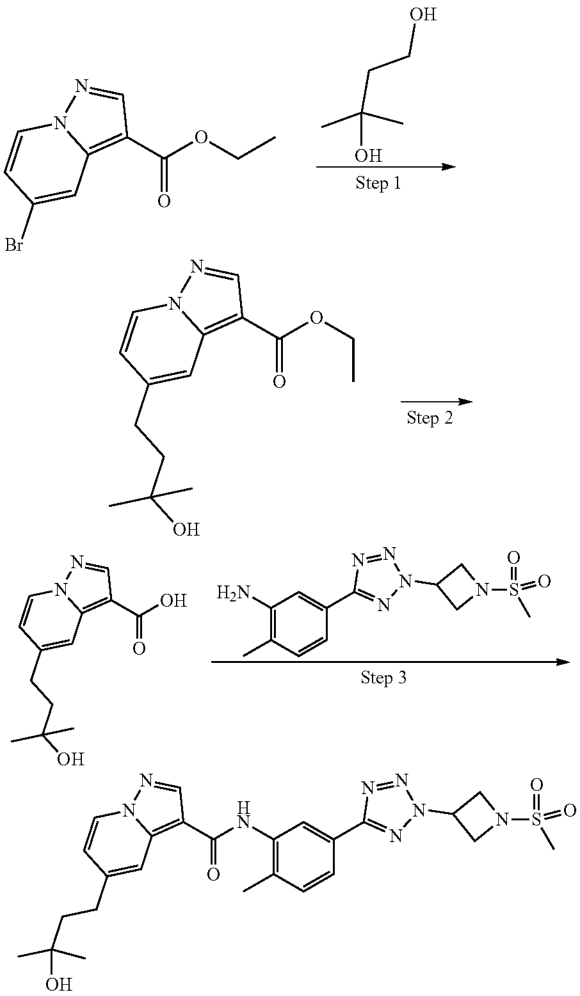

Step 1: Synthesis of ethyl 5-(3-hydroxy-3-methylbutyl)pyrazolo[1,5-a]pyridine-3-carboxylate The title compound was obtained as a yellow solid, 270 mg, 33.8% from 3-methylbutane-1,3-diol and ethyl-5-bromopyrazolo[1,5-a]pyridine-3-carboxylate following a similar procedure to that described in Example 58. LCMS: m/z=277 $[M+H]^+$.

Step 2: Synthesis of 5-(3-hydroxy-3-methylbutyl)pyrazolo[1,5-a]pyridine-3-carboxylic acid The title compound was obtained as a yellow solid, 100 mg, 40%, from ethyl 5-(3-hydroxy-3-methylbutyl)pyrazolo[1,5-a]pyridine-3-carboxylate, following the procedure described in Example 154, step 4. LCMS: m/z=249 $[M+H]^+$.

Step 3: Synthesis of 5-(3-hydroxy-3-methylbutyl)-N-(2-methyl-5-(2-(1-(methylsulfonyl)azetidin-3-yl)-2H-tetrazol-5-yl)phenyl)pyrazolo[1,5-a]pyridine-3-carboxamide The title compound was obtained as a white solid, 14.6 mg, from 5-(3-hydroxy-3-methylbutyl)pyrazolo[1,5-a]pyridine-3-carboxylic acid and Intermediate 39, Step 2, following the procedure described in Example 154, step 5. LCMS: m/z=539 $[M+H]^+$. $^1$H NMR (400 MHz, DMSO-$d_6$) δ 9.68 (s, 1H), 8.74 (d, 2H), 8.21 (d, 1H), 8.04 (s, 1H), 7.88 (dd, 1H), 7.49 (d, 1H), 6.99 (dd, 1H), 6.00-5.89 (m, 1H), 4.45 (dd, 4H), 4.33 (s, 1H), 3.18 (s, 3H), 2.80-2.71 (m, 2H), 2.44 (s, 3H), 2.37 (s, 2H), 1.16 (s, 6H).

Example 156

N-(5-(2-(3,3-difluorocyclobutyl)-2H-tetrazol-5-yl)-2,4-dimethylphenyl)-5-morpholinopyrazolo[1,5-a]pyridine-3-carboxamide

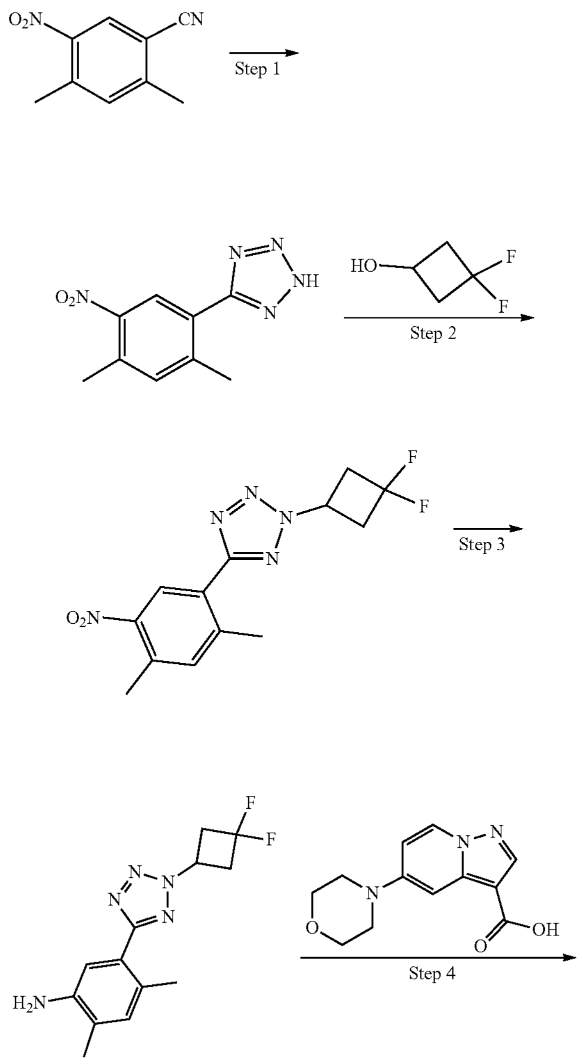

-continued

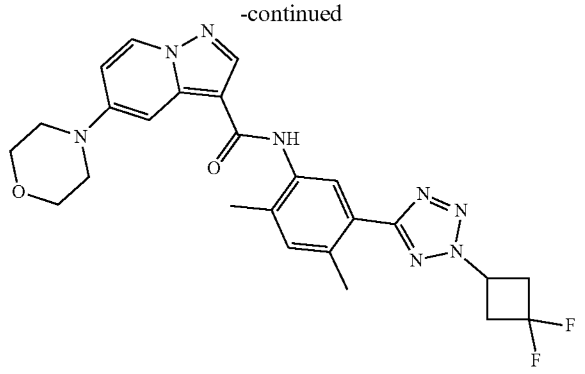

Steps 1 and 2: Synthesis of 2-(3,3-difluorocyclobutyl)-5-(2,4-dimethyl-5-nitrophenyl)-2H-tetrazole The title compound was obtained as a white solid, 600 mg, from 2,4-dimethyl-5-nitrobenzonitrile and 3,3-difluorocyclobutan-1-ol following a similar 2 step procedure to that described in Intermediate 10, steps 1 and 2. LCMS: m/z=310 $[M+H]^+$ Step 3: Synthesis of 5-(2-(3,3-difluorocyclobutyl)-2H-tetrazol-5-yl)-2,4-dimethylaniline Fe (651 mg, 11.64 mmol) was added to 2-(3,3-difluorocyclobutyl)-5-(2,4-dimethyl-5-nitrophenyl)-2H-tetrazole (600 mg, 1.94 mmol)) in EtOH (1 drop HCl (con) in 10 mL) and $H_2O$ (1 mL) at rt and the reaction was stirred at 80° C. for 16 h. The cooled mixture was filtered, the filtrate was extracted with EtOAc (2×100 mL) and the combined extracts washed with brine (50 mL), dried over anhydrous $Na_2SO_4$ and concentrated under vacuum. The residue was purified by prep-TLC with DCM:MeOH=10:1 to give the title compound (300 mg, 55.4%) as a yellow solid, LCMS: m/z=280 $[M+H]^+$ Step 4: Synthesis of N-(5-(2-(3,3-difluorocyclobutyl)-2H-tetrazol-5-yl)-2,4-dimethylphenyl)-5-morpholinopyrazolo[1,5-a]pyridine-3-carboxamide DMF (0.1 mL) was added to 5-morpholinopyrazolo[1,5-a]pyridine-3-carboxylic acid (Intermediate 25, 132 mg, 0.54 mmol) and $(COCl)_2$ (340 mg, 0.54 mmol) in DCM (10 mL) at 0° C. and the solution stirred at rt for 2 h. The reaction mixture was concentrated under vacuum and the residue added to 5-(2-(3,3-difluorocyclobutyl)-2H-tetrazol-5-yl)-2,4-dimethylaniline (150 mg, 0.54 mmol) in pyridine (10 mL) at rt. The reaction mixture was stirred at rt for 2 h then concentrated under vacuum. The crude product was purified by Prep-HPLC Method A, 37 to 62% gradient, to give the title compound (70.4 mg, 25.7%) as a white solid. LCMS: m/z=509 $[M+H]^+$. $^1$H NMR (400 MHz, DMSO-$d_6$) δ 9.46 (s, 1H), 8.59 (d, 2H), 8.02 (s, 1H), 7.45-7.21 (m, 2H), 6.98 (dd, 1H), 5.61 (p, 1H), 3.76 (t, 4H), 3.43 (dtd, 4H), 3.27 (t, 4H), 2.57 (s, 3H), 2.31 (s, 3H).

Example 157 methyl 3-(5-(4-chloro-3-(6-((2-methoxyethyl)amino)pyrazolo[1,5-a]pyridine-3-carboxamido)phenyl)-2H-tetrazol-2-yl)azetidine-1-carboxylate

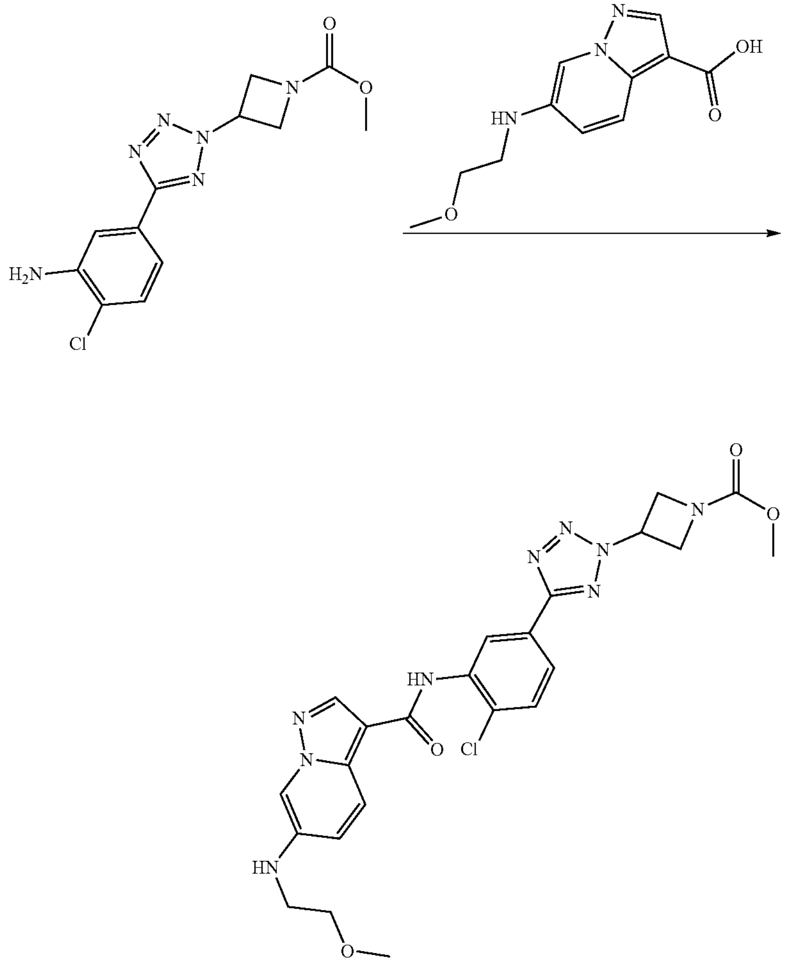

To a solution of Intermediate 23 (100 mg, 0.42 mmol) in DCM (5 mL), was added $SOCl_2$ (1 mL) at 0° C. and the solution stirred for 1 h. The mixture was concentrated to dryness, the residue was diluted with DCM (2 mL) and added to a solution of Intermediate 10 (131 mg, 0.42 mmol) and TEA (127 mg, 1.26 mmol) in DCM (5 mL). The resulting mixture was stirred for 16 h at rt. The reaction mixture was quenched with $H_2O$ (10 mL), extracted with DCM (3x30 mL), and the organic layer was concentrated to dryness. The crude product was purified by prep-TLC with EtOAc and then by prep-HPLC, Method I, 32% to 52% gradient, to give the title compound (24.0 mg) as a white solid, LCMS: m/z=526 $[M+H]^+$, $^1H$ NMR (400 MHz, DMSO-$d_6$) δ 9.44 (s, 1H), 8.54-8.48 (m, 2H), 8.41 (d, 1H), 7.91 (dd, 1H), 7.74 (d, 1H), 6.97 (d, 1H), 6.84 (t, 1H), 6.62 (dd, 1H), 5.94-5.92 (m, 1H), 4.57 (s, 2H), 4.40 (s, 2H), 3.63 (s, 3H), 3.55 (t, 2H), 3.30 (s, 3H), 3.28-3.26 (m, 2H).

Example 158

N-(2-methyl-5-(2-(2-(2,2,2-trifluoroethoxy)ethyl)-2H-tetrazol-5-yl)phenyl)pyrazolo[1,5-a]pyridine-3-carboxamide

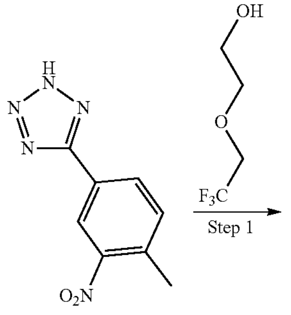

-continued

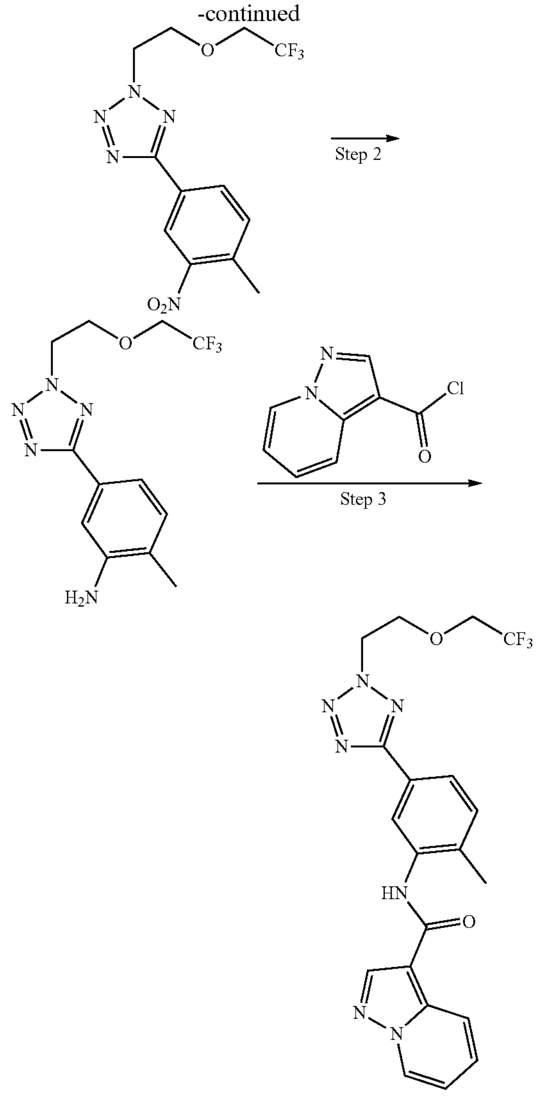

Step 1: Synthesis of 5-(4-methyl-3-nitrophenyl)-2-(2-(2,2,2-trifluoroethoxy)ethyl)-2H-tetrazole To a stirred solution of 2-(2,2,2-trifluoroethoxy)ethan-1-ol (800 mg, 5.55 mmol) and TEA (1.12 g, 11.1 mmol) in DCM (5 mL) was added MsCl (762 mg, 6.66 mmol) under $N_2$ at 0° C. The reaction was stirred for 2 h at rt and quenched with ice water. The mixture was extracted with DCM (3×50 mL) and the organic layer was evaporated under reduced pressure to give 2-(2,2,2-trifluoroethoxy)ethyl methanesulfonate (1.1 g; 89%) as a yellow oil.

To a solution of 5-(4-methyl-3-nitrophenyl)-2H-tetrazole (J. Med. Chem. 54(6), 1599-1612, 500 mg, 2.43 mmol) and 2-(2,2,2-trifluoroethoxy)ethyl methanesulfonate (646 mg, 2.91 mmol) in DMF (5 mL) was added $K_2CO_3$ (670 mg, 4.86 mmol) under $N_2$ at rt. The reaction was stirred for 2 h at 90° C. and cooled to rt. Water (10 mL) was added and the mixture was extracted with DCM (3×50 mL). The organic layer was washed with brine (30 mL) and concentrated under vacuum. The crude product was purified by Prep-TLC eluting with DCM:MeOH=10:1 to give the title compound (510 mg, 63%) as a white solid. LCMS m/z=332 $[M+H]^+$ Step 3: Synthesis of 2-methyl-5-(2-(2-(2,2,2-trifluoroethoxy)ethyl)-2H-tetrazol-5-yl)aniline The title compound was obtained as a white solid, 450 mg, 82%, from 5-(4-methyl-3-nitrophenyl)-2-(2-(2,2,2-trifluoroethoxy)ethyl)-2H-1,2,3,4-tetrazole, following the procedure described in Intermediate 13, step 2. LCMS m/z=302 $[M+H]^+$ Step 4: Synthesis of N-(2-methyl-5-(2-(2-(2,2,2-trifluoroethoxy)ethyl)-2H-tetrazol-5-yl)phenyl)pyrazolo[1,5-a]pyridine-3-carboxamide To a stirred solution of 2-methyl-5-(2-(2-(2,2,2-trifluoroethoxy)ethyl)-2H-tetrazol-5-yl)aniline (600 mg, 1.99 mmol) in pyridine (6 mL) was added pyrazolo[1,5-a]pyridine-3-carbonyl chloride (429 mg, 2.38 mmol) under $N_2$ at rt. The reaction was stirred for 15 mins at rt and concentrated under vacuum. The mixture was dissolved in DCM (50 mL) and washed with water (30 mL). The organic layer was concentrated and purified by Prep-HPLC, Method C, 30% to 55% gradient, to give the title compound (583 mg, 65%) as a white solid. LCMS: m/z=446 $[M+H]^+$, $^1H$ NMR (300 MHz, DMSO-$d_6$) δ 9.75 (s, 1H), 8.87 (dd, 1H), 8.80 (s, 1H), 8.26 (dt, 1H), 8.17 (d, 1H), 7.86 (dd, 1H), 7.59-7.44 (m, 2H), 7.13 (td, 1H), 4.98 (t, 2H), 4.27-4.06 (m, 4H), 2.37 (s, 3H).

Example 159 methyl 3-(5-(4-methyl-3-(6-morpholinopyrazolo[1,5-a]pyridine-3-carboxamido)phenyl)-2H-tetrazol-2-yl)azetidine-1-carboxylate

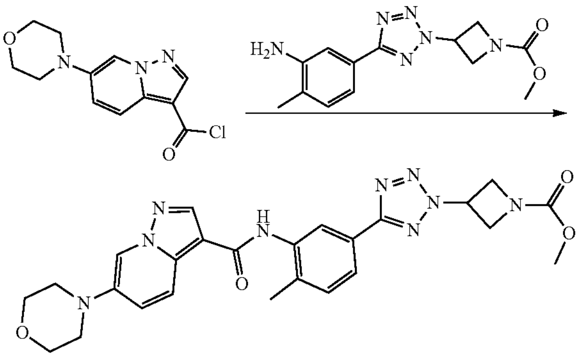

A mixture of Intermediate 27 (45 mg, 0.13 mmol), Intermediate 11, step 4, (38 mg, 0.13 mmol) and pyridine (53 mg, 0.66 mmol) in DCM (1 mL) was stirred at rt for 1 h. The mixture was concentrated in vacuo and the residue purified by reverse phase ISCO (5 to 100% MeCN/water containing 0.1% TFA). The product containing fractions were evaporated, triturated with $NaHCO_3$/water and filtered to give the title compound, 25 mg, 36.3% as tan-colored solid. LCMS m/z=518 $[M+H]^+$; 1H NMR (500 MHz, DMSO-$d_6$) δ 9.57 (s, 1H), 8.56 (s, 1H), 8.16 (s, 1H), 8.11 (s, 1H), 8.03 (d, 1H), 7.79 (d, 1H), 7.48 (d, 1H), 7.40 (d, 1H), 5.89-5.77 (m, 1H), 4.55-4.44 (m, 2H), 4.37-4.24 (m, 2H), 3.70 (t, 4H), 3.55 (s, 3H), 3.06 (t, 4H), 2.28 (s, 3H).

Example 160 methyl 3-(2-(4-methyl-3-(6-morpholinopyrazolo[1,5-a]pyridine-3-carboxamido)phenyl)-2H-1,2,3-triazol-4-yl)azetidine-1-carboxylate

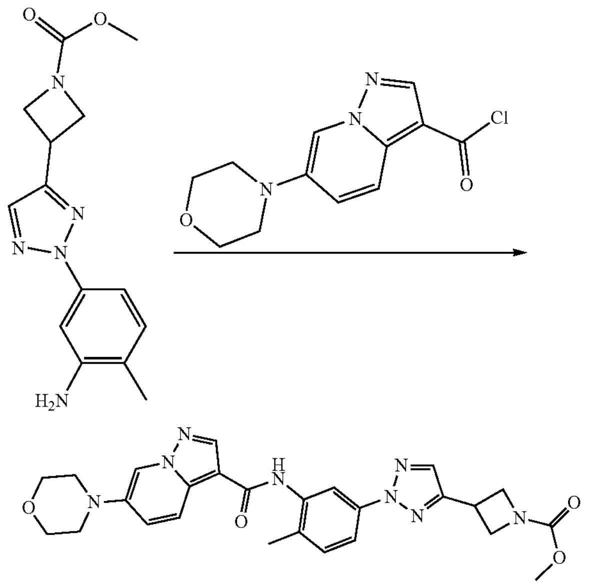

The title compound was obtained as an off-white solid, 10 mg, 20.5% from Intermediate 27 and Intermediate 18, step 5, following the procedure described in Example 159. LCMS m/z=517 $[M+H]^+$; 1H NMR (500 MHz, DMSO-$d_6$) δ 9.62 (s, 1H), 8.65 (d, 1H), 8.24 (s, 1H), 8.15 (d, 2H), 8.11 (dd, 1H), 7.76 (dd, 1H), 7.60-7.54 (m, 1H), 7.44 (d, 1H), 4.35 (s, 2H), 4.08 (t, 3H), 3.78 (s, 4H), 3.60 (s, 3H), 3.15 (q, 4H), 2.34 (s, 3H).

Example 161

N-(5-(4-(3,3-difluorocyclobutyl)-2H-1,2,3-triazol-2-yl)-2-methylphenyl)pyrazolo[1,5-a]pyridine-3-carboxamide

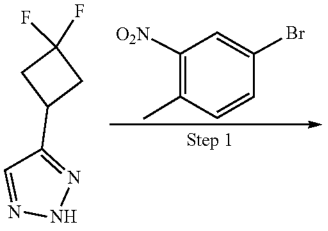

-continued

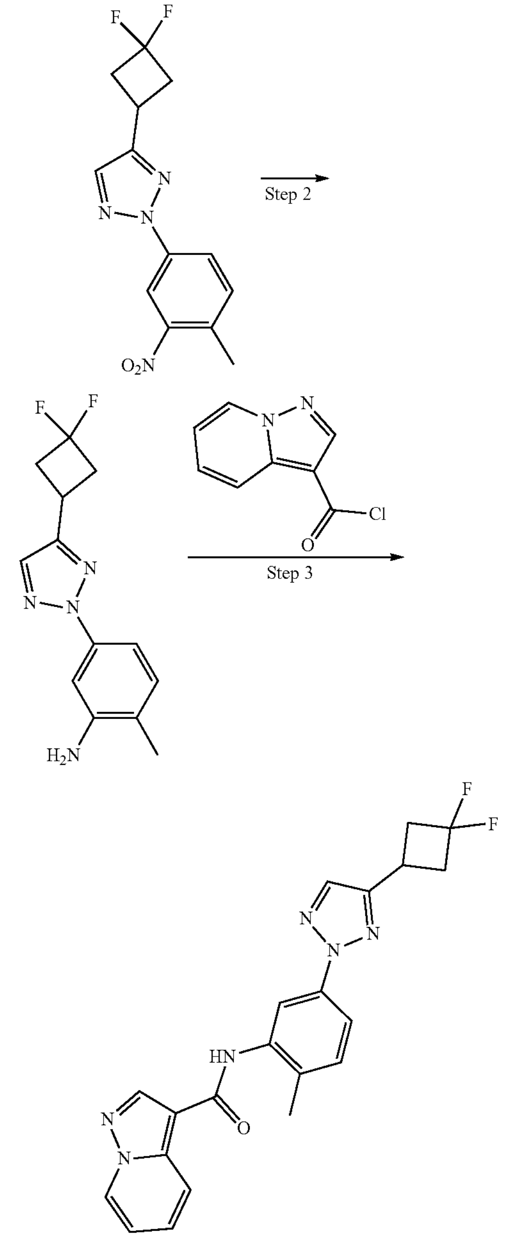

Step 1: Synthesis of 4-(3,3-difluorocyclobutyl)-2-(4-methyl-3-nitrophenyl)-2H-1,2,3-triazole A mixture of $Pd_2(dba)_3$ (2.12 mg) and $Me_4$tButylXphos (2.23 mg) in toluene (0.5 mL) was heated to 120° C. under $N_2$. This solution was added to a mixture of 4-bromo-1-methyl-2-nitrobenzene (50 mg, 0.23 mmol) and 4-(3,3-difluorocyclobutyl)-2H-1,2,3-triazole (44 mg, 0.28 mmol) in toluene (0.5 mL) under $N_2$ and the reaction mixture heated to 120° C. for 2 h. The cooled mixture was diluted with EtOAc, filtered through Celite® and the filtrate evaporated to give the crude product. This was purified by ISCO chromatography (0 to 40% EtOAc/Hex) to give the title compound as a colorless oil, 41 mg, 60.2%. LCMS m/z=295 $[M+H]^+$ Step 2: Synthesis of 5-(4-(3,3-Difluorocyclobutyl)-2H-1,2,3-triazol-2-yl)-2-methylaniline 1% Pt/2% V on carbon (4 mg) was added to a solution of 4-(3,3-difluorocyclobutyl)-2-(4-methyl-3-nitrophenyl)-2H-1,2,3-triazole (41 mg, 0.14 mmol) in MeOH (2 mL) and the mixture stirred under an atmosphere of $H_2$ for 1 h. The mixture was filtered through Celite® and the filtrate evaporated to give the title compound as a solid, 35 mg. LCMS m/z=266 $[M+H]^+$ Step 3: Synthesis of N-(5-(4-(3,3-difluorocyclobutyl)-2H-1,2,3-triazol-2-yl)-2-methylphenyl) pyrazolo[1,5-a]pyridine-3-carboxamide 5-(4-(3,3-Difluorocyclobutyl)-2H-1,2,3-triazol-2-yl)-2-methylaniline (35 mg, 0.132 mmol) was dissolved in pyridine (0.5 mL), pyrazolo[1,5-a]pyridine-3-carbonyl chloride (24 mg, 0.132 mmol) was added and the reaction mixture stirred at rt for 45 min. The mixture was concentrated in vacuo, the residue was partitioned between 5% MeOH/DCM and water and the layers separated. The organic layer was dried over $Na_2SO_4$, filtered and evaporated to give the crude product. The product was triturated with MeCN, the mixture filtered and the resulting solid dried to give the title compound as a white solid, 41 mg, 76% yield. LCMS m/z=409 $[M+H]^+$; 1H NMR (500 MHz, DMSO-$d_6$) δ 9.72 (s, 1H), 8.86 (d, 1H), 8.79 (d, 1H), 8.25 (d, 1H), 8.13 (d, 1H), 8.08 (d, 1H), 7.77 (dt, 1H), 7.54 (t, 1H), 7.45 (d, 1H), 7.13 (t, 1H), 3.66-3.56 (m, 1H), 3.15-3.03 (m, 2H), 2.95-2.82 (m, 2H), 2.35 (s, 3H).

Example 162 methyl 3-(5-(3-(5-((2,2-difluoroethoxy)methyl)pyrazolo[1,5-a]pyridine-3-carboxamido)-4-methylphenyl)-2H-tetrazol-2-yl)azetidine-1-carboxylate

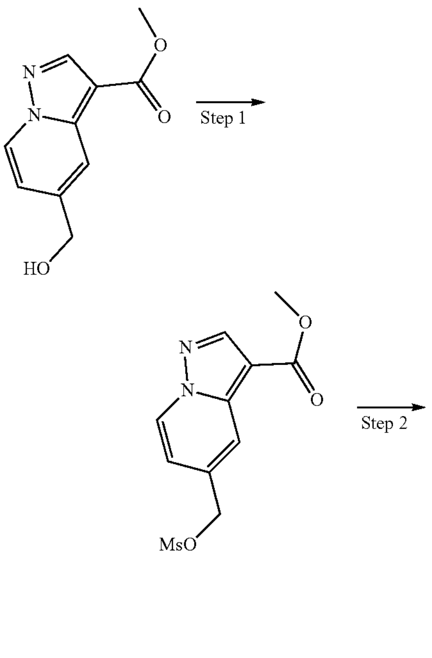

-continued

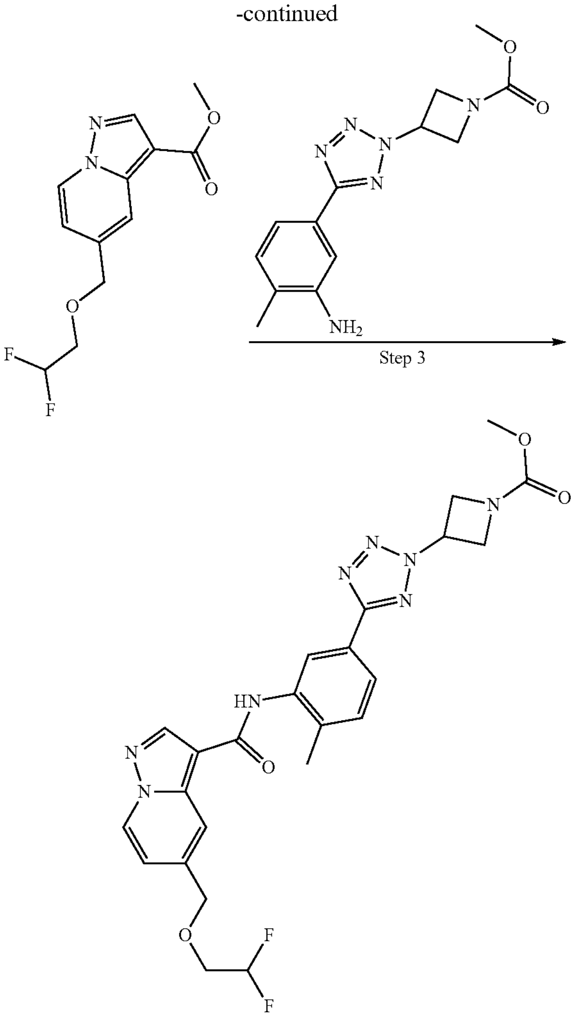

Step 1: Synthesis of methyl 5-(((methylsulfonyl)oxy)methyl)pyrazolo[1,5-a]pyridine-3-carboxylate The title compound was obtained as a yellow solid, 600 mg, 37.5% from methyl 5-(hydroxymethyl)pyrazolo[1,5-a]pyridine-3-carboxylate following the procedure described in Example 154, step 2. LCMS: m/z=285 $[M+H]^+$.

Step 2: Synthesis of methyl 5-((2,2-difluoroethoxy)methyl)pyrazolo[1,5-a]pyridine-3-carboxylate 2,2-Difluoroethan-1-ol (114 mg, 1.40 mmol) and $K_2CO_3$ (144 mg, 1.05 mmol) were added to methyl 5-(((methylsulfonyl)oxy)methyl)pyrazolo[1,5-a]pyridine-3-carboxylate (200 mg, 0.70 mmol) in DMF (10 mL) and the reaction mixture stirred at 30° C. for 10 h. The mixture was diluted with EtOAc (100 mL), washed with brine (50 mL×2), the organic layer was dried with $Na_2SO_4$ and concentrated under vacuum. The residue was purified by silica gel column with DCM:EtOAc=18:1 to give the title compound (100 mg, 50%) as a yellow solid. LCMS: m/z=271 $[M+H]^+$.

Step 3: Synthesis of methyl 3-(5-(3-(5-((2,2-difluoroethoxy)methyl)pyrazolo[1,5-a]pyridine-3-carboxamido)-4-methylphenyl)-2H-tetrazol-2-yl)azetidine-1-carboxylate $AlMe_3$ (52.6 mg, 0.33 mmol) was added to a mixture of methyl 5-((2,2-difluoroethoxy)methyl)pyrazolo[1,5-a]pyridine-3-carboxylate (60 mg, 0.22 mmol) and Intermediate 11, step 4 (52.6 mg, 0.33 mmol) in toluene and the reaction mixture was stirred at 100° C. for 3 h under $N_2$. The mixture was diluted with EtOAc (50 mL) and washed with brine (20 mL×2), the organic layer was dried with $Na_2SO_4$ and concentrated under vacuum. The residue was purified by silica gel column with DCM:MeOH=18:1. The product was further purified by prep-HPLC Method J, 40% to 51% gradient, to give the title compound (16 mg) as a yellow solid. LCMS: m/z=527 $[M+H]^+$; 1H NMR (400 MHz, DMSO-$d_6$) δ 9.76 (s, 1H), 8.86-8.80 (m, 2H), 8.25-8.17 (m, 2H), 7.88 (dd, 1H), 7.49 (d, 1H), 7.05 (dd, 1H), 6.24 (t, 1H), 5.97-5.86 (m, 1H), 4.75 (s, 2H), 4.56 (d, 2H), 4.38 (d, 2H), 3.82 (td, 2H), 3.63 (s, 3H), 2.37 (s, 3H).

Examples 163 to 170

The compounds in the following table were prepared from the appropriate ester and amine, following a similar procedure to that described in Example 162. Alternative purification conditions are described in the table below.

| Compound No | Name, Starting Materials (SM), Purification, Yield | Data |
|---|---|---|
| 163 | methyl 3-(5-(4-chloro-3-(6-morpholinopyrazolo[1,5-a]pyridine-3-carboxamido)phenyl)-2H-tetrazol-2-yl)azetidine-1-carboxylate<br>SM: Intermediate 27, step 1 and Intermediate 10<br>HPLC Method C, 34% to 54% gradient.<br>off-white solid | LCMS: m/z = 538 $[M + H]^+$; 1H NMR (400 MHz, DMSO-$d_6$) δ 9.82 (s, 1H), 8.68 (s, 1H), 8.44 (d, 1H), 8.25 (d, 1H), 8.10 (d, 1H), 7.96 (dd, 1H), 7.77 (d, 1H), 7.59 (dd, 1H), 5.93 (tt, 1H), 4.64-4.32 (m, 4H), 3.78 (t, 4H), 3.63 (s, 3H), 3.14 (t, 4H) |
| 164 | Methyl 3-(5-(4-chloro-3-(6-((2-methoxyethyl)amino)pyrazolo[1,5-a]pyridine-3-carboxamido)phenyl)-2H-tetrazol-2-yl)azetidine-1-carboxylate<br>SM: Intermediate 10 and Intermediate 42<br>Prep-HPLC Method C, 16% to 29% gradient<br>White solid, 4.6 mg, 4% | LCMS: m/z = 526 $[M + H]^+$; $^1H$ NMR (400 MHz, DMSO-$d_6$) δ 9.70 (s, 1H), 8.55 (s, 1H), 8.45 (d, 1H), 7.99-7.92 (m, 3H), 7.76 (d, 1H), 7.21 (dd, 1H), 5.97-5.87 (m, 2H), 4.56 (d, 2H), 4.39 (s, 2H), 3.63 (s, 3H), 3.55 (t, 2H), 3.31 (s, 3H), 3.21 (q, 2H). |
| 165 | N-(4-cyano-5-(2-(3,3-difluorocyclobutyl)-2H-tetrazol-5-yl)-2-methylphenyl)-5-morpholinopyrazolo[1,5-a]pyridine-3-carboxamide<br>SM: Intermediate 26 and Intermediate 31<br>yellow solid, 16 mg, 18% | LCMS: m/z = 520 $[M + H]^+$; 1H NMR (400 MHz, DMSO-$d_6$) δ 9.53 (s, 1H), 8.63 (d, 2H), 8.56 (s, 1H), 7.98 (s, 1H), 7.37 (d, 1H), 7.02 (dd, 1H), 5.67 (q, 1H), 3.76 (t, 4H), 3.44 (ddt, 4H), 3.31 (d, 4H), 2.44 (s, 3H). |
| 166 | N-(4-cyclopropyl-5-(2-(3,3-difluorocyclobutyl)-2H-tetrazol-5-yl)-2-methylphenyl)-5-morpholinopyrazolo[1,5-a]pyridine-3-carboxamide<br>SM: Intermediate 26 and Intermediate 32<br>yellow solid, 16 mg, | LCMS: m/z = 535 $[M + H]^+$; $^1H$ NMR (400 MHz, DMSO-$d_6$) δ 9.42 (s, 1H), 8.59 (d, 2H), 7.89 (s, 1H), 7.35 (d, 1H), 7.03-6.94 (m, 2H), 5.62 (td, 1H), 3.75 (t, 4H), 3.45 (d, 4H), 3.34 (s, 4H), 2.56 (ddd, 1H), 2.29 (s, 3H), 0.95 (dd, 2H), 0.96-0.87 (m, 2H). |
| 167 | N-(2,4-dichloro-5-(2-(3,3-difluorocyclobutyl)-2H-tetrazol-5-yl)phenyl)-5-morpholinopyrazolo[1,5-a]pyridine-3-carboxamide<br>SM: Intermediate 33 and Intermediate 26<br>white solid, 13.2 mg, 7.7% from | LCMS: m/z = 427 $[M + H]^+$; $^1H$ NMR (400 MHz, DMSO-$d_6$) δ 9.70 (s, 1H), 8.69-8.56 (m, 2H), 8.33 (s, 1H), 7.99 (s, 1H), 7.34 (d, 1H), 7.01 (dd, 1H), 5.75-5.57 (m, 1H), 3.76 (t, 4H), 3.55-3.36 (m, 4H), 3.29 (d, 4H). |
| 168 | N-(4-chloro-5-(2-(3,3-difluorocyclobutyl)-2H-tetrazol-5-yl)-2-methylphenyl)-5-morpholinopyrazolo[1,5-a]pyridine-3-carboxamide<br>SM: Intermediate 34 and Intermediate 26<br>HPLC method B, 40% to 60% gradient<br>white solid, 21 mg, 11.9% | LCMS: m/z = 529 $[M + H]^+$, 1H NMR (400 MHz, DMSO-$d_6$) δ 9.51 (s, 1H), 8.63-8.57 (m, 2H), 8.06 (s, 1H), 7.61 (s, 1H), 7.35 (d, 1H), 7.00 (dd, 1H), 5.65-5.61 (m, 1H), 3.76 (t, 4H), 3.53-3.40 (m, 4H), 3.33-3.26 (m, 4H), 2.36 (s, 3H). |
| 169 | N-(2-chloro-5-(2-(3,3-difluorocyclobutyl)-2H-tetrazol-5-yl)phenyl)-5-morpholinopyrazolo[1,5-a]pyridine-3-carboxamide<br>SM: Intermediate 26 and Intermediate 35<br>HPLC Method C, 49% to 64% gradient<br>white solid, 27.5 mg, 11.6% | LCMS: m/z = 515 $[M + H]^+$; $^1H$ NMR (400 MHz, DMSO-$d_6$) δ 9.62 (s, 1H), 8.66-8.58 (m, 2H), 8.47 (d, 1H), 7.92 (dd, 1H), 7.75 (d, 1H), 7.37 (d, 1H), 7.02 (dd, 1H), 5.62 (ddd, 1H), 3.76 (t, 4H), 3.53-3.37 (m, 4H), 3.30 (d, 4H). |
| 170 | N-(2-chloro-5-(2-(3,3-difluorocyclobutyl)-2H-tetrazol-5-yl)-4-methylphenyl)-5- | LCMS: m/z = 529 $[M + H]^+$; $^1H$ NMR (400 MHz, DMSO- |

-continued
| Compound No | Name, Starting Materials (SM), Purification, Yield | Data |
|---|---|---|
| | morpholinopyrazolo[1,5-a]pyridine-3-carboxamide<br>SM: Intermediate 36 and Intermediate 26<br>white solid | $d_6$) δ 9.60 (s, 1H), 8.64-8.57 (m, 2H), 8.26 (s, 1H), 7.64 (s, 1H), 7.35 (d, 1H), 7.00 (dd, 1H), 5.68-5.60 (m, 1H), 3.76 (t, 4H), 3.45 (s, 4H), 3.19 (s, 4H), 2.60 (s, 3H). |
Example 171
methyl 3-(5-(3-(6-fluoro-5-((2-methoxyethyl)amino) pyrazolo[1,5-a]pyridine-3-carboxamido)-4-methylphenyl)-2H-tetrazol-2-yl)azetidine-1-carboxylate
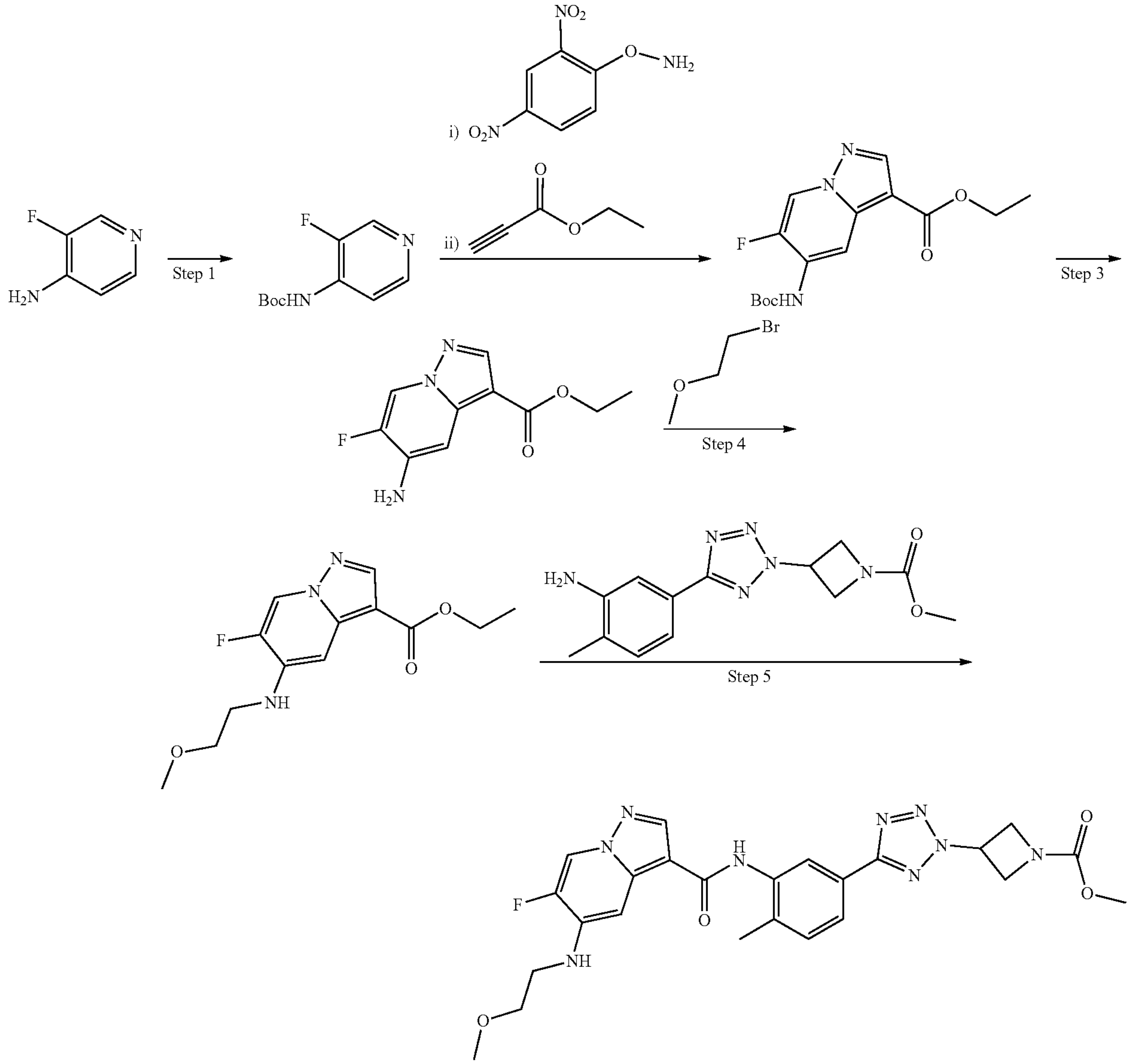

Steps 1 and 2: Synthesis of ethyl 5-((tert-butoxycarbonyl)amino)-6-fluoropyrazolo[1,5-a]pyridine-3-carboxylate The title compound was obtained as a white solid, 2.3 g, from 3-fluoropyridin-4-amine, following a similar 2 step procedure to that described in Intermediate 41. LCMS: m/z=324 $[M+H]^+$ Step 3: Synthesis of ethyl 5-amino-6-fluoropyrazolo[1,5-a]pyridine-3-carboxylate TFA (2 mL) was added to ethyl 5-((tert-butoxycarbonyl)amino)-6-fluoropyrazolo[1,5-a]pyridine-3-carboxylate (600 mg, 1.85 mmol) in DCM (8 mL) and the reaction mixture stirred at rt for 2 h. The reaction mixture was diluted with EtOAc (100 mL), washed with saturated aqueous $NaHCO_3$ (100 mL×3) and saturated brine (100 mL). The organic layer was dried over $Na_2SO_4$, filtered and evaporated to afford the title compound (350 mg, 84.9%) as a yellow solid. LCMS: m/z=224 $[M+H]^+$.

Step 4: Synthesis of ethyl 6-fluoro-5-((2-methoxyethyl)amino)pyrazolo[1,5-a]pyridine-3-carboxylate The title compound was obtained as a brown solid, 150 mg, 59.5% from ethyl 5-amino-6-fluoropyrazolo[1,5-a]pyridine-3-carboxylate and 1-bromo-2-methoxyethane, following the procedure described in Example 144, step 3. LCMS: m/z=282 $[M+H]^+$.

Step 6: Synthesis of methyl 3-(5-(3-(6-fluoro-5-((2-methoxyethyl)amino)pyrazolo[1,5-a]pyridine-3-carboxamido)-4-methylphenyl)-2H-tetrazol-2-yl)azetidine-1-carboxylate The title compound was obtained as a white solid, 8.5 mg, 4.5%, from ethyl 6-fluoro-5-((2-methoxyethyl)amino)pyrazolo[1,5-a]pyridine-3-carboxylate and Intermediate 11, step 4, following a similar procedure to that described in Example 162, step 3. The crude product was purified by Prep-HPLC, method A, 23% to 52% gradient. LCMS: m/z=524 $[M+H]^+$. $^1H$ NMR (400 MHz, DMSO-$d_6$) δ 9.42 (s, 1H), 8.92 (d, 1H), 8.55 (s, 1H), 8.19 (d, 1H), 7.85 (dd, 1H), 7.46 (d, 1H), 7.16 (d, 1H), 6.63 (s, 1H), 6.02-5.82 (m, 1H), 4.55 (d, 2H), 4.38 (s, 2H), 3.63 (s, 3H), 3.56 (t, 2H), 3.38-3.34 (m, 3H), 2.35 (s, 3H).

Example 172

N-(2-methyl-5-(2-(1-(methylsulfonyl)azetidin-3-yl)-2H-tetrazol-5-yl)phenyl)pyrazolo[1,5-a]pyridine-3-carboxamide

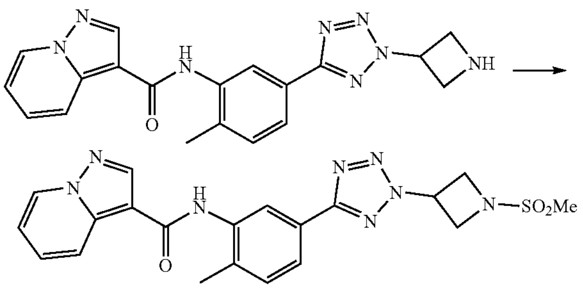

To a solution of Intermediate 15 (50 mg, 0.13 mmol) and 1M aq. $NaHCO_3$ (0.53 mL, 0.53 mmol) in THF (0.33 mL) and water (0.33 mL) was added methanesulfonyl chloride (22.9 mg, 0.20 mmol) at 0° C. and the reaction mixture stirred for 10 mins. The reaction mixture was diluted with EtOAc (3 mL), washed with water (3 mL×3) and saturated brine (3 mL). The organic layer was dried over $Na_2SO_4$, filtered and concentrated in vacuo. The crude product was purified by reverse prep-HPLC to yield the title compound (9.8 mg, 16.2%). LCMS m/z=453 $[M+H]^+$1H NMR (500 MHz, MeOD-$d_4$) δ 8.61-8.52 (m, 2H), 8.20 (d, 1H), 8.12 (d, 1H), 7.89 (dd, 1H), 7.45-7.36 (n, 21 h), 7.01 (t, 1H), 5.80 (p, 1H), 4.51-4.41 (m, 4H), 3.02 (d, 3H), 2.32 (s, 3H)

Examples 173 to 180

The compounds in the following table were prepared from Intermediate 15 and the appropriate sulfonyl chloride, following a similar procedure to that described in Example 172.

| Compound No | Structure, Sulfonyl chloride (SM), Yield | Data |
|---|---|---|
| 173 | N-(5-(2-(1-(ethylsulfonyl)azetidin-3-yl)-2H-tetrazol-5-yl)-2-methylphenyl)pyrazolo[1,5-a]pyridine-3-carboxamide<br>SM: ethanesulfonyl chloride<br>4.5 mg, 7.22% | LCMS m/z = 467 $[M + H]^+$; 1H NMR (500 MHz, MeOD-$d_4$) δ 8.73-8.64 (m, 2H), 8.32 (d, 1H), 8.24 (s, 1H), 8.01 (d, 1H), 7.57-7.48 (m, 2H), 7.13 (t, 1H), 5.96-5.86 (m, 1H), 4.63-4.51 (m, 4H), 3.23 (q, 2H), 2.44 (s, 3H), 1.44-1.37 (m, 3H). |
| 174 | N-(2-methyl-5-(2-(1-(propylsulfonyl)azetidin-3-yl)-2H-tetrazol-5-yl)phenyl)pyrazolo[1,5-alpyridine-3-carboxamide<br>SM: Propane-1-sulfonyl chloride<br>2.5 mg, 3.9% yield | LCMS m/z = 481 $[M + H]^+$<br>1H NMR (500 MHz, MeOD-$d_4$) δ 8.61-8.52 (m, 2H), 8.20 (d, 1H), 8.11 (s, 1H), 7.90 (d, 1H), 7.45-7.36 (m, 2H), 7.01 (t, 1H), 5.79 (p, 1H), 4.50-4.38 (m, 4H), 3.13-3.06 (m, 2H), 2.32 (s, 3H), 1.78 (h, 2H), 0.99 (t, 3H) |
| 175 | N-(2-methyl-5-(2-(1-((tetrahydrofuran-3-yl)sulfonyl)azetidin-3-yl)-2H-tetrazol-5-yl)phenyl)pyrazolo[1,5-a]pyridine-3-carboxamide<br>SM: tetrahydrofuran-3-sulfonyl chloride<br>12.3 mg, 16.5% | LCMS m/z = 509 $[M + H]^+$; 1H NMR (500 MHz, DMSO-$d_6$) δ 9.75 (d, 1H), 8.88-8.83 (m, 1H), 8.79 (d, 1H), 8.28-8.18 (m, 2H), 7.89 (d, 1H), 7.57-7.47 (m, 2H), 7.13 (t, 1H), 5.99 (t, 1H), 4.51 (q, 4H), 4.18 (s, 1H), 4.04-3.96 (m, 1H), 3.96-3.83 (m, 2H), 3.73 (q, 1H), 2.38 (d, 3H), 2.34-2.26 (m, 1H), 2.16 (dt, 1H). |
| 176 | N-(5-(2-(1-((2-(2,2-difluoroethoxy)ethyl)sulfonyl)azetidin-3-yl)-2H-tetrazol-5-yl)-2-methylphenyl)pyrazolo[1,5-a]pyridine-3-carboxamide<br>SM: 2-(2,2-difluoroethoxy)ethane-1-sulfonyl chloride<br>17.2 mg, 23.6%. | LCMS m/z = 547 $[M + H]^+$; 1H NMR (500 MHz, DMSO-$d_6$) δ 9.67 (s, 1H), 8.78 (d, 1H), 8.72 (d, 1H), 8.18 (d, 1H), 8.13 (s, 1H), 7.81 (d, 1H), 7.49-7.39 (m, 2H), 7.05 (t, 1H), 6.09 (tq, 1H), 5.85 (ddd, 1H), 4.47 (t, 2H), 4.40 (td, 2H), 3.86 (dt, 2H), 3.71 (tt, 3H), 2.30 (d, 3H). one proton obscured by solvent peak |
| 177 | N-(5-(2-(1-(isopropylsulfonyl)azetidin-3-yl)-2H-tetrazol-5-yl)-2-methylphenyl)pyrazolo[1,5-a]pyridine-3-carboxamide<br>SM: propane-2-sulfonyl chloride | LCMS m/z = 481 $[M + H]^+$; 1H NMR (500 MHz, DMSO-$d_6$) δ 9.68 (s, 1H), 8.78 (d, 1H), 8.71 (d, 1H), 8.18 (d, 1H), 8.11 (s, 1H), 7.81 (d, 1H), 7.49-7.39 (m, 2H), 7.05 (t, 1H), 5.90 (ddd, 1H), 4.39 (dd, 4H), 2.42-2.35 (m, 1H), 2.30 (d, 3H), 1.21 (dd, 6H) |
| 178 | N-(5-(2-(1-((2-methoxyethyl)sulfonyl)azetidin-3-yl)-2H-tetrazol-5-yl)-2-methylphenyl)pyrazolo[1,5- | LCMS m/z = 497 $[M + H]^+$; |

-continued

| Compound No | Structure, Sulfonyl chloride (SM), Yield | Data |
|---|---|---|
| | a]pyridine-3-carboxamide<br>SM: 2-methoxyethane-1-sulfonyl chloride<br>3.1 mg, 7.8% yield | |
| 179 | N-(5-(2-(1-(cyclopropylsulfonyl)azetidin-3-yl)-2H-tetrazol-5-yl)-2-methylphenyl)pyrazolo[1,5-a]pyridine-3-carboxamide<br>SM: cyclopropanesulfonyl chloride<br>2.7 mg, 7.0% yield | LCMS m/z = 479 $[M + H]^+$ |
| 180 | N-(5-(2-(1-((cyclobutylmethyl)sulfonyl)azetidin-3-yl)-2H-tetrazol-5-yl)-2-methylphenyl)pyrazolo[1,5-a]pyridine-3-carboxamide<br>SM: cyclobutylmethanesulfonyl chloride<br>8 mg, 19.7% yield | LCMS m/z = 507 $[M + H]^+$. 1H NMR (500 MHz, DMSO-$d_6$) δ 9.75 (s, 1H), 8.85 (d, 1H), 8.79 (d, 1H), 8.25 (d, 1H), 8.20 (s, 1H), 7.90 (d, 1H), 7.57-7.48 (m, 2H), 7.13 (t, 1H), 5.94 (ddt, 1H), 4.53-4.39 (m, 4H), 3.42-3.41 (m, 2H), 2.75 (h, 1H), 2.38 (s, 3H), 2.12 (dd, 2H), 1.96-1.82 (m, 3H), 1.78 (q, 1H). |

Example 181

N-(2-methyl-5-(2-(1-((1-methylcyclopropyl)sulfonyl)azetidin-3-yl)-2H-tetrazol-5-yl)phenyl)pyrazolo[1,5-a]pyridine-3-carboxamide

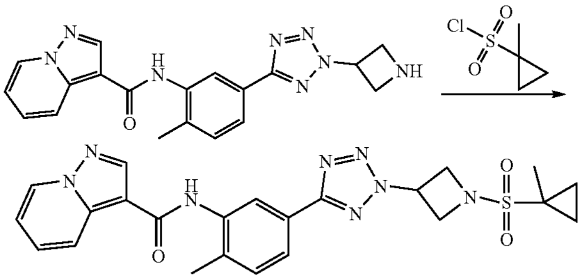

To a solution of Intermediate 15 (100 mg, 0.27 mmol) and TEA (53.9 mg, 0.53 mmol) in DCM (5 mL) was added 1-methylcyclopropane-1-sulfonyl chloride (61.8 mg, 0.40 mmol) at rt under $N_2$. The mixture was stirred for 2 h and then water (10 mL) was added. The resulting solution was extracted with DCM (3×20 mL), the organic layer was dried over $Na_2SO_4$ and concentrated under vacuum. The crude product was purified by Prep-HPLC, method F, 40% to 55% gradient, to give the title compound (41.9 mg, 32%) as a white solid. LCMS: m/z=493 $[M+H]^+$, $^1H$ NMR (400 MHz, DMSO-$d_6$) δ 9.76 (s, 1H), 8.86 (dt, 1H), 8.79 (s, 1H), 8.25 (dt, 1H), 8.19 (d, 1H), 7.88 (dd, 1H), 7.58-7.47 (m, 2H), 7.13 (td, 1H), 6.00 (p, 1H), 4.47 (d, 4H), 2.37 (s, 3H), 1.51 (s, 3H), 1.23-1.16 (m, 2H), 1.00-0.88 (m, 2H).

Examples 182 to 190

The following compounds were prepared from the appropriate azetidine and the appropriate sulfonyl chloride, following a similar procedure to that described in Example 181. Alternative purification conditions are described in the table below

| Compound No | Structure, Sulfonyl chloride (SM), Purification, yield | Data |
|---|---|---|
| 182 | N-(2-methyl-5-(2-(1-((trifluoromethyl)sulfonyl)azetidin-3-yl)-2H-tetrazol-5-yl)phenyl)pyrazolo[1,5-a]pyridine-3-carboxamide<br>SM: Intermediate 15 and trifluoromethanesulfonyl chloride<br>33.6 mg; 25% as a white solid. | LCMS: m/z = 507 $[M + H]^+$. 1H NMR (400 MHz, DMSO-$d_6$) δ 9.77 (s, 1H), 8.86 (dd, 1H), 8.79 (s, 1H), 8.25 (dt, 1H), 8.21 (d, 1H), 7.89 (dd, 1H), 7.58-7.48 (m, 2H), 7.13 (td, 1H), 6.12 (tt, 1H), 4.90 (t, 2H), 4.77 (dd, 2H), 2.38 (s, 3H). |
| 183 | N-(2-methyl-5-(2-(1-(oxetan-3-ylsulfonyl)azetidin-3-yl)-2H-tetrazol-5-yl)phenyl)pyrazolo[1,5-a]pyridine-3-carboxamide<br>SM: Intermediate 15 and oxetane-3-sulfonyl chloride<br>35.4 mg; 38% as a white solid | LCMS: m/z = 495 $[M + H]^+$; $^1H$ NMR (400 MHz, DMSO-$d_6$) δ 9.75 (s, 1H), 8.85 (dt, 1H), 8.79 (s, 1H), 8.29-8.19 (m, 2H), 7.89 (dd, 1H), 7.57-7.47 (m, 2H), 7.13 (td, 1H), 5.98 (tt, 1H), 5.10-4.98 (m, 1H), 4.90 (dd, 2H), 4.75 (dd, 2H), 4.57-4.44 (m, 4H), 2.37 (s, 3H). |
| 184 | N-(5-(2-(1-((3,3-difluoropropyl)sulfonyl)azetidin-3-yl)-2H-tetrazol-5-yl)-2-methylphenyl)pyrazolo[1,5-a]pyridine-3-carboxamide<br>SM: Intermediate 15 and 3,3-difluoropropane-1-sulfonyl chloride<br>off-white solid, 17.4 mg | LCMS m/z = 517 $[M + H]^+$; 1H NMR (500 MHz, DMSO-$d_6$) δ 9.74 (s, 1H), 8.86 (d, 1H), 8.79 (d, 1H), 8.26 (d, 1H), 8.20 (s, 1H), 7.89 (d, 1H), 7.58-7.45 (m, 2H), 7.13 (t, 1H), 6.40-6.11 (m, 1H), 6.02-5.91 (m, 1H), 4.61-4.47 (m, 4H), 3.48 (dd, 2H), 2.41-2.25 (m, 5H) |
| 185 | N-(5-(2-(1-((2-(2-methoxyethoxy)ethyl)sulfonyl)azetidin-3-yl)-2H-tetrazol-5-yl)-2-methylphenyl)pyrazolo[1,5-a]pyridine-3-carboxamide<br>SM: Intermediate 15 and 2-(2-methoxyethoxy)ethane-1-sulfonyl chloride<br>white foam, 29.1 mg, 57.5% yield | LCMS m/z = 541 $[M + H]^+$; 1H NMR (500 MHz, DMSO-$d_6$) δ 9.75 (s, 1H), 8.86 (d, 1H), 8.79 (d, 1H), 8.26 (d, 1H), 8.20 (s, 1H), 7.89 (d, 1H), 7.58-7.46 (m, 2H), 7.13 (t, 1H), 5.93 (p, 1H), 4.56 (t, 2H), 4.50-4.43 (m, 2H), 3.85-3.78 (m, 2H), 3.60 (td, 4H), 3.45 (p, 2H), 3.22 (s, 3H), 2.38 (s, 3H) |
| 186 | N-(5-(2-(1-((4-cyanobutyl)sulfonyl)azetidin-3-yl)-2H-tetrazol-5-yl)-2-methylphenyl)pyrazolo[1,5-a]pyridine-3-carboxamide<br>SM: Intermediate 15 and 4-cyanobutane-1-sulfonyl chloride<br>28.2 mg, 50.7% of white solid. | LCMS m/z = 520 $[M + H]^+$; 1H NMR (500 MHz, DMSO-$d_6$) δ 9.75 (s, 1H), 8.86 (d, 1H), 8.79 (s, 1H), 8.26 (d, 1H), 8.20 (s, 1H), 7.89 (d, 1H), 7.57-7.47 (m, 2H), 7.13 (t, 1H), 5.97 (p, 1H), 4.57-4.42 (m, 4H), 3.37 (t, 2H), 2.58 (t, 2H), 2.38 (s, 3H), 1.89-1.78 (m, 2H), 1.78-1.68 (m, 2H). |
| 187 | N-(2-chloro-5-(5-(1-(methylsulfonyl)azetidin-3-yl)-2H-tetrazol-2-yl)phenyl)pyrazolo[1,5-a]pyridine-3-carboxamide<br>SM: Intermediate 21 and methanesulfonyl chloride<br>HPLC method J, 37% to 47% gradient,<br>44.1 mg; 37% as a light green solid | LCMS: m/z = 473 $[M + H]^+$, $^1H$ NMR (400 MHz, DMSO-$d_6$) δ 9.97 (s, 1H), 8.92-8.82 (m, 2H), 8.56 (d, 1H), 8.26 (dt, 1H), 8.00 (dd, 1H), 7.88 (d, 1H), 7.63-7.54 (m, 1H), 7.17 (td, 1H), 4.52-4.25 (m, 3H), 4.25-4.17 (m, 2H), 3.11 (s, 3H). |
| 188 | N-(5-(5-(1-(cyclopropylsulfonyl)azetidin- | LCMS: m/z = 479 $[M + H]^+$, 1H NMR (400 MHz, DMSO-$d_6$) δ |

-continued

| Compound No | Structure, Sulfonyl chloride (SM), Purification, yield | Data |
|---|---|---|
| | 3-yl)-2H-tetrazol-2-yl)-2-methylphenyl)pyrazolo[1,5-a]pyridine-3-carboxamide<br>SM: Intermediate 17 and cyclopropanesulfonyl chloride<br>Prep-HPLC Method C, 31% to 54% gradient.<br>37.3 mg, 29% as a white solid | 9.77 (s, 1H), 8.90-8.84 (m, 1H), 8.81 (s, 1H), 8.29 (d, 1H), 8.28-8.22 (m, 1H), 7.88 (dd, 1H), 7.61-7.51 (m, 2H), 7.14 (td, 1H), 4.42-4.17 (m, 5H), 2.90-2.79 (m, 1H), 2.41 (s, 3H), 1.14-1.03 (m, 2H), 1.06-0.95 (m, 2H). |
| 189 | N-(5-(5-(1-((2-methoxyethyl)sulfonyl)azetidin-3-yl)-2H-tetrazol-2-yl)-2-methylphenyl)pyrazolo[1,5-a]pyridine-3-carboxamide<br>SM: Intermediate 17 and 2-methoxyethane-1-sulfonyl chloride<br>Prep-HPLC Method C, 28% to 50% gradient,<br>9.2 mg, 6% as a white solid. | LCMS: m/z = 497 $[M + H]^+$, 1H NMR (400 MHz, DMSO-$d_6$) δ 9.78 (s, 1H), 8.87 (dt, 1H), 8.81 (s, 1H), 8.31-8.22 (m, 2H), 7.88 (dd, 1H), 7.61-7.51 (m, 2H), 7.14 (td, 1H), 4.41-4.19 (m, 5H), 3.71 (t, 2H), 3.54 (t, 2H), 3.28 (s, 3H), 2.41 (s, 3H). |
| 190 | N-(2-methyl-5-(5-(1-(methylsulfonyl)azetidin-3-yl)-2H-tetrazol-2-yl)phenyl)pyrazolo[1,5-a]pyridine-3-carboxamide<br>SM: Intermediate 17 and methanesulfonyl chloride<br>Prep-HPLC Method C, 25% to 55% gradient, 41.7 mg; 23% as a white solid | LCMS: m/z = 453 $[M + H]^+$, 1H NMR (400 MHz, DMSO-$d_6$) δ 9.77 (s, 1H), 8.86 (dd, 1H), 8.80 (s, 1H), 8.31-8.21 (m, 2H), 7.88 (dd, 1H), 7.60-7.50 (m, 2H), 7.14 (td, 1H), 4.41-4.26 (m, 3H), 4.20 (dd, 2H), 3.11 (s, 3H), 2.40 (s, 3H). |

Example 191 methyl 3-(5-(4-methyl-3-(pyrazolo[1,5-a]pyridine-3-carboxamido)phenyl)-2H-tetrazol-2-yl)azetidine-1-carboxylate

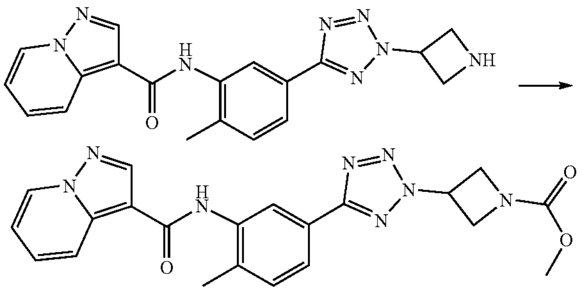

Methyl chloroformate (0.01 mL, 0.14 mmol) was added to a solution of Intermediate 15 (45 mg, 0.12 mmol) in DCM (1 mL) and pyridine (0.05 mL, 0.60 mmol) and the reaction mixture stirred at rt for 2 h. The mixture was diluted with water, washed with water and the organic layer dried over $Na_2SO_4$, filtered and evaporated to give the crude product. This was purified by reverse phase ISCO chromatography (5 to 100% MeCN/water containing 0.1% TFA). The product containing fractions were concentrated and the residue triturated with $NaHCO_3$ and water and then filtered and suction dried to give the title compound, 24.5 mg, 47% as a white solid. LCMS m/z=433 $[M+H]^+$; 1H NMR (500 MHz, DMSO-$d_6$) δ 9.74 (s, 1H), 8.86 (d, 1H), 8.79 (d, 1H), 8.26 (d, 1H), 8.19 (d, 1H), 7.93-7.83 (m, 1H), 7.59-7.45 (m, 2H), 7.13 (t, 1H), 5.92 (ddd, 1H), 4.57 (t, 2H), 4.39 (dd, 2H), 3.63 (s, 3H), 2.37 (s, 3H).

Example 192 to 194

The compounds in the following table were prepared from the appropriate azetidine and methyl chloroformate, following a similar procedure to that described in Example 191. Alternative purification conditions are described in the table below.

| Compound No | Name, Starting materials (SM), Purification, Yield | Data |
|---|---|---|
| 192 | methyl 3-(5-(4-chloro-3-(pyrazolo[1,5-a]pyridine-3-carboxamido)phenyl)-2H-tetrazol-2-yl)azetidine-1-carboxylate<br>SM: Intermediate 40<br>white solid, 23.4mg, 32.5% | LCMS m/z = 453 $[M + H]^+$ 1H NMR (500 MHz, DMSO-$d_6$) δ 9.91 (s, 1H), 8.87 (d, 1H), 8.82 (d, 1H), 8.46 (s, 1H), 8.27 (d, 1H), 7.97 (d, 1H), 7.78 (dd, 1H), 7.56 (t, 1H), 7.15 (t, 1H), 6.01-5.88 (m, 1H), 4.58 (t, 2H), 4.40 (dd, 2H), 3.64 (d, 3H) |
| 193 | methyl 3-(2-(4-chloro-3-(pyrazolo[1,5-a]pyridine-3-carboxamido)phenyl)-2H-1,2,3-triazol-4-yl)azetidine-1-carboxylate<br>SM: Intermediate 16<br>Prep-HPLC Method F, 40% to 65% gradient<br>18.5 mg, 23% as a white solid | LCMS: m/z = 452 $[M + H]^+$, 1H NMR (400 MHz, DMSO-$d_6$) δ 9.89 (s, 1H), 8.88 (dt, 1H), 8.83 (s, 1H), 8.42 (d, 1H), 8.29-8.20 (m, 2H), 7.88 (dd, 1H), 7.74 (d, 1H), 7.57 (ddd, 1H), 7.16 (td, 1H), 4.35 (s, 2H), 4.09 (s, 3H), 3.59 (s, 3H). |
| 194 | methyl 3-(2-(4-chloro-3-(pyrazolo[1,5-a]pyridine-3-carboxamido)phenyl)-2H-tetrazol-5-yl)azetidine-1-carboxylate<br>SM: Intermediate 21<br>Prep-HPLC Method F, 40% to 65% gradient<br>white solid, 24.3 mg, 26% yield | LCMS: m/z = 453 $[M + H]^+$, $^1H$ NMR (400 MHz, DMSO-$d_6$) δ 9.96 (s, 1H), 8.97-8.78 (m, 2H), 8.55 (d, 1H), 8.26 (dt, 1H), 7.99 (dd, 1H), 7.87 (d, 1H), 7.58 (ddd, 1H), 7.17 (td, 1H), 4.48-4.09 (m, 3H), 3.61 (s, 3H). |

Example 195

N-(2-chloro-5-(2-(1-(2,2,2-trifluoroethyl)azetidin-3-yl)-2H-tetrazol-5-yl)phenyl)pyrazolo[1,5-a]pyridine-3-carboxamide

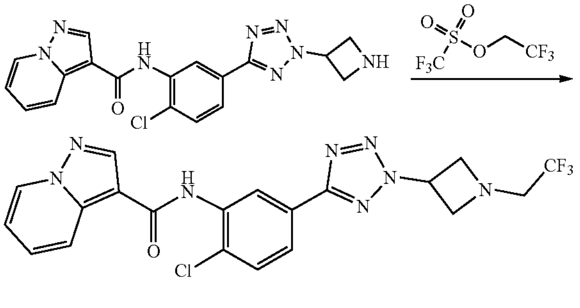

A mixture of Intermediate 40 (50 mg, 0.13 mmol), 2,2,2-trifluoroethyl trifluoromethanesulfonate (0.06 mL, 0.38 mmol) and DIPEA (0.03 mL, 0.51 mmol) in DMF (0.5 mL) was stirred for 1 h at 90° C. The mixture was concentrated in vacuo, the residue triturated with water and filtered to give a white solid, 48 mg. This was triturated with MeCN (1 mL), stirring for 30 mins, filtered and dried to give the title compound, 36.7 mg, 60.8%. LCMS m/z=477 $[M+H]^+$; 1H NMR (500 MHz, DMSO-$d_6$) δ 9.91 (s, 1H), 8.88 (d, 1H), 8.83 (d, 1H), 8.44 (d, 1H), 8.26 (d, 1H), 7.97 (dt, 1H), 7.78 (dd, 1H), 7.57 (t, 1H), 7.16 (t, 1H), 5.75 (p, 1H), 4.06 (t, 2H), 3.94 (t, 2H), 3.48-3.38 (m, 2H).

Example 196

N-(2-methyl-5-(2-(1-(2,2,2-trifluoroethyl)azetidin-3-yl)-2H-tetrazol-5-yl)phenyl)pyrazolo[1,5-a]pyridine-3-carboxamide

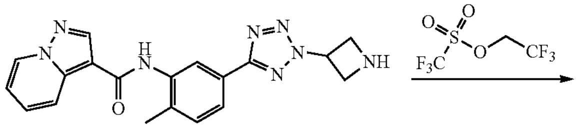

-continued

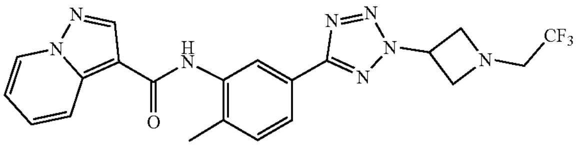

The title compound was obtained from Intermediate 15 and 2,2,2-trifluoroethyl trifluoromethanesulfonate, following a similar procedure to that described in Example 195. LCMS m/z=457 $[M+H]^+$; 1H NMR (500 MHz, DMSO-$d_6$) δ 9.74 (s, 1H), 8.86 (d, 1H), 8.79 (s, 1H), 8.25 (d, 1H), 8.18 (s, 1H), 7.88 (d, 1H), 7.54 (t, 1H), 7.49 (d, 1H), 7.13 (t, 1H), 5.73 (p, 1H), 4.06 (t, 2H), 3.93 (t, 2H), 3.42 (q, 2H), 2.37 (s, 3H).

Example 197

N-(2-methyl-5-(2-(2-(2,2,2-trifluoroethoxy)ethyl)-2H-tetrazol-5-yl)phenyl)-5-(1H-pyrazol-4-yl)pyrazolo[1,5-a]pyridine-3-carboxamide

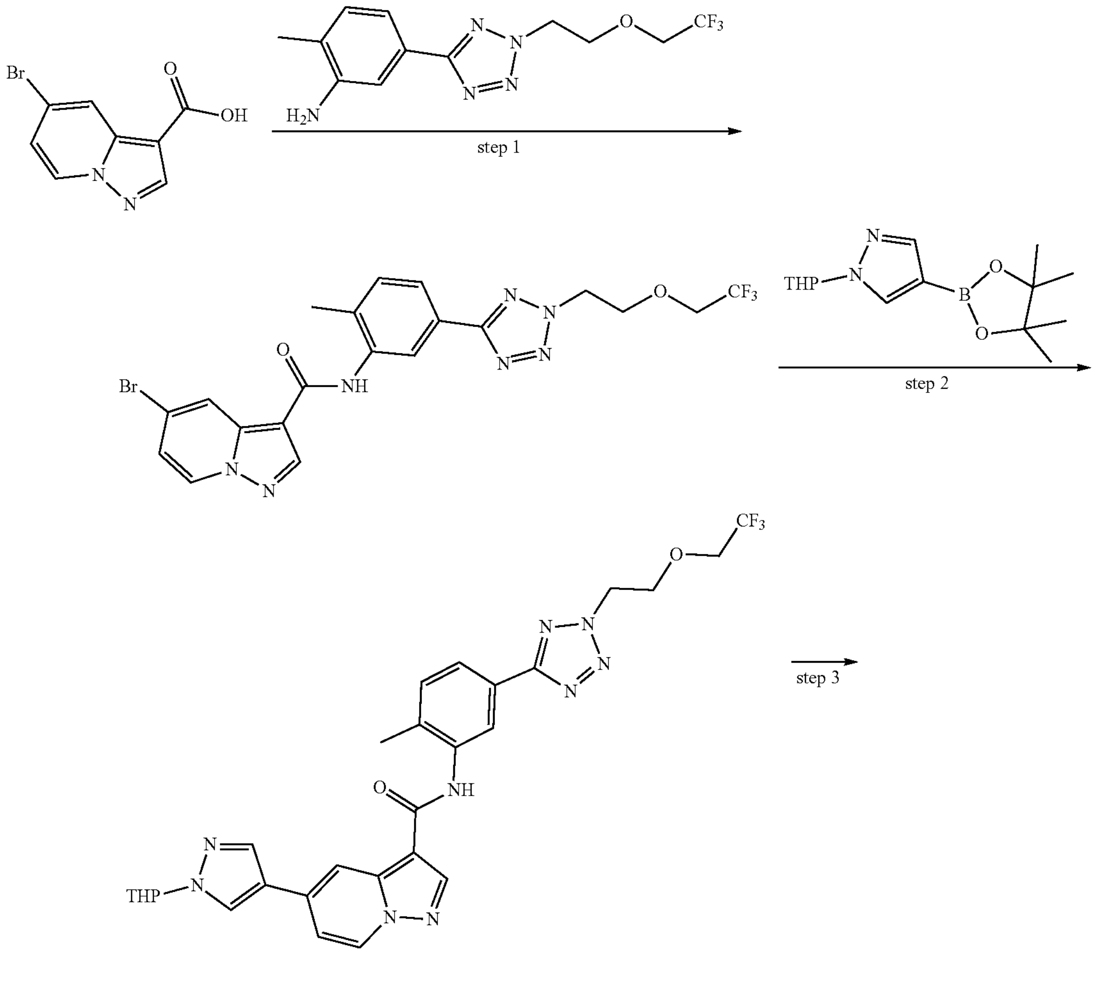

-continued

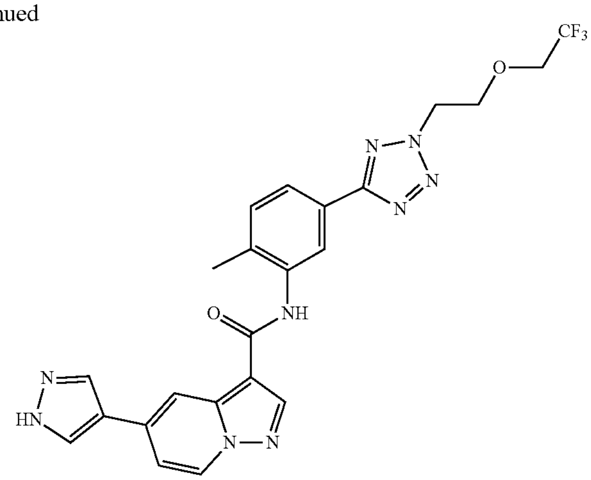

Step 1: Synthesis of 5-bromo-N-(2-methyl-5-(2-(2-(2,2,2-trifluoroethoxy)ethyl)-2H-tetrazol-5-yl)phenyl)pyrazolo[1,5-a]pyridine-3-carboxamide A suspension of 5-bromopyrazolo[1,5-a]pyridine-3-carboxylic acid (200 mg, 0.83 mmol) and DMF (0.1 mL) in DCM (10 mL) was cooled to 0° C. and treated slowly with oxalyl chloride (627 mg, 4.97 mmol). The mixture was removed from the cold bath and stirred at rt for 2.5 h. The mixture was filtered through filter paper to remove undissolved precipitates and then concentrated in vacuo to afford 5-bromopyrazolo[1,5-a]pyridine-3-carbonyl chloride crude, as a yellow solid. To a mixture of Example 158, Step 3 (249 mg, 0.83 mmol) in pyridine (8 mL) was added 5-bromopyrazolo[1,5-a]pyridine-3-carbonyl chloride (210 mg, 0.83 mmol) at 0° C. and the reaction mixture stirred at rt for 3 h. The resulting solution was concentrated in vacuo and the crude product was purified by silica gel column chromatography (eluting with DCM:MeOH 90:10) gave the title compound (180 mg, 41.3%) as a yellow solid. LCMS: m/z=427 $[M+H^+]$ Step 2: Synthesis of N-(2-methyl-5-(2-(2-(2,2,2-trifluoroethoxy)ethyl)-2H-tetrazol-5-yl)phenyl)-5-(1-(tetrahydro-2H-pyran-2-yl)-1H-pyrazol-4-yl)pyrazolo[1,5-a]pyridine-3-carboxamide A mixture of 5-bromo-N-(2-methyl-5-(2-(2-(2,2,2-trifluoroethoxy)ethyl)-2H-tetrazol-5-yl)phenyl)pyrazolo[1,5-a]pyridine-3-carboxamide (180 mg, 0.34 mmol), 1-(oxan-2-yl)-4-(4,4,5,5-tetramethyl-1,3,2-dioxaborolan-2-yl)-1H-pyrazole (105 mg, 0.38 mmol), Pd(dppf)$Cl_2$ (11.5 mg, 0.02 mmol) and $K_2CO_3$ (94.7 mg, 0.69 mmol) in dioxane (8 mL) and $H_2O$ (2 mL) was stirred at 80° C. for 3 h under $N_2$. The reaction mixture was cooled to rt, the resulting solution was diluted with water (25 mL) and extracted with EtOAc (2×40 mL). The combined organic layers were washed with brine (20 mL), dried over anhydrous $Na_2SO_4$ and concentrated in vacuo. The crude product was purified by column chromatography (eluting with DCM:MeOH 95:5) to give the title compound (150 mg, 73.5%) as a yellow solid. LCMS m/z=427 $[M+H]^+$ Step 3: Synthesis of N-(2-methyl-5-(2-(2-(2,2,2-trifluoroethoxy)ethyl)-2H-tetrazol-5-yl)phenyl)-5-(1H-pyrazol-4-yl)pyrazolo[1,5-a]pyridine-3-carboxamide A mixture of N-(2-methyl-5-(2-(2-(2,2,2-trifluoroethoxy)ethyl)-2H-tetrazol-5-yl)phenyl)-5-(1-(tetrahydro-2H-pyran-2-yl)-1H-pyrazol-4-yl)pyrazolo[1,5-a]pyridine-3-carboxamide (100 mg, 0.17 mmol) in TFA (3 mL) and DCM (6 mL) was stirred at rt for 1 h. The mixture was concentrated in vacuo and the residue was purified by prep-HPLC, Method E, 30% to 60% gradient, to give the title compound (29.4 mg, 34.2%) as a white solid. LCMS: m/z=427 $[M+H]^+$. 1H NMR (400 MHz, DMSO-$d_6$) δ 13.20 (s, 1H), 9.65 (s, 1H), 8.83 (dd, 1H), 8.74 (s, 1H), 8.46 (s, 1H), 8.36 (dd, 1H), 8.22 (d, 1H), 8.10 (s, 1H), 7.89-7.83 (m, 1H), 7.48 (d, 1H), 7.42 (dd, 1H), 4.98 (t, 2H), 4.33-4.08 (m, 4H), 2.38 (s, 3H).

Example 198

N-(5-(2-(3,3-difluorocyclobutyl)-2H-tetrazol-5-yl)-2-methylphenyl)-5-(1H-pyrazol-4-yl)pyrazolo[1,5-a]pyridine-3-carboxamide

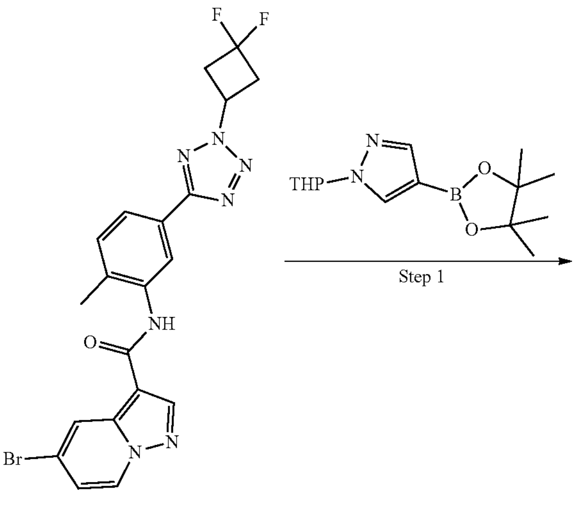

-continued

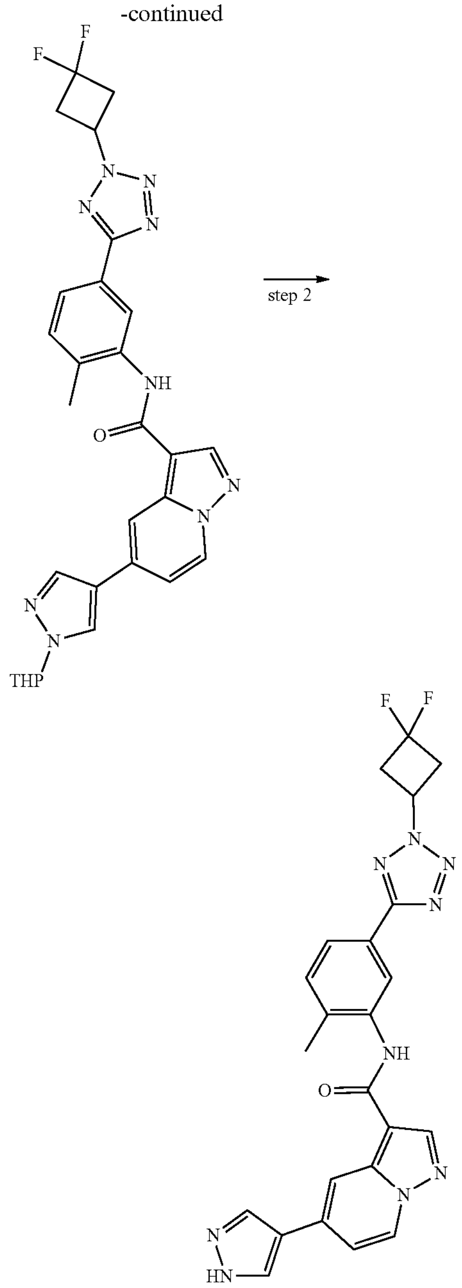

Step 1: Synthesis of N-(5-(2-(3,3-difluorocyclobutyl)-2H-tetrazol-5-yl)-2-methylphenyl)-5-(1-(tetrahydro-2H-pyran-2-yl)-1H-pyrazol-4-yl)pyrazolo[1,5-a]pyridine-3-carboxamide The title compound was obtained as a white solid, 180 mg, 78.6% yield from Intermediate 4 and 1-(oxan-2-yl)-4-(4,4,5,5-tetramethyl-1,3,2-dioxaborolan-2-yl)-1H-pyrazole, following the method described in Example 197, step 2. LCMS m/z=560 $[M+H]^+$ Step 2: Synthesis of N-(5-(2-(3,3-difluorocyclobutyl)-2H-tetrazol-5-yl)-2-methylphenyl)-5-(1H-pyrazol-4-yl)pyrazolo[1,5-a]pyridine-3-carboxamide A mixture of N-(5-(2-(3,3-difluorocyclobutyl)-2H-tetrazol-5-yl)-2-methylphenyl)-5-(1-(tetrahydro-2H-pyran-2-yl)-1H-pyrazol-4-yl)pyrazolo[1,5-a]pyridine-3-carboxamide (150 mg, 0.27 mmol) in TFA (3 mL) and DCM (6 mL) was stirred at rt for 1 h. The mixture was concentrated in vacuo and the residue was purified by prep-HPLC, Method J, 32% to 52% gradient, to give the title compound (84.3 mg, 66.3%) as a white solid. LCMS: m/z=476 $[M+H]^+$. 1H NMR (400 MHz, DMSO-$d_6$) δ 13.19 (s, 1H), 9.68 (s, 1H), 8.83 (d, 1H), 8.74 (s, 1H), 8.29 (dd, 4H), 7.87 (dd, 1H), 7.64-7.36 (m, 2H), 5.61 (q, 1H), 3.64-3.36 (m, 4H), 2.39 (s, 3H).

Example 199 methyl 3-(5-(3-(5-(2-hydroxyethoxy)pyrazolo[1,5-a]pyridine-3-carboxamido)-4-methylphenyl)-2H-tetrazol-2-yl)azetidine-1-carboxylate

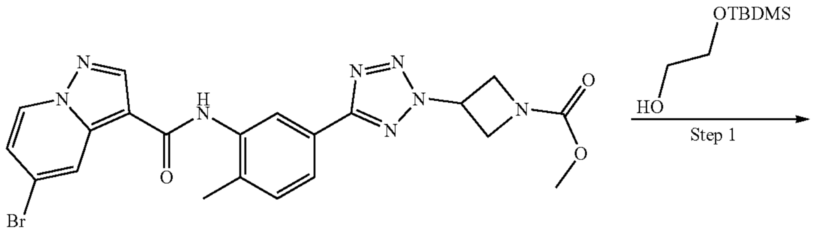

-continued

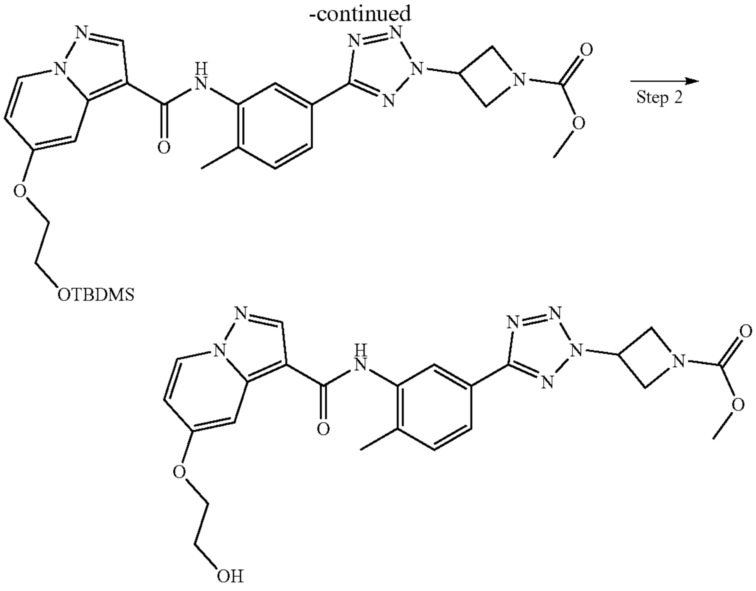

Step 1: Synthesis of methyl 3-(5-(3-(5-(2-((tert-butyldimethylsilyl)oxy)ethoxy)pyrazolo[1,5-a]pyridine-3-carboxamido)-4-methylphenyl)-2H-tetrazol-2-yl)azetidine-1-carboxylate The title compound was obtained as a white solid, 38.6 mg, 43.4%, from Intermediate 11 and 2-((tertbutyldimethylsilyl)oxy)ethan-1-ol, following a similar procedure to that described in Example 65.

Step 2: Synthesis of methyl 3-(5-(3-(5-(2-hydroxyethoxy)pyrazolo[1,5-a]pyridine-3-carboxamido)-4-methylphenyl)-2H-tetrazol-2-yl)azetidine-1-carboxylate Methyl 3-(5-(3-(5-(2-((tert-butyldimethylsilyl)oxy)ethoxy)pyrazolo[1,5-a]pyridine-3-carboxamido)-4-methylphenyl)-2H-tetrazol-2-yl)azetidine-1-carboxylate (38 mg, 0.06 mmol) was dissolved in THF (0.75 mL) and 1M TBAF in THF solution (0.19 mL, 0.19 mmol) added and the reaction mixture stirred at rt overnight. The reaction was diluted with EtOAc, washed with water and brine then dried over $Na_2SO_4$. The mixture was filtered and concentrated in vacuo to give the crude product. This was purified by reverse phase ISCO (5 to 100% MeCN/water containing 0.1% TFA). The product containing fractions were concentrated in vacuo, the residue triturated with aq $Na_2CO_3$ solution, the mixture filtered, washed with water and dried to give the title compound, 16.8 mg, 54.5%, as a white solid. LCMS m/z=493 $[M+H]^+$; 1H NMR (500 MHz, DMSO-$d_6$) δ 9.70 (s, 1H), 8.68 (d, 1H), 8.57 (d, 1H), 8.18 (s, 1H), 8.14 (dd, 1H), 7.88 (d, 1H), 7.49 (d, 1H), 7.34 (dd, 1H), 5.92 (ttd, 1H), 4.96 (s, 1H), 4.57 (t, 2H), 4.46-4.33 (m, 2H), 4.10 (t, 2H), 3.81-3.73 (m, 2H), 3.64 (d, 1H), 2.37 (s, 3H).

Example 200

N-(5-(2-((1r,3r)-3-(hydroxymethyl)cyclobutyl)-2H-tetrazol-5-yl)-2-methylphenyl)pyrazolo[1,5-a]pyridine-3-carboxamide

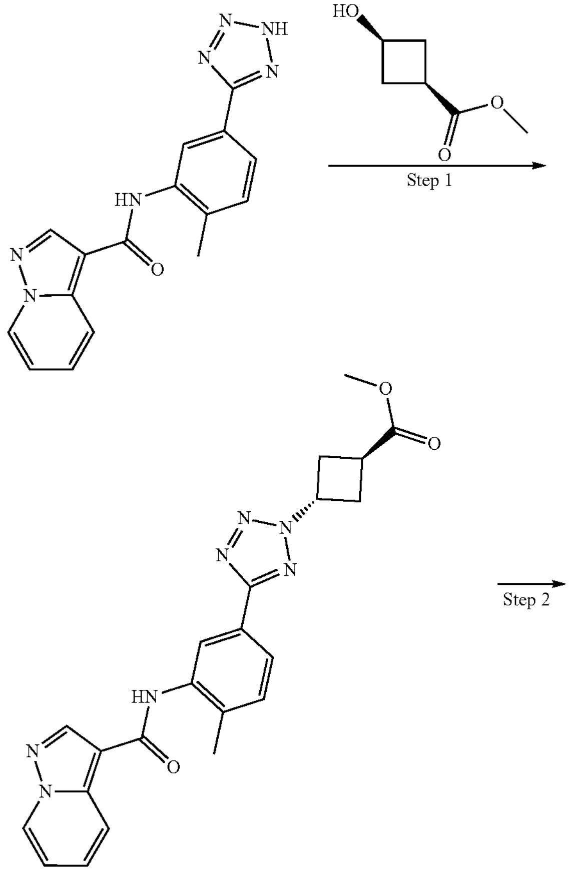

-continued

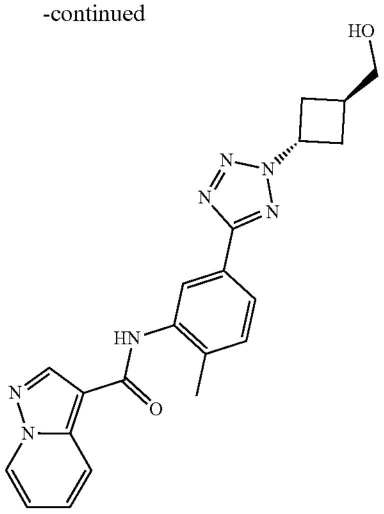

Step 1: Synthesis of methyl(1r,3r)-3-(5-(4-methyl-3-(pyrazolo[1,5-a]pyridine-3-carboxamido)phenyl)-2H-tetrazol-2-yl)cyclobutane-1-carboxylate DIAD (252 mg, 1.25 mmol) was added to Intermediate 1 (200 mg, 0.63 mmol), methyl(1s,3s)-3-hydroxycyclobutane-1-carboxylate (81 mg, 0.63 mmol) and $PPh_3$ (327 mg, 1.25 mmol) in THF (5 mL) at 0° C. under $N_2$ and the reaction was stirred at rt for 3 h. The reaction mixture was concentrated to dryness and the residue purified by silica gel column with 5% MeOH in DCM, to afford the title compound (100 mg, 37%) as a white solid. LCMS m/z=432 $[M+H]^+$ Step 2: Synthesis of N-(5-(2-((1r, 3r)-3-(hydroxymethyl)cyclobutyl)-2H-tetrazol-5-yl)-2-methylphenyl) pyrazolo[1,5-a]pyridine-3-carboxamide $NaBH_4$ (5 mg, 0.12 mmol) was added to a solution of methyl(1r,3r)-3-(5-(4-methyl-3-(pyrazolo[1,5-a]pyridine-3-carboxamido)phenyl)-2H-tetrazol-2-yl)cyclobutane-1-carboxylate (50 mg, 0.12 mmol) in MeOH (3 mL) and the reaction mixture stirred at rt for 3 h. The reaction was concentrated under vacuum and purified by Prep-HPLC, Method A, 29% to 42% gradient, to afford the title compound (36.9 mg, 37%) as white solid. LCMS: m/z=404 $[M+H]^+$, $^1H$ NMR (400 MHz, DMSO-$d_6$) δ 9.75 (s, 1H), 8.86 (d, 1H), 8.79 (s, 1H), 8.25 (dt, 1H), 8.16 (d, 1H), 7.86 (dd, 1H), 7.53 (ddd, 1H), 7.47 (d, 1H), 7.13 (td, 1H), 5.54 (p, 1H), 4.81 (t, 1H), 3.57 (t, 2H), 2.79-2.67 (m, 2H), 2.62-2.53 (m, 1H), 2.46 (d, 1H), 2.36 (s, 4H).

Example 201

N-(5-(2-((1r,3r)-3-(hydroxymethyl)cyclobutyl)-2H-tetrazol-5-yl)-2-methylphenyl)-5-((2-methoxyethyl)amino)pyrazolo[1,5-a]pyridine-3-carboxamide

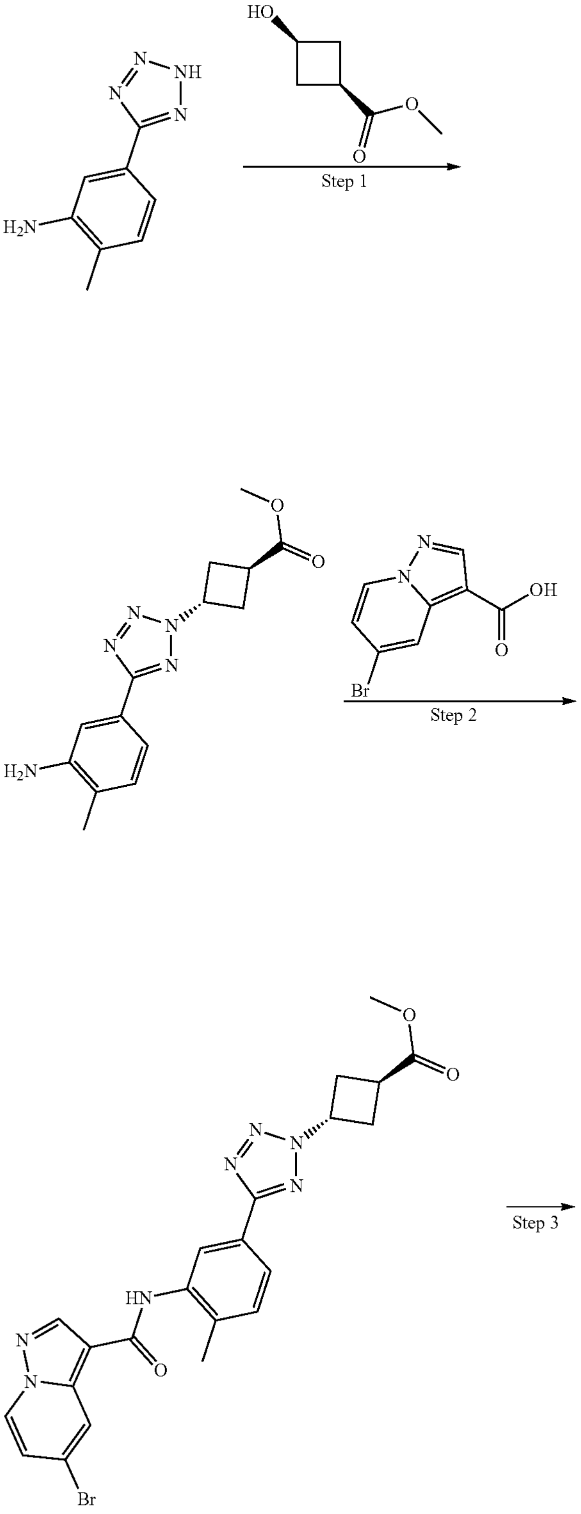

-continued

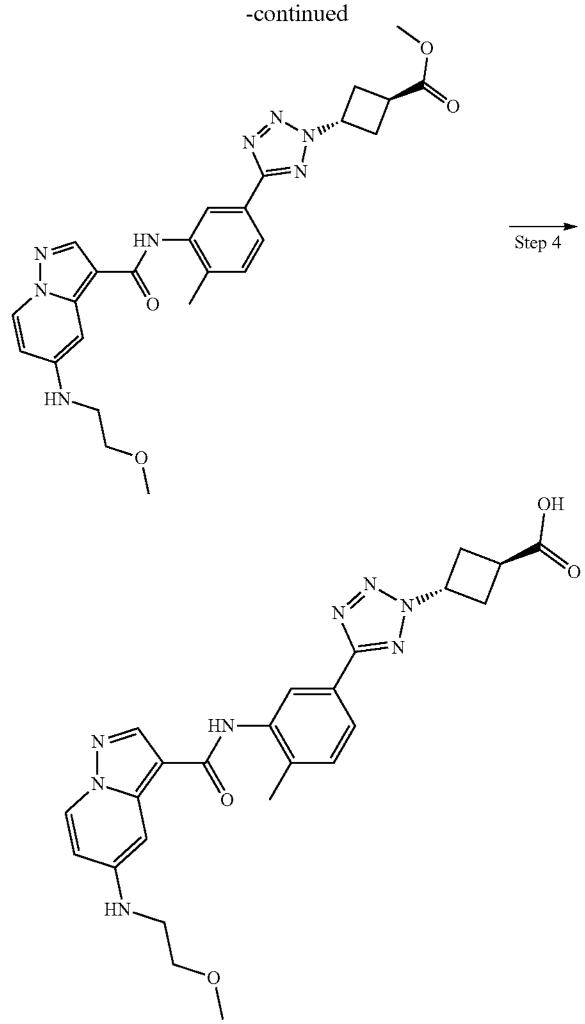

Step 1: Synthesis of methyl(1r,3r)-3-(5-(3-amino-4-methylphenyl)-2H-tetrazol-2-yl)cyclobutane-1-carboxylate The title compound was obtained as a brown solid, 60 mg, 31% from 2-methyl-5-(2H-tetrazol-5-yl)aniline and methyl (1s,3s)-3-hydroxycyclobutane-1-carboxylate, following the procedure described in Intermediate 7, step 2. LCMS: m/z=288 [M+H]$^+$.

Step 2: Synthesis of methyl(1r,3r)-3-(5-(3-(5-bromopyrazolo[1,5-a]pyridine-3-carboxamido)-4-methylphenyl)-2H-tetrazol-2-yl)cyclobutane-1-carboxylate To a stirred solution of methyl(1r,3r)-3-(5-(3-amino-4-methylphenyl)-2H-tetrazol-2-yl)cyclobutane-1-carboxylate (30 mg, 0.10 mmol) in MeCN (2 mL) were added 5-bromopyrazolo[1,5-a]pyridine-3-carboxylic acid (37.6 mg, 0.16 mmol), N-methylimidazole (29.8 mg, 0.36 mmol) and TCFH (34.7 mg, 0.12 mmol) and the reaction mixture stirred for 2 h at rt. The mixture was diluted with EtOAc (5 mL) and water (5 mL) and the layers separated. The water phase was extracted with EtOAc (3×3 mL) and the combined organic phase was washed with brine (10 mL). The organic layer was dried with $Na_2SO_4$ and concentrated under vacuum. The residue was purified by Prep-TLC with PE:EtOAc=2:3 to give the title compound (30 mg; 57%) as a yellow solid. LCMS: m/z=528 [M+H]$^+$.

Step 3: Synthesis of methyl(1r,3r)-3-(5-(5-(5-((2-methoxyethyl)amino)pyrazolo[1,5-a]pyridine-3-carboxamido)-4-methylphenyl)-2H-tetrazol-2-yl)cyclobutane-1-carboxylate The title compound was obtained as a yellow solid, 20 mg, 67%, from methyl(1r,3r)-3-(5-(3-(5-bromopyrazolo[1,5-a]pyridine-3-carboxamido)-4-methylphenyl)-2H-tetrazol-2-yl)cyclobutane-1-carboxylate and 2-methoxyethan-1-amine, following the procedure described in Example 115, step 4. LCMS: m/z=505 [M+H]$^+$.

Step 4: Synthesis of N-(5-(2-((1r, 3r)-3-(hydroxymethyl)cyclobutyl)-2H-tetrazol-5-yl)-2-methylphenyl)-5-((2-methoxyethyl)amino)pyrazolo[1,5-a]pyridine-3-carboxamide The title compound was obtained as a white solid, 1.3 mg, 7% from methyl(1r,3r)-3-(5-(5-(5-((2-methoxyethyl)amino) pyrazolo[1,5-a]pyridine-3-carboxamido)-4-methylphenyl)-2H-tetrazol-2-yl)cyclobutane-1-carboxylate, following a similar procedure to that described in Example 200, step 2, except the crude product was purified by HPLC Method F, 21% to 44% gradient. LCMS: m/z=477 [M+H]$^+$, 1H NMR (400 MHz, DMSO-$d_6$) δ 9.32 (s, 1H), 8.49 (s, 1H), 8.39 (d, 1H), 8.18 (d, 1H), 7.82 (dd, 1H), 7.44 (d, 1H), 6.97 (d, 1H), 6.77 (t, 1H), 6.60 (dd, 1H), 5.53 (p, 1H), 4.81 (t, 1H), 3.56 (dt, 4H), 3.32-3.22 (m, 6H), 2.79-2.67 (m, 4H), 2.35 (s, 3H).

Example 202

N-(4-fluoro-5-(2-((1r,3r)-3-(hydroxymethyl)cyclobutyl)-2H-tetrazol-5-yl)-2-methylphenyl)-5-((2-methoxyethyl)amino)pyrazolo[1,5-a]pyridine-3-carboxamide

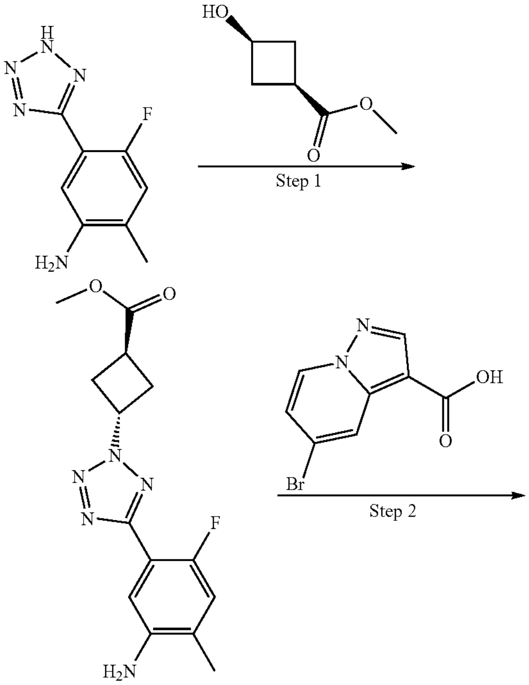

-continued

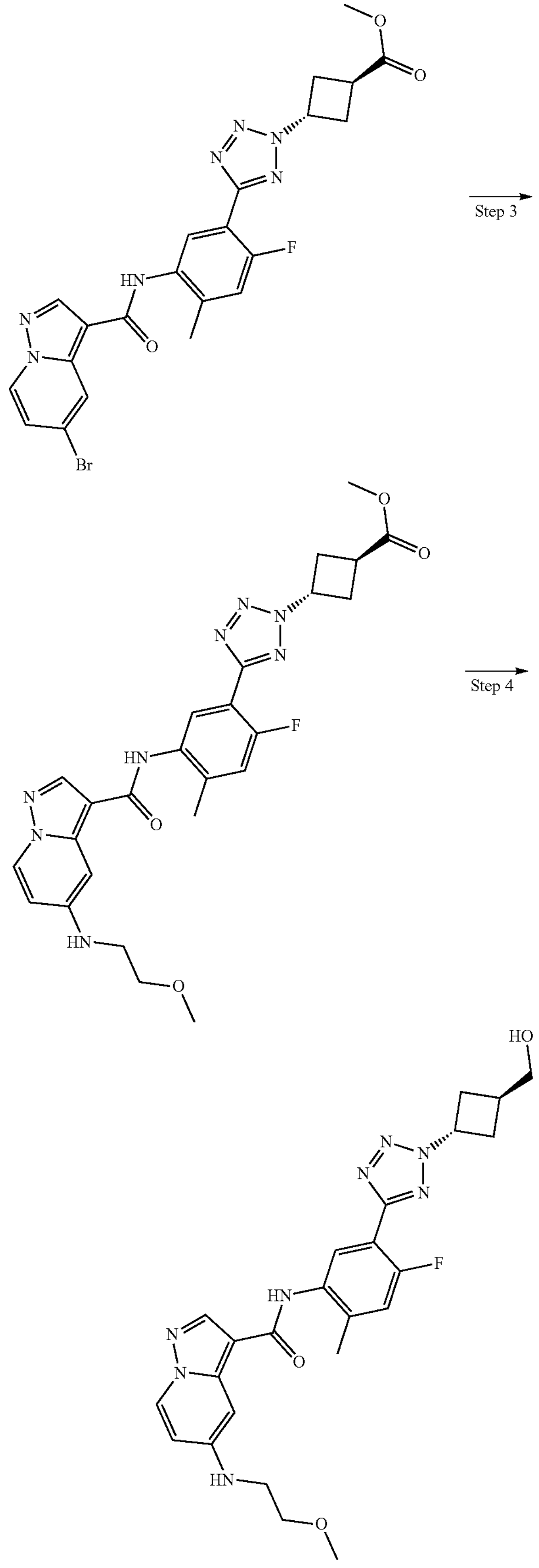

The title compound was obtained as a white solid, from Intermediate 7, step 1, methyl(1s,3s)-3-hydroxycyclobutane-1-carboxylate, 5-bromopyrazolo[1,5-a]pyridine-3-carboxylic acid and 2-methoxyethan-1-amine following a similar 4 step procedure to that described in Example 200. The crude product was purified by HPLC, Method C, 15% to 45% gradient. LCMS: m/z=495 $[M+H]^+$. 1H NMR (400 MHz, DMSO-$d_6$) δ 9.38 (s, 1H), 8.47 (s, 1H), 8.39 (d, 1H), 8.08 (d, 1H), 7.38 (d, 1H), 6.95 (d, 1H), 6.79 (t, 1H), 6.60 (dd, 1H), 5.62-5.50 (m, 1H), 4.83 (t, 1H), 3.56 (dt, 4H), 3.31-3.21 (m, 5H), 2.73 (dd, 2H), 2.58 (dt, 1H), 2.47 (dd, 1H), 2.34 (s, 3H).

Example 203

N-(5-(2-(1-((2-hydroxyethyl)sulfonyl)azetidin-3-yl)-2H-tetrazol-5-yl)-2-methylphenyl)pyrazolo[1,5-a]pyridine-3-carboxamide

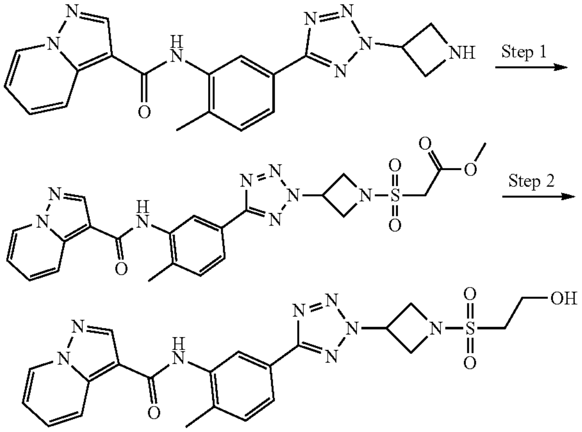

Step 1: Synthesis of methyl 2-((3-(5-(4-methyl-3-(pyrazolo[1,5-a]pyridine-3-carboxamido)phenyl)-2H-tetrazol-2-yl)azetidin-1-yl)sulfonyl)acetate To a stirred solution of Intermediate 15, step 2 (20 mg, 0.05 mmol) and TEA (10.1 mg, 0.06 mmol) in DCM (1 mL) was added methyl 2-(chlorosulfonyl)acetate (10.1 mg, 0.06 mmol) at 0° C. under $N_2$ and the reaction was stirred for 2 h and quenched with ice water. The mixture was extracted with DCM (3×50 mL), the combined organic layer was concentrated under vacuum and purified by Prep-HPLC, method C, 25% to 60%, to give the title compound (8.7 mg, 31%) as a white solid. LCMS: m/z=511 [M+H]+,

Step 2: Synthesis of N-(5-(2-(1-((2-hydroxyethyl)sulfonyl)azetidin-3-yl)-2H-tetrazol-5-yl)-2-methylphenyl)pyrazolo[1,5-a]pyridine-3-carboxamide To a stirred solution of methyl 2-((3-(5-(4-methyl-3-(pyrazolo[1,5-a]pyridine-3-carboxamido)phenyl)-2H-tetrazol-2-yl)azetidin-1-yl)sulfonyl)acetate (90 mg, 0.18 mmol) in MeOH (2 mL) was added $NaBH_4$ (12.6 mg, 0.35 mmol) at 0° C. under $N_2$ and the reaction was stirred for 2 h at rt. The mixture was quenched with ice water and extracted with EtOAc (3×20 mL). The organic layer was concentrated and purified by Prep-HPLC, Method C, 20% to 43% gradient, to give the title compound (39.8 mg, 46%) as a white solid.

LCMS: m/z=483 $[M+H]^+$, $^1H$ NMR (400 MHz, DMSO-$d_6$) δ 9.75 (s, 1H), 8.89-8.77 (m, 2H), 8.29-8.18 (m, 2H), 7.89 (dd, 1H), 7.57-7.46 (m, 2H), 7.13 (td, 1H), 5.91 (tt, 1H), 5.15 (t, 1H), 4.58-4.42 (m, 4H), 3.82 (q, 2H), 3.45 (t, 2H), 2.37 (s, 3H).

Example 204

(S)—N-(2-methyl-5-(4-methyl-2H-1,2,3-triazol-2-yl)phenyl)-5-(1-(morpholin-2-ylmethyl)-1H-pyrazol-4-yl)pyrazolo[1,5-a]pyridine-3-carboxamide

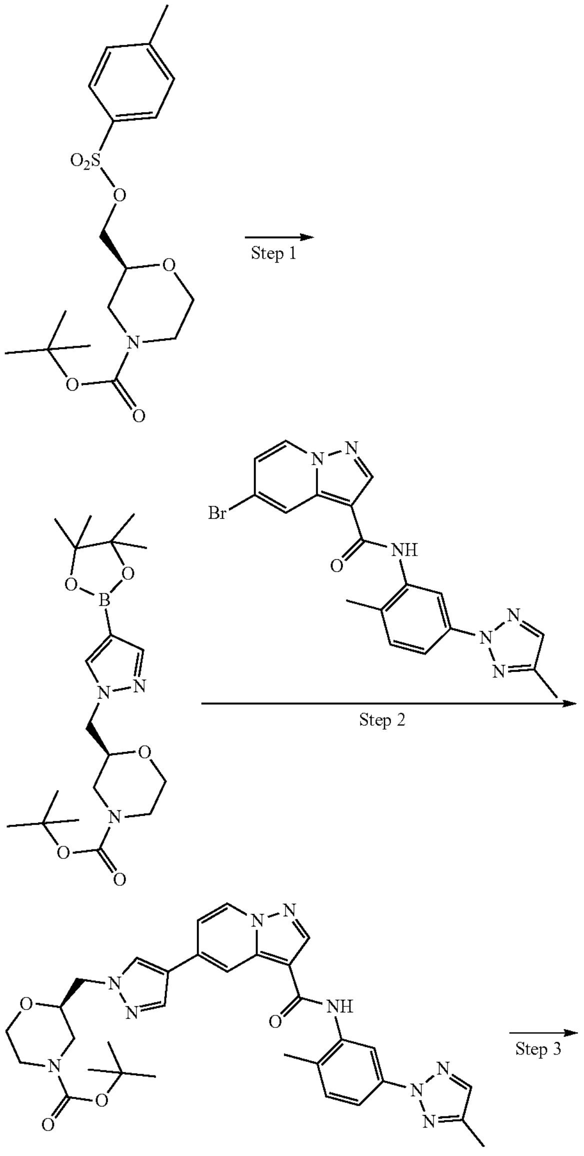

-continued

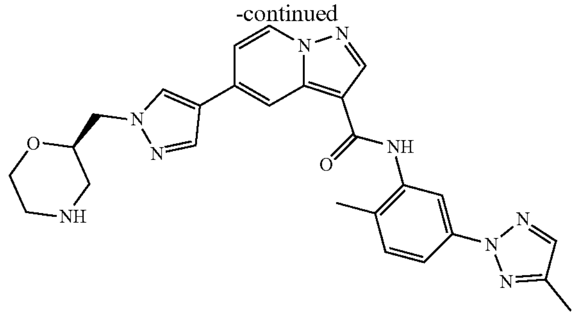

Step 1: Synthesis of tert-butyl (S)-2-((4-(4,4,5,5-tetramethyl-1,3,2-dioxaborolan-2-yl)-1H-pyrazol-1-yl)methyl)morpholine-4-carboxylate 4-(4,4,5,5-Tetramethyl-1,3,2-dioxaborolan-2-yl)-1H-pyrazole (100 mg, 0.52 mmol), tert-butyl (S)-2-((tosyloxy)methyl)morpholine-4-carboxylate (211 mg, 0.57 mmol) and $Cs_2CO_3$ (235 mg, 0.72 mmol) were combined in MeCN (1.5 mL) and heated to 90° C. for 3 h. The mixture was diluted with EtOAc, filtered through Celite® and the filtrate evaporated. The crude product was purified by silica gel using ISCO (0 to 75% EtOAc/Hex) to give the title compound, (112 mg, 55%) as a colorless film. LCMS: m/z=394 $[M+H]^+$.

Step 2: Synthesis of tert-butyl (S)-2-((4-(3-((2-methyl-5-(4-methyl-2H-1,2,3-triazol-2-yl)phenyl)carbamoyl)pyrazolo[1,5-a]pyridin-5-yl)-1H-pyrazol-1-yl)methyl)morpholine-4-carboxylate Example 57, step 1 (96 mg, 0.23 mmol), tert-butyl (S)-2-((4-(4,4,5,5-tetramethyl-1,3,2-dioxaborolan-2-yl)-1H-pyrazol-1-yl)methyl)morpholine-4-carboxylate (110 mg, 0.28 mmol), $PdCl_2$(dppf) (8.54 mg, 0.01 mmol) and $Na_2CO_3$ (74 mg, 0.70 mmol) were combined under $N_2$ in dioxane/water (0.75 mL/0.25 mL) and heated to 90° C. overnight. The cooled mixture was diluted with EtOAc and water then filtered through Celite® and the layers separated. The organic layer was washed with brine and dried over $Na_2SO_4$, filtered and evaporated to give the crude product. This was purified by ISCO chromatography (10 to 100% EtOAc/Hex) to give the title compound, 99 mg, 71% as colorless film.

Step 3: Synthesis of (S)—N-(2-methyl-5-(4-methyl-2H-1,2,3-triazol-2-yl)phenyl)-5-(1-(morpholin-2-ylmethyl)-1H-pyrazol-4-yl)pyrazolo[1,5-a]pyridine-3-carboxamide A solution of tert-butyl (S)-2-((4-(3-((2-methyl-5-(4-methyl-2H-1,2,3-triazol-2-yl)phenyl)carbamoyl)pyrazolo[1,5-a]pyridin-5-yl)-1H-pyrazol-1-yl)methyl)morpholine-4-carboxylate (99 mg, 0.17 mmol) in DCM (2 mL) and TFA (0.26 mL, 3.31 mmol) was stirred at rt for 2 h. The mixture was evaporated under reduced pressure, the residue partitioned between 10% MeOH/DCM and aq $NaHCO_3$. The organic layer was dried over $Na_2SO_4$, filtered and evaporated to give the title compound as a pale-yellow foam (75 mg, 91%). LCMS: m/z=499 $[M+H]^+$. $^1H$ NMR (500 MHz, DMSO-$d_6$) δ 9.60 (s, 1H), 8.82 (d, 1H), 8.74 (s, 1H), 8.41 (s, 1H), 8.34 (s, 1H), 8.21 (s, 1H), 8.07 (s, 1H), 7.88 (s, 1H), 7.74 (d, 1H), 7.43 (d, 1H), 7.38 (d, 1H), 4.16 (d, 2H), 3.75 (dd, 2H), 3.40 (t, 1H), 2.78 (d, 1H), 2.69-2.57 (m, 2H), 2.46-2.32 (m, 8H).

Example 205

(R)—N-(2-methyl-5-(4-methyl-2H-1,2,3-triazol-2-yl)phenyl)-5-(1-(morpholin-2-ylmethyl)-1H-pyrazol-4-yl)pyrazolo[1,5-a]pyridine-3-carboxamide

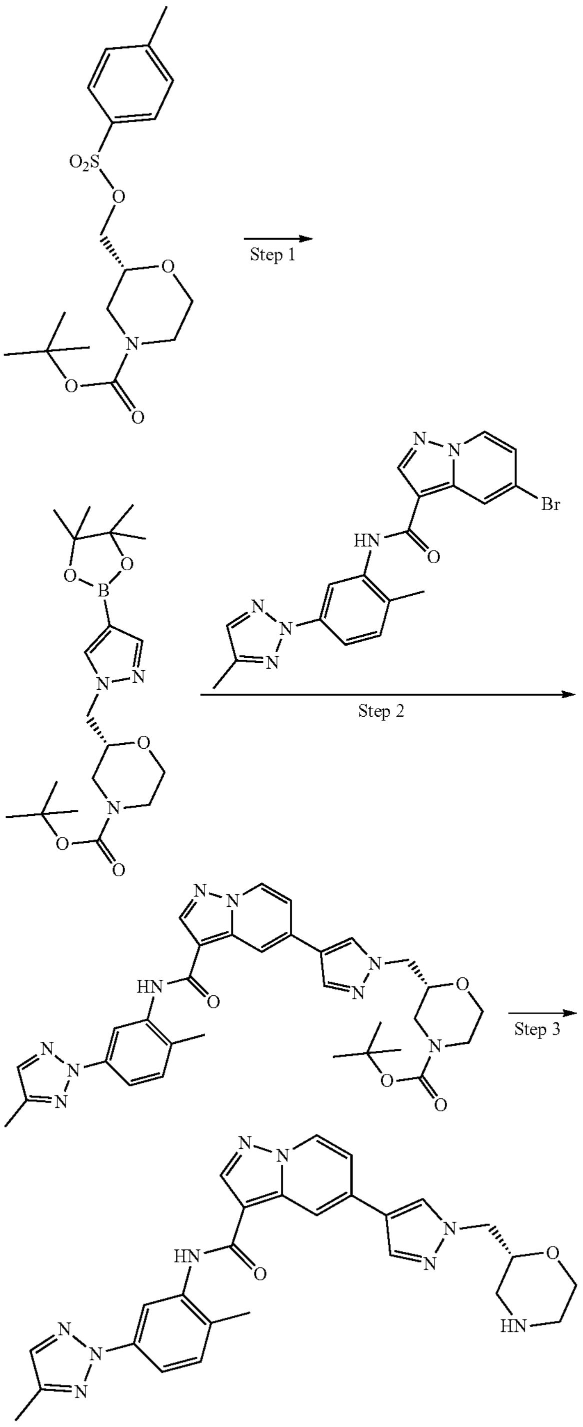

The title compound was prepared using the same method as described in Steps 1 to 3 for Example 204 starting with tert-butyl (R)-2-(hydroxymethyl)morpholine-4-carboxylate. LCMS: m/z=499 $[M+H]^+$. $^1H$ NMR (500 MHz, DMSO-$d_6$) δ 9.60 (s, 1H), 8.82 (d, 1H), 8.74 (s, 1H), 8.41 (s, 1H), 8.34 (s, 1H), 8.21 (s, 1H), 8.07 (s, 1H), 7.88 (s, 1H), 7.74 (d, 1H), 7.44 (d, 1H), 7.38 (d, 1H), 4.16 (d, 2H), 3.75 (dd, 2H), 3.40 (t, 1H), 2.78 (d, 1H), 2.70-2.57 (m, 2H), 2.43-2.37 (m, 8H).

Example 206

N-(5-(2-cyclopropyl-2H-tetrazol-5-yl)-2-methylphenyl)-5-(1-((4-hydroxytetrahydro-2H-pyran-4-yl)methyl)-1H-pyrazol-4-yl)pyrazolo[1,5-a]pyridine-3-carboxamide

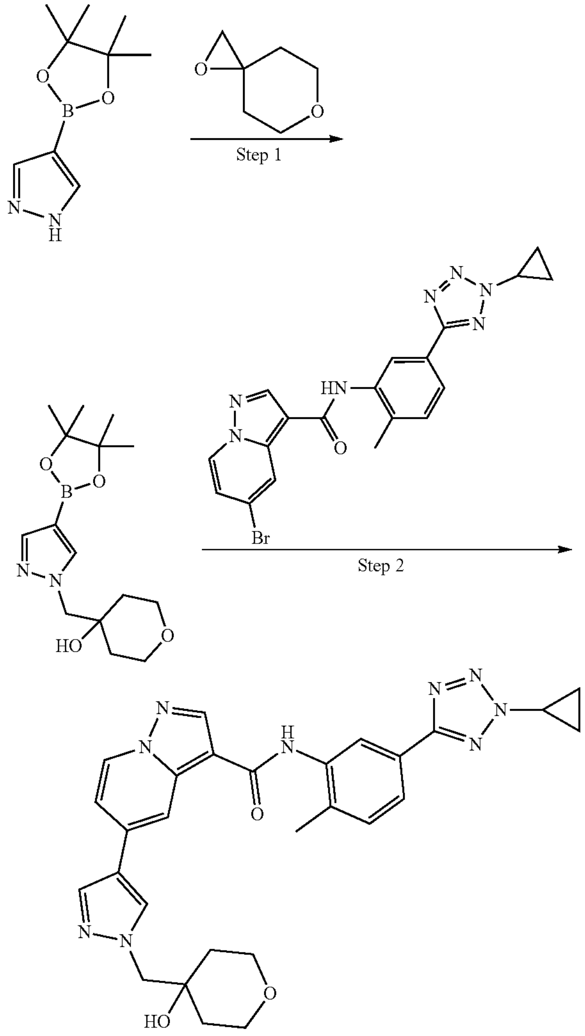

Step 1: Synthesis of 4-((4-(4,4,5,5-tetramethyl-1,3,2-dioxaborolan-2-yl)-1H-pyrazol-1-yl)methyl)tetrahydro-2H-pyran-4-ol The title compound was obtained as a light yellow solid, 1.5 g, 22% from 4-(4,4,5,5-tetramethyl-1,3,2-dioxaborolan- 2-yl)-1H-pyrazole and 1,6-dioxaspiro[2.5]octane, following a similar procedure to that described in Example 154, step 3. LCMS: m/z=309 [M+H]$^+$ Step 2: Synthesis of N-(5-(2-cyclopropyl-2H-tetrazol-5-yl)-2-methylphenyl)-5-(1-((4-hydroxytetrahydro-2H-pyran-4-yl)methyl)-1H-pyrazol-4-yl)pyrazolo[1,5-a]pyridine-3-carboxamide The title compound was obtained as a white solid, 300 mg, 30.4%, from Intermediate 30, and 4-((4-(4,4,5,5-tetramethyl-1,3,2-dioxaborolan-2-yl)-1H-pyrazol-1-yl)methyl)tetrahydro-2H-pyran-4-ol, following a similar procedure to that described in Example 47. LCMS: m/z=540 [M+H]$^+$; 1H NMR (400 MHz, DMSO-$d_6$) δ 9.64 (s, 1H), 8.82 (dd, 1H), 8.74 (s, 1H), 8.34 (d, 2H), 8.19 (d, 1H), 8.06 (d, 1H), 7.82 (dd, 1H), 7.50-7.34 (m, 2H), 4.83 (s, 1H), 4.47 (tt, 1H), 4.13 (s, 2H), 3.70-3.52 (m, 4H), 2.38 (s, 3H), 1.66-1.50 (m, 2H), 1.44-1.38 (m, 2H), 1.36-1.25 (m, 4H).

Example 207

N-(5-(2-cyclopropyl-2H-tetrazol-5-yl)-4-fluoro-2-methylphenyl)-5-(1-(2-hydroxy-2-methylpropyl)-1H-pyrazol-4-yl)pyrazolo[1,5-a]pyridine-3-carboxamide

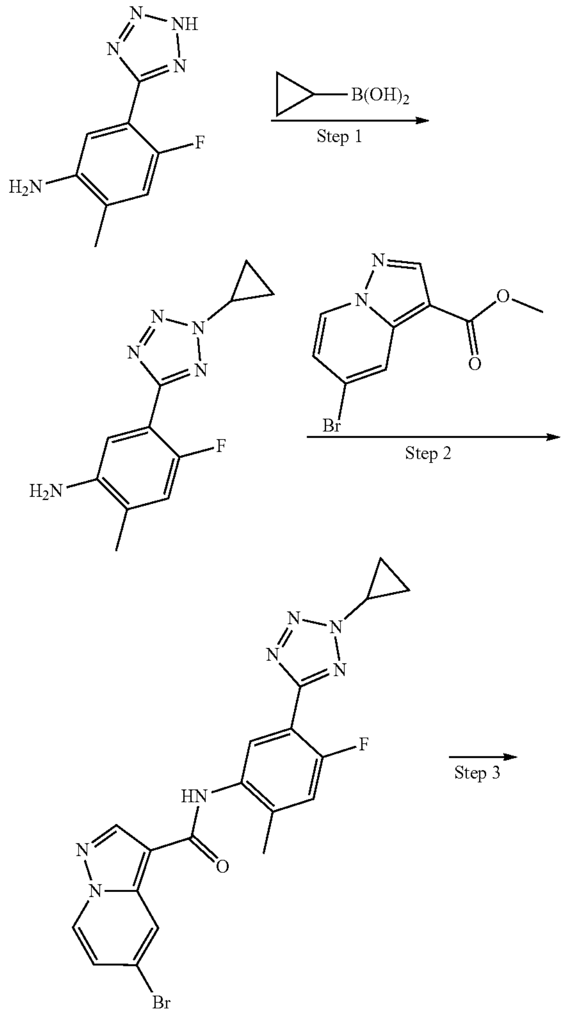

-continued

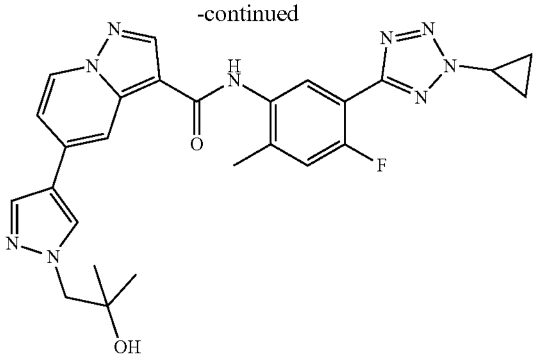

Step 1: Synthesis of 5-(2-cyclopropyl-2H-tetrazol-5-yl)-4-fluoro-2-methylaniline To a stirred solution of Intermediate 7, step 1 (300 mg, 1.55 mmol) in DCE (10 mL) was added $K_2CO_3$ (641 mg, 4.65 mmol), $[Cu(OH)-(TMEDA)]_2Cl_2$ (143 mg, 0.31 mmol) and cyclopropylboronic acid (266 mg, 3.10 mmol) and the reaction mixture was stirred overnight under $O_2$ at 60° C. The cooled mixture was filtered and the filter cake washed with DCM. The filtrate was concentrated in vacuo and the crude product was purified by silica gel column with PE:EtOAc=2:1 to give the title compound (60 mg, 17%) as a yellow solid. LCMS: m/z=234 [M+H]$^+$ Step 2: Synthesis of 5-bromo-N-(5-(2-cyclopropyl-2H-tetrazol-5-yl)-4-fluoro-2-methylphenyl)pyrazolo[1,5-a]pyridine-3-carboxamide To a stirred solution of 5-(2-cyclopropyl-2H-tetrazol-5-yl)-4-fluoro-2-methylaniline (60 mg, 0.26 mmol) in toluene (1 mL) was added methyl 5-bromopyrazolo[1,5-a]pyridine-3-carboxylate (78.5 mg, 0.31 mmol) and $AlMe_3$ (37.0 mg, 0.51 mmol) and the reaction mixture stirred for 3 h under $N_2$ at 100° C. The mixture was cooled to rt and 1N NaOH solution was added. The resulting solution was extracted with DCM and the organic layer was dried with $Na_2SO_4$ and concentrated in vacuo. The crude product was purified by silica gel column with PE:EtOAc=1:1 to give the title compound (100 mg, 85%) as a yellow solid. LCMS: m/z=456 [M+H]$^+$ Step 3: Synthesis of N-(5-(2-cyclopropyl-2H-tetrazol-5-yl)-4-fluoro-2-methylphenyl)-5-(1-(2-hydroxy-2-methylpropyl)-1H-pyrazol-4-yl)pyrazolo[1,5-a]pyridine-3-carboxamide To a stirred solution of 5-bromo-N-(5-(2-cyclopropyl-2H-tetrazol-5-yl)-4-fluoro-2-methylphenyl)pyrazolo[1,5-a]pyridine-3-carboxamide (60 mg, 0.13 mmol), 2-methyl-1-(4-(4,4,5,5-tetramethyl-1,3,2-dioxaborolan-2-yl)-1H-pyrazol-1-yl)propan-2-ol (52.1 mg, 0.2 mmol) in dioxane (1 mL) and $H_2O$ (0.2 mL) was added $Pd(dppf)Cl_2$ (9.6 mg, 13 mmol) and $Cs_2CO_3$ (85.3 mg, 0.26 mmol) and the reaction mixture was stirred for 2 h at 100° C. under $N_2$. The cooled mixture was concentrated and purified by silica gel column with DCM:MeOH=10:1. The crude product was purified by Prep-HPLC Method B, 27% to 52% gradient, to give the title compound (35.3 mg, 52%) as an off-white solid. LCMS: m/z=516 [M+H]$^+$, 1H NMR (400 MHz, DMSO-$d_6$) δ 9.70 (s, 1H), 8.82 (dd, 1H), 8.71 (s, 1H), 8.36-8.29 (m, 2H), 8.10 (d, 1H), 8.05 (s, 1H), 7.44-7.36 (m, 2H), 4.78 (s, 1H), 4.49

(tt, 1H), 4.06 (s, 2H), 2.37 (s, 3H), 1.46-1.32 (m, 2H), 1.34-1.21 (m, 2H), 1.10 (s, 6H).

Example 208

N-(5-(2-cyclopropyl-2H-tetrazol-5-yl)-2-methylphenyl)-5-(1-(2-hydroxyethyl)-3,5-dimethyl-1H-pyrazol-4-yl)pyrazolo[1,5-a]pyridine-3-carboxamide

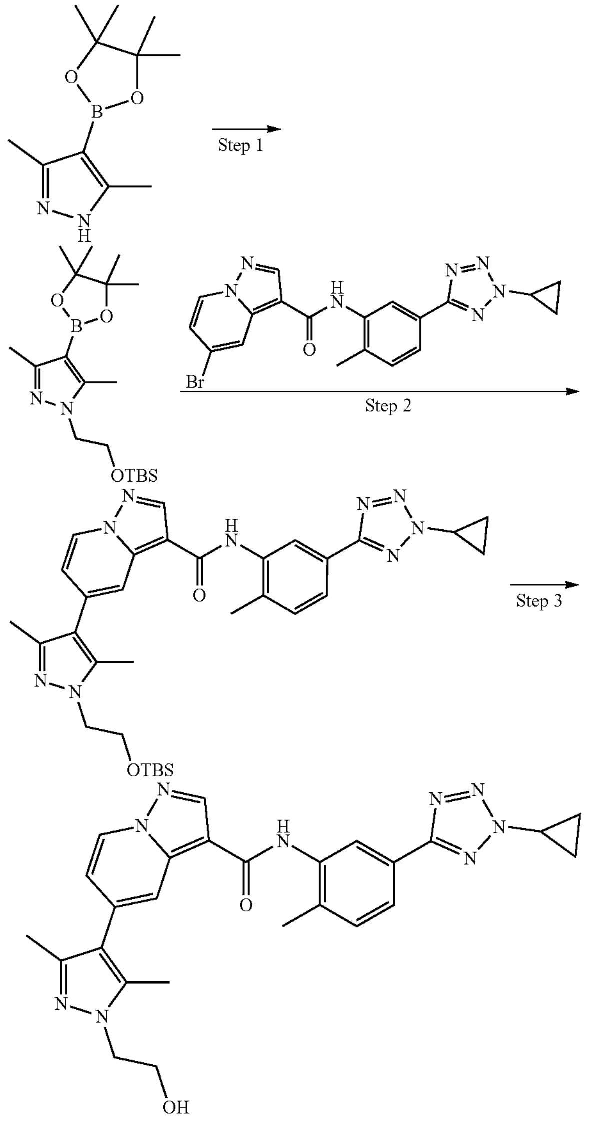

Step 1: Synthesis of 1-(2-((tert-butyldimethylsilyl)oxy)ethyl)-3,5-dimethyl-4-(4,4,5,5-tetramethyl-1,3,2-dioxaborolan-2-yl)-1H-pyrazole A mixture of 3,5-dimethyl-4-(4,4,5,5-tetramethyl-1,3,2-dioxaborolan-2-yl)-1H-pyrazole (1.00 g, 4.50 mmol), (2-bromoethoxy)(tert-butyl)dimethylsilane (2.15 g, 9.0 mmol), $K_2CO_3$ (1.24 g, 9.0 mmol) and MeCN (20 mL) was stirred at 80° C. for 16 h. The cooled mixture was quenched with water at 0° C. and extracted with EtOAc (3×20 mL). The combined organic layer was concentrated under reduced pressure and the residue was purified by prep-TLC with DCM:MeOH=25:1 to afford the title compound (378.9 mg, 22.1%) as a white solid. LCMS: m/z=381 $[M+H]^+$

Step 2: Synthesis of 5-(1-(2-((tert-butyldimethylsilyl)oxy)ethyl)-3,5-dimethyl-1H-pyrazol-4-yl)-N-(5-(2-cyclopropyl-2H-tetrazol-5-yl)-2-methylphenyl)pyrazolo[1,5-a]pyridine-3-carboxamide The title compound was obtained as a white solid, 190 mg, 80.9% from Intermediate 30 and (1-(2-((tert-butyldimethylsilyl)oxy)ethyl)-3,5-dimethyl-4-(4,4,5,5-tetramethyl-1,3,2-dioxaborolan-2-yl)-1H-pyrazole (195 mg, 0.51 mmol) following a similar procedure to that described in Example 197, step 2. LCMS: m/z=612 $[M+H]^+$

Step 3: Synthesis of N-(5-(2-cyclopropyl-2H-tetrazol-5-yl)-2-methylphenyl)-5-(1-(2-hydroxyethyl)-3,5-dimethyl-1H-pyrazol-4-yl)pyrazolo[1,5-a]pyridine-3-carboxamide TBAF (0.25 mL, 1M) was added to 5-(1-(2-((tert-butyldimethylsilyl)oxy)ethyl)-3,5-dimethyl-1H-pyrazol-4-yl)-N-(5-(2-cyclopropyl-2H-tetrazol-5-yl)-2-methylphenyl)pyrazolo[1,5-a]pyridine-3-carboxamide (100 mg, 0.16 mmol) in THF (1 mL) and the solution stirred for 2 h at 90° C. The cooled mixture was quenched with water at 0° C. and extracted with EtOAc (3×2 mL). The combined organic extracts were evaporated under reduced pressure. The residue was purified on prep-TLC with DCM:MeOH=10:1 and the product further purified by prep-HPLC Method A, 24% to 49% gradient, to afford the title compound (31.3 mg, 38.5%) as a white solid. LCMS: m/z=498 $[M+H]^+$; 1H NMR (400 MHz, DMSO-$d_6$) δ 9.70 (s, 1H), 8.84 (d, 1H), 8.78 (s, 1H), 8.12 (d, 1H), 8.06 (d, 1H), 7.82 (dd, 1H), 7.46 (d, 1H), 7.07 (dd, 1H), 4.89 (t, 1H), 4.46 (tt, 1H), 4.07 (t, 2H), 3.72 (q, 2H), 2.34 (d, 6H), 2.23 (s, 3H), 1.40 (p, 2H), 1.33-1.16 (m, 2H).

Examples 209-226

The compounds in the following table can be prepared from the appropriate starting materials and intermediates, following procedures described herein.

| Cmpd No | Name, Starting materials | Data LCMS (m/z = $[M+H]^+$) | General Scheme |
|---|---|---|---|
| 209 | 5-(1-(2-hydroxy-2-methylpropyl)-1H-pyrazol-4-yl)-N-(2-methyl-5-(5-methyl-2H-tetrazol-2-yl)phenyl)pyrazolo[1,5-a]pyridine-3-carboxamide<br>SM: Intermediate 37 and 2-methyl-1-(4-(4,4,5,5-tetramethyl-1,3,2-dioxaborolan-2-yl)-1H-pyrazol-1-yl)propan-2-ol | 472 | 16 |
| 210 | N-(2-chloro-5-(2-methyl-2H-tetrazol-5-yl)phenyl)-5-(1-(2-hydroxy-2-methylpropyl)-1H-pyrazol-4-yl)pyrazolo[1,5-a]pyridine-3-carboxamide<br>SM: Intermediate 44 and 2-chloro-5-(2-methyl-2H-tetrazol-5-yl)aniline (CAS 1858603-80-1), which can be synthesized similarly to Intermediate 74 | 492 | 19 |
| 211 | (R)-N-(5-(5-(2,2-difluorocyclopropyl)-2H-tetrazol-2-yl)-2-methylphenyl)-5-(1-(2-hydroxyethyl)-1H-pyrazol-4-yl)pyrazolo[1,5-a]pyridine-3-carboxamide or (S)-N-(5-(5-(2,2- | 506 | 16 Isomer 1 |

-continued

| Cmpd No | Name, Starting materials | Data LCMS (m/z = [M + H]+) | General Scheme |
|---|---|---|---|
| | difluorocyclopropyl)-2H-tetrazol-2-yl)-2-methylphenyl)-5-(1-(2-hydroxyethyl)-1H-pyrazol-4-yl)pyrazolo[1,5-a]pyridine-3-carboxamide SM: 5-bromo-N-(5-(5-(2,2-difluorocyclopropyl)-2H-tetrazol-2-yl)-2-methylphenyl)pyrazolo[1,5-a]pyridine-3-carboxamide, which can be synthesized similarly to Intermediate 37 starting with 5-(2,2-difluorocyclopropyl)-2H-tetrazole (which can be made from 2,2-difluorocyclopropanecarbonitrile (CAS 36597-03-2) and tributyltin azide (CAS 36597-03-2)), and 2-(4-(4,4,5,5-tetramethyl-1,3,2-dioxaborolan-2-yl)-1H-pyrazol-1-yl)ethan-1-ol, CAS 1040377-08-9 | | |
| 212 | N-(2-chloro-5-(5-methyl-2H-tetrazol-2-yl)phenyl)-5-(1-(2-hydroxy-2-methylpropyl)-1H-pyrazol-4-yl)pyrazolo[1,5-a]pyridine-3-carboxamide SM: Intermediate 44 and 2-chloro-5-(5-methyl-2H-tetrazol-2-yl)aniline, which can be synthesized similarly to Intermediate 37, step 1 or Intermediate 21, step 1 | 492 | 19 |
| 213 | N-(2-fluoro-5-(2-methyl-2H-tetrazol-5-yl)phenyl)-5-(1-(2-hydroxy-2-methylpropyl)-1H-pyrazol-4-yl)pyrazolo[1,5-a]pyridine-3-carboxamide SM: Intermediate 44 and 2-fluoro-5-(2-methyl-2H-tetrazol-5-yl)aniline, CAS 2439265-96-8 | 476 | 19 |
| 214 | 4-fluoro-6-(1-(2-hydroxy-2-methylpropyl)-1H-pyrazol-4-yl)-N-(2-methyl-5-(2-methyl-2H-tetrazol-5-yl)phenyl)pyrazolo[1,5-a]pyridine-3-carboxamide SM: Example 277, step 1, and Intermediate 13, step 2, and 2-methyl-1-(4-(4,4,5,5-tetramethyl-1,3,2-dioxaborolan-2-yl)-1H-pyrazol-1-yl)propan-2-ol, CAS 1082503-77-2 | 490 | 16 |
| 215 | N-(5-(2-cyclopropyl-2H-tetrazol-5-yl)-2-fluoro-4-methylphenyl)-5-(1-(2-hydroxy-2-methylpropyl)-1H-pyrazol-4-yl)pyrazolo[1,5-a]pyridine-3-carboxamide SM: Intermediate 44 and 5-(2-cyclopropyl-2H-tetrazol-5-yl)-2-fluoro-4-methylaniline, which can be synthesized similarly to Intermediate 73 starting with 5-amino-4-fluoro-2-methylbenzonitrile, CAS 1824053-65-7 | 516 | 19 |
| 216 | N-(2-chloro-5-(5-cyclopropyl-2H-tetrazol-2-yl)phenyl)-5-(1-(2-hydroxy-2-methylpropyl)-1H-pyrazol-4-yl)pyrazolo[1,5-a]pyridine-3-carboxamide SM: Intermediate 44 and 2-chloro-5-(5-cyclopropyl-2H-tetrazol-2-yl)aniline, which can be synthesized similarly to Intermediate 21, Step 1 starting with 5-cyclopropyl-2H-tetrazole, CAS 27943-07-3 | 518 | 19 |
| 217 | N-(5-(5-cyclopropyl-2H-tetrazol-2-yl)-2-fluorophenyl)-5-(1-(2-hydroxy-2-methylpropyl)-1H-pyrazol-4-yl)pyrazolo[1,5-a]pyridine-3-carboxamide SM: Intermediate 44 and 5-(5-cyclopropyl-2H-tetrazol-2-yl)-2-fluoroaniline, which can be synthesized similarly to Intermediate 21, Step 1 starting with 5-cyclopropyl-2H-tetrazole, CAS 27943-07-3, and (3-amino-4-fluorophenyl)boronic acid, CAS 873566-75-7 | 502 | 19 |
| 218 | N-(2-chloro-5-(2-methyl-2H-tetrazol-5-yl)phenyl)-5-(1-(2-hydroxyethyl)-1H-pyrazol-4-yl)pyrazolo[1,5-a]pyridine-3-carboxamide SM: Methyl 5-(1-(2-hydroxyethyl)-1H-pyrazol-4-yl)pyrazolo[1,5-a]pyridine-3-carboxylate, which can be synthesized similarly to Intermediate 44 starting with 2-(4-(4,4,5,5-tetramethyl-1,3,2-dioxaborolan-2-yl)-1H-pyrazol-1-yl)ethan-1-ol, CAS 1040377-08-9, and 2-chloro-5-(2-methyl-2H-tetrazol-5-yl)aniline (CAS 1858603-80-1), which can be synthesized similarly to Intermediate 74 | 464 | 19 |
| 219 | N-(5-(2-cyclopropyl-2H-tetrazol-5-yl)-2-methylphenyl)-5-(1-(2-(4-methylpiperazin-1-yl)ethyl)-1H-pyrazol-4-yl)pyrazolo[1,5-a]pyridine-3-carboxamide SM: Intermediate 30 and 1-methyl-4-(2-(4-(4,4,5,5-tetramethyl-1,3,2-dioxaborolan-2-yl)-1H-pyrazol-1-yl)ethyl)piperazine, CAS 1392419-83-8 | 552 | 16 |
| 220 | N-(5-(2-cyclopropyl-2H-tetrazol-5-yl)-2-methylphenyl)-5-(1-(3-morpholinopropyl)-1H-pyrazol-4-yl)pyrazolo[1,5-a]pyridine-3-carboxamide SM: Intermediate 30 and 4-(3-(4-(4,4,5,5-tetramethyl-1,3,2-dioxaborolan-2-yl)-1H-pyrazol-1-yl)propyl)morpholine, CAS 1092500-87-2 | 553 | 16 |
| 221 | 5-(1-(3-(dimethylphosphoryl)propyl)-1H-pyrazol-4-yl)-N-(2-methyl-5-(2-methyl-2H-tetrazol-5-yl)phenyl)pyrazolo[1,5-a]pyridine-3-carboxamide SM: Intermediate 13 and (3-(4-bromo-1H-pyrazol-1-yl)propyl)dimethylphosphine oxide (treated with $(BPin)_2$, $Pd(dppf)Cl_2$, and $CsCO_3$) | | 16 |
| 222 | N-(5-(5-(2-fluorocyclopropyl)-2H-tetrazol-2-yl)-2-methylphenyl)-5-(1-(2-hydroxy-2-methylpropyl)-1H-pyrazol-4-yl)pyrazolo[1,5-a]pyridine-3-carboxamide SM: Intermediate 44 and 5-(5-(2-fluorocyclopropyl)-2H-tetrazol-2-yl)-2-methylaniline, which can be synthesized similarly to Intermediate 71 | 516 | 19 |
| 223 | methyl 3-(5-(2-fluoro-5-(6-(2-hydroxyethoxy)pyrazolo[1,5-a]pyridine-3-carboxamido)-4-methylphenyl)-2H-tetrazol-2-yl)azetidine-1-carboxylate SM: Example 114, step 1 and methyl 6-(2-hydroxyethoxy)pyrazolo[1,5-a]pyridine-3-carboxylate, which can be synthesized similarly to Intermediate 42 | 511 | 18 |
| 224 | methyl 3-(5-(2-fluoro-4-methyl-5-(6-morpholinopyrazolo[1,5-a]pyridine-3-carboxamido)phenyl)-2H-tetrazol-2-yl)azetidine-1-carboxylate SM: Example 114, step 1 and methyl 6-morpholinopyrazolo[1,5-a]pyridine-3-carboxylate, which can be synthesized similarly to Intermediate 42 | 536 | 18 |
| 225 | N-(5-(5-cyclopropyl-2H-tetrazol-2-yl)-2-methylphenyl)-5-(1-(2-hydroxy-2-methylpropyl)-1H-pyrazol-4-yl)pyrazolo[1,5-a]pyridine-3-carboxamide SM: Intermediate 44 and Example 152, step 1 | 498 | 19 |
| 226 | N-(4-chloro-5-(2-cyclopropyl-2H-tetrazol-5-yl)-2-methylphenyl)-5-(1-(2-hydroxy-2-methylpropyl)-1H-pyrazol-4-yl)pyrazolo[1,5-a]pyridine-3-carboxamide SM: Intermediate 44 and 4-chloro-5-(2-cyclopropyl-2H-tetrazol-5-yl)-2-methylaniline, which can be synthesized similarly to Intermediate 34, step 1 and Intermediate 49 | | 19 |

Example 227

N-(2-chloro-5-(2-cyclopropyl-2H-tetrazol-5-yl)-4-methylphenyl)-5-(1-(2-hydroxy-2-methylpropyl)-1H-pyrazol-4-yl)pyrazolo[1,5-a]pyridine-3-carboxamide

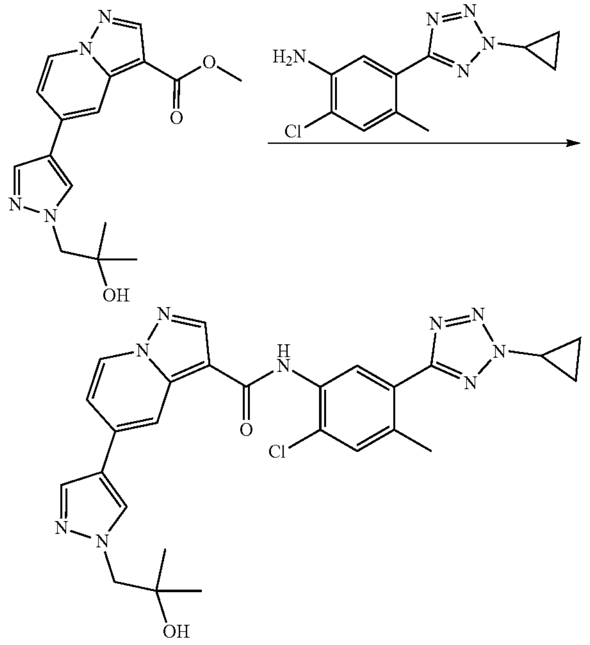

The title compound was obtained as a white solid, 26 mg, 19%, from Intermediate 43 and Intermediate 44 following a similar procedure to that described in Example 162, step 3. The crude product was purified by HPLC, Method B2, Gradient: 38% to 63%. LCMS: m/z=532 $[M+H]^+$, $^1H$ NMR (400 MHz, DMSO-$d_6$) δ 9.80 (s, 1H), 8.82 (d, 1H), 8.75 (s, 1H), 8.36-8.29 (m, 2H), 8.25 (s, 1H), 8.05 (s, 1H), 7.64 (s, 1H), 7.40 (dd, 1H), 4.77 (s, 1H), 4.50 (tt, 1H), 4.06 (s, 2H), 2.59 (s, 3H), 1.42 (q, 2H), 1.39-1.21 (m, 3H), 1.10 (s, 6H).

Examples 228-233

The compounds in the following table can be prepared from the appropriate starting materials and intermediates, following procedures described herein.

-continued

| Cmpd No | Name, Starting Material | Data LCMS (m/z = $[M + H]^+$) | General Scheme |
|---|---|---|---|
| 228 | 5-(1-(2-hydroxyethyl)-3-methyl-1H-pyrazol-4-yl)-N-(2-methyl-5-(2-methyl-2H-tetrazol-5-yl)phenyl)pyrazolo[1,5-a]pyridine-3-carboxamide<br>SM: Example 238, step 1 and Intermediate 13 | 458 | 21 |
| 229 | (R)-N-(5-(2-cyclopropyl-2H-tetrazol-5-yl)-2-methylphenyl)-5-(1-(morpholin-2-ylmethyl)-1H-pyrazol-4-yl)pyrazolo[1,5-a]pyridine-3-carboxamide<br>SM: Example 204, step 1 and Intermediate 30 | 525 | 21 |
| 230 | (R)-5-(3-methyl-1-(morpholin-2-ylmethyl)-1H-pyrazol-4-yl)-N-(2-methyl-5-(5-methyl-2H-tetrazol-2-yl)phenyl)pyrazolo[1,5-a]pyridine-3-carboxamide<br>SM: Intermediate 37 and tert-butyl (R)-2-((3-methyl-4-(4,4,5,5-tetramethyl-1,3,2-dioxaborolan-2-yl)-1H-pyrazol-1-yl)methyl)morpholine-4-carboxylate, which can be synthesized similarly to Example 204, step 1 and Example 238, step 1 | | 21 |
| 231 | 5-((1H-pyrazol-4-yl)amino)-N-(2-methyl-5-(5-methyl-2H-tetrazol-2-yl)phenyl)pyrazolo[1,5-a]pyridine-3-carboxamide<br>SM: Intermediate 37 and 1H-pyrazol-4-amine, CAS 28466-26-4 | 415 | 21 |
| 232 | N-(2-methyl-5-(2-methyl-2H-tetrazol-5-yl)phenyl)-5-(1-(3-(S-methylsulfonimidoyl)propyl)-1H-pyrazol-4-yl)pyrazolo[1,5-a]pyridine-3-carboxamide<br>SM: Intermediate 13 treated with $(BPin)_2$, $Pd(dppf)Cl_2$, and $CsCO_3$ and (3-(4-bromo-1H-pyrazol-1-yl)propyl)(imino)(methyl)-$\lambda^6$-sulfanone | 519 | 22 |
| 233 | (S)-N-(5-(5-(2,2-difluorocyclopropyl)-2H-tetrazol-2-yl)-2-methylphenyl)-5-(1-(2-hydroxyethyl)-1H-pyrazol-4-yl)pyrazolo[1,5-a]pyridine-3-carboxamide or (R)-N-(5-(5-(2,2-difluorocyclopropyl)-2H-tetrazol-2-yl)-2-methylphenyl)-5-(1-(2-hydroxyethyl)-1H-pyrazol-4-yl)pyrazolo[1,5-a]pyridine-3-carboxamide<br>SM: 5-bromo-N-(5-(5-(2,2-difluorocyclopropyl)-2H-tetrazol-2-yl)-2-methylphenyl)pyrazolo[1,5-a]pyridine-3-carboxamide, which can be synthesized similarly to Intermediate 37 starting with 5-(2,2-difluorocyclopropyl)-2H-tetrazole (which can be made from 2,2-difluorocyclopropanecarbonitrile (CAS 36597-03-2) and tributyltin azide (CAS 36597-03-2)), and 2-(4-(4,4,5,5-tetramethyl-1,3,2-dioxaborolan-2-yl)-1H-pyrazol-1-yl)ethan-1-ol, CAS 1040377-08-9 | 506 | 16 Isomer 2 |

Example 234

N-(2-chloro-5-(2-cyclopropyl-2H-tetrazol-5-yl)phenyl)-5-(1-(2-hydroxy-2-methylpropyl)-1H-pyrazol-4-yl)pyrazolo[1,5-a]pyridine-3-carboxamide

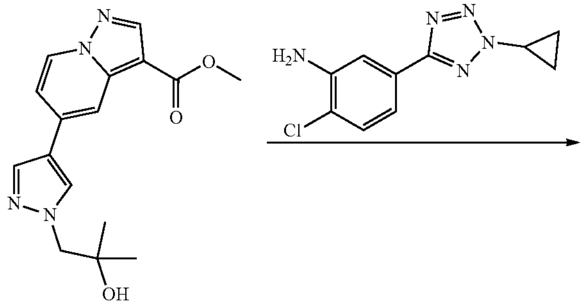

-continued

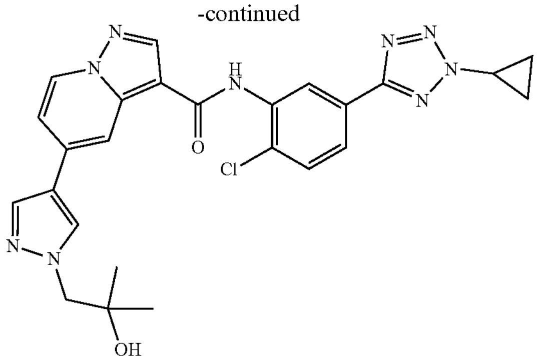

The title compound was obtained as an off-white solid, 54.3 mg, 31%, from Intermediate 46 and Intermediate 44 following a similar procedure to that described in Example 162, step 3. The crude product was purified by HPLC, Method B2, Gradient: 31% to 59% to yield the title compound (54.3 mg, 31%) as an off-white solid. LCMS: m/z=518 $[M+H]^+$, $^1H$ NMR (400 MHz, DMSO-$d_6$) δ 9.82 (s, 1H), 8.84 (d, 1H), 8.77 (s, 1H), 8.46 (d, 1H), 8.38-8.32 (m, 2H), 8.07 (s, 1H), 7.91 (dd, 1H), 7.75 (d, J=8.4 Hz, 1H), 7.42 (dd, 1H), 4.77 (s, 1H), 4.50 (tt, 1H), 4.07 (s, 2H), 1.43 (p, 2H), 1.31 (dt, 2H), 1.11 (s, 6H).

Example 235

N-(2-chloro-5-(2-cyclopropyl-2H-tetrazol-5-yl)-4-methylphenyl)-5-(1-((4-hydroxytetrahydro-2H-pyran-4-yl)methyl)-3-methyl-1H-pyrazol-4-yl)pyrazolo[1,5-a]pyridine-3-carboxamide

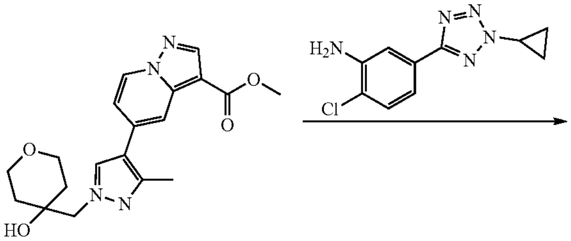

-continued

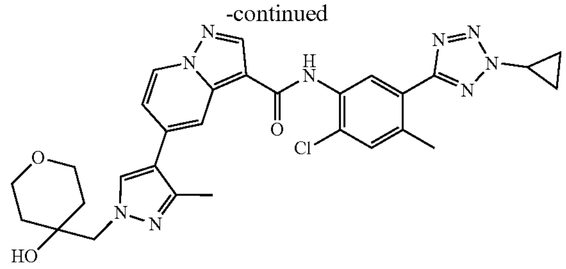

To a mixture of Intermediate 45 (200 mg, 0.539 mmol) and Intermediate 43 (147 mg, 0.592 mmol) in toluene (10 mL) was added LiHMDS (1 M in toluene, 2 mL). The reaction mixture was stirred at 30° C. for 2 h. The mixture was quenched with water (2 mL), concentrated to dryness and the residue was purified on prep-TLC with DCM: MeOH=20:1. The crude product was purified by HPLC, Method B2, Gradient: 33% to 60% to afford title compound (178.3 mg, 56.3%) as a yellow solid. LCMS: m/z=588 $[M+H]^+$; $^1H$ NMR (400 MHz, DMSO-$d_6$) δ 9.84 (s, 1H), 8.86-8.74 (m, 2H), 8.26 (d, 1H), 8.19 (d, 2H), 7.64 (s, 1H), 7.28 (dd, 1H), 4.82 (s, 1H), 4.50 (tt, 1H), 4.04 (s, 2H), 3.60 (dt, 4H), 2.59 (s, 3H), 2.41 (s, 3H), 1.64-1.52 (m, 2H), 1.42 (p, 2H), 1.31 (ddt, 4H).

Example 236

N-(2-chloro-5-(2-cyclopropyl-2H-tetrazol-5-yl)phenyl)-5-(1-((4-hydroxytetrahydro-2H-pyran-4-yl)methyl)-1H-pyrazol-4-yl)pyrazolo[1,5-a]pyridine-3-carboxamide

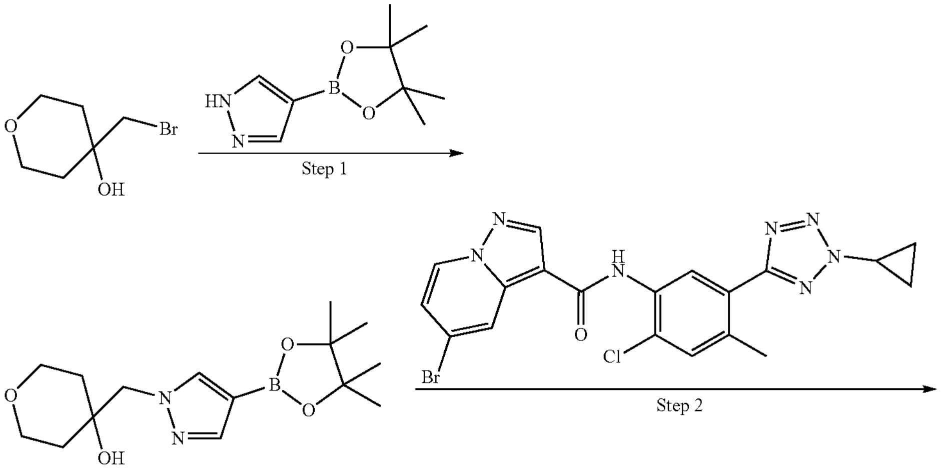

-continued

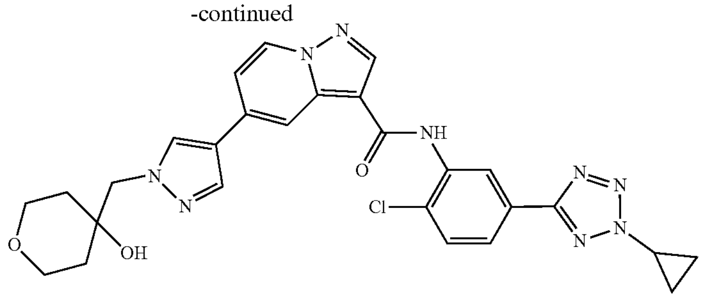

Step 1: Synthesis of 4-((4-(4,4,5,5-tetramethyl-1,3,2-dioxaborolan-2-yl)-1H-pyrazol-1-yl)methyl)tetrahydro-2H-pyran-4-ol NaH (81.6 mg, 2.04 mmol) was added portionwise to 4-(bromomethyl)tetrahydro-2H-pyran-4-ol (200 mg, 1.02 mmol) and 4-(4,4,5,5-tetramethyl-1,3,2-dioxaborolan-2-yl)-1H-pyrazole (296 mg, 1.53 mmol) in DMF (10 mL) at 0° C. The resulting mixture was stirred at 80° C. for 2 h. The mixture was diluted with DCM (100 mL) and washed with aq. $NaHCO_3$ (2×50 mL). The organic layer was dried with $Na_2SO_4$ and concentrated under vacuum. The residue was purified by a silica gel column with DCM:EtOAc=25:1 to give the title compound (90 mg, 66%) as a white solid. LCMS: m/z=309 $[M+H]^+$.

Step 2: Synthesis of N-(2-chloro-5-(2-cyclopropyl-2H-tetrazol-5-yl)phenyl)-5-(1-((4-hydroxytetrahydro-2H-pyran-4-yl)methyl)-1H-pyrazol-4-yl)pyrazolo[1,5-a]pyridine-3-carboxamide The title compound was obtained as an off-white solid, 28.8 mg, 34%, from Intermediate 47 and 4-((4-(4,4,5,5-tetramethyl-1,3,2-dioxaborolan-2-yl)-1H-pyrazol-1-yl)methyl)tetrahydro-2H-pyran-4-ol (Step 1) following a similar procedure to that described in Example 46. The crude product was purified by HPLC, Method B2, Gradient: 30% to 55% to give the title compound (28.8 mg, 34%) as an off-white solid. LCMS: m/z=560 $[M+H]^+$, $^1H$ NMR (400 MHz, DMSO-$d_6$) δ 9.79 (s, 1H), 8.83 (dd, 1H), 8.76 (s, 1H), 8.46 (d, 1H), 8.38-8.32 (m, 2H), 8.07 (d, 1H), 7.90 (dd, 1H), 7.75 (d, 1H), 7.41 (dd, 1H), 4.81 (s, 1H), 4.49 (tt, 1H), 4.14 (s, 2H), 3.64-3.55 (m, 4H), 1.58 (dt, 2H), 1.47-1.38 (m, 2H), 1.37-1.21 (m, 5H).

Example 237

(S)—N-(2-chloro-5-(2-cyclopropyl-2H-tetrazol-5-yl)phenyl)-5-(1-(2-hydroxy-3-methoxypropyl)-1H-pyrazol-4-yl)pyrazolo[1,5-a]pyridine-3-carboxamide

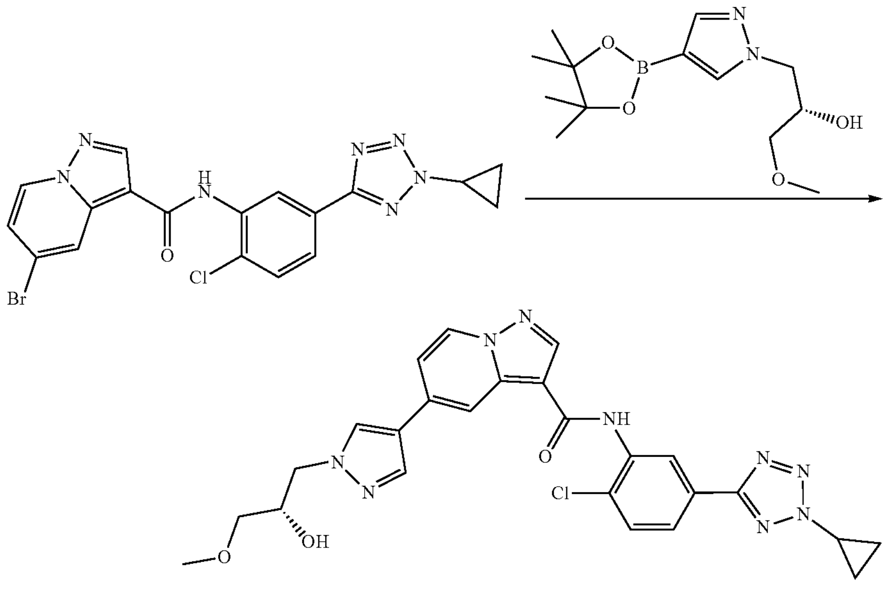

To a stirred solution of Intermediate 47 (5 g, 10.9 mmol) in dioxane (30 mL) and $H_2O$ (8 mL) was added Intermediate 48 (4.59 g, 16.3 mmol), $K_2CO_3$ (3.00 g, 21.8 mmol) and Pd(dppf)$Cl_2$ (797 mg, 1.09 mmol) at rt. The reaction mixture was stirred at 80° C. for 3 h under $N_2$. The mixture was diluted with EtOAc (100 mL) and water (100 mL). The aqueous layer was extracted with EtOAc (3×50 mL). The combined organic layers were washed with brine, dried with $Na_2SO_4$ and concentrated under vacuum. The residue was purified by silica gel column with DCM:MeOH=25:1 to give the title compound (1.76 g, 30%) as an off white solid. LCMS: m/z=534 $[M+H]^+$. $^1H$ NMR (400 MHz, DMSO-$d_6$) δ 9.78 (s, 1H), 8.83 (dd, 1H), 8.76 (s, 1H), 8.46 (d, 1H), 8.39 (s, 1H), 8.34 (dd, 1H), 8.07 (d, 1H), 7.91 (dd, 1H), 7.75 (d, 1H), 7.40 (dd, 1H), 5.18 (d, 1H), 4.49 (tt, 1H), 4.22 (dd, 1H), 4.12-3.96 (m, 2H), 3.32-3.29 (m, 5H), 1.47-1.34 (m, 2H), 1.37-1.25 (m, 2H).

Example 238

N-[2-chloro-5-(2-cyclopropyl-2H-1,2,3,4-tetrazol-5-yl)phenyl]-5-[1-(2-hydroxyethyl)-3-methyl-1H-pyrazol-4-yl]pyrazolo[1,5-a]pyridine-3-carboxamide

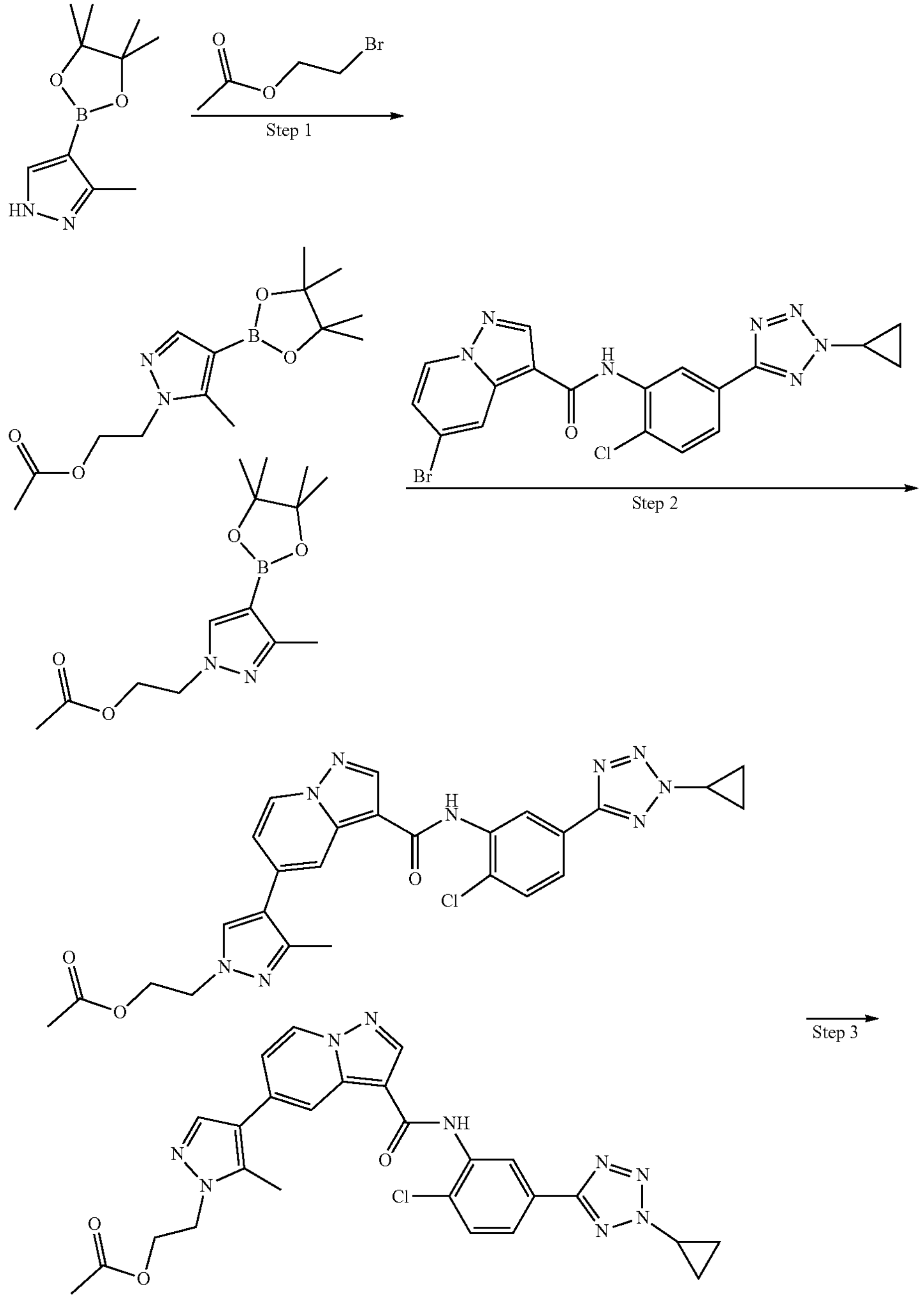

-continued

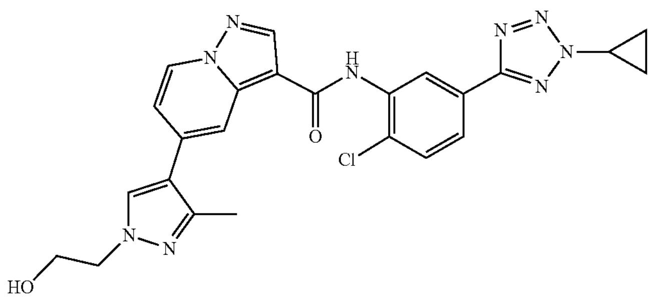

Step 1: Synthesis of 2-(3-methyl-4-(4,4,5,5-tetramethyl-1,3,2-dioxaborolan-2-yl)-1H-pyrazol-1-yl) ethyl acetate and 2-(5-methyl-4-(4,4,5,5-tetramethyl-1,3,2-dioxaborolan-2-yl)-1H-pyrazol-1-yl) ethyl acetate A mixture of $Cs_2CO_3$ (9.35 g, 28.7 mmol), KI (954 mg, 5.75 mmol), 3-methyl-4-(4,4,5,5-tetramethyl-1,3,2-dioxaborolan-2-yl)-1H-pyrazole (2.4 g, 11.5 mmol) and 2-bromoethyl acetate (2.87 g, 17.2 mmol) in DMF (200 mL) was heated at 60° C. for 16 h. The reaction mixture was diluted with EtOAc (300 mL), washed with water (3×200 mL) and saturated brine (200 mL). The organic layer was dried over $Na_2SO_4$, filtered and evaporated to afford crude product which was purified by Prep-TLC with DCM:MeOH=20:1 to afford the title compound (2.9 g, 85.7%) as a light yellow oil. LCMS: m/z=295 $[M+H]^+$.

Step 2: Synthesis of 2-(4-(3-((2-chloro-5-(2-cyclopropyl-2H-tetrazol-5-yl)phenyl)carbamoyl)pyrazolo[1,5-a]pyridin-5-yl)-3-methyl-1H-pyrazol-1-yl)ethyl acetate and 2-(4-(3-((2-chloro-5-(2-cyclopropyl-2H-tetrazol-5-yl)phenyl)carbamoyl)pyrazolo[1,5-a]pyridin-5-yl)-5-methyl-1H-pyrazol-1-yl)ethyl acetate The title compound was obtained as a brown solid from the reaction mixture of Step 1 and Intermediate 47 following a similar procedure to that described in Example 46. The crude product was used in the next step without purification. LCMS: m/z=546 $[M+H]^+$.

Step 3: Synthesis of N-(2-chloro-5-(2-cyclopropyl-2H-tetrazol-5-yl)phenyl)-5-(1-(2-hydroxyethyl)-3-methyl-1H-pyrazol-4-yl)pyrazolo[1,5-a]pyridine-3-carboxamide and N-(2-chloro-5-(2-cyclopropyl-2H-tetrazol-5-yl)phenyl)-5-(1-(2-hydroxyethyl)-5-methyl-1H-pyrazol-4-yl)pyrazolo[1,5-a]pyridine-3-carboxamide $K_2CO_3$ (150 mg, 1.09 mmol) was added to the mixture of Step 2 (300 mg, 0.549 mmol) in MeOH (15 mL) at rt and the reaction mixture was stirred at rt for 2 h, then concentrated under vacuum. The crude product was purified by a silica gel column eluting with DCM:MeOH=10:1. The residue was purified by HPLC, Method B2, Gradient: 30% to 57% to afford an isomeric mixture (100 mg) as a white solid. This mixture was purified further by chiral-HPLC with following condition: Column: CHIRALPAK IG, 2*25 cm, 5 μm; Mobile Phase A: Hex (0.5% 2M $NH_3$-MeOH), Mobile Phase B: EtOH:DCM=1:1; Flow rate: 20 mL/min; 50% isocratic gradient to yield N-(2-chloro-5-(2-cyclopropyl-2H-tetrazol-5-yl)phenyl)-5-(1-(2-hydroxyethyl)-3-methyl-1H-pyrazol-4-yl)pyrazolo[1,5-a]pyridine-3-carboxamide, Peak 1, 31.8 mg, 11%, as a white solid. LCMS: m/z=504 $[M+H]^+$, $^1H$ NMR (400 MHz, DMSO-$d_6$) δ 9.85 (s, 1H), 8.87-8.81 (m, 1H) 8.80-8.77 (m, 1H), 8.39 (d, 1H), 8.30-8.24 (m, 2H), 7.91 (dd, 1H), 7.75 (d, 1H), 7.29 (dd, 1H), 4.94 (t, 1H), 4.49 (tt, 1H), 4.11 (t, 2H), 3.76 (q, 2H), 2.42 (s, 3H), 1.47-1.34 (m, 2H), 1.34-1.21 (m, 2H).

Peak 2 was identified as N-(2-chloro-5-(2-cyclopropyl-2H-tetrazol-5-yl)phenyl)-5-(1-(2-hydroxyethyl)-5-methyl-1H-pyrazol-4-yl)pyrazolo[1,5-a]pyridine-3-carboxamide.

Example 239 and 240

N-(5-(2-cyclopropyl-2H-tetrazol-5-yl)-4-fluoro-2-methylphenyl)-5-(1-(2-hydroxy-2-methylpropyl)-3-methyl-1H-pyrazol-4-yl)pyrazolo[1,5-a]pyridine-3-carboxamide and N-(5-(2-cyclopropyl-2H-tetrazol-5-yl)-4-fluoro-2-methylphenyl)-5-(1-(2-hydroxy-2-methylpropyl)-5-methyl-1H-pyrazol-4-yl)pyrazolo[1,5-a]pyridine-3-carboxamide

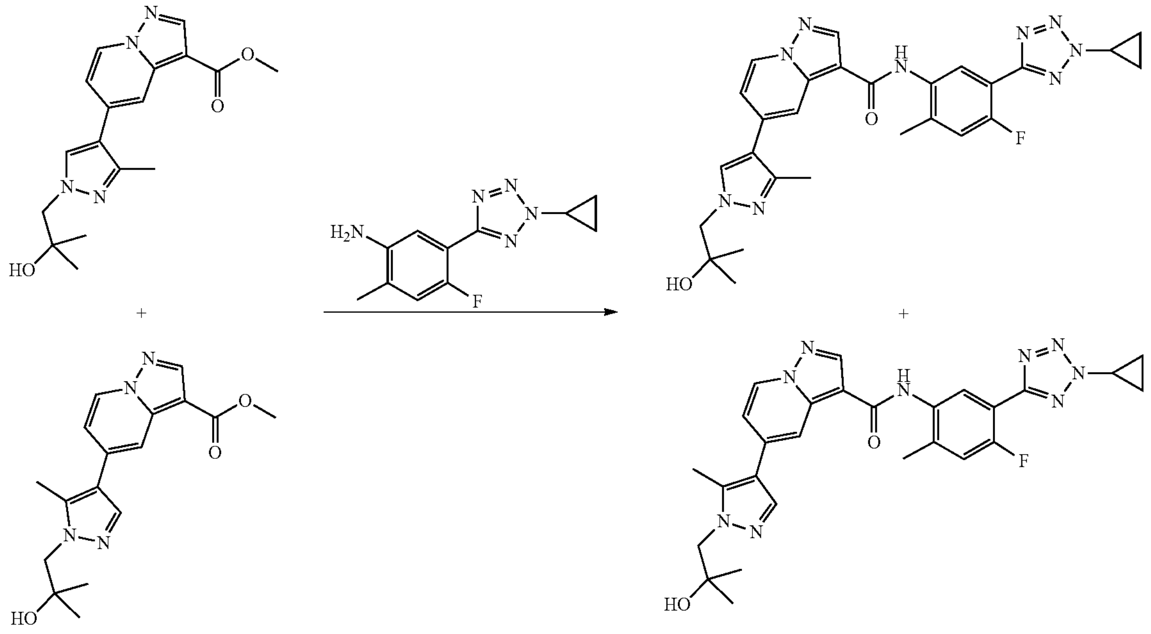 [SMILES: COC(=O)c1cnn2ccc(-c3cn(CC(C)(C)O)nc3C)cc12 ; Cc1cc(F)c(-c2nnn(C3CC3)n2)cc1N ; Cc1cc(F)c(-c2nnn(C3CC3)n2)cc1NC(=O)c1cnn2ccc(-c3cn(CC(C)(C)O)nc3C)cc12 ; COC(=O)c1cnn2ccc(-c3cnn(CC(C)(C)O)c3C)cc12 ; Cc1cc(F)c(-c2nnn(C3CC3)n2)cc1NC(=O)c1cnn2ccc(-c3cnn(CC(C)(C)O)c3C)cc12]

To a stirred solution of Intermediate 51 (0.6 g, 1.82 mmol) and Intermediate 49 (466 mg, 2.0 mmol) in toluene (8 mL) was added 2 M $Me_3Al$ in toluene (262 mg, 3.64 mmol) at 0° C. The reaction mixture was stirred at 100° C. for 2 h, then cooled to rt. The mixture was concentrated and purified by a silica gel column with DCM:MeOH=10:1. The crude product was purified by prep-SFC using following condition: Column: Green Sep Basic 3*15 cm, 5 μm; Mobile Phase A: $CO_2$, Mobile Phase B: ACN:MeOH=4:1 (0.1% 2M $NH_3$-MeOH); Flow rate: 75 mL/min; Gradient: isocratic 27% B to yield N-(5-(2-cyclopropyl-2H-tetrazol-5-yl)-4-fluoro-2-methylphenyl)-5-(1-(2-hydroxy-2-methylpropyl)-3-methyl-1H-pyrazol-4-yl)pyrazolo[1,5-a]pyridine-3-carboxamide (Peak 1, 458 mg; 47%) as a white solid: LCMS: m/z=530 $[M+H]^+$, $^1H$ NMR (400 MHz, DMSO-$d_6$) δ 9.72 (s, 1H), 8.81 (d, 1H), 8.73 (s, 1H), 8.27 (d, 1H), 8.16 (s, 1H), 8.06 (d, 1H), 7.40 (d, 1H), 7.26 (dd, 1H), 4.74 (s, 1H), 4.49 (tt, 1H), 3.98 (s, 2H), 2.40 (s, 3H), 2.36 (s, 3H), 1.41 (q, 2H), 1.29 (td, 2H), 1.10 (s, 6H), and N-(5-(2-cyclopropyl-2H-tetrazol-5-yl)-4-fluoro-2-methylphenyl)-5-(1-(2-hydroxy-2-methylpropyl)-5-methyl-1H-pyrazol-4-yl)pyrazolo[1,5-a]pyridine-3-carboxamide (Peak 2, 205 mg, 21%) as a white solid: LCMS: m/z=530 $[M+H]^+$, (400 MHz, Chloroform-d) δ 8.54 (d, 1H), 8.41 (d, 1H), 8.34 (s, 1H), 8.26 (s, 1H), 7.79 (s, 1H), 7.42 (s, 1H), 7.15 (d, 1H), 7.05 (dd, 1H), 4.27 (tt, 1H), 4.12 (s, 2H), 2.51 (s, 3H), 2.41 (s, 3H), 1.55 (t, 2H), 1.28 (td, 2H), 1.22 (s, 6H). $^1H$ NMR (400 MHz, DMSO-d6) δ 9.73 (s, 1H), 8.83 (d, 1H), 8.74 (s, 1H), 8.20 (d, 1H), 8.05 (d, J 1H), 7.86 (s, 1H), 7.40 (d, 1H), 7.25 (dd, 1H), 4.70 (s, 1H), 4.49 (tt, 1H), 4.05 (s, 2H), 2.35 (s, 3H), 1.45-1.33 (m, 2H), 1.36-1.21 (m, 2H), 1.14 (s, 6H). Methyl protons obscured by DMSO peak.

Example 241

5-(3-cyclopropyl-1-(2-hydroxy-2-methylpropyl)-1H-pyrazol-4-yl)-N-(5-(2-cyclopropyl-2H-tetrazol-5-yl)-4-fluoro-2-methylphenyl)pyrazolo[1,5-a]pyridine-3-carboxamide

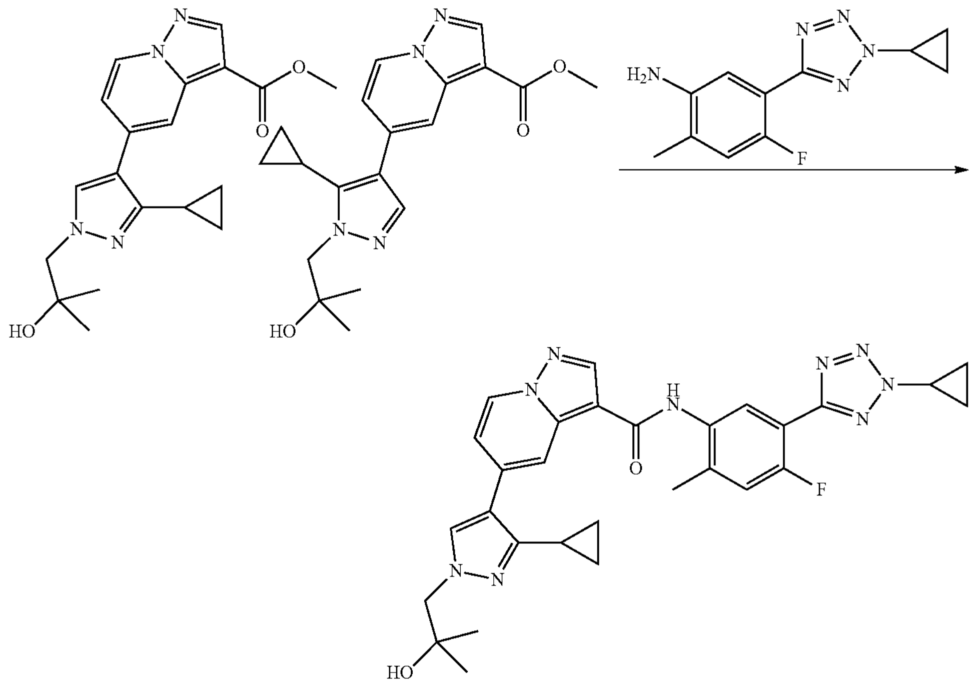

The title compound was obtained as an off-white solid, 69.9 mg, 45%, from Intermediate 49 and Intermediate 54, following a similar procedure to that described in Example 162. The crude product was purified by chiral HPLC as following condition: Column: CHIRALPAK IC, 2*25 cm, 5 μm; Mobile Phase A: Hex (0.5% 2M $NH_3$-MeOH), Mobile Phase B: MeOH:DCM=1:1; Flow rate: 20 mL/min; 40% isocratic gradient to yield 5-(3-cyclopropyl-1-(2-hydroxy-2-methylpropyl)-1H-pyrazol-4-yl)-N-(5-(2-cyclopropyl-2H-tetrazol-5-yl)-4-fluoro-2-methylphenyl)pyrazolo[1,5-a]pyridine-3-carboxamide (Peak 1, 69.9 mg, 45%) as a white solid. LCMS: m/z=556 $[M+H]^+$. $^1H$ NMR (400 MHz, DMSO-$d_6$) δ 9.73 (s, 1H), 8.82 (d, 1H), 8.73 (s, 1H), 8.55 (d, 1H), 8.12 (s, 1H), 8.05 (d, 1H), 7.40 (d, 1H), 7.34 (dd, 1H), 4.72 (s, 1H), 4.49 (tt, J=7.5, 3.8 Hz, 1H), 3.96 (s, 2H), 2.35 (s, 3H), 1.99 (tt, 1H), 1.40 (q, 2H), 1.36-1.22 (m, 2H), 1.07 (s, 6H), 0.99-0.88 (m, 2H), 0.87-0.77 (m, 2H).

Peak 2 was identified as 5-(5-cyclopropyl-1-(2-hydroxy-2-methylpropyl)-1H-pyrazol-4-yl)-N-(5-(2-cyclopropyl-2H-tetrazol-5-yl)-4-fluoro-2-methylphenyl)pyrazolo[1,5-a]pyridine-3-carboxamide.

Example 242

N-(5-(2-cyclopropyl-2H-tetrazol-5-yl)-2-methylphenyl)-5-(1-(2-hydroxy-2-methylpropyl)-1H-pyrazol-4-yl)pyrazolo[1,5-a]pyridine-3-carboxamide

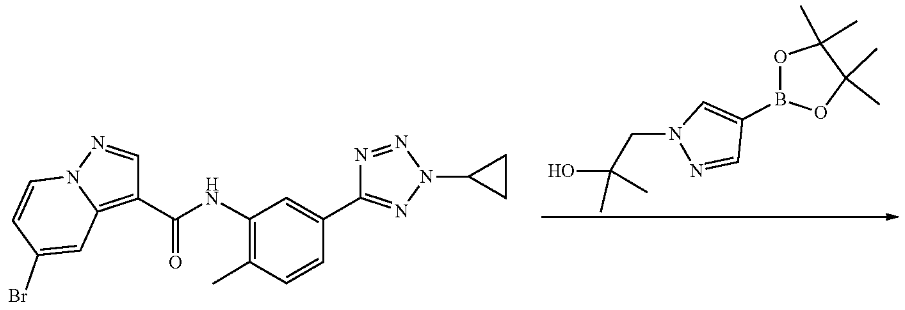

-continued

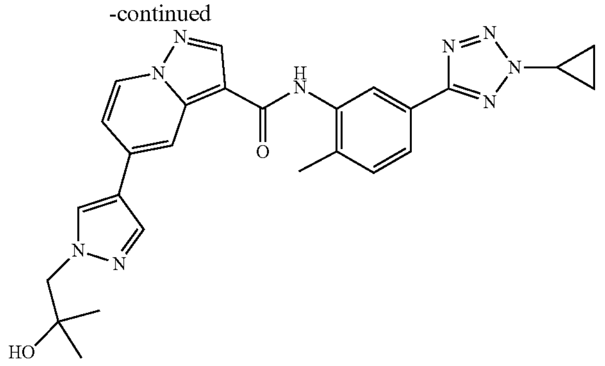

A mixture of Intermediate 56 (150 mg, 0.342 mmol), 2-methyl-1-(4-(4,4,5,5-tetramethyl-1,3,2-dioxaborolan-2-yl)-1H-pyrazol-1-yl)propan-2-ol (109 mg, 0.41 mmol), Pd(dppf)$Cl_2$ (25 mg, 0.034 mmol) and $Na_2CO_3$ (70.9 mg, 0.513 mmol) in dioxane (1.6 mL) and $H_2O$ (0.4 mL) was stirred at 100° C. for 3 h under $N_2$. The reaction mixture was cooled to rt, diluted with water (2 mL), extracted with EtOAc (2×4 mL) and washed with brine (2 mL). The mixture was dried over $Na_2SO_4$ and concentrated under vacuum. The residue was purified by HPLC, Method B2, Gradient: 24% to 51% to yield the title compound (81.9 mg, 48.1%) as a white solid. LCMS: m/z=498 $[M+H]^+$. $^1$H NMR (400 MHz, DMSO-$d_6$) δ 9.64 (s, 1H), 8.82 (dd, 1H), 8.73 (s, 1H), 8.40-8.29 (m, 2H), 8.19 (d, 1H), 8.05 (s, 1H), 7.82 (dd, 1H), 7.46 (d, 1H), 7.39 (dd, 1H), 4.76 (s, 1H), 4.47 (tt, 1H), 4.07 (s, 2H), 2.37 (s, 3H), 1.41 (p, 2H), 1.32-1.25 (m, 2H), 1.10 (s, 6H).

Example 243

(S)-5-(3-cyclopropyl-1-(2-hydroxy-3-methoxypropyl)-1H-pyrazol-4-yl)-N-(5-(2-cyclopropyl-2H-tetrazol-5-yl)-2-methylphenyl)pyrazolo[1,5-a]pyridine-3-carboxamide

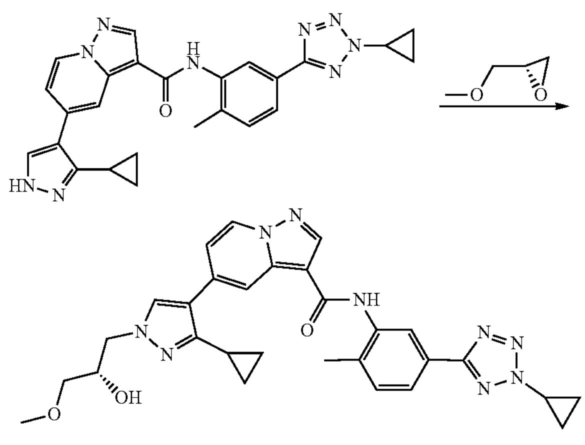

To a stirred solution of Intermediate 57 (200 mg, 0.429 mmol) in DMF (3 mL) were added (S)-2-(methoxymethyl)oxirane (75.5 mg, 0.858 mmol) and $K_2CO_3$ (118 mg, 0.858 mmol). The mixture was stirred at 100° C. for 16 h, then diluted with EtOAc (25 mL) and water (25 mL). The aqueous layer was extracted with EtOAc (3×20 mL). The combined organic layers were washed with brine, dried with $Na_2SO_4$ and concentrated under vacuum. The residue was purified by silica gel column with DCM:MeOH=10:1 and the product further purified by prep-SFC as following condition: Mobile Phase A: $CO_2$, Mobile Phase B: MeCN:MeOH=4:1(0.1% 2M $NH_3$-MeOH); Flow rate: 60 mL/min; Gradient: isocratic 50% B; to provide the title compound (Peak 2, 42.5 mg, 18%) as a yellow solid. LCMS: m/z=554 $[M+H]^+$. $^1$H NMR (400 MHz, Methanol-$d_4$) δ 8.68-8.59 (m, 3H), 8.13 (d, 1H), 8.01 (s, 1H), 7.91 (dd, 1H), 7.46 (d, 1H), 7.37 (dd, 1H), 4.38 (tt, 1H), 4.22 (dt, 1H), 4.14-4.03 (m, 2H), 3.37 (s, 3H), 3.37 (d, 2H), 2.41 (s, 3H), 2.06 (tt, 1H), 1.52-1.44 (m, 2H), 1.44-1.24 (m, 3H), 1.03 (dt, 2H), 0.92-0.83 (m, 2H).

Peak 1 was identified as (S)-5-(5-cyclopropyl-1-(2-hydroxy-3-methoxypropyl)-1H-pyrazol-4-yl)-N-(5-(2-cyclopropyl-2H-tetrazol-5-yl)-2-methylphenyl)pyrazolo[1,5-a]pyridine-3-carboxamide.

Example 244

5-(1-(2-hydroxy-2-methylpropyl)-3,5-dimethyl-1H-pyrazol-4-yl)-N-(2-methyl-5-(5-methyl-2H-tetrazol-2-yl)phenyl)pyrazolo[1,5-a]pyridine-3-carboxamide

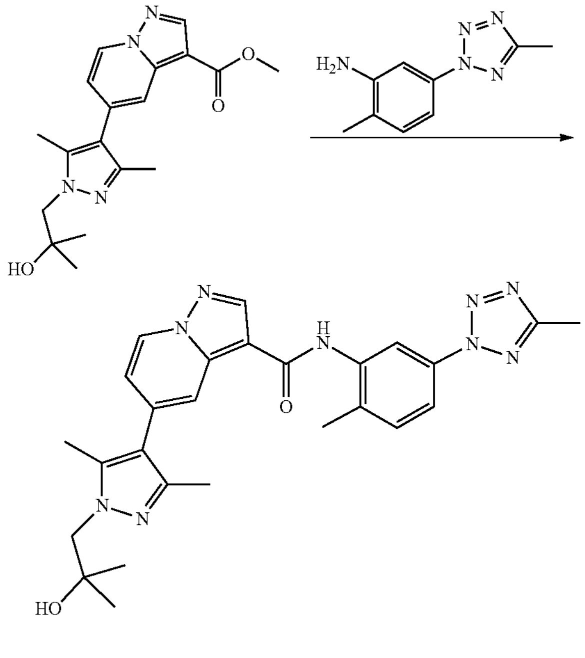

To a solution of Intermediate 59 (271 mg, 0.792 mmol) and Intermediate 37 (100 mg, 0.528 mmol) in toluene (10 mL) was added LiHMDS (1M in THF, 1.8 mL) at 0° C. The reaction mixture was stirred at 35° C. for 16 h, then hydrolysed with water (5 mL). The solvent was evaporated and the residue was purified on prep-TLC with DCM: MeOH=30:1. The crude product was purified by HPLC, Method B2, Gradient: 25% to 51% to afford the title compound (103.6 mg, 39.1%) as a white solid. LCMS: m/z=500 $[M+H]^+$; $^1H$ NMR (400 MHz, DMSO-$d_6$) δ 9.72 (s, 1H), 8.85 (d, 1H), 8.80 (s, 1H), 8.25 (d, 1H), 8.07 (d, 1H), 7.83 (dd, 1H), 7.54 (d, 1H), 7.09 (dd, 1H), 4.70 (s, 1H), 3.96 (s, 2H), 2.59 (s, 3H), 2.37 (d, 6H), 2.24 (s, 3H), 1.14 (s, 6H).

Example 245

(S)-5-(1-(2-hydroxy-3-methoxypropyl)-3,5-dimethyl-1H-pyrazol-4-yl)-N-(2-methyl-5-(2-methyl-2H-tetrazol-5-yl)phenyl)pyrazolo[1,5-a]pyridine-3-carboxamide

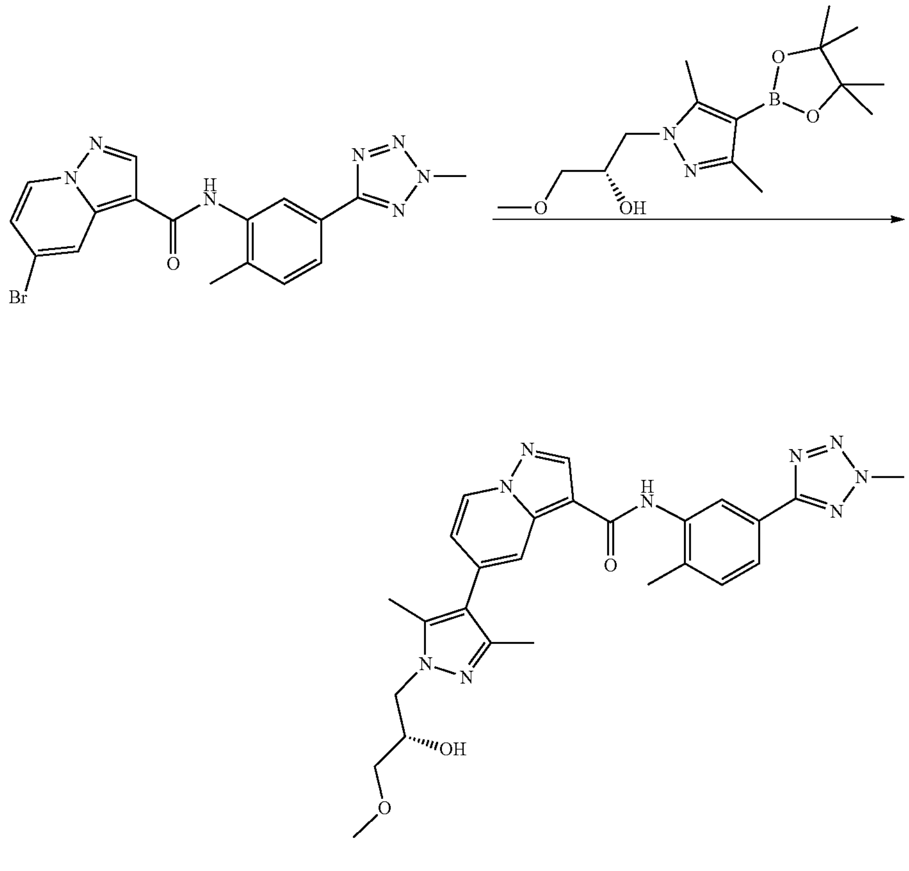

The title compound was obtained as a white solid, 67.8 mg, 54.5%, from Intermediate 13 and Intermediate 61, following a similar procedure to that described in Example 207, step 3, except HPLC Method B2 was used. LCMS: m/z=516 $[M+H]^+$; $^1H$ NMR (400 MHz, DMSO-$d_6$) δ 9.70 (s, 1H), 8.85 (dd, 1H), 8.79 (s, 1H), 8.16 (d, 1H), 8.07 (dd, 1H), 7.83 (dd, 1H), 7.46 (d, 1H), 7.07 (dd, 1H), 5.13 (d, 1H), 4.43 (s, 3H), 4.07 (m, 1H), 3.98 (m, 2H), 3.33-3.30 (m, 2H), 3.29 (s, 3H), 2.35 (d, 6H), 2.23 (s, 3H).

Example 246

N-(5-(2-ethyl-2H-tetrazol-5-yl)-4-fluoro-2-methylphenyl)-5-(1-(2-hydroxy-2-methylpropyl)-3,5-dimethyl-1H-pyrazol-4-yl)pyrazolo[1,5-a]pyridine-3-carboxamide

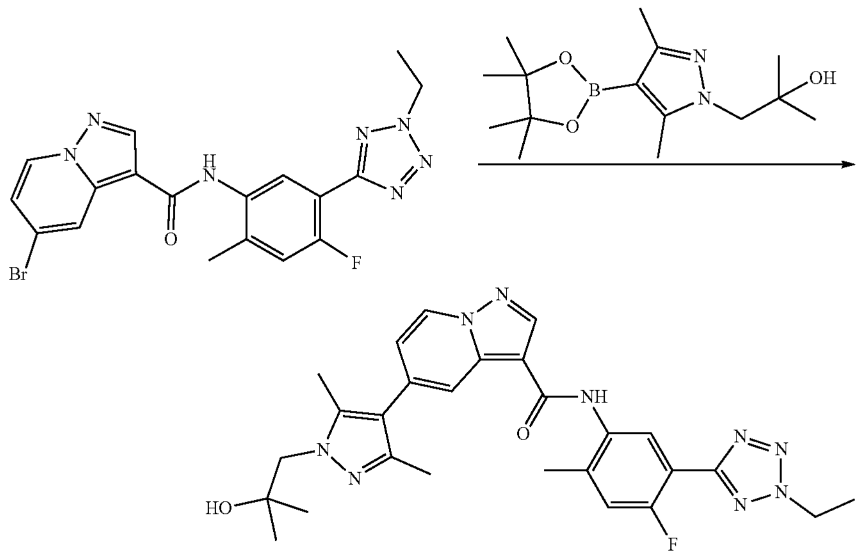

A reaction mixture of Intermediate 77 (100 mg, 225 μmol), Intermediate 58 (99.0 mg, 337 μmol), $Pd(dppf)Cl_2$ (16.3 mg, 22.5 μmol) and $K_2CO_3$ (62.0 mg, 450 μmol) in dioxane/$H_2O$ (5 mL/0.5 mL) was stirred for 2 h at 80° C. under $N_2$. Water (10 mL) was added to the cooled mixture and the resulting solution was extracted with EtOAc (3×10 mL). The combined organic extracts were dried over $Na_2SO_4$ and concentrated. The crude product was purified by prep-TLC (DCM:MeOH=10:1) and prep-HPLC (Method B2, 28% to 53% gradient) to give the title compound (71.6 mg; 60%) as a white solid. LCMS: m/z=532 $[M+H]^+$; 1H NMR (400 MHz, DMSO-$d_6$) δ 9.76 (s, 1H), 8.85 (d, 1H), 8.77 (s, 1H), 8.11-8.03 (m, 2H), 7.40 (d, 1H), 7.08 (dd, 1H), 4.79 (q, 2H), 4.71 (s, 1H), 3.95 (s, 2H), 2.35 (s, 6H), 2.23 (s, 3H), 1.58 (t, 3H), 1.14 (s, 6H)

Examples 247 to 248

The compounds in the following table were prepared from the appropriate 5-bromo-pyrazolo[1,5-a]pyridine and boronate ester, following the procedure described in Example 246. The compounds were further purified using the HPLC conditions indicated.

| Example No | Name, Structure | Starting materials (SM), Data |
|---|---|---|
| 247[A] | N-(5-(2-cyclopropyl-2H-tetrazol-5-yl)-4-fluoro-2-methylphenyl)-6-fluoro-5-(1-(2-hydroxy-2-methylpropyl)-3-methyl-1H-pyrazol-4-yl)pyrazolo[1,5-a]pyridine-3-carboxamide | SM: Intermediates 50 and 76 Peak 1 LCMS: m/z = 548 $[M + H]^+$; 1H NMR (400 MHz, DMSO-$d_6$) δ 9.81 (s, 1H), 9.27 (d, 1H), 8.77 (s, 1H), 8.29 (d, 1H), 8.07-8.01 (m, 2H), 7.40 (d, 1H), 4.74 (s, 1H), 4.49 (tt, 1H), 4.02 (s, 2H), 2.35 (s, 3H), 2.34 (s, 3H), 1.45-1.33 (m, 2H), 1.33-1.21 (m, 2H), 1.10 (s, 6H). |
| 248[B] | (S)-N-(2-chloro-5-(2-cyclopropyl-2H-tetrazol-5-yl)phenyl)-5-(1-(2-hydroxy-3-methoxypropyl)-5-methyl-1H-pyrazol-4-yl)pyrazolo[1,5-a]pyridine-3-carboxamide | Intermediate 47 and 64 Peak 1 LCMS: m/z = 548 $[M + H]^+$, 1H NMR (400 MHz, DMSO-$d_6$) δ 9.88 (s, 1H), 8.85 (dd, 1H), 8.80 (s, 1H), 8.38 (d, 1H), 8.23-8.18 (m, 1H), 7.95-7.86 (m, 2H), 7.76 (d, 1H), 7.27 (dd, 1H), 5.17 (d, 1H), 4.49 (tt, , 1H), 4.16 (dd, 2H), 4.03-3.95 (m, 1H), 3.34 (m, 2H), 3.25 (m, 3H), 2.42 (s, 3H), 1.42 (p, 2H), 1.34-1.21 (m, 2H). |

A-CHIRALPAK IG, 2*25 cm, 5 μm; Mobile Phase A: Hex (0.5% 2M $NH_3$-MeOH), Mobile Phase B: EtOH: DCM=1:1; Flow rate: 20 mL/min; Isocratic Gradient: 50% B in 15 min B-CHIRALPAK IG, 2*25 cm, 5 μm; Mobile Phase A: HEX (0.5% 2M $NH_3$-MeOH), Mobile Phase B: EtOH: DCM=1:1; Flow rate: 20 mL/min; Isocratic Gradient: 60% B in 11 min;

Example 249

(S)—N-(5-(2-cyclopropyl-2H-tetrazol-5-yl)-4-fluoro-2-methylphenyl)-5-(1-(2-hydroxy-3-methoxy-2-methylpropyl)-3-methyl-1H-pyrazol-4-yl)pyrazolo[1,5-a]pyridine-3-carboxamide or (R)—N-(5-(2-cyclopropyl-2H-tetrazol-5-yl)-4-fluoro-2-methylphenyl)-5-(1-(2-hydroxy-3-methoxy-2-methylpropyl)-3-methyl-1H-pyrazol-4-yl)pyrazolo[1,5-a]pyridine-3-carboxamide

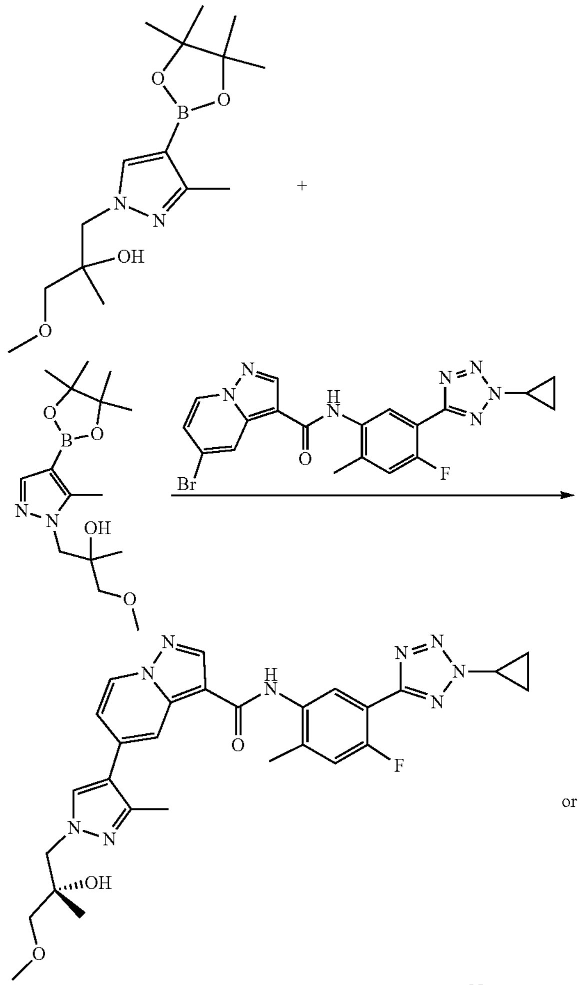

or

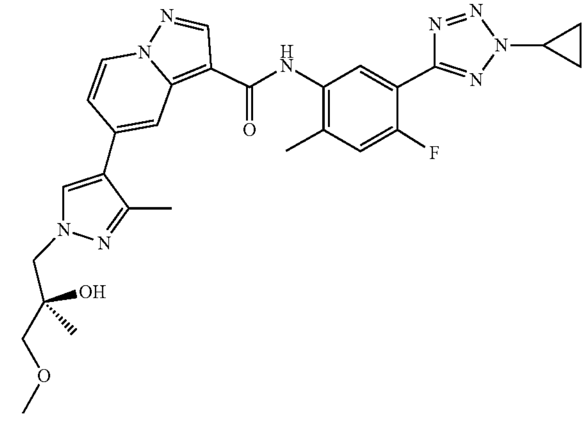

The title compound was obtained as Peak 1, as a white solid, from Intermediate 67 and Example 207, step 2, following a similar procedure to that described in Example 246 except, prep-chiral-HPLC (Column: CHIRALPAK AD3; Mobile Phase A: Hex (0.2% DEA): IPA=50:50; Flow rate: 1 mL/min isocratic gradient, was used. LCMS: m/z=560 $[M+H]^+$. $^1H$ NMR (400 MHz, DMSO-$d_6$) δ 9.73 (s, 1H), 8.84-8.78 (m, 1H), 8.73 (s, 1H), 8.27 (d, 1H), 8.12 (s, 1H), 8.06 (d, 1H), 7.40 (d, 1H), 7.26 (dd, 1H), 4.90 (s, 1H), 4.49 (tt, 1H), 4.04 (s, 2H), 3.30 (s, 3H), 3.14 (s, 2H), 2.41 (s, 3H), 2.36 (s, 3H), 1.41 (dq, 2H), 1.33-1.26 (m, 2H), 1.03 (s, 3H).

Example 250

N-(2-chloro-5-(2-cyclopropyl-2H-tetrazol-5-yl)phenyl)-5-(1-(2-hydroxy-2-methylpropyl)-3-methyl-1H-pyrazol-4-yl)pyrazolo[1,5-a]pyridine-3-carboxamide

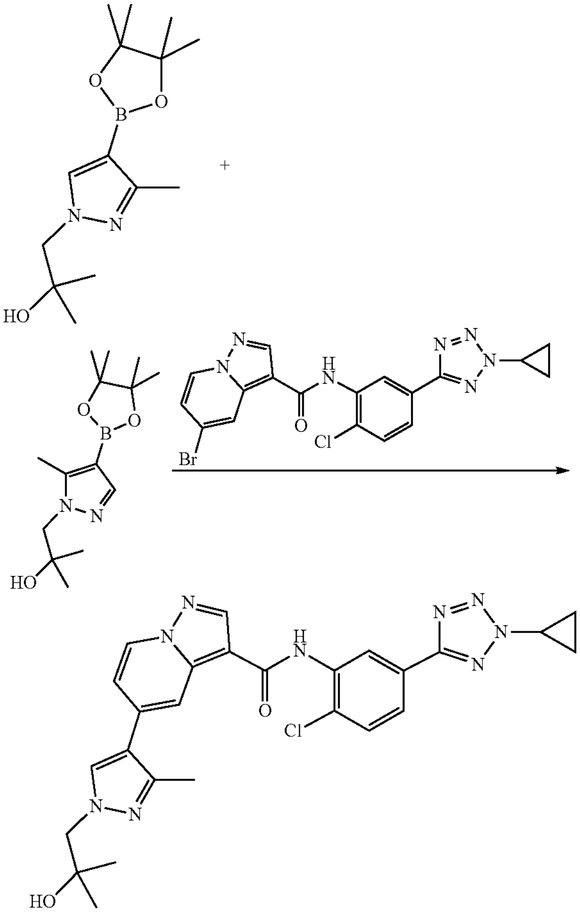

A mixture of Intermediate 47 (150 mg, 327 μmol), Intermediate 50 (137 mg, 490 μmol), $Cs_2CO_3$ (159 mg, 490 μmol) and Pd(dppf)$Cl_2$ (27.0 mg, 32.7 μmol) in dioxane (9 mL) and water (3 mL) was stirred at 100° C. for 3 h. The cooled mixture was evaporated under reduced pressure and the residue was purified on prep-TLC with DCM: MeOH=20:1. The product was further purified on prep-achiral-SFC, Column: DAICEL DCpak P4VP 3*25 cm, 5 μm; Mobile Phase A: $CO_2$, Mobile Phase B: MeOH (0.1% 2M $NH_3$-MeOH); Flow rate: 60 mL/min; Isocratic Gradient 38% B; Column Temperature (° C.): 35; to afford Peak 1, the title compound, (53.2 mg) as a white solid. LCMS: m/z=532

[M+H]$^+$; $^1$H NMR (400 MHz, DMSO-$d_6$) δ 9.87 (s, 1H), 8.86-8.77 (m, 2H), 8.39 (d, 1H), 8.28 (d, 1H), 8.19 (s, 1H), 7.91 (dd, 1H), 7.76 (d, 1H), 7.30 (dd, 1H), 4.76 (s, 1H), 4.49 (m, 1H), 3.99 (s, 2H), 2.42 (s, 3H), 1.42 (s, 2H), 1.34-1.21 (m, 2H), 1.10 (s, 6H).

And Peak 2, N-(2-chloro-5-(2-cyclopropyl-2H-tetrazol-5-yl)phenyl)-5-(1-(2-hydroxy-2-methylpropyl)-5-methyl-1H-pyrazol-4-yl)pyrazolo[1,5-a]pyridine-3-carboxamide (39.1 mg) as a white solid.

Example 251

N-(2-chloro-5-(2-cyclopropyl-2H-tetrazol-5-yl)-4-fluorophenyl)-5-(1-(2-hydroxy-2-methylpropyl)-3-methyl-1H-pyrazol-4-yl)pyrazolo[1,5-a]pyridine-3-carboxamide

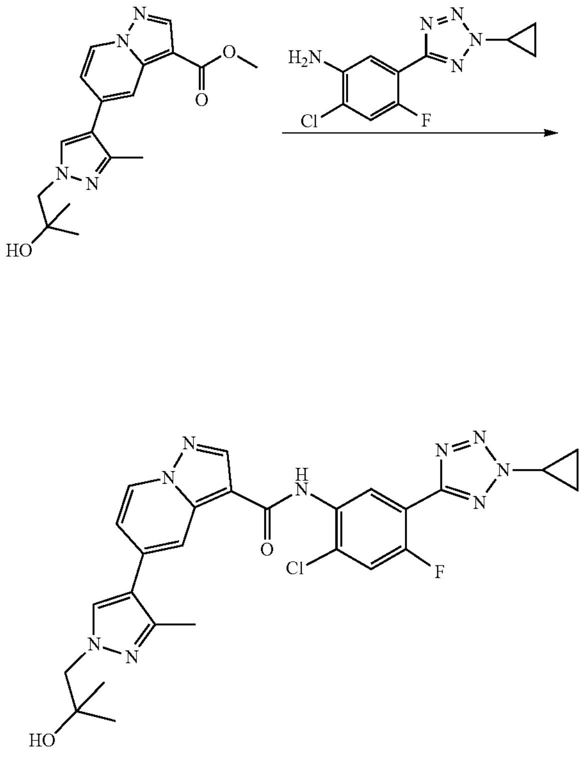

The title compound was obtained as a white solid, 20 mg, 9%, from Intermediates 73 and 51B, following a similar procedure to that described in Example 162, step 3, except HPLC (Method B2, 32% to 57% B) was used. LCMS m/z=550 [M+H]$^+$. $^1$H NMR (400 MHz, DMSO-$d_6$) δ 9.93 (s, 1H), 8.82 (dd, 1H), 8.76 (s, 1H), 8.33-8.24 (m, 2H), 8.17 (s, 1H), 7.85 (d, 1H), 7.29 (dd, 1H), 4.74 (s, 1H), 4.51 (tt, 1H), 3.98 (s, 2H), 2.41 (s, 3H), 1.47-1.34 (m, 2H), 1.37-1.21 (m, 2H), 1.10 (s, 6H).

Example 252

(S)—N-(2-chloro-5-(2-cyclopropyl-2H-tetrazol-5-yl)-4-methylphenyl)-5-(1-(2-hydroxy-3-methoxypropyl)-1H-pyrazol-4-yl)pyrazolo[1,5-a]pyridine-3-carboxamide

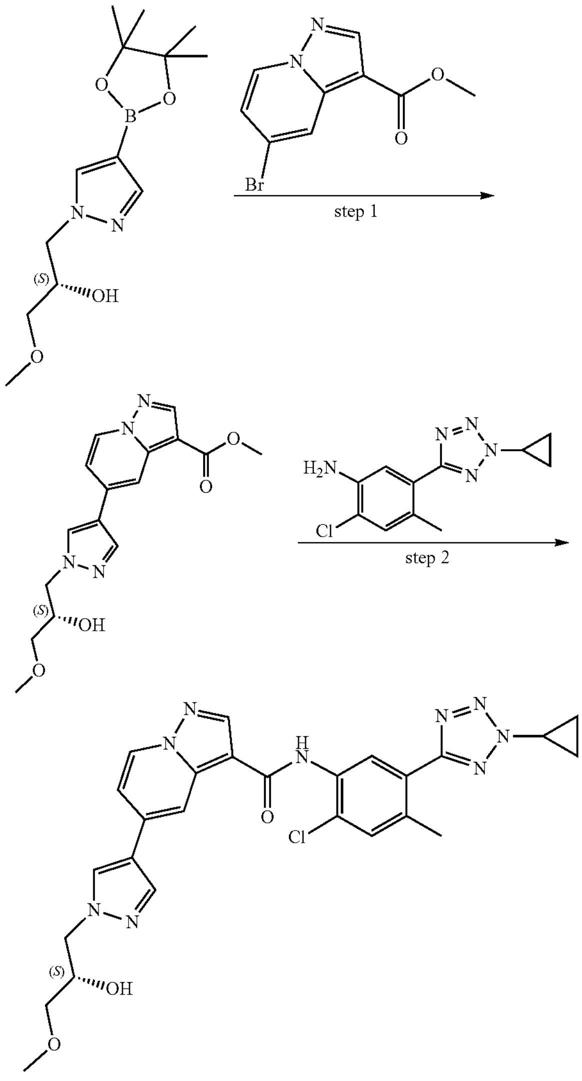

Step 1: Synthesis of methyl (S)-5-(1-(2-hydroxy-3-methoxypropyl)-1H-pyrazol-4-yl)pyrazolo[1,5-a]pyridine-3-carboxylate The title compound was obtained as a solid, 550 mg, 85%, from methyl 5-bromopyrazolo[1,5-a]pyridine-3-carboxylate and Intermediate 48, following the procedure described in Intermediate 69, step 3. LCMS: m/z=331 [M+H]$^+$.

Step 2: Synthesis of (S)—N-(2-chloro-5-(2-cyclopropyl-2H-tetrazol-5-yl)-4-methylphenyl)-5-(1-(2-hydroxy-3-methoxypropyl)-1H-pyrazol-4-yl)pyrazolo[1,5-a]pyridine-3-carboxamide The title compound was obtained as a solid, from methyl (S)-5-(1-(2-hydroxy-3-methoxypropyl)-1H-pyrazol-4-yl)

pyrazolo[1,5-a]pyridine-3-carboxylate and Intermediate 43, following a similar procedure to that described in Example 162, step 3, except prep-HPLC, (Method E, 24% to 52% B) was used. LCMS: m/z=548 $[M+H]^+$; $^1H$ NMR (400 MHz, DMSO-$d_6$) δ 9.81 (s, 1H), 8.83 (d, 1H), 8.75 (s, 1H), 8.38 (s, 1H), 8.31 (d, 1H), 8.24 (s, 1H), 8.06 (s, 1H), 7.64 (s, 1H), 7.39 (m, 1H), 5.22 (d, 1H), 4.50 (m, 1H), 4.22 (m, 1H), 4.12-3.98 (m, 2H), 3.30 (m, 5H), 2.59 (s, 3H), 1.47-1.22 (m, 4H).

Example 253

(S)—N-(2-chloro-5-(2-ethyl-2H-tetrazol-5-yl)phenyl)-5-(1-(2-hydroxypropyl)-3,5-dimethyl-1H-pyrazol-4-yl)pyrazolo[1,5-a]pyridine-3-carboxamide

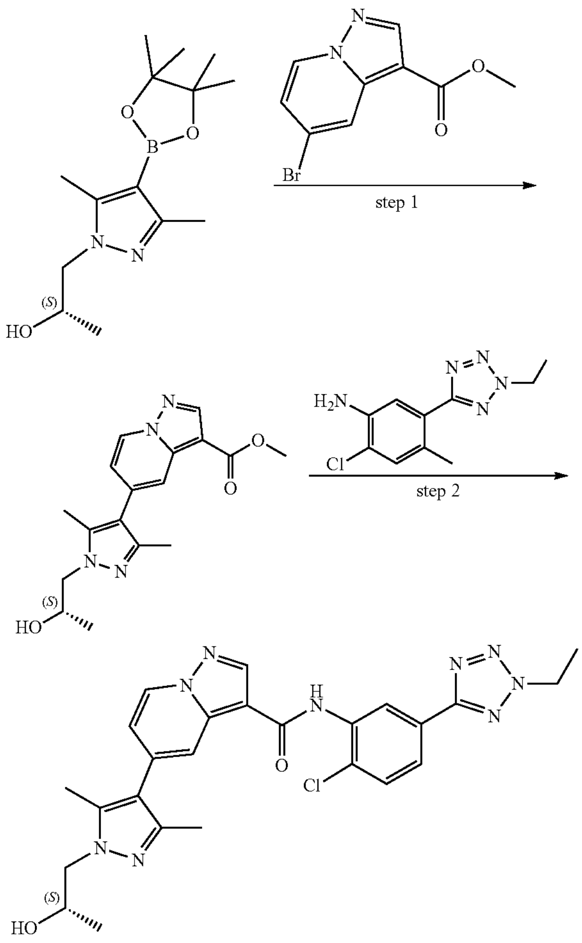

The title compound was obtained as a white solid, from Intermediate 62 and Intermediate 74, following a similar 2 step procedure to that described in Example 252, except HPLC (Method B2, 30% to 55% B) was used. LCMS: m/z=520 $[M+H]^+$; 1H NMR (400 MHz, DMSO-$d_6$) δ 9.88 (s, 1H), 8.90-8.80 (m, 2H), 8.41 (d, 1H), 8.06 (d, 1H), 7.93 (dd, 1H), 7.76 (d, 1H), 7.10 (dd, 1H), 4.91 (d, 1H), 4.78 (q, 2H), 4.03-3.90 (m, 3H), 2.34 (s, 3H), 2.23 (s, 3H), 1.58 (t, 3H), 1.10 (d, 3H).

Example 254

(S)—N-(5-(2-cyclopropyl-2H-tetrazol-5-yl)-4-fluoro-2-methylphenyl)-5-(1-(2-hydroxypropyl)-3,5-dimethyl-1H-pyrazol-4-yl)pyrazolo[1,5-a]pyridine-3-carboxamide

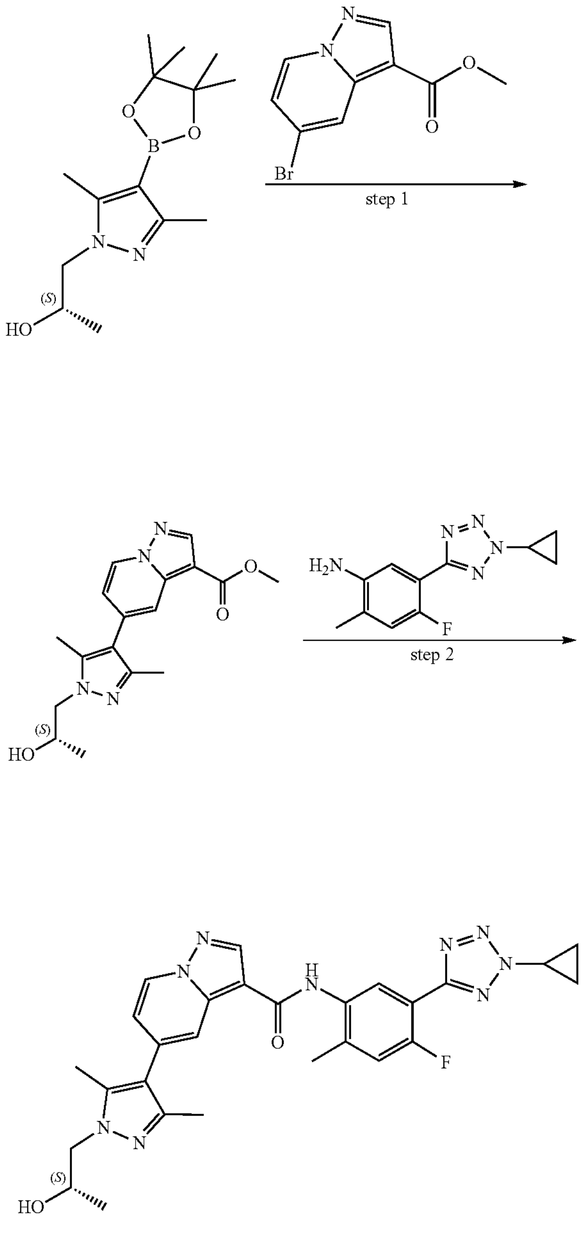

The title compound was obtained as a white solid, 65.7 mg, 58%, from Intermediate 49 and Intermediate 62, following a similar procedure to that described in Example 252, except HPLC (Method B2, 27% to 52% B) was used. LCMS: m/z=530 $[M+H]^+$; 1H NMR (400 MHz, DMSO-$d_6$) δ 9.74 (s, 1H), 8.84 (dd, 1H), 8.76 (s, 1H), 8.07-8.01 (m, 2H), 7.39 (d, 1H), 7.07 (dd, 1H), 4.90 (d, 1H), 4.49 (tt, 1H), 4.05-3.95 (m, 1H), 3.95-3.86 (m, 2H), 2.34 (d, 6H), 2.22 (s, 3H), 1.43-1.38 (m, 2H), 1.32-1.25 (m, 2H), 1.10 (d, 3H).

Example 255

(R)—N-(5-(2-cyclopropyl-2H-tetrazol-5-yl)-4-fluoro-2-methylphenyl)-5-(1-(2-hydroxypropyl)-3-methyl-1H-pyrazol-4-yl)pyrazolo[1,5-a]pyridine-3-carboxamide

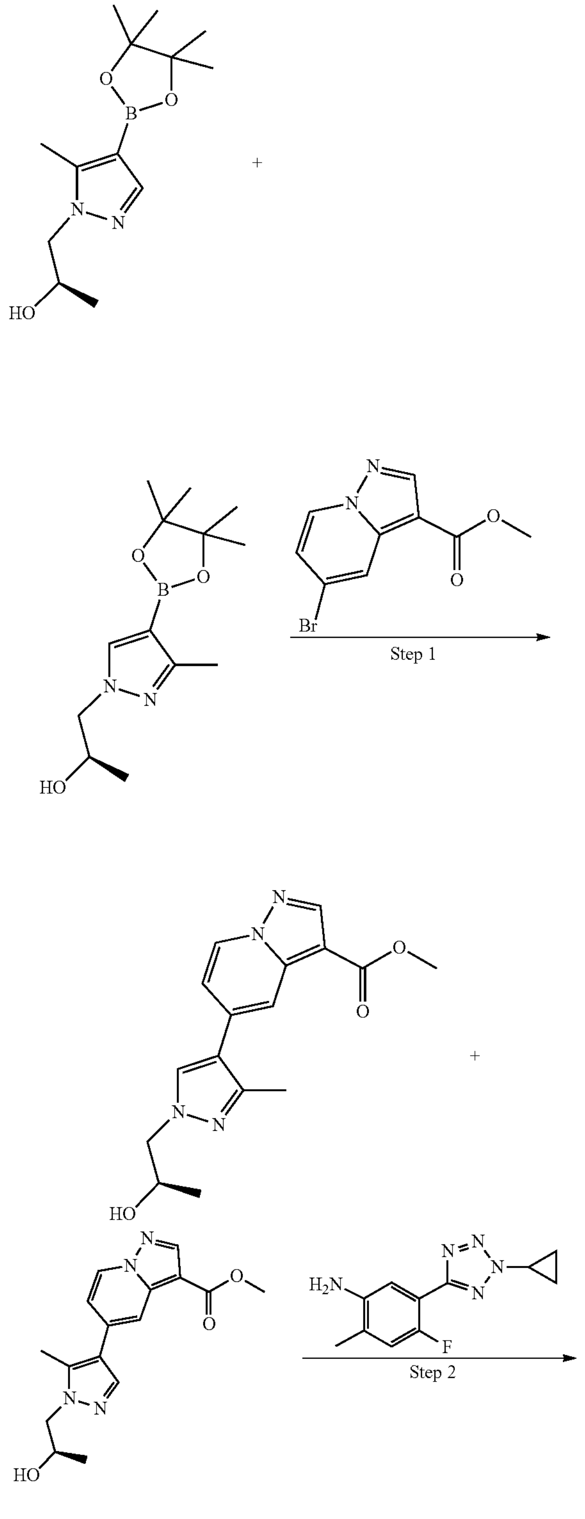

-continued

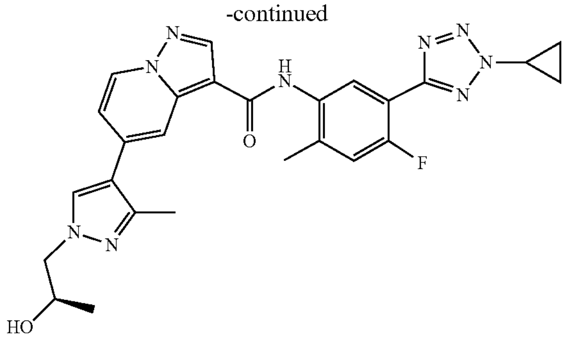

Step 1: Synthesis of mixture of methyl (R)-5-(1-(2-hydroxypropyl)-3-methyl-1H-pyrazol-4-yl)pyrazolo[1,5-a]pyridine-3-carboxylate and methyl (R)-5-(1-(2-hydroxypropyl)-5-methyl-1H-pyrazol-4-yl)pyrazolo[1,5-a]pyridine-3-carboxylate To a stirred mixture of Intermediate 63 (500 mg, 1.87 mmol), $K_2CO_3$ (520 mg, 3.76 mmol) and methyl 5-bromopyrazolo[1,5-a]pyridine-3-carboxylate (575 mg, 2.25 mmol) in dioxane/$H_2O$ (4 mL/1 mL) was added Pd(dppf)$Cl_2$ (307 mg, 0.375 mmol) and the reaction mixture was stirred for 2 h at 80° C. Water (10 mL) was added to the cooled reaction and the mixture was extracted with EtOAc (10 mL×3). The combined organic phase was dried over $Na_2SO_4$ and concentrated. The crude product was purified by prep-TLC (DCM:MeOH=20:1) to give the title compound (576.3 mg, 97%) as a brown oil. LCMS: m/z=315 $[M+H]^+$.

Step 2: Synthesis of (R)—N-(5-(2-cyclopropyl-2H-tetrazol-5-yl)-4-fluoro-2-methylphenyl)-5-(1-(2-hydroxypropyl)-3-methyl-1H-pyrazol-4-yl)pyrazolo[1,5-a]pyridine-3-carboxamide The title compound was obtained as Peak 1, as a solid, 26.7 mg, 8%, from the compound mixture from step 1 and Intermediate 49, following a similar procedure to that described in Example 162, step 3, except HPLC (CHIRALPAK IG, 2*25 cm, 5 μm; Mobile Phase A: Hex (0.5% 2M $NH_3$-MeOH), Mobile Phase B: EtOH:DCM=1:1; Flow rate: 20 mL/min; Isocratic Gradient: 50% B in 12 min) was used. LCMS: m/z=516 $[M+H]^+$; $^1H$ NMR (400 MHz, DMSO-$d_6$) δ 9.74 (s, 1H), 8.83 (d, 1H), 8.74 (s, 1H), 8.19 (d, 1H), 8.05 (d, 1H), 7.85 (s, 1H), 7.40 (d, 1H), 7.25 (dd, 1H), 4.93 (d, 1H), 4.49 (tt, 1H), 4.02 (tq, 3H), 2.49 (s, 2H), 2.36 (s, 3H), 1.46-1.21 (m, 4H), 1.10 (d, 3H).

Example 256

(S)—N-(5-(2-cyclopropyl-2H-tetrazol-5-yl)-4-fluoro-2-methylphenyl)-5-(1-(2-hydroxypropyl)-3-methyl-1H-pyrazol-4-yl)pyrazolo[1,5-a]pyridine-3-carboxamide

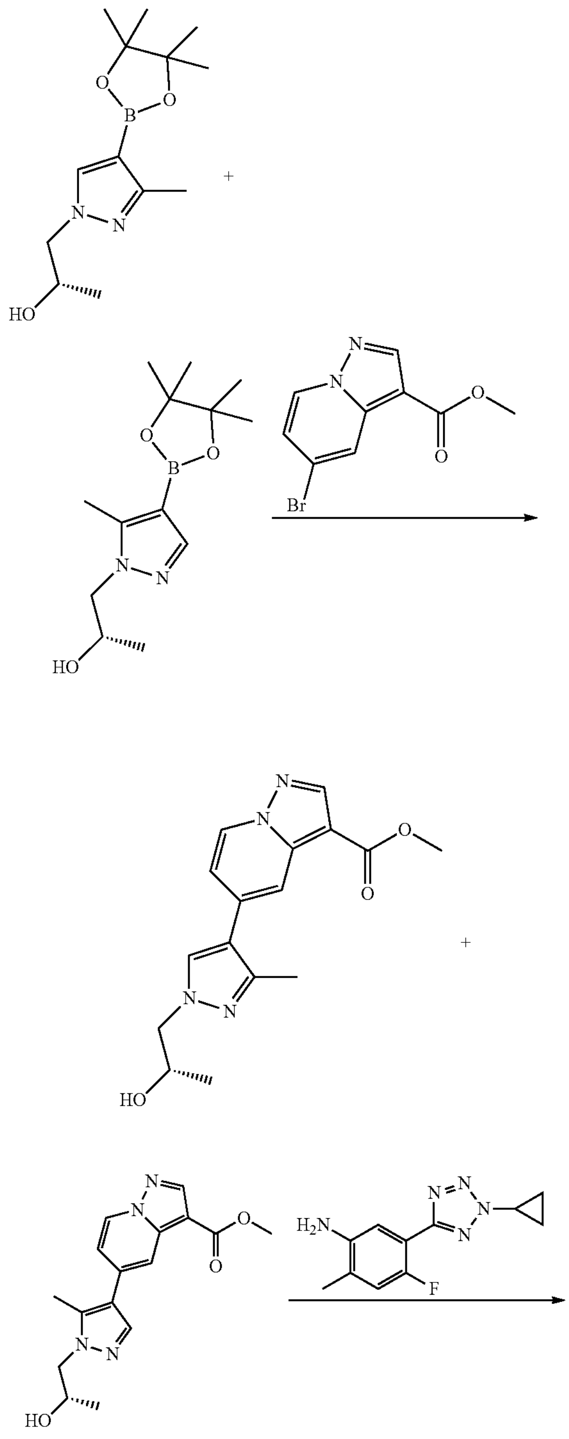

-continued

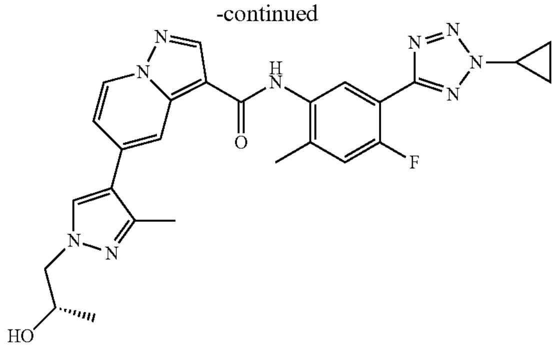

Step 1: Synthesis of mixture of methyl (S)-5-(1-(2-hydroxypropyl)-3-methyl-1H-pyrazol-4-yl)pyrazolo[1,5-a]pyridine-3-carboxylate and methyl (S)-5-(I-(2-hydroxypropyl)-5-methyl-1H-pyrazol-4-yl)pyrazolo[1,5-a]pyridine-3-carboxylate The title compound was obtained as an oil, 566.4 mg, 95%, from Intermediate 65 and methyl 5-bromopyrazolo[1,5-a]pyridine-3-carboxylate, following the procedure described in Example 255, step 1. LCMS: m/z=315 $[M+H]^+$.

Step 2: Synthesis of (S)—N-(5-(2-cyclopropyl-2H-tetrazol-5-yl)-4-fluoro-2-methylphenyl)-5-(1-(2-hydroxypropyl)-3-methyl-1H-pyrazol-4-yl)pyrazolo[1,5-a]pyridine-3-carboxamide The title compound was obtained as a white solid, as Peak 1, 55.8 mg, 15%, from the compound mixture from step 1 and Intermediate 49, following a similar procedure to that described in Example 162, step 3, except HPLC (CHIRALPAK IA, 2*25 cm, 5 μm; Mobile Phase A: Hex (0.5% 2M $NH_3$-MeOH), Mobile Phase B: EtOH:DCM=1:1; Flow rate: 20 mL/min; Isocratic Gradient: 50% B in 12 min, was used. LCMS: m/z=516 $[M+H]^+$; H NMR (400 MHz, DMSO-$d_6$) δ 9.72 (s, 1H), 8.81 (d, 1H), 8.73 (s, 1H), 8.26 (d, 1H), 8.21 (s, 1H), 8.06 (d, 1H), 7.40 (d, 1H), 7.26 (dd, 1H), 4.95 (d, 1H), 4.49 (tt, 1H), 4.02 (dd, 1H), 4.00-3.89 (m, 2H), 2.38 (d, 6H), 1.41 (q, 2H), 1.36-1.21 (m, 2H), 1.07 (d, 3H).

Example 257
(S)-5-(3-cyclopropyl-1-(2-hydroxy-3-methoxypropyl)-1H-pyrazol-4-yl)-N-(5-(2-cyclopropyl-2H-tetrazol-5-yl)-4-fluoro-2-methylphenyl)pyrazolo[1,5-a]pyridine-3-carboxamide
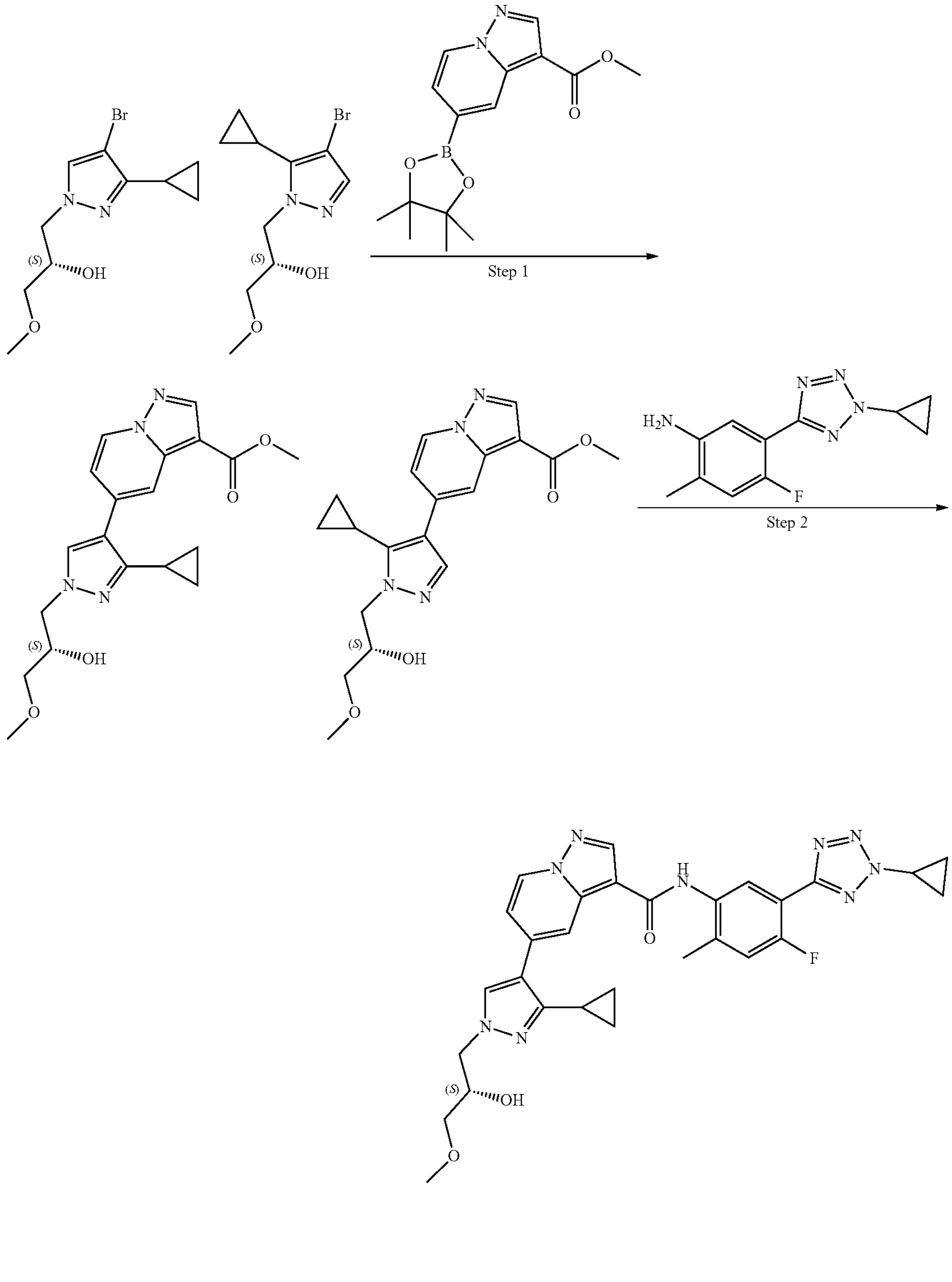

Step 1: Synthesis of methyl (S)-5-(3-cyclopropyl-1-(2-hydroxy-3-methoxypropyl)-1H-pyrazol-4-yl) pyrazolo[1,5-a]pyridine-3-carboxylate with methyl (S)-5-(5-cyclopropyl-1-(2-hydroxy-3-methoxypropyl)-1H-pyrazol-4-yl)pyrazolo[1,5-a]pyridine-3-carboxylate A mixture of Intermediate 60 (3.2 g, 11.6 mmol), Intermediate 53 (3.8 g, 11.6 mmol), $Pd(dppf)Cl_2$ (170 mg, 232 μmol) and $Cs_2CO_3$ (2.7 g, 11.6 mmol) in dioxane (50 mL) and $H_2O$ (10 mL) was stirred at 100° C. for 16 h. The cooled mixture was evaporated under reduced pressure and the residue was purified by silica gel column (60% EtOAc in PE) to afford the title compound (3.2 g, 40.9%) as a yellow oil. LCMS: m/z=371 $[M+H]^+$.

Step 2: Synthesis of (S)-5-(3-cyclopropyl-1-(2-hydroxy-3-methoxypropyl)-1H-pyrazol-4-yl)-N-(5-(2-cyclopropyl-2H-tetrazol-5-yl)-4-fluoro-2-methylphenyl)pyrazolo[1,5-a]pyridine-3-carboxamide The title compound was obtained as Peak 1, as a solid, 38.7 mg, 16%, from Intermediate 49 and the compound mixture from step 1, following a similar procedure to that described in Example 162, step 3, except prep-chiral-HPLC (Column: CHIRALPAK SA 2*25 cm, 5 μm; Mobile Phase A: Hex (0.5% 2 mM $NH_3$-MeOH), Mobile Phase B: EtOH: DCM=1:1; Flow rate: 20 mL/min; Isocratic Gradient: 50% B in 12 min) was used. LCMS: m/z=572 $[M+H]^+$; $^1H$ NMR (400 MHz, DMSO-$d_6$) δ 9.72 (s, 1H), 8.82 (dd, 1H), 8.73 (s, 1H), 8.56 (dd, 1H), 8.16 (s, 1H), 8.04 (d, 1H), 7.40 (d, 1H), 7.33 (dd, 1H), 5.16 (d, 1H), 4.49 (tt, 1H), 4.16-4.05 (m, 1H), 4.01-3.90 (m, 2H), 3.28 (s, 1H), 3.27 (s, 4H), 2.35 (s, 3H), 1.98 (tt, 1H), 1.45-1.33 (m, 2H), 1.33-1.21 (m, 2H), 1.03-0.89 (m, 2H), 0.89-0.76 (m, 2H).

Example 258

(S)-5-(3-cyclopropyl-1-(2,3-dihydroxy-3-methylbutyl)-1H-pyrazol-4-yl)-N-(5-(2-cyclopropyl-2H-tetrazol-5-yl)-4-fluoro-2-methylphenyl)pyrazolo[1,5-a]pyridine-3-carboxamide Example 259

(R)-5-(3-cyclopropyl-1-(2,3-dihydroxy-3-methylbutyl)-1H-pyrazol-4-yl)-N-(5-(2-cyclopropyl-2H-tetrazol-5-yl)-4-fluoro-2-methylphenyl)pyrazolo[1,5-a]pyridine-3-carboxamide

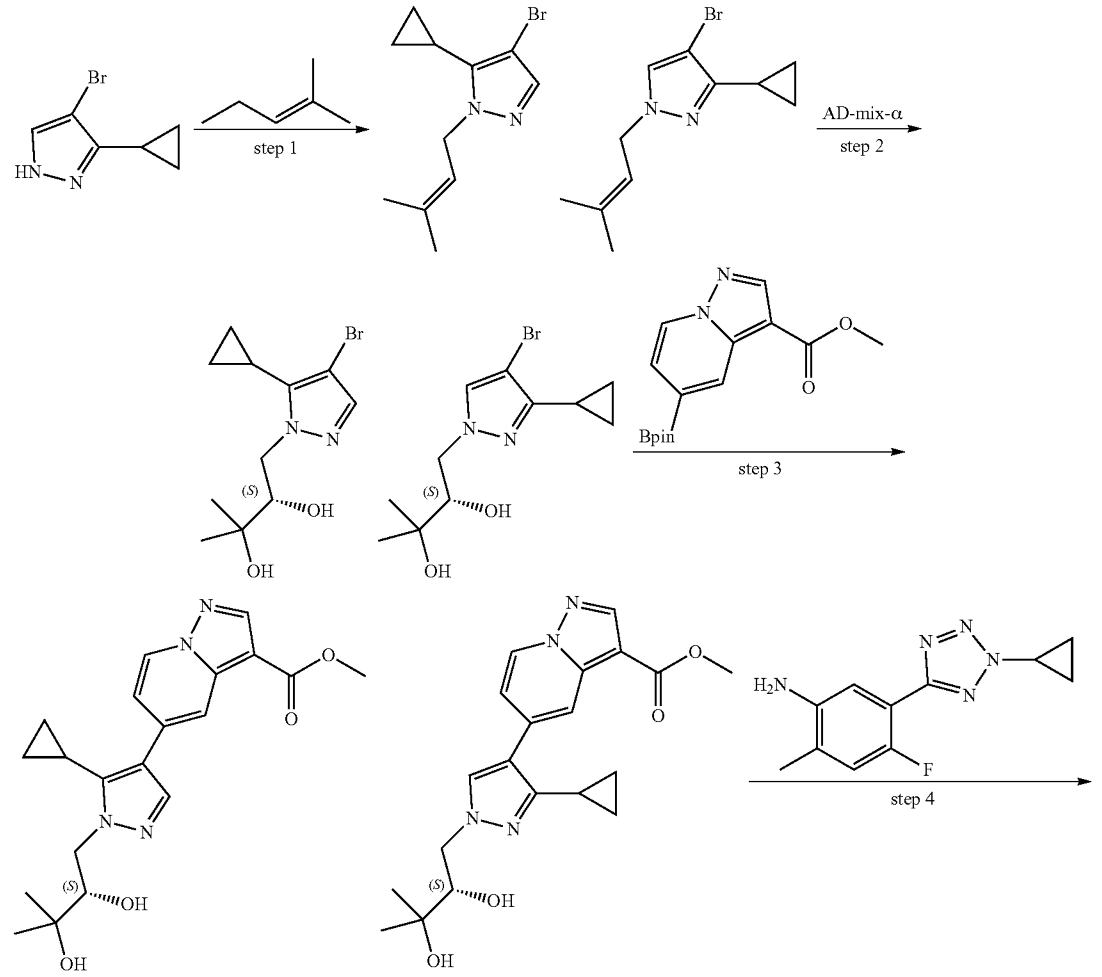

-continued

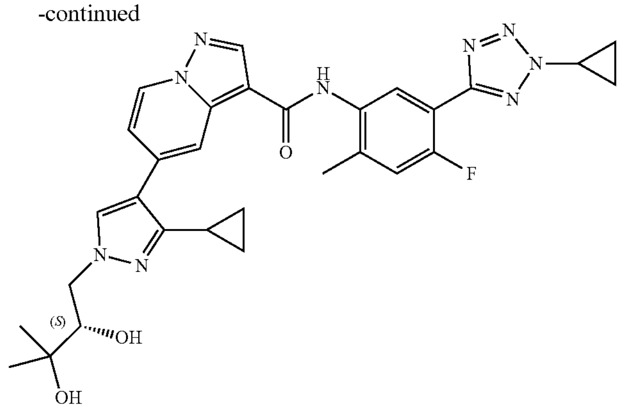

Step 1: Synthesis of 4-bromo-3-cyclopropyl-1-(3-methylbut-2-en-1-yl)-1H-pyrazole and 4-bromo-5-cyclopropyl-1-(3-methylbut-2-en-1-yl)-1H-pyrazole A mixture of 4-bromo-3-cyclopropyl-1H-pyrazole (3 g, 16.0 mmol), 1-chloro-3-methylbut-2-ene (3.34 g, 32.0 mmol) and $Cs_2CO_3$ (10.4 g, 32.0 mmol) in MeCN (90 mL) was stirred at 80° C. for 2 h. The cooled mixture was concentrated in vacuo and the residue was purified on silica gel column (5% MeOH in DCM) to afford the title compound (2.5 g, 61.2%) as a colorless oil. LCMS: m/z=255, 257 $[M+H]^+$.

Step 2: Synthesis of (S)-1-(4-bromo-3-cyclopropyl-1H-pyrazol-1-yl)-3-methylbutane-2,3-diol and (S)-1-(4-bromo-5-cyclopropyl-1H-pyrazol-1-yl)-3-methylbutane-2,3-diol A mixture of the compounds from step 1 (1.3 g, 5.09 mmol), AD-mix-α (4.15 g, 5.09 mmol) in tBuOH (50 mL) and $H_2O$ (20 mL) was stirred at 30° C. for 48 h. The cooled mixture was concentrated in vacuo and the residue was purified on silica gel column (10% MeOH in DCM) to afford the title compounds (500 mg, 34.0%) as a colorless oil. LCMS: m/z=289, 291 $[M+H]^+$.

Step 3: Synthesis of methyl (S)-5-(3-cyclopropyl-1-(2,3-dihydroxy-3-methylbutyl)-1H-pyrazol-4-yl)pyrazolo[1,5-a]pyridine-3-carboxylate with methyl (S)-5-(5-cyclopropyl-1-(2,3-dihydroxy-3-methylbutyl)-1H-pyrazol-4-yl)pyrazolo[1,5-a]pyridine-3-carboxylate A mixture of the compounds from step 2 (500 mg, 1.72 mmol), Intermediate 53 (571 mg, 1.89 mmol), $Pd(dppf)Cl_2$ (80 mg, 97.9 μmol) and $Cs_2CO_3$ (1.12 g, 3.44 mmol) in dioxane (25 mL) and $H_2O$ (5 mL) was stirred at 100° C. for 2 h. The cooled mixture was concentrated in vacuo and the residue was purified on silica gel column (10% MeOH in DCM) to afford title compound (470 mg, 71.1%) as a white solid. LCMS: m/z=385 $[M+H]^+$ Step 4: Synthesis of (S)-5-(3-cyclopropyl-1-(2,3-dihydroxy-3-methylbutyl)-1H-pyrazol-4-yl)-N-(5-(2-cyclopropyl-2H-tetrazol-5-yl)-4-fluoro-2-methylphenyl)pyrazolo[1,5-a]pyridine-3-carboxamide $AlMe_3$ (1M in Tol, 2 mL) was added to a mixture of the compounds from step 3 (400 mg, 1.04 mmol) and Intermediate 49 (265 mg, 1.14 mmol) in toluene (25 mL) and the reaction mixture was stirred at 100° C. for 16 h. The cooled reaction was quenched with water and the mixture concentrated in vacuo. The residue was purified on prep-TLC with DCM:MeOH=30:1. The product was separated on prep-achiral-SFC with Column: DAICEL DCpak P4VP 3*25 cm, 5 μm; Mobile Phase A: $CO_2$, Mobile Phase B: MeOH (0.1% 2M $NH_3$-MeOH); Flow rate: 60 mL/min; isocratic gradient 44% B, to afford Peak 1, the title compound (200 mg, 75% ee) as a white solid.

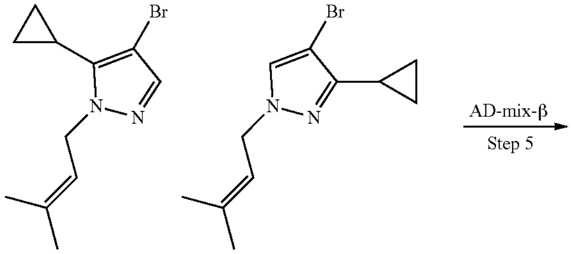

-continued

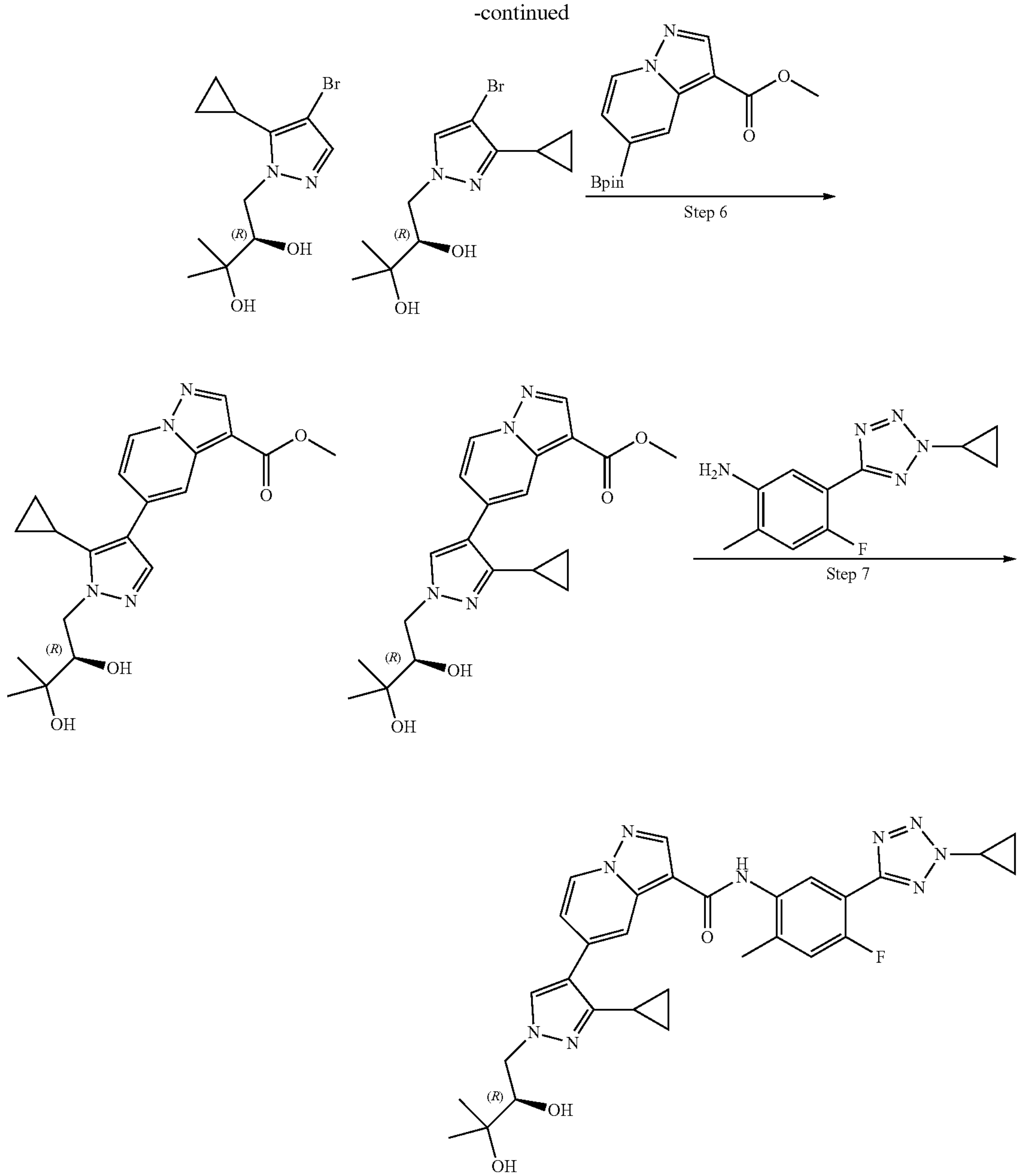

(R)-5-(3-cyclopropyl-1-(2,3-dihydroxy-3-methylbutyl)-1H-pyrazol-4-yl)-N-(5-(2-cyclopropyl-2H-tetrazol-5-yl)-4-fluoro-2-methylphenyl)pyrazolo[1,5-a]pyridine-3-carboxamide was obtained as Peak 1, (120 mg, 80% ee) from 4-bromo-3-cyclopropyl-1-(3-methylbut-2-en-1-yl)-1H-pyrazole and 4-bromo-5-cyclopropyl-1-(3-methylbut-2-en-1-yl)-1H-pyrazole and AD-mix-0, following the same 3 step procedure described in Steps 2 to 4 above.

(S)-5-(3-cyclopropyl-1-(2,3-dihydroxy-3-methylbutyl)-1H-pyrazol-4-yl)-N-(5-(2-cyclopropyl-2H-tetrazol-5-yl)-4-fluoro-2-methylphenyl)pyrazolo[1,5-a]pyridine-3-carboxamide (200 mg, 75% ee) and (R)-5-(3-cyclopropyl-1-(2,3-dihydroxy-3-methylbutyl)-1H-pyrazol-4-yl)-N-(5-(2-cyclopropyl-2H-tetrazol-5-yl)-4-fluoro-2-methylphenyl)pyrazolo[1,5-a]pyridine-3-carboxamide (120 mg, 80% ee) were further purified by prep-chiral-HPLC, Column: CHIRALPAK IC, 2*25 cm, 5 μm; Mobile Phase A: Hex (0.5% 2M $NH_3$-MeOH), Mobile Phase B: EtOH:DCM=1:1; Flow rate: 20 mL/min; 50% B isocratic gradient to afford Peak 1, Example 258 (173.7 mg, 100% ee) as a white solid LCMS: m/z=586 $[M+H]^+$; Chiral-HPLC: tR=1.863 min; 1H NMR (400 MHz, DMSO-$d_6$) δ 9.72 (s, 1H), 8.81 (d, 1H), 8.73 (s, 1H), 8.57 (d, 1H), 8.19 (s, 1H), 8.04 (d, 1H), 7.42-7.32 (m, 2H), 5.03 (d, 1H), 4.54-4.44 (m, 2H), 4.36-4.28 (m, 1H), 3.84 (m, 1H), 3.55 (t, 1H), 2.35 (s, 3H), 1.98 (m, 1H), 1.40 (m, 2H), 1.29 (m, 2H), 1.13 (s, 3H), 1.07 (s, 3H), 0.94 (m, 2H), 0.92-0.83 (m, 1H), 0.81 (m, 1H).

and Peak 2, Example 259, (82.7 mg, 100% ee) as a white solid. LCMS: m/z=586 $[M+H]^+$; Chiral-HPLC: tR=2.544 min; 1H NMR (400 MHz, DMSO-$d_6$) δ 9.72 (s, 1H), 8.81 (d, 1H), 8.73 (s, 1H), 8.57 (d, 1H), 8.19 (s, 1H), 8.04 (d, 1H), 7.43-7.30 (m, 2H), 5.03 (s, 1H), 4.49 (m, 2H), 4.32 (dd, 1H), 3.84 (m, 1H), 3.55 (d, 1H), 2.35 (s, 3H), 2.04-1.93 (m, 1H), 1.40 (m, 2H), 1.29 (m, 2H), 1.13 (s, 3H), 1.07 (s, 3H), 0.98-0.89 (m, 2H), 0.86 (m, 1H), 0.84-0.76 (m, 1H).

Example 260

N-(2-chloro-5-(2-cyclopropyl-2H-tetrazol-5-yl)-4-fluorophenyl)-5-(1-(2-hydroxy-2-methylpropyl)-3-methyl-1H-pyrazol-4-yl)pyrazolo[1,5-a]pyridine-3-carboxamide

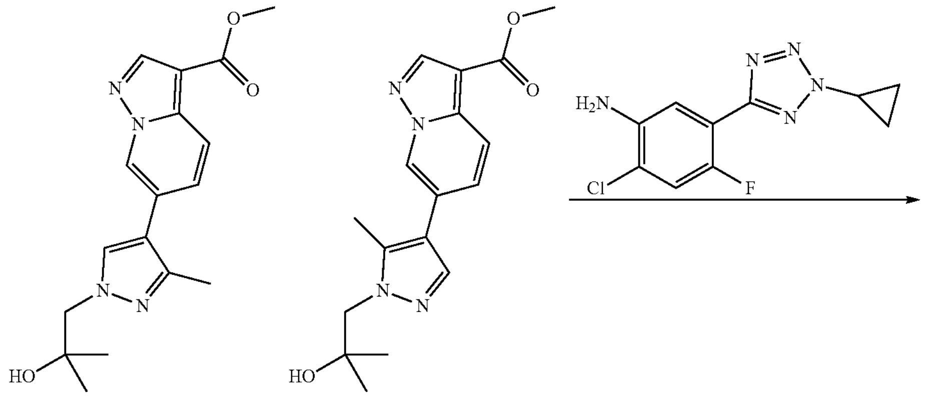

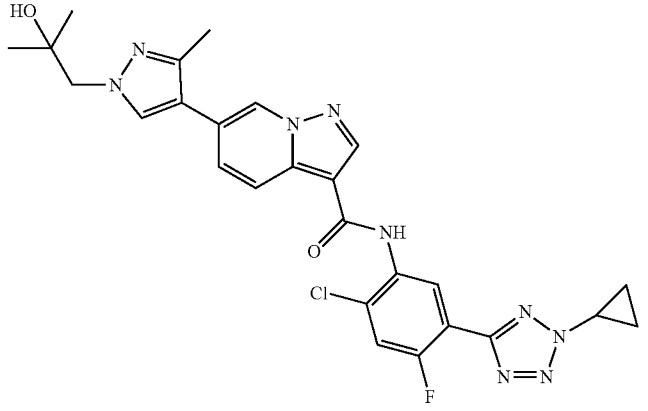

To a mixture of Intermediate 70 (450 mg, 1.37 mmol) and Intermediate 73 (696 mg, 2.12 mmol) in toluene (10 mL) was added LiHMDS (5 mL) at 0° C. under $N_2$ and the reaction mixture was stirred at rt for 16 h. Water (10 mL) was added and the resulting solution was extracted with EtOAc (3×10 mL). The combined organic layer was dried over $Na_2SO_4$ and concentrated. The residue was purified by silica gel column (DCM:MeOH, 100/0 to 90/10) and the product further purified by prep-achiral-SFC (Column: GreenSep Naphthyl, 3*25 cm, 5 μm; Mobile Phase A: $CO_2$, Mobile Phase B: MeOH (0.1% 2M $NH_3$-MeOH); Flow rate: 75 mL/min; Gradient: isocratic 26% B; Column Temperature (° C.): 35;) to give Peak 1, the title compound (99.8 mg, 10.1%) as a white solid and N-(2-chloro-5-(2-cyclopropyl-2H-tetrazol-5-yl)-4-fluorophenyl)-6-(1-(2-hydroxy-2-methylpropyl)-5-methyl-1H-pyrazol-4-yl)pyrazolo[1,5-a]pyridine-3-carboxamide (50 mg, 13.1%) as a white solid. LCMS: m/z=550 $[M+H]^+$; $^1H$ NMR (400 MHz, DMSO-$d_6$) δ 9.96 (s, 1H), 8.85 (t, 1H), 8.78 (s, 1H), 8.32 (d, 1H), 8.22 (d, 1H), 8.05 (s, 1H), 7.85 (d, 1H), 7.70 (dd, 1H), 4.72 (s, 1H), 4.52 (tt, 1H), 3.98 (s, 2H), 2.38 (s, 3H), 1.47-1.35 (m, 2H), 1.35-1.21 (m, 2H), 1.11 (s, 6H).

Example 261

(S)—N-(2-chloro-5-(2-cyclopropyl-2H-tetrazol-5-yl)-4-methylphenyl)-5-(1-(2-hydroxy-3-(2-methoxy-ethoxy)propyl)-1H-pyrazol-4-yl)pyrazolo[1,5-a]pyridine-3-carboxamide

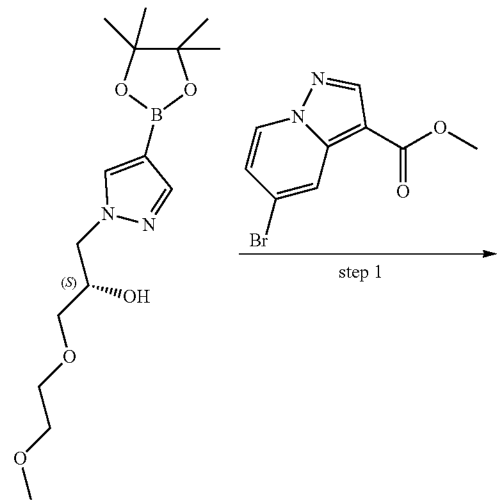

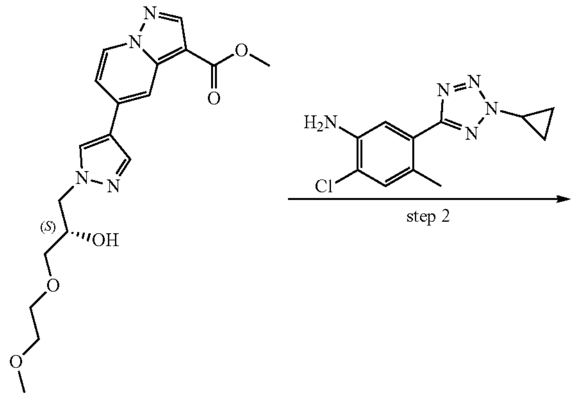

-continued

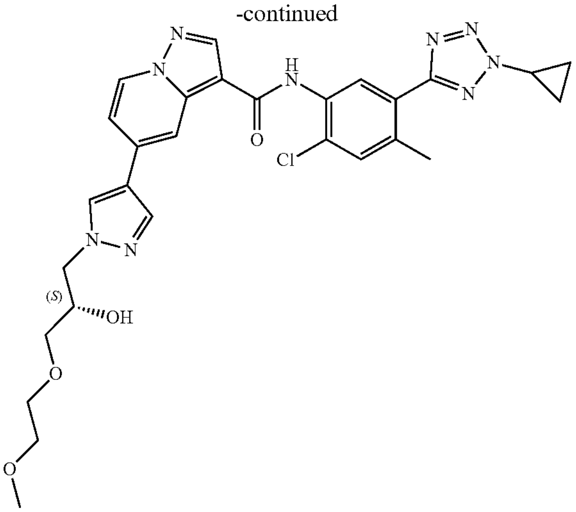

Step 1: Synthesis of methyl (S)-5-(1-(2-hydroxy-3-(2-methoxyethoxy)propyl)-1H-pyrazol-4-yl)pyrazolo[1,5-a]pyridine-3-carboxylate The title compound was obtained as a yellow solid, 70 mg, 61.4%, from Intermediate 68 and methyl 5-bromopyrazolo[1,5-a]pyridine-3-carboxylate, following the procedure described in Intermediate 69, step 3. LCMS: m/z=375 $[M+H]^+$.

Step 4: Synthesis of (S)—N-(2-chloro-5-(2-cyclopropyl-2H-tetrazol-5-yl)-4-methylphenyl)-5-(1-(2-hydroxy-3-(2-methoxyethoxy)propyl)-1H-pyrazol-4-yl)pyrazolo[1,5-a]pyridine-3-carboxamide The title compound was obtained as a white solid, 18.5 mg, 15.6%, from the product from step 1 and Intermediate 43, following a similar procedure to that described in Example 235, except Prep-HPLC (Method D, 36% to 56% B) was used. LCMS: m/z=375 $[M+H]^+$; 1H NMR (400 MHz, DMSO-$d_6$) δ 9.81 (s, 1H), 8.83 (dd, 1H), 8.75 (s, 1H), 8.39 (s, 1H), 8.31 (dd, 1H), 8.25 (s, 1H), 8.06 (d, 1H), 7.65 (s, 1H), 7.39 (dd, 1H), 5.21 (d, 1H), 4.50 (tt, 1H), 4.23 (dd, 1H), 4.12-3.96 (m, 1H), 4.00 (s, 1H), 3.58-3.48 (m, 2H), 3.46 (m, 2H), 3.40-3.34 (m, 2H), 3.25 (s, 3H), 2.59 (s, 3H), 1.46-1.38 (m, 2H), 1.35-1.23 (m, 2H).

Example 262

(S)—N-(2-chloro-5-(2-cyclopropyl-2H-tetrazol-5-yl)-4-methylphenyl)-5-(1-(2-hydroxy-3-methoxypropyl)-5-methyl-1H-pyrazol-4-yl)pyrazolo[1,5-a]pyridine-3-carboxamide

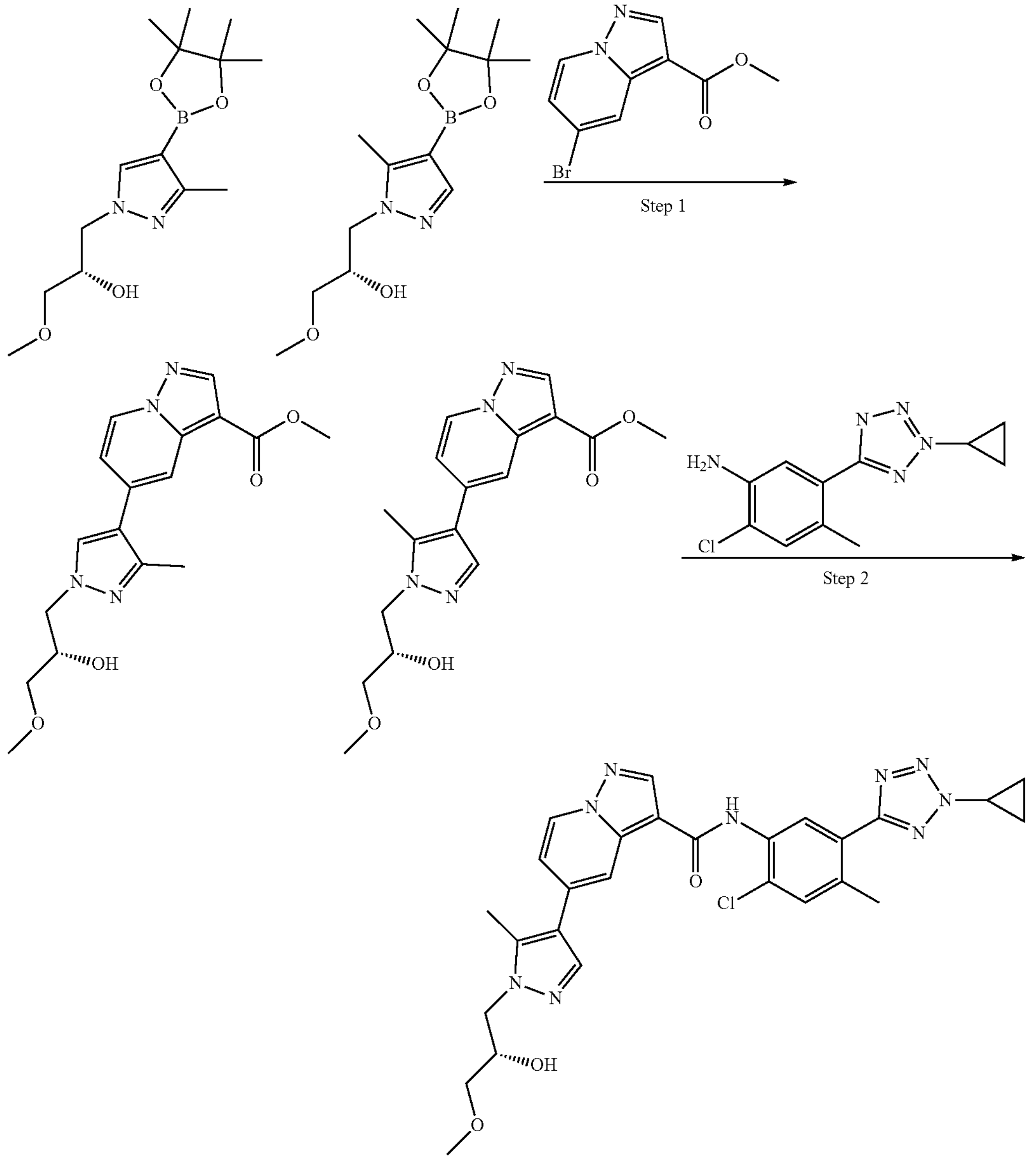

Step 1: Synthesis of methyl (S)-5-(1-(2-hydroxy-3-methoxypropyl)-3-methyl-1H-pyrazol-4-yl)pyrazolo[1,5-a]pyridine-3-carboxylate and methyl (S)-5-(1-(2-hydroxy-3-methoxypropyl)-5-methyl-1H-pyrazol-4-yl)pyrazolo[1,5-a]pyridine-3-carboxylate The title compound was obtained as a yellow solid, 320 mg, 68.9%, from Intermediate 64 and methyl 5-bromopyrazolo[1,5-a]pyridine-3-carboxylate, following the procedure described in Intermediate 69, step 3. LCMS: m/z=345 $[M+H]^+$.

Step 2: Synthesis of (S)—N-(2-chloro-5-(2-cyclopropyl-2H-tetrazol-5-yl)-4-methylphenyl)-5-(1-(2-hydroxy-3-methoxypropyl)-5-methyl-1H-pyrazol-4-yl)pyrazolo[1,5-a]pyridine-3-carboxamide The title compound was obtained as Peak 1, 56.6 mg, 23.1% as an off-white solid, from the product from step 1 and Intermediate 43, following a similar reaction to that described in Example 235, except achiral-SFC, (Column: DAICEL DCpak P4VP 3*25 cm, 5 μm; Mobile Phase A: $CO_2$, Mobile Phase B: MeOH (0.1% 2M $NH_3$-MeOH); Flow rate: 60 mL/min; Gradient: isocratic 45% B) was used.

LCMS: m/z=562 [M+H]$^+$; 1H NMR (400 MHz, DMSO-$d_6$) δ 9.85 (s, 1H), 8.87-8.76 (m, 2H), 8.18 (d, 2H), 7.87 (s, 1H), 7.65 (s, 1H), 7.26 (dd, 1H), 5.16 (d, 1H), 4.50 (tt, 1H), 4.16 (dd, 1H), 4.07 (dd, 1H), 3.97 (s, 1H), 3.39-3.30 (m, 1H), 3.28 (s, 4H), 2.59 (s, 3H), 2.48 (s, 3H), 1.42 (m, 2H), 1.36-1.21 (m, 2H).

Example 263

(S)—N-(2-chloro-5-(2-cyclopropyl-2H-tetrazol-5-yl)phenyl)-5-(1-(2-hydroxy-3-methoxypropyl)-3-methyl-1H-pyrazol-4-yl)pyrazolo[1,5-a]pyridine-3-carboxamide

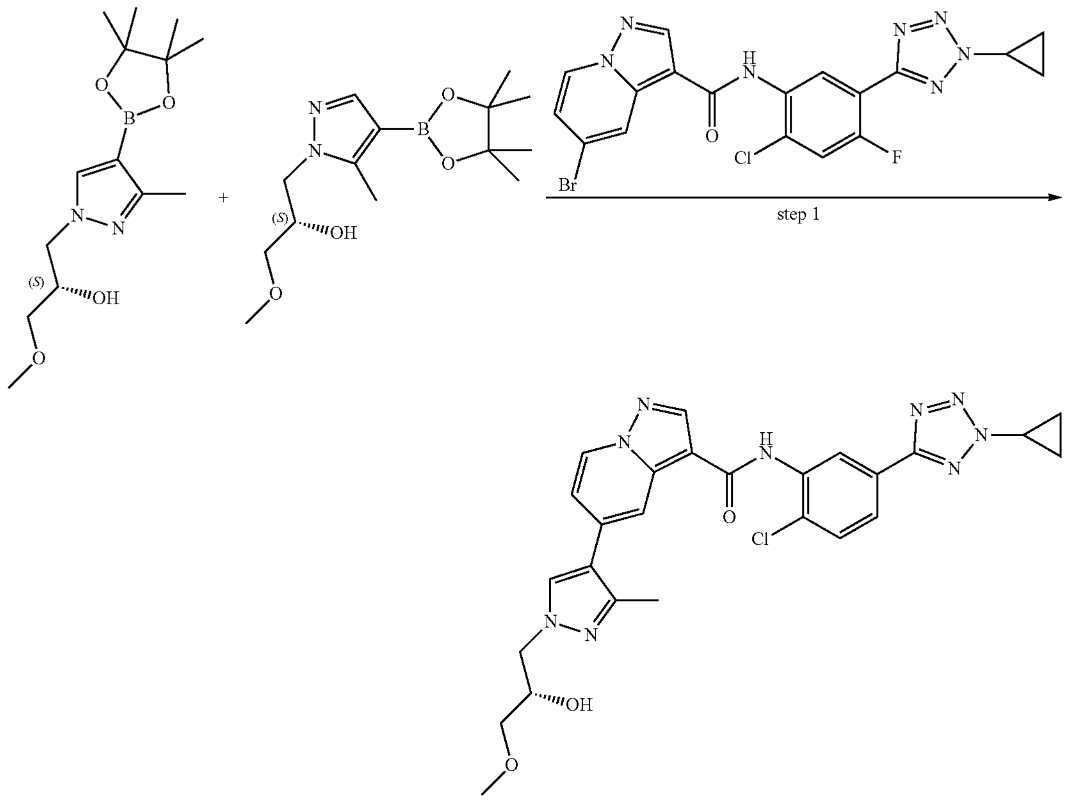

A mixture of Pd(dppf)$Cl_2$ (35.5 mg, 43.6 μmol), $K_2CO_3$ (90.2 mg, 654 μmol), Intermediate 47 (200 mg, 436 μmol) and Intermediate 64 (129 mg, 436 μmol) in dioxane/$H_2O$ (8 mL/2 mL) was heated at 80° C. for 3 h under $N_2$. The cooled reaction mixture was diluted with EtOAc (120 mL) and washed with water (60 mL). The organic layer was dried over $Na_2SO_4$, filtered and concentrated under vacuum. The crude product was purified by prep-TLC (DCM:MeOH=20:1) and the residue was further purified by Prep-HPLC (Method B2, 34% to 52% B) to give a white solid, 120 mg. The product was purified by Chiral-HPLC (Column: CHIRALPAK IG, 2*25 cm, 5 μm; Mobile Phase A: Hex (0.5% 2M $NH_3$-MeOH), Mobile Phase B: EtOH:DCM=1:1; Flow rate: 20 mL/min; Isocratic Gradient: 60% B in 11 min; to give Peak 1, the title compound, (39.8 mg) as a white solid LCMS: m/z=548 [M+H]$^+$, 1H NMR (400 MHz, DMSO-$d_6$) δ 9.87 (s, 1H), 8.87-8.77 (m, 2H), 8.39 (d, 1H), 8.28 (dd, 1H), 8.23 (s, 1H), 7.92 (dd, 1H), 7.76 (d, 1H), 7.29 (dd, 1H), 5.20 (d, 1H), 4.50 (tt, 1H), 4.14 (t, 1H), 4.02-3.93 (m, 2H), 3.31 (d, 5H), 2.42 (s, 3H), 1.42 (q, 2H), 1.37-1.22 (m, 2H).

Example 264

(S)—N-(2-chloro-5-(2-cyclopropyl-2H-tetrazol-5-yl)-4-fluorophenyl)-5-(1-(2-hydroxypropyl)-5-methyl-1H-pyrazol-4-yl)pyrazolo[1,5-a]pyridine-3-carboxamide

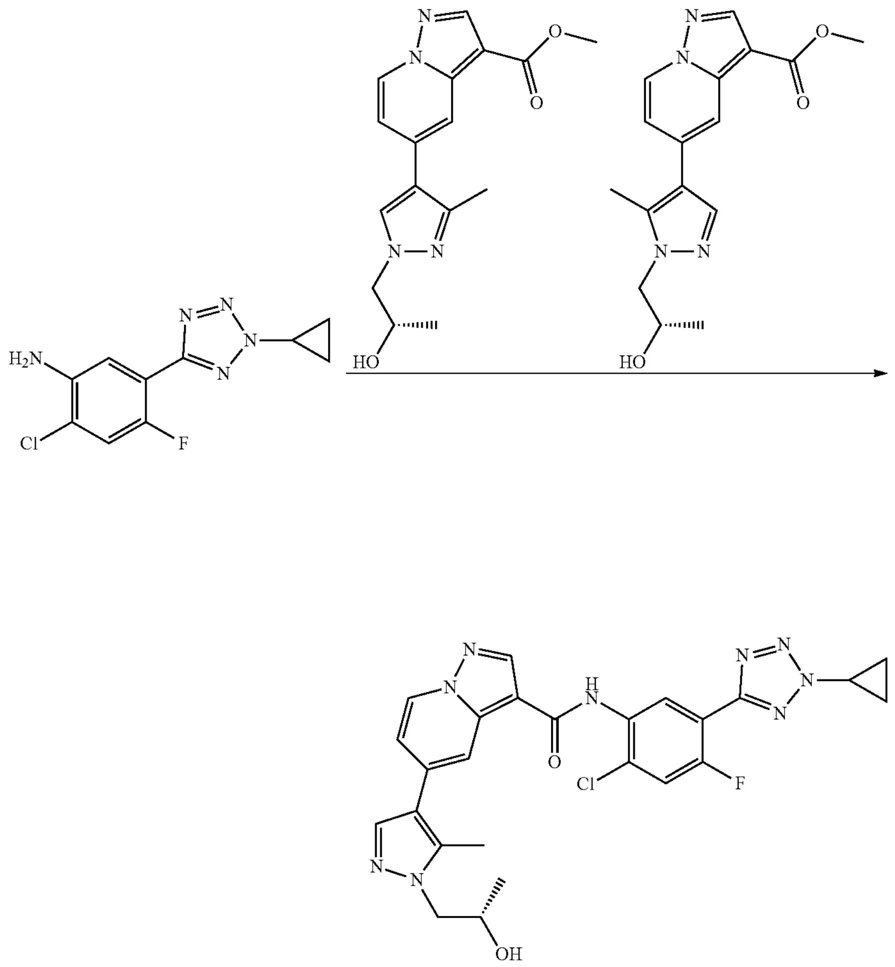

The title compound was obtained, as Peak 2, 19.8 mg, 24.6%, as a white solid, from Intermediate 73 and Example 256, step 1, following a similar procedure to that described in Example 235, except Prep-HPLC (Column: GreenSep Naphthyl, 3*25 cm, 5 μm; Mobile Phase A: $CO_2$, Mobile Phase B: MeOH (0.1% 2M NH3-MeOH); Flow rate: 75 mL/min; Gradient: isocratic 33% B; was used. LCMS: m/z=536 $[M+H]^+$; 1H NMR (400 MHz, DMSO-$d_6$) δ 9.92 (s, 1H), 8.84 (dd, 1H), 8.77 (s, 1H), 8.30 (d, 1H), 8.18 (dd, 1H), 7.84 (d, 2H), 7.26 (dd, 1H), 4.91 (d, 1H), 4.51 (tt, 1H), 4.02 (ddt, 3H), 1.47-1.34 (m, 2H), 1.34-1.21 (m, 2H), 1.10 (d, 3H).

Example 265

N-(2-chloro-5-(2-ethyl-2H-tetrazol-5-yl)-4-fluorophenyl)-5-(1-(2-hydroxy-2-methylpropyl)-3-methyl-1H-pyrazol-4-yl)pyrazolo[1,5-a]pyridine-3-carboxamide

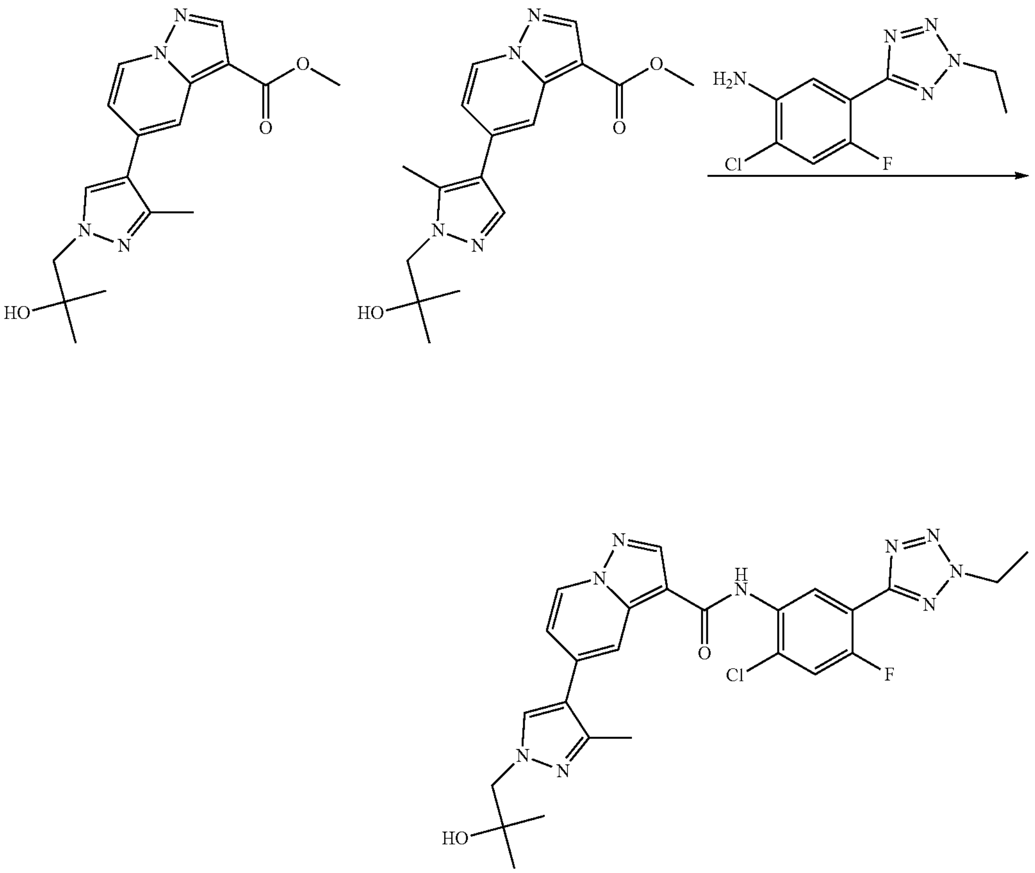

LiHMDS (1 mL, 304 μmol) was added dropwise to a mixture of Intermediate 75 (73.5 mg, 304 μmol) and Intermediate 51 (99.8 mg, 304 μmol) in toluene (7 mL) at rt and the reaction mixture was stirred at 50° C. for 16 h under $N_2$. The reaction mixture was diluted with EtOAc (120 mL) and washed with water (60 mL). The organic layer was dried over $Na_2SO_4$, filtered and concentrated under vacuum. The crude product was purified by prep-TLC with DCM: MeOH=20:1 and the residue was further purified by Prep-HPLC (Method B2, 28% to 55% B). The product was further purified by prep-SFC (DAICEL DCpak P4VP 3*25 cm, 5 μm; Mobile Phase A: $CO_2$, Mobile Phase B: MeOH (0.1% 2M $NH_3$-MeOH); Flow rate: 60 mL/min; Gradient: isocratic 35% B; Column Temperature (° C.): 35; to give Peak 1, the title compound, (12.9 mg) as a white solid. LCMS: m/z=538 $[M+H]^+$; 1H NMR (400 MHz, DMSO-$d_6$) δ 9.93 (s, 1H), 8.82 (d, 1H), 8.77 (s, 1H), 8.33 (d, 1H), 8.26 (d, 1H), 8.18 (s, 1H), 7.86 (d, 1H), 7.29 (dd, 1H), 4.81 (q, 3H), 3.98 (s, 2H), 2.41 (s, 3H), 1.59 (t, 3H), 1.24 (d, 1H), 1.10 (s, 6H).

Example 266

(R)—N-(2-chloro-5-(2-cyclopropyl-2H-tetrazol-5-yl)phenyl)-5-(1-(2,3-dihydroxy-2-methylpropyl)-1H-pyrazol-4-yl)pyrazolo[1,5-a]pyridine-3-carboxamide

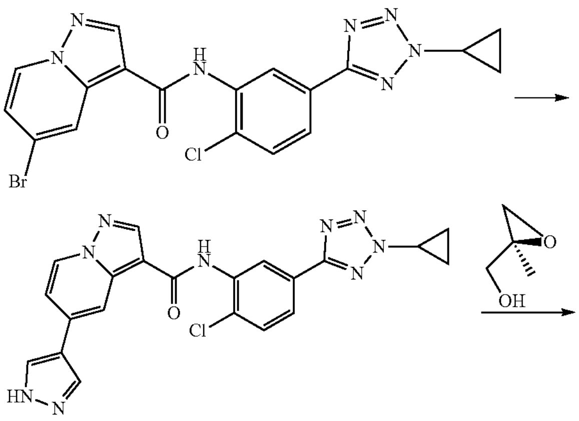

-continued

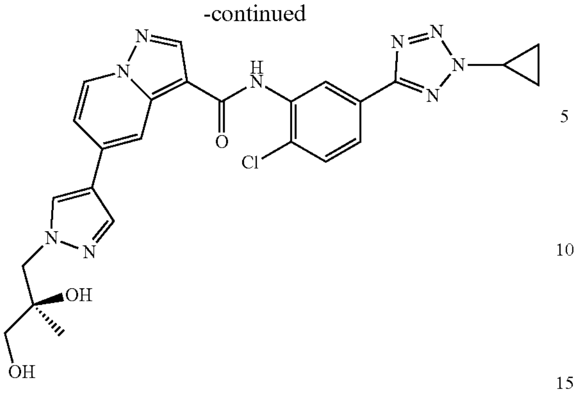

Step 1: Synthesis of N-(2-chloro-5-(2-cyclopropyl-2H-tetrazol-5-yl)phenyl)-5-(H-pyrazol-4-yl)pyrazolo[1,5-a]pyridine-3-carboxamide The title compound was obtained as a yellow solid, 100 mg, 42%, from Intermediate 47 and 4-(4,4,5,5-tetramethyl-1,3,2-dioxaborolan-2-yl)-1H-pyrazole, following the procedure described in Example 237. LCMS: m/z=446 $[M+H]^+$.

Step 2: Synthesis of (R)—N-(2-chloro-5-(2-cyclopropyl-2H-tetrazol-5-yl)phenyl)-5-(1-(2,3-dihydroxy-2-methylpropyl)-1H-pyrazol-4-yl)pyrazolo[1,5-a]pyridine-3-carboxamide To a stirred solution of the product from step 1 (100 mg, 224 μmol) and (S)-2-(methoxymethyl)oxirane (29.6 mg, 336 μmol) in DMF (2 mL) was added NaH (10.7 mg, 448 μmol) and the reaction mixture was stirred for 2 h at 60° C. Ice cooled water (10 mL) was added to the cooled reaction and the mixture was extracted with EtOAc (3×10 mL). The combined organic phase was dried over anhydrous $Na_2SO_4$ and concentrated. The crude product was purified by Prep-TLC with DCM:MeOH=10:1 and Prep-HPLC (Method B2, 55% to 70% B) to give the title compound (50.3 mg; 42%) as a white solid. LCMS: m/z=534 $[M+H]^+$; $^1H$ NMR (400 MHz, DMSO-$d_6$) δ 9.82 (s, 1H), 8.83 (d, 1H), 8.77 (s, 1H), 8.45 (d, 1H), 8.33 (d, 2H), 8.07 (s, 1H), 7.91 (dd, 1H), 7.75 (d, 1H), 7.41 (dd, 1H), 4.84 (t, 1H), 4.70 (s, 1H), 4.49 (tt, 1H), 4.16 (d, 1H), 4.10 (d, 1H), 3.23 (h, 2H), 1.42 (q, 2H), 1.38-1.21 (m, 2H), 0.98 (s, 3H).

Example 267

(R)—N-(5-(2-cyclopropyl-2H-tetrazol-5-yl)-2-methylphenyl)-5-(1-(2-hydroxy-3-methoxy-2-methylpropyl)-1H-pyrazol-4-yl)pyrazolo[1,5-a]pyridine-3-carboxamide or (S)—N-(5-(2-cyclopropyl-2H-tetrazol-5-yl)-2-methylphenyl)-5-(1-(2-hydroxy-3-methoxy-2-methylpropyl)-1H-pyrazol-4-yl)pyrazolo[1,5-a]pyridine-3-carboxamide Example 268

(S)—N-(5-(2-cyclopropyl-2H-tetrazol-5-yl)-2-methylphenyl)-5-(1-(2-hydroxy-3-methoxy-2-methylpropyl)-1H-pyrazol-4-yl)pyrazolo[1,5-a]pyridine-3-carboxamide or (R)—N-(5-(2-cyclopropyl-2H-tetrazol-5-yl)-2-methylphenyl)-5-(1-(2-hydroxy-3-methoxy-2-methylpropyl)-1H-pyrazol-4-yl)pyrazolo[1,5-a]pyridine-3-carboxamide

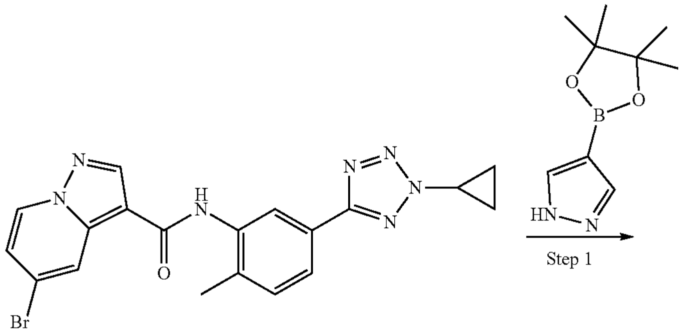

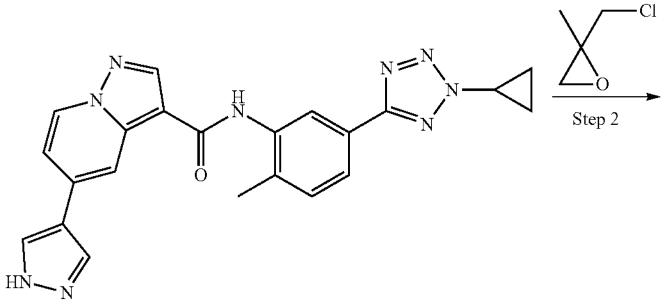

-continued

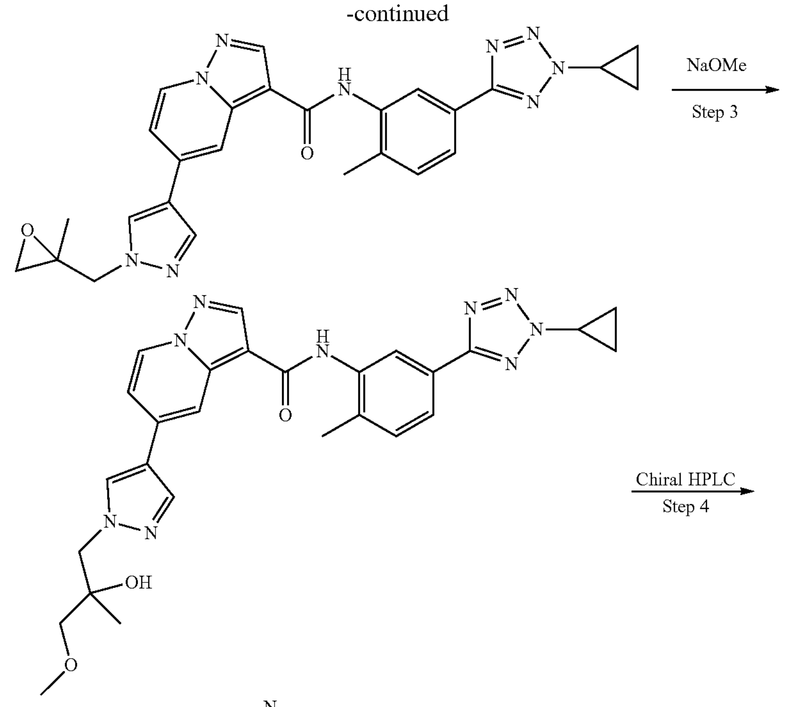

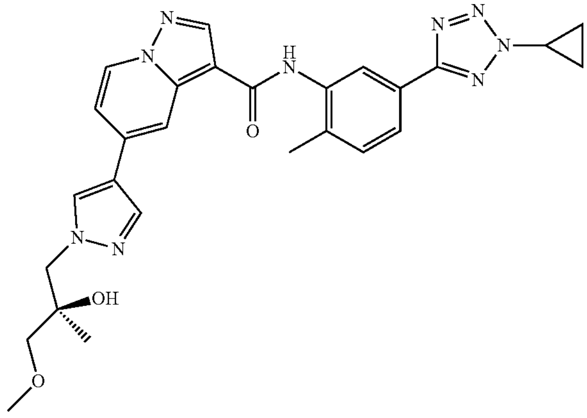

and

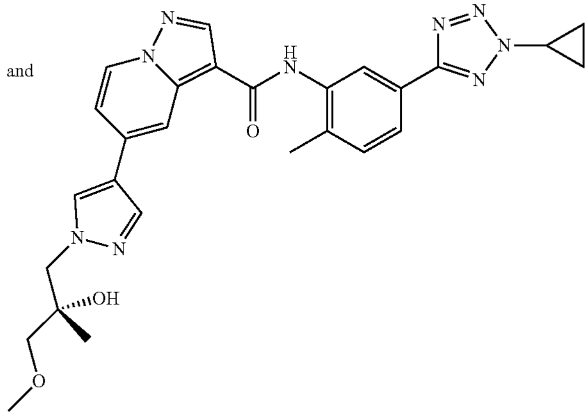

Step 1: Synthesis of N-(5-(2-cyclopropyl-2H-tetrazol-5-yl)-2-methylphenyl)-5-(1H-pyrazol-4-yl)pyrazolo[1,5-a]pyridine-3-carboxamide The title compound was obtained as a brown solid, 150 mg, 77%, from Intermediate 56 and 4-(4,4,5,5-tetramethyl-1,3,2-dioxaborolan-2-yl)-1H-pyrazole, following the procedure described in Example 237. LCMS m/z=426 $[M+H]^+$

Step 2: Synthesis of N-(5-(2-cyclopropyl-2H-tetrazol-5-yl)-2-methylphenyl)-5-(1-((2-methyloxiran-2-yl)methyl)-1H-pyrazol-4-yl)pyrazolo[1,5-a]pyridine-3-carboxamide To a solution of the compound from step 1 (100 mg, 235 μmol) in DMF (3 mL) was added NaH (11.2 mg, 470 μmol) and the mixture was stirred for 30 min at rt. 2-(Chloromethyl)-2-methyloxirane (3.75 mg, 35.2 μmol) was added and the reaction mixture was stirred for 2 h at 60° C. Water (10 mL) was added and the mixture was extracted with EtOAc (3×10 mL). The combined organic layer was concentrated and purified by Prep-TLC (PE:EtOAc=1:1) to give the title compound (80 mg, 68%) as a brown solid. LCMS: m/z=496 $[M+H]^+$.

Step 3: Synthesis of N-(5-(2-cyclopropyl-2H-tetrazol-5-yl)-2-methylphenyl)-5-(1-(2-hydroxy-3-methoxy-2-methylpropyl)-1H-pyrazol-4-yl)pyrazolo[1,5-a]pyridine-3-carboxamide To a stirred solution of the compound from step 2 (80 mg, 161 μmol) in MeOH (3 mL) was added $CH_3ONa$ (17.3 mg, 322 μmol) and the reaction mixture was stirred for 2 h at rt. Water (10 mL) was added and the mixture was extracted with EtOAc (3×10 mL). The combined organic layer was dried over $Na_2SO_4$ and concentrated. The crude product was purified by prep-TLC (DCM:MeOH=10:1) to give the title compound (50 mg; 58%) as a yellow solid. LCMS: m/z=528 $[M+H]^+$.

Step 4: Synthesis of (R)—N-(5-(2-cyclopropyl-2H-tetrazol-5-yl)-2-methylphenyl)-5-(1-(2-hydroxy-3-methoxy-2-methylpropyl)-1H-pyrazol-4-yl)pyrazolo[1,5-a]pyridine-3-carboxamide or (S)—N-(5-(2-cyclopropyl-2H-tetrazol-5-yl)-2-methylphenyl)-5-(1-(2-hydroxy-3-methoxy-2-methylpropyl)-1H-pyrazol-4-yl)pyrazolo[1,5-a]pyridine-3-carboxamide The compound from step 3 (50 mg, 94.7 μmol) was purified by Prep-Chiral-HPLC (Column: CHIRALPAK IF, 2*25 cm, 5 μm; Mobile Phase A: MTBE (0.5% 2M $NH_3$-MeOH), Mobile Phase B: MeOH; Flow rate: 18 mL/min; isocratic gradient: 50% B in 30 min; to give Peak 1, 20.7 mg, 41%, as a white solid. LCMS: m/z=528 $[M+H]^+$; $^1H$ NMR (400 MHz, DMSO-$d_6$) δ 9.65 (s, 1H), 8.85-8.79 (m, 1H), 8.73 (s, 1H), 8.35-8.28 (m, 2H), 8.18 (d, 1H), 8.06 (s, 1H), 7.82 (dd, 1H), 7.46 (d, 1H), 7.38 (dd, 1H), 4.93 (s, 1H), 4.47 (tt, 1H), 4.13 (s, 2H), 3.30 (s, 3H), 3.15 (s, 2H), 2.37 (s, 3H), 1.41 (p, 2H), 1.37-1.21 (m, 2H), 1.03 (s, 3H). Further elution provided Peak 2, 18.6 mg, 37% as a white solid. LCMS: m/z=528 $[M+H]^+$, 1H NMR (400 MHz, DMSO-$d_6$) δ 9.65 (s, 1H), 8.82 (d, 1H), 8.73 (s, 1H), 8.35-8.28 (m, 2H), 8.18 (d, 1H), 8.06 (s, 1H), 7.82 (dd, 1H), 7.46 (d, 1H), 7.38 (dd, 1H), 4.92 (s, 1H), 4.47 (tt, 1H), 4.12 (s, 2H), 3.30 (s, 3H), 3.14 (s, 2H), 2.37 (s, 3H), 1.41 (p, 2H), 1.35-1.21 (m, 2H), 1.03 (s, 3H).

Example 269

N-(5-(2-cyclopropyl-2H-tetrazol-5-yl)-2-methylphenyl)-5-(1-((2R,3S)-3-hydroxybutan-2-yl)-3-methyl-1H-pyrazol-4-yl)pyrazolo[1,5-a]pyridine-3-carboxamide or N-(5-(2-cyclopropyl-2H-tetrazol-5-yl)-2-methylphenyl)-5-(1-((2S,3R)-3-hydroxybutan-2-yl)-3-methyl-1H-pyrazol-4-yl)pyrazolo[1,5-a]pyridine-3-carboxamide

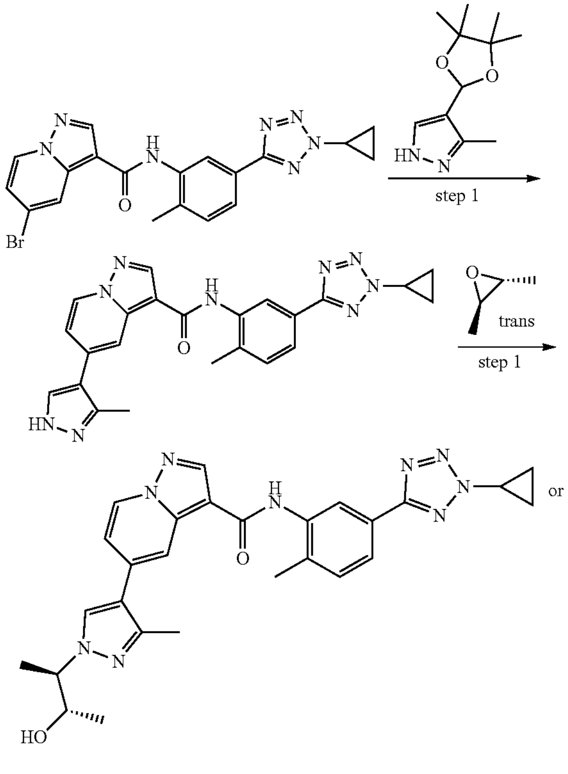

-continued

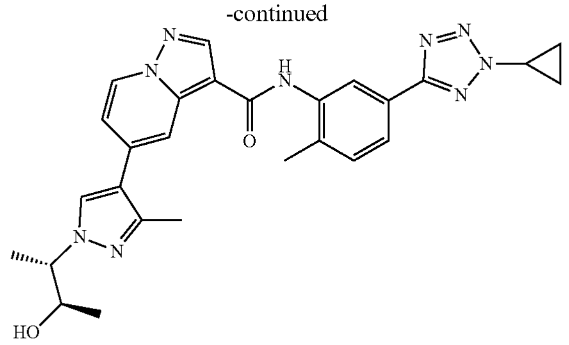

Step 1: Synthesis of N-(5-(2-cyclopropyl-2H-tetrazol-5-yl)-2-methylphenyl)-5-(3-methyl-1H-pyrazol-4-yl)pyrazolo[1,5-a]pyridine-3-carboxamide The title compound was obtained as a yellow solid, 950 mg, 55.9%, from Intermediate 56 and 3-methyl-4-(4,4,5,5-tetramethyl-1,3-dioxolan-2-yl)-1H-pyrazole, following the procedure described in Example 255, step 1. LCMS: m/z=440 $[M+H]^+$.

Step 2: Synthesis of N-(5-(2-cyclopropyl-2H-tetrazol-5-yl)-2-methylphenyl)-5-(1-((2R,3S)-3-hydroxybutan-2-yl)-3-methyl-1H-pyrazol-4-yl)pyrazolo[1,5-a]pyridine-3-carboxamide or N-(5-(2-cyclopropyl-2H-tetrazol-5-yl)-2-methylphenyl)-5-(1-((2S,3R)-3-hydroxybutan-2-yl)-3-methyl-1H-pyrazol-4-yl)pyrazolo[1,5-a]pyridine-3-carboxamide A reaction mixture of N-(5-(2-cyclopropyl-2H-tetrazol-5-yl)-2-methylphenyl)-5-(3-methyl-1H-pyrazol-4-yl)pyrazolo[1,5-a]pyridine-3-carboxamide (470 mg, 1.06 mmol), rac-(2R,3R)-2,3-dimethyloxirane (114 mg, 1.59 mmol), NaH (76.3 mg, 1.59 mmol) in DMF (40 mL) was stirred at 100° C. for 3 h under $N_2$. The cooled reaction was diluted with water (20 mL), the mixture was extracted with EtOAc (2×50 mL) and washed with saturated brine (10 mL). The organic layer was dried with $Na_2SO_4$ and concentrated under vacuum. The crude product was purified by Prep-HPLC (Method B2, 26% to 53% B) and was further purified by Prep-chiral HPLC (CHIRALPAK IE, 2*25 cm, 5 μm; Mobile Phase A: Hex (0.5% 2M $NH_3$-MeOH), Mobile Phase B: MeOH:DCM=1:1; Flow rate: 20 mL/min; isocratic Gradient: 50% B in 20 min; to afford a mixture of Peak 1 and 2, a mixture of N-(5-(2-cyclopropyl-2H-tetrazol-5-yl)-2-methylphenyl)-5-(1-((2R,3S)-3-hydroxybutan-2-yl)-3-methyl-1H-pyrazol-4-yl)pyrazolo[1,5-a]pyridine-3-carboxamide and N-(5-(2-cyclopropyl-2H-tetrazol-5-yl)-2-methylphenyl)-5-(1-((2S,3R)-3-hydroxybutan-2-yl)-3-methyl-1H-pyrazol-4-yl)pyrazolo[1,5-a]pyridine-3-carboxamide (90 mg), Peak 3 and Peak 4, N-(5-(2-cyclopropyl-2H-tetrazol-5-yl)-2-methylphenyl)-5-(1-((2R,3S)-3-hydroxybutan-2-yl)-5-methyl-1H-pyrazol-4-yl)pyrazolo[1,5-a]pyridine-3-carboxamide and N-(5-(2-cyclopropyl-2H-tetrazol-5-yl)-2-methylphenyl)-5-(1-((2S,3R)-3-hydroxybutan-2-yl)-5-methyl-1H-pyrazol-4-yl)pyrazolo[1,5-a]pyridine-3-carboxamide.

The mixture of Peak 1 and 2 was further purified by Prep-chiral HPLC (CHIRALPAK IE, 2*25 cm, 5 μm; Mobile Phase A: Hex (0.5% 2M $NH_3$-MeOH), Mobile Phase B: MeOH:DCM=1:1; Flow rate: 20 mL/min; Isocratic Gradient: 50% B for 20 min; to give Peak 1, the title compound (31.9 mg, 5.8%) as a white solid and Peak 2, N-(5-(2-cyclopropyl-2H-tetrazol-5-yl)-2-methylphenyl)-5-(1-((2S,3R)-3-hydroxybutan-2-yl)-3-methyl-1H-pyrazol-4-yl)pyrazolo[1,5-a]pyridine-3-carboxamide or N-(5-(2-cyclopropyl-2H-tetrazol-5-yl)-2-methylphenyl)-5-(1-((2R,3S)-3-hydroxybutan-2-yl)-3-methyl-1H-pyrazol-4-yl)pyrazolo[1,5-a]pyridine-3-carboxamide (26.5 mg, 4.9%) as a white solid. LCMS: m/z=512 $[M+H]^+$; $^1H$ NMR (400 MHz, DMSO-$d_6$) δ 8.81 (d, 1H), 8.75 (s, 1H), 8.31-8.25 (m, 2H), 8.14 (d, 1H), 7.83 (dd, 1H), 7.46 (d, 1H), 7.29 (dd, 1H), 4.96 (d, 1H), 4.47 (tt, 1H), 4.07 (p, 1H), 3.86 (h, 1H), 2.39 (d, 6H), 1.46 (d, 3H), 1.41 (p, 2H), 1.29 (dt, 2H), 0.93 (d, 3H).

Example 270

N-(5-(2-cyclopropyl-2H-tetrazol-5-yl)-2-methylphenyl)-5-(1-((2S,3S)-3-hydroxybutan-2-yl)-5-methyl-1H-pyrazol-4-yl)pyrazolo[1,5-a]pyridine-3-carboxamide or N-(5-(2-cyclopropyl-2H-tetrazol-5-yl)-2-methylphenyl)-5-(1-((2R,3R)-3-hydroxybutan-2-yl)-5-methyl-1H-pyrazol-4-yl)pyrazolo[1,5-a]pyridine-3-carboxamide

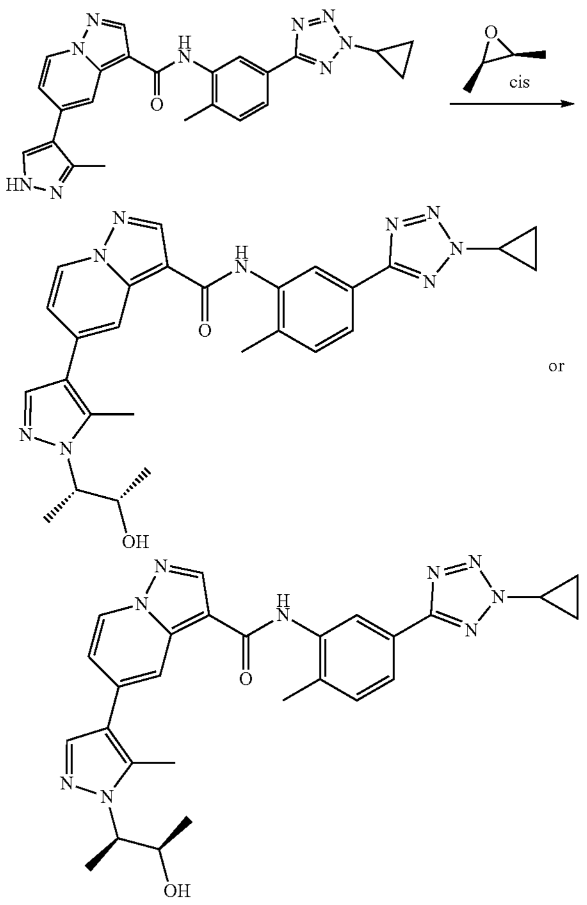

or

A reaction mixture of Example 269, step 1 (470 mg, 1.06 mmol), rac-(2R,3S)-2,3-dimethyloxirane (114 mg, 1.59 mmol), NaH (76.3 mg, 1.59 mmol) in DMF (40 mL) was stirred at 100° C. for 3 h under $N_2$. The cooled reaction mixture was diluted with water (10 mL) of water, then extracted with EtOAc (2×50 mL). The combined organic layers were washed with brine (20 mL), dried over anhydrous $Na_2SO_4$ and concentrated under vacuum. The crude product was purified by HPLC (Method B2, 26% to 53% B). The product was further purified by Prep-HPLC (Column: Lux3umCellulose2; Mobile Phase A: Hex (0.2% DEA): (EtOH:MeOH=1:1)=60:40; Flow rate: 1 mL/min; Gradient: isocratic) to give a mixture of Peak 1 and 2 (100 mg), Peak 3 (21.9 mg) and Peak 4 (26.2 mg). The mixture of Peak 1 and 2 was further purified by Prep-chiral HPLC (CHIRALPAK IE, 2*25 cm, 5 μm; Mobile Phase A: Hex (0.5% 2M $NH_3$-MeOH), Mobile Phase B: MeOH:DCM=1:1; Flow rate: 20 mL/min; Isocratic Gradient: 50% B over 20 min; to give Peak 1, the title compound, (39.7 mg, 7.3%) as a white solid and Peak 2, N-(5-(2-cyclopropyl-2H-tetrazol-5-yl)-2-methylphenyl)-5-(1-((2R,3R)-3-hydroxybutan-2-yl)-5-methyl-1H-pyrazol-4-yl)pyrazolo[1,5-a]pyridine-3-carboxamide or N-(5-(2-cyclopropyl-2H-tetrazol-5-yl)-2-methylphenyl)-5-(1-((2S,3S)-3-hydroxybutan-2-yl)-5-methyl-1H-pyrazol-4-yl)pyrazolo[1,5-a]pyridine-3-carboxamide (36.5 mg, 6.7%) as a white solid. LCMS: m/z=512 $[M+H]^+$; $^1H$ NMR (400 MHz, DMSO-$d_6$) δ 9.69 (s, 1H), 8.20 (d, 1H), 8.13 (d, 1H), 7.87-7.77 (m, 2H), 7.46 (d, 1H), 7.24 (dd, 1H), 4.71 (d, 1H), 4.47 (tt, 1H), 4.24 (p, 1H), 3.84 (q, 1H), 2.48 (s, 3H), 2.36 (s, 3H), 1.39 (dd, 5H), 1.29 (dt, 2H), 1.14 (d, 3H).

Example 271

N-(2-chloro-5-(5-((1R,2S)-2-fluorocyclopropyl)-2H-tetrazol-2-yl)phenyl)-5-(1-((4-hydroxytetrahydro-2H-pyran-4-yl)methyl)-1H-pyrazol-4-yl)pyrazolo[1,5-a]pyridine-3-carboxamide or N-(2-chloro-5-(5-((1S,2R)-2-fluorocyclopropyl)-2H-tetrazol-2-yl)phenyl)-5-(1-((4-hydroxytetrahydro-2H-pyran-4-yl)methyl)-1H-pyrazol-4-yl)pyrazolo[1,5-a]pyridine-3-carboxamide

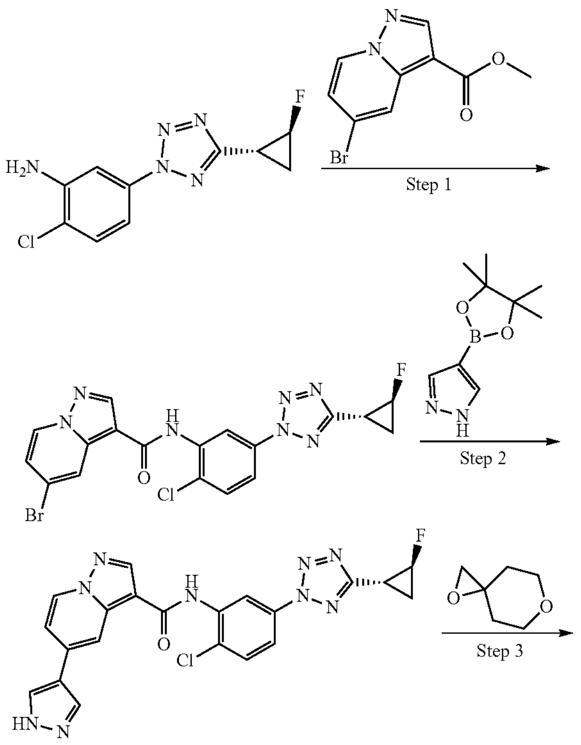

-continued

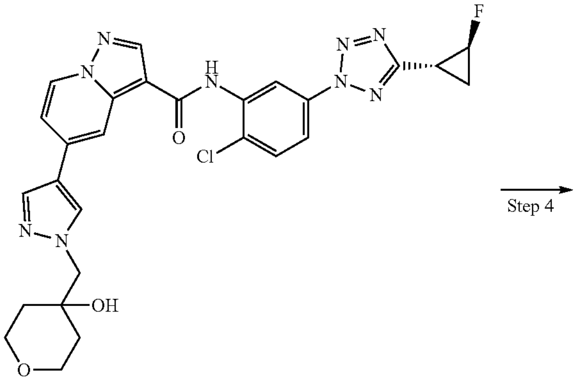

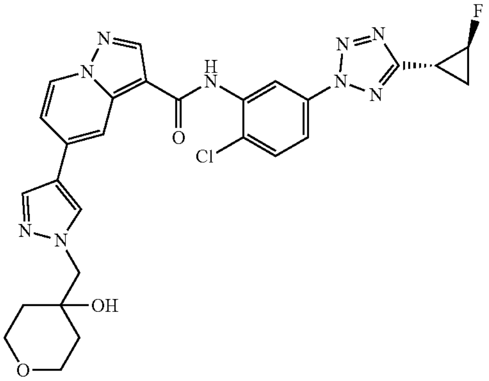

or

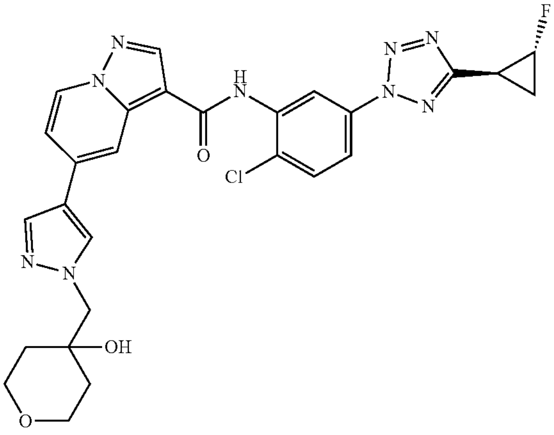 [SMILES: O=C(Nc1cc(-n2nnc([C@@H]3C[C@H]3F)n2)ccc1Cl)c1cnn2ccc(-c3cnn(CC4(O)CCOCC4)c3)cc12]

Step 1: Synthesis of rac-5-bromo-N-(2-chloro-5-(5-((1R,2S)-2-fluorocyclopropyl)-2H-tetrazol-2-yl)phenyl)pyrazolo[1,5-a]pyridine-3-carboxamide To a solution of Intermediate 71 (100 mg, 394 μmol) and methyl 5-bromopyrazolo[1,5-a]pyridine-3-carboxylate (110 mg, 433 μmol) in toluene (3 mL) was added $Me_3Al$ (42.5 mg, 591 μmol) and the reaction mixture was stirred for 2 h at 100° C. 1 M NaOH solution (10 mL) was added to the cooled reaction and the mixture extracted with EtOAc (3×10 mL). The combined organic layer was dried with $Na_2SO_4$, concentrated under vacuum and the crude product purified by prep-TLC (EtOAc:PE=1:1) to give the title compound (150 mg; 80%) as a yellow solid. LCMS m/z=476 $[M+H]^+$ Step 2: Synthesis of Rac-N-(2-chloro-5-(5-((1R,2S)-2-fluorocyclopropyl)-2H-tetrazol-2-yl)phenyl)-5-(1H-pyrazol-4-yl)pyrazolo[1,5-a]pyridine-3-carboxamide The title compound was obtained as a solid, 120 mg, 82%, from the product of step 1 and 4-(4,4,5,5-tetramethyl-1,3,2-dioxaborolan-2-yl)-1H-pyrazole, following the procedure described in Example 237. LCMS: m/z=464 $[M+H]^+$.

Step 3: Synthesis of Rac-N-(2-chloro-5-(5-((1R,2S)-2-fluorocyclopropyl)-2H-tetrazol-2-yl)phenyl)-5-(1-((4-hydroxytetrahydro-2H-pyran-4-yl)methyl)-1H-pyrazol-4-yl)pyrazolo[1,5-a]pyridine-3-carboxamide The title compound was obtained as a white solid, 53 mg, 35%, from the product from step 2 and 1,6-dioxaspiro[2.5]octane, following the procedure described in Example 266, step 2. LCMS: m/z=578 $[M+H]^+$.

Step 4: Synthesis of N-(2-chloro-5-(5-((1R,2S)-2-fluorocyclopropyl)-2H-tetrazol-2-yl)phenyl)-5-(1-((4-hydroxytetrahydro-2H-pyran-4-yl)methyl)-1H-pyrazol-4-yl)pyrazolo[1,5-a]pyridine-3-carboxamide or N-(2-chloro-5-(5-((1S,2R)-2-fluorocyclopropyl)-2H-tetrazol-2-yl)phenyl)-5-(1-((4-hydroxytetrahydro-2H-pyran-4-yl)methyl)-1H-pyrazol-4-yl)pyrazolo[1,5-a]pyridine-3-carboxamide The product from step 3 (53 mg, 91.6 μmol) was separated by prep-Chiral-HPLC (Column: CHIRALPAK IF, 2*25 cm, 5 μm; Mobile Phase A: MTBE (0.5% 2M $NH_3$-MeOH), Mobile Phase B: MeOH:DCM=1:1; Flow rate: 20 mL/min; Isocratic Gradient: 30% B in 18 min) to give Peak 1, the title compound, 19.2 mg, 36% as a white solid. LCMS: m/z=578 $[M+H]^+$; $^1H$ NMR (400 MHz, DMSO-$d_6$) δ 9.88 (s, 1H), 8.88-8.81 (m, 1H), 8.78 (s, 1H), 8.55 (d, 1H), 8.39-8.31 (m, 2H), 8.08 (s, 1H), 7.92 (dd, 1H), 7.85 (d, 1H), 7.43 (dd, 1H), 5.29-5.22 (m, 1H), 5.10 (ddd, 1H), 4.84 (s, 1H), 4.14 (s, 2H), 3.64-3.54 (m, 4H), 2.95 (dddd, 1H), 1.91-1.75 (m, 1H), 1.64-1.53 (m, 2H), 1.46 (dq, 1H), 1.33 (d, 2H).

Example 272
N-(2-chloro-5-(5-((1R,2S)-2-fluorocyclopropyl)-2H-tetrazol-2-yl)phenyl)-5-(1-((4-hydroxytetrahydro-2H-pyran-4-yl)methyl)-3-methyl-1H-pyrazol-4-yl) pyrazolo[1,5-a]pyridine-3-carboxamide or N-(2-chloro-5-(5-((1S,2R)-2-fluorocyclopropyl)-2H-tetrazol-2-yl)phenyl)-5-(1-((4-hydroxytetrahydro-2H-pyran-4-yl)methyl)-3-methyl-1H-pyrazol-4-yl) pyrazolo[1,5-a]pyridine-3-carboxamide
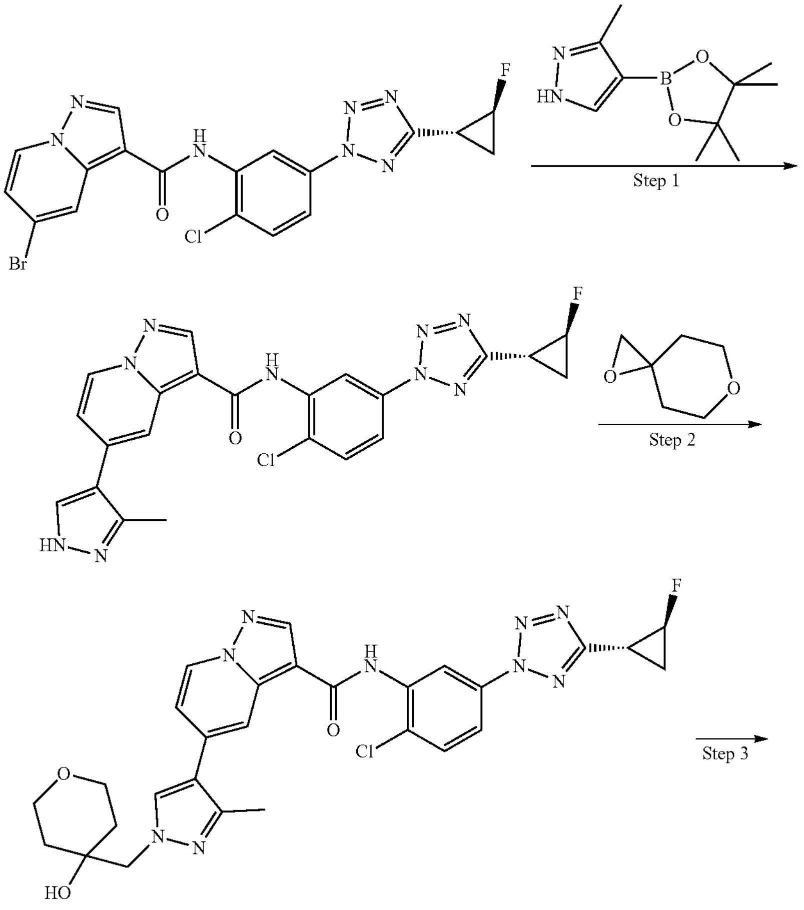
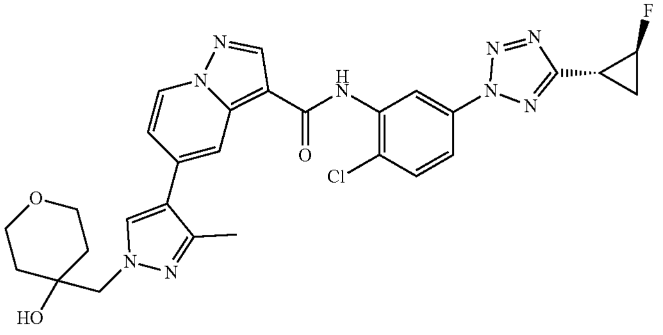
or -continued

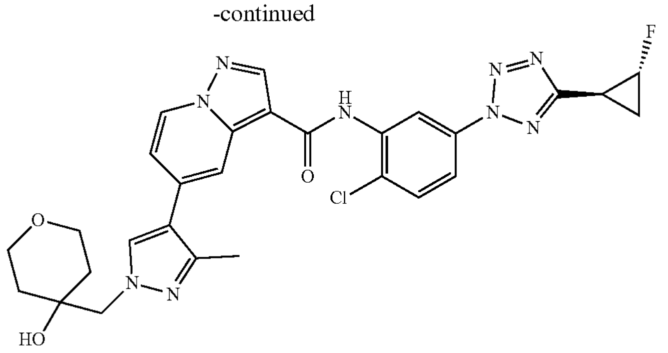

The title compound was obtained as a white solid, as Peak 1, from Example 271, step 1 and 3-methyl-4-(4,4,5,5-tetramethyl-1,3,2-dioxaborolan-2-yl)-1H-pyrazole, following a similar 3 step procedure to that described in Example 271, step 2 to 4. LCMS: m/z=592 $[M+H]^+$; 1H NMR (400 MHz, DMSO-$d_6$) δ 9.92 (s, 1H), 8.87-8.78 (m, 2H), 8.48 (d, 1H), 8.28 (d, 1H), 8.19 (s, 1H), 7.93 (dd, 1H), 7.85 (d, 1H), 7.30 (dd, 1H), 5.25 (dt, 0.5H), 5.09 (dt, 0.5H), 4.82 (s, 1H), 4.05 (s, 2H), 3.66-3.54 (m, 4H), 2.95 (dddd, 1H), 2.42 (s, 3H), 1.82 (dddd, 1H), 1.59 (ddd, 2H), 1.46 (dq, 1H), 1.33 (d, 2H).

Example 273

N-(2-chloro-5-(5-((1S,2R)-2-fluorocyclopropyl)-2H-tetrazol-2-yl)phenyl)-5-(1-((R)-2,3-dihydroxy-2-methylpropyl)-1H-pyrazol-4-yl)pyrazolo[1,5-a]pyridine-3-carboxamide or N-(2-chloro-5-(5-((1R,2S)-2-fluorocyclopropyl)-2H-tetrazol-2-yl)phenyl)-5-(1-((R)-2,3-dihydroxy-2-methylpropyl)-1H-pyrazol-4-yl)pyrazolo[1,5-a]pyridine-3-carboxamide

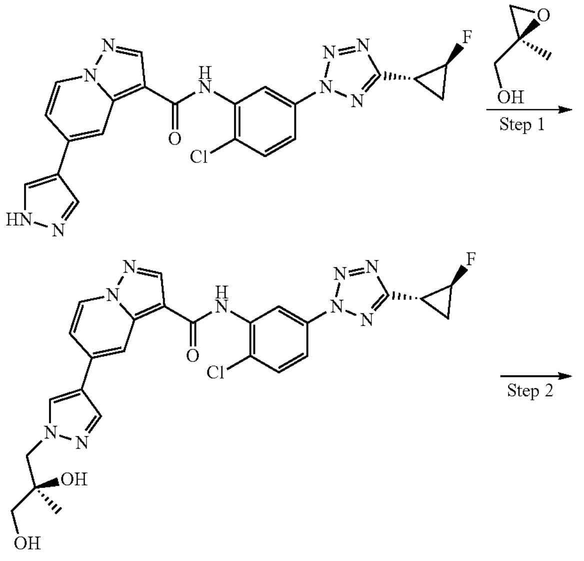

-continued

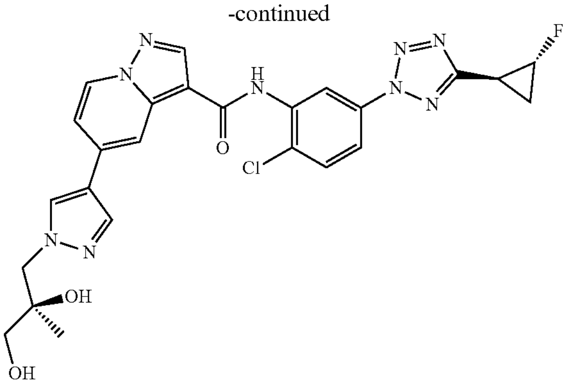

or

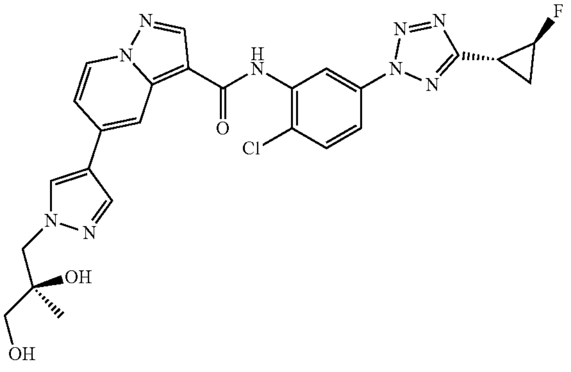

The title compound was obtained as Peak 2, 2.6 mg, 8%, from Example 271, step 1 and (S)-(2-methyloxiran-2-yl)methanol, following a similar 2 step procedure to that described in Example 271, steps 3 and 4, except prep-HPLC (Column: CHIRALPAK IF, 2*25 cm, 5 μm; Mobile Phase A: MTBE (0.5% 2M $NH_3$-MeOH), Mobile Phase B: MeOH; Flow rate: 18 mL/min; Isocratic Gradient: 50% B over 30 min), was used. LCMS: m/z=552 $[M+H]^+$; $^1H$ NMR (400 MHz, DMSO-$d_6$) δ 9.90 (s, 1H), 8.84 (d, 1H), 8.78 (s, 1H), 8.55 (d, 1H), 8.37-8.30 (m, 2H), 8.07 (s, 1H), 7.93 (dd, 1H), 7.85 (d, 1H), 7.42 (dd, 1H), 5.26 (dt, 0.5H), 5.13-5.06 (m, 0.5H), 4.94-4.82 (m, 1H), 4.72 (s, 1H), 4.26-4.06 (m, 2H), 3.20 (t, 2H), 2.95 (dddd, 1H), 1.83 (dddd, 1H), 1.46 (dq, 1H), 0.99 (s, 3H).

Example 274

(R)—N-(2-chloro-5-(2-cyclopropyl-2H-tetrazol-5-yl)phenyl)-5-(3,5-dimethyl-1-((4-methylmorpholin-2-yl)methyl)-1H-pyrazol-4-yl)pyrazolo[1,5-a]pyridine-3-carboxamide

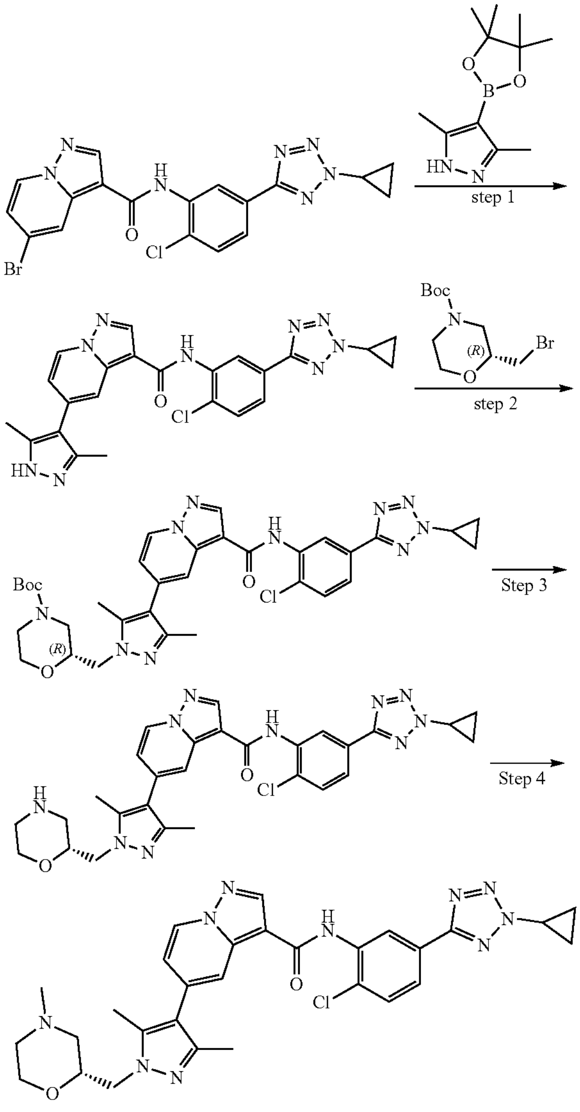

Step 1: Synthesis of N-(2-chloro-5-(2-cyclopropyl-2H-tetrazol-5-yl)phenyl)-5-(3,5-dimethyl-1H-pyrazol-4-yl)pyrazolo[1,5-a]pyridine-3-carboxamide The title compound was obtained as an off-white solid, from Intermediate 47 and 3,5-dimethyl-4-(4,4,5,5-tetramethyl-1,3,2-dioxaborolan-2-yl)-1H-pyrazole, following the procedure described in Example 237. LCMS: m/z=474 $[M+H]^+$.

Step 2: Synthesis of tert-butyl (R)-2-((4-(3-((2-chloro-5-(2-cyclopropyl-2H-tetrazol-5-yl)phenyl)carbamoyl)pyrazolo[1,5-a]pyridin-5-yl)-3,5-dimethyl-1H-pyrazol-1-yl)methyl)morpholine-4-carboxylate $K_2CO_3$ (130 mg, 949 μmol) was added to the solution of N-(2-chloro-5-(2-cyclopropyl-2H-tetrazol-5-yl)phenyl)-5-(3,5-dimethyl-1H-pyrazol-4-yl)pyrazolo[1,5-a]pyridine-3-carboxamide (300 mg, 633 μmol) and tert-butyl (R)-2-(bromomethyl)morpholine-4-carboxylate (453 mg, 781 μmol) in DMF (10 mL) and the reaction mixture was stirred at 80° C. for 3 h. The cooled mixture was diluted with EtOAc (100 mL) and washed with brine (50 mL×2). The organic layer was dried with $Na_2SO_4$ and concentrated in vacuo. The residue was purified by silica gel column (DCM:EtOAc=15:1) to give the title compound (150 mg) as a light-yellow solid. LCMS: m/z=673 $[M+H]^+$.

Step 3: Synthesis of (R)—N-(2-chloro-5-(2-cyclopropyl-2H-tetrazol-5-yl)phenyl)-5-(3,5-dimethyl-1-(morpholin-2-ylmethyl)-1H-pyrazol-4-yl)pyrazolo[1,5-a]pyridine-3-carboxamide TFA (3 mL) was added to the product from step 2 (70 mg, 103 μmol) in DCM (10 mL) and the reaction mixture was stirred at rt for 2 h. The mixture was diluted with DCM (100 mL) and washed with aq. $NaHCO_3$ (50 mL×2), the organic layer was dried with $Na_2SO_4$ and concentrated under vacuum. The residue was purified by silica gel column (DCM:EtOAc=25:1) and the product further purified by prep-HPLC (Method B2, 32% to 57% B) to give the title compound (13.9 mg) as a white solid. LCMS: m/z=573 $[M+H]^+$;

Step 4: Synthesis of (R)—N-(2-chloro-5-(2-cyclopropyl-2H-tetrazol-5-yl)phenyl)-5-(3,5-dimethyl-1-((4-methylmorpholin-2-yl)methyl)-1H-pyrazol-4-yl)pyrazolo[1,5-a]pyridine-3-carboxamide HCHO (4.36 mg, 156 μmol) was added to the product from step 3 (60 mg, 104 μmol) in ice cold MeOH (3 mL) and the solution was stirred at rt for 0.5 h. $NaBH_3CN$ (5.83 mg, 104 μmol) was added and the reaction mixture was stirred at rt for 1.5 h. The mixture was diluted with EtOAc (50 mL), washed with brine (20 mL×2), the organic layer was dried with $Na_2SO_4$ and concentrated in vacuo. The residue was purified by prep-HPLC with DCM:MeOH=18:1 and the product further purified by prep-HPLC (Method B2, 60% to 77% B) to give the title compound (16.8 mg) as a white solid. LCMS: m/z=587 $[M+H]^+$; $^1H$ NMR (400 MHz, DMSO-$d_6$) δ 9.84 (s, 1H), 8.85 (dd, 1H), 8.81 (s, 1H), 8.38 (d, 1H), 8.05 (dd, 1H), 7.91 (dd, 1H), 7.74 (d, 1H), 7.10 (dd, 1H), 4.48 (tt, 1H), 4.16-4.01 (m, 2H), 3.79 (td, 2H), 3.46 (td, 1H), 2.70 (d, 1H), 2.56 (d, 2H), 2.32 (s, 3H), 2.23 (s, 3H), 2.17 (s, 3H), 1.98 (td, 1H), 1.85-1.75 (m, 1H), 1.41 (q, 2H), 1.36-1.27 (m, 2H), 1.31-1.21 (m, 2H).

Example 275

(S)—N-(2-chloro-5-(2-cyclopropyl-2H-tetrazol-5-yl)phenyl)-5-(1-(2,3-dihydroxypropyl)-3,5-dimethyl-1H-pyrazol-4-yl)pyrazolo[1,5-a]pyridine-3-carboxamide

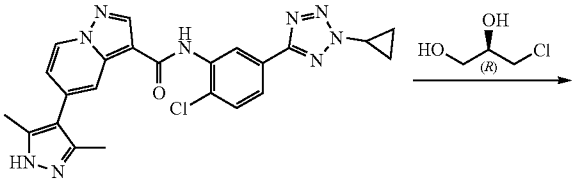

-continued

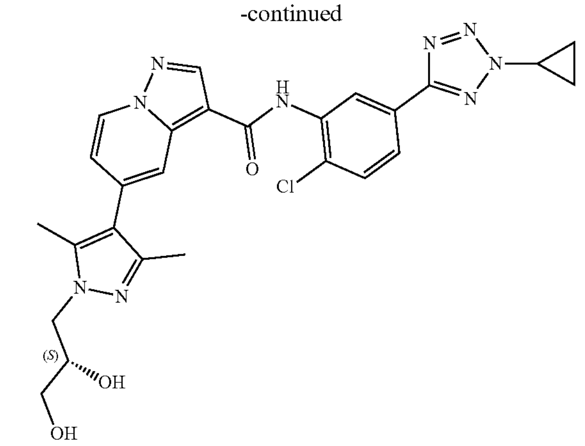

The title compound was obtained as a white solid, 53.3 mg, 24.9%, from Example 274, step 1 and (2R)-3-chloropropane-1,2-diol, following the procedure described in Example 266, step 2. LCMS: m/z=548.4 $[M+H]^+$; 1H NMR (400 MHz, DMSO-$d_6$) δ 9.89 (s, 1H), 8.87 (dd, 1H), 8.82 (s, 1H), 8.38 (d, 1H), 8.06 (dd, 1H), 7.92 (d, 0H), 7.90 (d, 1H), 7.75 (d, 1H), 4.98 (d, 1H), 4.76 (t, 1H), 4.49 (tt, 1H), 4.12 (dd, 1H), 3.94 (dd, 1H), 3.86 (dd, 1H), 3.44-3.36 (m, 1H), 2.35 (s, 3H), 2.24 (s, 3H), 1.42 (p, 2H), 1.32-1.25 (m, 2H).

Example 276

N-(2-chloro-5-(2-cyclopropyl-2H-tetrazol-5-yl)phenyl)-5-(1-(1,3-dihydroxypropan-2-yl)-3,5-dimethyl-1H-pyrazol-4-yl)pyrazolo[1,5-a]pyridine-3-carboxamide

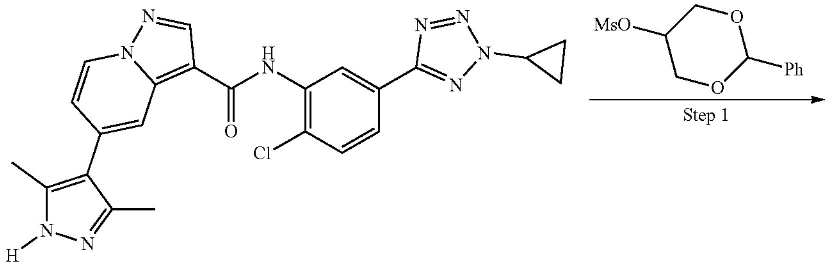

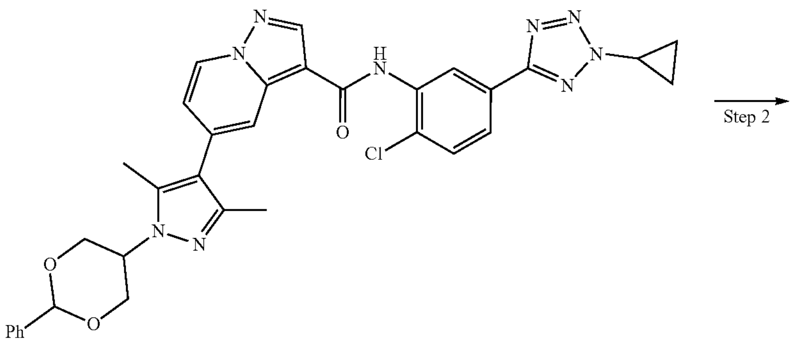

-continued

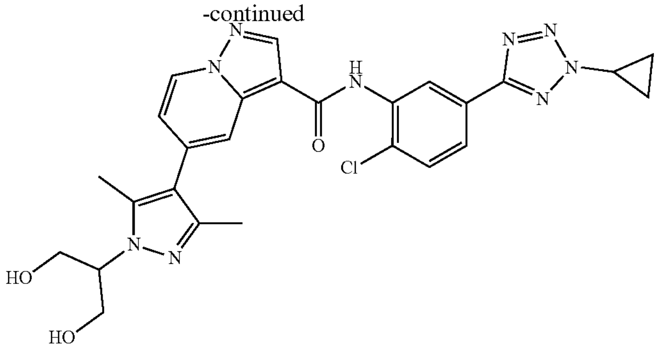

Step 1: Synthesis of N-(2-chloro-5-(2-cyclopropyl-2H-tetrazol-5-yl)phenyl)-5-(3,5-dimethyl-1-(2-phenyl-1,3-dioxan-5-yl)-1H-pyrazol-4-yl)pyrazolo[1,5-a]pyridine-3-carboxamide The reaction mixture of Example 275, step 1 (200 mg, 422 μmol), 2-phenyl-1,3-dioxan-5-yl methanesulfonate (325 mg, 1.26 mmol) and $Cs_2CO_3$ (206 mg, 632 μmol) in DMF (10 mL) was heated at 80° C. for 2 h. The cooled reaction mixture was extracted with EtOAc (3×100 mL) and washed with saturated brine (100 mL). The organic layer was dried with $Na_2SO_4$ and concentrated under vacuum. The crude product was purified by a prep-TLC (DCM:MeOH=30:1) to give the title compound (30 mg, 11%) as a yellow solid. LCMS: m/z=636 [M+H]+

Step 2: Synthesis of N-(2-chloro-5-(2-cyclopropyl-2H-tetrazol-5-yl)phenyl)-5-(1-(1,3-dihydroxypropan-2-yl)-3,5-dimethyl-1H-pyrazol-4-yl)pyrazolo[1,5-a]pyridine-3-carboxamide HCl (2M) in $H_2O$ (2 mL) was added to the product from step 1 (30 mg, 47.1 μmol) in dioxane (2 mL) at 0° C. and the reaction mixture was stirred at rt for 2 h. The reaction was extracted with EtOAc (3×50 mL), the combined organic layer was dried with $Na_2SO_4$ and concentrated under vacuum. The crude product was purified by Prep-HPLC (Method B2, 28% to 53% B) to give the title compound (4.8 mg, 18%) as a white solid. LCMS: m/z=548 [M+H]+$^1$H NMR (400 MHz, DMSO-$d_6$) δ 9.88 (s, 1H), 8.86 (d, 1H), 8.82 (s, 1H), 8.37 (d, 1H), 8.05 (d, 1H), 7.91 (dd, 1H), 7.75 (d, 1H), 7.10 (dt, 1H), 4.99-4.72 (m, 2H), 4.49 (tt, 1H), 4.29-4.07 (m, 1H), 3.99-3.81 (m, 1H), 3.76 (dt, 1H), 3.70-3.64 (m, 1H), 3.38 (dd, 1H), 2.34 (d, 3H), 2.24 (d, 3H), 1.42 (p, 2H), 1.37-1.25 (m, 2H).

Example 277

N-(5-(5-cyclopropyl-2H-tetrazol-2-yl)-2-methylphenyl)-4-fluoro-6-(1-((4-hydroxytetrahydro-2H-pyran-4-yl)methyl)-1H-pyrazol-4-yl)pyrazolo[1,5-a]pyridine-3-carboxamide

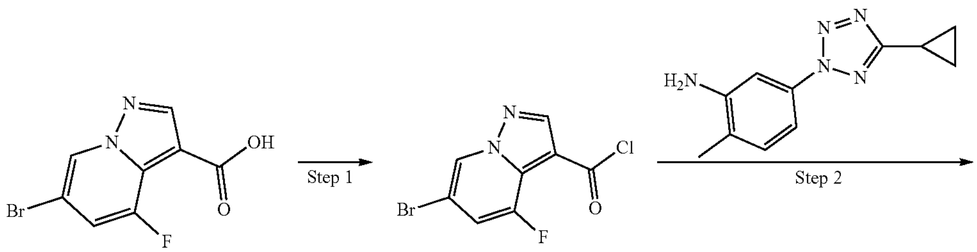

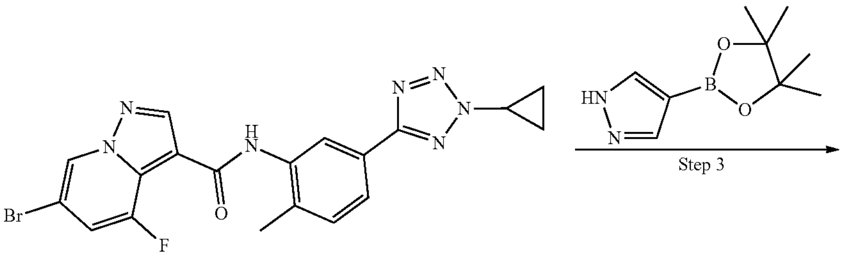

-continued

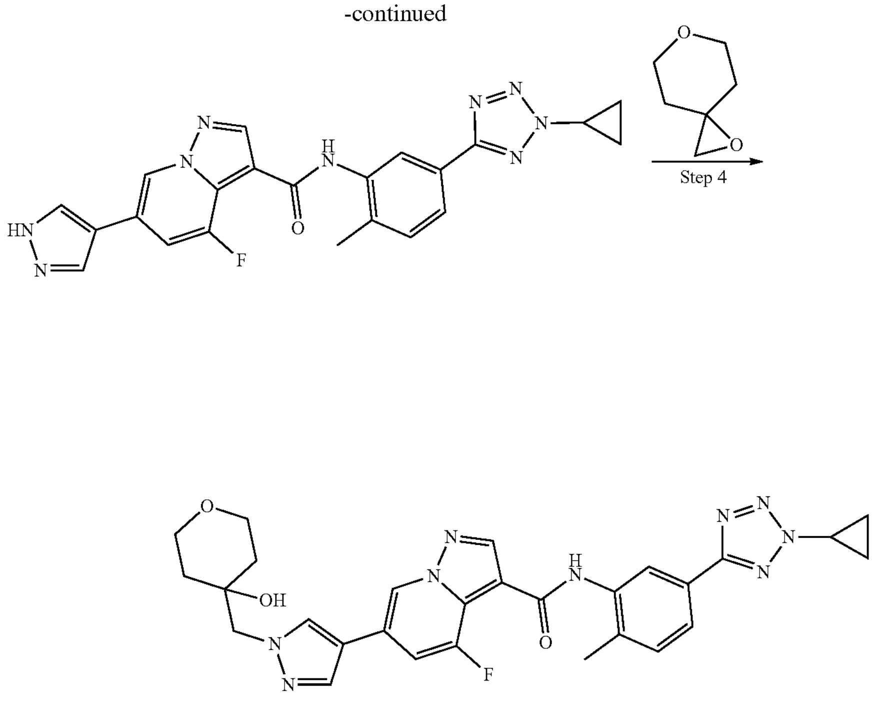

Step 1: Synthesis of 6-bromo-4-fluoropyrazolo[1,5-a]pyridine-3-carbonyl chloride To a suspension of 6-bromo-4-fluoropyrazolo[1,5-a]pyridine-3-carboxylic acid (500 mg, 1.93 mmol) in DCM (6.43 mL), was added oxalyl dichloride (1.93 mL, 3.86 mmol) and a drop of DMF. The reaction mixture was stirred at rt overnight, then evaporated under reduced pressure to give the title compound, (512 mg, crude).

Step 2: Synthesis of 6-bromo-N-(5-(5-cyclopropyl-2H-tetrazol-2-yl)-2-methylphenyl)-4-fluoropyrazolo[1,5-a]pyridine-3-carboxamide To a solution of 5-(2-cyclopropyl-2H-tetrazol-5-yl)-2-methylaniline (180 mg, 0.84 mmol) in pyridine (4 mL) was added 6-bromo-4-fluoropyrazolo[1,5-a]pyridine-3-carbonyl chloride (278 mg, 1.0 mmol) at rt and the reaction stirred for 1 h. The reaction was poured into ice water and the mixture stirred for 30 mins. The resulting solid was filtered off and washed with water to give the title compound (378 mg, crude). LCMS m/z=457 $[M+H]^+$ Step 3: Synthesis of N-(5-(5-cyclopropyl-2H-tetrazol-2-yl)-2-methylphenyl)-4-fluoro-6-(1H-pyrazol-4-yl)pyrazolo[1,5-a]pyridine-3-carboxamide To a solution of 6-bromo-N-(5-(5-cyclopropyl-2H-tetrazol-2-yl)-2-methylphenyl)-4-fluoropyrazolo[1,5-a]pyridine-3-carboxamide (323 mg, 0.71 mmol) and 4-(4,4,5,5-tetramethyl-1,3,2-dioxaborolan-2-yl)-1H-pyrazole (412 mg, 2.12 mmol) in dioxane (2.65 mL) and water (0.885 mL), was added $PdCl_2(dppf)-CH_2Cl_2$ (57.8 mg, 0.071 mmol) and $Na_2CO_3$ (375 mg, 3.54 mmol) and the reaction mixture was stirred at 80° C. overnight. The cooled reaction was diluted with water, the mixture stirred and the resulting solid, filtered off to give the title compound, crude. LCMS m/z=444 $[M+H]^+$ Step 4: Synthesis of N-(5-(5-cyclopropyl-2H-tetrazol-2-yl)-2-methylphenyl)-4-fluoro-6-(1-((4-hydroxytetrahydro-2H-pyran-4-yl)methyl)-1H-pyrazol-4-yl)pyrazolo[1,5-a]pyridine-3-carboxamide To a solution of N-(5-(2-cyclopropyl-2H-tetrazol-5-yl)-2-methylphenyl)-4-fluoro-6-(1H-pyrazol-4-yl)pyrazolo[1,5-a]pyridine-3-carboxamide (50 mg, 0.113 mmol) in DMF (1 mL), was added $K_2CO_3$ (46.7 mg, 0.338 mmol) and 1,6-dioxaspiro[2.5]octane (19.31 mg, 0.169 mmol) and the reaction was stirred at 90° C. overnight. The cooled mixture was filtered and the residue was purified by reverse phase HPLC and further purified by prep-TLC (DCM:MeOH) to give the title compound, 6.3 mg, 10%. LCMS mz=558 [M+H]+; 1H NMR (500 MHz, DMSO-$d_6$) δ 9.72 (s, 1H), 9.13 (s, 1H), 8.60-8.53 (m, 1H), 8.34 (s, 1H), 8.30 (s, 1H), 8.13 (d, 1H), 7.84-7.77 (m, 2H), 7.46 (d, 1H), 4.83 (d, 1H), 4.47 (tt, 1H), 4.12 (s, 2H), 3.62 (d, 4H), 2.38 (s, 3H), 1.59 (dt, 2H), 1.42 (q, 2H), 1.35 (d, 2H), 1.29 (d, 2H).

Example 278

(S)—N-(2-chloro-5-(2-cyclopropyl-2H-tetrazol-5-yl)phenyl)-5-(1-(2-hydroxypropyl)-3-methyl-1H-pyrazol-4-yl)pyrazolo[1,5-a]pyridine-3-carboxamide

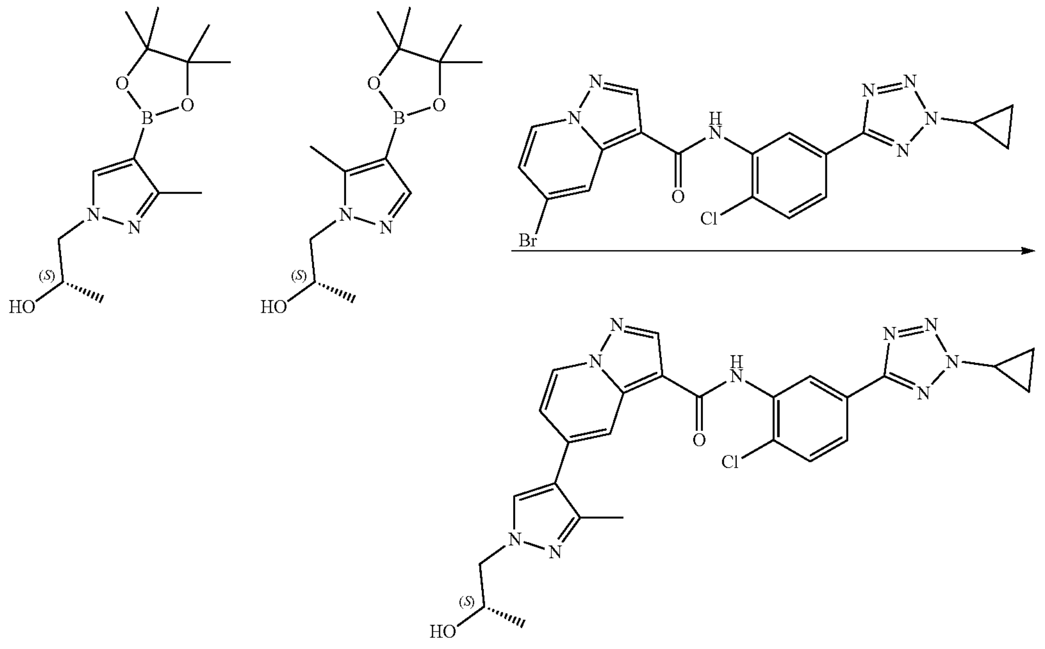

A mixture of Intermediate 47 (150 mg, 327 μmol) and Intermediate 65 (130 mg, 490 μmol), $Cs_2CO_3$ (159 mg, 490 μmol) and Pd(dppf)$Cl_2$ (19 mg, 32.7 μmol) in dioxane (9 mL) and $H_2O$ (3 mL) was stirred at 100° C. for 3 h. The reaction mixture was evaporated under reduced pressure and the residue was purified by prep-TLC with DCM:MeOH=20:1. The product was further purified by prep-SFC (Column: DAICEL DCpak P4VP 3*25 cm, 5 μm; Mobile Phase A: $CO_2$, Mobile Phase B: MeOH (0.1% 2M $NH_3$-MeOH); Flow rate: 60 mL/min; isocratic gradient: 44% B), to afford Peak 1, the title compound (44.5 mg) as an off-white solid. LCMS: m/z=518 $[M+H]^+$; $^1H$ NMR (400 MHz, DMSO-$d_6$) δ 9.86 (s, 1H), 8.86-8.77 (m, 2H), 8.39 (d, 1H), 8.30-8.21 (m, 2H), 7.91 (dd, 1H), 7.76 (d, 1H), 7.29 (dd, 1H), 4.96 (d, 1H), 4.49 (m, 1H), 4.03-3.89 (m, 3H), 2.42 (s, 3H), 1.47-1.32 (m, 2H), 1.34-1.27 (m, 1H), 1.31-1.21 (m, 1H), 1.07 (d, 3H).

Example 279

(R)—N-(2-chloro-5-(2-cyclopropyl-2H-tetrazol-5-yl)-4-fluorophenyl)-5-(1-(2-hydroxy-3-methoxypropyl)-3-methyl-1H-pyrazol-4-yl)pyrazolo[1,5-a]pyridine-3-carboxamide

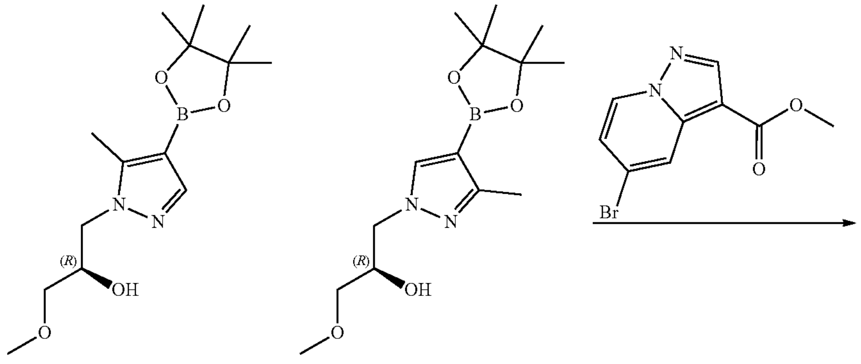

-continued

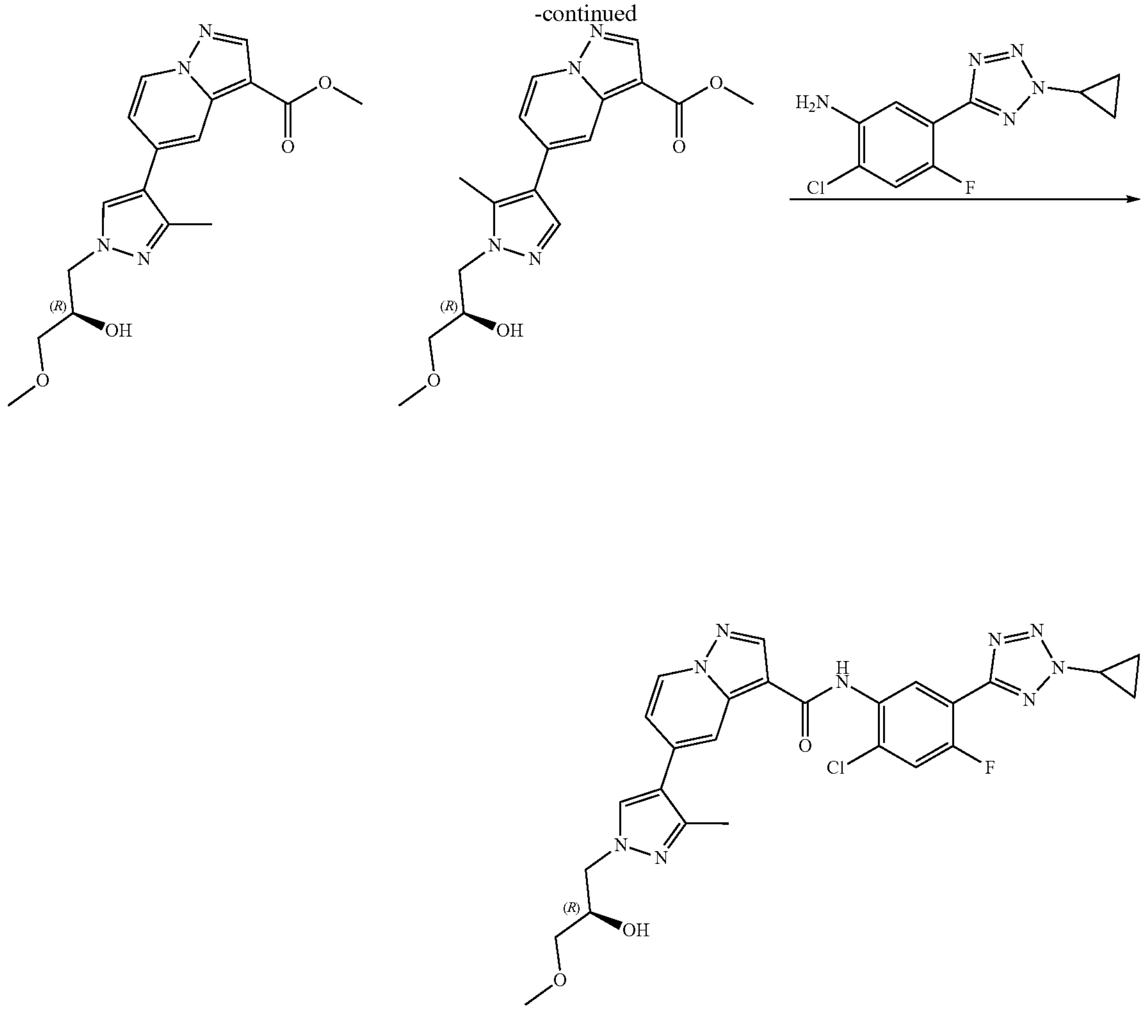

Step 1: Synthesis of methyl (R)-5-(1-(2-hydroxy-3-methoxypropyl)-3-methyl-1H-pyrazol-4-yl)pyrazolo[1,5-a]pyridine-3-carboxylate and methyl (R)-5-(1-(2-hydroxy-3-methoxypropyl)-5-methyl-1H-pyrazol-4-yl)pyrazolo[1,5-a]pyridine-3-carboxylate To a mixture of Intermediate 66 (300 mg, 1.01 mmol) and methyl 5-bromopyrazolo[1,5-a]pyridine-3-carboxylate (334 mg, 1.31 mmol) in $H_2O$ (2 mL) and dioxane (8 mL) was added Pd(dppf)$Cl_2$ (73.2 mg, 101 μmol) and $K_2CO_3$ (418 mg, 3.03 mmol) and the reaction mixture was stirred at 80° C. for 3 h. The mixture was concentrated in vacuo and the residue purified by silica gel column (MeOH:DCM 0:100 to 20:80) to give the title compound (200 mg, 57.6%) as a yellow oil. LCMS: m/z=345 $[M+H]^+$.

Step 2: Synthesis of (R)—N-(2-chloro-5-(2-cyclopropyl-2H-tetrazol-5-yl)-4-fluorophenyl)-5-(1-(2-hydroxy-3-methoxypropyl)-3-methyl-1H-pyrazol-4-yl)pyrazolo[1,5-a]pyridine-3-carboxamide To a mixture of the compound from step 1 (160 mg, 472 μmol) and Intermediate 73 in toluene (5 mL) was added LiHMDS (1 mL) and the reaction mixture stirred at rt for 3 h. The resulting mixture was concentrated under reduced pressure and the residue was purified by silica gel column (DCM:MeOH 100:0 to 90:10). The product was further purified by Prep-HPLC (Method B2, 42% to 72% B). The product was further purified using Prep-Achiral-SFC (Column: GreenSep Naphthyl, 3*25 cm, 5 μm; Mobile Phase A: $CO_2$, Mobile Phase B: MeOH (0.1% 2M $NH_3$-MeOH); Flow rate: 75 mL/min; Gradient: isocratic 30% B; Column Temperature (° C.): 35; and further purified by Chiral-Prep-HPLC (Column: CHIRALPAK IF, 2*25 cm, 5 μm; Mobile Phase A: Hex (0.5% 2M $NH_3$-MeOH), Mobile Phase B: EtOH:DCM=1:1; Flow rate: 20 mL/min; Isocratic Gradient: 50% B in 24 min; to give Peak 1, the title compound (14.4 mg, 23.8%) as a white solid. LCMS: m/z=566 $[M+H]^+$; 1H NMR (400 MHz, DMSO-$d_6$) δ 9.91 (s, 1H), 8.82 (dd, 1H), 8.76 (s, 1H), 8.30 (d, 1H), 8.26 (dd, 1H), 8.21 (s, 1H), 7.84 (d, 1H), 7.28 (dd, 1H), 5.17 (d, 1H), 4.51 (tt, 1H), 4.19-4.08 (m, 1H), 4.05-3.92 (m, 2H), 3.30 (d, 2H), 3.28 (s, 3H), 2.41 (s, 3H), 1.47-1.36 (m, 2H), 1.36-1.24 (m, 2H).

Example 280 (S)—N-(2-chloro-5-(2-cyclopropyl-2H-tetrazol-5-yl)-4-fluorophenyl)-5-(1-(2-hydroxy-propyl)-3-methyl-1H-pyrazol-4-yl)pyrazolo[1,5-a]pyridine-3-carboxamide

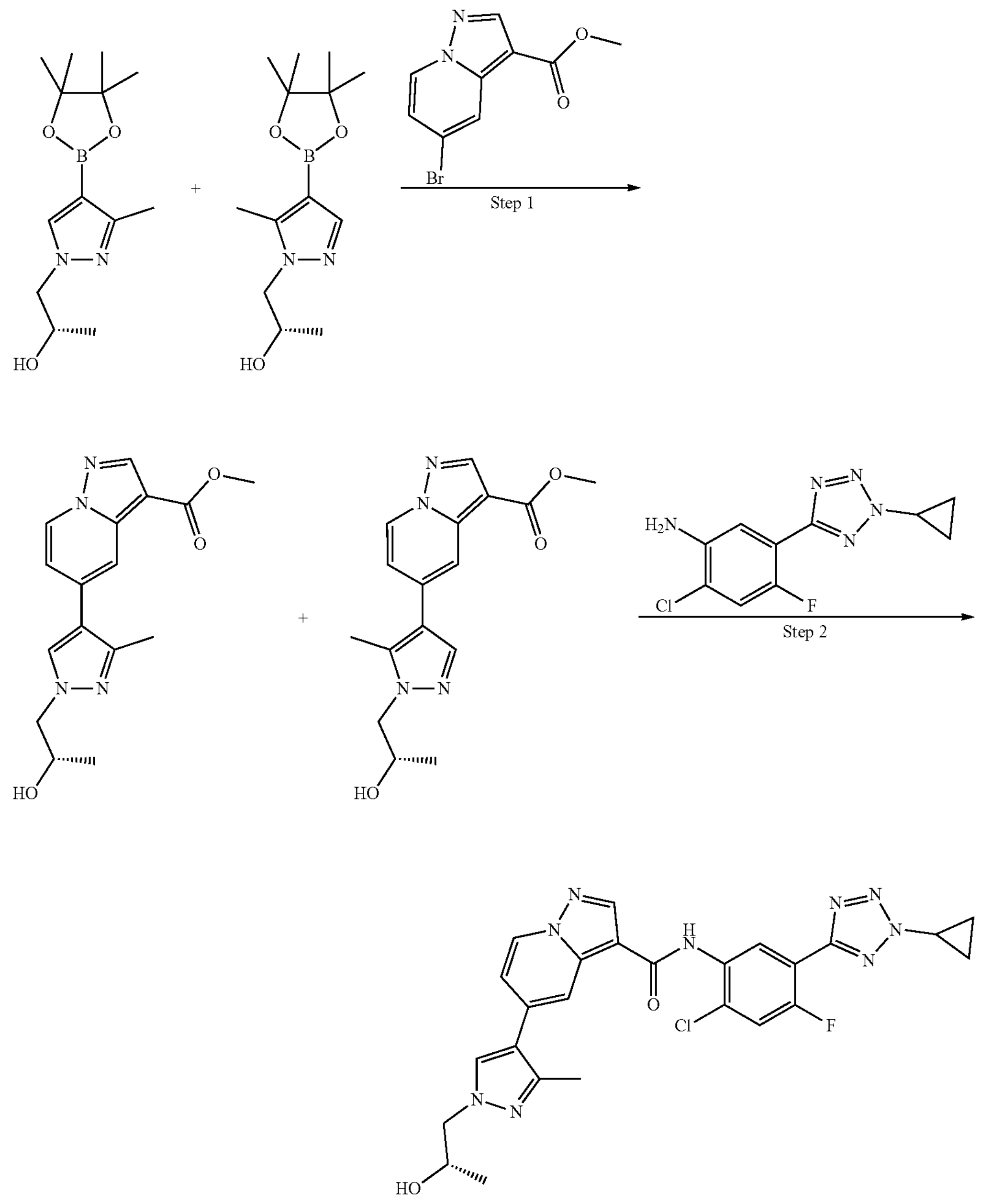

The title compound was obtained as Peak 1, as a white solid, from Intermediate 65, methyl 5-bromopyrazolo[1,5-a]pyridine-3-carboxylate and Intermediate 73, following a similar 2 step procedure as described in Example 279. LCMS: m/z=536 $[M+H]^+$; 1H NMR (400 MHz, $CDCl_3$) δ 9.22 (d, 1H), 8.53 (dd, 1H), 8.39 (d, 1H), 8.30 (s, 1H), 8.01 (s, 1H), 7.74 (s, 1H), 7.37 (d, 1H), 7.07 (dd, 1H), 4.35-4.18 (m, 3H), 4.03 (dd, 1H), 2.55 (s, 3H), 1.62-1.54 (m, 2H), 1.38-1.25 (m, 5H).

Example 281

(R)—N-(2-chloro-5-(2-cyclopropyl-2H-tetrazol-5-yl)-4-fluorophenyl)-5-(1-(2-hydroxypropyl)-3-methyl-1H-pyrazol-4-yl)pyrazolo[1,5-a]pyridine-3-carboxamide

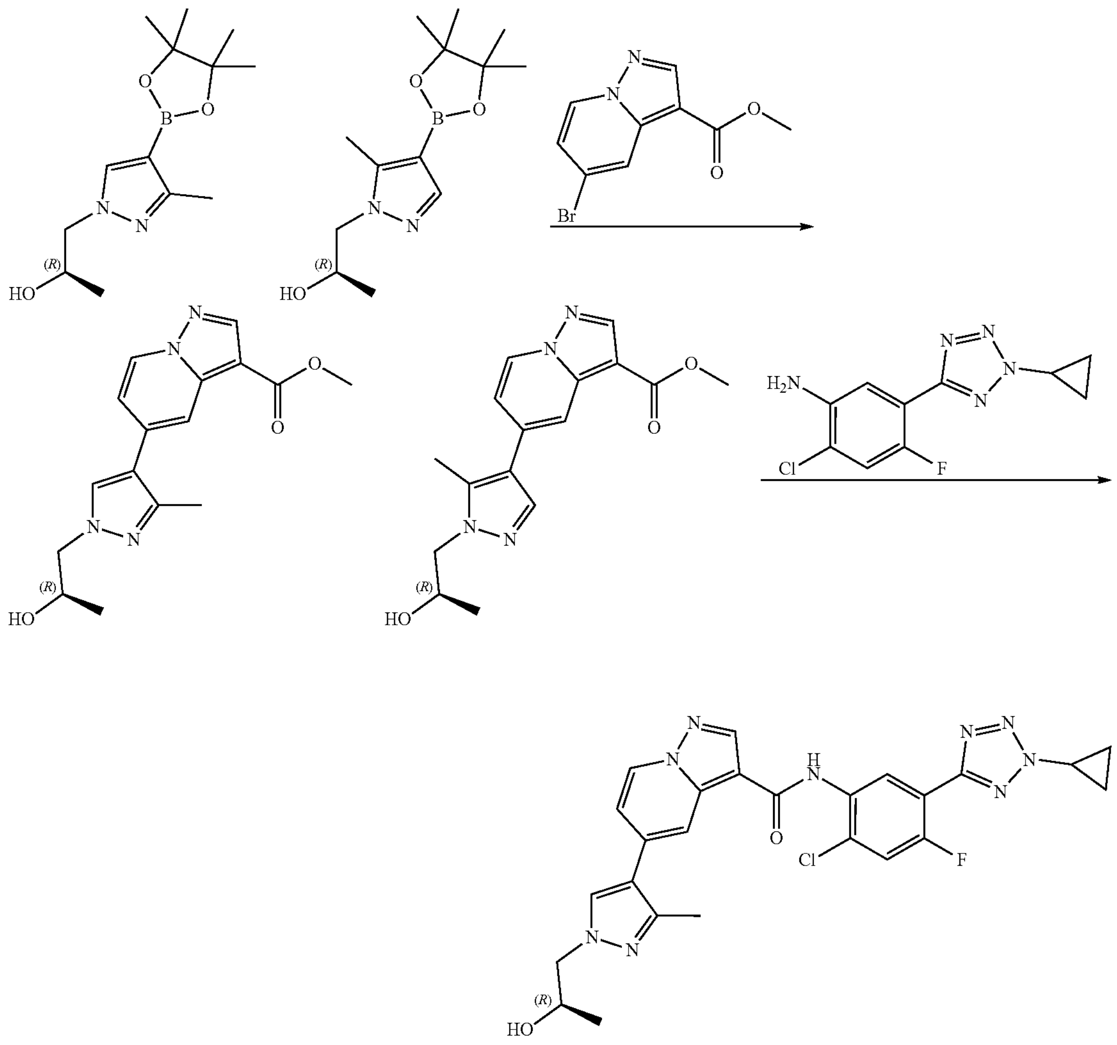

Step 1: Synthesis of methyl (R)-5-(1-(2-hydroxypropyl)-3-methyl-1H-pyrazol-4-yl)pyrazolo[1,5-a]pyridine-3-carboxylate and methyl (R)-5-(1-(2-hydroxypropyl)-5-methyl-1H-pyrazol-4-yl)pyrazolo[1,5-a]pyridine-3-carboxylate The title compound was obtained as a yellow oil, 250 mg, 71%, from Intermediate 63 and methyl 5-bromopyrazolo[1,5-a]pyridine-3-carboxylate, following the procedure described in Example 279, step 1.

Step 2: Synthesis of (R)—N-(2-chloro-5-(2-cyclopropyl-2H-tetrazol-5-yl)-4-fluorophenyl)-5-(1-(2-hydroxypropyl)-3-methyl-1H-pyrazol-4-yl)pyrazolo[1,5-a]pyridine-3-carboxamide To a mixture of the compound from step 1 (100 mg, 394 μmol) and Intermediate 73 (148 mg, 472 μmol) in toluene (10 mL) was added LiHMDS (2 mL) and the reaction mixture was stirred at rt for 16 h. The resulting mixture was concentrated under reduced pressure and the residue was purified by Prep-HPLC (Method B2, 27% to 55% B). The residue was further purified by Prep-Chiral-HPLC (Method P, Gradient: 50% B) to give Peak 1, the title compound, (25.8 mg, 14.8%) as a white solid. LCMS: m/z=536 $[M+H]^+$. 1H NMR (400 MHz, DMSO-$d_6$) δ 9.91 (s, 1H), 8.82 (dd, 1H), 8.76 (s, 1H), 8.30 (d, 1H), 8.27-8.19 (m, 2H), 7.84 (d, 1H), 7.28 (dd, 1H), 4.94 (d, 1H), 4.51 (tt, 1H), 4.05-3.89 (m, 3H), 2.41 (s, 3H), 1.47-1.38 (m, 2H), 1.38-1.21 (m, 3H), 1.07 (d, 3H).

Example 282

(S)—N-(2-chloro-5-(2-ethyl-2H-tetrazol-5-yl)-4-fluorophenyl)-5-(1-(2-hydroxy-3-methoxypropyl)-3-methyl-1H-pyrazol-4-yl)pyrazolo[1,5-a]pyridine-3-carboxamide

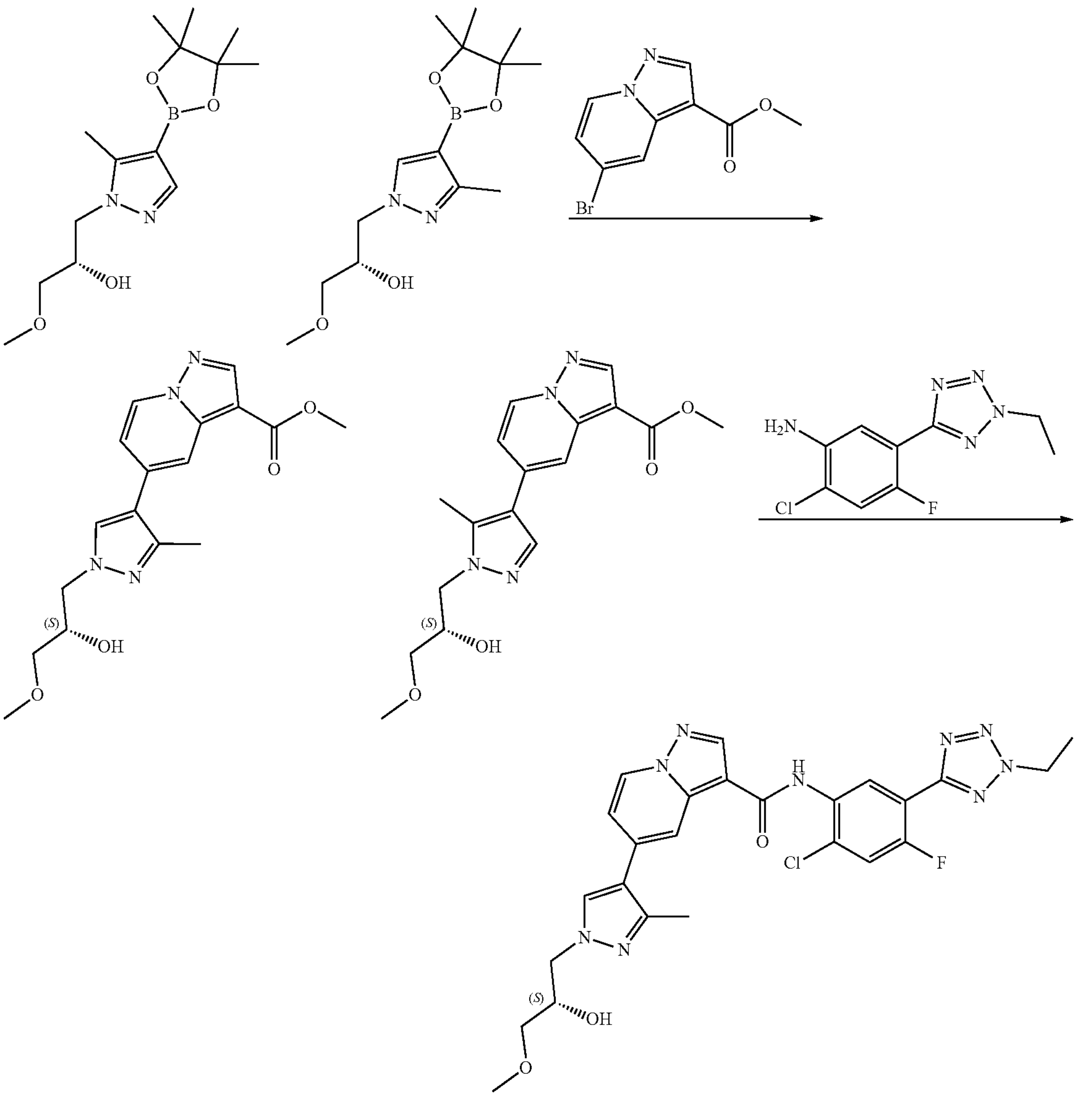

Step 1: Synthesis of methyl (S)-5-(1-(2-hydroxy-3-methoxypropyl)-3-methyl-1H-pyrazol-4-yl)pyrazolo[1,5-a]pyridine-3-carboxylate and methyl (S)-5-(1-(2-hydroxy-3-methoxypropyl)-5-methyl-1H-pyrazol-4-yl)pyrazolo[1,5-a]pyridine-3-carboxylate The title compound was obtained as a yellow solid, 320 mg, 68.9%, from Intermediate 64 (400 mg, 1.35 mmol) and methyl 5-bromopyrazolo[1,5-a]pyridine-3-carboxylate, following a similar procedure to that described in Example 279, step 1. LCMS: m/z=345 $[M+H]^+$.

Step 2: Synthesis of (S)—N-(2-chloro-5-(2-ethyl-2H-tetrazol-5-yl)-4-fluorophenyl)-5-(1-(2-hydroxy-3-methoxypropyl)-3-methyl-1H-pyrazol-4-yl)pyrazolo[1,5-a]pyridine-3-carboxamide The title compound was obtained as Peak 1, as a white solid, 69 mg, 24.2%, from Intermediate 75 and the compound mixture from step 1, following a similar procedure to that described in Example 281, step 2. LCMS: m/z=459 $[M+H]^+$; 1H NMR (400 MHz, DMSO-$d_6$) δ 9.94 (s, 1H), 8.82 (dd, 2H), 8.33 (d, 3H), 7.86 (d, 1H), 7.28 (dd, 1H), 5.20 (d, 1H), 4.81 (q, 2H), 4.19-4.09 (m, 3H), 2.53 (m, 2H), 3.28 (s, 3H), 2.41 (s, 3H), 1.59 (t, 3H).

Example 283

(S)—N-(2-chloro-5-(2-ethyl-2H-tetrazol-5-yl)-4-fluorophenyl)-5-(1-(2-hydroxy-3-(2-methoxyethoxy)propyl)-3-methyl-1H-pyrazol-4-yl)pyrazolo[1,5-a]pyridine-3-carboxamide

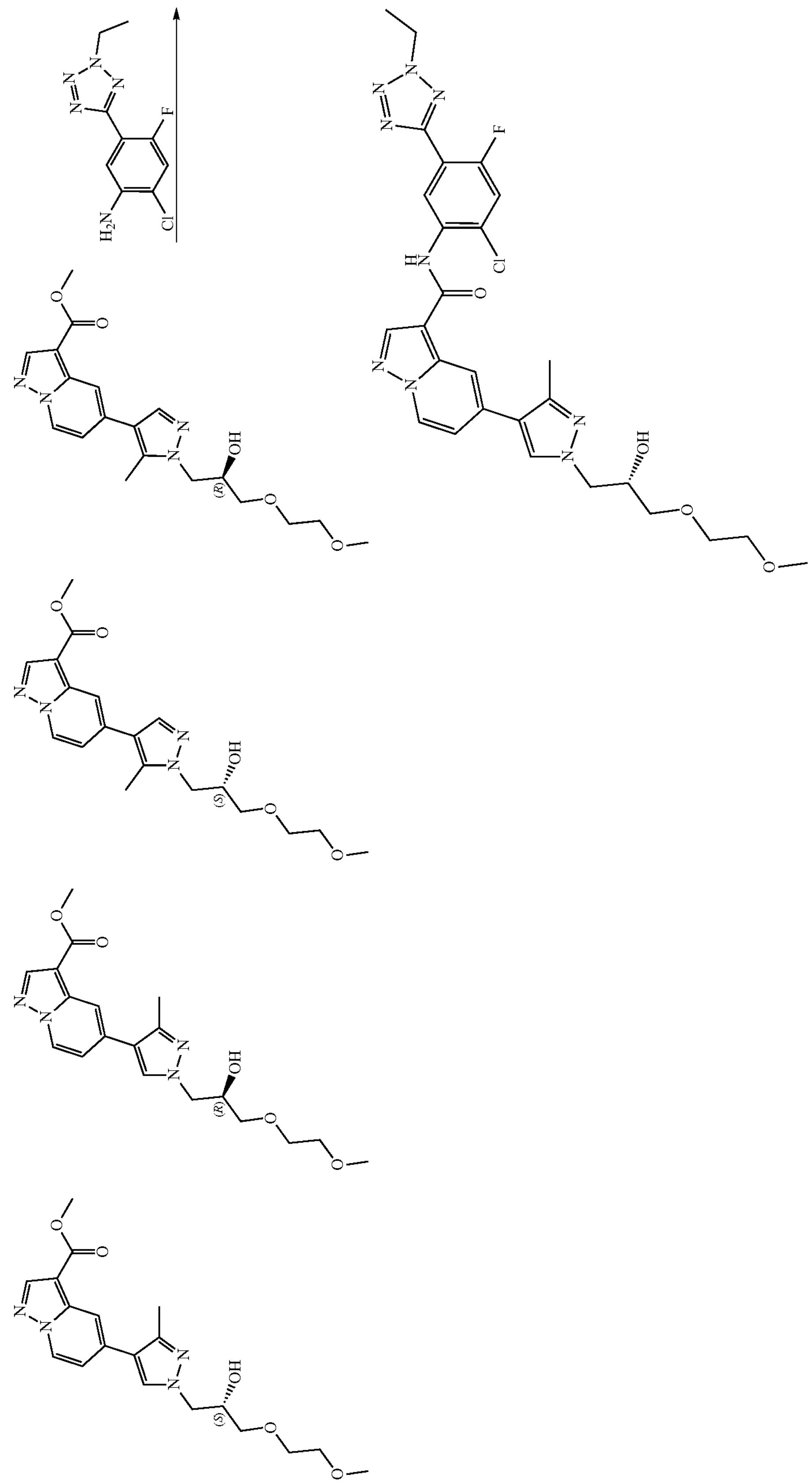

LiHMDS (1 mL, 331 μmol) was added dropwise to a mixture of Intermediate 75 (80 mg, 331 μmol) and Intermediate 69 (128 mg, 331 μmol) in toluene (7 mL) and the reaction mixture was stirred at rt for 16 h under $N_2$. The reaction was diluted with EtOAc (120 mL) and washed with water (60 mL). The organic layer was dried over $Na_2SO_4$, filtered and concentrated under vacuum. The crude product was purified by prep-TLC (DCM:MeOH=20:1) and further purified by prep-HPLC (Column: XBridge Shield RP18 OBD Column, 19*250 mm, 5 μm; Mobile Phase A: Water (0.05% TFA), Mobile Phase B: MeCN; Flow rate: 25 mL/min; Gradient: 39% B to 53% B in 7 min) to give a white solid. This was further purified by HPLC (Method P, Gradient: 50% B), to give Peak 1, (S)—N-(2-chloro-5-(2-ethyl-2H-tetrazol-5-yl)-4-fluorophenyl)-5-(1-(2-hydroxy-3-(2-methoxyethoxy)propyl)-3-methyl-1H-pyrazol-4-yl)pyrazolo[1,5-a]pyridine-3-carboxamide (20.1 mg, ee %: 50%) as a white solid.

This product was separated by Prep-Chiral-HPLC (Method R, Isocratic Gradient: 60% B) to give Peak 1, the title compound, 11.6 mg. LCMS: m/z=598 $[M+H]^+$, 1H NMR (400 MHz, DMSO-$d_6$) δ 9.93 (s, 1H), 8.86-8.80 (m, 1H), 8.77 (s, 1H), 8.33 (d, 1H), 8.26 (s, 1H), 8.22 (s, 1H), 7.86 (d, 1H), 7.28 (dd, 1H), 5.18 (d, 1H), 4.81 (q, 2H), 4.21-4.08 (m, 1H), 3.98 (d, 2H), 3.54 (dd, 2H), 3.49-3.42 (m, 2H), 3.25 (s, 2H), 3.17 (d, 3H), 2.41 (s, 3H), 1.59 (t, 3H), 1.23 (s, 1H).

Example 284

(S)—N-(2-chloro-5-(2-ethyl-2H-tetrazol-5-yl)phenyl)-5-(1-(2-hydroxy-3-methoxypropyl)-3-methyl-1H-pyrazol-4-yl)pyrazolo[1,5-a]pyridine-3-carboxamide

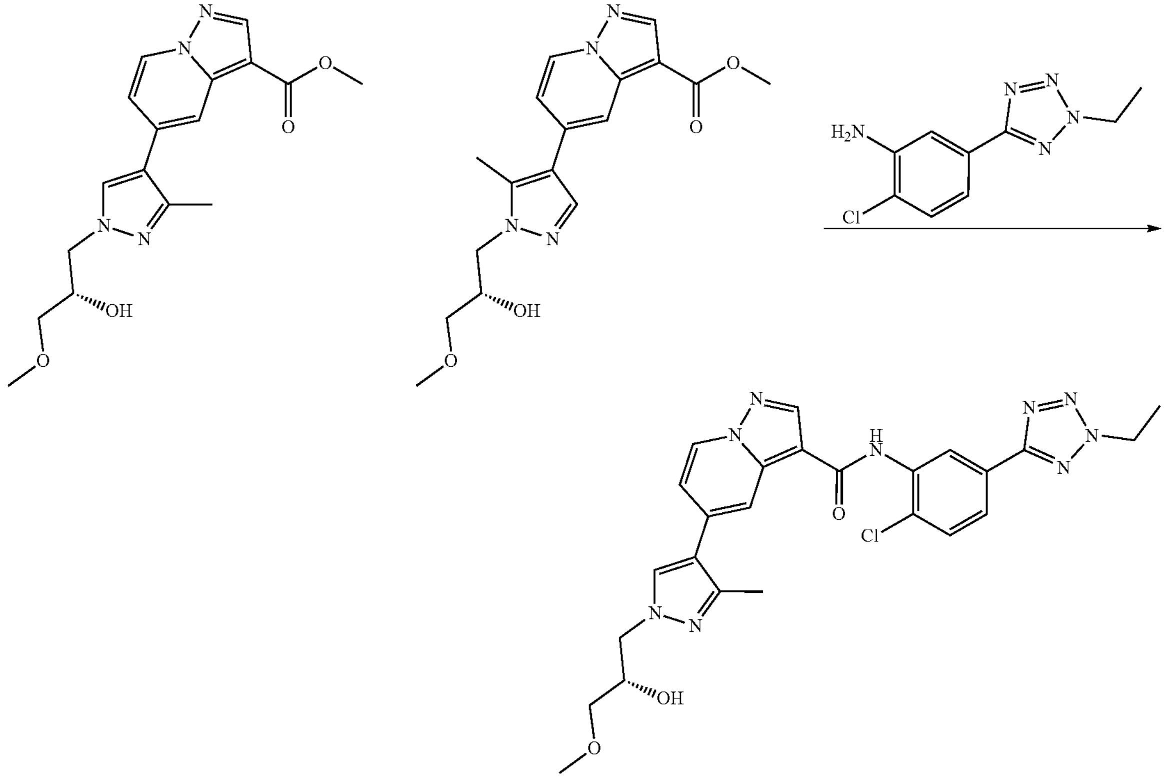

To a mixture of Example 282, step 1 (200 mg, 580 μmol) and Intermediate 74 (150 mg, 670 μmol) in toluene (10 mL) was added $AlMe_3$ (1M in Tol, 2 mL) and the reaction mixture stirred at 100° C. for 2 h. The reaction was quenched with water and the mixture evaporated under reduced pressure. The residue was purified on prep-TLC (DCM:MeOH=30:1) and separated by achiral-SFC (Column: YMC-Pack Polyamine II 3*25 cm, 5 μm; Mobile Phase A: $CO_2$, Mobile Phase B: MeCN:MeOH=4:1 (0.1% 2M NH3-MeOH); Flow rate: 75 mL/min; Gradient: isocratic 25% B; to afford peak 1, the title compound. LCMS: m/z=536 $[M+H]^+$; 1H NMR (400 MHz, DMSO-$d_6$) δ 9.86 (s, 1H), 8.83 (d, 1H), 8.80 (s, 1H), 8.42 (d, 1H), 8.28 (d, 1H), 8.22 (s, 1H), 7.93 (dd, 1H), 7.76 (d, 1H), 7.29 (dd, 1H), 5.19 (d, 1H), 4.78 (q, 2H), 4.20-4.09 (m, 1H), 4.02-3.93 (m, 2H), 3.30 (m, 2H), 3.29 (s, 3H), 2.42 (s, 3H), 1.59 (t, 3H).

Example 285

(S)—N-(2-chloro-5-(2-cyclopropyl-2H-tetrazol-5-yl)-4-fluorophenyl)-5-(1-(2-hydroxy-3-(2-methoxy-ethoxy)propyl)-3-methyl-1H-pyrazol-4-yl)pyrazolo[1,5-a]pyridine-3-carboxamide And Example 286

(R)—N-(2-chloro-5-(2-cyclopropyl-2H-tetrazol-5-yl)-4-fluorophenyl)-5-(1-(2-hydroxy-3-(2-methoxy-ethoxy)propyl)-3-methyl-1H-pyrazol-4-yl)pyrazolo[1,5-a]pyridine-3-carboxamide

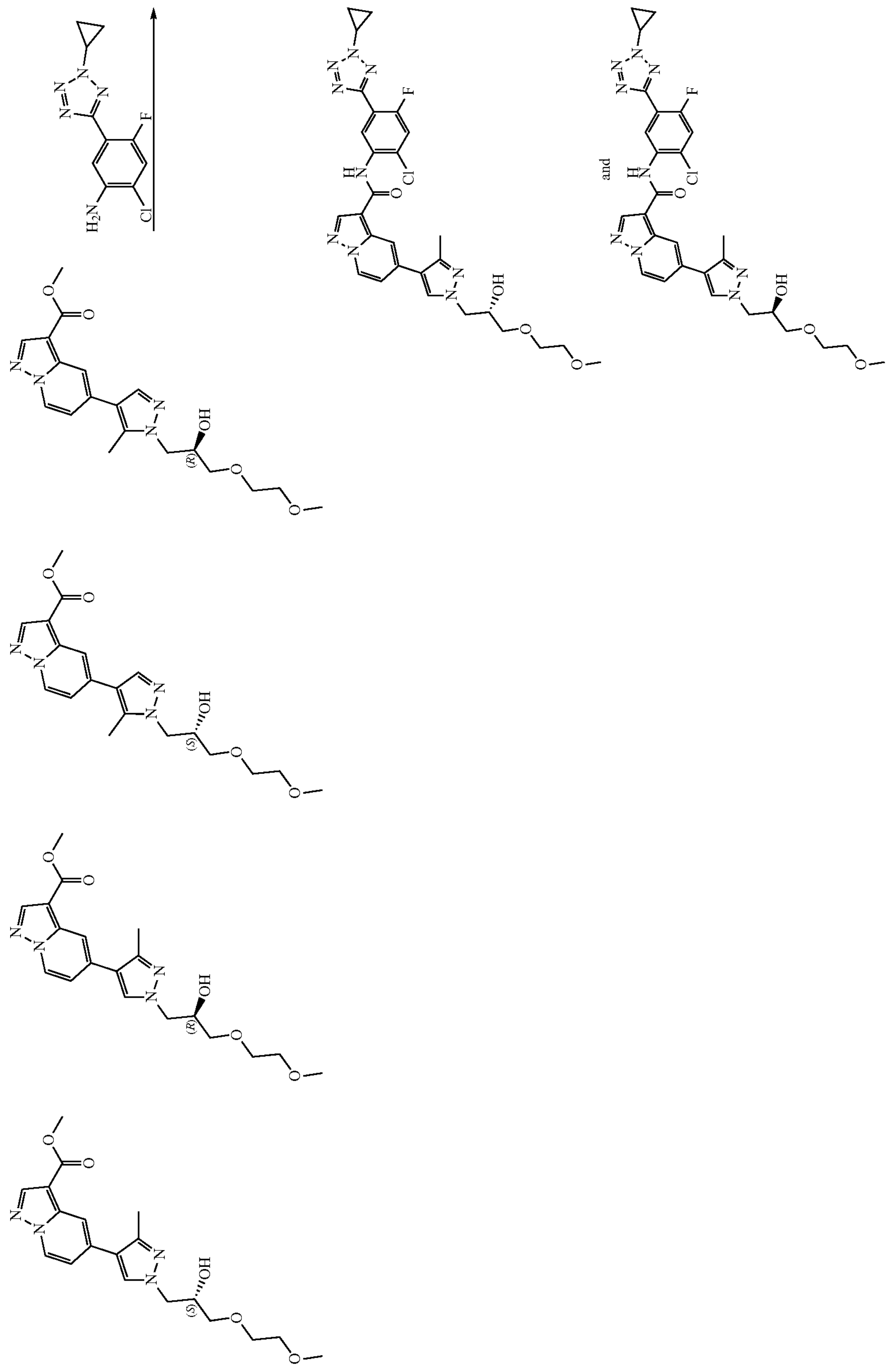
and

To a solution of Intermediate 69 (330 mg, 849 μmol) and Intermediate 73 (279 mg, 1.10 mmol) in toluene (10 mL) was added $AlMe_3$ (1 mL) at 0° C. under $N_2$ and the reaction mixture was heated at 100° C. for 16 h. The cooled mixture was extracted with EtOAc (3×100 mL), the combined organic layers were washed with brine (2×100 mL) dried over anhydrous $Na_2SO_4$ and concentrated under reduced pressure. The residue was purified by Prep-HPLC (Method B2, 27% to 57% B) and the product was further purified by Prep-achiral-SFC (Column: DAICEL DCpak P4VP 3*25 cm, 5 μm; Mobile Phase A: $CO_2$, Mobile Phase B: MeOH (0.1% 2M $NH_3$-MeOH); Flow rate: 60 mL/min; isocratic Gradient 37% B, to give N-(2-chloro-5-(2-cyclopropyl-2H-tetrazol-5-yl)-4-fluorophenyl)-5-(1-(2-hydroxy-3-(2-methoxyethoxy)propyl)-3-methyl-1H-pyrazol-4-yl)pyrazolo[1,5-a]pyridine-3-carboxamide (60 mg, ee %: 50%) as a white solid and N-(2-chloro-5-(2-cyclopropyl-2H-tetrazol-5-yl)-4-fluorophenyl)-5-(1-(2-hydroxy-3-(2-methoxyethoxy)propyl)-5-methyl-1H-pyrazol-4-yl)pyrazolo[1,5-a]pyridine-3-carboxamide (35 mg, ee %: 50%) as a white solid.

N-(2-chloro-5-(2-cyclopropyl-2H-tetrazol-5-yl)-4-fluorophenyl)-5-(1-(2-hydroxy-3-(2-methoxyethoxy)propyl)-3-methyl-1H-pyrazol-4-yl)pyrazolo[1,5-a]pyridine-3-carboxamide (60 mg, ee %: 50%) was further purified by Prep-Chiral-HPLC (Method Q, Gradient: 50% B) to give Peak 1, (S)—N-(2-chloro-5-(2-cyclopropyl-2H-tetrazol-5-yl)-4-fluorophenyl)-5-(1-(2-hydroxy-3-(2-methoxyethoxy)propyl)-3-methyl-1H-pyrazol-4-yl)pyrazolo[1,5-a]pyridine-3-carboxamide (32.3 mg, 16.1%) as a white solid. Absolute configuration was assigned based on enantiopure epoxide used as the starting material for Intermediate 69. LCMS: m/z=610 $[M+H]^+$; 1H NMR (400 MHz, DMSO-$d_6$) δ 9.91 (s, 1H), 8.82 (d, 1H), 8.76 (s, 1H), 8.30 (d, 1H), 8.26 (d, 1H), 8.21 (s, 1H), 7.84 (d, 1H), 7.28 (dd, 1H), 5.16 (d, 1H), 4.51 (tt, 1H), 4.21-4.10 (m, 1H), 3.98 (qd, 2H), 3.55 (dd, 2H), 3.46 (dd, 2H), 3.37 (dd, 2H), 3.25 (s, 3H), 2.41 (s, 3H), 1.47-1.33 (m, 2H), 1.33-1.21 (m, 2H). and Peak 2, (R)—N-(2-chloro-5-(2-cyclopropyl-2H-tetrazol-5-yl)-4-fluorophenyl)-5-(1-(2-hydroxy-3-(2-methoxyethoxy)propyl)-3-methyl-1H-pyrazol-4-yl)pyrazolo[1,5-a]pyridine-3-carboxamide (10.9 mg, 5.42%) as a white solid. LCMS: m/z=610 $[M+H]^+$; 1H NMR (400 MHz, DMSO-$d_6$) δ 9.91 (s, 1H), 8.82 (dd, 1H), 8.76 (s, 1H), 8.30 (d, 1H), 8.26 (dd, 1H), 8.21 (s, 1H), 7.84 (d, 1H), 7.28 (dd, 1H), 5.16 (d, 1H), 4.51 (tt, 1H), 4.21-4.10 (m, 1H), 4.03-3.93 (m, 2H), 3.58-3.51 (m, 2H), 3.46 (dd, 2H), 3.37 (dd, 2H), 3.25 (s, 3H), 2.41 (s, 3H), 1.42 (p, 2H), 1.37-1.25 (m, 2H).

Example 287

N-(2-chloro-5-(2-cyclopropyl-2H-tetrazol-5-yl)-4-fluorophenyl)-5-(1-((2R,3R)-3-hydroxybutan-2-yl)-3-methyl-1H-pyrazol-4-yl)pyrazolo[1,5-a]pyridine-3-carboxamide or N-(2-chloro-5-(2-cyclopropyl-2H-tetrazol-5-yl)-4-fluorophenyl)-5-(1-((2S,3S)-3-hydroxybutan-2-yl)-3-methyl-1H-pyrazol-4-yl)pyrazolo[1,5-a]pyridine-3-carboxamide And Example 288

N-(2-chloro-5-(2-cyclopropyl-2H-tetrazol-5-yl)-4-fluorophenyl)-5-(1-((2S,3S)-3-hydroxybutan-2-yl)-3-methyl-1H-pyrazol-4-yl)pyrazolo[1,5-a]pyridine-3-carboxamide or N-(2-chloro-5-(2-cyclopropyl-2H-tetrazol-5-yl)-4-fluorophenyl)-5-(1-((2R,3R)-3-hydroxybutan-2-yl)-3-methyl-1H-pyrazol-4-yl)pyrazolo[1,5-a]pyridine-3-carboxamide

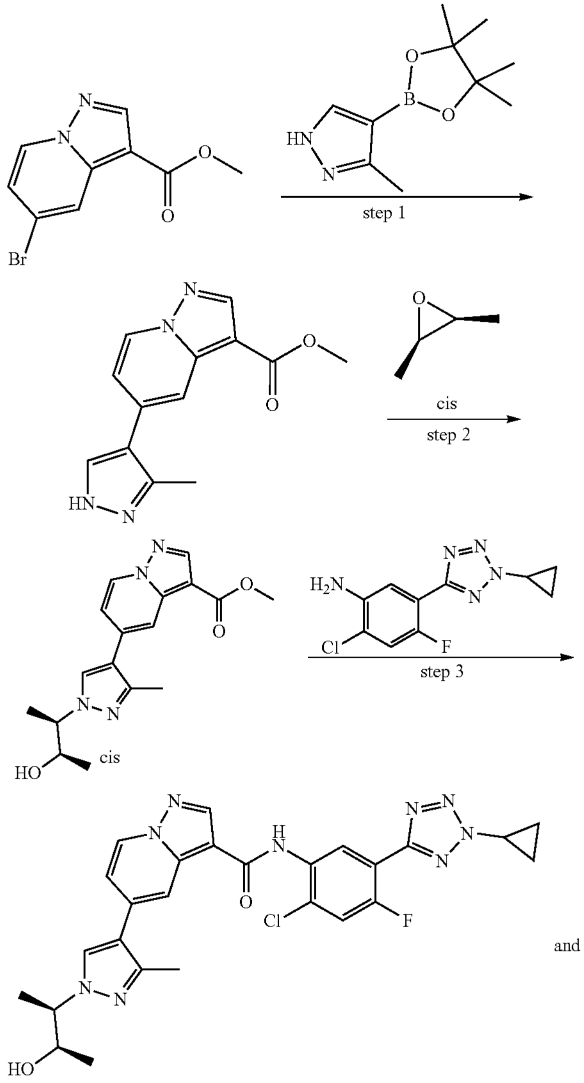

and

-continued

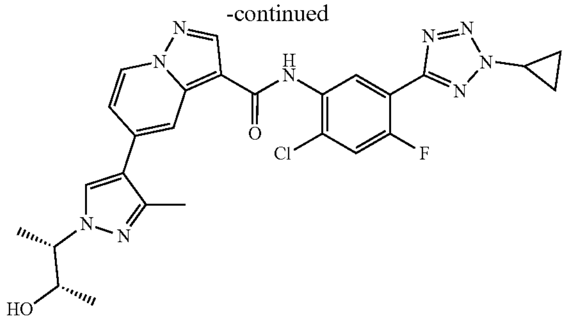

Step 1: Synthesis of methyl 5-(3-methyl-1H-pyrazol-4-yl)pyrazolo[1,5-a]pyridine-3-carboxylate The title compound was obtained as a yellow solid, 400 mg, 66.4%, from methyl 5-bromopyrazolo[1,5-a]pyridine-3-carboxylate and 3-methyl-4-(4,4,5,5-tetramethyl-1,3,2-dioxaborolan-2-yl)-1H-pyrazole, following a similar procedure to that described in Example 279, step 1. LCMS: m/z=257 $[M+H]^+$.

Step 2: Synthesis of Rac-methyl 5-(1-((2R,3R)-3-hydroxybutan-2-yl)-3-methyl-1H-pyrazol-4-yl)pyrazolo[1,5-a]pyridine-3-carboxylate The title compound was obtained as a yellow solid, 100 mg, 39%, from methyl 5-(3-methyl-1H-pyrazol-4-yl)pyrazolo[1,5-a]pyridine-3-carboxylate and (2R,3S)-2,3-dimethyloxirane, following a similar procedure to that described in Intermediate 50. LCMS: m/z=329 $[M+H]^+$.

Step 3: Synthesis of N-(2-chloro-5-(2-cyclopropyl-2H-tetrazol-5-yl)-4-fluorophenyl)-5-(1-((2R,3R)-3-hydroxybutan-2-yl)-3-methyl-1H-pyrazol-4-yl)pyrazolo[1,5-a]pyridine-3-carboxamide and N-(2-chloro-5-(2-cyclopropyl-2H-tetrazol-5-yl)-4-fluorophenyl)-5-(1-((2S,3S)-3-hydroxybutan-2-yl)-3-methyl-1H-pyrazol-4-yl)pyrazolo[1,5-a]pyridine-3-carboxamide $Me_3Al$ (0.4 mL, 788 μmol, 2 M) was added to a mixture of the compound from step 2 (90 mg, 274 μmol), and Intermediate 73 (69.5 mg, 274 μmol) in toluene (5 mL) at 0° C., and the reaction mixture was stirred at 100° C. for 3 h under $N_2$. The cooled mixture was diluted with EtOAc (10 mL) and washed with water (10 mL). The aqueous phase was extracted with EtOAc (3×15 mL) and the combined organic phase was washed with brine, dried with $Na_2SO_4$ and concentrated under vacuum. The residue was purified by Prep-TLC (DCM:MeOH=10:1) and the product further purified by prep-HPLC (Method R, Isocratic Gradient: 40% B) to give Peak 1, Example 287 (9.1 mg, 6%) as a white solid and Peak 2, Example 288 (10.4 mg, 6.9%) as a white solid.

Peak 1: LCMS: m/z=550 $[M+H]^+$; 1H NMR (400 MHz, DMSO-$d_6$) δ 9.93 (s, 1H), 8.93-8.71 (m, 2H), 8.36-8.17 (m, 3H), 7.85 (d, 1H), 7.31 (dd, 1H), 4.86 (d, 1H), 4.52 (tt, 1H), 4.15 (p, 1H), 3.88 (q, 1H), 2.41 (s, 3H), 1.47-1.35 (m, 5H), 1.30 (td, 2H), 1.02 (d, 3H).

Peak 2, LCMS: m/z=550 $[M+H]^+$; 1H NMR (400 MHz, DMSO-$d_6$) δ 9.86 (s, 1H), 8.75 (d, 1H), 8.69 (s, 1H), 8.23 (d, 1H), 8.20-8.15 (m, 2H), 7.79 (d, 1H), 7.25 (dd, 1H), 4.80 (d, 1H), 4.45 (tt, 1H), 4.08 (p, 1H), 3.82 (q, 1H), 2.34 (s, 3H), 1.34 (dd, 5H), 1.23 (td, 2H), 0.96 (d, 3H).

Example 289

N-(2-chloro-5-(2-cyclopropyl-2H-tetrazol-5-yl)-4-fluorophenyl)-5-(1-((2R,3S)-3-hydroxybutan-2-yl)-3-methyl-1H-pyrazol-4-yl)pyrazolo[1,5-a]pyridine-3-carboxamide or N-(2-chloro-5-(2-cyclopropyl-2H-tetrazol-5-yl)-4-fluorophenyl)-5-(1-((2S,3R)-3-hydroxybutan-2-yl)-3-methyl-1H-pyrazol-4-yl)pyrazolo[1,5-a]pyridine-3-carboxamide

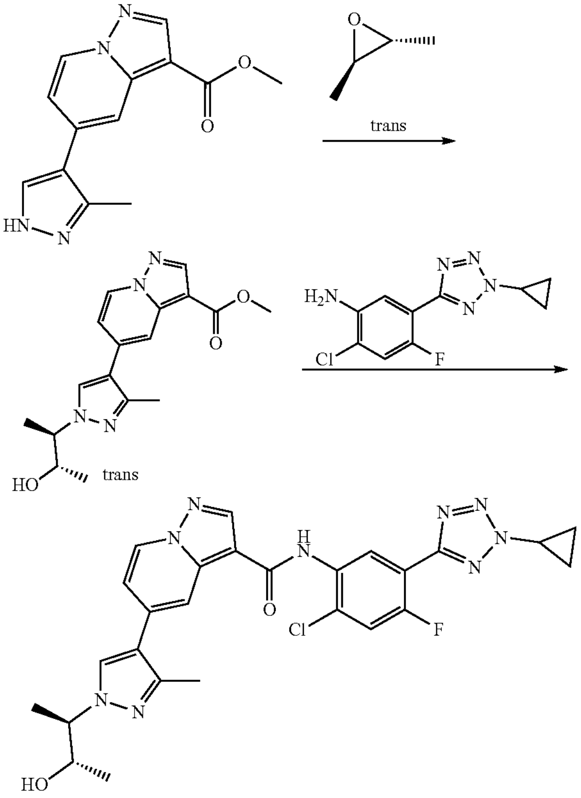

or

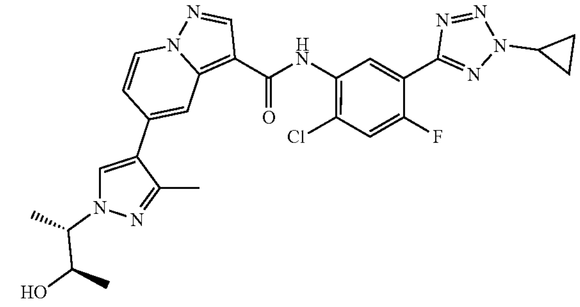

Step 1: Synthesis of Rac methyl 5-(1-((2R,3)-3-hydroxybutan-2-yl)-3-methyl-1H-pyrazol-4-yl)pyrazolo[1,5-a]pyridine-3-carboxylate The title compound was obtained, 100 mg, 39%, from trans-2,3-dimethyloxirane and Example 287 and 288, step 1, following the procedure described in Example 287 and 288, step 2. LCMS m/z=329 $[M+H]^+$ Step 2: Synthesis of N-(2-chloro-5-(2-cyclopropyl-2H-tetrazol-5-yl)-4-fluorophenyl)-5-(1-((2R,3S)-3-hydroxybutan-2-yl)-3-methyl-1H-pyrazol-4-yl)pyrazolo[1,5-a]pyridine-3-carboxamide or N-(2-chloro-5-(2-cyclopropyl-2H-tetrazol-5-yl)-4-fluorophenyl)-5-(1-((2S,3R)-3-hydroxybutan-2-yl)-3-methyl-1H-pyrazol-4-yl)pyrazolo[1,5-a]pyridine-3-carboxamide Rac-N-(2-chloro-5-(2-cyclopropyl-2H-tetrazol-5-yl)-4-fluorophenyl)-5-(1-((2R,3S)-3-hydroxybutan-2-yl)-3-methyl-1H-pyrazol-4-yl)pyrazolo[1,5-a]pyridine-3-carboxamide was obtained from the compound from step 1 and Intermediate 73, following a similar procedure to that described in Example 287 and 288, step 3. The racemate was separated by Chiral Prep-Chiral-HPLC (Method Q, Isocratic Gradient: 40% B) to give Peak 1, the title compound, 6.5 mg, 4.3% as a white solid. LCMS: m/z=550 $[M+H]^+$; 1H NMR (400 MHz, DMSO-$d_6$) δ 9.92 (s, 1H), 8.84-8.74 (m, 2H), 8.33-8.22 (m, 3H), 7.85 (d, 1H), 7.30 (dd, 1H), 4.97 (d, 1H), 4.51 (tt, 1H), 4.07 (p, 1H), 3.88-3.80 (m, 1H), 2.41 (s, 3H), 1.48-1.40 (m, 5H), 1.30 (td, 2H), 0.92 (d, 3H).

Example 290—Compounds of the Disclosure Inhibit Wild Type c-Kit in a Biochemical Phospho c-Kit Inhibition Assay The ability of compounds of the disclosure (described herein as test compounds) to inhibit autophosphorylation of wild type c-kit was measures using either a PathScan phospho c-kit (Tyr719) sandwich ELISA (CST #7298) or a Phospho c-Kit (Tyr721) Assay Whole Cell Lysate Kit (MSD: 515DPD/catalog number K15119D-2).

For the PathScan phospho c-kit (Tyr719) sandwich ELISA: M-07e cells were resuspended at $2\times10^6$ cells/mL in phenol red free, serum-free, GM-CSF-free Iscove's Modified Dulbecco's Medium (IMDM) media with 1% Penicillin-Streptomycin. The cells were then dispensed into the wells of a U-bottom, 96-well plate at 50 uL per well using a multichannel pipet. The plate was allowed to incubate at 37° C. in a humidified tissue culture incubator for 4 hours.

After 4 hours of incubation, each well was dosed with 6.25 uL of test compound at a final DMSO concentration of 0.25% for 60 min at 37° C. to generate an 8-point dose concentration series of test compounds in duplicate. Cells were then incubated for 1 hour at 37° C. in a humidified tissue culture incubator. Next, human SCF at 500 ng/mL was added to the appropriate wells at 6.25 uL/well and the plate was shaken at 450 rpm at room temperature for 10 minutes. AlphaLISA 5× Lysis Buffer supplemented with 1× protease and phosphatase inhibitor was then added at 16 uL/well. The plate was sealed with an adherent cover and shaken at 4° C. at 600 rpm for 30 minutes. After this period of lysis, the plate was stored at −80° C.

When the 96-well plate containing M07e lysates was ready to be processed, the plate was brought to room temperature and 40 μl from each well was transferred to the wells of a PathScan Phospho-c-Kit (Tyr719) Sandwich ELISA plate (CST, Catalog #7298). The ELISA plate was sealed with an adherent cover and incubated for 2 hours at 37° C. Next, the wells were washed 4 times with the provided 1× Wash Buffer, and 100 uL/well of reconstituted Detection Antibody was added to each well, the plate sealed with an adherent cover, and incubated at 37° C. for 1 hour. The wash procedure was repeated and 100 uL/well of reconstituted HRP-Linked secondary antibody was added. The plate was sealed with an adherent cover and incubated at 37° C. for 1 hour. The wash procedure was repeated and 100 uL/well of TMB Substrate was added. The plate was incubated for 10 minutes at room temperature or until the positive reaction elicited a blue color in the appropriate wells. 100 uL/well of STOP solution was added and shaken gently for a few seconds a microplate reader or conventional spectrophotometer e.g., a Perkin Elmer Envision multimode plate reader, part #2105-0010.

For the MSD Phospho c-Kit (Tyr721) Assay Whole Cell Lysate Kit: M-07e cells were maintained in Iscove's Modified Dulbecco's Medium (IMDM) media supplemented with 10% FBS, 5 ng/ml granulocyte-macrophage colony-stimulating factor (GM-CSF) and 100 units/mL Penicillin-Streptomycin, and grown in a 37° C., 5% CO2 in a humidified tissue culture incubator. M-07e cells were washed with phenol red-free, serum-free, GM-CSF-free IMDM and seeded in the same media at 100,000 cells well in a volume of 50 ul in a 96-well U-bottom plate. The cells were incubated for 4 hours, followed by the addition of test compound at a final DMSO concentration of 0.25% for 60 min at 37° C. to generate an 8-point dose concentration series of test compounds. The cells were stimulated with 50 ng/ml human SCF for 10 min at room temperature. Cells were then lysed by the addition of 16.5 ul of PerkinElmer 5× AlphaLISA Lysis Buffer supplemented with Cell Signaling Technologies protease/phosphatase inhibitor. Lysis was encouraged by shaking at 4° C. for 30 minutes.

25 ul of lysate was transferred to the MSD plate and the plate was shaken at 700 rpm at room temperature for one hour, followed by washing 3 times with Tris wash buffer. Next, 25 ul of detection antibody solution (diluted from 50× stock in antibody dilution buffer) was added. After shaking at 700 rpm at room temperature for one hour, the plate was washed 3 times with Tris wash buffer. The plate was then read on MSD Sector Imager immediately after 150 ul of reading buffer added to each well.

For both assays, the raw data was normalized using the values derived with 10 μM staurosporine as 100% inhibition of c-kit phosphorylation and DMSO as 0% inhibition of c-kit phosphorylation. An IC50 was calculated using a 4-parameter logistic nonlinear regression.

Table 2 shows the activity of the exemplified compounds in the pKIT assay according to the ELISA assay (or Meso Scale Discovery (MSD) assay if marked with *) described herein.

Some compounds of the disclosure are substrates of the human P-glycoprotein (P-gp). The potential for compounds prepared according to the examples to be substrates of P-gp was evaluated using in vitro on Multidrug Resistance Mutation 1-Mardin-Darby Canine Kidney (MDCK-MDR1)) (Mardin-Darby Canine Kidney) cell monolayers overexpressing P-gp grown on permeable supports. A higher efflux ratio of P-gp means that the compound is pushed out of the brain tissue by the transporter.

Preparation for cell seeding: MDCK-MDR1 cell culture medium consisting of Dulbecco's Modified Eagle's Medium (DMEM) with high glucose and L-glutamine supplemented with: 10% FBS, 0.1 mg/mL of streptomycin, 0.6 μg/mL of Kanamycin sulfate and 100 units of penicillin was prepared. 50 μL of culture medium was added to each well of the Transwell insert. The Transwell insert was removed from the reservoir and 25 mL of culture medium was added. After incubation at 37° C., 5% CO2 for 1 hour, the plates were ready for cell seeding. The cells were cultivated in T-75 flasks in a cell culture incubator set at 37° C., 5% CO2, 95% relative humidity until they reached 80-90% confluence before detaching and splitting. The cultivated cells were rinsed in T-75 flasks with 5 mL PBS and aspirated off, and then 1.5 mL trypsin/EDTA was added and incubated at 37° C. for approximately 5 to 10 minutes or until the cells detach and float. The trypsin/EDTA was inactived by adding excess serum containing medium. The cell suspension was transferred to a conical tube and the cells pelleted by centrifugation at 120×g for 10 minutes. The cells were resuspended in seeding medium at a density of $1.56\times10^6$ cells/mL. This cell concentration was used to seed $5.45\times10^5$ cells/$cm^2$.

Seeding and feeding of MDCK-MDR1 cells into transwell plates: 50 μL of the above cell suspension was added to each well of a previously prepared Transwell plate and the plate was incubated for 4-8 days, replacing the medium every other day beginning no sooner than 48 hours after initial plating. The medium must be replaced on the day before conducting the experiment, and the procedure for medium changes was carried out as follows. The plate was removed from the incubator and placed in a hood. The medium was aspirated from a reservoir and each Transwell was inserted. 100 μL of culture medium was added to each well of the Transwell inserts and 25 mL of culture medium to reservoir tray. The plate was returned to the incubator.

Assessment of cell monolayer integrity: When the 4-day cultured MDCK-MDR1 cells reached confluence and were differentiated, the medium was removed from the reservoir and Transwell inserts. 100 μL of prewarmed culture medium was added to each transwell insert and 25 mL was added to the reservoir tray. The electrical resistance across the monolayer was measured using a Millicell Epithelial Volt-Ohm measuring system. The electrical resistance for each well was measured and then the plate was returned to the incubator. TEER values were calculated using this formula: TEER measurement (ohms)×Area of membrane (cm2) =TEER value (ohm·cm2). Any monolayer with a TEER value<42 ohms·cm2, indicating poor monolayer formation, was discarded.

Performing the drug transport assay: The MDCK-MDR1 plate was removed from the incubator and the monolayer was washed, exchanging the volume two times using prewarmed HBSS (Hank's balanced salt solution) (10 mM HEPES, pH 7.4). The plate was then incubated at 37° C. for 30 minutes. A 1 μM compound working solution was prepared as follows: Added 2 L of stock solution (10 mM in DMSO) of test compound and control compounds (Metoprolol, Prazosin and Imatinib) in one 96 well plate, then added 98 μL of DMSO into the same well to obtain 0.2 mM stock solutions (note a stock solution was further diluted 1:10 for eventually making a 0.1 uM compound working solution). Transfered 3 μL of 0.2 mM solution into 597 μL of transport buffer in one 96 well plate to prepare the 1 μM compound working solution. The plate was shaken at 1000 rpm for 10 min. The final concentration of DMSO in the incubation system was 0.5%. The rate of drug transport in the apical to basolateral direction was carried out as follows: Added 125 μL of the 1 μM working solution to the Transwell insert (apical compartment), and transferred 50 μL of sample immediately from the apical compartment to 250 μL of quenching solvents in a new 96-well plate as the initial donor sample (A-B). The plate was shaken at 1000 rpm for 5 minutes. The wells in the receiver plate (basolateral compartment) were filled with 235 μL of transport buffer.

The rate of drug transport in the basolateral to apical direction was carried out as follows: Added 285 μL of the 1 μM working solution to the receiver plate wells (basolateral compartment), and transferred 50 μL of sample immediately from the basolateral compartment to 250 μL quenching solvents in a new 96-well plate as the initial donor sample (B-A). Filled the Transwell insert (apical compartment) with 75 μL of transport buffer. The plate was shaken at 1000 rpm 5 minutes.

The multiwell insert plate was placed into the basolateral receiver plate and the plate was placed into the incubator, incubating at 37° C. for 2 hours. At the end of the transport period, 50 μL of samples was transferred from donor sides (apical compartment for Ap→Bl flux, and basolateral compartment for Bl→Ap flux) to 250 μL quenching solvents in a new 96-well plate. 50 μL was removed directly from receiver sides (basolateral compartment for Ap→Bl flux, and apical compartment for Bl→Ap flux) and transfered to new 96-well plates with 250 μL quenching solvents. The samples were vortexed at 1000 rpm for 5 minutes and then centrifuged at 4,000 rpm for 20 minutes. An aliquot of 100 μL of the supernatant mixed with 100 μL of pure water was used for LC/MS/MS analysis. All incubations were performed in duplicates. To determine the Lucifer Yellow leakage after 2-hour transport period, stock solutions of Lucifer yellow in water were prepared and diluted with HBSS containing 25 mM HEPES, pH 7.4 to reach the final concentration of 100 μM. 100 μL of the Lucifer yellow solution was added to the Transwell insert (apical compartment) and the wells in the receiver plate (basolateral compartment) were filled with 300 μL of HBSS containing 25 mM HEPES, pH 7.4., incubating at 37° C. for 30 mins. 80 μL was removed directly from the apical and basolateral wells (using the basolateral access holes) and transfered to new 96 wells plates. Lucifer Yellow fluorescence was measured (to monitor monolayer integrity) in a fluorescence plate reader at 485 nM excitation and 530 nM emission.

Data calculations: All calculations were carried out using Microsoft Excel. Peak areas were determined from extracted ion chromatograms. The Lucifer yellow leakage of MDCK-MDR1 cell monolayers was calculated using the following equation: LY Leakage=({Iacceptor×0.3}/{Iacceptor×0.3+Idonor×0.1})×100%, where Iacceptor is the fluorescence intensity in the acceptor well (0.3 mL), and Idonor is the fluorescence intensity in the donor well (0.1 mL) and expressed as % leakage. Any monolayer that produces a Lucifer yellow leakage>1%, indicating poor monolayer formation, was excluded from the evaluation.

The apparent permeability (Papp), in units of centimeter per second, was calculated for MDCK-MDR1 drug transport assays using the following equation: Papp={$V_A$/(Area×time)}×{[drug]acceptor}/{[drug]initial,donor}, where $V_A$ is the volume (in mL) in the acceptor well (0.235 mL for Ap→Bl flux and 0.075 mL for Bl→Ap flux), Area is the surface area of the membrane (0.143 cm2 for HTS Transwell-96 Well Permeable Supports), and time is the total transport time in seconds.

The efflux ratio was determined using the following equation: Efflux Ratio=Papp (B−A)/Papp (A−B), where Papp (B−A) indicates the apparent permeability coefficient in basolateral to apical direction, and Papp (A−B) indicates the apparent permeability coefficient in apical to basolateral direction.

The recovery rate was determined using the following equation: Recovery %=({[drug]acceptor×VA+[drug]donor×VD}/{[drug]initial,donor×VD})×100, where VA is the volume (in mL) in the acceptor well (0.235 mL for Ap→Bl flux, and 0.075 mL for Bl→Ap), VD is the volume (in mL) in the donor well (0.075 mL for Ap→Bl flux, and 0.235 mL for Bl→Ap).

Table 2 shows pgp efflux ratio data at 1 uM concentration of compound or 0.1 uM (denoted by **).

TABLE 2

| Compound No | pKIT IC50 (nM) | Pgp Efflux Ratio, 1 uM |
|---|---|---|
| 1 | 3.8 | |
| 2 | 4.8 | |
| 3 | 8.4* | |
| 4 | 2.6* | |
| 5 | 5.0* | |
| 6 | 4.5* | |
| 7 | 13.6 | |
| 8 | 2.7* | |
| 9 | 4.8 | |
| 10 | 3.8 | |
| 11 | 2.5 | |
| 12 | 2.4 | |
| 13 | 1.6* | |
| 14 | 28.6 | |
| 15 | 4.2 | |
| 16 | 2.3 | |
| 17 | 6.5 | |
| 18 | 29.6 | |
| 19 | 7.5 | |
| 20 | 50.9 | |
| 21 | 6.4 | |
| 22 | 1.9* | |
| 23 | 2.6* | |
| 24 | 2.1* | |
| 25 | 7.6* | |
| 26 | 2.4* | |
| 27 | 19.3 | |
| 28 | 9.1* | |
| 29 | 11.1 | |
| 30 | 2.7* | |
| 31 | 8.3* | |
| 32 | 2.5* | |
| 33 | 2.7* | |
| 34 | 9.5* | |
| 35 | 3.8* | |
| 36 | 8.5 | |
| 37 | 6.2* | |
| 38 | 7.2* | |
| 39 | 9.1* | |
| 40 | 3.1* | |
| 41 | 1.8* | |
| 42 | 3.8* | |
| 43 | 5.4* | 11.9 |
| 44 | 1.5* | 15.9 |
| 45 | 70.2 | |
| 46 | 0.6* | 42.5 |
| 47 | 9.8 | 16.0 |
| 48 | 3.6 | 7.1 |
| 49 | 1.3 | 14.0 |
| 50 | 8.0* | 6.5 |
| 51 | 27.4 | 5.5 |
| 52 | 0.7 | 5.9 |
| 53 | 1.5 | 10.9 |
| 54 | 1.4 | 8.4 |
| 55 | 1.1* | 19.7 |
| 56 | 1.1* | 24.5 |
| 57 | 4.0 | 3.4 |
| 58 | 125.6 | 4.1 |
| 59 | 4.5 | |
| 60 | 1.8 | 23.9 |
| 61 | 3.2 | 16.4 |
| 62 | 6.1 | 11.0 |
| 63 | 10.5 | |
| 64 | 3.7 | 39.3 |
| 65 | 33.7 | 23.5 |
| 66 | 64.9 | 13.5 |
| 67 | 22.7 | |
| 68 | 61.3 | 28.2 |
| 69 | 50.1 | 11.7 |
| 70 | 53.1 | |
| 71 | 41.6 | |
| 72 | 38.4 | |
| 73 | 46.6 | |
| 74 | 63.9 | |
| 75 | 9.6 | |
| 76 | 55.6 | |
| 77 | 60.7 | |

TABLE 2-continued

| Compound No | pKIT IC50 (nM) | Pgp Efflux Ratio, 1 uM |
|---|---|---|
| 78 | 9.6 | 13.1 |
| 79 | 3.9* | |
| 80 | 9.2 | 4.0 |
| 81 | 19.0 | 16.9 |
| 82 | 23.4 | |
| 83 | 50.4 | |
| 84 | 21.9 | 51.9 |
| 85 | 25.0 | 7.1 |
| 86 | 8.6 | |
| 87 | 34.5 | |
| 88 | 3.2 | |
| 89 | 71.0 | 43.1 |
| 90 | 87.7 | 33.9 |
| 91 | 50.9 | 39.3 |
| 92 | 22.1 | 11.4 |
| 93 | 29.0 | 11.4 |
| 94 | 130.9 | 22.3 |
| 95 | 30.5 | 21.5 |
| 96 | 37.1 | 9.5 |
| 97 | 111.5 | 23.2 |
| 98 | 47.8 | 15.5 |
| 99 | | |
| 100 | 33.8 | |
| 101 | 5.2 | 16.0 |
| 102 | 2.6 | 40.3 |
| 103 | 2.4 | 22.5 |
| 104 | 3.5 | 11.6 |
| 105 | 3.5 | |
| 106 | 5.8 | 37.4 |
| 107 | 5.5 | 28.9 |
| 108 | 11.6 | 4.0 |
| 109 | 4.9 | 15.4 |
| 110 | 17.7 | 8.7 |
| 111 | 11.8 | |
| 112 | 43.4 | 15.7 |
| 113 | 6.4 | 3.4 |
| 114 | 31.3 | 14.6 |
| 115 | 12.4 | 6.8 |
| 116 | 3.2 | |
| 117 | 52.7 | |
| 118 | 22.7 | |
| 119 | 2.3 | 3.9 |
| 120 | 4.1 | 35.9 |
| 121 | 11.9 | |
| 122 | 0.6 | 12.8 |
| 123 | 3.4 | 4.1 |
| 124 | 1.8 | 3.8 |
| 125 | 7.2 | 5.2 |
| 126 | 10.3 | 15.9 |
| 127 | 30.2 | |
| 128 | 47.4 | |
| 129 | 29.6 | |
| 130 | 34.7 | |
| 131 | 49.0 | |
| 132 | 21.4 | |
| 133 | 34.5 | |
| 134 | 32.4 | |
| 135 | 53.8 | |
| 136 | 76.2 | |
| 137 | 16.8 | 5.4 |
| 138 | 13.4 | |
| 139 | 26.3 | 18.9 |
| 140 | 24.1 | 72.2 |
| 141 | 7.6 | 36.4 |
| 142 | 17.1 | 21.8 |
| 143 | 10.5 | 4.0 |
| 144 | 23.4 | 4.8 |
| 145 | 157.4 | 6.4 |
| 146 | 88.8 | 15.4 |
| 147 | 31.6 | |
| 148 | 34.8 | 24.9 |
| 149 | 38.6 | 30.1 |
| 150 | 3.4 | |
| 151 | 4.1 | 4.8 |
| 152 | 3.6* | |
| 153 | 4.5* | 3.9 |
| 154 | 18.8 | 37.6 |

TABLE 2-continued

| Compound No | pKIT IC50 (nM) | Pgp Efflux Ratio, 1 uM |
|---|---|---|
| 155 | 55.9 | 57.9 |
| 156 | 22.1 | |
| 157 | 6.4 | 5.9 |
| 158 | 5.7* | |
| 159 | 20.1 | |
| 160 | 14.9 | |
| 161 | 9.0 | |
| 162 | 18.0 | 5.3 |
| 163 | 9.3 | |
| 164 | 8.0 | |
| 165 | 26.6 | 6.6 |
| 166 | 37.7 | |
| 167 | 7.3 | |
| 168 | 9.2 | 3.2 |
| 169 | 4.7 | |
| 170 | 6.3 | |
| 171 | 34.3 | 6.0 |
| 172 | 35.4 | 5.5 |
| 173 | 12.0 | 3.5 |
| 174 | 28.5 | |
| 175 | 77.8 | |
| 176 | 47.9 | |
| 177 | 8.8 | |
| 178 | 17.6 | 4.7 |
| 179 | 4.9 | |
| 180 | 13.4 | |
| 181 | 6.4* | 3.1 |
| 182 | 4.0* | |
| 183 | 45.4 | |
| 184 | 6.2 | |
| 185 | 160.8 | |
| 186 | 103.4 | |
| 187 | 6.2* | |
| 188 | 2.9* | |
| 189 | 4.9* | |
| 190 | 22.8 | |
| 191 | 41.3 | |
| 192 | 10.6 | |
| 193 | 5.2* | |
| 194 | 11.6* | |
| 195 | 8.7 | |
| 196 | 9.1 | |
| 197 | 1.4* | 41.0 |
| 198 | 1.7* | 16.6 |
| 199 | 29.6 | 36.6 |
| 200 | 16.9 | |
| 201 | 15.6 | |
| 202 | 14.8 | 19.1 |
| 203 | 16.7* | 12.8 |
| 204 | 10.1 | 62.1 |
| 205 | 8.2 | 33.1 |
| 206 | 1.2 | 22.6 |
| 207 | 1.4 | 16.2 |
| 208 | 0.4 | 4.1 |
| 209 | 6.9 | 4.3 |
| 210 | 7.4 | |
| 211 | 2.6 | |
| 212 | 5.6 | |
| 213 | 16.0 | |
| 214 | 2.7 | |
| 215 | 23.7 | |
| 216 | 2.4 | |
| 217 | 8.1 | |
| 218 | 5.2 | |
| 219 | 1.1 | 53.5 |
| 220 | 1.8 | 12.4 |
| 221 | | |
| 222 | 2.7 | |
| 223 | 23.4 | |
| 224 | 27.0 | 9.1 |
| 225 | 1.7 | 3.3 |
| 226 | 0.5 | |
| 227 | 1.9 | 5.0** |
| 228 | 1.5 | |
| 229 | 0.7 | |
| 230 | 0.8 | 116.3 |
| 231 | 3.6 | |

TABLE 2-continued

| Compound No | pKIT IC50 (nM) | Pgp Efflux Ratio, 1 uM |
|---|---|---|
| 232 | 26.0 | |
| 233 | 2.2 | 6.3 |
| 234 | 0.5 | 3.8** |
| 235 | 1.6 | 3.9 |
| 236 | 0.6 | |
| 237 | 0.5 | 3.2 |
| 238 | 0.2 | 5.9** |
| 239 | 0.3 | 13.2 |
| 240 | 0.6 | 7.4 |
| 241 | 0.2 | 6.3** |
| 242 | 0.5 | 11.9 |
| 243 | 0.1 | 13.5 |
| 244 | 0.4 | |
| 245 | 0.8 | 2.3 |
| 246 | 0.7 | |
| 247 | 0.5 | |
| 248 | 0.6 | 3.5 |
| 249 | 0.7 | |
| 250 | 0.4 | |
| 251 | 0.4 | 1.8** |
| 252 | 3.7 | 5.1 |
| 253 | 0.4 | |
| 254 | 0.4 | |
| 255 | 0.3 | 8.1 |
| 256 | 0.5 | 13.5 |
| 257 | 0.7 | 8.9 |
| 258 | 0.4 | |
| 259 | 0.4 | |
| 260 | 0.6 | |
| 261 | 1.7 | |
| 262 | 1.1 | |
| 263 | 0.2 | 3.0 |
| 264 | 0.5 | |
| 265 | 0.8 | |
| 266 | 0.3 | 3.4 |
| 267 | 1.4 | 2.9 |
| 268 | 1.6 | 5.2 |
| 269 | 0.3 | |
| 270 | 0.5 | |
| 271 | 0.3 | 2.2 |
| 272 | 0.9 | 7.0 |
| 273 | 0.5 | 4.9 |
| 274 | 0.6 | 1.7 |
| 275 | 0.1 | |
| 276 | 0.3 | |
| 277 | 0.5 | 3.0 |
| 278 | 0.3 | 3.6 |
| 279 | 0.6 | |
| 280 | 0.2 | |
| 281 | 0.4 | |
| 282 | 0.2 | |
| 283 | 0.7 | |
| 284 | 0.2 | |
| 285 | 1.0 | |
| 286 | 0.3 | |
| 287 | 0.9 | |
| 288 | 0.4 | |
| 289 | 0.6 | |

Example 291: Compounds of the Disclosure Inhibit Exon 9 and Exon 11 KIT

Exon 9 assay: The NIH3T3 cell lines that overexpressed the kit mutation exon 9 (or parental cells) were resuscitated and well cultured, and the cells were collected and seeded in 96-well plates at 3000/well, then the compounds were added to the 96 well plates in a gradient dilution, and the plates were incubated in an incubator for 72 hours. After 72 hours of incubation, an equal volume of CellCounting Lite 2.0 Luminescent Cell Viability reagent was added to the 96-well plates to detect the cell viability. The data were analyzed using GraphPad Prism 7.0 software, and the nonlinear S-curve regression was used to fit the data to obtain the dose-effect curve, and the IC50 value was calculated accordingly.

Exon 11 HMC1.1 autophosphorylation assay: 50,000 HMC1.1 cells were incubated in 50 ul culture media (phenol-red free IMDM, no iron, no serum) in each well of a 96-well plate and serum starved 4 hours in a tissue culture incubator (5% CO2, 37° C.). An 8-point dose concentration series of compound were then added to the cells in a volume of 7 ul to each well. After 90 minutes, 14 ul of 5× AlphaLISA Lysis Buffer (Perkin Elmer) supplemented with a protease and phosphatase inhibitor cocktail (Cell Signaling Technologies) was added to each well and shaken at 2500×g for 5 minutes at 4° C. Phospho-Y719 c-KIT ELISA kit from Cell Signaling Technology was used to assess levels of phospho KIT. Data was normalized to 0% and 100% inhibition controls and the IC50 was calculated using Four Parameter Logistic IC50 curve fitting.

TABLE 3

| | IC50 (nM) | | |
|---|---|---|---|
| Compound Number | NIH3T3 parental | NIH3T3-cKit-AY502-3dup | HMC1.1 pKIT |
| 81 | | | 6.4 |
| 148 | | | 1.0 |
| 237 | | 15.6 | 0.7 |
| 239 | | | 0.9 |
| 263 | 122.6 | 2.0 | 0.2 |
| 278 | | | 0.2 |
| 280 | 412.8 | 10.0 | |
| 284 | 161 | 7.5 | 0.2 |
| 286 | 480.2 | 42.5 | |

What is claimed is:

1. A compound having the structure of Formula (I):

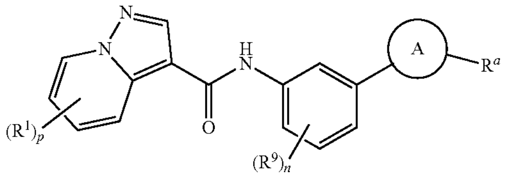

(I)

or a pharmaceutically acceptable salt thereof, wherein:

Ring A is selected from tetrazole or triazole, wherein said tetrazole or triazole is optionally substituted with $R^a$;

wherein $R^a$ is selected from hydrogen, $C_{1-6}$ alkyl, $C_{1-6}$haloalkyl, $C_{0-5}$alkylphenyl, $C_{0-5}$alkyl$C_{3-6}$cycloalkyl, $C_{0-5}$alkyl$C_{6-10}$spirocycloalkyl, $C_{0-5}$alkyl$C_{5-10}$bridgedbicycloalkyl, and $C_{0-5}$alkyl(4-6 membered heterocycle), or $C_{0-5}$alkyl(7-10 membered spiroheterocycle) or $C_{0-5}$alkyl(5-10 membered bridgedbicycloheterocycle, each containing at least one N or O, wherein said alkyl, haloalkyl, phenyl, cycloalkyl, spirocycloalkyl, bridgedbicycloalkyl, heterocycle, spiroheterocycle, or bridgedbicycloheterocycle is optionally substituted with 1-5 $R^b$, wherein:

each $R^b$ is independently selected from OH, CN, $C_{1-6}$alkoxy, $C_{1-6}$haloalkoxy, $C_{3-5}$cycloalkoxy, $SO_2C_{1-4}$alkyl, $SO_2C_{1-4}$haloalkyl, $C(O)OC_{1-4}$alkyl, $SO_2(C_{0-2}$alkyl)(4-6 membered heterocycle containing at least one O or N), $SO_2(C_{1-4}$alkyl)$C_{1-4}$haloalkoxy, $SO_2(C_{1-4}$alkyl)$C_{1-4}$alkoxy ($C_{0-1}$alkoxy), $SO_2(C_{1-4}$alkyl)OH, $SO_2(C_{0-2}$alkyl)$C_{3-6}$cycloalkyl, $C_{1-3}$alkyl, $C_{1-5}$haloalkyl, halogen, and $C_{1-2}$alkylOH, further wherein said cycloalkyl is optionally substituted with $C_{1-3}$alkyl;

each $R^1$ is independently selected from halogen, $C_{1-6}$alkyl, $C_{1-6}$haloalkyl, $C_{3-6}$cycloalkyl, $C_{0-4}$alkylOH, $C_{6-10}$spirocycloalkyl, $C_{0-6}$alkyl$C_{1-6}$alkoxy, $C_{0-4}$alkyl$C_{1-6}$haloalkoxy, $NH_2$, $NHC_{1-6}$alkyl, $N(C_{1-6}$alkyl$)_2$, NH-(4-6 membered heterocycle or 5-6 membered heteroaryl containing at least one O or N), and 4-6 membered heterocycle or 7-10 membered fused bicycloheterocycle or 7-10 membered spiroheterocycle, each containing at least one O or N, or 5-6 membered heteroaryl containing at least two N, wherein said alkyl, haloalkyl, alkoxy, cycloalkyl, spirocycloalkyl, heterocycle, or heteroaryl is optionally substituted with 1-3 $R^e$;

each $R^e$ is independently selected from deuterium, deuterated $C_{1-4}$alkyl, deuterated $C_{1-4}$alkoxy, $C_{1-4}$haloalkoxy, halogen, $C_{0-3}$alkyl-$S(O)_2C_{1-3}$alkyl, $C_{0-3}$alkyl-S(O)(NH) $C_{1-3}$alkyl, ($C_{1-4}$alkyl)P(O)($C_{1-3}$alkyl$)_2$, $C_{1-4}$alkyl, CN, $CHF_2$, $C_{3-6}$cycloalkyl, $C_{1-4}$haloalkyl, $C_{0-4}$alkylOH, $C_{2-5}$alkyl$(OH)_2$, $C_{1-4}$alkyl(OH)($C_1$-$C_4$alkoxy), $C_{2-5}$alkyl(OH)($C_{1-5}$alkoxy) ($C_{1-5}$alkoxy), $C_{0-4}$alkyl$C_{1-4}$alkoxy, $C_{1-3}$alkyoxy $C_{1-3}$alkoxy, $NH_2$, NH($C_{1-6}$alkyl), $N(C_{1-6}$alkyl$)_2$, and ($C_{0-4}$alkyl)-(4-6 membered heterocycle containing at least one O or N), wherein said heterocycle is optionally substituted with 1-3 $C_{0-3}$alkylOH, or $C_{1-3}$alkyl;

each $R^9$ is independently selected from $C_{1-3}$alkyl, $C_{1-3}$haloalkyl, halogen, CN, and $C_{3-4}$cycloalkyl;

n is 1 or 2; and p is 0, 1 or 2.

2. The compound of claim 1 or a pharmaceutically acceptable salt thereof, wherein:

each $R^e$ is independently selected from deuterium, deuterated $C_{1-4}$alkyl, deuterated $C_{1-4}$alkoxy, $C_{1-4}$haloalkoxy, halogen, $C_{0-3}$alkyl-$S(O)_2C_{1-3}$alkyl, $C_{0-3}$alkyl-S(O)(NH)$C_{1-3}$alkyl, ($C_{1-4}$alkyl)P(O)($C_{1-3}$alkyl$)_2$, $C_{1-4}$alkyl, CN, $CHF_2$, $C_{3-6}$cycloalkyl, $C_{1-4}$haloalkyl, $C_{0-4}$alkylOH, $C_{1-4}$alkyl(OH)($C_1$-$C_4$alkoxy), $C_{0-4}$alkyl$C_{1-4}$alkoxy, $C_{1-3}$alkyoxy$C_{1-3}$alkoxy, $NH_2$, NH($C_{1-6}$alkyl), $N(C_{1-6}$alkyl$)_2$, and ($C_{0-4}$alkyl)-(4-6 membered heterocycle containing at least one O or N), wherein said heterocycle is optionally substituted with 1-3 $C_{0-3}$alkylOH.

3. The compound of claim 1 having the structure of Formula (IIa):

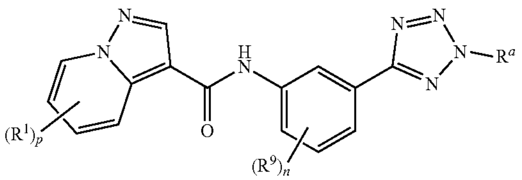

(IIa)

or a pharmaceutically acceptable salt thereof.

4. The compound of claim 1 having the structure of Formula (IIb):

(IIb)

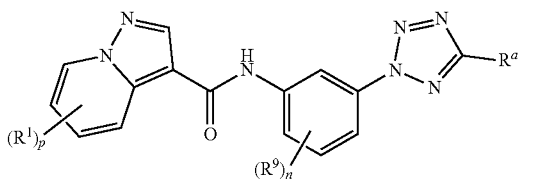

or a pharmaceutically acceptable salt thereof.

5. The compound of claim 1 having the structure of Formula (IIIa):

(IIIa)

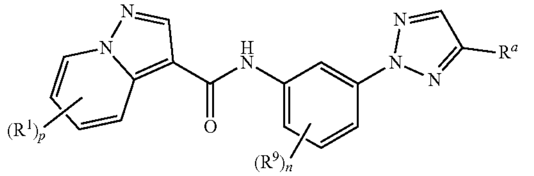

or a pharmaceutically acceptable salt thereof.

6. The compound of claim 1 having the structure of Formula (IIIb):

(IIIb)

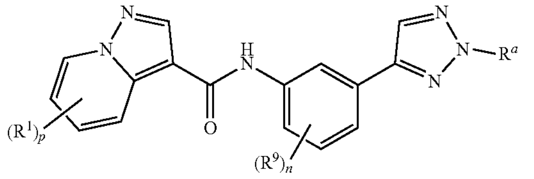

or a pharmaceutically acceptable salt thereof.

7. The compound of claim 1 or a pharmaceutically acceptable salt thereof, wherein p is 0.

8. The compound of claim 1 or a pharmaceutically acceptable salt thereof, wherein p is 1 or 2.

9. The compound of claim 1 or a pharmaceutically acceptable salt thereof, wherein:

$R^a$ is selected from hydrogen, $C_{1-6}$alkyl, $C_{1-6}$haloalkyl, $C_{0-3}$alkylphenyl, $C_{0-4}$alkyl$C_{3-6}$cycloalkyl, $C_{0-3}$alkyl $C_{6-10}$spirocycloalkyl, $C_{0-3}$alkyl($C_{5-8}$ bridgedbicycloalkyl), $C_{0-5}$alkyl(4-6 membered heterocycle containing at least one N or O), $C_{0-3}$alkyl(7-10 membered spiroheterocycle containing at least one N or O), and $C_{0-3}$alkyl (5-10 membered bridged bicycloheterocycle containing at least one O or N), wherein:

i) said alkyl or haloalkyl is optionally substituted with 1-5 $R^b$ each independently selected from $C_{1-5}$alkoxy, $C_{1-5}$haloalkoxy, OH and CN;

ii) said cycloalkyl, spirocycloalkyl, or phenyl is optionally substituted with 1-2 $R^b$ each independently selected from methyl, halogen, $C_{1-3}$haloalkyl, $C_{1-3}$alkoxy, and $C_{0-3}$alkylOH; and iii) said heterocycle is optionally substituted with one $R^b$ selected from $SO_2C_{1-4}$alkyl, $SO_2C_{1-4}$haloalkyl, $C(O)OC_{1-4}$alkyl, $SO_2$(4-6 membered heterocycle containing at least one O or N), $SO_2(C_{1-3}$alkyl)$C_{1-3}$haloalkoxy, $SO_2(C_{1-3}$alkyl) $C_{1-3}$alkoxy, $SO_2(C_{1-4}$alkyl)OH, $SO_2(C_{1-3}$alkyl) $C_{1-3}$alkoxy(methoxy), $SO_2(C_{0-2}$alkyl)$C_{3-6}$cycloalkyl and $C_{1-4}$ haloalkyl, further wherein said cycloalkyl is optionally substituted with $C_{1-2}$alkyl.

10. The ocmpound of claim 1 or a pharmaceutically acceptable salt thereof, wherein each $R^9$ is independently selected from $CH_3$, Cl, F, $CD_3$, CN, and cyclopropyl.

11. The compound of claim 1 or a pharmaceutically acceptable salt thereof, wherein the compound is selected from any one of the compounds in the table below:

| Compound No | Structure |
|---|---|
| 1 | 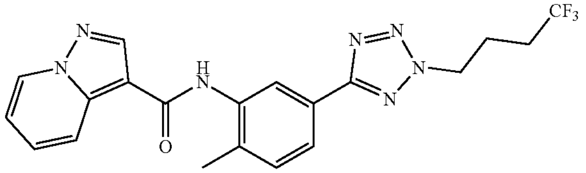 [SMILES: Cc1ccc(-c2nnn(CCCC(F)(F)F)n2)cc1NC(=O)c1cnn2ccccc12] |
| 2 | 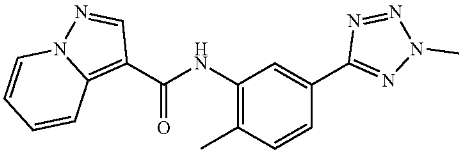 [SMILES: Cc1ccc(-c2nnn(C)n2)cc1NC(=O)c1cnn2ccccc12] |
| 3 | 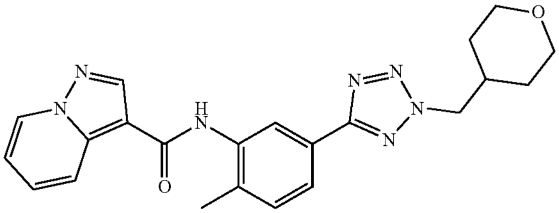 [SMILES: Cc1ccc(-c2nnn(CC3CCOCC3)n2)cc1NC(=O)c1cnn2ccccc12] |

-continued
| Compound No | Structure |
|---|---|
| 4 | 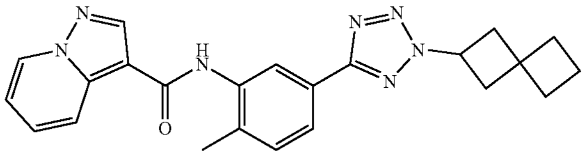 [SMILES: Cc1ccc(-c2nnn(C3CC4(CCC4)C3)n2)cc1NC(=O)c1cnn2ccccc12] |
| 5 | 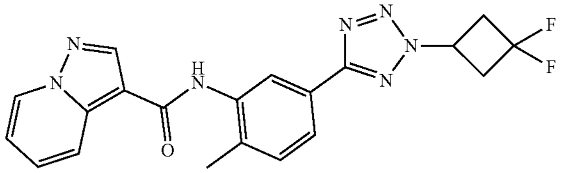 [SMILES: Cc1ccc(-c2nnn(C3CC(F)(F)C3)n2)cc1NC(=O)c1cnn2ccccc12] |
| 6 | 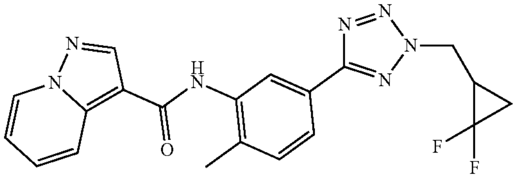 [SMILES: Cc1ccc(-c2nnn(CC3CC3(F)F)n2)cc1NC(=O)c1cnn2ccccc12] |
| 7 | 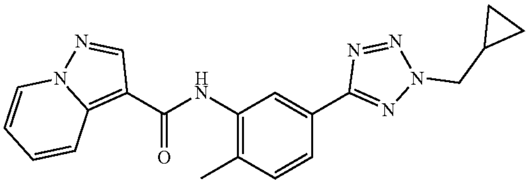 [SMILES: Cc1ccc(-c2nnn(CC3CC3)n2)cc1NC(=O)c1cnn2ccccc12] |
| 8 | 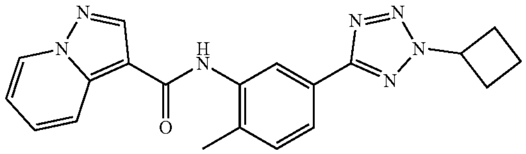 [SMILES: Cc1ccc(-c2nnn(C3CCC3)n2)cc1NC(=O)c1cnn2ccccc12] |
| 9 | 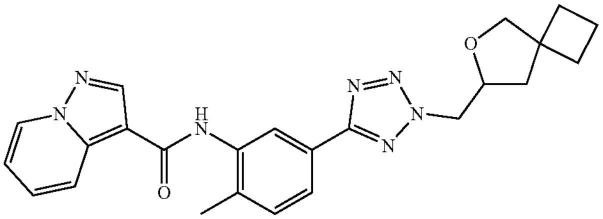 [SMILES: Cc1ccc(-c2nnn(CC3CC4(CCC4)CO3)n2)cc1NC(=O)c1cnn2ccccc12] |
| 10 | 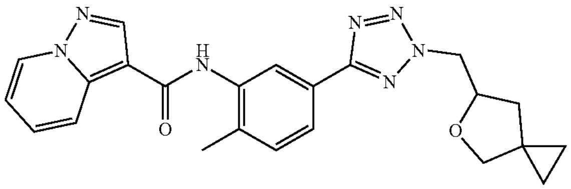 [SMILES: Cc1ccc(-c2nnn(CC3CC4(CC4)CO3)n2)cc1NC(=O)c1cnn2ccccc12] |
| 11 | 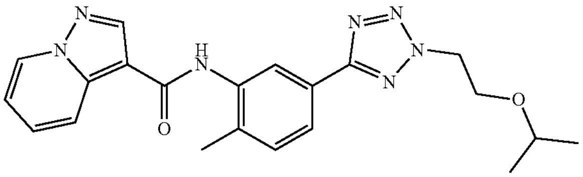 [SMILES: Cc1ccc(-c2nnn(CCOC(C)C)n2)cc1NC(=O)c1cnn2ccccc12] |

-continued
| Compound No | Structure |
|---|---|
| 12 | 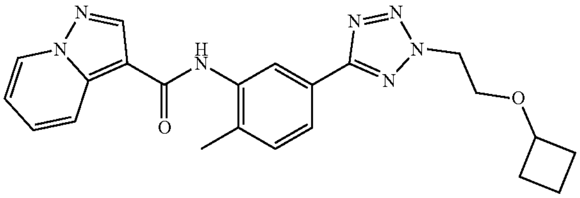 [SMILES: Cc1ccc(-c2nnn(CCOC3CCC3)n2)cc1NC(=O)c1cnn2ccccc12] |
| 13 | 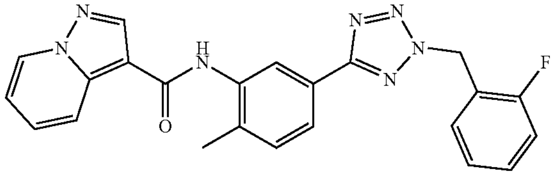 [SMILES: Cc1ccc(-c2nnn(Cc3ccccc3F)n2)cc1NC(=O)c1cnn2ccccc12] |
| 14 | 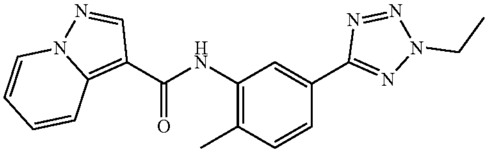 [SMILES: CCn1nnc(-c2ccc(C)c(NC(=O)c3cnn4ccccc34)c2)n1] |
| 15 | 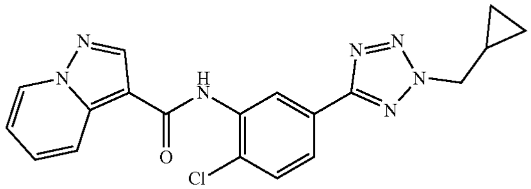 [SMILES: O=C(Nc1cc(-c2nnn(CC3CC3)n2)ccc1Cl)c1cnn2ccccc12] |
| 16 | 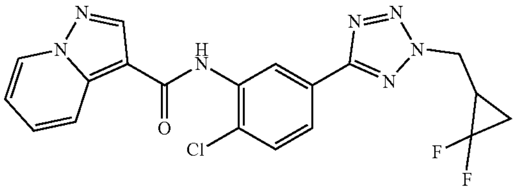 [SMILES: O=C(Nc1cc(-c2nnn(CC3CC3(F)F)n2)ccc1Cl)c1cnn2ccccc12] |
| 17 | 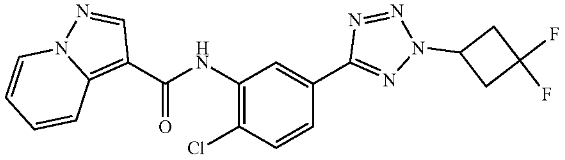 [SMILES: O=C(Nc1cc(-c2nnn(C3CC(F)(F)C3)n2)ccc1Cl)c1cnn2ccccc12] |
| 18 | 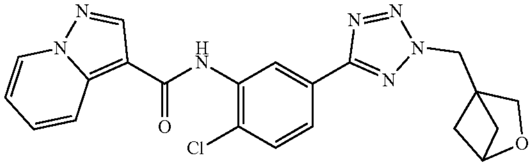 [SMILES: O=C(Nc1cc(-c2nnn(CC34COC(C3)C4)n2)ccc1Cl)c1cnn2ccccc12] |
| 19 | 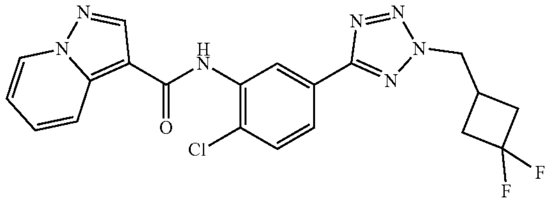 [SMILES: O=C(Nc1cc(-c2nnn(CC3CC(F)(F)C3)n2)ccc1Cl)c1cnn2ccccc12] |

-continued
| Compound No | Structure |
|---|---|
| 20 | 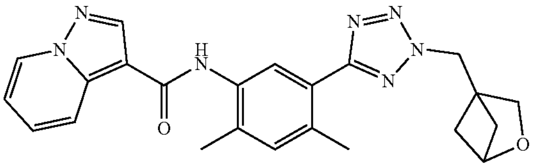 |
| 21 | 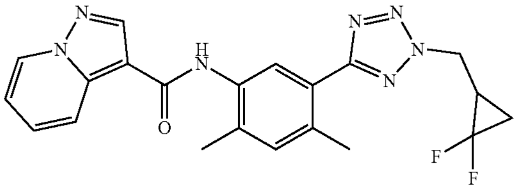 |
| 22 | 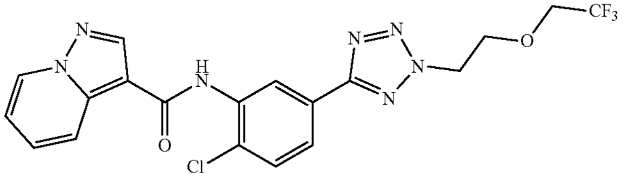 [SMILES: O=C(Nc1cc(-c2nnn(CCOCC(F)(F)F)n2)ccc1Cl)c1cnn2ccccc12] |
| 23 | 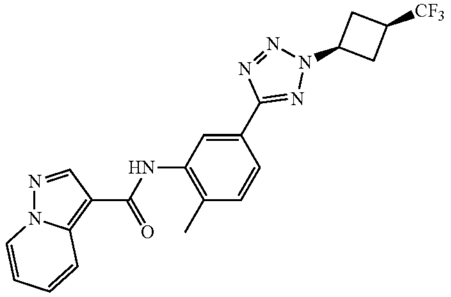 Or 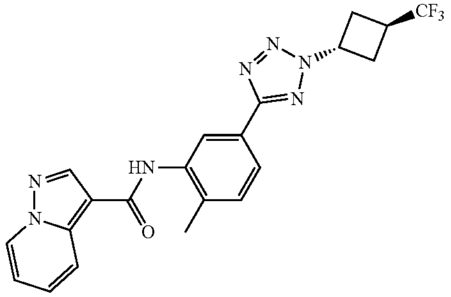 |
| 24 | 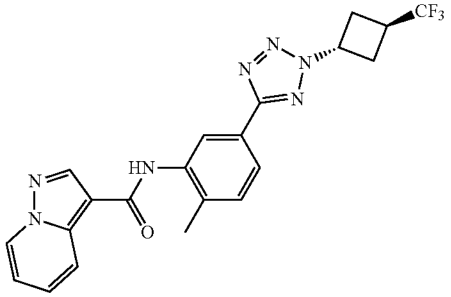 Or 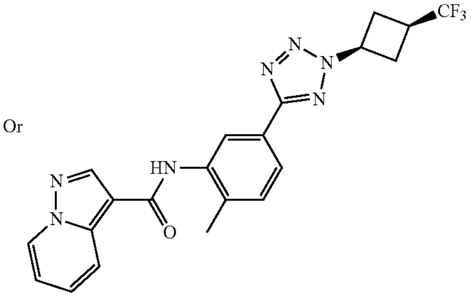 |
| 25 | 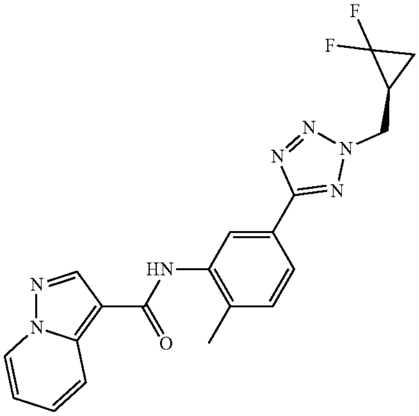 or 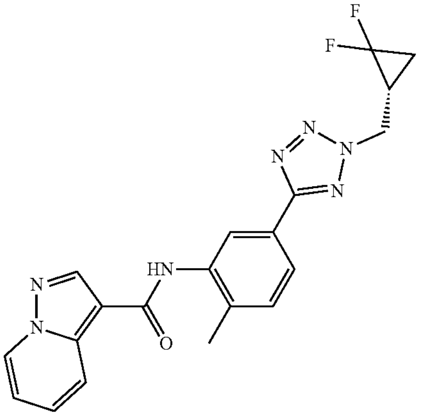 |

-continued
| Compound No | Structure |
|---|---|
| 26 | 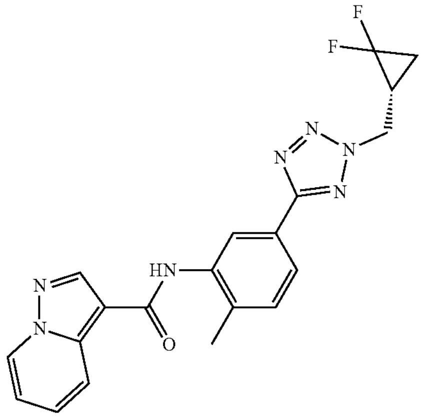 or 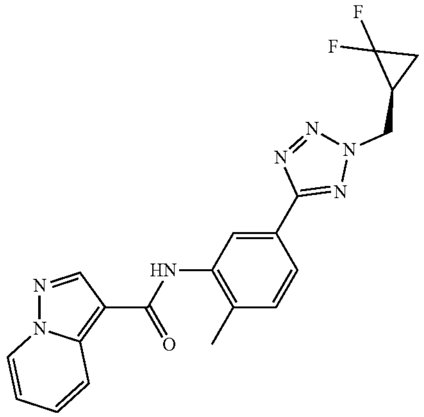 |
| 27 | 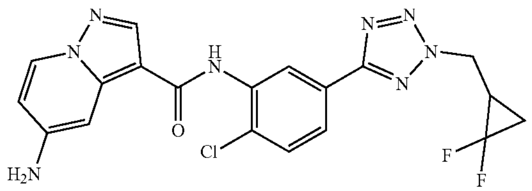 [SMILES: Nc1ccn2ncc(C(=O)Nc3cc(-c4nnn(CC5CC5(F)F)n4)ccc3Cl)c2c1] |
| 28 | 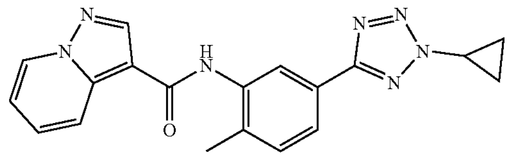 [SMILES: Cc1ccc(-c2nnn(C3CC3)n2)cc1NC(=O)c1cnn2ccccc12] |
| 29 | 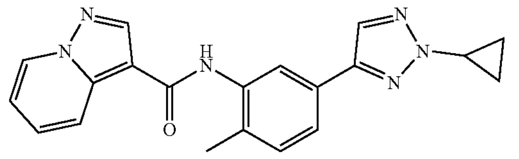 [SMILES: Cc1ccc(-c2cnn(C3CC3)n2)cc1NC(=O)c1cnn2ccccc12] |
| 30 | 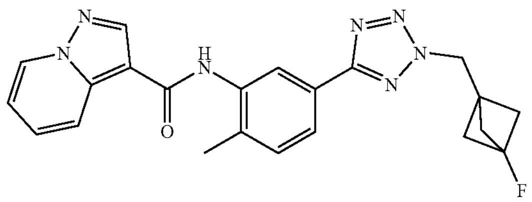 [SMILES: Cc1ccc(-c2nnn(CC34CC(F)(C3)C4)n2)cc1NC(=O)c1cnn2ccccc12] |
| 31 | 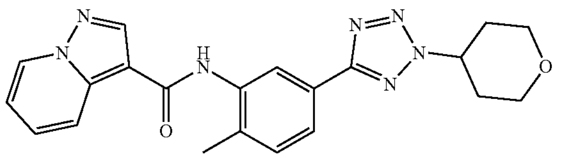 [SMILES: Cc1ccc(-c2nnn(C3CCOCC3)n2)cc1NC(=O)c1cnn2ccccc12] |
| 32 | 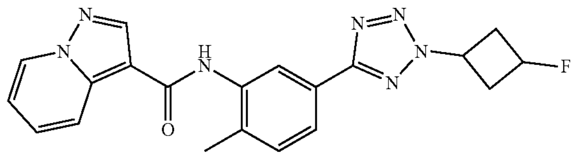 [SMILES: Cc1ccc(-c2nnn(C3CC(F)C3)n2)cc1NC(=O)c1cnn2ccccc12] |

-continued
| Compound No | Structure |
|---|---|
| 33 | 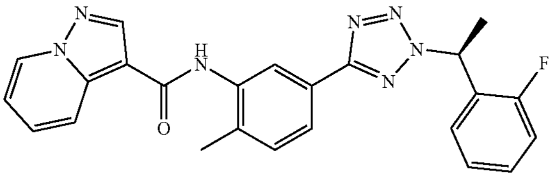 [SMILES: Cc1ccc(-c2nnn([C@@H](C)c3ccccc3F)n2)cc1NC(=O)c1cnn2ccccc12] |
| 34 | 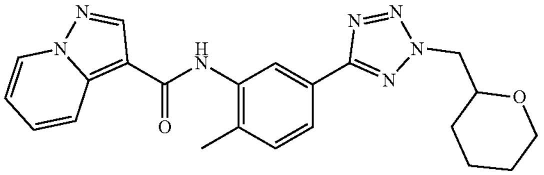 [SMILES: Cc1ccc(-c2nnn(CC3CCCCO3)n2)cc1NC(=O)c1cnn2ccccc12] |
| 35 | 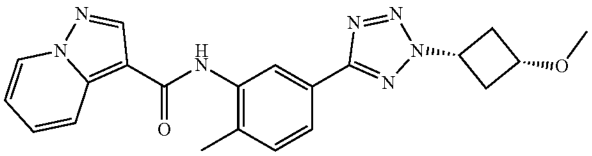 [SMILES: CO[C@H]1C[C@@H](n2nnc(-c3ccc(C)c(NC(=O)c4cnn5ccccc45)c3)n2)C1] |
| 36 | 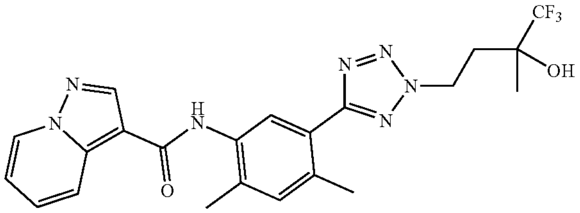 [SMILES: Cc1cc(C)c(-c2nnn(CCC(C)(O)C(F)(F)F)n2)cc1NC(=O)c1cnn2ccccc12] |
| 37 | 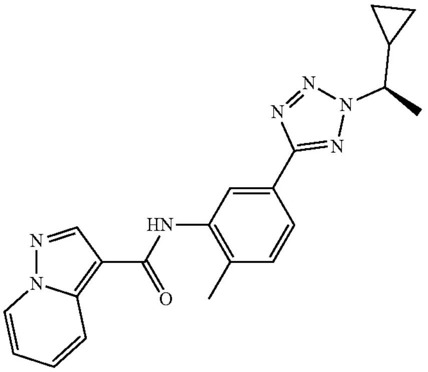 or 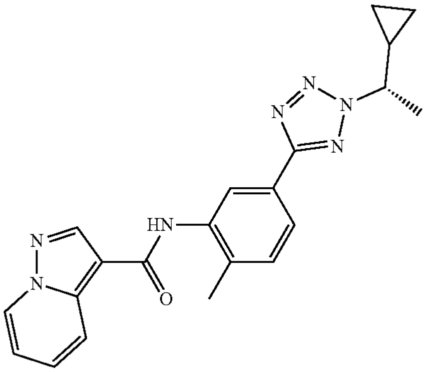 |
| 38 | 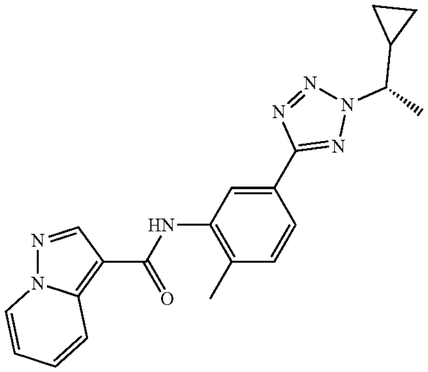 or 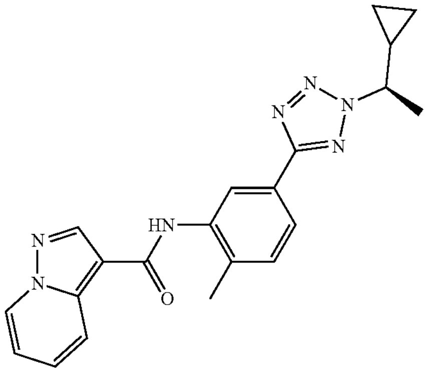 |

-continued
| Compound No | Structure |
| --- | --- |
| 39 | 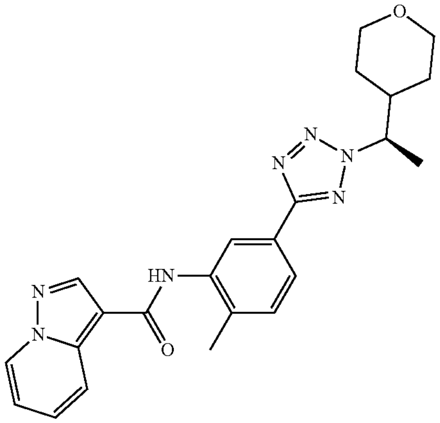 Or 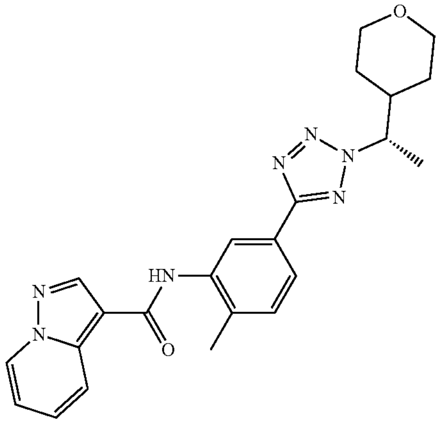 |
| 40 | 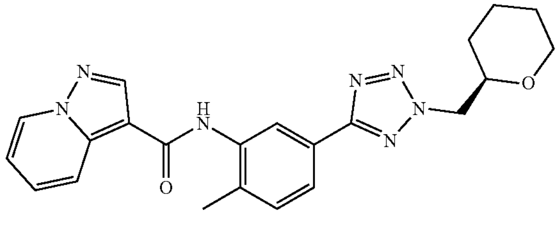 OR 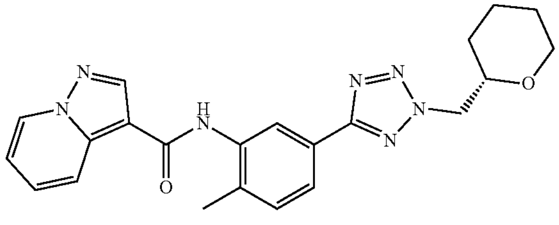 |
| 41 | 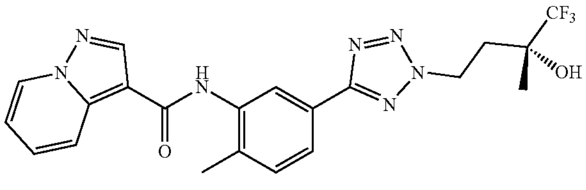 OR 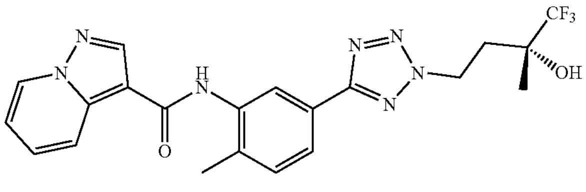 |

-continued
| Compound No | Structure |
|---|---|
| 42 | 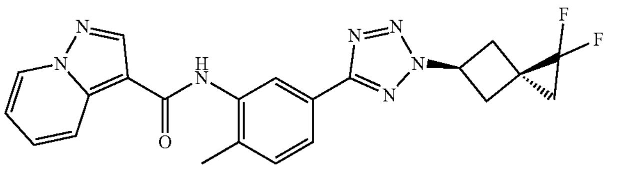<br>OR<br>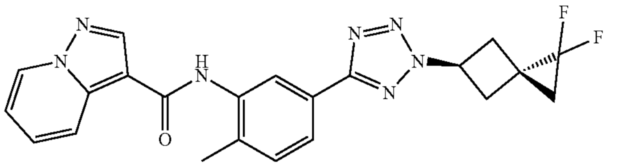 |
| 43 | 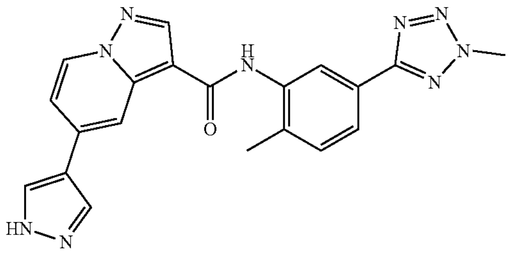 [SMILES: Cc1ccc(-c2nnn(C)n2)cc1NC(=O)c1cnn2ccc(-c3cn[nH]c3)cc12] |
| 44 | 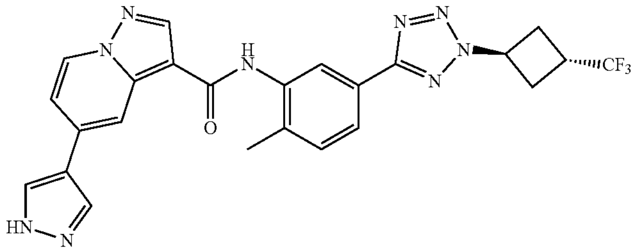<br>OR<br>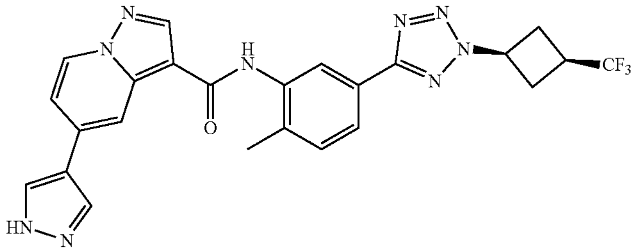 |
| 45 | 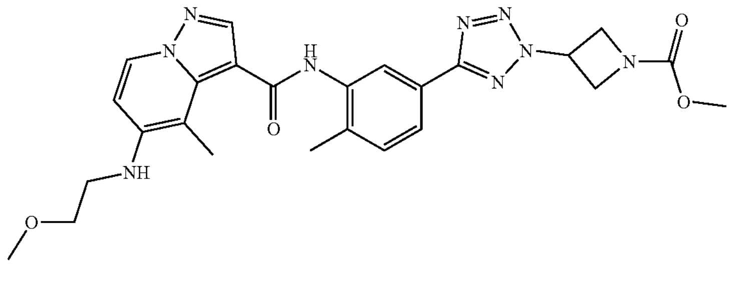 |

-continued
| Compound No | Structure |
|---|---|
| 46 | 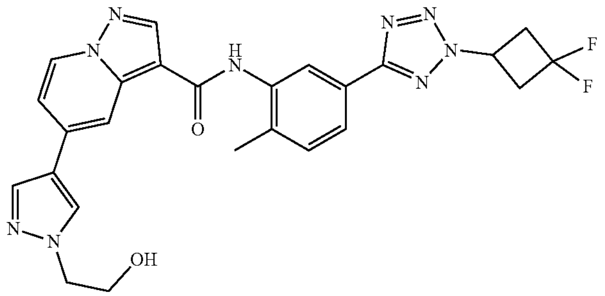 [SMILES: Cc1ccc(-c2nnn(C3CC(F)(F)C3)n2)cc1NC(=O)c1cnn2ccc(-c3cnn(CCO)c3)cc12] |
| 47 | 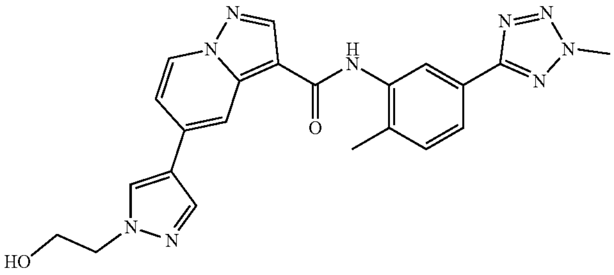 [SMILES: Cc1ccc(-c2nnn(C)n2)cc1NC(=O)c1cnn2ccc(-c3cnn(CCO)c3)cc12] |
| 48 | 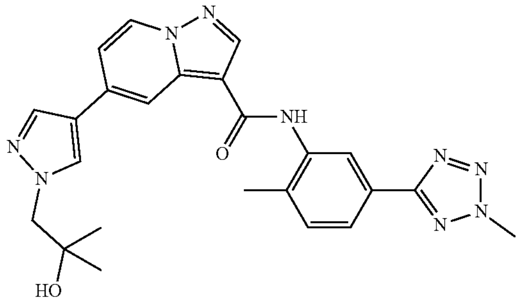 [SMILES: Cc1ccc(-c2nnn(C)n2)cc1NC(=O)c1cnn2ccc(-c3cnn(CC(C)(C)O)c3)cc12] |
| 49 | 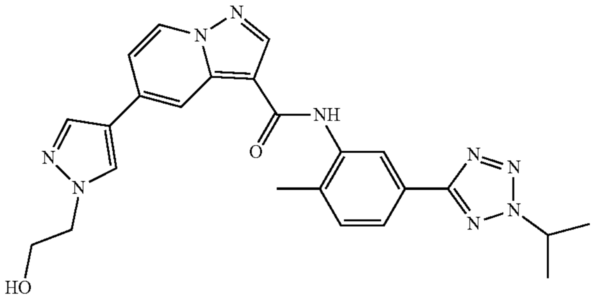 [SMILES: Cc1ccc(-c2nnn(C(C)C)n2)cc1NC(=O)c1cnn2ccc(-c3cnn(CCO)c3)cc12] |
| 50 | 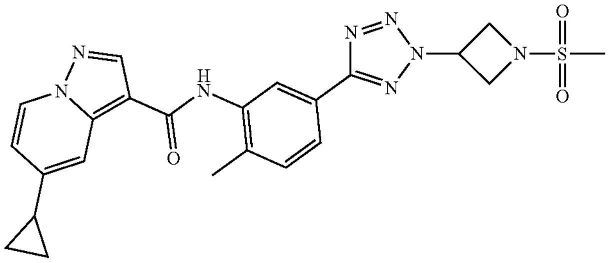 [SMILES: Cc1ccc(-c2nnn(C3CN(S(C)(=O)=O)C3)n2)cc1NC(=O)c1cnn2ccc(C3CC3)cc12] |

-continued
| Compound No | Structure |
|---|---|
| 51 | 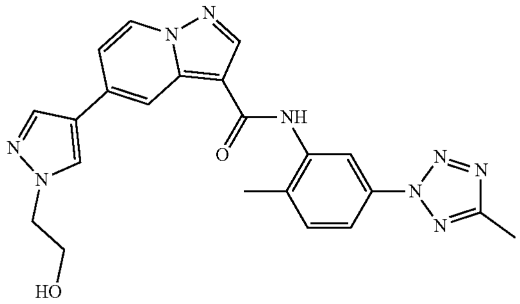 [SMILES: Cc1nnn(-c2ccc(C)c(NC(=O)c3cnn4ccc(-c5cnn(CCO)c5)cc34)c2)n1] |
| 52 | 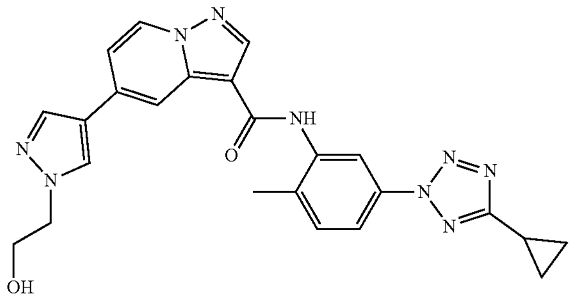 [SMILES: Cc1ccc(-n2nnc(C3CC3)n2)cc1NC(=O)c1cnn2ccc(-c3cnn(CCO)c3)cc12] |
| 53 | 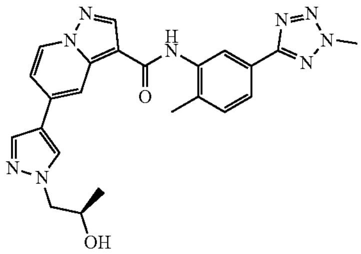 OR 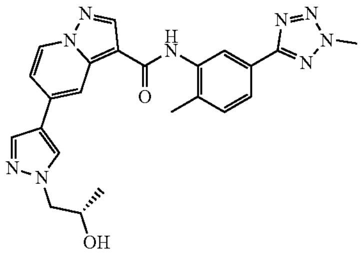 |
| 54 | 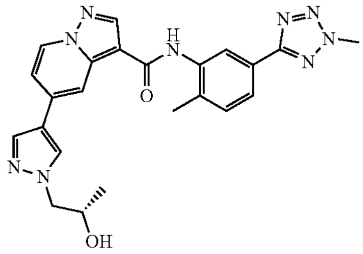 OR 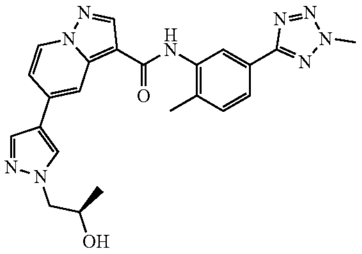 |
| 55 | 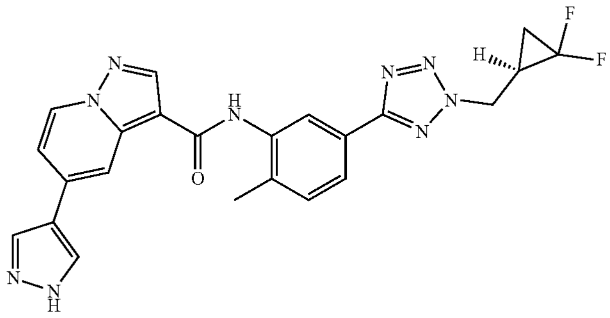 Or |

-continued
| Compound No | Structure |
| --- | --- |
| | 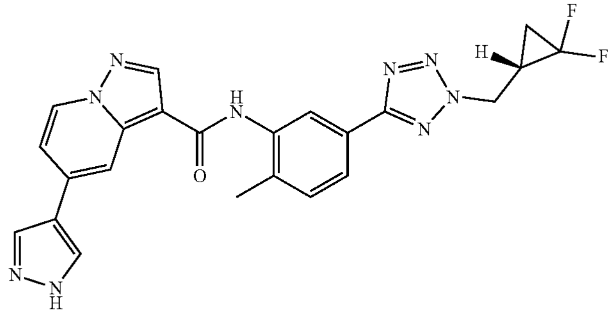 |
| 56 | 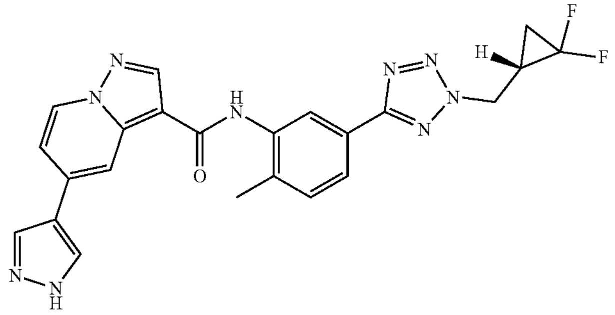 Or 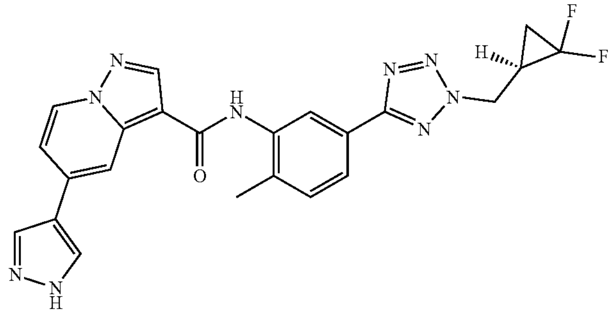 |
| 57 | 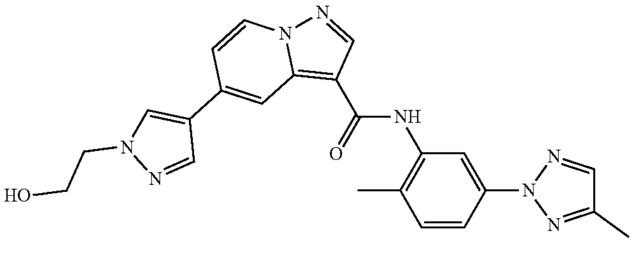 [SMILES: Cc1cnn(-c2ccc(C)c(NC(=O)c3cnn4ccc(-c5cnn(CCO)c5)cc34)c2)n1] |
| 58 | 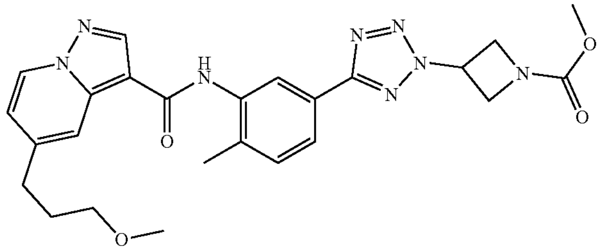 [SMILES: COCCCc1ccn2ncc(C(=O)Nc3cc(-c4nnn(C5CN(C(=O)OC)C5)n4)ccc3C)c2c1] |

-continued
| Compound No | Structure |
| --- | --- |
| 59 | 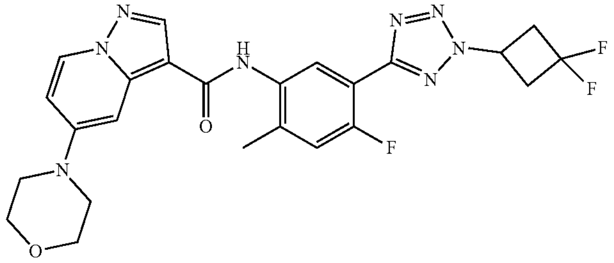 [SMILES: Cc1cc(F)c(-c2nnn(C3CC(F)(F)C3)n2)cc1NC(=O)c1cnn2ccc(N3CCOCC3)cc12] |
| 60 | 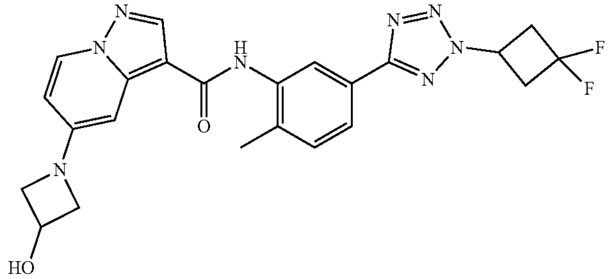 [SMILES: Cc1ccc(-c2nnn(C3CC(F)(F)C3)n2)cc1NC(=O)c1cnn2ccc(N3CC(O)C3)cc12] |
| 61 | 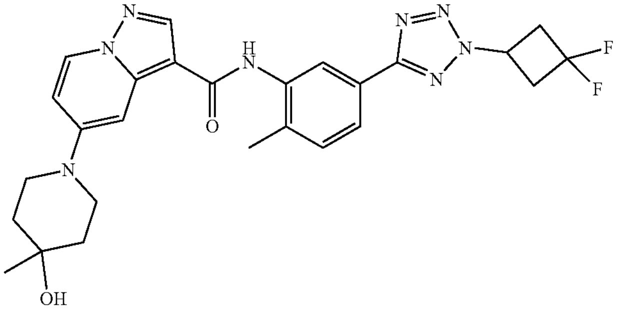 [SMILES: Cc1ccc(-c2nnn(C3CC(F)(F)C3)n2)cc1NC(=O)c1cnn2ccc(N3CCC(C)(O)CC3)cc12] |
| 62 | 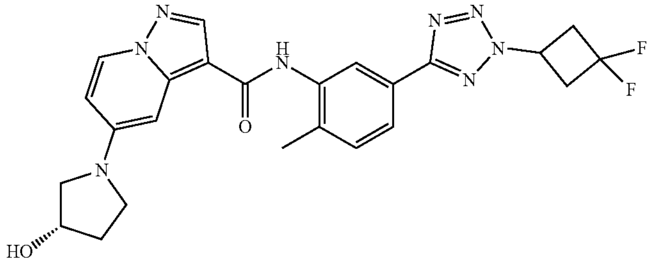 [SMILES: Cc1ccc(-c2nnn(C3CC(F)(F)C3)n2)cc1NC(=O)c1cnn2ccc(N3CC[C@H](O)C3)cc12] |
| 63 | 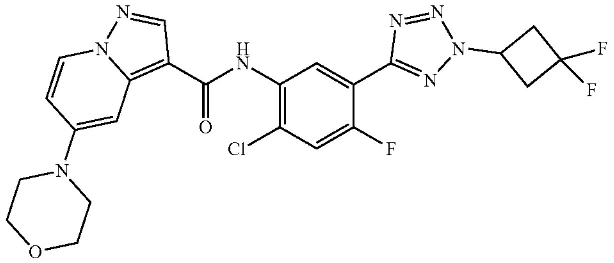 [SMILES: O=C(Nc1cc(-c2nnn(C3CC(F)(F)C3)n2)c(F)cc1Cl)c1cnn2ccc(N3CCOCC3)cc12] |

-continued
| Compound No | Structure |
|---|---|
| 64 | 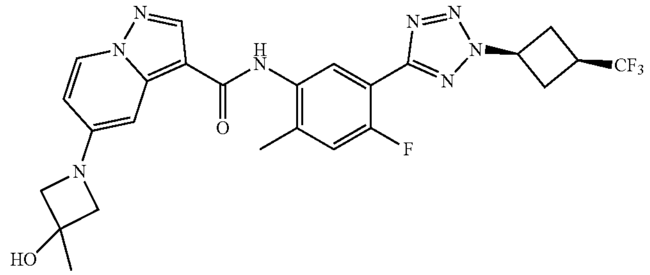 [SMILES: Cc1cc(F)c(-c2nnn([C@H]3C[C@@H](C(F)(F)F)C3)n2)cc1NC(=O)c1cnn2ccc(N3CC(C)(O)C3)cc12] |
| 65 | 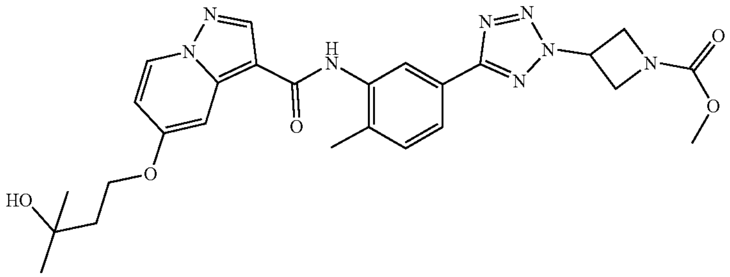 [SMILES: COC(=O)N1CC(n2nnc(-c3ccc(C)c(NC(=O)c4cnn5ccc(OCCC(C)(C)O)cc45)c3)n2)C1] |
| 66 | 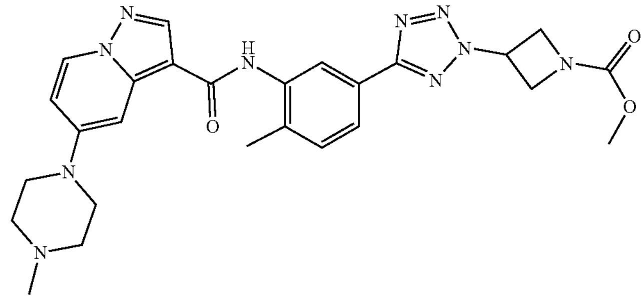 [SMILES: COC(=O)N1CC(n2nnc(-c3ccc(C)c(NC(=O)c4cnn5ccc(N6CCN(C)CC6)cc45)c3)n2)C1] |
| 67 | 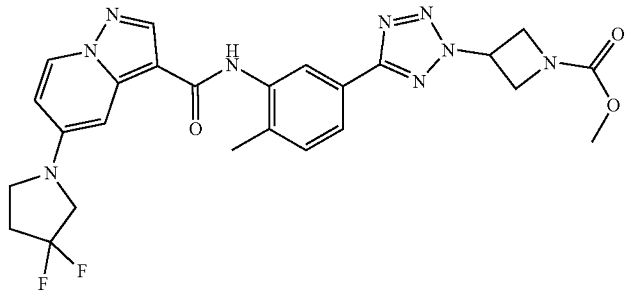 [SMILES: COC(=O)N1CC(n2nnc(-c3ccc(C)c(NC(=O)c4cnn5ccc(N6CCC(F)(F)C6)cc45)c3)n2)C1] |
| 68 | 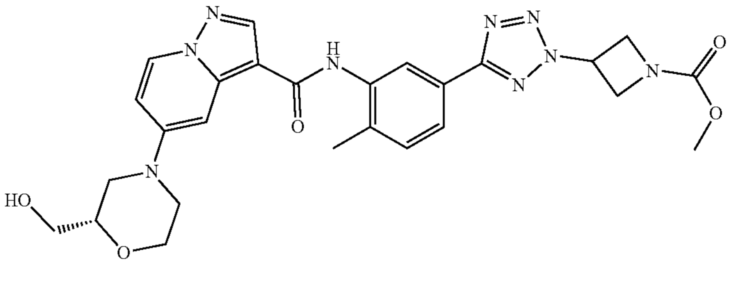 [SMILES: COC(=O)N1CC(n2nnc(-c3ccc(C)c(NC(=O)c4cnn5ccc(N6CCO[C@H](CO)C6)cc45)c3)n2)C1] |

-continued
| Compound No | Structure |
| --- | --- |
| 69 | 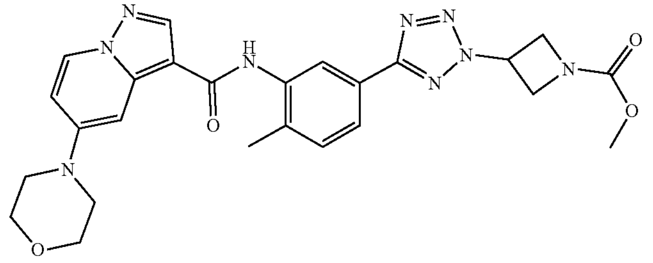 [SMILES: COC(=O)N1CC(n2nnc(-c3ccc(C)c(NC(=O)c4cnn5ccc(N6CCOCC6)cc45)c3)n2)C1] |
| 70 | 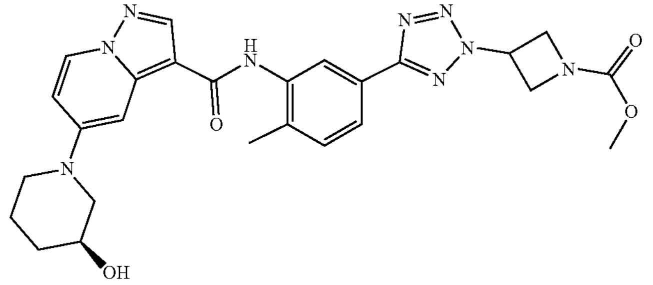 [SMILES: COC(=O)N1CC(n2nnc(-c3ccc(C)c(NC(=O)c4cnn5ccc(N6CCC[C@H](O)C6)cc45)c3)n2)C1] |
| 71 | 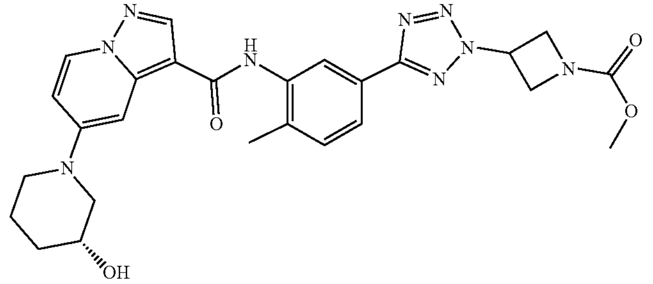 [SMILES: COC(=O)N1CC(n2nnc(-c3ccc(C)c(NC(=O)c4cnn5ccc(N6CCC[C@@H](O)C6)cc45)c3)n2)C1] |
| 72 | 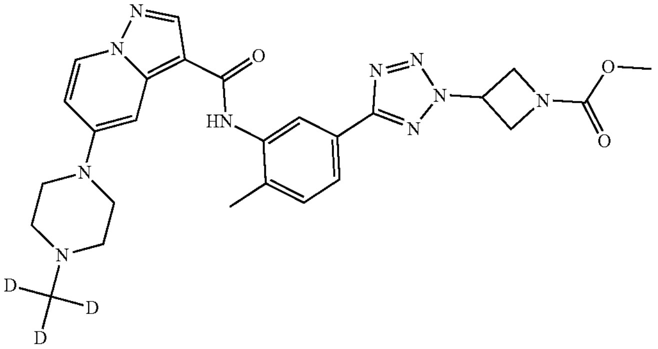 [SMILES: [2H]C([2H])([2H])N1CCN(c2ccn3ncc(C(=O)Nc4cc(-c5nnn(C6CN(C(=O)OC)C6)n5)ccc4C)c3c2)CC1] |
| 73 | 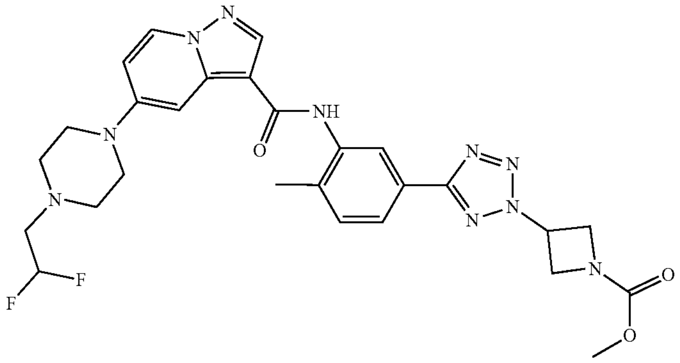 [SMILES: COC(=O)N1CC(n2nnc(-c3ccc(C)c(NC(=O)c4cnn5ccc(N6CCN(CC(F)F)CC6)cc45)c3)n2)C1] |

-continued
| Compound No | Structure |
|---|---|
| 74 | 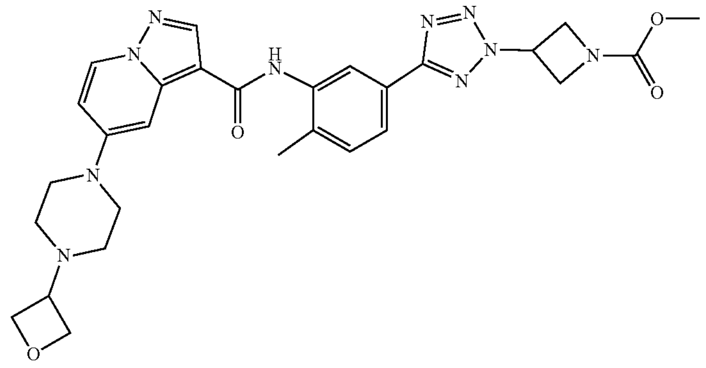 [SMILES: COC(=O)N1CC(n2nnc(-c3ccc(C)c(NC(=O)c4cnn5ccc(N6CCN(C7COC7)CC6)cc45)c3)n2)C1] |
| 75 | 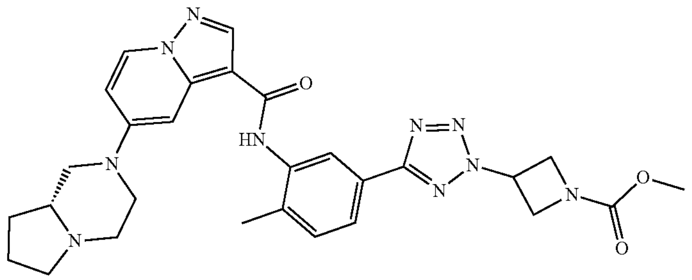 [SMILES: COC(=O)N1CC(n2nnc(-c3ccc(C)c(NC(=O)c4cnn5ccc(N6CCN7CCC[C@@H]7C6)cc45)c3)n2)C1] |
| 76 | 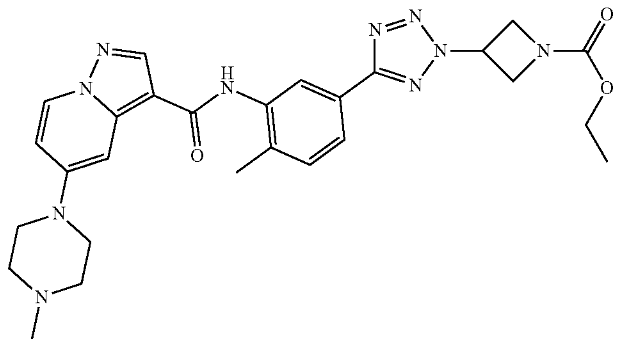 [SMILES: CCOC(=O)N1CC(n2nnc(-c3ccc(C)c(NC(=O)c4cnn5ccc(N6CCN(C)CC6)cc45)c3)n2)C1] |
| 77 | 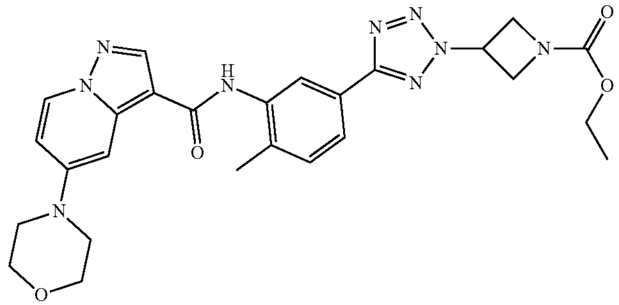 [SMILES: CCOC(=O)N1CC(n2nnc(-c3ccc(C)c(NC(=O)c4cnn5ccc(N6CCOCC6)cc45)c3)n2)C1] |

-continued
| Compound No | Structure |
| --- | --- |
| 78 | 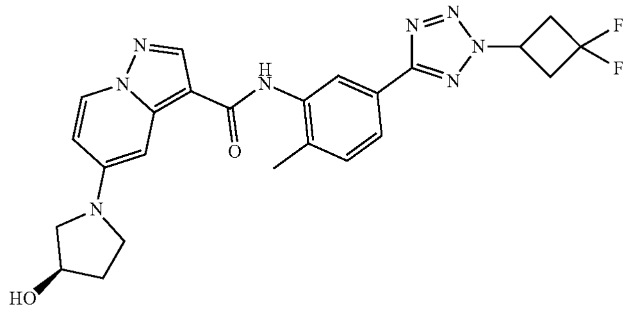 |
| 79 | 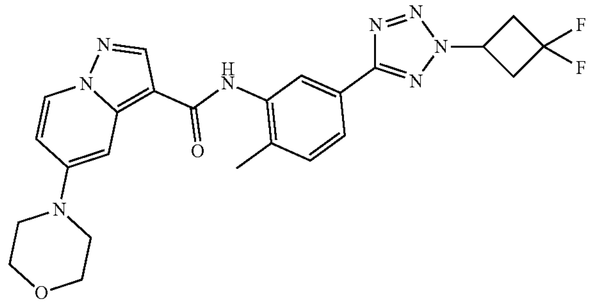 |
| 80 | 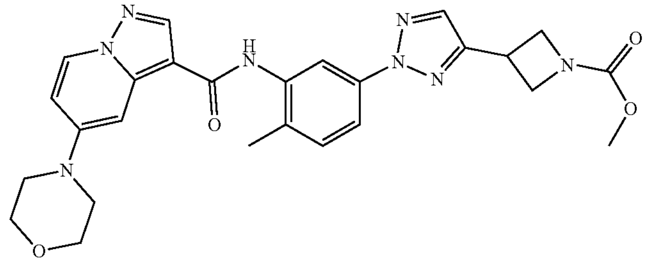 [SMILES: COC(=O)N1CC(c2cnn(-c3ccc(C)c(NC(=O)c4cnn5ccc(N6CCOCC6)cc45)c3)n2)C1] |
| 00 | 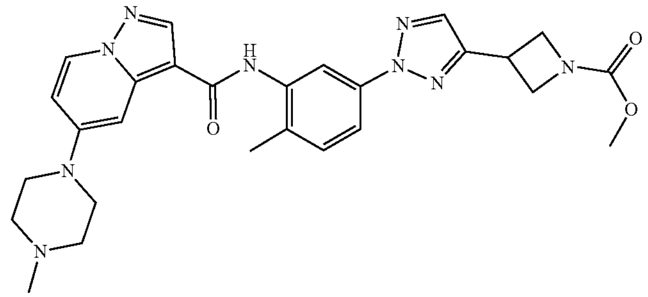 [SMILES: COC(=O)N1CC(c2cnn(-c3ccc(C)c(NC(=O)c4cnn5ccc(N6CCN(C)CC6)cc45)c3)n2)C1] |
| 82 | 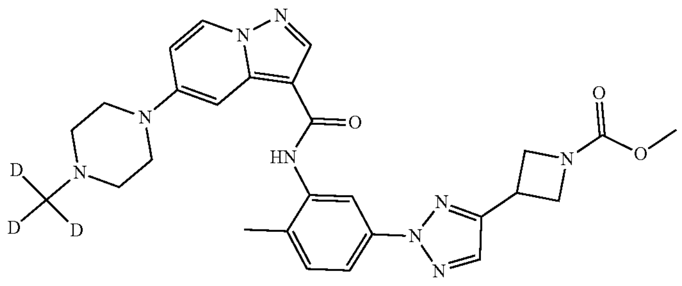 [SMILES: [2H]C([2H])([2H])N1CCN(c2ccn3ncc(C(=O)Nc4cc(-n5ncc(C6CN(C(=O)OC)C6)n5)ccc4C)c3c2)CC1] |

-continued
| Compound No | Structure |
| --- | --- |
| 83 | 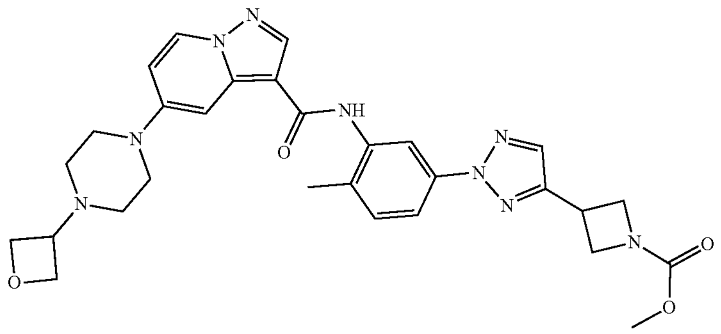 [SMILES: COC(=O)N1CC(c2cnn(-c3ccc(C)c(NC(=O)c4cnn5ccc(N6CCN(C7COC7)CC6)cc45)c3)n2)C1] |
| 84 | 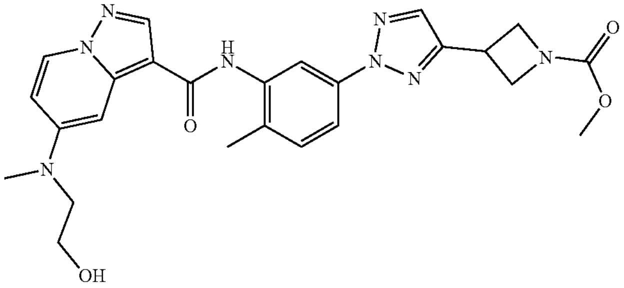 [SMILES: COC(=O)N1CC(c2cnn(-c3ccc(C)c(NC(=O)c4cnn5ccc(N(C)CCO)cc45)c3)n2)C1] |
| 85 | 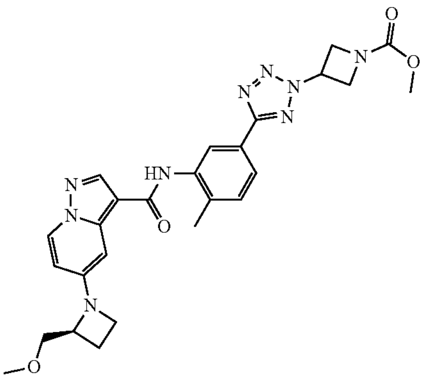 or 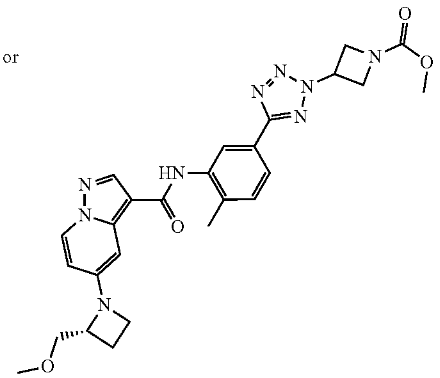 |
| 86 | 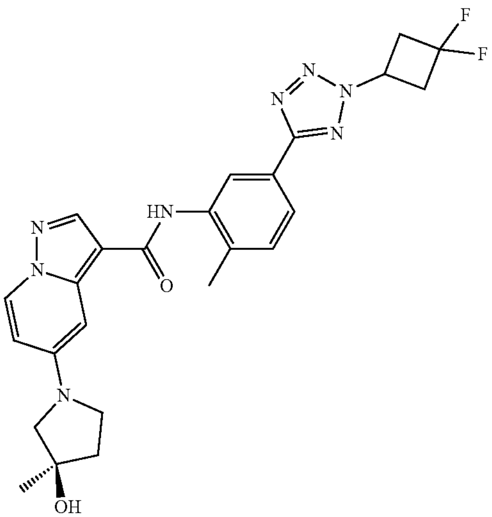 or 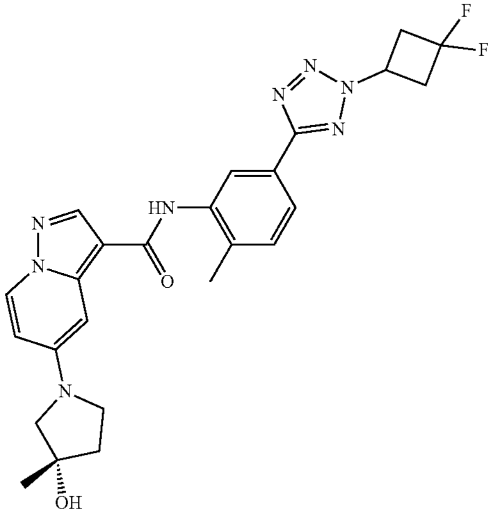 |

-continued
| Compound No | Structure |
|---|---|
| 87 | 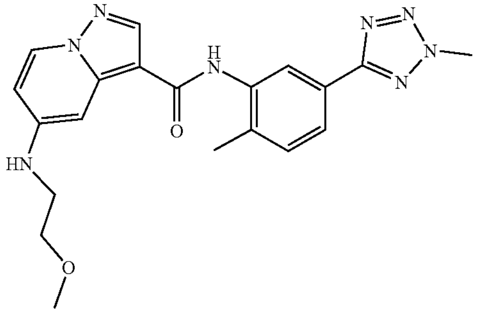 [SMILES: COCCNc1ccn2ncc(C(=O)Nc3cc(-c4nnn(C)n4)ccc3C)c2c1] |
| 88 | 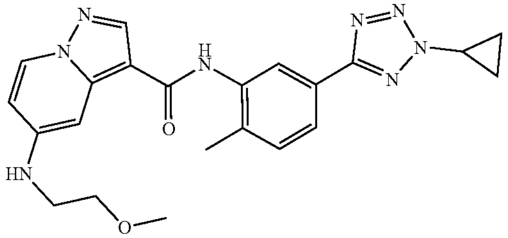 [SMILES: COCCNc1ccn2ncc(C(=O)Nc3cc(-c4nnn(C5CC5)n4)ccc3C)c2c1] |
| 89 | 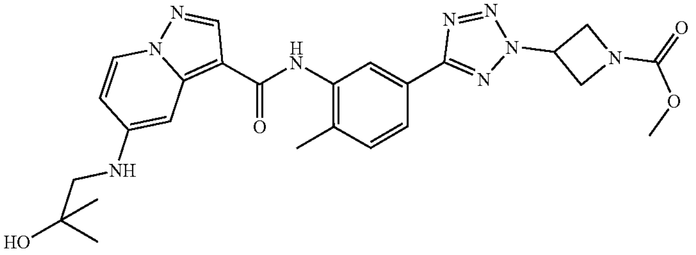 [SMILES: COC(=O)N1CC(n2nnc(-c3ccc(C)c(NC(=O)c4cnn5ccc(NCC(C)(C)O)cc45)c3)n2)C1] |
| 90 | 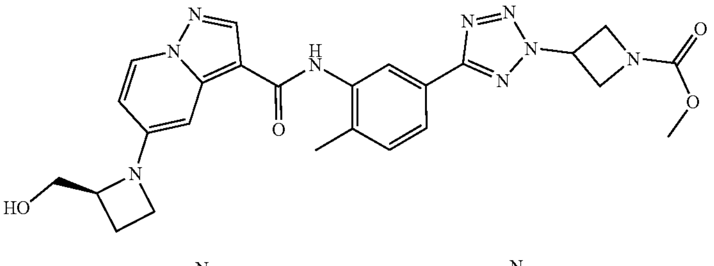 |
| 91 | 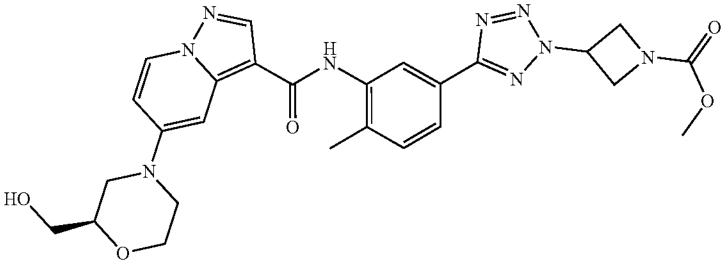 [SMILES: COC(=O)N1CC(n2nnc(-c3ccc(C)c(NC(=O)c4cnn5ccc(N6CCO[C@@H](CO)C6)cc45)c3)n2)C1] |
| 92 | 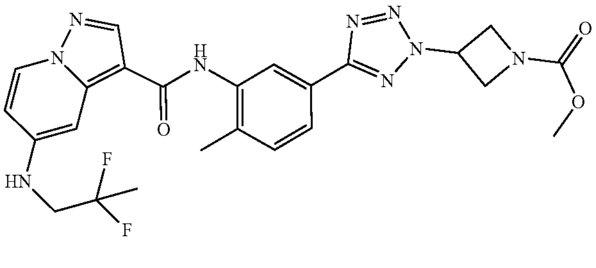 [SMILES: COC(=O)N1CC(n2nnc(-c3ccc(C)c(NC(=O)c4cnn5ccc(NCC(C)(F)F)cc45)c3)n2)C1] |

-continued
| Compound No | Structure |
|---|---|
| 93 | 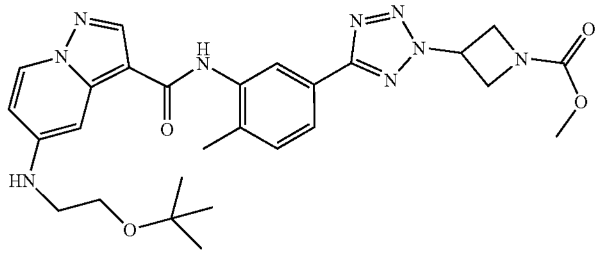 [SMILES: COC(=O)N1CC(n2nnc(-c3ccc(C)c(NC(=O)c4cnn5ccc(NCCOC(C)(C)C)cc45)c3)n2)C1] |
| 94 | 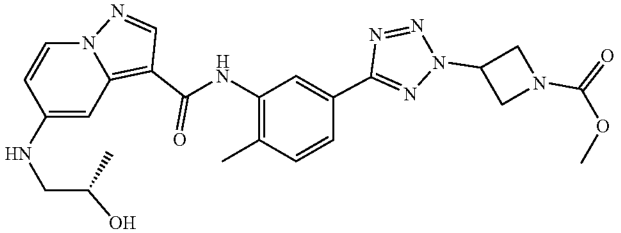 [SMILES: COC(=O)N1CC(n2nnc(-c3ccc(C)c(NC(=O)c4cnn5ccc(NC[C@H](C)O)cc45)c3)n2)C1] |
| 95 | 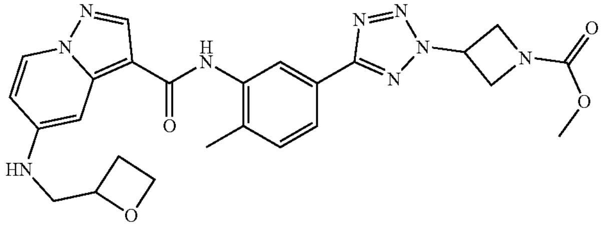 [SMILES: COC(=O)N1CC(n2nnc(-c3ccc(C)c(NC(=O)c4cnn5ccc(NCC6CCO6)cc45)c3)n2)C1] |
| 96 | 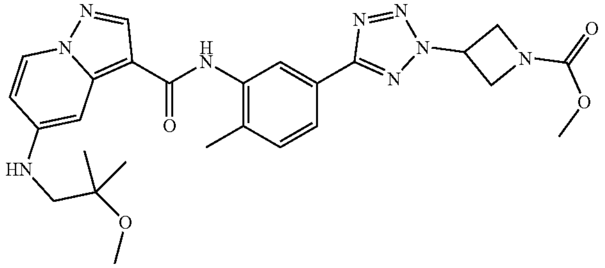 [SMILES: COC(=O)N1CC(n2nnc(-c3ccc(C)c(NC(=O)c4cnn5ccc(NCC(C)(C)OC)cc45)c3)n2)C1] |
| 97 | 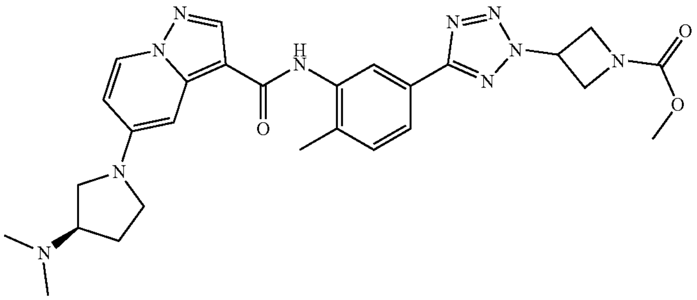 [SMILES: COC(=O)N1CC(n2nnc(-c3ccc(C)c(NC(=O)c4cnn5ccc(N6CC[C@@H](N(C)C)C6)cc45)c3)n2)C1] |

-continued
| Compound No | Structure |
|---|---|
| 98 | 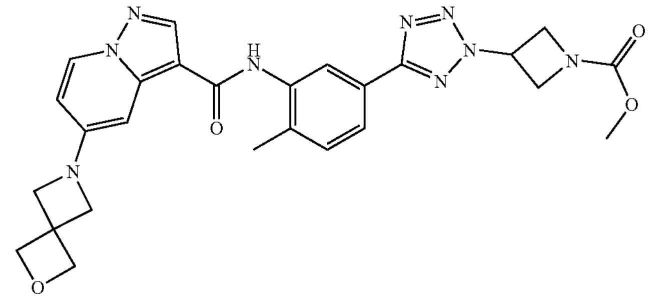 [SMILES: COC(=O)N1CC(n2nnc(-c3ccc(C)c(NC(=O)c4cnn5ccc(N6CC7(COC7)C6)cc45)c3)n2)C1] |
| 99 | 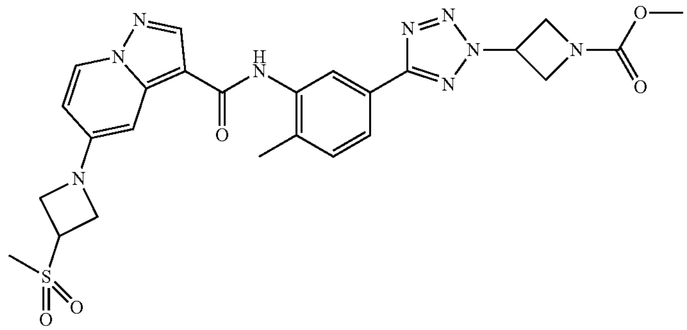 |
| 100 | 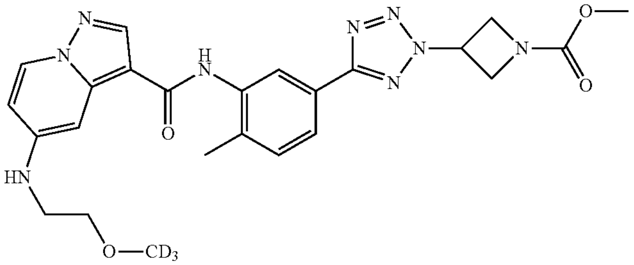 [SMILES: [2H]C([2H])([2H])OCCNc1ccn2ncc(C(=O)Nc3cc(-c4nnn(C5CN(C(=O)OC)C5)n4)ccc3C)c2c1] |
| 101 | 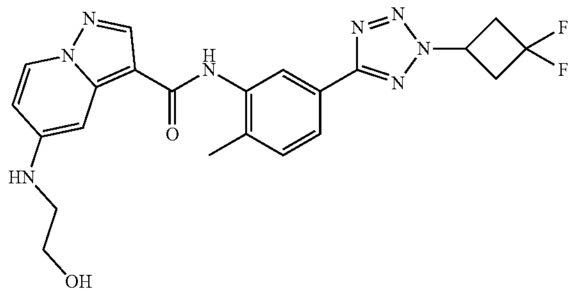 [SMILES: Cc1ccc(-c2nnn(C3CC(F)(F)C3)n2)cc1NC(=O)c1cnn2ccc(NCCO)cc12] |
| 102 | 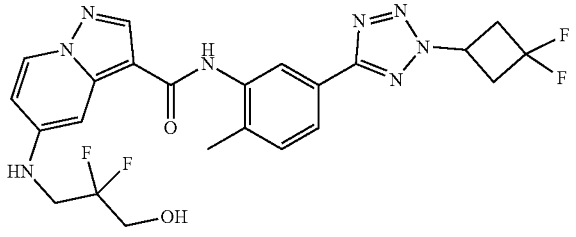 [SMILES: Cc1ccc(-c2nnn(C3CC(F)(F)C3)n2)cc1NC(=O)c1cnn2ccc(NCC(F)(F)CO)cc12] |

-continued
| Compound No | Structure |
| --- | --- |
| 103 | 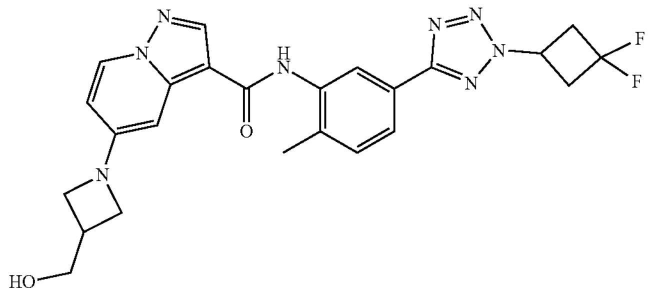 [SMILES: Cc1ccc(-c2nnn(C3CC(F)(F)C3)n2)cc1NC(=O)c1cnn2ccc(N3CC(CO)C3)cc12] |
| 104 | 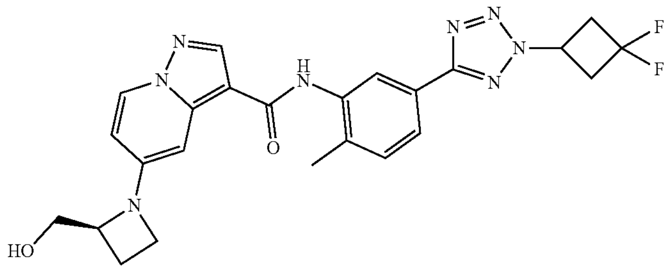 [SMILES: Cc1ccc(-c2nnn(C3CC(F)(F)C3)n2)cc1NC(=O)c1cnn2ccc(N3CC[C@H]3CO)cc12] |
| 105 | 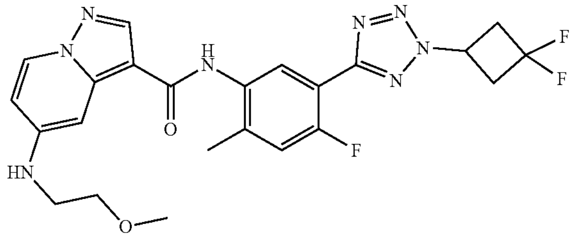 [SMILES: COCCNc1ccn2ncc(C(=O)Nc3cc(-c4nnn(C5CC(F)(F)C5)n4)c(F)cc3C)c2c1] |
| 106 | 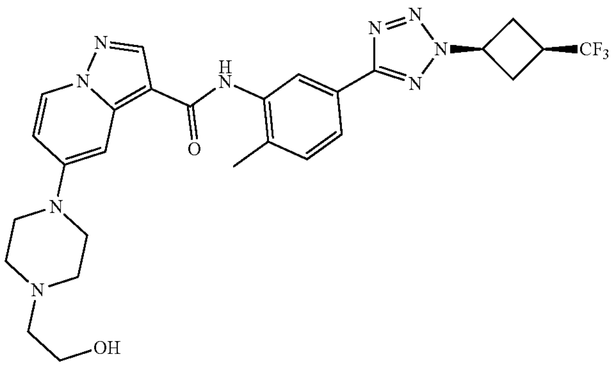 [SMILES: Cc1ccc(-c2nnn([C@H]3C[C@@H](C(F)(F)F)C3)n2)cc1NC(=O)c1cnn2ccc(N3CCN(CCO)CC3)cc12] |
| 107 | 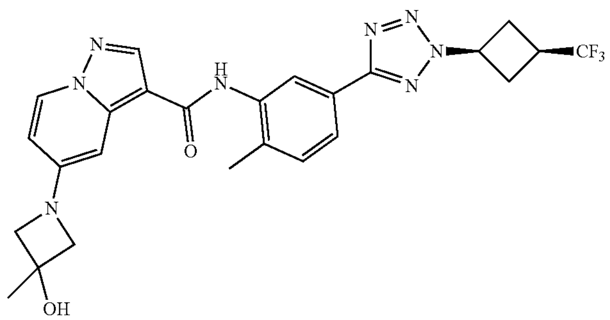 [SMILES: Cc1ccc(-c2nnn([C@H]3C[C@@H](C(F)(F)F)C3)n2)cc1NC(=O)c1cnn2ccc(N3CC(C)(O)C3)cc12] |

-continued
| Compound No | Structure |
| --- | --- |
| 108 | 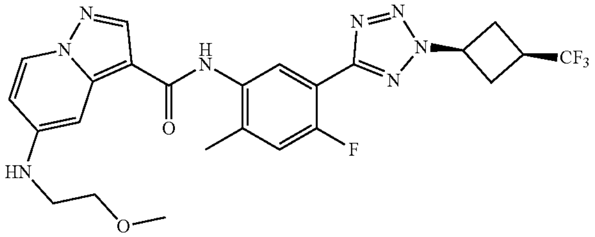 [SMILES: COCCNc1ccn2ncc(C(=O)Nc3cc(-c4nnn([C@H]5C[C@@H](C(F)(F)F)C5)n4)c(F)cc3C)c2c1] |
| 109 | 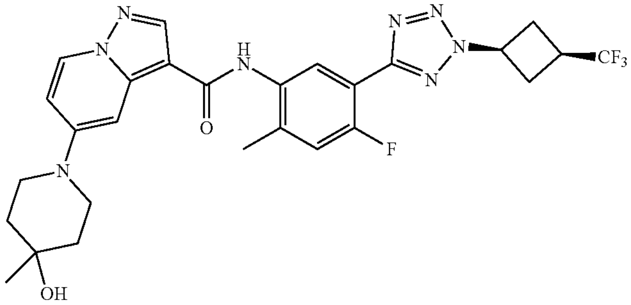 [SMILES: Cc1cc(F)c(-c2nnn([C@H]3C[C@@H](C(F)(F)F)C3)n2)cc1NC(=O)c1cnn2ccc(N3CCC(C)(O)CC3)cc12] |
| 110 | 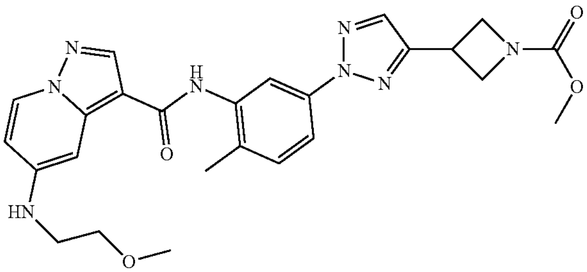 [SMILES: COCCNc1ccn2ncc(C(=O)Nc3cc(-n4ncc(C5CN(C(=O)OC)C5)n4)ccc3C)c2c1] |
| 111 | 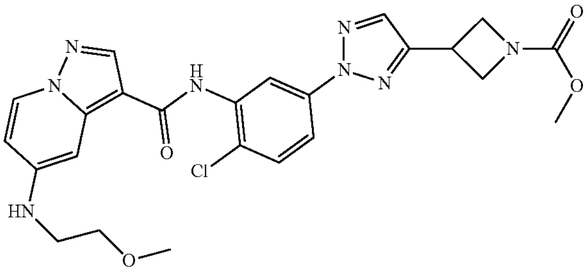 [SMILES: COCCNc1ccn2ncc(C(=O)Nc3cc(-n4ncc(C5CN(C(=O)OC)C5)n4)ccc3Cl)c2c1] |
| 112 | 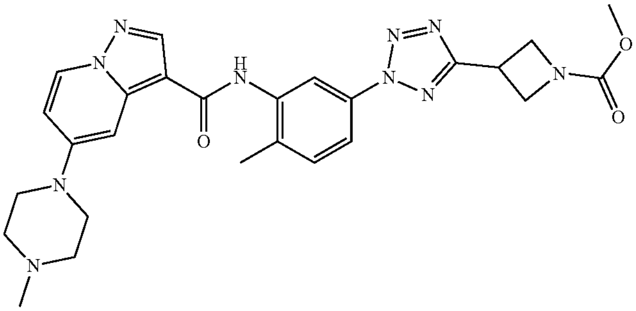 [SMILES: COC(=O)N1CC(c2nnn(-c3ccc(C)c(NC(=O)c4cnn5ccc(N6CCN(C)CC6)cc45)c3)n2)C1] |

-continued
| Compound No | Structure |
| --- | --- |
| 113 | 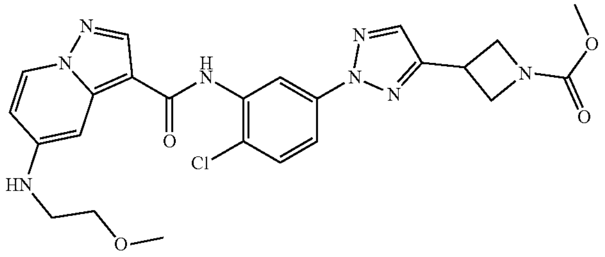 [SMILES: COCCNc1ccn2ncc(C(=O)Nc3cc(-n4ncc(C5CN(C(=O)OC)C5)n4)ccc3Cl)c2c1] |
| 114 | 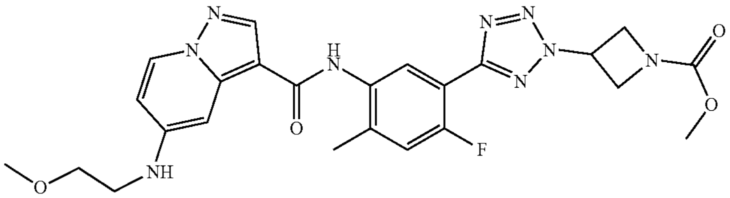 [SMILES: COCCNc1ccn2ncc(C(=O)Nc3cc(-c4nnn(C5CN(C(=O)OC)C5)n4)c(F)cc3C)c2c1] |
| 115 | 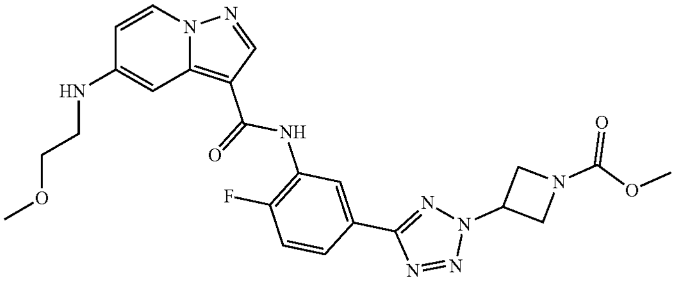 |
| 116 | 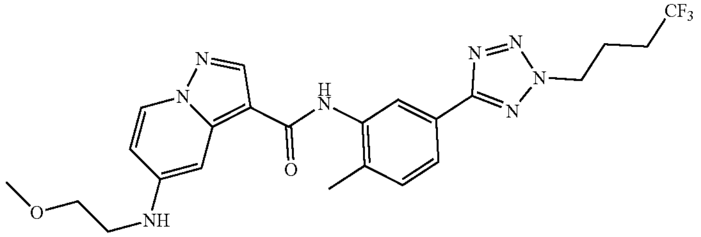 [SMILES: COCCNc1ccn2ncc(C(=O)Nc3cc(-c4nnn(CCCC(F)(F)F)n4)ccc3C)c2c1] |
| 117 | 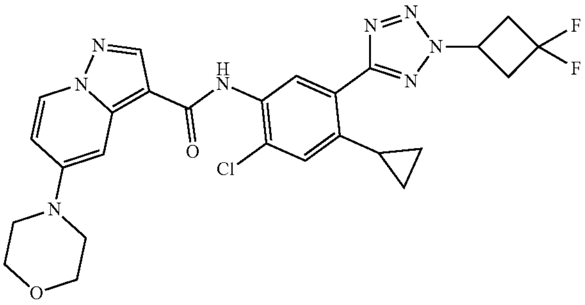 |
| 118 | 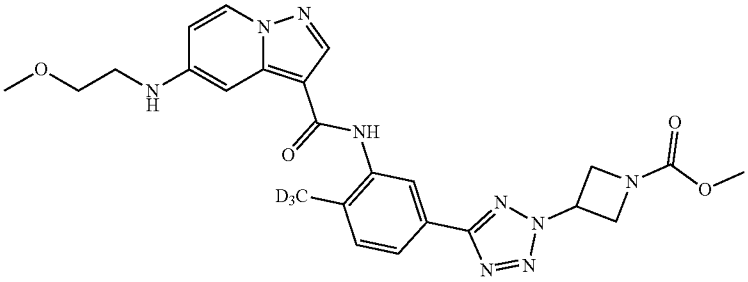 |

-continued
| Compound No | Structure |
|---|---|
| 119 | 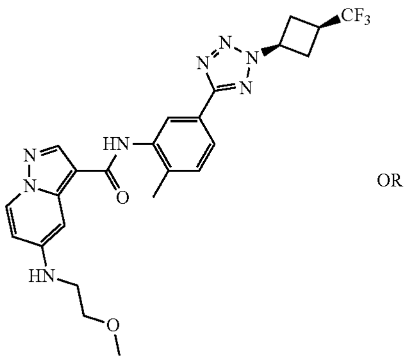 OR 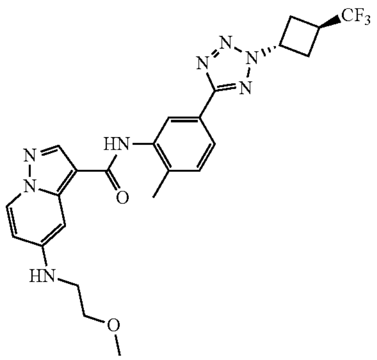 |
| 120 | 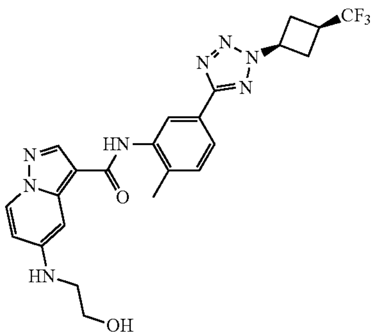 OR 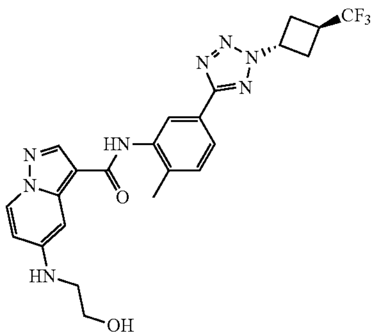 |
| 121 | 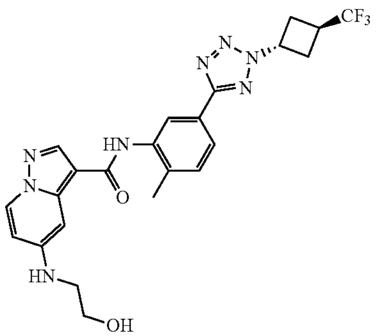 OR 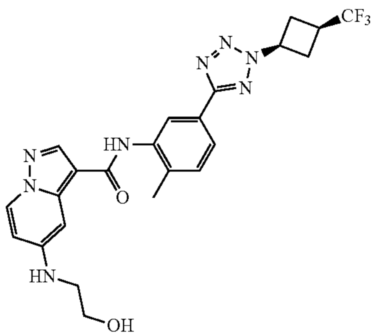 |
| 122 | 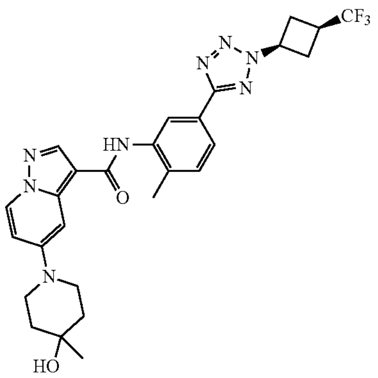 OR 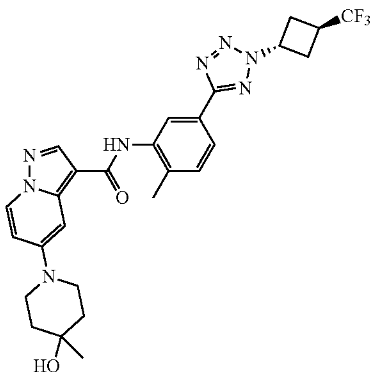 |

-continued
| Compound No | Structure |
|---|---|
| 123 | 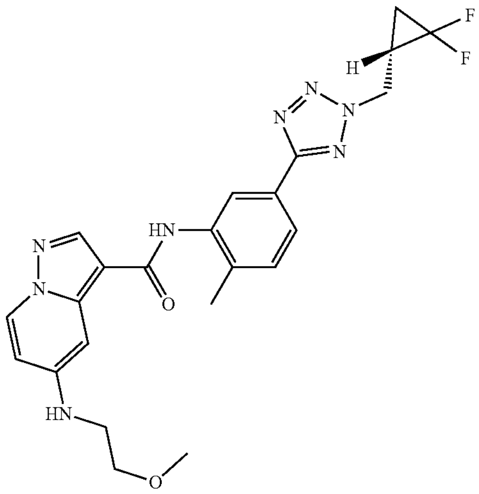 Or 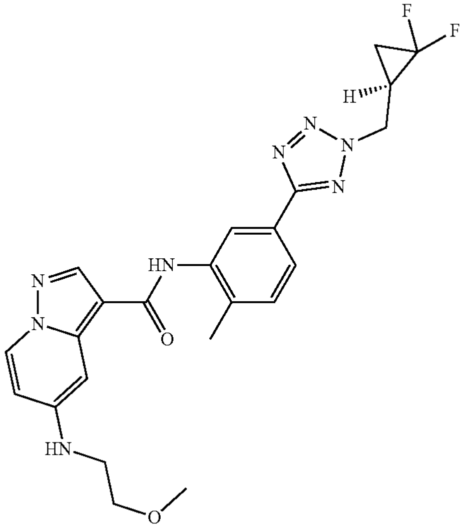 |
| 124 | 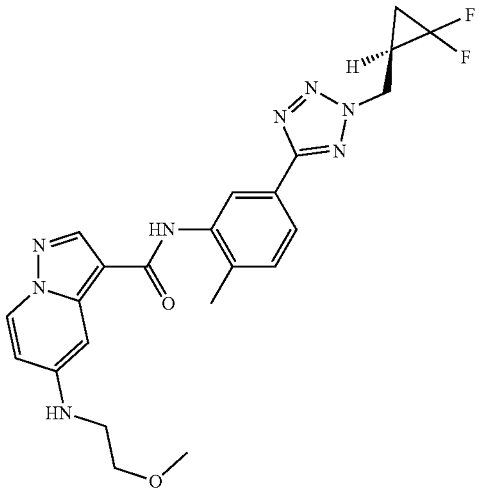 Or 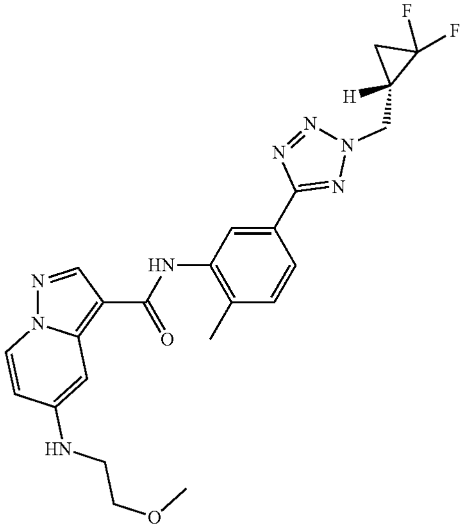 |
| 125 | 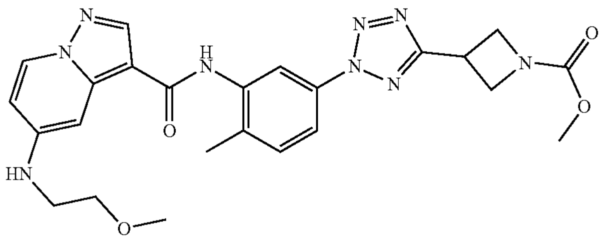 [SMILES: COCCNc1ccn2ncc(C(=O)Nc3cc(-n4nnc(C5CN(C(=O)OC)C5)n4)ccc3C)c2c1] |
| 126 | 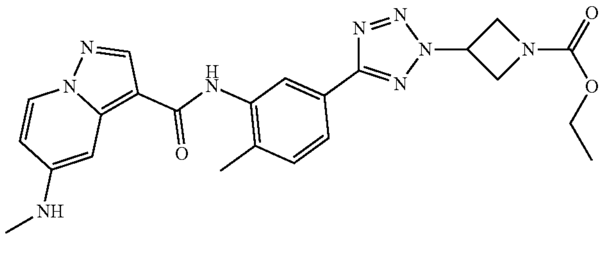 [SMILES: CCOC(=O)N1CC(n2nnc(-c3ccc(C)c(NC(=O)c4cnn5ccc(NC)cc45)c3)n2)C1] |

-continued
| Compound No | Structure |
|---|---|
| 127 | 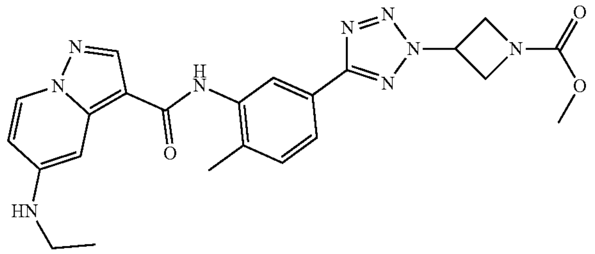 [SMILES: CCNc1ccn2ncc(C(=O)Nc3cc(-c4nnn(C5CN(C(=O)OC)C5)n4)ccc3C)c2c1] |
| 128 | 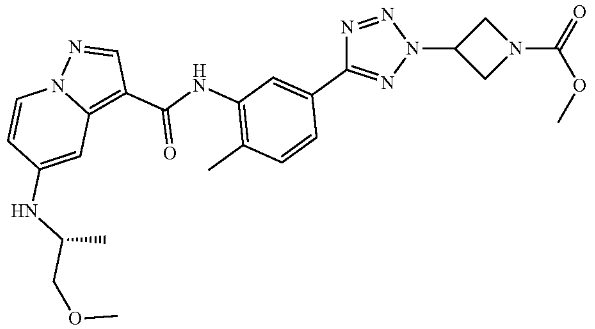 [SMILES: COC[C@@H](C)Nc1ccn2ncc(C(=O)Nc3cc(-c4nnn(C5CN(C(=O)OC)C5)n4)ccc3C)c2c1] |
| 129 | 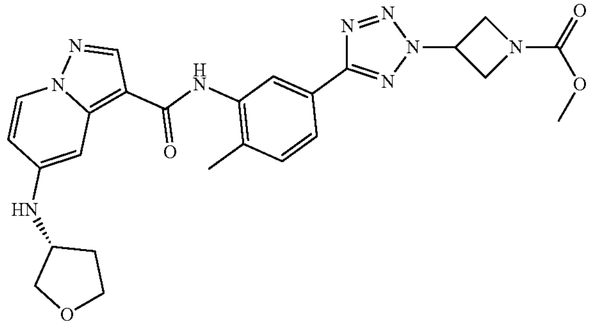 [SMILES: COC(=O)N1CC(n2nnc(-c3ccc(C)c(NC(=O)c4cnn5ccc(N[C@@H]6CCOC6)cc45)c3)n2)C1] |
| 130 | 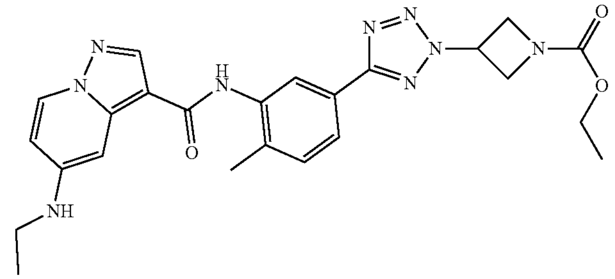 [SMILES: CCNc1ccn2ncc(C(=O)Nc3cc(-c4nnn(C5CN(C(=O)OCC)C5)n4)ccc3C)c2c1] |
| 131 | 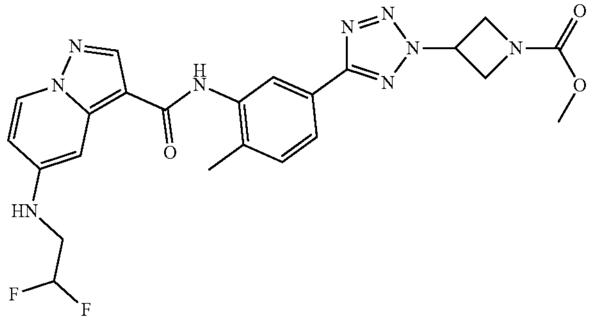 [SMILES: COC(=O)N1CC(n2nnc(-c3ccc(C)c(NC(=O)c4cnn5ccc(NCC(F)F)cc45)c3)n2)C1] |

-continued
| Compound No | Structure |
| --- | --- |
| 132 | 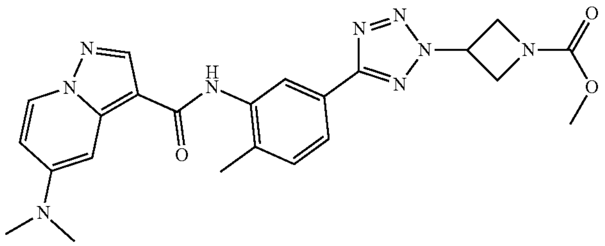 [SMILES: COC(=O)N1CC(n2nnc(-c3ccc(C)c(NC(=O)c4cnn5ccc(N(C)C)cc45)c3)n2)C1] |
| 133 | 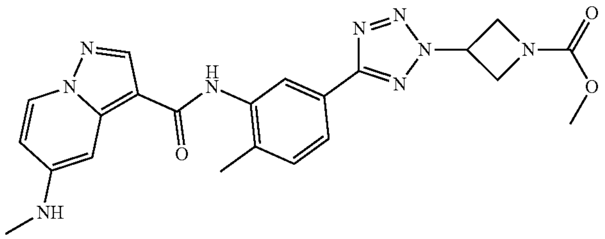 [SMILES: CNc1ccn2ncc(C(=O)Nc3cc(-c4nnn(C5CN(C(=O)OC)C5)n4)ccc3C)c2c1] |
| 134 | 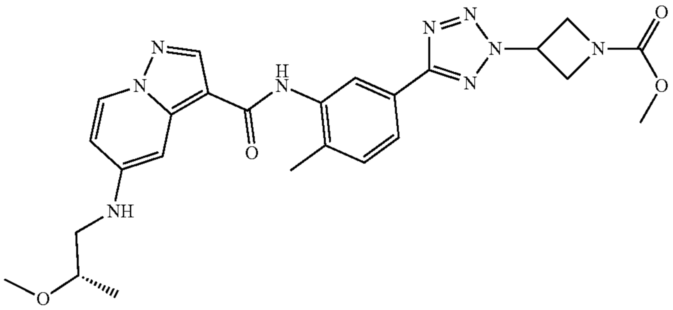 [SMILES: COC(=O)N1CC(n2nnc(-c3ccc(C)c(NC(=O)c4cnn5ccc(NC[C@H](C)OC)cc45)c3)n2)C1] |
| 135 | 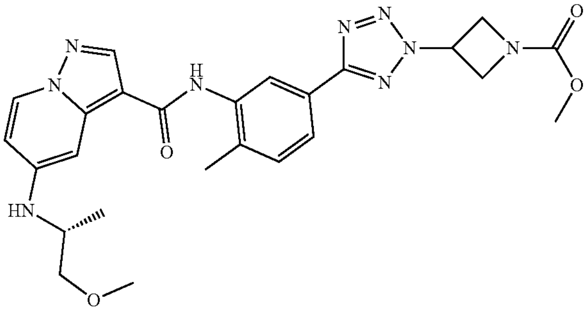 [SMILES: COC[C@@H](C)Nc1ccn2ncc(C(=O)Nc3cc(-c4nnn(C5CN(C(=O)OC)C5)n4)ccc3C)c2c1] |
| 136 | 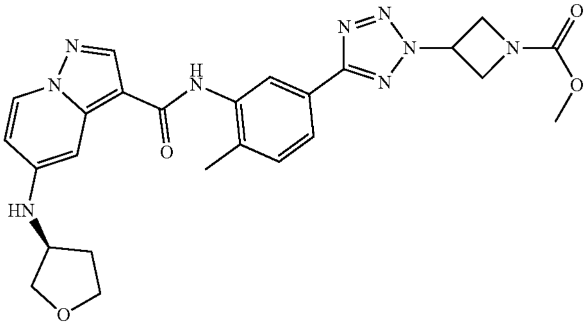 [SMILES: COC(=O)N1CC(n2nnc(-c3ccc(C)c(NC(=O)c4cnn5ccc(N[C@H]6CCOC6)cc45)c3)n2)C1] |

-continued
| Compound No | Structure |
|---|---|
| 137 | 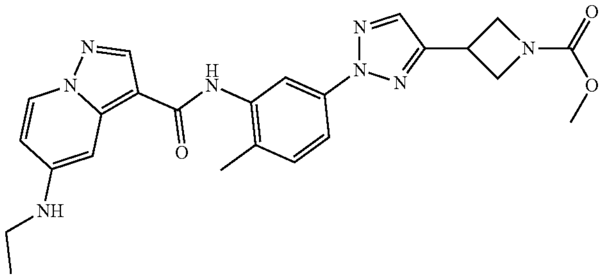 [SMILES: CCNc1ccn2ncc(C(=O)Nc3cc(-n4ncc(C5CN(C(=O)OC)C5)n4)ccc3C)c2c1] |
| 138 | 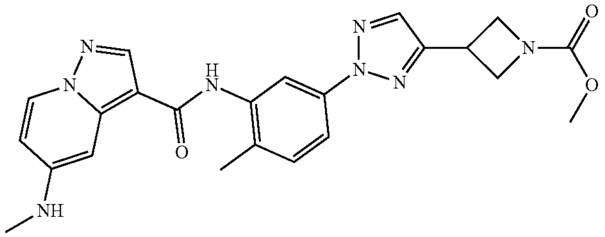 [SMILES: CNc1ccn2ncc(C(=O)Nc3cc(-n4ncc(C5CN(C(=O)OC)C5)n4)ccc3C)c2c1] |
| 139 | 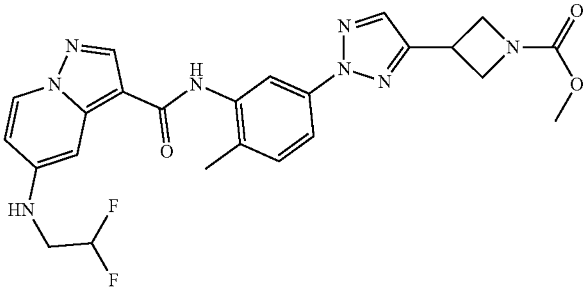 [SMILES: COC(=O)N1CC(c2cnn(-c3ccc(C)c(NC(=O)c4cnn5ccc(NCC(F)F)cc45)c3)n2)C1] |
| 140 | 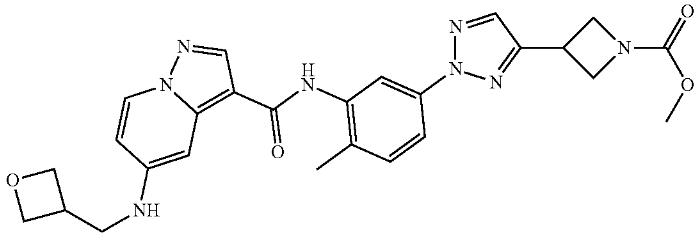 [SMILES: COC(=O)N1CC(c2cnn(-c3ccc(C)c(NC(=O)c4cnn5ccc(NCC6COC6)cc45)c3)n2)C1] |
| 141 | 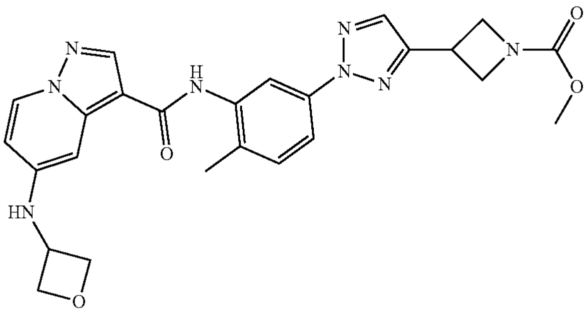 [SMILES: COC(=O)N1CC(c2cnn(-c3ccc(C)c(NC(=O)c4cnn5ccc(NC6COC6)cc45)c3)n2)C1] |

-continued
| Compound No | Structure |
| --- | --- |
| 142 | 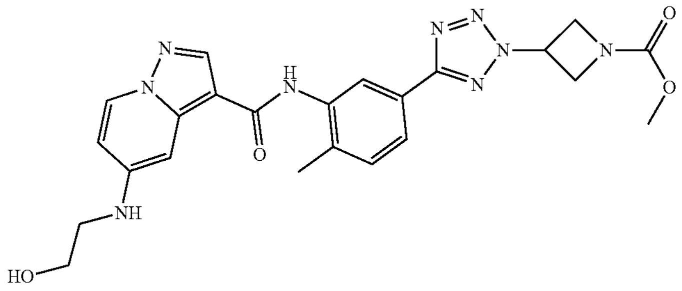 [SMILES: COC(=O)N1CC(n2nnc(-c3ccc(C)c(NC(=O)c4cnn5ccc(NCCO)cc45)c3)n2)C1] |
| 143 | 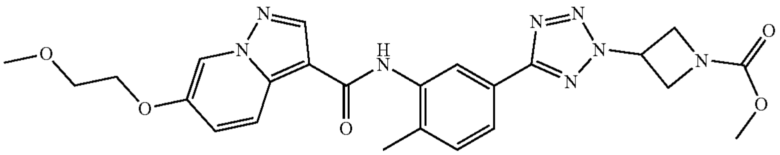 [SMILES: COCCOc1ccc2c(C(=O)Nc3cc(-c4nnn(C5CN(C(=O)OC)C5)n4)ccc3C)cnn2c1] |
| 144 | 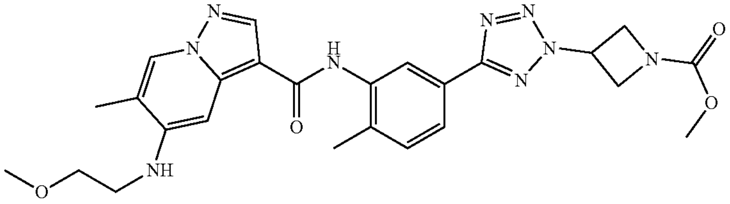 [SMILES: COCCNc1cc2c(C(=O)Nc3cc(-c4nnn(C5CN(C(=O)OC)C5)n4)ccc3C)cnn2cc1C] |
| 145 | 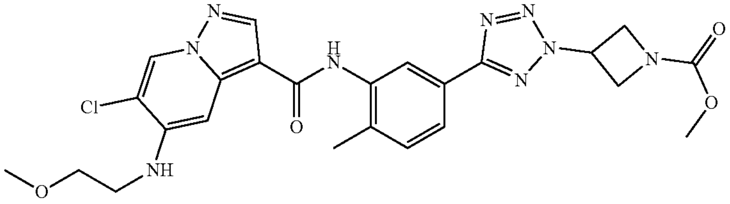 [SMILES: COCCNc1cc2c(C(=O)Nc3cc(-c4nnn(C5CN(C(=O)OC)C5)n4)ccc3C)cnn2cc1Cl] |
| 146 | 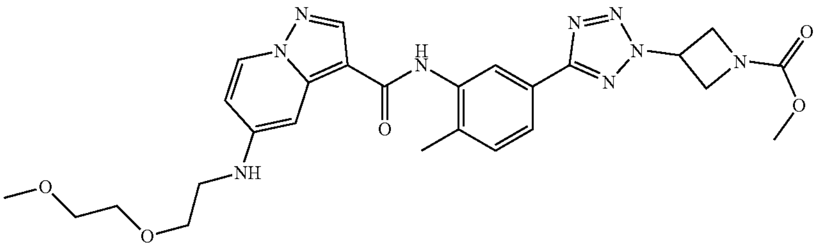 [SMILES: COCCOCCNc1ccn2ncc(C(=O)Nc3cc(-c4nnn(C5CN(C(=O)OC)C5)n4)ccc3C)c2c1] |
| 147 | 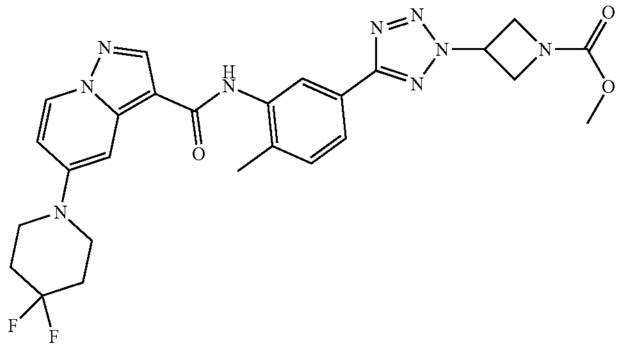 [SMILES: COC(=O)N1CC(n2nnc(-c3ccc(C)c(NC(=O)c4cnn5ccc(N6CCC(F)(F)CC6)cc45)c3)n2)C1] |

-continued
| Compound No | Structure |
|---|---|
| 148 | 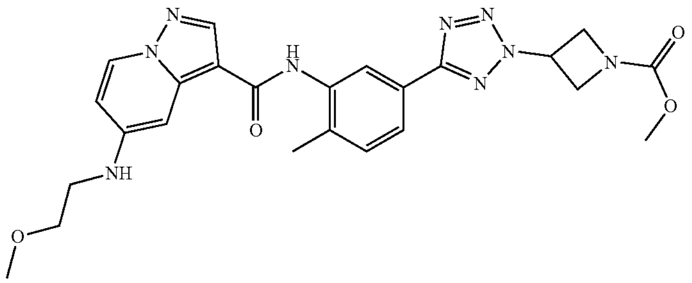 [SMILES: COCCNc1ccn2ncc(C(=O)Nc3cc(-c4nnn(C5CN(C(=O)OC)C5)n4)ccc3C)c2c1] |
| 149 | 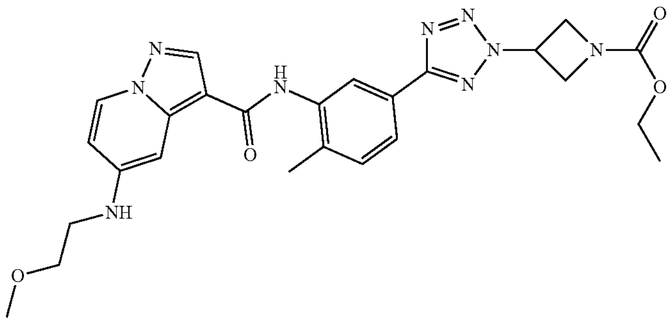 [SMILES: CCOC(=O)N1CC(n2nnc(-c3ccc(C)c(NC(=O)c4cnn5ccc(NCCOC)cc45)c3)n2)C1] |
| 150 | 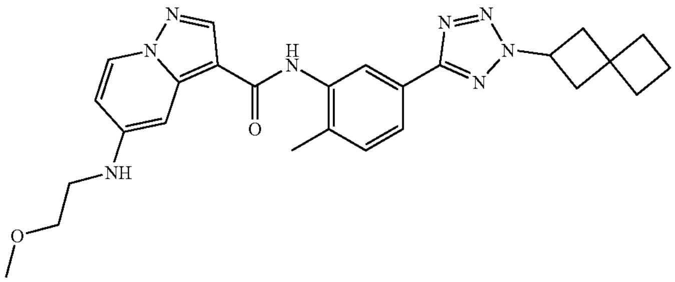 [SMILES: COCCNc1ccn2ncc(C(=O)Nc3cc(-c4nnn(C5CC6(CCC6)C5)n4)ccc3C)c2c1] |
| 151 | 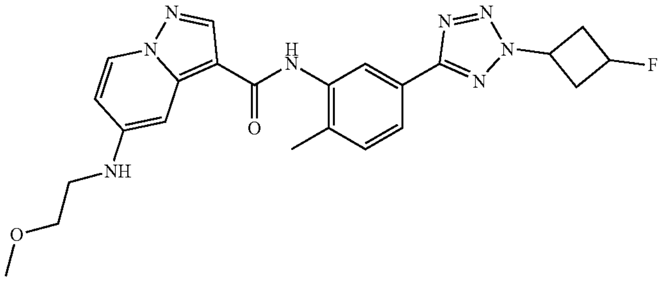 [SMILES: COCCNc1ccn2ncc(C(=O)Nc3cc(-c4nnn(C5CC(F)C5)n4)ccc3C)c2c1] |
| 152 | 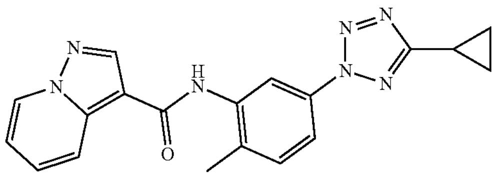 [SMILES: Cc1ccc(-n2nnc(C3CC3)n2)cc1NC(=O)c1cnn2ccccc12] |
| 153 | 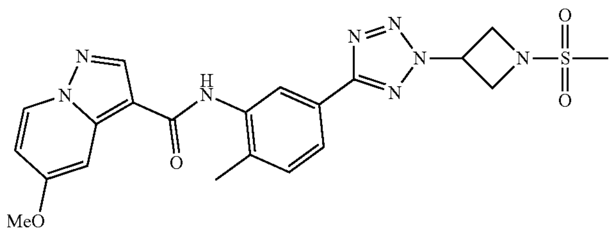 [SMILES: COc1ccn2ncc(C(=O)Nc3cc(-c4nnn(C5CN(S(C)(=O)=O)C5)n4)ccc3C)c2c1] |

-continued
| Compound No | Structure |
|---|---|
| 154 | 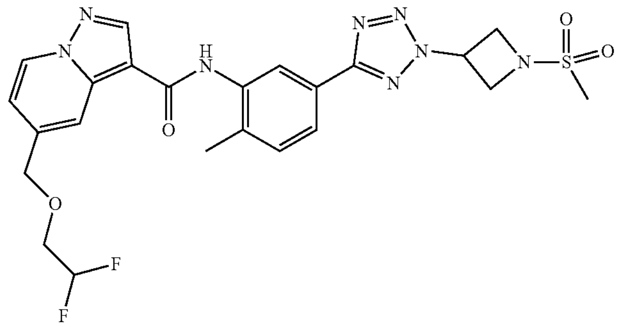 [SMILES: Cc1ccc(-c2nnn(C3CN(S(C)(=O)=O)C3)n2)cc1NC(=O)c1cnn2ccc(COCC(F)F)cc12] |
| 155 | 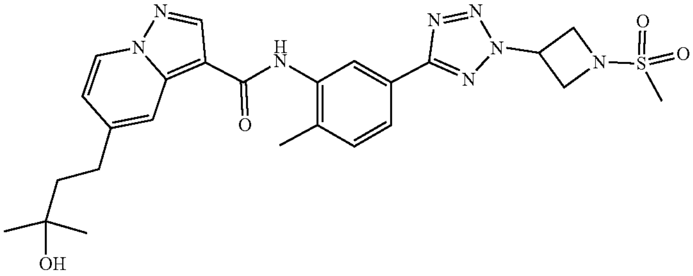 [SMILES: Cc1ccc(-c2nnn(C3CN(S(C)(=O)=O)C3)n2)cc1NC(=O)c1cnn2ccc(CCC(C)(C)O)cc12] |
| 156 | 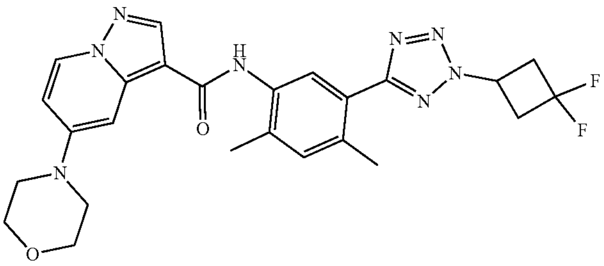 [SMILES: Cc1cc(C)c(-c2nnn(C3CC(F)(F)C3)n2)cc1NC(=O)c1cnn2ccc(N3CCOCC3)cc12] |
| 157 | 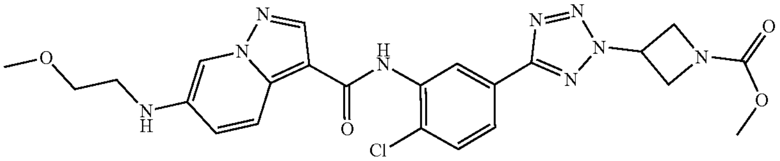 [SMILES: COCCNc1ccc2c(C(=O)Nc3cc(-c4nnn(C5CN(C(=O)OC)C5)n4)ccc3Cl)cnn2c1] |
| 158 | 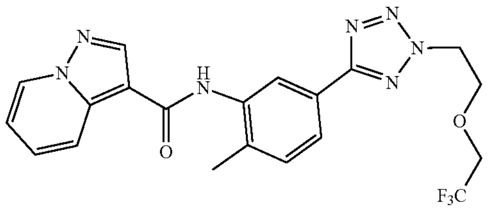 [SMILES: Cc1ccc(-c2nnn(CCOCC(F)(F)F)n2)cc1NC(=O)c1cnn2ccccc12] |
| 159 | 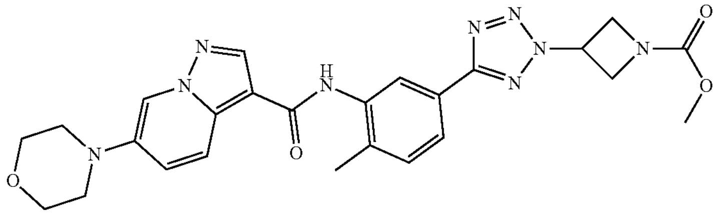 |

-continued
| Compound No | Structure |
|---|---|
| 160 | 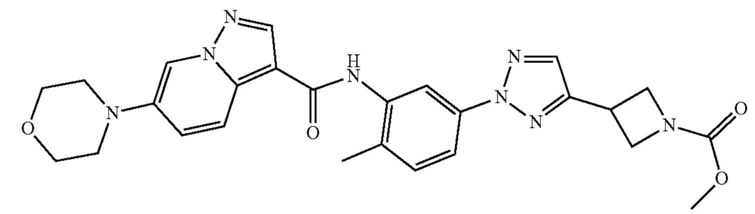 [SMILES: COC(=O)N1CC(c2cnn(-c3ccc(C)c(NC(=O)c4cnn5cc(N6CCOCC6)ccc45)c3)n2)C1] |
| 161 | 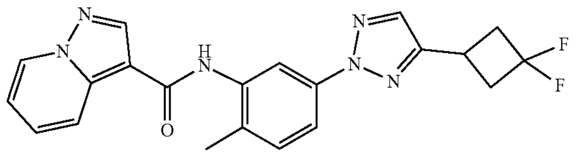 [SMILES: Cc1ccc(-n2ncc(C3CC(F)(F)C3)n2)cc1NC(=O)c1cnn2ccccc12] |
| 162 | 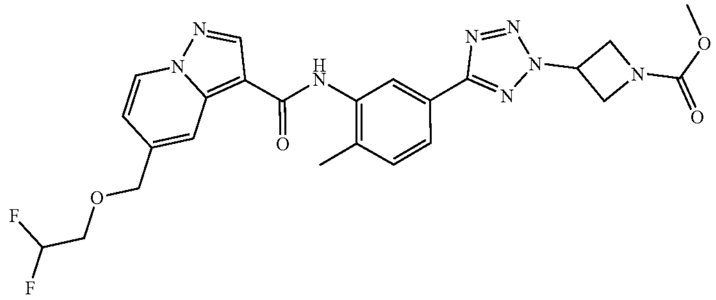 [SMILES: COC(=O)N1CC(n2nnc(-c3ccc(C)c(NC(=O)c4cnn5ccc(COCC(F)F)cc45)c3)n2)C1] |
| 163 | 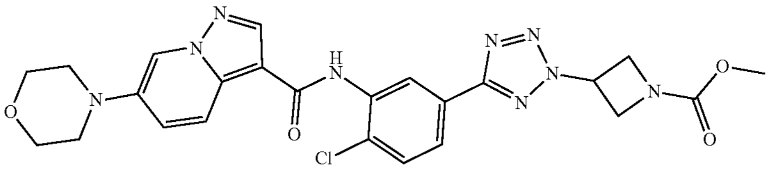 [SMILES: COC(=O)N1CC(n2nnc(-c3ccc(Cl)c(NC(=O)c4cnn5cc(N6CCOCC6)ccc45)c3)n2)C1] |
| 164 | 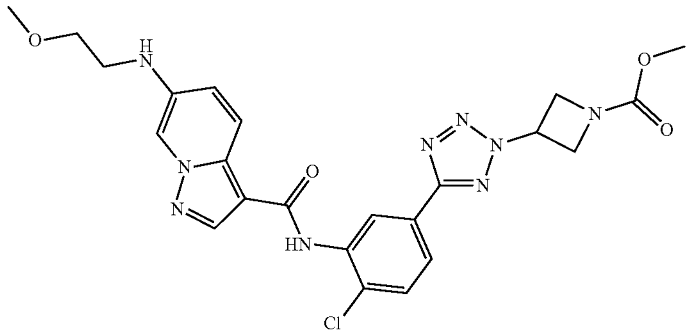 |
| 165 | 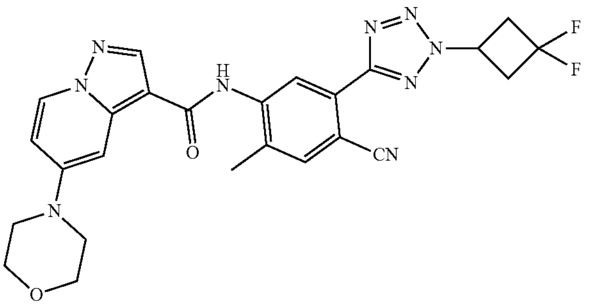 [SMILES: Cc1cc(C#N)c(-c2nnn(C3CC(F)(F)C3)n2)cc1NC(=O)c1cnn2ccc(N3CCOCC3)cc12] |

-continued
| Compound No | Structure |
|---|---|
| 166 | 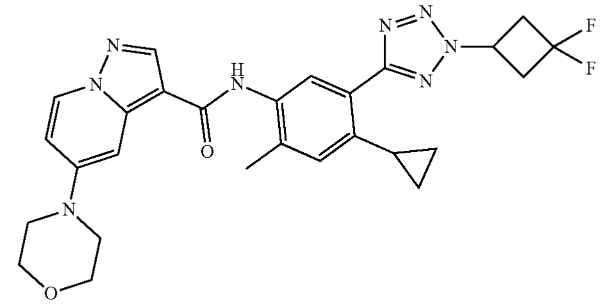 [SMILES: Cc1cc(C2CC2)c(-c2nnn(C3CC(F)(F)C3)n2)cc1NC(=O)c1cnn2ccc(N3CCOCC3)cc12] |
| 167 | 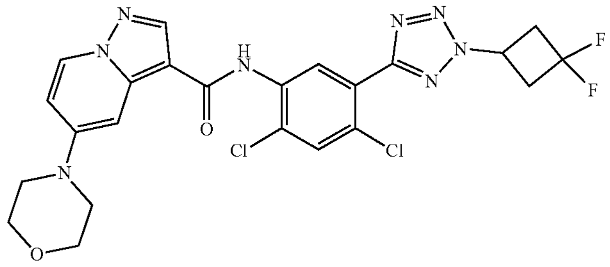 [SMILES: O=C(Nc1cc(-c2nnn(C3CC(F)(F)C3)n2)c(Cl)cc1Cl)c1cnn2ccc(N3CCOCC3)cc12] |
| 168 | 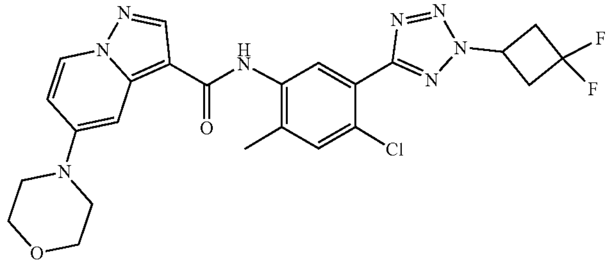 [SMILES: Cc1cc(Cl)c(-c2nnn(C3CC(F)(F)C3)n2)cc1NC(=O)c1cnn2ccc(N3CCOCC3)cc12] |
| 169 | 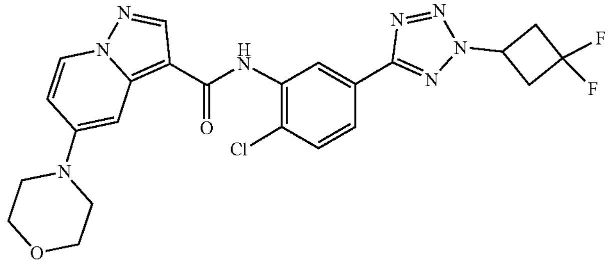 [SMILES: O=C(Nc1cc(-c2nnn(C3CC(F)(F)C3)n2)ccc1Cl)c1cnn2ccc(N3CCOCC3)cc12] |
| 170 | 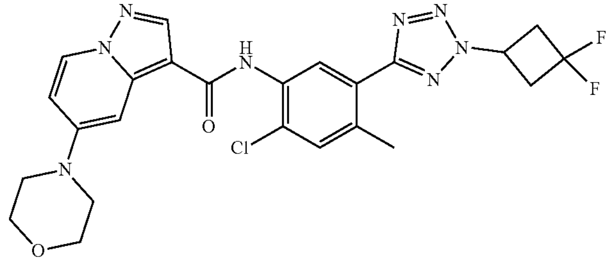 [SMILES: Cc1cc(Cl)c(NC(=O)c2cnn3ccc(N4CCOCC4)cc23)cc1-c1nnn(C2CC(F)(F)C2)n1] |

-continued
| Compound No | Structure |
|---|---|
| 171 | 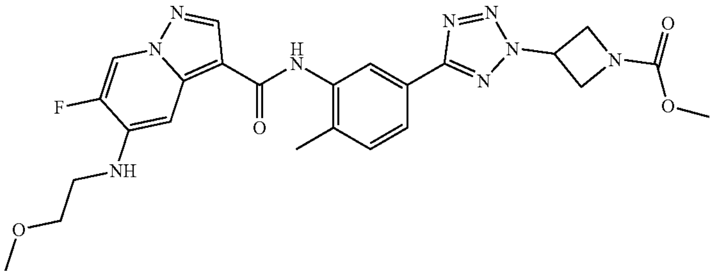 |
| 172 | 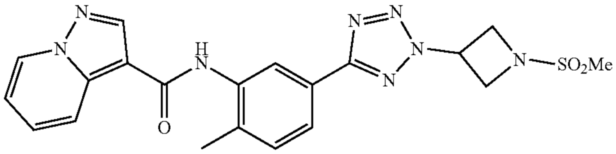 [SMILES: Cc1ccc(-c2nnn(C3CN(S(C)(=O)=O)C3)n2)cc1NC(=O)c1cnn2ccccc12] |
| 173 | 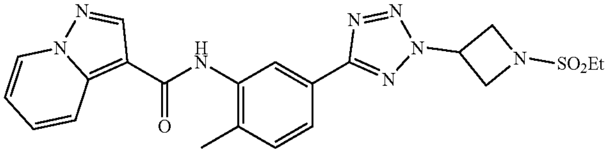 |
| 174 | 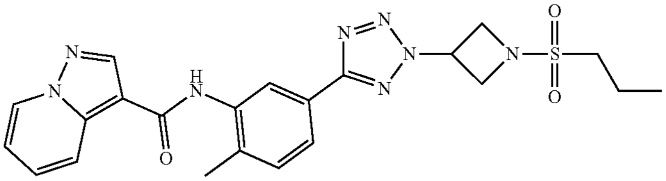 [SMILES: CCCS(=O)(=O)N1CC(n2nnc(-c3ccc(C)c(NC(=O)c4cnn5ccccc45)c3)n2)C1] |
| 175 | 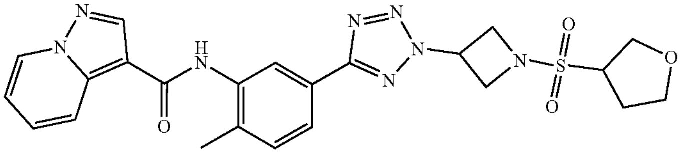 [SMILES: Cc1ccc(-c2nnn(C3CN(S(=O)(=O)C4CCOC4)C3)n2)cc1NC(=O)c1cnn2ccccc12] |
| 176 | 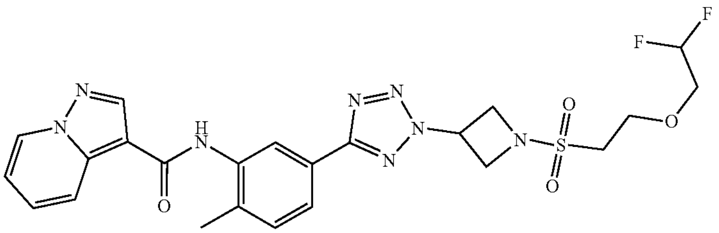 [SMILES: Cc1ccc(-c2nnn(C3CN(S(=O)(=O)CCOCC(F)F)C3)n2)cc1NC(=O)c1cnn2ccccc12] |
| 177 | 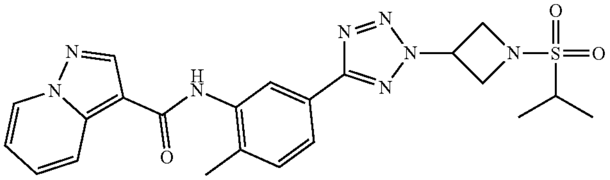 [SMILES: Cc1ccc(-c2nnn(C3CN(S(=O)(=O)C(C)C)C3)n2)cc1NC(=O)c1cnn2ccccc12] |

-continued
| Compound No | Structure |
|---|---|
| 178 | 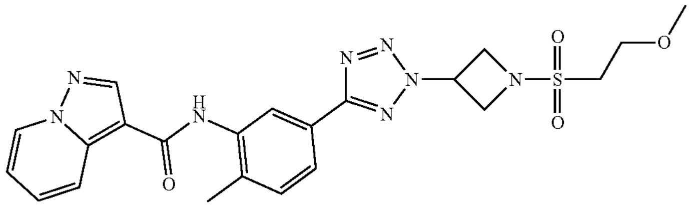 [SMILES: COCCS(=O)(=O)N1CC(n2nnc(-c3ccc(C)c(NC(=O)c4cnn5ccccc45)c3)n2)C1] |
| 179 | 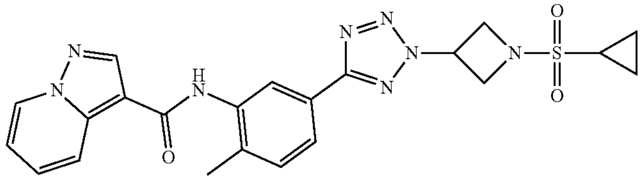 [SMILES: Cc1ccc(-c2nnn(C3CN(S(=O)(=O)C4CC4)C3)n2)cc1NC(=O)c1cnn2ccccc12] |
| 180 | 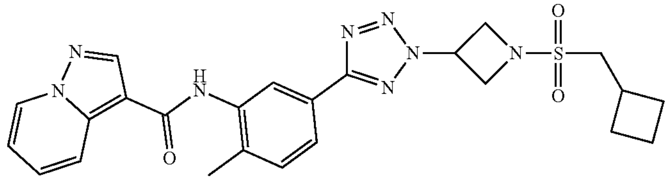 [SMILES: Cc1ccc(-c2nnn(C3CN(S(=O)(=O)CC4CCC4)C3)n2)cc1NC(=O)c1cnn2ccccc12] |
| 181 | 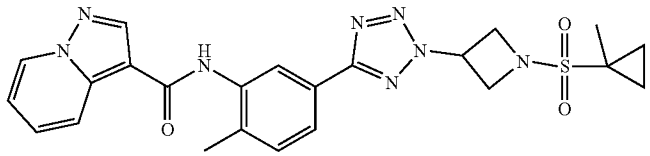 [SMILES: Cc1ccc(-c2nnn(C3CN(S(=O)(=O)C4(C)CC4)C3)n2)cc1NC(=O)c1cnn2ccccc12] |
| 182 | 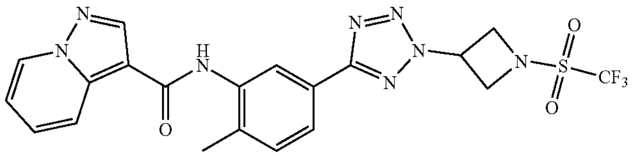 [SMILES: Cc1ccc(-c2nnn(C3CN(S(=O)(=O)C(F)(F)F)C3)n2)cc1NC(=O)c1cnn2ccccc12] |
| 183 | 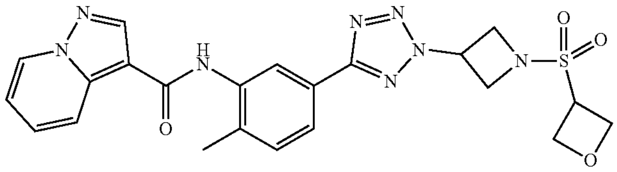 [SMILES: Cc1ccc(-c2nnn(C3CN(S(=O)(=O)C4COC4)C3)n2)cc1NC(=O)c1cnn2ccccc12] |
| 184 | 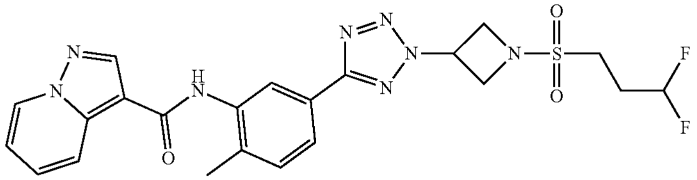 [SMILES: Cc1ccc(-c2nnn(C3CN(S(=O)(=O)CCC(F)F)C3)n2)cc1NC(=O)c1cnn2ccccc12] |
| 185 | 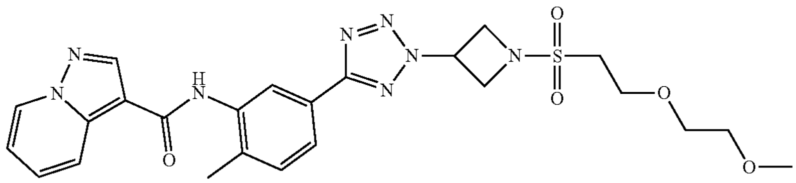 [SMILES: COCCOCCS(=O)(=O)N1CC(n2nnc(-c3ccc(C)c(NC(=O)c4cnn5ccccc45)c3)n2)C1] |

-continued
| Compound No | Structure |
|---|---|
| 186 | 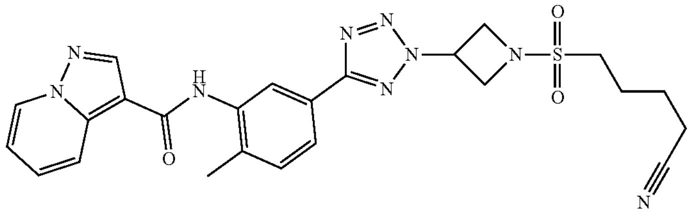 [SMILES: Cc1ccc(-c2nnn(C3CN(S(=O)(=O)CCCCC#N)C3)n2)cc1NC(=O)c1cnn2ccccc12] |
| 187 | 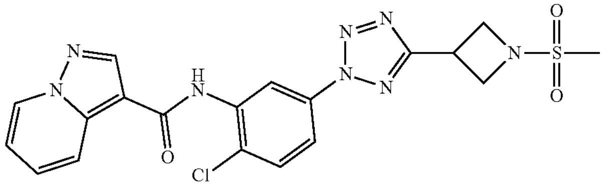 [SMILES: CS(=O)(=O)N1CC(c2nnn(-c3ccc(Cl)c(NC(=O)c4cnn5ccccc45)c3)n2)C1] |
| 188 | 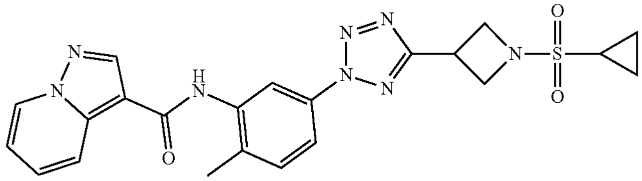 [SMILES: Cc1ccc(-n2nnc(C3CN(S(=O)(=O)C4CC4)C3)n2)cc1NC(=O)c1cnn2ccccc12] |
| 189 | 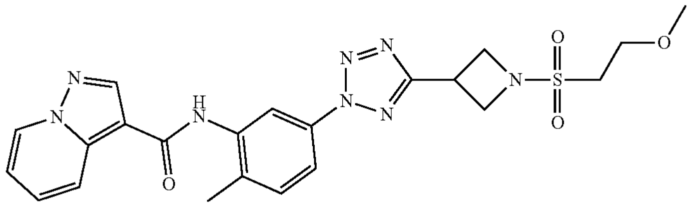 [SMILES: COCCS(=O)(=O)N1CC(c2nnn(-c3ccc(C)c(NC(=O)c4cnn5ccccc45)c3)n2)C1] |
| 190 | 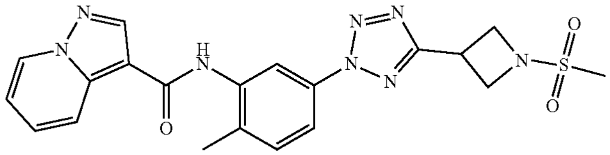 [SMILES: Cc1ccc(-n2nnc(C3CN(S(C)(=O)=O)C3)n2)cc1NC(=O)c1cnn2ccccc12] |
| 191 | 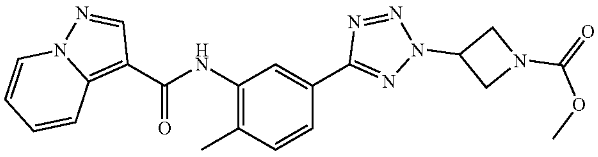 [SMILES: COC(=O)N1CC(n2nnc(-c3ccc(C)c(NC(=O)c4cnn5ccccc45)c3)n2)C1] |
| 192 | 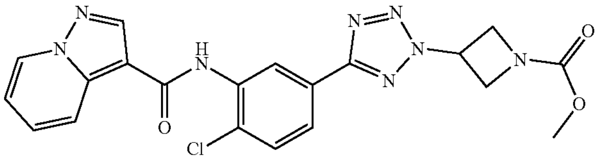 [SMILES: COC(=O)N1CC(n2nnc(-c3ccc(Cl)c(NC(=O)c4cnn5ccccc45)c3)n2)C1] |
| 193 | 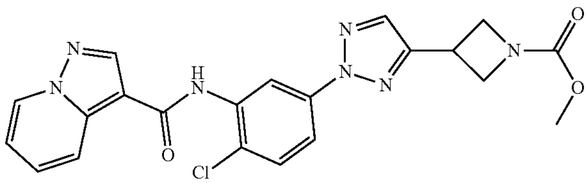 [SMILES: COC(=O)N1CC(c2cnn(-c3ccc(Cl)c(NC(=O)c4cnn5ccccc45)c3)n2)C1] |

-continued
| Compound No | Structure |
| --- | --- |
| 194 | 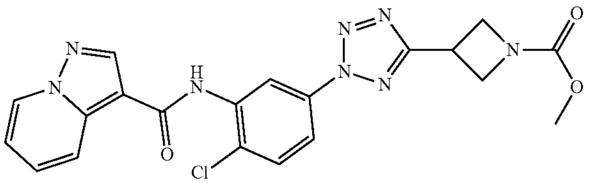 [SMILES: COC(=O)N1CC(c2nnn(-c3ccc(Cl)c(NC(=O)c4cnn5ccccc45)c3)n2)C1] |
| 195 | 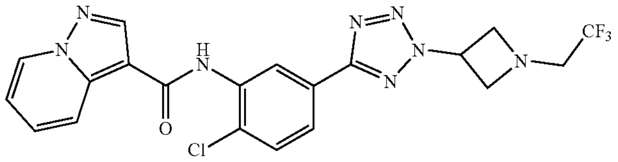 [SMILES: O=C(Nc1cc(-c2nnn(C3CN(CC(F)(F)F)C3)n2)ccc1Cl)c1cnn2ccccc12] |
| 196 | 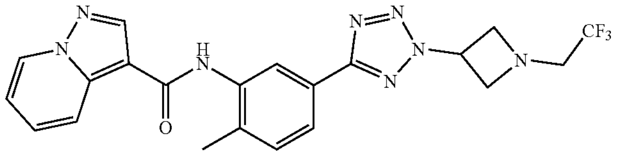 [SMILES: Cc1ccc(-c2nnn(C3CN(CC(F)(F)F)C3)n2)cc1NC(=O)c1cnn2ccccc12] |
| 197 | 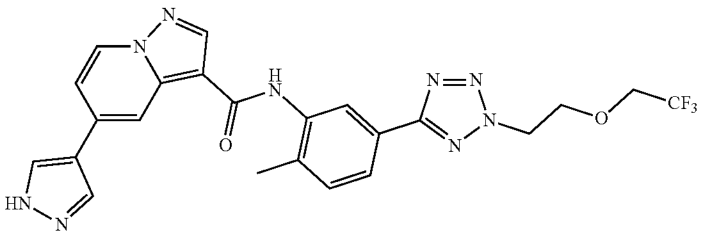 [SMILES: Cc1ccc(-c2nnn(CCOCC(F)(F)F)n2)cc1NC(=O)c1cnn2ccc(-c3cn[nH]c3)cc12] |
| 198 | 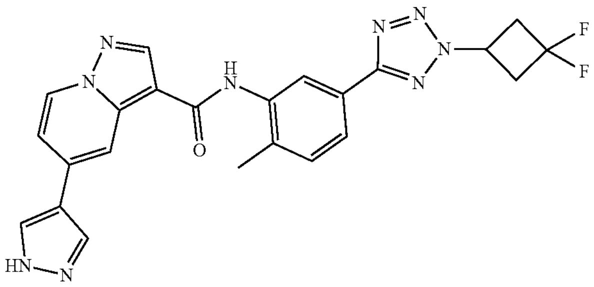 [SMILES: Cc1ccc(-c2nnn(C3CC(F)(F)C3)n2)cc1NC(=O)c1cnn2ccc(-c3cn[nH]c3)cc12] |
| 199 | 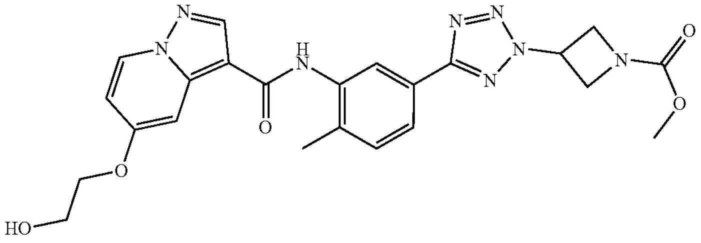 [SMILES: COC(=O)N1CC(n2nnc(-c3ccc(C)c(NC(=O)c4cnn5ccc(OCCO)cc45)c3)n2)C1] |
| 200 | 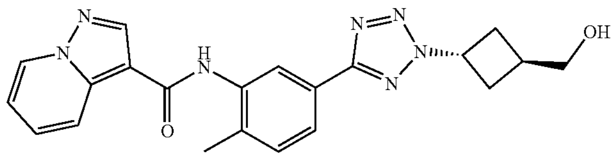 [SMILES: Cc1ccc(-c2nnn([C@H]3C[C@H](CO)C3)n2)cc1NC(=O)c1cnn2ccccc12] |

-continued
| Compound No | Structure |
|---|---|
| 201 | 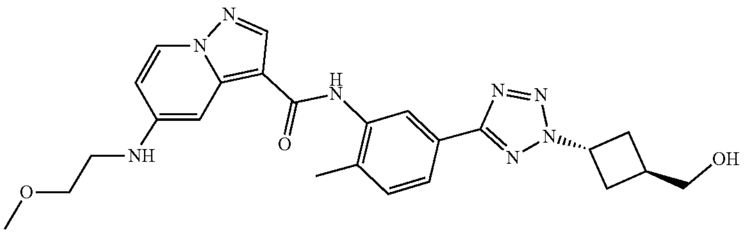 [SMILES: COCCNc1ccn2ncc(C(=O)Nc3cc(-c4nnn([C@H]5C[C@H](CO)C5)n4)ccc3C)c2c1] |
| 202 | 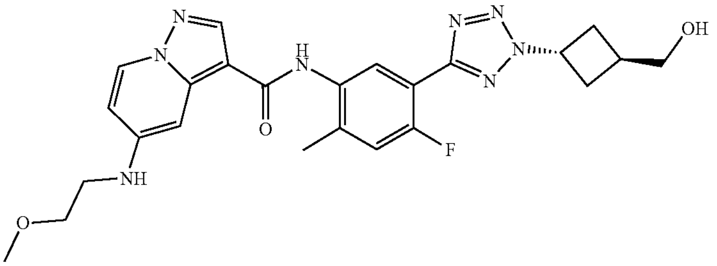 [SMILES: COCCNc1ccn2ncc(C(=O)Nc3cc(-c4nnn([C@H]5C[C@H](CO)C5)n4)c(F)cc3C)c2c1] |
| 203 | 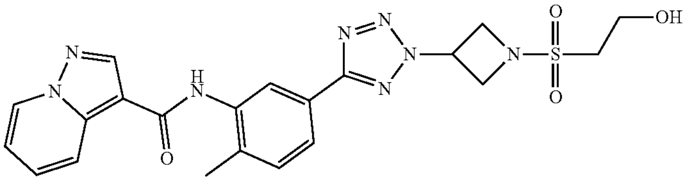 [SMILES: Cc1ccc(-c2nnn(C3CN(S(=O)(=O)CCO)C3)n2)cc1NC(=O)c1cnn2ccccc12] |
| 204 | 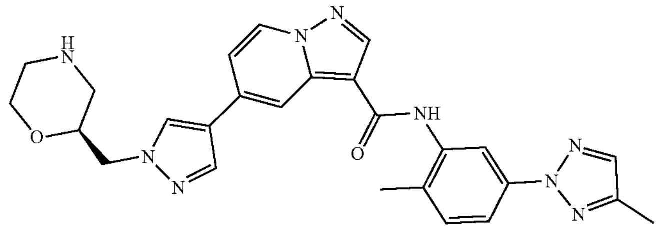 [SMILES: Cc1cnn(-c2ccc(C)c(NC(=O)c3cnn4ccc(-c5cnn(C[C@@H]6CNCCO6)c5)cc34)c2)n1] |
| 205 | 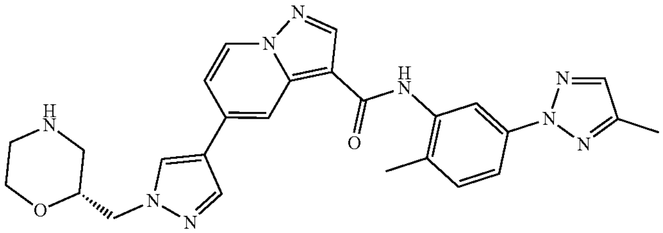 [SMILES: Cc1cnn(-c2ccc(C)c(NC(=O)c3cnn4ccc(-c5cnn(C[C@H]6CNCCO6)c5)cc34)c2)n1] |
| 206 | 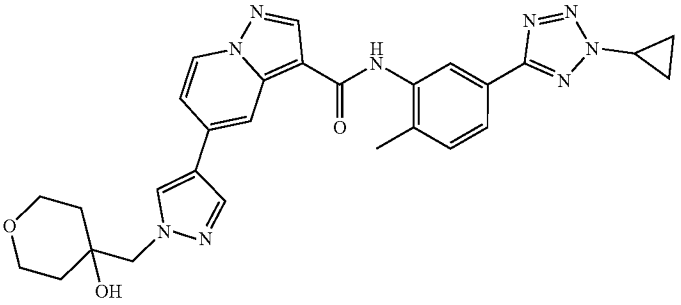 [SMILES: Cc1ccc(-c2nnn(C3CC3)n2)cc1NC(=O)c1cnn2ccc(-c3cnn(CC4(O)CCOCC4)c3)cc12] |

-continued
| Compound No | Structure |
| --- | --- |
| 207 | 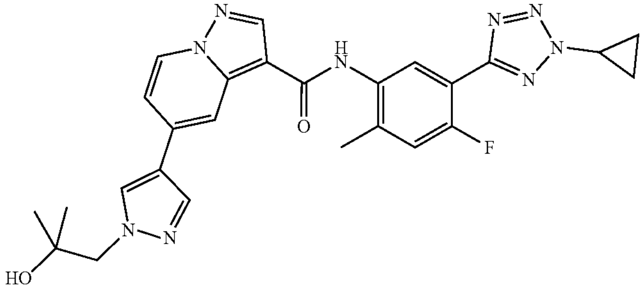 [SMILES: Cc1cc(F)c(-c2nnn(C3CC3)n2)cc1NC(=O)c1cnn2ccc(-c3cnn(CC(C)(C)O)c3)cc12] |
| 208 | 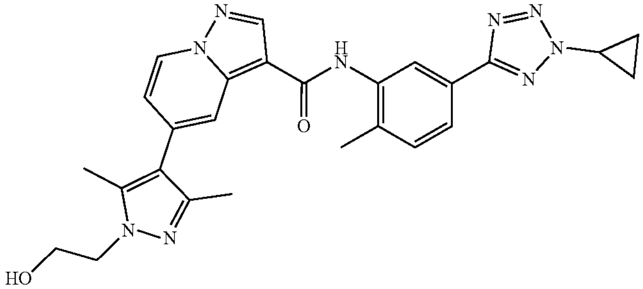 [SMILES: Cc1ccc(-c2nnn(C3CC3)n2)cc1NC(=O)c1cnn2ccc(-c3c(C)nn(CCO)c3C)cc12] |
| 209 | 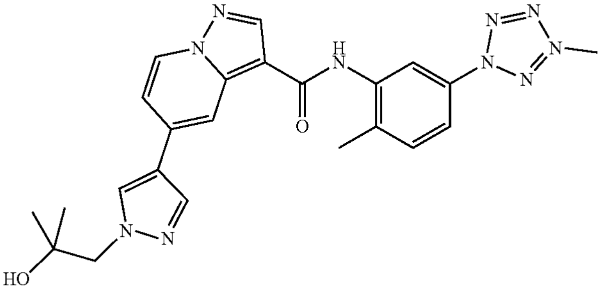 |
| 210 | 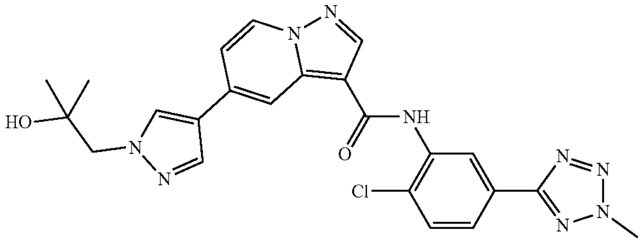 [SMILES: Cn1nnc(-c2ccc(Cl)c(NC(=O)c3cnn4ccc(-c5cnn(CC(C)(C)O)c5)cc34)c2)n1] |
| 211 | 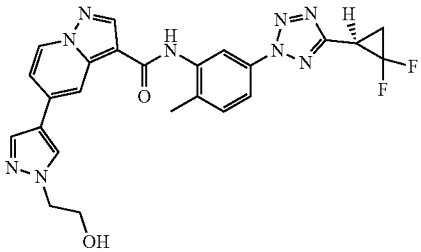 Or 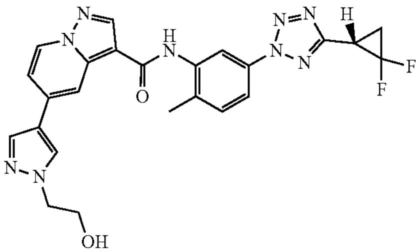 |

-continued
| Compound No | Structure |
| --- | --- |
| 212 | 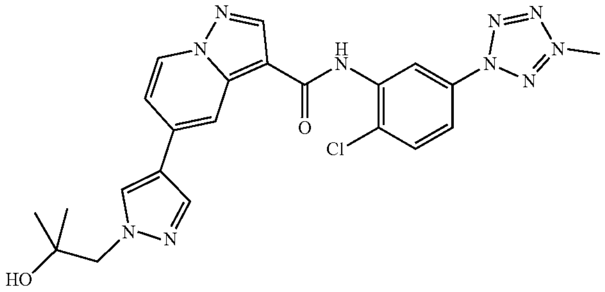 |
| 213 | 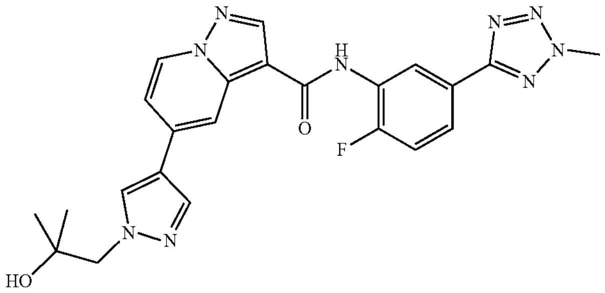 [SMILES: Cn1nnc(-c2ccc(F)c(NC(=O)c3cnn4ccc(-c5cnn(CC(C)(C)O)c5)cc34)c2)n1] |
| 214 | 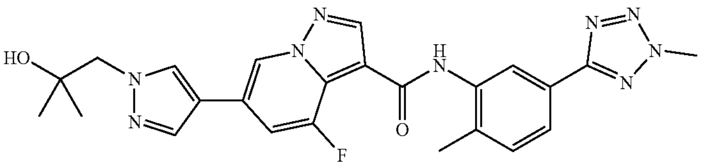 [SMILES: Cc1ccc(-c2nnn(C)n2)cc1NC(=O)c1cnn2cc(-c3cnn(CC(C)(C)O)c3)cc(F)c12] |
| 215 | 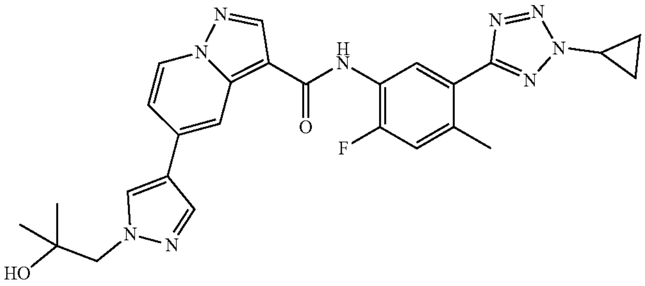 [SMILES: Cc1cc(F)c(NC(=O)c2cnn3ccc(-c4cnn(CC(C)(C)O)c4)cc23)cc1-c1nnn(C2CC2)n1] |
| 216 | 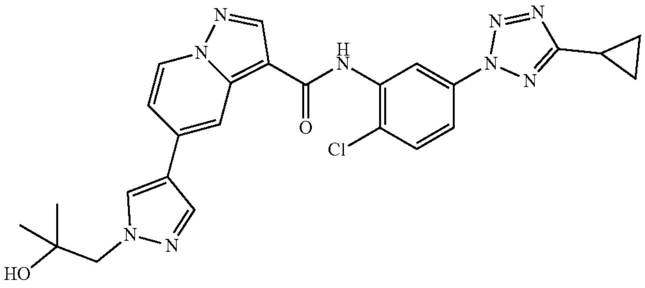 [SMILES: CC(C)(O)Cn1cc(-c2ccn3ncc(C(=O)Nc4cc(-n5nnc(C6CC6)n5)ccc4Cl)c3c2)cn1] |

-continued
| Compound No | Structure |
|---|---|
| 217 | 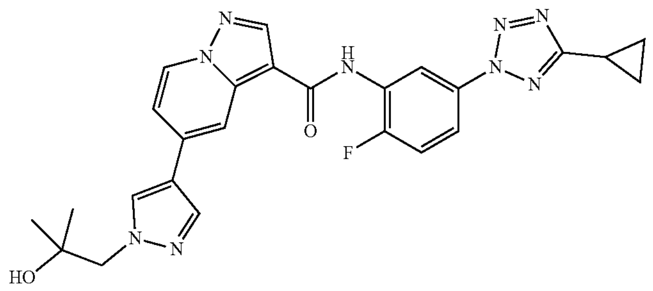 [SMILES: CC(C)(O)Cn1cc(-c2ccn3ncc(C(=O)Nc4cc(-n5nnc(C6CC6)n5)ccc4F)c3c2)cn1] |
| 218 | 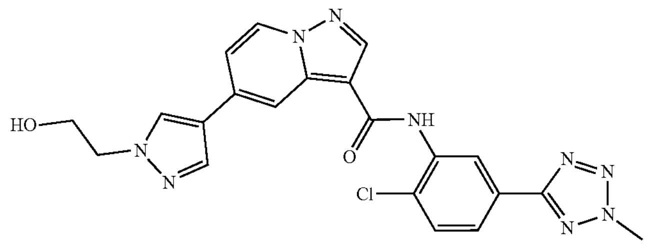 |
| 219 | 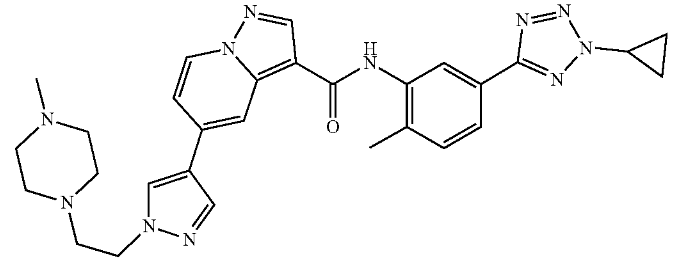 [SMILES: Cc1ccc(-c2nnn(C3CC3)n2)cc1NC(=O)c1cnn2ccc(-c3cnn(CCN4CCN(C)CC4)c3)cc12] |
| 220 | 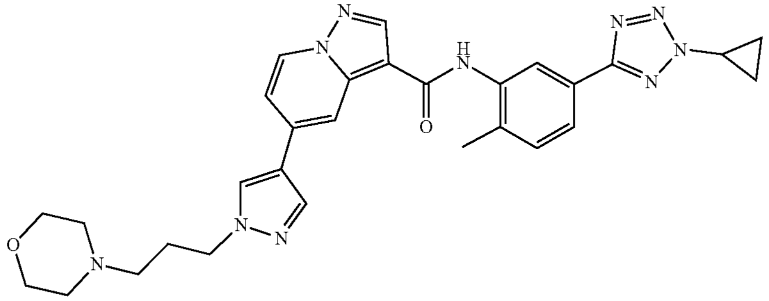 [SMILES: Cc1ccc(-c2nnn(C3CC3)n2)cc1NC(=O)c1cnn2ccc(-c3cnn(CCCN4CCOCC4)c3)cc12] |
| 221 | 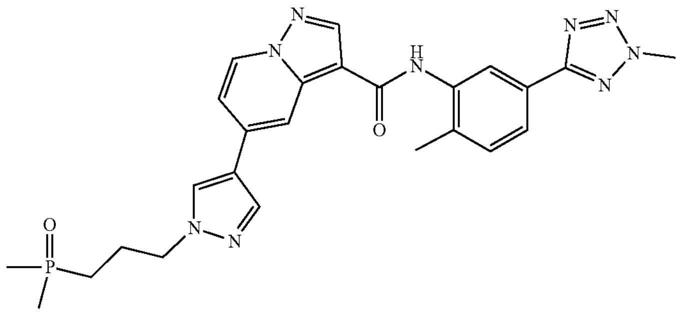 |

-continued
| Compound No | Structure |
| --- | --- |
| 222 | 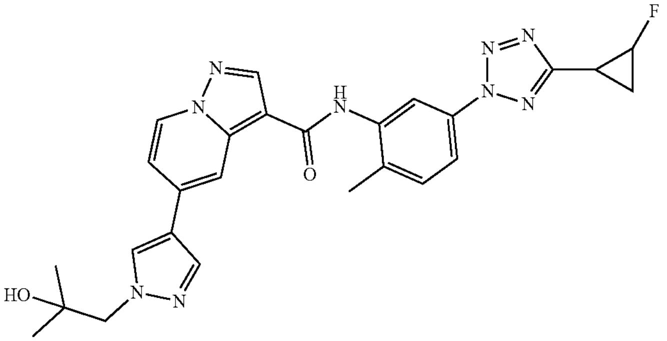 [SMILES: Cc1ccc(-n2nnc(C3CC3F)n2)cc1NC(=O)c1cnn2ccc(-c3cnn(CC(C)(C)O)c3)cc12] |
| 223 | 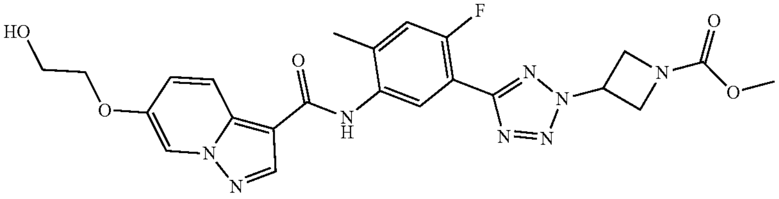 [SMILES: COC(=O)N1CC(n2nnc(-c3cc(NC(=O)c4cnn5cc(OCCO)ccc45)c(C)cc3F)n2)C1] |
| 224 | 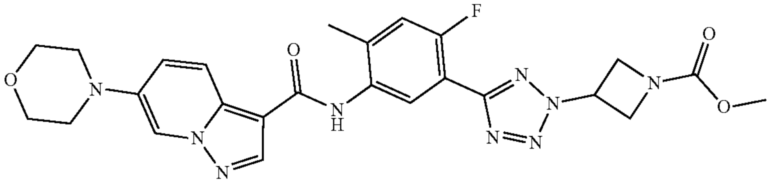 [SMILES: COC(=O)N1CC(n2nnc(-c3cc(NC(=O)c4cnn5cc(N6CCOCC6)ccc45)c(C)cc3F)n2)C1] |
| 225 | 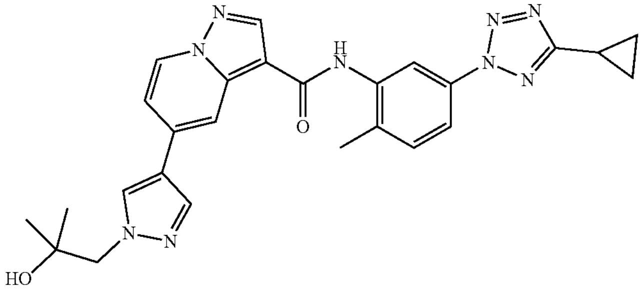 [SMILES: Cc1ccc(-n2nnc(C3CC3)n2)cc1NC(=O)c1cnn2ccc(-c3cnn(CC(C)(C)O)c3)cc12] |
| 226 | 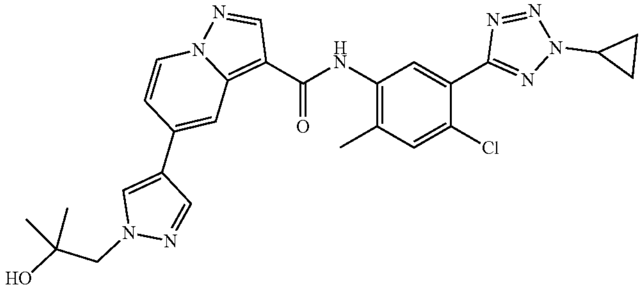 [SMILES: Cc1cc(Cl)c(-c2nnn(C3CC3)n2)cc1NC(=O)c1cnn2ccc(-c3cnn(CC(C)(C)O)c3)cc12] |

-continued
| Compound No | Structure |
|---|---|
| 227 | 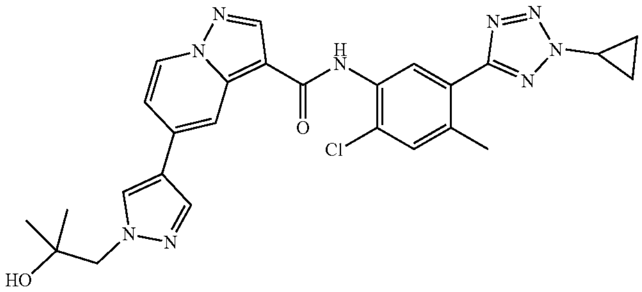 [SMILES: Cc1cc(Cl)c(NC(=O)c2cnn3ccc(-c4cnn(CC(C)(C)O)c4)cc23)cc1-c1nnn(C2CC2)n1] |
| 228 | 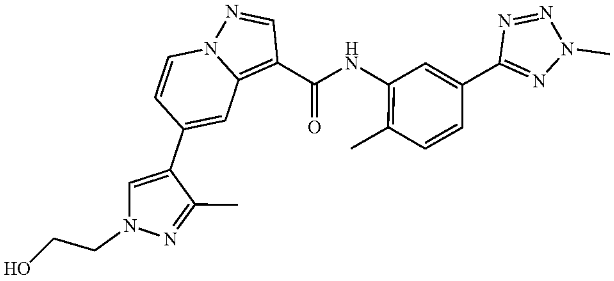 [SMILES: Cc1ccc(-c2nnn(C)n2)cc1NC(=O)c1cnn2ccc(-c3cn(CCO)nc3C)cc12] |
| 229 | 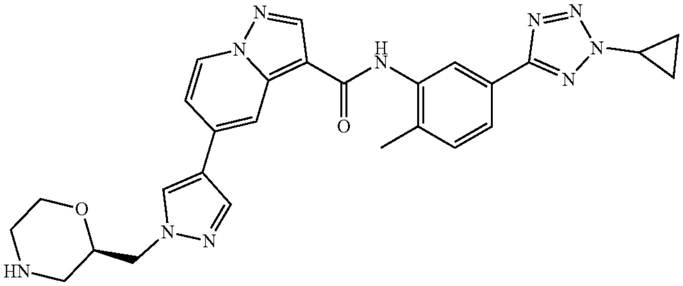 [SMILES: Cc1ccc(-c2nnn(C3CC3)n2)cc1NC(=O)c1cnn2ccc(-c3cnn(C[C@H]4CNCCO4)c3)cc12] |
| 230 | 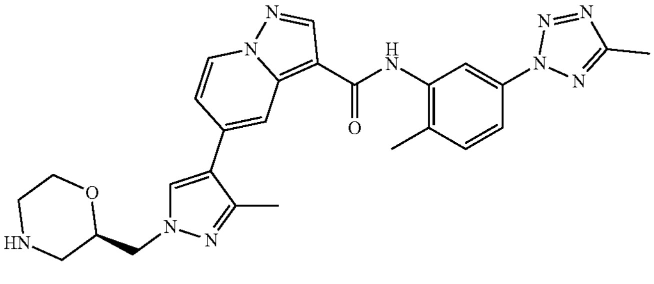 [SMILES: Cc1nnn(-c2ccc(C)c(NC(=O)c3cnn4ccc(-c5cn(C[C@H]6CNCCO6)nc5C)cc34)c2)n1] |
| 231 | 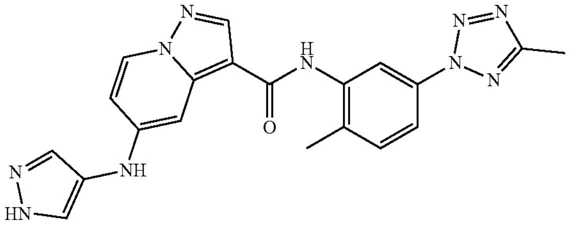 [SMILES: Cc1nnn(-c2ccc(C)c(NC(=O)c3cnn4ccc(Nc5cn[nH]c5)cc34)c2)n1] |

-continued
| Compound No | Structure |
|---|---|
| 232 | 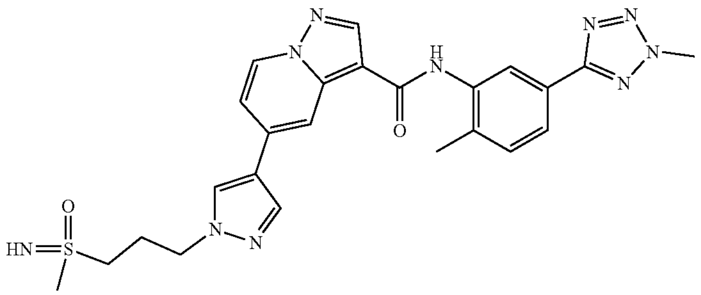 [SMILES: Cc1ccc(-c2nnn(C)n2)cc1NC(=O)c1cnn2ccc(-c3cnn(CCCS(C)(=N)=O)c3)cc12] |
| 233 | 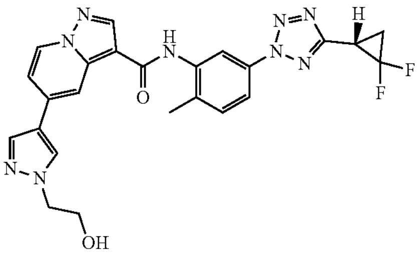 Or 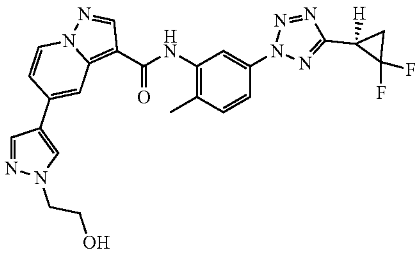 |
| 234 | 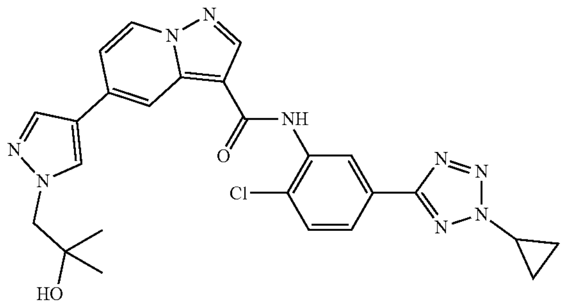 [SMILES: CC(C)(O)Cn1cc(-c2ccn3ncc(C(=O)Nc4cc(-c5nnn(C6CC6)n5)ccc4Cl)c3c2)cn1] |
| 235 | 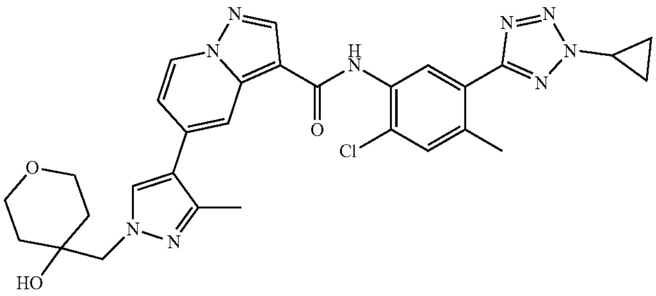 |
| 236 | 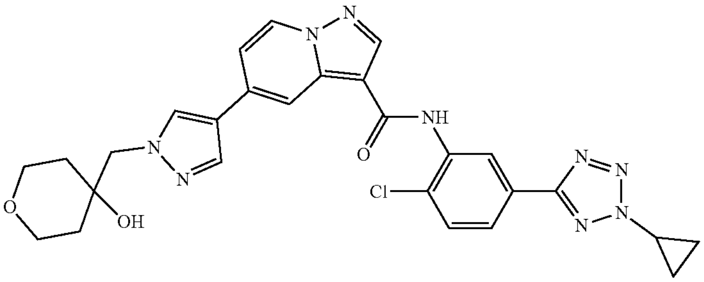 [SMILES: O=C(Nc1cc(-c2nnn(C3CC3)n2)ccc1Cl)c1cnn2ccc(-c3cnn(CC4(O)CCOCC4)c3)cc12] |

-continued
| Compound No | Structure |
| --- | --- |
| 237 | 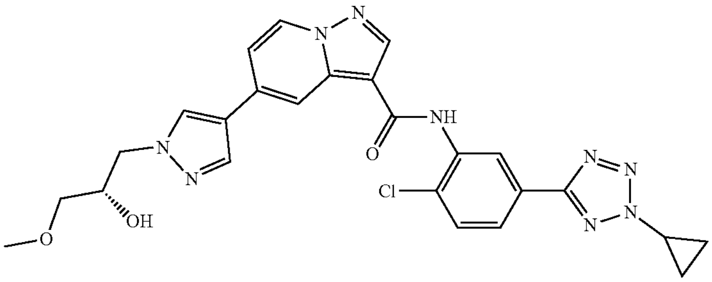 [SMILES: COC[C@@H](O)Cn1cc(-c2ccn3ncc(C(=O)Nc4cc(-c5nnn(C6CC6)n5)ccc4Cl)c3c2)cn1] |
| 238 | 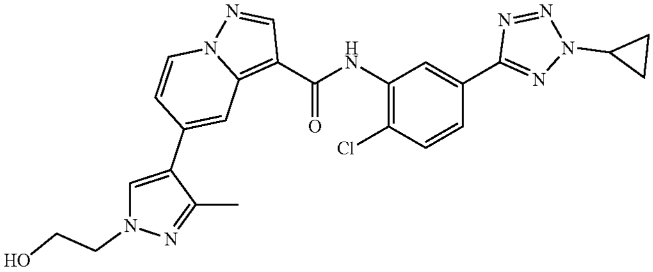 [SMILES: Cc1nn(CCO)cc1-c1ccn2ncc(C(=O)Nc3cc(-c4nnn(C5CC5)n4)ccc3Cl)c2c1] |
| 239 | 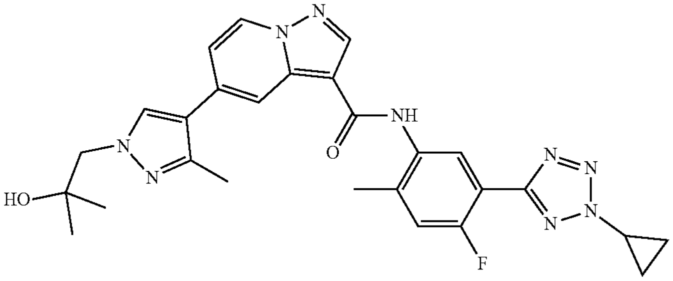 [SMILES: Cc1cc(F)c(-c2nnn(C3CC3)n2)cc1NC(=O)c1cnn2ccc(-c3cn(CC(C)(C)O)nc3C)cc12] |
| 240 | 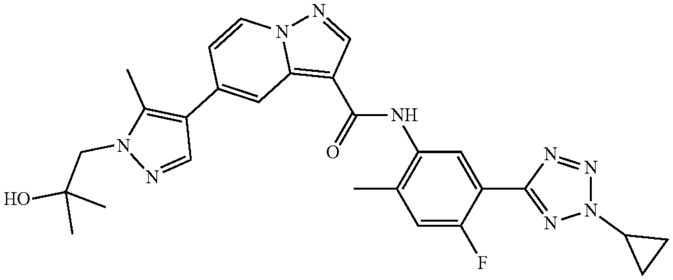 [SMILES: Cc1cc(F)c(-c2nnn(C3CC3)n2)cc1NC(=O)c1cnn2ccc(-c3cnn(CC(C)(C)O)c3C)cc12] |
| 241 | 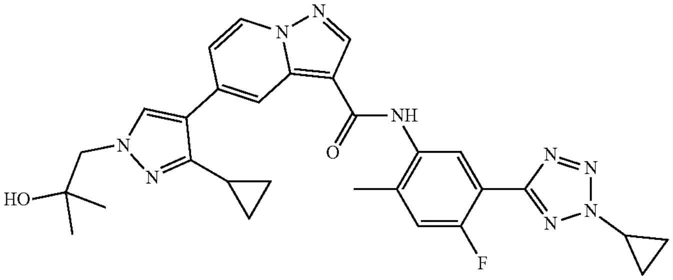 [SMILES: Cc1cc(F)c(-c2nnn(C3CC3)n2)cc1NC(=O)c1cnn2ccc(-c3cn(CC(C)(C)O)nc3C3CC3)cc12] |

-continued

| Compound No | Structure |
| --- | --- |
| 242 | 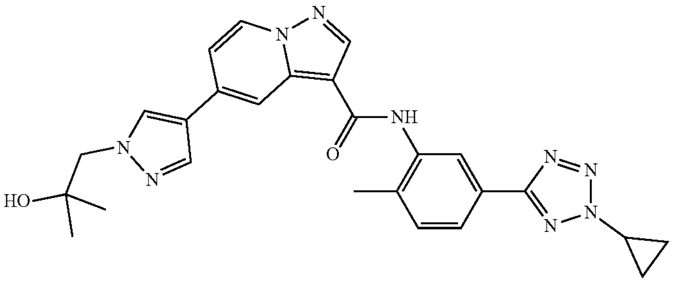 [SMILES: Cc1ccc(-c2nnn(C3CC3)n2)cc1NC(=O)c1cnn2ccc(-c3cnn(CC(C)(C)O)c3)cc12] |
| 243 | 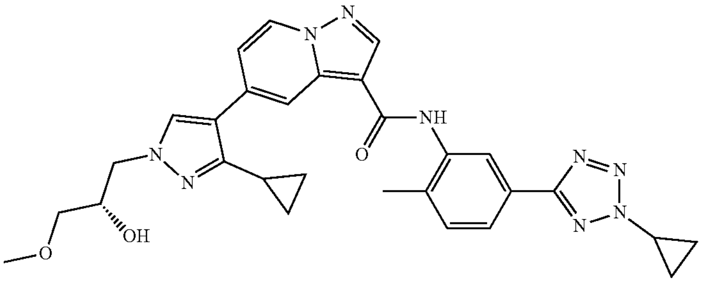 [SMILES: COC[C@@H](O)Cn1cc(-c2ccn3ncc(C(=O)Nc4cc(-c5nnn(C6CC6)n5)ccc4C)c3c2)c(C2CC2)n1] |
| 244 | 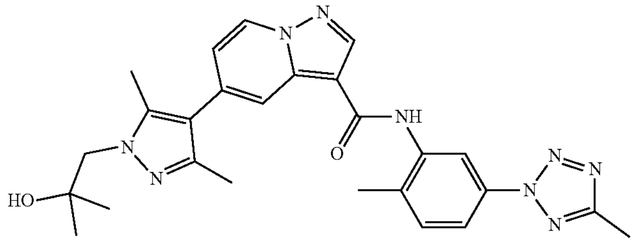 . |

12. A pharmaceutical composition comprising a compound of claim 1 or a pharmaceutically acceptable salt thereof and at least one pharmaceutically acceptable carrier or excipient.

13. The ocmpound of claim 1 or a pharmaceutically acceptable salt thereof, wherein the compound is:

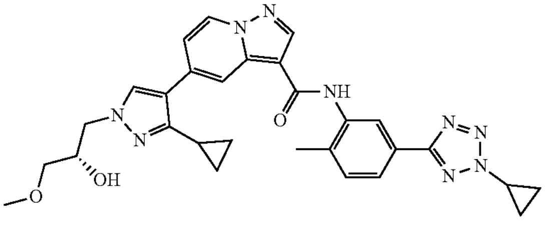

.

14. The compound of claim 1, wherein the compound is:

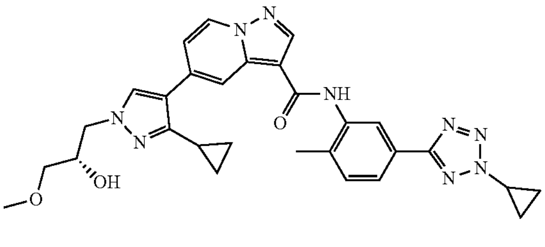

.

15. The compound of claim 1 or a pharmaceutically acceptable salt thereof, wherein the compound is:

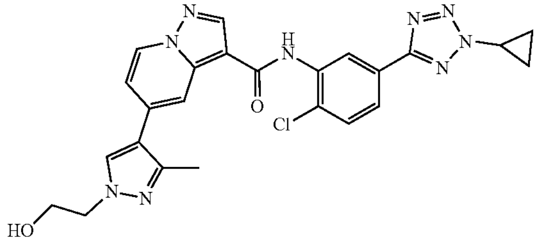

.

16. The compound of claim 1, wherein the compound is:

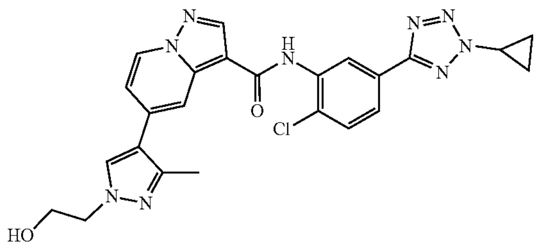

.

17. The compound of claim 1 or a pharmaceutically acceptable salt thereof, wherein the compound is:

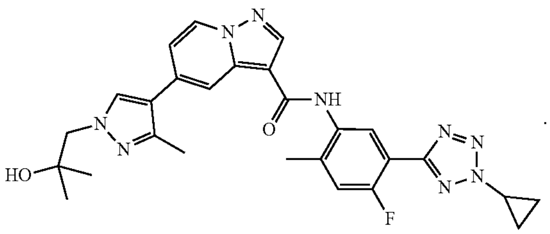 [SMILES: Cc1cc(F)c(-c2nnn(C3CC3)n2)cc1NC(=O)c1cnn2ccc(-c3cn(CC(C)(C)O)nc3C)cc12]

.

18. The compound of claim 1, wherein the compound is:

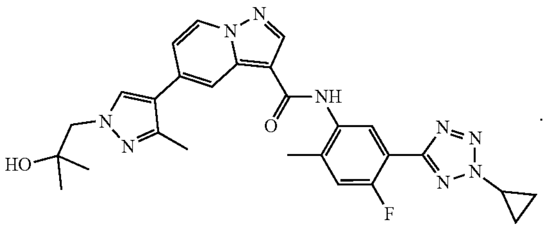 [SMILES: Cc1cc(F)c(-c2nnn(C3CC3)n2)cc1NC(=O)c1cnn2ccc(-c3cn(CC(C)(C)O)nc3C)cc12]

.

19. The compound of claim 1 or a pharmaceutically acceptable salt thereof, wherein the compound is:

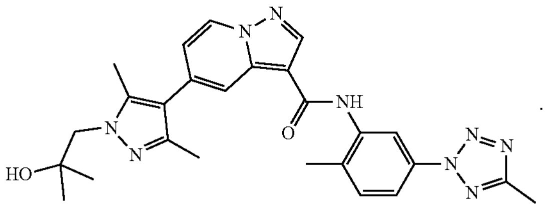 [SMILES: Cc1nnn(-c2ccc(C)c(NC(=O)c3cnn4ccc(-c5c(C)nn(CC(C)(C)O)c5C)cc34)c2)n1]

.

20. The compound of claim 1, wherein the compound is:

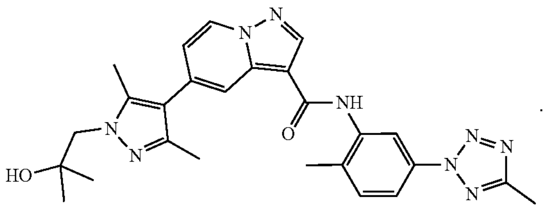 [SMILES: Cc1nnn(-c2ccc(C)c(NC(=O)c3cnn4ccc(-c5c(C)nn(CC(C)(C)O)c5C)cc34)c2)n1]

.

21. The compound of claim 1 or a pharmaceutically acceptable salt thereof, wherein the compound is:

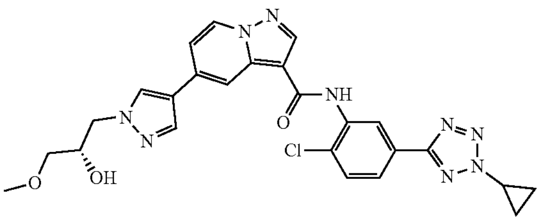

.

22. The compound of claim 1, wherein the compound is:

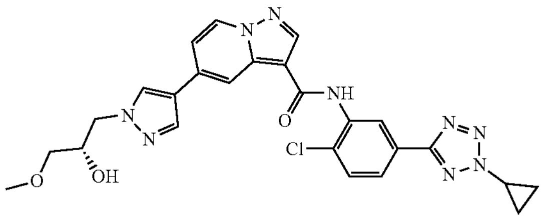

.

23. The compound of claim 1 or a pharmaceutically acceptable salt thereof, wherein the compound is:

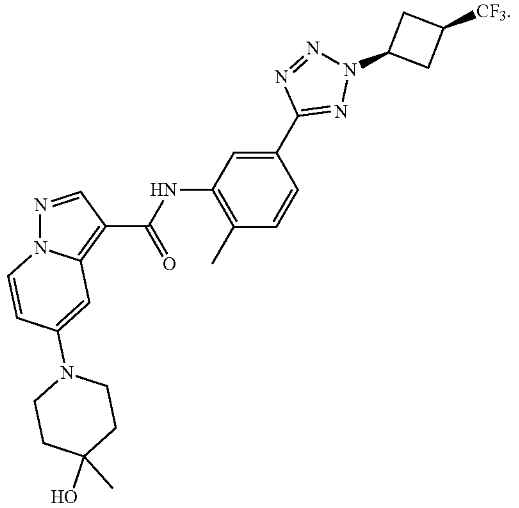 [SMILES: Cc1ccc(-c2nnn([C@H]3C[C@@H](C(F)(F)F)C3)n2)cc1NC(=O)c1cnn2ccc(N3CCC(C)(O)CC3)cc12]

24. The compound of claim 1, wherein the compound is:

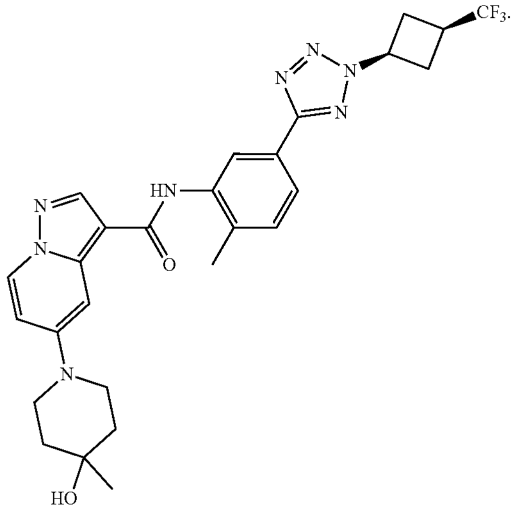 [SMILES: Cc1ccc(-c2nnn([C@H]3C[C@@H](C(F)(F)F)C3)n2)cc1NC(=O)c1cnn2ccc(N3CCC(C)(O)CC3)cc12]

25. The compound of claim 1 or a pharmaceutically acceptable salt thereof, wherein the compound is:

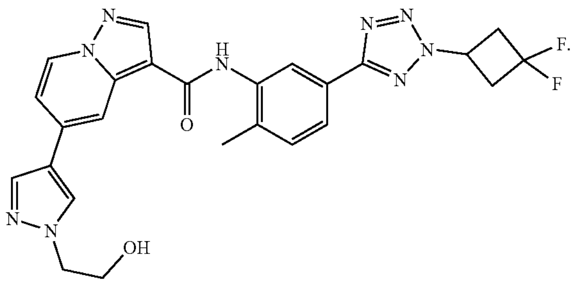 [SMILES: Cc1ccc(-c2nnn(C3CC(F)(F)C3)n2)cc1NC(=O)c1cnn2ccc(-c3cnn(CCO)c3)cc12]

26. The compound of claim 1, wherein the compound is:

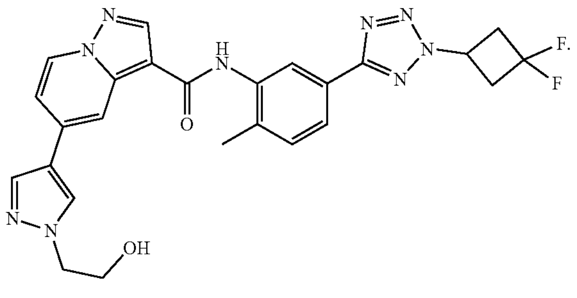 [SMILES: Cc1ccc(-c2nnn(C3CC(F)(F)C3)n2)cc1NC(=O)c1cnn2ccc(-c3cnn(CCO)c3)cc12]

27. The compound of claim 1 or a pharmaceutically acceptable salt thereof, wherein the compound is:

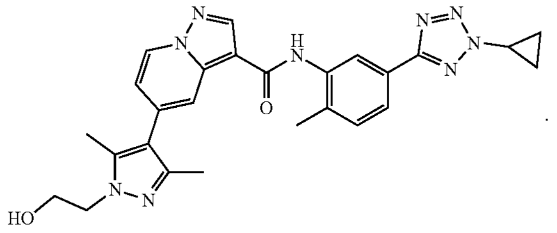 [SMILES: Cc1ccc(-c2nnn(C3CC3)n2)cc1NC(=O)c1cnn2ccc(-c3c(C)nn(CCO)c3C)cc12]

28. The compound of claim 1, wherein the compound is:

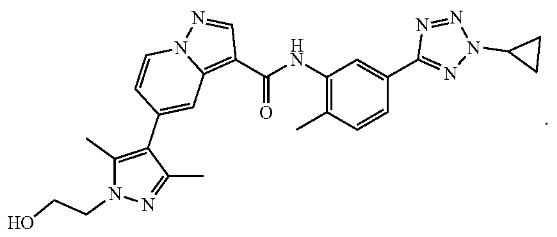 [SMILES: Cc1ccc(-c2nnn(C3CC3)n2)cc1NC(=O)c1cnn2ccc(-c3c(C)nn(CCO)c3C)cc12]

29. The compound of claim 1 or a pharmaceutically acceptable salt thereof, wherein the compound is:

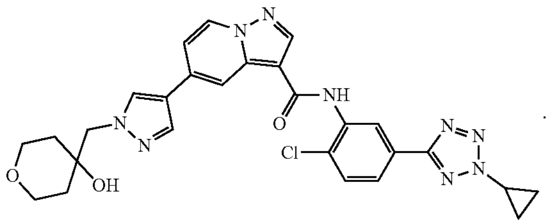 [SMILES: O=C(Nc1cc(-c2nnn(C3CC3)n2)ccc1Cl)c1cnn2ccc(-c3cnn(CC4(O)CCOCC4)c3)cc12]

30. The compound of claim 1, wherein the compound is:

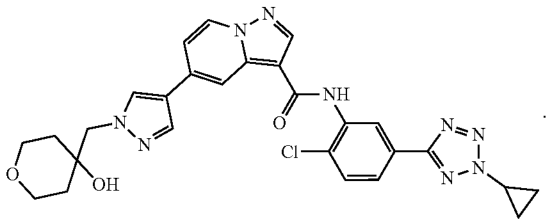 [SMILES: O=C(Nc1cc(-c2nnn(C3CC3)n2)ccc1Cl)c1cnn2ccc(-c3cnn(CC4(O)CCOCC4)c3)cc12]

31. The compound of claim 1 or a pharmaceutically acceptable salt thereof, wherein the compound is:

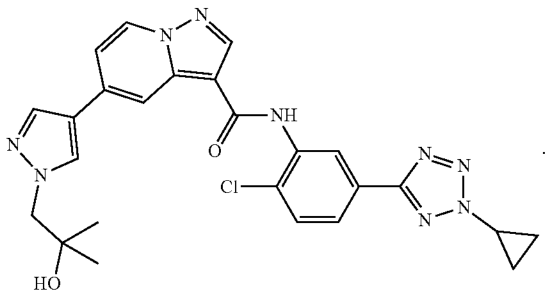 [SMILES: CC(C)(O)Cn1cc(-c2ccn3ncc(C(=O)Nc4cc(-c5nnn(C6CC6)n5)ccc4Cl)c3c2)cn1]

32. The compound of claim 1, wherein the compound is:

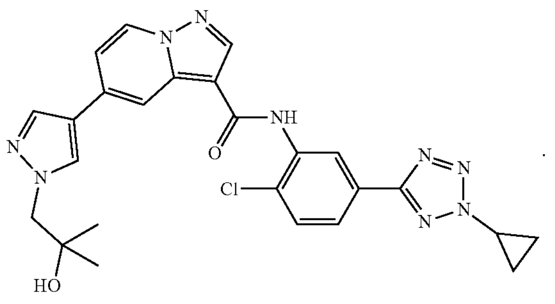 [SMILES: CC(C)(O)Cn1cc(-c2ccn3ncc(C(=O)Nc4cc(-c5nnn(C6CC6)n5)ccc4Cl)c3c2)cn1]

33. The compound of claim 1 or a pharmaceutically acceptable salt thereof, wherein:

each $R^1$ is independently selected from halogen, $C_{1-4}$alkyl, $C_{1-4}$haloalkyl, $C_{0-4}$alkylOH, $C_{0-4}$alkyl$C_{1-6}$alkoxy, $C_{0-4}$alkyl$C_{1-6}$haloalkoxy, $C_{3-4}$cycloalkyl, $NH_2$, $NHC_{1-5}$alkyl, $N(C_{1-3}alkyl)_2$, NH-(4-6 membered heterocycle containing at least one O), NH-(5-6 membered heteroaryl containing at least one N), 4-6 membered heterocycle, 7-9 mebered fused bicycloheterocycle, 7-10 membered spiroheterocycle, and 5-6 membered heteroaryl containing at least two N, wherein said heterocycle, fused bicycloheterocycle and spiroheterocycle contain at least one O or N, and wherein:

i) said alkyl, haloalkyl, or alkoxy is optionally substituted with 1-3 $R^e$ each independently selected from deuterium, deuterated $C_{1-3}$alkoxy, $C_{1-3}$alkyl, $C_{1-4}$haloalkoxy, $C_{1-4}$alkoxy, $C_{1-2}$alkoxy$C_{1-2}$alkoxy, OH, halogen, and 4-6 membered heterocycle containing at least one O or N;

ii) said heterocycle or cycloalkyl is optionally substituted with 1-3 $R^e$ each independently selected from deuterated $C_{1-3}$alkyl, di($C_{1-3}$alkyl)amine, $S(O)_2C_{1-3}$alkyl, halogen, 4-6 membered heterocycle containing one O, $C_{1-3}$alkyl, $C_{0-4}$alkyl, $C_{0-4}$alkylOH, and $C_{1-2}$alkyl $C_{1-3}$alkoxy; and iii) said heteroaryl is optionally substituted with 1-3 $R^e$ each independently selected from $C_{1-4}$alkyl, CN, $CHF_2$, cyclopropyl, $C_{1-4}$alkylOH, $C_{2-4}$alkyl(OH)(methoxy), $S(O)_2C_{1-3}$alkyl, $C_{1-3}$alkyl-S(O)(NH)$C_{1-3}$alkyl, ($C_{1-3}$alkyl)P(O)($C_{1-3}$alkyl)$_2$, and ($C_{1-3}$alkyl)-(4-6 membered heterocycle containing at least one O or N), wherein said heterocycle is optionally substituted with 1-2 OH.

* * * * *